United States Patent [19]

Brannigan et al.

[11] Patent Number: 5,162,537
[45] Date of Patent: Nov. 10, 1992

[54] BENZHYDRYL COMPOUNDS AS HERBICIDE ANTIDOTES

[75] Inventors: Lawrence H Brannigan, Olivette; Ronald J. Brinker; Robert J. Kaufman, both of St. Louis; Suzanne Metz, Chesterfield, all of Mo.

[73] Assignee: Monsanto Company, St. Louis, Mo.

[21] Appl. No.: 550,002

[22] Filed: Jul. 9, 1990

Related U.S. Application Data

[62] Division of Ser. No. 853,301, Apr. 17, 1986, Pat. No. 4,964,893.

[51] Int. Cl.$^5$ .................... C07C 69/76; C07C 59/40; C07D 211/34
[52] U.S. Cl. .................... 546/239; 560/57; 560/58; 562/468; 71/108
[58] Field of Search .................... 546/239; 560/57, 58; 562/468

[56] References Cited

PUBLICATIONS

Warkentin, J. et al Can. J. Chem. 45(24) 3035-43 1967.
Kolovos, M. et al Tetrahedron Lett. 25(35) 3909-12 1984.

*Primary Examiner*—Paul J. Killos
*Attorney, Agent, or Firm*—J. Timothy Keane; William I. Andress

[57] ABSTRACT

Acids, esters, amides and salts of benzhydryl compounds are antidotes for thiocarbamate and acetamide herbicides. These antidote compounds are especially effective to safen acetamide herbicides used to control grassy weeds and broadleaf weeds in rice, sorghum, corn and wheat.

22 Claims, No Drawings

BENZHYDRYL COMPOUNDS AS HERBICIDE ANTIDOTES

RELATED APPLICATION

This application is a division of U.S. Ser. No. 06/853,301 filed Apr. 17, 1986, U.S. Pat. No. 4,964,893.

FIELD OF THE INVENTION

Herbicide antidotes are well-known crop protection chemicals. Of particular interest herein is a class of acids, esters, amides and salts of benzhydryl compounds found effective as antidotes for protecting crop plants from herbicide injury.

BACKGROUND OF THE INVENTION

Herbicides may injure crop plants at herbicide application rates necessary to control weed growth. Accordingly, many herbicides cannot be used for controlling weeds in the presence of certain crops. Uncontrolled weed growth, however, results in lower crop yield and reduced crop quality inasmuch as weeds compete with crops for light, water and soil nutrients. Reduction of herbicidal injury to crops without an unacceptable corresponding reduction of herbicidal action on the weeds can be accomplished by use of crop protectants known as herbicide "antidotes" or "safeners".

Many benzhydryl compounds and derivatives are known for treatment of human central nervous system diseases. For example, U.S. Pat. No. 3,544,557 to Nauta describes tenzhydryl ether, acid-addition and quaternary ammonium salt compounds useful as anti-Parkinson disease agents. In particular, alkyl benzhydrylacetate compounds are shown as intermediates to obtain the Nauta '557 compounds. U.S. Pat. No. 4,003,932 to Gootjes describes diphenylmethoxyethylamine compounds as having dopaminergic properties for use in Parkinson-syndrome treatment. The Gootjes '932 compounds are mentioned as prepared from starting materials and intermediates selected from unsubstituted halo/-lower-alkyl-substituted diphenylmethoxyacetamides and lower alkyl esters. In particular, the amide starting material is shown as prepared from 2-[bis-(p-fluorophenyl)methoxy]acetic acid. U.S. Pat. No. 4,066,686 to Lafon describes benzhydrylsulphinyl derivatives useful for treating central nervous systems disturbances. In particular, Lafon '686 shows the following as intermediate or product compounds: benzhydrylthioacetic acid, ethyl benzhydrylthioacetate, benzhydrylsulphinylacetic acid, methyl benzhydrylsulphinylacetate, and N-[2-(benzhydrylsulphinyl)ethyl]-piperidine hydrochloride. U.S. Pat. No. 4,202,896 to Gootjes describes N-benzhydryloxyethyl-N-phenylpropylpiperazine compounds for use in Parkinson-syndrome treatment. These compounds are prepared from starting materials selected from unsubstituted or halo/lower-alkyl/lower-alkoxy-substituted diphenylmethoxyacetic/propanoic acid compounds. In particular, there is mentioned as a starting material the compound methyl diphenylmethoxyacetate.

Benzhydryl compounds and derivatives are known also for other human-related pharmaceutical purposes. For example, U.S. Pat. No. 4,205,087 to Waring describes benzhydrylacetic acid derivatives for use in anti-arthritic treatment. In particular, the compound methyl bis(4-chlorophenyl)methoxyacetate is shown. U.S. Pat. No. 4,427,590 to Allgeier et al describes triazolobenzodiazepine derivatives and oxides useful as tranquilizers and as anticonvulsant agents. An intermediate compound specifically shown is diphenylmethoxyacetic acid hydrazide. Japanese Kokai No. 74/81,379 of Kono et al shows benzhydryloxyalkylpenicillin compounds for pharmaceutical uses which are prepared from diphenylmethoxyacetic acid. A monograph by C. Van der Stelt et al [Arzneim.-Forsch., 17(11), pp. 1446-1449 (1967)], relating to guanidine and amidoxime derivatives of diphenylmethyl and tricyclic ethers, mentions the compound 2-(diphenylmethoxy)acetamide.

None of the aforementioned publications describes benzhydryl compounds for agricultural-related uses, much less for use as herbicide antidotes.

For a herbicide product to be accepted commercially, the herbicide product must provide a relatively high level of control of weeds in crops, such as rice, wheat, corn or sorghum, in addition to meeting several other criteria. For example, the herbicide must possess relatively high unit activity so that lower rates of herbicide application are feasible. Lower application rates are desirable in order to minimize exposure of the environment to the herbicide. At the same time, such herbicide must be selective in herbicidal effect so as not to injure the crops. Herbicidal selectivity can be enhanced by use of an appropriate antidote in combination with the herbicide. But identification of an antidote having high safening activity suitable for a commercially-effective herbicide is a highly complicated task. Whether a compound or class of compounds provides efficacious antidotal or safening activity is not a theoretical determination but must be done empirically. Safening activity is determined empirically by observing the complex interaction of several biological and chemical factors, namely: the type of herbicide compound; the type of weed to be controlled; the type of crop to be protected from weed competition and herbicidal injury; and the antidote compound itself. Moreover, the herbicide and antidote must each possess chemical and physical properties enabling preparation of an efficacious, stable formulation which is environmentally safe and easy to apply to the field.

DESCRIPTION OF THE INVENTION

A family of compounds useful as antidotes against herbicide injury to crop plants is provided by acids, esters, amides and salts of benzhydryl-type ether compounds having the general structural formula

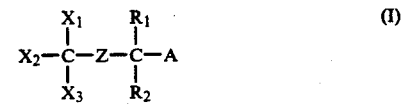

wherein each of $X_1$, $X_2$ and $X_3$ is independently selected from hydrido, alkyl, cycloalkyl, haloalkyl, phenyl, furanyl, thienyl, thiazolyl, pyridinyl, N-oxidepyridinyl, and phenyl substituted by one or more radicals, $R_4$ and $R_9$ selected from alkyl, alkoxy, halo, haloalkoxy, nitro, haloalkyl and alkyolamino; wherein Z is selected from oxygen atom, sulfur atom,

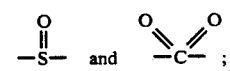

wherein each of $R_1$ and $R_2$ is independently selected from hydrido and alkyl; wherein A is selected from cyano, oxazolinyl, alkyloxazolinyl, oximinoalkyl, and radicals represented by

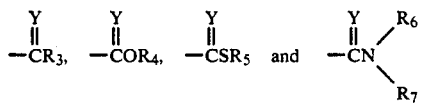

with Y selected from oxygen atom and sulfur atom; wherein each of $R_3$, $R_4$ and $R_5$ is a substituent independently selected from hydrido, alkyl, alkenyl, alkynyl, haloalkyl, cycloalkyl, oxiranyl, alkoxyalkyl, alkoxycarbonylalkyl, alkylthioalkyl, hydroxyalkyl, phenyl, benzyl, benzodioxolyl, benzodioxolylalkyl, thienyl, thienylalkyl, furanyl, furanylalkyl, hydroxyalkylfuranylalkyl, pyridinyl, pyridinylalkyl, dioxolanyl, alkyldioxolanyl, alkyldioxolanylalkyl, and hydrated and non-hydrated agriculturally-acceptable alkali metal cations including sodium and potassium cations, alkaline earth cations including calcium and magnesium cations, onium cations including ammonium, morpholinium and piperazinium cations and ammonium or morpholinium or piperazinium cations substituted with one or more groups selected from alkyl, cycloalkyl, hydroxyalkyl, phenylalkyl, diphenylalkyl, triphenylalkyl, aminoalkyl, cyanoalkyl, alkoxyalkyl and hydroxyalkoxyalkyl; wherein any one of said $R_3$, $R_4$ and $R_5$ substituents having a substitutable position may be substituted with one or more radicals selected from alkyl, cycloalkyl, alkoxy, halo, haloalkyl, phenyl, halophenyl, alkoxyphenyl, cyano and nitro; wherein each of $R_6$ and $R_7$ is a substituent independently selected from hydrido, alkyl, alkenyl, amino, hydroxyl, haloalkyl, hydroxyalkyl, alkoxyl and phenyl; wherein $R_6$ and $R_7$ may be taken together to form piperazinyl; wherein any of said $R_6$ and $R_7$ substituents alone, or taken together, and having a substitutable position, may be substituted with one or more radicals selected from alkyl, halo, haloalkyl, phenyl, halophenyl, phenylalkoxyalkylcarbonyl, diphenylalkoxyalkylcarbonyl and alkoxyphosphorylalkylisocyano.

Preferred compounds within the class defined by formula I are compounds wherein each of $X_1$ and $X_2$ is independently selected from phenyl and phenyl substituted by one or more groups selected from alkyl, alkoxy, halo, nitro, haloalkyl and alkylamino; wherein $X_3$ is hydrido; wherein Z is oxygen atom; wherein each of $R_1$ and $R_2$ is hydrido; wherein A is selected from

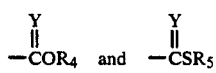

wherein Y is oxygen atom; wherein each of $R_4$ and $R_5$ is independently selected from hydrido, alkyl, alkoxyalkyl, cycloalkoxyalkyl, alkoxycarbonylalkyl, alkylthioalkyl, alkenyl, alkynyl, haloalkyl, phenyl, benzyl, benzodioxolyl, benzodioxolylalkyl, thienyl, thienylalkyl, furanyl, furanylalkyl, hydroxyalkylfuranylalkyl, pyridinyl, pyridinylalkyl, dioxolanyl, alkyldioxolanyl, alkyldioxolanylalkyl, and agriculturally-acceptable cations selected from sodium, ammonium and ammonium substituted with one or more alkyl groups; and wherein any one of said $R_4$ and $R_5$ substituents having a substitutable position may be substituted with one or more radicals selected from alkyl, cyano, cycloalkyl, haloalkyl, halo, alkoxy, phenyl, halophenyl and haloalkyl.

Particularly preferred compounds within formula I comprise a class of compounds of formula II

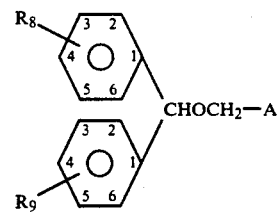

wherein each of $R_8$ and $R_9$ independently represents one or more substituents selected from alkyl, alkoxy, alkylamino, halo, haloalkyl and nitro; wherein A is selected from

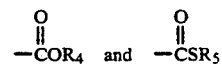

wherein each of $R_4$ and $R_5$ is independently selected from hydrido, alkyl, haloalkyl, cyanoalkyl, alkenyl, alkynyl, phenyl, nitrophenyl, benzyl, halobenzyl, pyridinylalkyl and alkylammonium.

More particularly preferred compounds within formula II are those wherein each of $R_4$ and $R_5$ is independently selected from hydrido, methyl, ethyl, 1-methylethyl, 1,1-dimethylethyl, n-propyl, 2-propenyl, 1 TM methyl-2-propynyl, 1-ethyl-2-propynyl, 2,2,2-trifluoroethyl, 1-methyl-2,2,2-trifluoroethyl, 2,2,3,3-tetrafluoropropyl, 2-cyanoethyl, 1-cyano-1-methylethyl, phenyl, 3-nitrophenyl, benzyl, 4-chlorobenzyl, 3-pyridinylmethyl, and 1,1 TM dimethylethylammonium, and wherein each of $R_8$ and $R_9$ represents substituents independently selected from 2-methyl, 2,6-dimethyl, 4-chloro, 2-trifluoromethyl, 3-trifluoromethyl and 5-trifluoromethyl.

The compounds of the foregoing classes are believed to be novel with the exclusion of certain acids, esters, amides and other groups of benzhydryl compounds defined as follows:

when each of $X_1$ and $X_2$ is phenyl, $X_3$ is hydrido, Z is oxygen atom, $R_1$ is hydrido, $R_2$ is hydrido, methyl, or ethyl, and $R_4$ is hydrido, then each of $R_8$ and $R_9$ cannot be hydrido, methyl, fluoro, chloro or bromo;

when each of $X_1$ and $X_2$ is phenyl, Z is oxygen atom, each of $X_3$ and $R_1$ is hydrido, $R_2$ is hydrido, methyl or 2-propyl, and $R_4$ is methyl, ethyl, 2-dimethylaminoethyl, 2-ethoxyethyl or diphenylmethyl, then each of $R_8$ and $R_9$ cannot be hydrido, chloro, fluoro, bromo or trifluoromethyl;

when each of $R_6$ and $R_7$ is hydrido, methyl or ethyl, Z is oxygen atom, each of $X_1$ and $X_2$ is phenyl, $X_3$ is hydrido, and each of $R_1$ and $R_2$ is hydrido, then each of $R_8$ and $R_9$ cannot be hydrido, fluoro, chloro, methyl, tert-butyl, methoxy or amino;

when each of $R_8$ and $R_9$ is dimethylamino or diethylamino, Z is oxygen atom, each of $X_1$ and $X_2$ is phenyl, and each of $X_3$, $R_1$, $R_2$ and $R_6$ is hydrido, then $R_4$ cannot be ethyl, 2-ethoxyethyl or benzyl, and $R_7$ cannot be hydrido, methyl, phenyl or chlorophenyl;

when each of $X_1$ and $X_2$ is phenyl, each of $X_3$, $R_1$ and $R_2$ is hydrido, and each of $R_8$ and $R_9$ is hydrido or methyl, then A cannot be

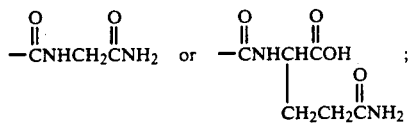

when Z is either sulfur atom or sulfinyl, each of $X_1$ and $X_2$ is phenyl, each of $X_3$, $R_1$, $R_2$ and $R_6$ is hydrido, then $R_4$ cannot be hydrido, methyl or ethyl, $R_7$ cannot be hydroxyl, and A cannot be cyano; and when Z is oxygen atom, each of $X_1$ and $X_2$ is phenyl, each of $X_3$, $R_1$ and $R_2$ is hydrido, and each of $R_8$ and $R_9$ is fluoro, then A cannot be cyano.

Where the term "alkyl" is used, either alone or within another term such as "haloalkyl", the term "alkyl" embraces linear or branched radicals having one to ten carbon atoms. The term "cycloalkyl", embraces radicals having three to ten carbon atoms, such as cyclopropyl and cyclobutyl. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are trifluoromethyl, 2,2,2-trifluoroethyl, perfluoroethyl and 2,2,3,3-tetrafluoropropyl groups. The terms "alkylol" and "hydroxyalkyl" embrace linear or branched alkyl groups having one to ten carbon atoms any one of which may be substituted with one or more hydroxyl groups. The term "alkenyl" embraces linear or branched radicals having two to ten carbon atoms and containing at least one carbon-carbon double bond. The term "alkynyl" embraces linear or branched radicals having two to ten carbon atoms and containing at least one carbon-carbon triple bond. The term "alkylthioalkyl" embraces radicals containing two linear or branched alkyl groups, each of one to ten carbon atoms, which alkyl groups are connected to a divalent sulfur atom. The terms "alkoxy" and "alkoxyalkyl" embrace linear or branched oxy-containing radicals having alkyl portions of one to ten carbon atoms, such as a methoxy group. The "alkoxy" or "alkoxyalkyl" radicals may be further substituted with one or more halo atoms, such as fluoro, chloro or bromo, to provide haloalkoxy or haloalkoxyalkyl groups. The term "oxiranyl" embraces a three-membered ring containing an oxygen atom and two carbon atoms. The term "alkoxycarbonylalkyl" embraces linear or branched radicals containing at least one oxy group and at least one carbonyl moiety separated by alkyl groups of one to ten carbon atoms. The terms "benzyl" and "phenylmethyl" are interchangeable. The terms "halophenyl","alkylphenyl","alkoxyphenyl" and "nitrophenyl" embrace substituted phenyl radicals having one or more of the respective substituents, e.g., "halophenyl" embraces monohalo-, dihalo-, trihalo-, tetrahalo- and pentahalo-phenyl. The term "agriculturally-acceptable cations" embraces cations commonly used to form addition salts of the free acids, examples of such cations being alkali metal cations such as sodium and potassium, alkaline earth cations such as magnesium and calcium, onium cations such as ammonium, substituted ammonium, morpholinium and piperazinium cations and their substituted derivatives. The term "addition salts" includes the salts of acids and quaternary-type salts.

Each of the following radicals is described by a general word term, and then exemplified by a specific name and structure. It is intended that such specific name and structure are for purposes of exemplification, only, and that many other radicals may be embraced by the general term:

| General Term for Radical | Specific Name Exemplification | Specific Structural Exemplification |
| --- | --- | --- |
| dioxolanyl | 1,3-dioxolan-4-yl | |
| alkyldioxolanyl | 2,2-dimethyl-1,3-dixolan-4-yl | |
| alkyldioxolanylalkyl | (2,2-dimethyl-1,3-dioxolan-4-yl)methyl | |
| benzodioxolyl | 1,3-benzodioxol-5-yl | |
| benzodioxolylalkyl | 1,3-benzodioxol-5-yl-methyl | |

-continued

| General Term for Radical | Specific Name Exemplification | Specific Structural Exemplification |
|---|---|---|
| thienyl | 2-thienyl | (2-thienyl ring structure with S) |
| thienylalkyl | 2-thienylmethyl | —CH₂— (2-thienylmethyl ring structure with S) |
| furanyl | 3-furanyl | (3-furanyl ring structure with O) |
| furanylalkyl | 3-furanylmethyl | —CH₂— (3-furanylmethyl ring structure with O) |
| hydroxyalkylfuranylalkyl | 5-(hydroxymethyl)-2-furanylmethyl | —CH₂— (furan ring with O and CH₂OH) |
| thiazolyl | 2-thiazolyl | (2-thiazolyl ring with S and N) |
| oxazolinyl | 2-oxazolin-2-yl | (2-oxazolin-2-yl ring with O and N) |
| alkyloxazolinyl | 4,4-dimethyl-2-oxazolin-2-yl | (ring with O, N, and two CH₃ groups) |
| pyridinyl | 2-pyridinyl | (2-pyridinyl ring with N) |
| pyridinylalkyl | 3-pyridinylmethyl | —CH₂— (3-pyridinylmethyl ring with N) |
| N-oxidepyridinyl | 4-pyridinyl-N-oxide | (pyridine ring with N→O) |
| oximinoalkyl | oximinomethyl | —CH=NOH |
| alkoxyphosphoryl-alkylisocyano | methoxyphosphoryl-ethylisocyano | —N=C(CH₃)—P(=O)(OCH₃)(OCH₃) |

Also included in this invention are the stereo and optical isomers of compounds within the class defined by formula I.

The terms "antidote", "safening agent", "safener", "antagonistic agent", "interferant", "crop protectant" and "crop protective", are often-used terms denoting a compound capable of reducing the phytotoxicity of a herbicide to a crop plant or crop seed. The terms "crop protectant" and "crop protective" are sometimes used to denote a herbicide-antidote combination which provides protection from competitive weed growth by reducing herbicidal injury to a valuable crop plant while at the same time controlling or suppressing weed growth occurring in the presence of the crop plant. An "antidotally-effective amount" of an antidote is that amount which protects crop plants by interfering with the herbicidal action of a herbicide on the crop plants, but without interfering with the herbicidal action on weeds, so as to render the herbicide selective to weed plants emerging or growing in the presence of crop plants.

Herbicides which may be used with benefit in combination with an antidote of the described class include a large variety of herbicides such as thiocarbamates, triazines, diphenylethers, benzoic acid derivatives, phenylureas, nitroanilines, benzene sulfonamides, sulfonylureas and acetamides. To achieve control of a broad spectrum of narrow and broadleaf weeds, it may be desirable to use a combination of two or more herbicides along with one or more antidotes. The antidote(s) may act to safen only one of the herbicides of such combination, but such combination can be highly useful in providing a trio of advantages, namely, crop safety, herbicide selectivity and broad spectrum weed control. Such combinations can be used to obtain selective weed control with low crop injury in several species of monocotyledonous crop plants such as corn, grain sorghum (milo), and cereals such as wheat, rice, barley, oats and rye, as well as in several varieties of dicotyledonous crop plants including oil-seed crops such as soybeans and cotton.

Examples of thiocarbamate herbicides are the following:
cis-/trans-2,3-dichloroallyl-diisopropylthiolcarbamate (common name "diallate");
ethyl dipropylthiocarbamate (common name "EPTC");
2,3,3-trichloroallyl-diisopropylthiolcarbamate (common name "triallate");
S-ethyl diisobutylthiocarbamate (common name "butylate");
S-propyl dipropylthiocarbamate (common name "vernolate");
S-4-chlorobenzyl diethylthiocarbamate (common name "benthiocarb");
S-ethyl hexahydro-1H-azepine-1-carbothioate (common name "molinate");
S-($\alpha,\alpha$-dimethylbenzyl)-1-piperazinecarbothioate (common name "dimeperate").

Examples of triazine herbicides are the following:
2-chloro-4,6-bis(ethylamino)-1,3,5-triazine (common name "simazine");
2-chloro-4-ethylamino-6-isopropylamino-sym-triazine (common name "atrazine");
2-chloro-4-(1-cyano)-1-methyl(ethylamino)-6-ethylamino-1,3,5-triazine (common name "cyanazine");
6-chloro-N-(1-methylethyl)-N'-ethyl-N'-(2-methyl-1-propenyl)-1,3,5-triazine;
2,4-bis(ethylamino)-6-(methylthio)-sym-triazine (common name "simetryne").

Examples of diphenyl ether herbicides are the following:
2,4-dichlorophenyl-4'-nitrophenyl ether (common name "nitrofen");
2,4,6-trichlorophenyl-4-nitrophenyl ether (common name "CNP");
2-chloro-1-(3'-ethoxy-4'-nitrophenoxy)-4-trifluoromethylbenzene (common name "oxyfluorfen");
2',4'-dichlorophenyl-3-methoxy-4-nitrophenyl ether (common name "chloromethoxynil");
methyl 2-[4'-(2'',4''-dichlorophenoxy)phenoxy)propionate; methyl 5-(2',4'-dichlorophenoxy)-2-nitrobenzoate (common name "bifenox");
N-(2'-methoxyethyl)-2-[5'-(2''-chloro-4''-trifluoromethyl-phenoxy)phenoxy]propionamide;
5-[2-chloro-4-(trifluoromethyl)phenoxy]-N-(methylsulfonyl)-2-nitrobenzamide (common name "fomesafen");
5-(2'-chloro-4'-trifluoromethylphenoxy)-2-nitrobenzoic acid (common name "acifluorfen");

Examples of benzoic acid type herbicides are the following:
3,6-dichloro-o-anisic acid and the sodium or dimethylamine salts thereof (common name "dicamba").

Examples of phenylurea herbicides are the following:
N-(3'-isopropylphenyl)-N',N'-dimethylurea (common name "isoproturon");
1-(3,4-dichlorophenyl)-3,3-dimethylurea (common name "diuron");
N-(3',4'-dimethylbenzyl)-N'-4-tolylurea (common name "dimuron");
N'-(3,4-dichlorophenyl)-N-methoxy-N-methylurea (common name "linuron");
N-(3'-chloro-4'-isopropylphenyl)-N',N'-(3-methylpentamethylen-1,5-yl)urea.

Examples of nitroaniline herbicides are the following:
2,6-dinitro-N,N-dipropyl-4-trifluoromethylaniline (common name "trifluralin");
4-(dipropylamino)-3,5-dinitrobenzenesulfonamide (common name "oryzalin");
N-(1'-ethylpropyl)-2,6-dinitro-3,4-xylidine (common name "pendimethalin").

An example of a benzenesulfonamide herbicide is the following:
2-chloro-N-{[4-methoxy-6-methyl-1,3,5-triazine-2-yl-amino]carbonyl}benzenesulfonamide (common name DPX-4189);

An example of a sulfonylurea herbicide is the following:
methyl 2-[{[{[(4,6-dimethoxy-2-pyrimidinyl)amino]carbonyl}amino]sulfonyl}methyl]benzoate (common name "DPX TM 5384").

Examples of phenoxyacetic acid type herbicides are the following:
(2,4-dichlorophenoxy)acetic acid (common name "2,4-D");
(4-chloro-2-methylphenoxy)acetic acid (common name "MCPA").

Examples of acetamide herbicides are the following:
2-chloro-N-isopropylacetanilide (common name "propachlor");
2-chloro-N-[2-(1,1-dimethylethyl)-6-methylphenyl]-acetamide;
2-chloro-2'-(1,1-dimethylethyl)-6'-methyl-N-(methoxymethyl)acetanilide;
N-(butoxymethyl)-2-chloro-N-[2-(1,1-dimethylethyl)-6-methylphenyl]acetamide (common name "terbuchlor");
2-chloro-2',6'-diethyl-N-(methoxymethyl)acetanilide (common name "alachlor");
2-chloro-N-(isobutoxymethyl)-2',6'-acetoxylidide;
2-chloro-2',6'-diethyl-N-(butoxymethyl)acetanilide (common name "butachlor");
2-chloro-N-(ethoxymethyl)-6'-ethyl-o-acetotoluidide (common name "acetochlor");
2-chloro-N-(2,6-dimethyl-1-cyclohexen-1-yl)-N-(2-ethoxyethyl)acetamide;
ethyl ester of N-chloroacetyl-N-(2,6-diethylphenyl) glycine (common name "diethatyl ethyl");
2-chloro-N-(2,6-dimethylphenyl)-N-(2-methoxyethyl) acetamide (common name "dimethachlor");
2-chloro-N-(2-methoxy-1-methylethyl)-6'-ethyl-o-acetotoluidide (common name "metolachlor");

2-chloro-2',6'-diethyl-N-(2-propoxyethyl)acetanilide (common name "pretilachlor");
2-chloro-2',3'-dimethyl-N-(isopropyl)acetanilide;
2-chloro-2'-methyl-6'-methoxy-N-(propoxymethyl)-acetanilide;
2-chloro-2'-methyl-6'-methoxy-N-(isopropoxymethyl) acetanilide;
2-chloro-2'-methyl-6'-ethoxy-N-(propoxymethyl)-acetanilide;
N-(ethoxymethyl)-N-(2-ethyl-6-methyl-1-cyclohexen-yl)-2-chloroacetamide;
2-chloro-2,6'-dimethyl-N-(1H-pyrazol-1-ylmethyl)-acetanilide (common name "metazachlor");
2-chloro-N-(2,6-dimethyl-1-cyclohexen-1-yl)-N-(1H-pyrazol-1-ylmethyl)acetamide;
2-chloro-6'-trifluoromethyl-N-(isopropoxymethyl) acetanilide;
2-chloro-2'-methyl-6'-trifluoromethyl-N-(ethoxymethyl) acetanilide;
2-chloro-2'-trifluoromethyl-6-methyl-N-(propoxymethyl)-acetanilide;
2-chloro-2'-methyl-6'-(1-methylethoxy)-N-(ethoxymethyl)acetanilide;
2-chloro-2'-methyl-6'-trifluoromethyl-N-(isopropoxymethyl)acetanilide;
2-chloro-2'-(3-methylbutoxy)-6'-methyl-N-(methyl)-acetanilide;
2-chloro-2'-isobutoxy-6'-methyl-N-(propoxymethyl) acetanilide;
2-chloro-2'-methyl-6'-propoxy-N-(methyl)acetanilide;
2-chloro-2'-butoxy-6'-methyl-N-(methyl)acetanilide;
2-chloro-2'-methyl-6'-propoxy-N-(ethoxymethyl)-acetanilide;
2-chloro-2'-butoxy-6'-ethyl-N-(methyl)acetanilide;
α-chloro-N-(ethoxymethyl)-N-[2-methyl-1-(1-methylethyl)-1-propenyl]acetamide;
2-chloro-2'-methoxy-3',6'-dimethyl-N-[(1-methylethoxy)-methyl]acetamide;
2-chloro-2'-ethyl-6'-(2-methylpropoxy)-N-(ethoxymethyl)-acetanilide;
2-chloro-2'-methyl-6'-(1-methylbutoxy)-N-(methyl)acetanilide;
2-chloro-2'-ethyl-6'-(1-methylpropyl)-N-(methyl)acetanilide;
2-chloro-2'-(1,3-dimethylbutoxy)-6'-methyl-N-(methyl)acetanilide;
2-chloro-2'-methyl-6'-(1-methylpropyl)-N-(methyl)acetanilide;
2-chloro-2'-ethyl-6'-trifluoromethyl-N-(1-pyrazolyl-1-ylmethyl)acetanilide;
2-chloro-N-[1-(2-chloro-6-fluorophenyl)-2-methyl-1-propen-1-yl]-N-(2-propynyl)acetamide;
2chloro-N-isopropyl-N-(3,5,5-trimethylcyclohexen-1-yl) acetamide (common name "trimexachlor");

Examples of other miscellaneous herbicides are the following:
2,6-dichlorobenzonitrile (common name "dichlobenil");
3,5-dichloro-4-hydroxybenzonitrile (common name "bromoxynil");
N-(α,α-dimethylbenzyl)-2-bromo-tert-butylamide (common name "bromobutamide");
N-(3,4-dichlorophenyl)propanamide (common name "propanil");
3-[2,4-dichloro-5-(1-methylethoxy)phenyl]-5-(1,1-dimethylethyl)-1,3,4-oxadiazol-2-(3H)-one (common name "oxadiazon");
4-(2,4-dichlorobenzoyl)-1,3-dimethyl-5-pyrazolyl-p-toluenesulfonate (common name "pyrazolate");
2-(2,4-dichloro-3-methylphenoxy)propionamide (common name "MY-15");
4-(2,4-dichloro-3-methylbenzoyl)-1,3-dimethyl-5-methylphenacyloxypyrazole (common name "MY-71");
α-(2-naphthoxy)propionanilide (common name "naproanilide");
1,3-dimethyl-4-(2,4-dichlorobenzoyl)-5-phenacyloxypyrazole (common name "SL-49").

Several of the mentioned herbicides are known in the art. Diallate and triallate herbicides are described in U.S. Pat. Nos. 3,330,643 and No. 3,330,821. Atrazine herbicide is described in U.K. Patent No. 814,947. Alachlor, butachlor and acetochlor herbicides are described in U.S. Pat. Nos. 3,442,945 and No. 3,547,620. Propachlor herbicide is described in U.S. Pat. No. 2,863,752 and Reissue Patent No. 26,961. Metolachlor herbicide is described in U.S. Pat. No. 3,937,730. Pretilachlor is described in U.S. Pat. No. 4,168,965. Metazachlor herbicide is described in U.S. Pat. No. 4,249,935. Trimexachlor herbicide is described in U.S. Pat. No. 4,319,918.

U.S Pat. No. 4,351,667 describes the herbicides N-(ethoxymethyl)-N-(2-ethyl-6-methyl-1-cyclohexen-1-yl)-2-chloroacetamide and N-(ethoxymethyl)-N-(2,5-dimethyl-1-cyclopenten-1-yl)-2-chloroacetamide. U.K. Patent No. 2,072,175 describes the herbicide 2-chloro-2'-methyl-6'-methoxy-N-(isopropoxymethyl)acetanilide. U.K. Patent No. 2,072,181 describes the herbicide 2-chloro-2'-methyl-6'trifluoromethyl-N-(ethoxymethyl)acetanilide.

Combinations may be made of any one or more of the described antidote compounds with any one or more of the herbicide compounds mentioned herein.

Antidote compounds of the described class are effective to reduce herbicidal injury to grain sorghum (milo), wheat, rice, soybean and corn, especially where herbicide injury is associated with pre-emergent application of the herbicides. Antidote compounds of the invention have been found particularly effective to reduce injury to rice caused by butachlor herbicide. Also, the antidote compounds have been found particularly effective to reduce injury to sorghum and wheat caused by alachlor herbicide. Also, the antidote compounds are particularly effective to reduce injury to corn caused by the acetamide herbicides acetochlor and 2-chloro-2'-methyl-6'-methoxy-N-(isopropoxymethyl)acetanilide, both of which are highly active acetanilide herbicides.

Antidote compounds of the invention are effective to reduce injury to direct-seeded upland rice, puddle-seeded rice, rice grown in seedbeds for subsequent transplanting and to transplant rice. Tank-mix combinations of butachlor and antidote applied preemergent to puddle-seeded rice and seedbeds for transplant rice are particularly effective. Antidote compounds of the invention generally do not reduce the performance of the herbicide on weeds.

Antidote Compound Preparation

Table I shows 284 benzhydryl-type antidote compounds by name and structure which were synthesized. Also indicated are methods of preparation and physical-chemical analysis for each antidote compound. The methods of preparation, designated "A" through "DD",are described below in schematic form. Raw materials utilized in the methods were obtained from commercial sources such as Aldrich Chemical Co. Preparation of non-commercially-available starting materials are shown in methods following Method "DD". Abbreviations of reagents or radicals specified in the methods are as follows:

Abbreviation Key

TsOH = toluenesulfonic acid
THF = tetrahydrofuran
DMF = dimethylformamide
Me = methyl
Et = ethyl
OAc = acetate
DCC = dicyclohexylcarbodiimide
DMAP = 4-dimethylaminopyridine
MCPBA = m-chloroperbenzoic acid
Bu$_4$NBr = tetrabutyl ammonium bromide
n-BuLi = n-butyl lithium
t-BuOK = potassium tert-butoxide
$\phi$ = phenyl Method "A":

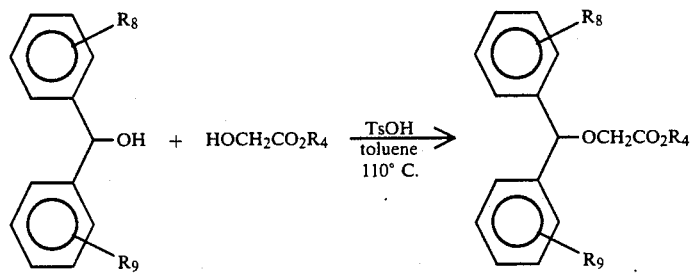

R$_8$ and R$_9$ = H, 2-methyl, 4-methyl, 4-chloro, 3-fluoro, 4-fluoro, 3,5-dichloro; R$_4$ = methyl, ethyl.

Method "B":

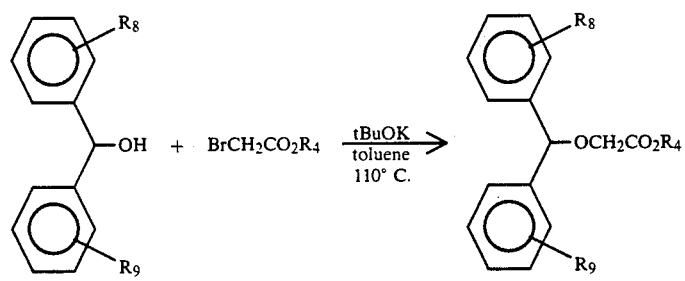

R$_8$ and R$_9$ = H, 2-trifluoromethyl, 3-trifluoromethyl, 4-trifluoromethyl; R$_4$ = methyl, ethyl.

Method "C":

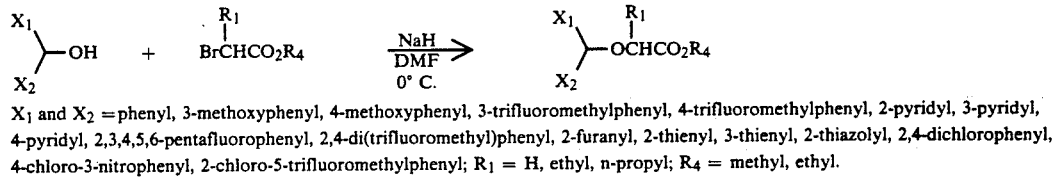

X$_1$ and X$_2$ = phenyl, 3-methoxyphenyl, 4-methoxyphenyl, 3-trifluoromethylphenyl, 4-trifluoromethylphenyl, 2-pyridyl, 3-pyridyl, 4-pyridyl, 2,3,4,5,6-pentafluorophenyl, 2,4-di(trifluoromethyl)phenyl, 2-furanyl, 2-thienyl, 3-thienyl, 2-thiazolyl, 2,4-dichlorophenyl, 4-chloro-3-nitrophenyl, 2-chloro-5-trifluoromethylphenyl; R$_1$ = H, ethyl, n-propyl; R$_4$ = methyl, ethyl.

Method "D":

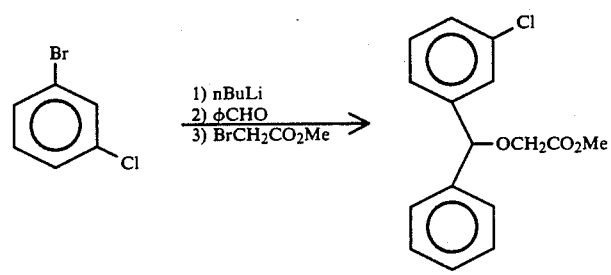

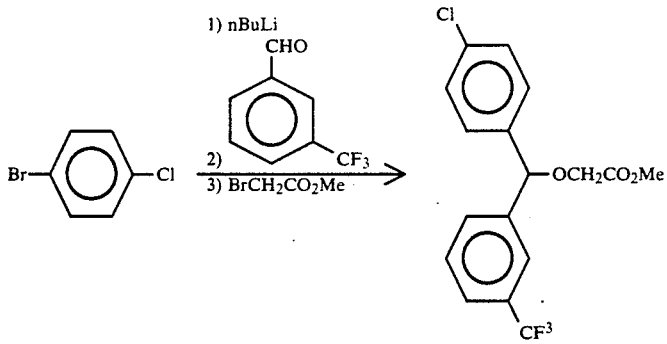

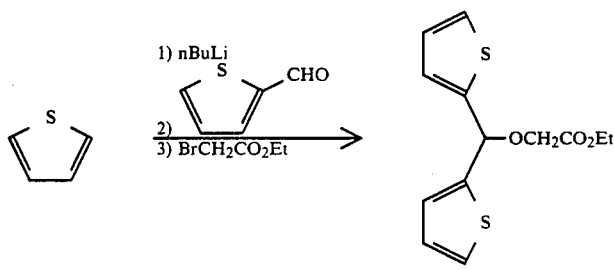

Method "E":

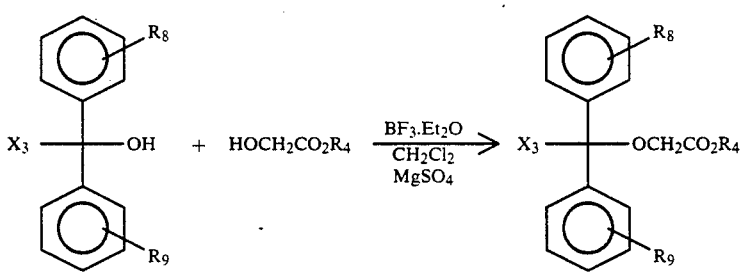

$X_3$ = H, methyl, trifluoromethyl; $R_8$ and $R_9$ = H, 2-methyl, 2,6-dimethyl, 3,5-dimethyl, 2,4,6-trimethyl, 2-chloro, 4-chloro, 3,5-dichloro; $R_4$ = methyl, ethyl.

Method "F":

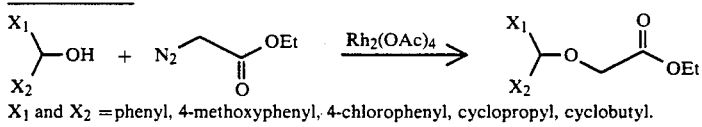

$X_1$ and $X_2$ = phenyl, 4-methoxyphenyl, 4-chlorophenyl, cyclopropyl, cyclobutyl.

Method "G":

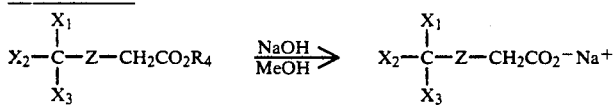

$X_1$, $X_2$ and $X_3$ = H, phenyl; Z = O, S; $R_4$ = methyl, ethyl.

Method "H":

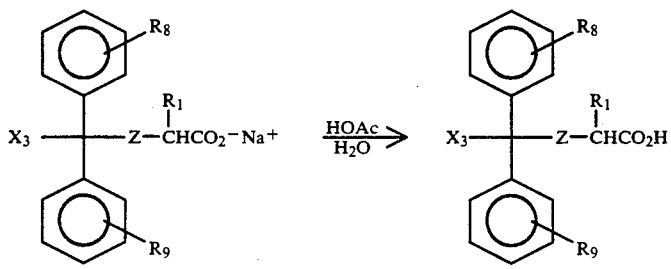

$R_1$ = H, n-propyl; $R_8$ and $R_9$ = H, 2-methyl, 2,6-dimethyl, 3,5-dimethyl, 2,4,6-trimethyl, 4-chloro, 3-trifluoromethyl, 2-chloro-5-trifluoromethyl; $X_3$ = H, phenyl; Z = O, S.

Method "I":

-continued

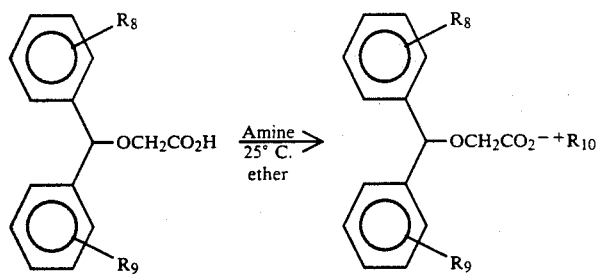

$R_8$ and $R_9$ = H, 3-trifluoromethyl; $R_{10}$ = amine cation of selected amine starting material (see Table I, Method of Preparation "I" compounds showing product amine cations).

Method "J":

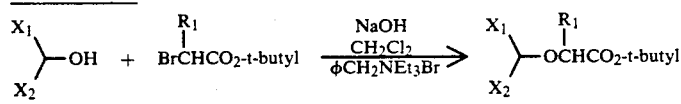

$X_1$ and $X_2$ = phenyl, 4-(dimethylamino)phenyl, 2-trifluoromethylphenyl, 3-trifluoromethylphenyl, 4-methoxyphenyl, 3-pyridyl, cyclopropyl; $R_1$ = H, methyl.

Method "K":

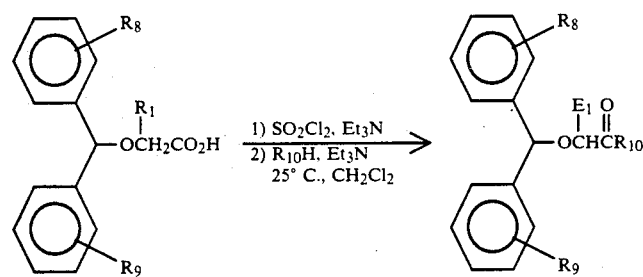

$R_1$ = H, n-propyl; $R_8$ and $R_9$ = H, 2-methyl, 2,6-dimethyl, 4-chloro, 3,5-dichloro, 3-trifluoromethyl.

$R_{10}$ = $\phi CH_2O-$     $3-CF_3\phi CH_2O-$ $CH_3CH_2CH_2O-$     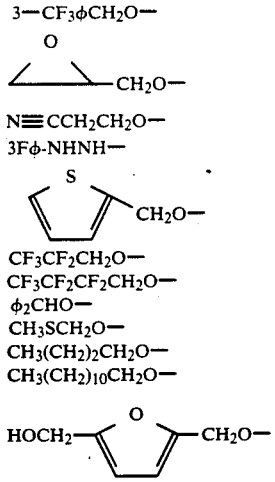

$(CH_3)_2CHO-$     $N\equiv CCH_2CH_2O-$ $CF_3CH_2O-$     $3F\phi-NHNH-$ $(CH_3)_2CHS-$     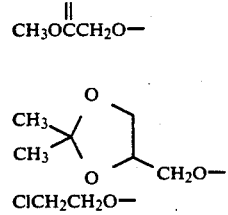

$CH_3CH_2S-$     $CF_3CF_2CH_2O-$
$CHF_2CF_2CH_2O-$     $CF_3CF_2CF_2CH_2O-$
$Cl\phi CH_2O-$     $\phi_2CHO-$
$CH_3NH-$     $CH_3SCH_2O-$
$(CH_2=CH-CH_2)_2N-$     $CH_3(CH_2)_2CH_2O-$
$Cl_3CCH_2O-$     $CH_3(CH_2)_{10}CH_2O-$ $CH_3O\overset{O}{\overset{\|}{C}}CH_2O-$     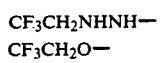

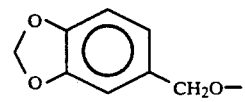

$ClCH_2CH_2O-$     $CF_3CH_2NHNH-$
    $CF_3CH_2O-$

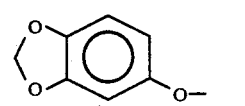

$HC\equiv CCH_2O-$

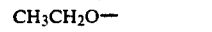

$CH_3CH_2O-$     $(CH_3)_3CNH-$
    $CH_2=CHCH_2O-$

-continued

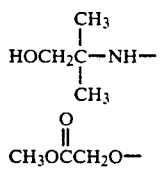　　φCH$_2$ONH—

CH$_3$OCCH$_2$O—　　(CF$_3$)$_2$CHO—

4-CH$_3$φCH$_2$O—
4-ClφCH$_2$O—
4-CH$_3$OφCH$_2$O—

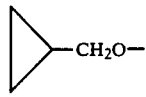　　4-NO$_2$φCH$_2$O—

CH$_3$CHO—
 |
 CF$_3$
2-ClφCH$_2$O—　　3-CH$_3$φCH$_2$O—
3-CH$_3$OφCH$_2$O—　　2-NO$_2$φCH$_2$O—
(CH$_3$)$_2$N—NH—　　3-NO$_2$φCH$_2$O—
φNH—　　2-CH$_3$φCH$_2$O—
　　2-CH$_3$OφCH$_2$O—

Method "L":

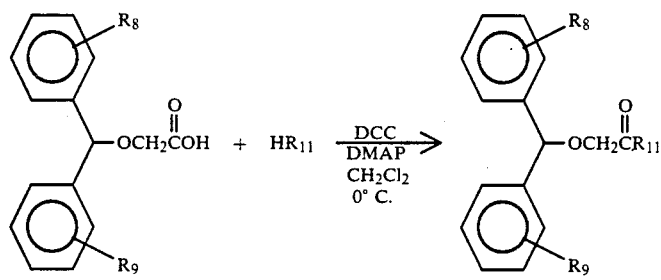

R$_{11}$ = phenyloxy　　　　　　　　N≡CCH$_2$CH$_2$O—
　　phenylthio　　　　　　　　　　(CH$_3$)$_2$CHS—
　　3-nitrophenyloxy　　　　　　　HC≡CCHO—
　　　　　　　　　　　　　　　　　　　 |
　　　　　　　　　　　　　　　　　　　CH$_3$
　　3-pyridyloxy　　　　　　　　　3-chlorophenyloxy
　　(CH$_3$)$_2$CO—　　　　　　　　2-methoxyphenyloxy
　　　　 |
　　　　C≡N
　　HC≡C—CHO—　　　　　　　2-nitrophenyloxy
　　　　　　 |
　　　　　　CH$_2$CH$_3$
　　4-nitrophenyloxy　　　　　　　3-methoxyphenyloxy
　　2-chlorophenyloxy　　　　　　4-methoxyphenyloxy
　　n-propylthio　　　　　　　　　3-methylphenyloxy
　　4-chlorophenyloxy　　　　　　2-methylphenyloxy
　　4-methylphenyloxy　　　　　　4-fluorobenzyloxy O
　　　　　　　　　　　　　　　　　　 ⟨　⟩
　　　　　　　　　　　　　　　　　　　O　 CH$_2$O—
　　3-trifluorophenyloxy　　　　　CH$_3$CH$_2$S—
　　4-fluorophenyloxy　　　　　　CH$_3$(CH$_2$)$_2$CHO—
　　4-chlorobenzyloxy CH$_3$
　　　　　　　　　　　　　　　　　　　　　 |
　　3-trifluoromethylbenzyloxy　　H≡C—C—O—
　　　　　　　　　　　　　　　　　　　　　 |
　　　　　　　　　　　　　　　　　　　　　CH$_3$ CH$_3$CHO—　　　　　　　　CH$_3$OCH$_2$CH$_2$O
　　　 |
　　　C≡N
　　Cl$_3$CCH$_2$O—　　　　　　　(CH$_3$)$_2$CHO—
　　CH$_3$CH$_2$CH$_2$O—　　　　　CH$_3$CH$_2$CHO—
　　　　　　　　　　　　　　　　　　　 |
　　　　　　　　　　　　　　　　　　　CH$_3$ 3-pyridylmethoxy CF₃CH₂O—      HC≡C—CH₂O—
benzyloxy      H₂C=CHCH₂O—
Method "M":
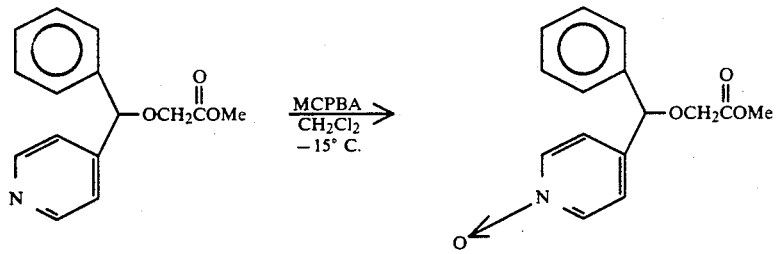
Method "N":
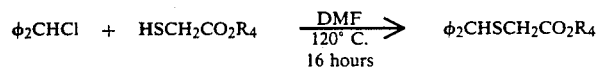
R₄ = methyl, ethyl.
Method "O":
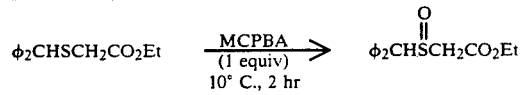
Method "P":
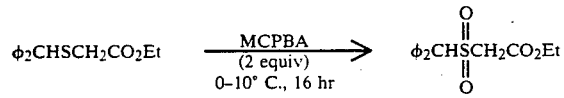
Method "Q":
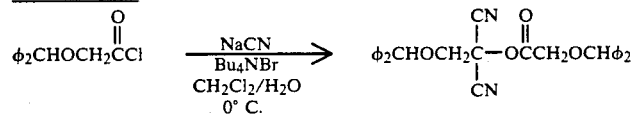
Method "R":
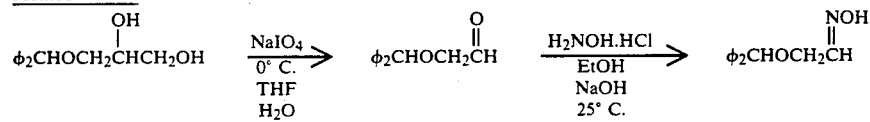
Method "S":
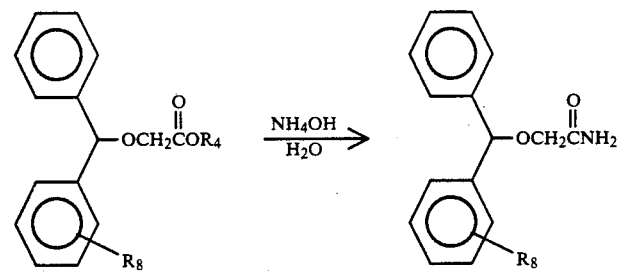
R₈ = H, 4-chloro, 3-trifluoromethyl; R₄ = methyl, ethyl.
Method "T":
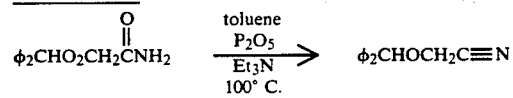
Method "U":
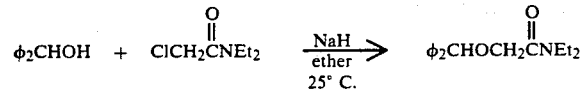
Method "V":

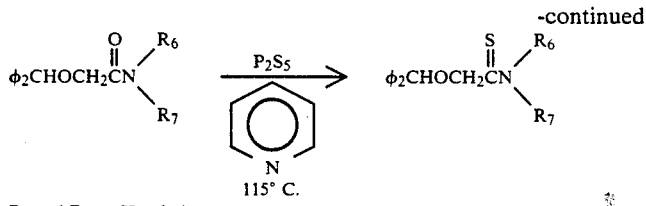
$R_6$ and $R_7 = H$, ethyl.
Method "W":
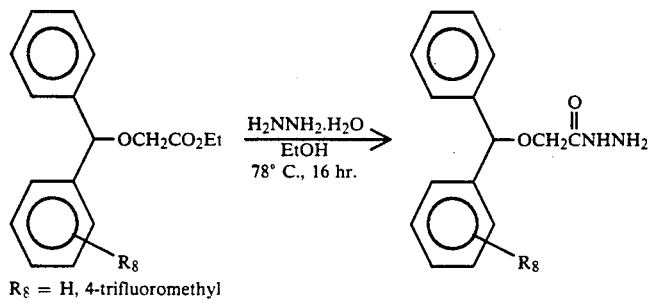
$R_8 = H$, 4-trifluoromethyl
Method "X":
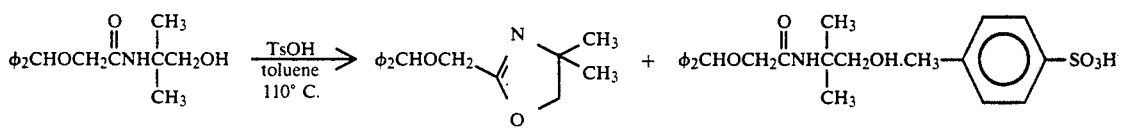
Method "Y":
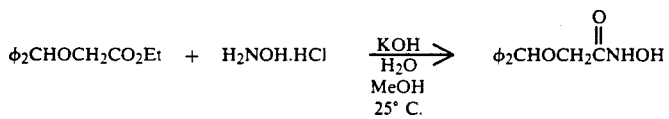
Method "Z":
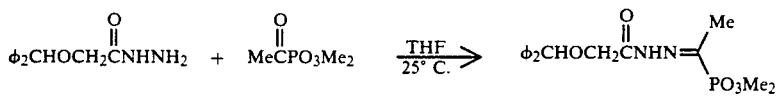
Method "AA":
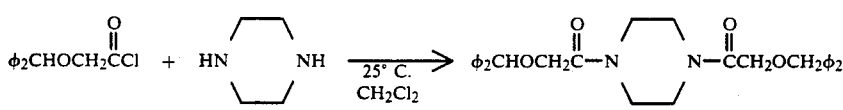
Method "BB":
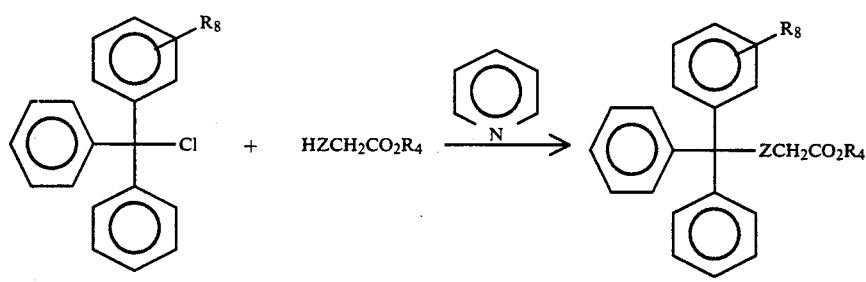
$R_8 = H$, 4-methoxy; $R_4 =$ methyl, ethyl; $Z = O, S$.
Method "CC":
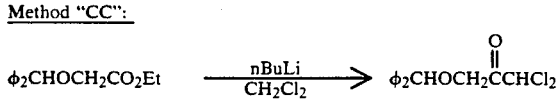
Method "DD":

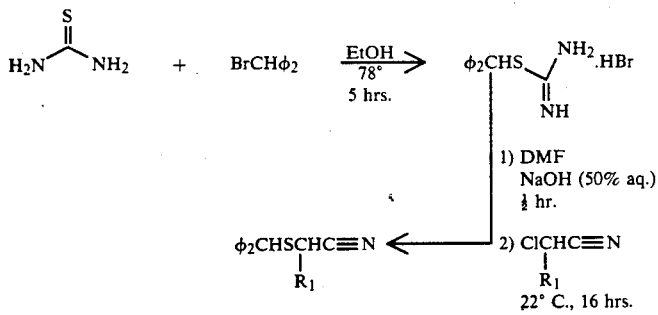

$R_1$ = H, methyl.

Starting Materials for Methods "A", "B", "C", "D" and "E"

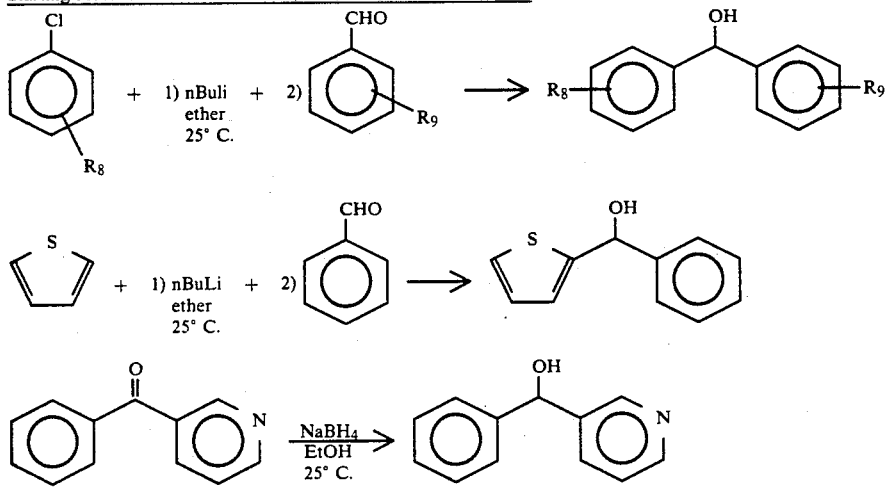

The following Examples 1–36 are detailed descriptions of the methods of preparation of those antidote compounds which were found in biological evaluation to show the most significant safening utility of the 284 specific antidote compounds disclosed herein. These detailed preparations fall within the scope of, and serve to exemplify, the more generally described Methods "A" through "DD". These Examples 1–36 are presented for illustrative purposes only and are not intended as a restriction on the scope of the invention. All parts are by weight unless otherwise indicated. Most of the commercially-available starting materials were obtained from Aldrich Chemical Co., Milwaukee, Wis. Table I sets forth analytical data for specific compounds prepared in accordance with the procedures of Example 1–36.

EXAMPLE 1

A reaction vessel was charged with 200 ml of benzene and 4.5 g (50 mmol) of methyl glycolate. This solution was concentrated under reduced pressure to remove water. Then, 100 ml of dimethylformamide containing 10.1 g (50 mmol) of benzhydryl chloride was added to the reaction vessel and the resulting solution was heated to 120° C. After 8½ hours of heating at 120° C., 9.0 g (100 mmol) of methyl glycolate was added to the reaction mixture. After heating the reaction mixture at 120° C. for a total of 16 hours, the reaction appeared complete. The reaction product was poured into a vessel containing 200 ml of water and 200 ml of ethyl ether. After separation of the mixture into layers, the ethyl ether layer was washed with 200 ml of water, then dried with sodium sulfate and concentrated under reduced pressure. The concentrated material was triturated with cyclohexane, and then distilled (122–124° C.@0.5 mm) to provide 7.9 g of product identified in Table I.

EXAMPLE 2

A reaction vessel was charged with 100 ml of methylene chloride, 9.2 g (50 mmol) of benzhydrol, 9.7 g (50 mmol) of t-butyl bromoacetate, 8 g of benzyl triethylammonium chloride and 50 ml of 10% sodium hydroxide. This reaction mixture was stirred at room temperature for about 15 hours. The mixture was filtered, then washed successively with 5% hydrochloric acid, 5% sodium bicarbonate and brine. The organic material was dried with sodium sulfate and then concentrated under reduced pressure. The solid residue was recrystallized from ethanol to provide 8.5 g of product identified in Table I.

EXAMPLE 3

A reaction vessel was charged with 300 ml of dimethylformamide, 300 ml of benzene and 191.8 g (1.8 mol) of ethyl glycolate. This mixture was azeotroped for 4 hours with a Dean-Stark trap to remove water. With the reaction mixture at 130° C., 291.9 g (1.44 mol) chlorodiphenylmethane was added in one batch. The reaction mixture was heated at 145° C. overnight. Some of the dimethylformamide was removed under reduced pressure and the residue was poured into ice water and then extracted with methylene chloride. The methylene chloride portion of the mixture was washed with 700 ml water, dried over sodium sulfate, concentrated under reduced pressure, and then subjected to Kugelrohr distillation to remove dimethylformamide. About 10 g of the crude product was purified by HPLC using 1% ethylacetate-in-toluene eluent to provide product identified in Table I.

EXAMPLE 4

A dry reaction vessel was charged with 100 ml of tetrahydrofuran and 10.3 g (92 mmol) of potassium tert-butoxide. The vessel and contents were cooled to about 0° C. and then a mixture of 200 ml of dry tetrahydrofuran and 22.7 g (90 mmol) of meta-trifluoromethylbenzhydrol was added dropwise to the vessel contents. The reaction mixture was stirred for 2 hours without further cooling. Then 14.9 g (7.7 ml) of methyl bromoacetate was added dropwise to the reaction mixture and the mixture was refluxed for one hour. The mixture was cooled to room temperature and then 200 ml of water and 200 ml of methylene chloride were added. The methylene chloride layer was dried over sodium sulfate and then concentrated under reduced pressure to provide 27.6 g of a light amber oil. This oil was purified by HPLC using a 1% ethyl acetate-in-hexane eluent to provide 6.1 g of product identified in Table I.

EXAMPLE 5

A dry reaction vessel was charged with 300 ml of tetrahydrofuran and 160 g (143 mmol) of potassium tert-butoxide. The vessel and contents were cooled to about 0 ° C. and then a mixture of 200 ml of ethyl ether containing 30 g (119 mmol) of ortho-trifluoromethyl benzhydrol was added dropwise to the vessel contents. The reaction mixture was stirred for two hours at 0° C. Then, 12.0 ml (143 mmol) of methyl bromoacetate was added dropwise to the reaction mixture at 0° C. The mixture was stirred for one hour, cooling was discontinued, and the mixture was stirred one more hour. Then, 200 ml of water and 200 ml of ethyl ether were added. The ether layer was dried over magnesium sulfate, then solvent was removed under reduced pressure to provide 33.9 g of a light-yellow oil. This oil was purified by HPLC using a 5% ethyl acetate-in-hexane eluent to provide product identified in Table I.

EXAMPLE 6

A reaction vessel was charged with 100 ml of methylene chloride, 10 ml of triethylamine and 13 g (50 mmol) of benzyl alcohol. Then, a mixture of 100 ml of benzene containing 13 g (50 mmol) benzhydryloxyacetic acid chloride was added dropside to the vessel contents with vigorous stirring. The reaction mixture became cloudy with precipitate. The mixture was stirred 4 hours and then washed twice with 300 ml of water. The benzene layer was dried over magnesium sulfate and then concentrated under reduced pressure to provide a light yellow oil. This oil was triturated in 100 ml of pentane, then recrystallized in 100 ml of hexane to provide 8.9 g of product identified in Table I.

EXAMPLE 7

A reaction vessel was charged with 100 ml of methylene chloride, 2.5 ml of n-propanol and 6 ml (43 mmol) of triethylamine. Then, a mixture of 20 ml of methylene chloride containing 10 g (38.4 mmol) of benzhydryloxyacetic acid chloride was added dropwise to the vessel contents. The reaction mixture was stirred for 72 hours, then washed twice with 200 ml of water, dried over magnesium sulfate and concentrated under reduced pressure to provide 10.3 g of a light amber oil. This oil was purified by HPLC using 2% ethyl acetate-in-hexane eluent to provide 8 g of product identified in Table I.

EXAMPLE 8

By the procedure of Example 7, a reaction of 25 ml of isopropanol, 10 g (38.4 mmol) of benzhydryloxyacetic acid chloride and 6 ml of triethylamine yielded an oil which was purified by HPLC using 2% ethyl acetate-in-hexane eluent to provide 7.6 g of product identified in Table I.

EXAMPLE 9

By the procedure of Example 7, a reaction of 3.1 ml (40 mmol) of 2,2,2-trifluoroethyl alcohol, 10 g (38.4 mmol) of benzhydryloxyacetic acid chloride and 6 ml triethylamine yielded an oil which was purified by HPLC using 2% ethyl acetate-in-hexane eluent to provide 10.1 g of product identified in Table I.

EXAMPLE 10

To a reaction vessel containing 6.2 g (260 mmol) of sodium hydride powder, there was added dropwise a mixture of 300 ml tetrahydrofuran containing 52 g (240 mmol) of 4-chlorobenzhydrol with vigorous stirring. Immediate gas evolution and a temperature rise to 32° C. were observed. The reaction mixture was stirred for 5 hours. The reaction mixture appeared as a clear solution in contact with a small amount of sodium hydride. Then, over a period of ½ hour, a mixture of 100 ml tetrahydrofuran containing 43.4 g (260 mmol) ethyl bromoacetate was added to the vessel contents. A solid material formed immediately. The mixture was stirred for hours and then refluxed one hour. Then, 300 ml of methylene chloride and 400 ml of water were added to the mixture which was stirred vigorously. Methylene chloride was concentrated under reduced pressure to provide 80.5 g of an amber oil which was purified by HPLC using 2% ethyl acetate-in-hexane eluent to provide product identified in Table I.

EXAMPLE 11

A reaction vessel was charged with 20 ml of ethyl ether, 2 g (6.4 mmol) of 3-trifluoromethyl benzhydryloxyacetic acid and 0.7 ml of tert-butyl amine. The reaction mixture was stirred overnight at room temperature. No precipitate was observed. The solvent was allowed to evaporate. The solid material left was triturated with pentane to provide 2.1 g of a white solid product identified in Table I.

EXAMPLE 12

A reaction vessel was charged with 200 ml of methylene chloride, 4 ml (64 mmol) of 2-propanethiol and 5.6 ml (40 mmol) triethylamine. Then, a mixture of 75 ml methylene chloride containing 9.7 g (36 mmol) of benzhydryloxyacetic acid chloride was added dropwise to the vessel contents under stirring. The reaction mixture was stirred for 2 hours, washed twice with 600 ml water, dried over magnesium sulfate, and concentrated under reduced pressure to yield 9.4 g of a yellow solid material. This material was recrystallized from 7.5 ml cyclohexane to provide 3.4 g light-yellow crystal product identified in Table I.

EXAMPLE 13

A reaction vessel was charged with 7.5 ml of methylene chloride, 7.5 g (31 mmol) of benzylhydryloxyacetic acid chloride, 3.1 g (32.5 mmol) of phenol and 0.3 g of dimethylaminopyridine. The reaction vessel and contents were cooled to 0° C. and then a mixture of 50 ml of methylene chloride containing 6.7 g (32.5 mmol) of dicyclohexylcarbodiimide was added dropwise. The reaction mixture was stirred overnight and allowed to reach room temperature. The solid material was removed by filtration. The filtrate was concentrated under reduced pressure to provide a white solid material. This material was triturated with ethyl ether, then filtered, and the ether removed under reduced pressure to provide 8.6 g of a white solid material. This material was recrystallized from 50 ml of cyclohexane to provide white crystals identified in Table I.

EXAMPLE 14

A reaction vessel was charged with 100 ml of methylene chloride, 10 g (41 mmol) of benzhydryloxyacetic acid, 4.7 g (43 mmol) of thiophenol and 0.3 g of 4-dimethylaminopyridine. The reaction vessel and contents were cooled to $-30°$ C. and then a mixture of 50 ml of methylene chloride containing 8.9 g (43 mmol) of dicyclohexylcarbodiimide was added dropwise with vigorous stirring of the reaction vessel contents. With the temperature of the reaction mixture at 0° C., a white solid precipitate formed. The mixture was stirred overnight and then filtered. The filtrate was concentrated under reduced pressure to provide a white solid material. This material was triturated with ethyl ether and filtered to remove 3.4 g of white solid material. The ether filtrate was concentrated under reduced pressure to provide 9.6 g of white solid material. The combined solid materials were recrystallized from 150 ml cyclohexane, filtered and then dried under reduced pressure to provide product identified in Table I.

EXAMPLE 15

A reaction vessel was charged with 100 ml of benzene, 5.2 g (20.5 mmol) of 4,4'-dichlorobenzhydrol, 2.8 g (30.8 mmol) of methyl glycolate and 0.3 g of para-toluenesulfonic acid. The reaction mixture was refluxed for 2 hours with a Dean-Stark trap after which time 0.5 ml water was collected. The reaction mixture was cooled to room temperature, washed with 200 ml water, dried over magnesium sulfate, and concentrated under reduced pressure to provide a light-yellow oil. This oil was purified by HPLC using a 2% ethyl acetate-in-hexane eluent to provide product identified in Table I.

EXAMPLE 16

A reaction vessel was charged with 100 ml of methylene chloride, 3 ml of ethyl mercaptan and 5.6 ml of triethylamine. Then, a mixture of 50 ml methylene chloride containing 10 g (38.4 mmol) of benzhydryloxyacetic acid chloride was added dropwise to the reaction vessel contents. The mixture was stirred in a closed vessel overnight, then washed twice with 200 ml of water, dried over magnesium sulfate, and then concentrated under reduced pressure to provide a yellow oil. This oil was triturated with pentane to provide a solid material which was then recrystallized from cyclohexane to give 7.0 g of yellow crystal product identified in Table I.

EXAMPLE 17

By the procedure of Example 6, a reaction of 7 g (27 mmol) of benzhydryloxyacetic acid chloride, 3.7 g (28 mmol) of 1H,1H,3H-tetrafluoropropanol and 4 ml of triethylamine yielded 6.3 g of clear colorless oil product identified in Table I.

EXAMPLE 18

A dry reaction vessel was charged with 200 ml of dimethylformamide and 17.2 g (60 mmol) of 2-chloro-5-trifluoromethylbenzhydrol. The vessel and contents were cooled to $-30°$ C. and the contents placed under a nitrogen blanket. Then, 2.2 g (90 mmol) of sodium hydride was added in one batch. The mixture warmed to 0° C. and slow gas evolution was observed. The mixture, under a nitrogen blanket, was stirred overnight at room temperature. The vessel and contents were cooled to $-30°$ C. and 8.5 ml (90 mmol) of methyl bromoacetate was added dropwise. The reaction mixture was allowed to reach room temperature during a two-hour stirring period. Then, 200 ml of ethyl ether and 100 ml of water were added. The ether portion of the mixture was washed with an additional 500 ml of water, dried over magnesium sulfate, and then concentrated under reduced pressure to provide 22.1 g of light-yellow oil which was purified by HPLC using a 3.7% ethyl acetate-in-hexane eluent to provide product identified in Table I.

EXAMPLE 19

A reaction vessel was charged with 100 ml of methylene chloride, 3.3 ml (35 mmol) of isopropyl mercaptan, and 4.9 ml (35 mmol) of triethylamine. Then, a mixture of 50 ml of methylene chloride containing 9.8 g (30 mmol) of benzhydryloxyacetic acid chloride was added dropwise to the vessel contents. The reaction mixture was stirred overnight in a closed vessel, then washed with water, dried over magnesium sulfate, and concentrated under reduced pressure leaving an oil which was purified by HPLC using a 2% ethyl acetate-in-hexane eluent to provide 8.9 g of a yellow oil product identified in Table I.

EXAMPLE 20

A reaction vessel was charged with 200 ml methylene chloride, 4.6 g (40 mmol) of 1,1,1-trifluoro-2-propanol and 6 ml of triethylamine. Then, a mixture of 100 ml of methylene chloride containing 12 g (36.5 mmol) of 3-trifluoromethylbenzhydrylacetic acid chloride was added dropwise to the vessel contents. The reaction mixture was stirred in a closed vessel for 72 hours. The mixture was washed with 500 ml of water, dried over magnesium sulfate, and then concentrated under reduced pressure to provide 14.4 g of oil purified by HPLC using 1% ethyl acetate-in-hexane to give product identified in Table I.

EXAMPLE 21

A reaction vessel was charged with 100 ml of methylene chloride, 4.0 g (28 mmol) of para-chlorobenzyl alcohol and 2.83 g of triethylamine. Then, a mixture of 75 ml of methylene chloride containing 7.0 g (27 mmol) of benzhydryloxyacetic acid chloride was dropwise to the vessel contents with stirring continuing overnight. The reaction mixture was washed with water, dried over magnesium sulfate, and concentrated under reduced pressure to provide an off-white and oily solid which was recrystallized from hexane to provide white crystal product identified in Table I.

EXAMPLE 22

A reaction vessel was charged with 150 ml of toluene, 20.0 g (83 mmol) of 2,6,2'6'-tetramethylbenzhydrol, 17.3 g (166 mmol) of ethyl glycolate and 0.6 g (3 mmol) of para-toluenesulfonic acid. The reaction mixture was heated to reflux and held at reflux for 3 hours, after which time 2.8 ml of water was collected (Dean-Stark trap). The mixture was concentrated under reduced pressure to provide 19 g of a brown oil. This oil was dissolved in methanol, cooled to 0° C. and then 6 g of potassium hydroxide was added in one batch to the methanol-oil mixture. This mixture was stirred at 0° C. for one hour and then stirred at room temperature for two hours. Methanol was concentrated under reduced pressure to provide a light brown oil. This oil was partitioned between water and ethyl ether. The aqueous layer was acidified with 10% hydrochloric acid and a cloudy oil rose to the top of the aqueous layer. The aqueous layer was extracted with ethyl ether, the ether layer was dried with magnesium sulfate, and concentrated under reduced pressure to provide 11.8 g of a white solid which was recrystallized from methylcyclohexane to give product identified in Table I.

EXAMPLE 23

By the procedure of Example 13, a reaction of 8.50 g (35 mmol) of benzhydryloxyacetic acid, 4.87 g (35 mmol) of 3-nitrophenol, 7.24 g (35 mmol) of dicyclohexylcarbodiimide and 0.61 g (5 mmol) of 4-dimethylamino pyridine yielded 7.97 g of white solid which was recrystallized from methylcyclohexane/toluene (20:1) to give product identified in Table I.

EXAMPLE 24

A reaction vessel was charged with 250 ml of toluene, 8.0 g (33 mmol) of 2,2',6,6'-tetramethylbenzhydrol, 4.16 g (40 mmol) of ethyl glycolate and 1.9 g (10 mmol) of para-toluenesulfonic acid. The reaction mixture was heated to reflux under a nitrogen blanket and a Dean-Stark trap was used to collect water of reaction. After a four-hour reflux period, the reaction mixture was washed with aqueous sodium bicarbonate. Then, the organic layer was separated, dried with magnesium sulfate, and concentrated under reduced pressure to provide an oil. This oil was purified by HPLC using a 20:1 hexane:ethyl acetate eluent to provide a solid material, which when recrystallized from hexane-ether, yielded a white solid product identified in Table I.

EXAMPLE 25

By the procedure of Example 13, a reaction of 40.0 g of (170 mmol) of benzhydryloxyacetic acid, 21.8 g (200 mmol) of 3-pyridinylcarbinol, 41.2 g (200 mmol) of dicyclohexylcarbodiimide and 2.44 g (20 mmol) of 4-dimethylaminopyridine yielded 32.6 g of crystal product identified in Table I.

EXAMPLE 26

By the procedure of Example 13, a reaction of 8.1 g (32 mmol) of 2-methylbenzhydryloxyacetic acid, 2.94 g (47 mmol) of ethanethiol, 6.6 g (32 mmol) of dicyclohexylcarbodiimide and 0.8 g (6 mmol) of 4-dimethylaminopyridine yielded 7.7 g of a clear oil product identified in Table I.

EXAMPLE 27

By the procedure of Example 13, a reaction of 7.0 g (30 mmol) of benzhydryloxyacetic acid, 2.55 g (30 mmol) of acetone cyanohydrin, 6.18 g (30 mmol) of dicyclohexylcarbodiimide and 0.12 g (1 mmol) of -dimethylaminopyridine yielded 2.3 g of white crystal product identified in Table I.

EXAMPLE 28

By the procedure of Example 13, a reaction of 6.0 g (20 mmol) of 2,2'6,6'-tetramethylbenzhydryloxyacetic acid, 1.25 g (20 mmol) of ethanethiol, 4.2 g (20 mmol) of dicyclohexylcarbodiimide and 0.5 g (4 mmol) of para-dimethylaminopyridine yielded 3.95 g of white crystal product identified in Table I.

EXAMPLE 29

By the procedure of Example 13, a reaction of 7 g (29 mmol) of benzhydryloxyacetic acid, 2.2 g (31 mmol) of 3-hydroxypropionitrile, 6.4 g (31 mmol) of dicyclohexylcarbodiimide and 0.5 g (4 mmol) of 4-dimethylaminopyridine yielded 3.0 g of a yellow oil product identified in Table I.

EXAMPLE 30

By the procedure of Example 13, a reaction of 10 g (30 mmol) of 2,2'6,6' -tetramethylbenzhydryloxyacetic acid, 3.0 g (35 mmol) of acetone cyanohydrin, 7.2 g (35 mmol) of dicyclohexylcarbodiimide and 0.37 g (3 mmol) of 4-dimethylaminopyridine yielded 5.4 g of a white crystal product identified in Table I.

EXAMPLE 31

By the procedure of Example 13, a reaction of 12 g (40 mmol) of 2,2',6,6'-tetramethylbenzhydryloxyacetic acid, 2.66 g (35 mmol) of 2-propanethiol, 8.25 g (40 mmol) of dicyclohexylcarbodiimide and 0.49 g (4 mmol) of 4-dimethylaminopyridine yielded 6.17 g of white crystal product identified in Table I.

EXAMPLE 32

By the procedure of Example 13, a reaction of 10.4 g (40 mmol) of benzhydryloxyacetic acid, 3.15 g (45 mmol) of 3-butyn-2-ol, 10.3 g (50 mmol) of dicyclohexylcarbodiimide and 0.49 g (4 mmol) of 4-dimethylaminopyridine yielded 8.34 of a clear, colorless oil product identified in Table I.

EXAMPLE 33

By the procedure of Example 13, a reaction of 7.0 g (25 mmol) of 4-chlorobenzhydryloxyacetic acid, 3.5 g (25 mmol) of meta-nitrophenol, 5.6 g (27 mmol) of dicyclohexylcarbodiimide and 0.37 g (3 mmol) of 4-dimethylaminopyridine yielded 3.4 g of a yellow, viscous oil product identified in Table I.

EXAMPLE 34

By the procedure of Example 13, a reaction of 7.0 g (25 mmol) of 4-chlorobenzylhydryloxyacetic acid, 2.13 g (25 mmol) of acetone cyanohydrin, 5.6 g (27 mmol) of dicyclohexylcarbodiimide and 0.37 g (3 mmol) of 4-dimethylaminopyridine yielded 5.0 g of a clear, colorless oil product identified in Table I.

EXAMPLE 35

By the procedure of Example 13, a reaction of 6.5 g (27 mmol) of benzhydryloxyacetic acid, 2.3 g (27 mmol)

of ethyl ethynylcarbinol, 5.7 g (28 mmol) of dicyclohexylcarbodiimide and 0.4 g (3 mmol) of 4-dimethylaminopyridine yielded 7.1 g of a clear, colorless oil product identified in Table I.

EXAMPLE 36

A reaction vessel was charged with 400 ml of methylene chloride, 10.0 g (36 mmol) of 4-chlorobenzhydryloxyacetic acid, 2.1 g (35 mmol) of allyl alcohol and 0.47 g (4 mmol) of 4-dimethylaminopyridine. While this mixture was being stirred, 7.6 g (37 mmol) of dicyclohexylcarbodiimide was added slowly to the reaction vessel. After stirring overnight, the mixture was filtered. The filtrate was concentrated under reduced pressure and the residue was purified by HPLC using a 25:1 hexane:ethyl acetate eluent to provide 9.0 g of a clear light-yellow oil identified in Table I.

TABLE I

| Antidote Example Compound # | Name | Structure | Method of Prep. | Analysis (%) Calc'd | Analysis (%) Found | M.P./B.P. °C. |
|---|---|---|---|---|---|---|
| 1 | methyl diphenylmethoxyacetate | 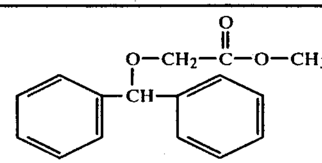 | A | C 74.98<br>H 6.29 | | 121-124 @ 0.50t |
| 2 | 1,1-dimethylethyl diphenylmethoxyacetate | 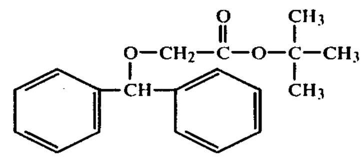 | J | C 76.48<br>H 7.43 | 76.47<br>7.34 | 60-64 |
| 3 | ethyl diphenylmethoxyacetate | 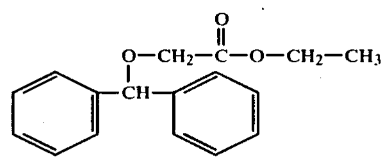 | A | C 75.53<br>H 6.71 | 75.25<br>6.77 | oil |
| 4 | methyl phenyl[3-(trifluoromethyl)-phenyl]methoxyacetate | 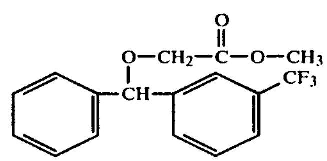 | B | C 62.96<br>H 4.66<br>F 17.58 | 63.10<br>4.81 | oil |
| 5 | methyl phenyl[2-(trifluoromethyl)-phenyl]methoxyacetate | 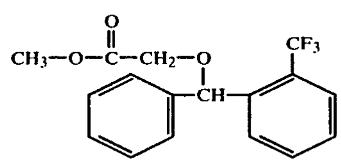 | B | C 62.96<br>H 4.66<br>F 17.58 | 62.94<br>4.68 | oil |
| 6 | benzyl diphenylmethoxyacetate | 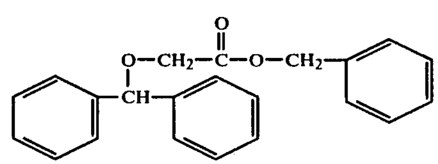 | K | C 79.50<br>H 6.07 | 79.40<br>6.10 | 52-54 |

| | | | | | |
|---|---|---|---|---|---|
| 7 | propyl diphenylmethoxyacetate | 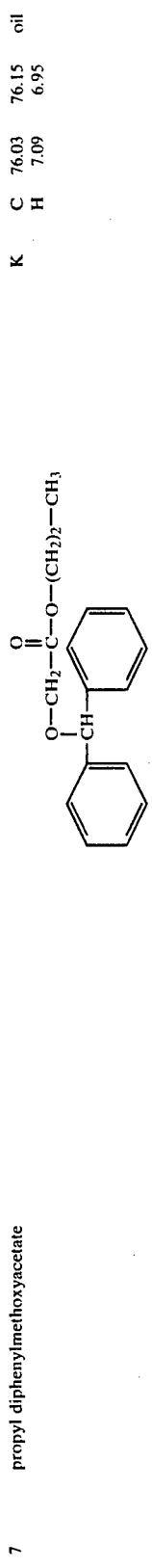 | K | C 76.03 H 7.09 | 76.15 6.95 | oil |
| 8 | 1-methylethyl diphenylmethoxyacetate | 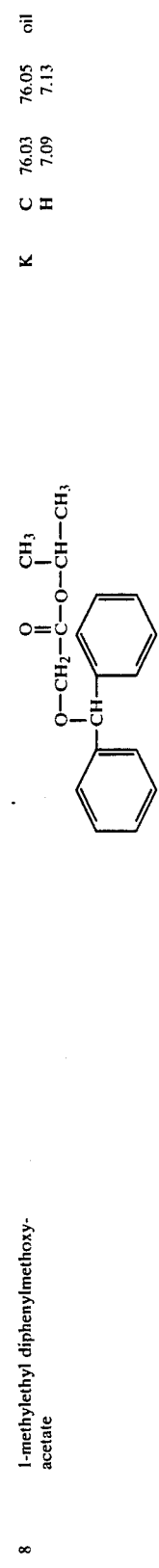 | K | C 76.03 H 7.09 | 76.05 7.13 | oil |
| 9 | 2,2,2-(trifluoroethyl) diphenylmethoxyacetate | 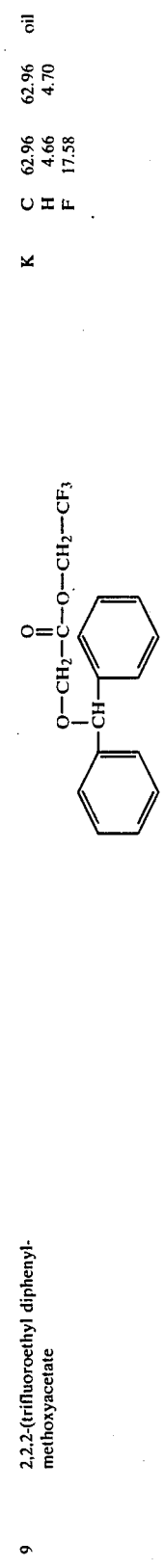 | K | C 62.96 H 4.66 F 17.58 | 62.96 4.70 | oil |
| 10 | ethyl (4-chlorophenyl)phenylmethoxyacetate | 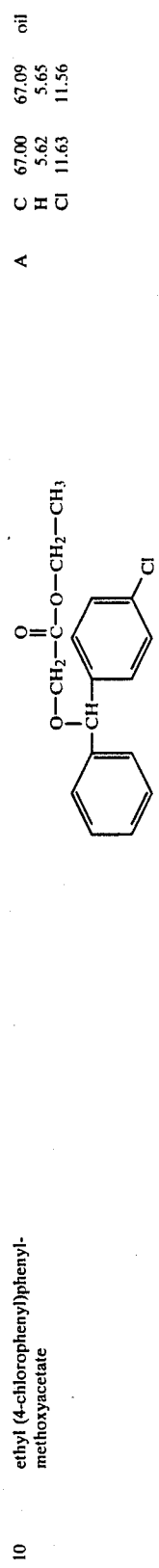 | A | C 67.00 H 5.62 Cl 11.63 | 67.09 5.65 11.56 | oil |
| 11 | 1,1-dimethylethylammonium phenyl-[3-(trifluoromethyl)phenyl]methoxyacetate | 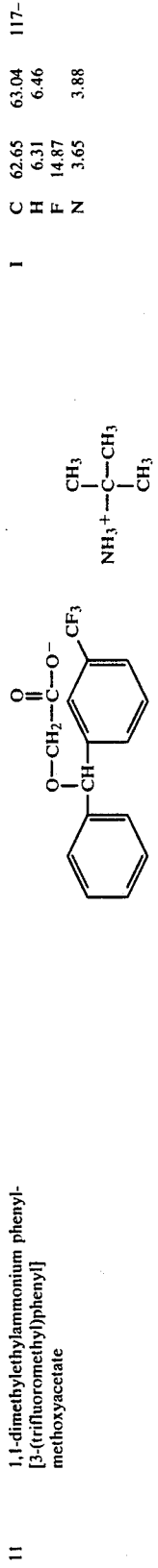 | I | C 62.65 H 6.31 F 14.87 N 3.65 | 63.04 6.46 3.88 | 117–120 |
| 12 | S-1-methylethyl 2-(diphenylmethoxy)ethanethioate | 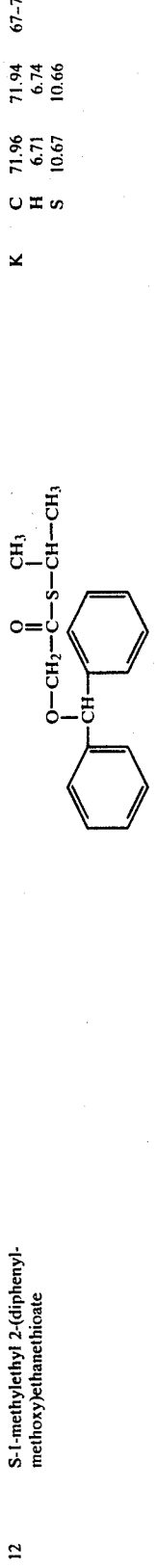 | K | C 71.96 H 6.71 S 10.67 | 71.94 6.74 10.66 | 67–70 |

| | | | | | |
|---|---|---|---|---|---|
| 13 | phenyl diphenylmethoxyacetate |  | L | C 79.23 79.21<br>H 5.70 5.70 | 59-61 |
| 14 | S-phenyl 2-(diphenylmethoxy)-ethanethioate | 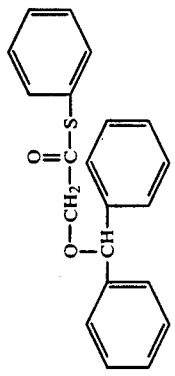 | L | C 75.42 75.33<br>H 5.43 5.45<br>S 9.59 9.56 | 81-82 |
| 15 | methyl bis(4-chlorophenyl)-methoxyacetate | 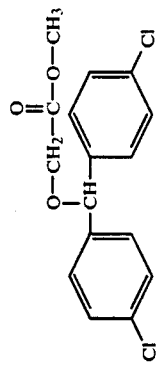 | A | C 59.10 59.13<br>H 4.34 4.34<br>Cl 21.80 21.79 | oil |
| 16 | S-ethyl 2-(diphenylmethoxy)-ethanethioate | 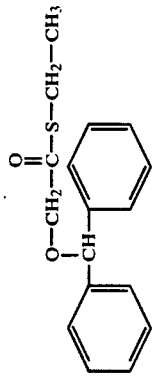 | K | C 71.29 71.23<br>H 6.34 6.37<br>S 11.20 11.19 | 55-59 |
| 17 | 2,2,3,3-tetrafluoropropyl diphenylmethoxyacetate | 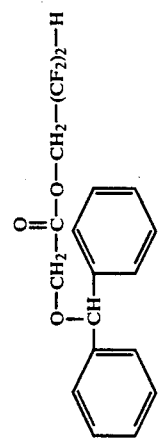 | K | C 60.67 60.43<br>H 4.53 4.40<br>F 21.33 | oil |

-continued

| | | | | Analysis | | |
|---|---|---|---|---|---|---|
| 18 | methyl [2-chloro-5-(trifluoro-methyl)phenyl]phenylmethoxy-acetate | 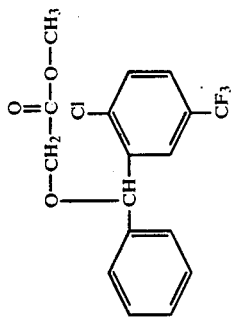 | C | C<br>H<br>Cl<br>F | 56.92<br>3.93<br>9.88<br>15.89 | 56.92<br>4.04<br>9.86 | 54-56 |
| 19 | S-1-methylethyl phenyl[3-trifluoromethyl)phenyl]methoxy-ethanethioate | 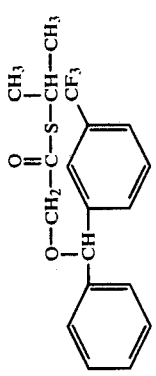 | K | C<br>H<br>F<br>S | 61.94<br>5.20<br>15.47<br>8.70 | 62.03<br>5.22<br>8.77 | oil |
| 20 | 1-methyl-2,2,2-trifluoroethyl phenyl[3-(trifluoromethyl)phenyl]-methoxyacetate | 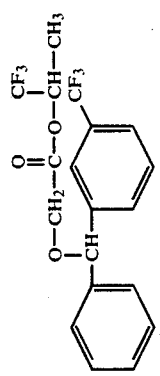 | K | C<br>H<br>F | 56.16<br>3.97<br>28.06 | 56.30<br>3.98 | oil |
| 21 | 4-chlorobenzyl diphenylmethoxy-acetate | 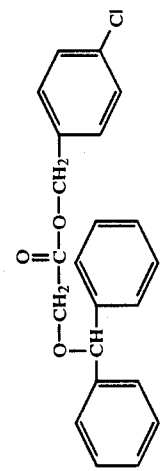 | K | C<br>H<br>Cl | 72.03<br>5.22<br>9.66 | 71.77<br>5.38 | 78.5-79 |
| 22 | bis(2,6-dimethylphenyl)methoxy-acetic acid | | H | C<br>H | 76.48<br>7.43 | 76.25<br>7.48 | 116-118 |

-continued
| | | | | | |
|---|---|---|---|---|---|
| 23 | 3-nitrophenyl diphenylmethoxy-acetate | 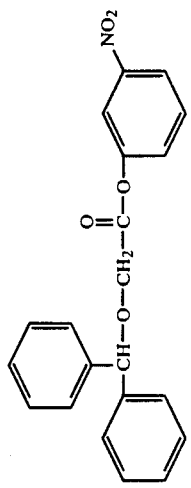 | L | C 69.41 69.41<br>H 4.72 4.74<br>N 3.85 3.84 | 88–89 |
| 24 | ethyl bis(2,6-dimethylphenyl)-methoxyacetate | 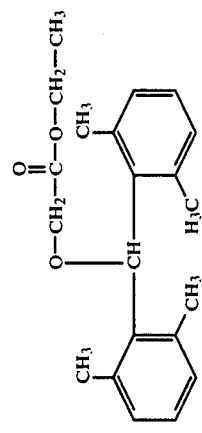 | E | C 77.27 76.89<br>H 8.03 8.06 | 68–69 |
| 25 | 3-pyridinylmethyl diphenyl-methoxyacetate | 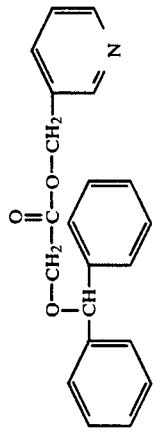 | L | C 75.66 75.46<br>H 5.74 5.79<br>N 4.20 4.19 | 34–35 |
| 26 | S-ethyl 2-[(2-methylphenyl)-phenylmethoxy]ethanethioate | 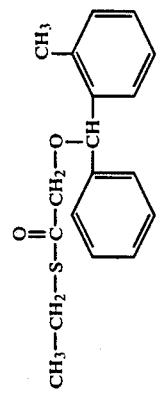 | K | C 71.96 72.00<br>H 6.71 6.72<br>S 10.67 10.63 | oil |
| 27 | 1-cyano-1-methylethyl diphenyl-methoxyacetate | 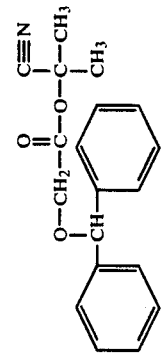 | L | C 73.77 73.50<br>H 6.19 6.20<br>N 4.53 4.50 | 75–77 |

-continued

| | | | Analysis | | m.p. °C |
|---|---|---|---|---|---|
| 28 | S-ethyl 2-bis[(2,6-dimethyl-phenyl)methoxy]ethanethioate | 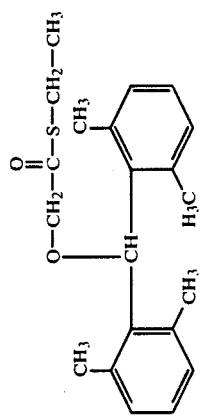 | K | C 73.64<br>H 7.65<br>S 9.36 | 73.68<br>7.66<br>66–67 |
| 29 | 2-cyanoethyl diphenylmethoxy-acetate | 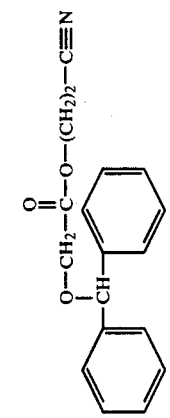 | L | C 73.20<br>H 5.80<br>N 4.74 | 73.11<br>5.84<br>4.71 oil |
| 30 | 1-cyano-1-methylethyl bis(2,6-dimethylphenyl)methoxyacetate | 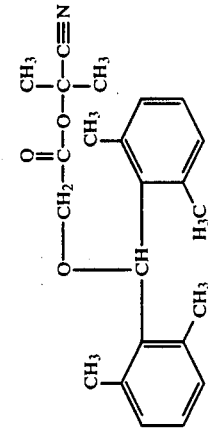 | L | C 75.59<br>H 7.45<br>N 3.83 | 75.42<br>7.69<br>3.82 106–110 |
| 31 | S-1-methylethyl 2-[bis(2,6-dimethylphenyl)methoxy]ethane-thioate | 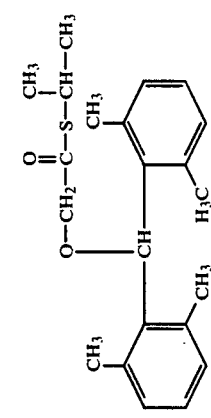 | L | C 74.11<br>H 7.92<br>S 8.99 | 73.93<br>7.96<br>9.05 76–78 |
| 32 | 1-methyl-2-propynyl diphenyl-methoxyacetate | 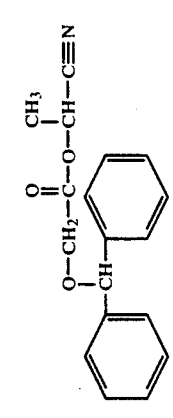 | L | C 77.53<br>H 6.16 | 77.50<br>6.18 oil |

-continued

| | | | | | |
|---|---|---|---|---|---|
| 33 | 3-nitrophenyl (4-chlorophenyl)-phenylmethoxyacetate | 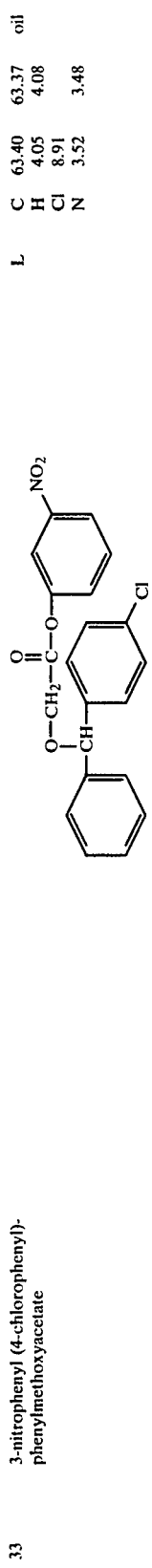 | L | C 63.40 63.37<br>H 4.05 4.08<br>Cl 8.91<br>N 3.52 3.48 | oil |
| 34 | 1-cyano-1-methylethyl (4-chlorophenyl)phenylmethoxyacetate | 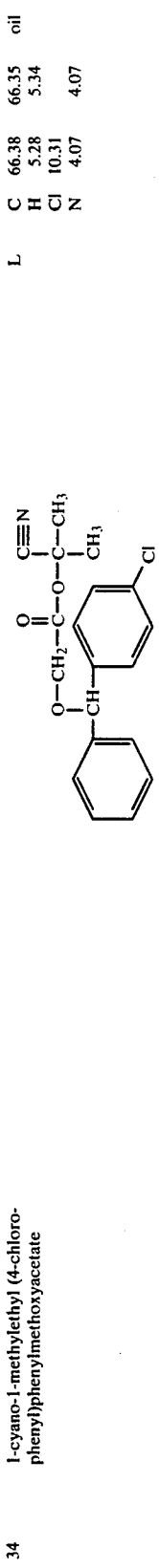 | L | C 66.38 66.35<br>H 5.28 5.34<br>Cl 10.31<br>N 4.07 4.07 | oil |
| 35 | 1-ethyl-2-propynyl diphenylmethoxyacetate | 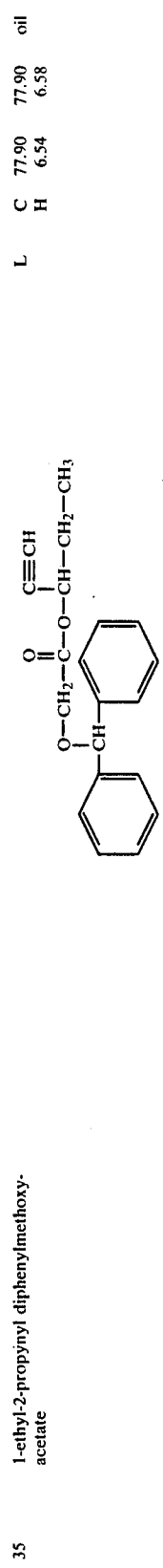 | L | C 77.90 77.90<br>H 6.54 6.58 | oil |
| 36 | 2-propenyl (4-chlorophenyl)phenylmethoxyacetate | 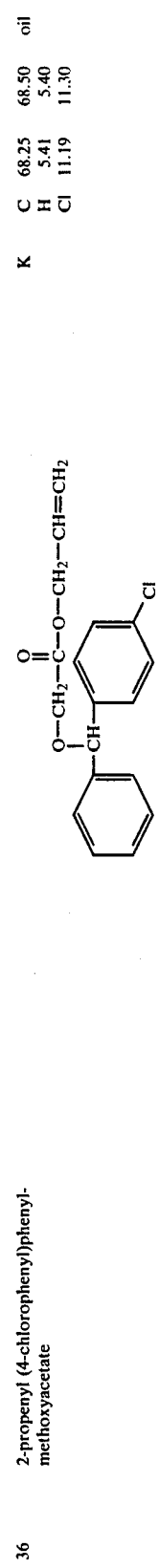 | K | C 68.25 68.50<br>H 5.41 5.40<br>Cl 11.19 11.30 | oil |
| 37 | sodium diphenylmethoxyacetate hemihydrate | 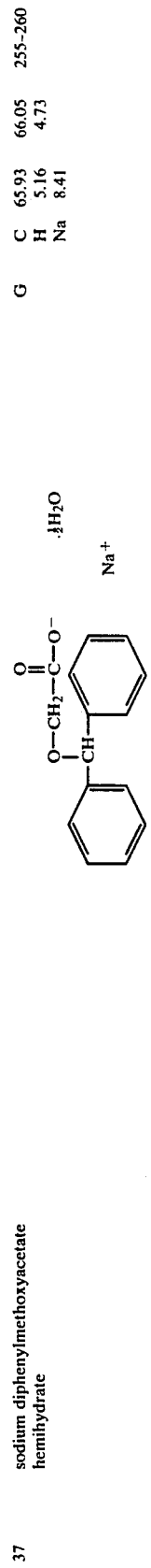 | G | C 65.93 66.05<br>H 5.16 4.73<br>Na 8.41 | 255–260 |
| 38 | diphenylmethoxyacetic acid | 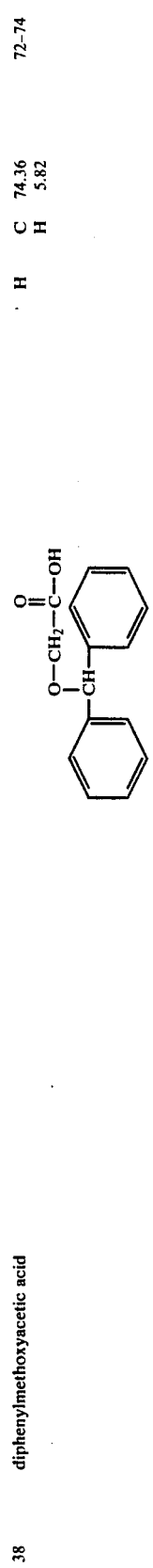 | H | C 74.36<br>H 5.82 | 72–74 |

-continued
| | | | | | |
|---|---|---|---|---|---|
| 39 | 1,1-dimethylethyl 2-(diphenylmethoxy)-propanoate |  | J | C 76.89 76.46<br>H 7.74 7.74 | 148–152<br>@ 0.05t |
| 40 | ethyl triphenylmethoxyacetate | 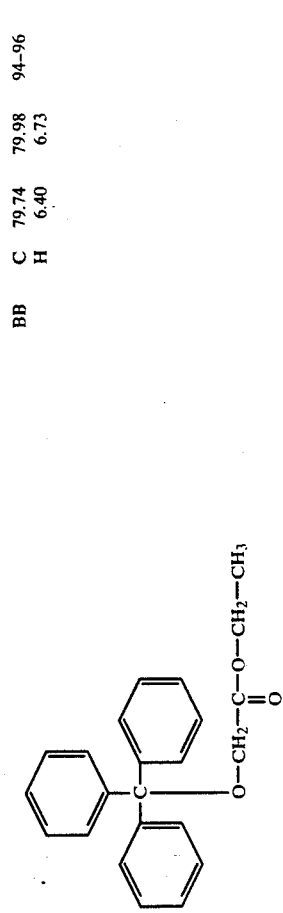 | BB | C 79.74 79.98<br>H 6.40 6.73 | 94–96 |
| 41 | methyl triphenylmethoxyacetate | 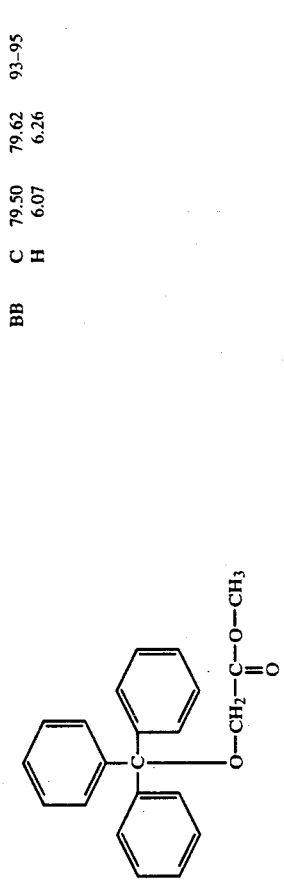 | BB | C 79.50 79.62<br>H 6.07 6.26 | 93–95 |
| 42 | sodium triphenylmethoxyacetate | 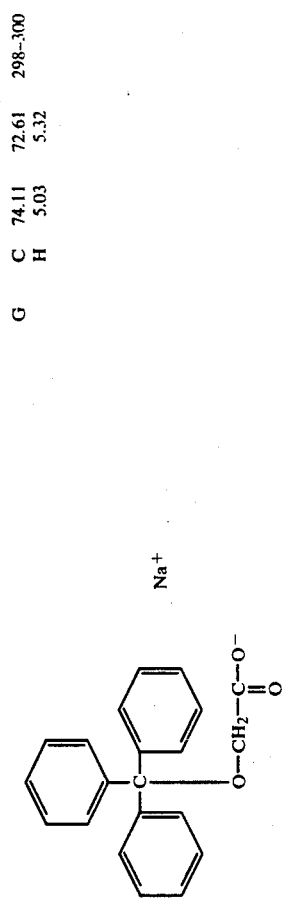 | G | C 74.11 72.61<br>H 5.03 5.32 | 298–300 |

| | | | | |
|---|---|---|---|---|
| 43 | triphenylmethoxyacetic acid | 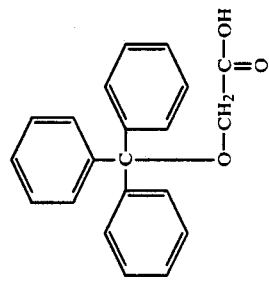 | H | C 79.23 79.22<br>H 5.70 5.72 | 150–151 |
| 44 | 2-(diphenylmethoxy)acetamide | 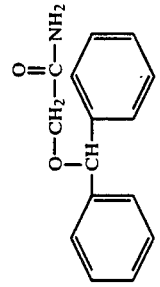 | S | C 74.67<br>H 6.27<br>N 5.81 | 133–135 |
| 45 | ethyl [(diphenylmethyl)thio]acetate | 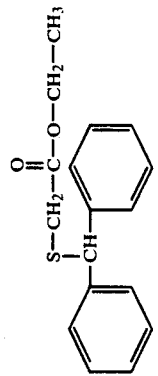 | N | C 71.29 71.33<br>H 6.34 6.35<br>S 11.20 11.19 | oil |
| 46 | ethyl 2-(diphenylmethoxy)butanoate | 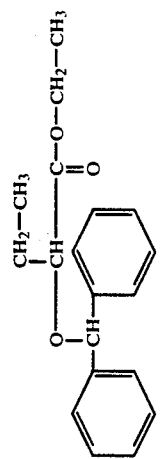 | C | C 76.48 76.51<br>H 7.43 7.46 | 129 @ 0.20t |
| 47 | 2-(diphenylmethoxy)-N,N-diethyl-acetamide | 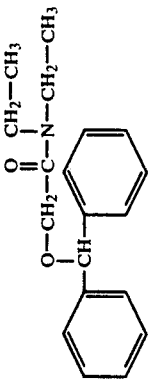 | U | C 76.74 76.60<br>H 7.80 7.86<br>N 4.71 4.73 | 155 @ 0.02t |

-continued
| | | | | | |
|---|---|---|---|---|---|
| 48 | 2-(diphenylmethoxy)-N,N-diethyl-ethanethioamide | 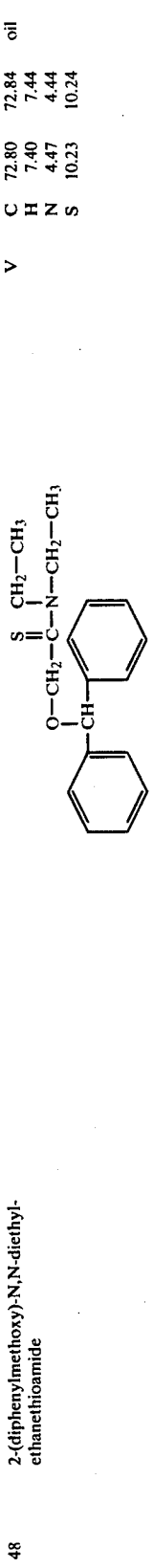 | V | C 72.80 72.84<br>H 7.40 7.44<br>N 4.47 4.44<br>S 10.23 10.24 | oil |
| 49 | 2-(diphenylmethoxy)-N-methylacetamide | | K | C 75.27 75.31<br>H 6.71 6.77<br>N 5.49 5.45 | 77–79 |
| 50 | 2-(diphenylmethoxy)-N,N-bis(2-propenyl)-acetamide | | K | C 78.47 78.22<br>H 7.21 7.27<br>N 4.36 4.34 | oil |
| 51 | ethyl [(diphenylmethyl)sulfonyl]acetate | | P | C 64.13 64.13<br>H 5.70 5.73<br>S 10.07 10.07 | 81–84 |
| 52 | sodium [(diphenylmethyl)thio]acetate | | G | C 64.27 62.52<br>H 4.67 4.77<br>S 11.44 10.48<br>Na 8.20 | 300 |
| 53 | [(diphenylmethyl)thio]acetic acid | | H | C 69.74 69.61<br>H 5.46 5.48<br>S 12.41 12.44 | 126.5–128 |

-continued
| | | | | | |
|---|---|---|---|---|---|
| 54 | ethyl [(diphenylmethyl)sulfinyl]acetate |  | O | C 67.52 67.53<br>H 6.00 6.00<br>S 10.60 10.62 | 76–79 |
| 55 | diphenylmethoxyacetic acid hydrazide |  | W | C 70.29 70.26<br>H 6.29 6.33<br>N 10.93 10.91 | 106–107 |
| 56 | 1,1-dimethyl-2-hydroxy-1-ethylammonium diphenylmethoxyacetate | 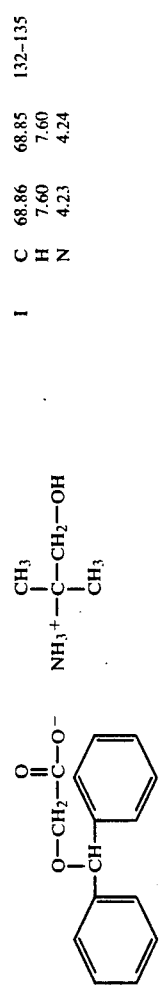 | I | C 68.86 68.85<br>H 7.60 7.60<br>N 4.23 4.24 | 132–135 |
| 57 | methyl (4-methylphenyl)phenyl-methoxyacetate |  | A | C 75.53 75.30<br>H 6.71 6.45 | oil |
| 58 | methyl bis(4-methoxyphenyl)-methoxyacetate |  | C | C 68.34 68.27<br>H 6.37 6.38 | oil |
| 59 | 2-[((4-chlorophenyl)phenylmethoxy]-acetamide |  | S | C 65.34 65.38<br>H 5.12 5.14<br>Cl 12.86<br>N 5.08 5.04 | 78–90 |

-continued
| | | | | | |
|---|---|---|---|---|---|
| 60 | (4-chlorophenyl)phenylmethoxyacetic acid | 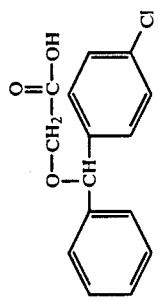 | H | C 65.11 H 4.74 Cl 12.81 | C 65.06 H 4.76 Cl 12.82 | 73–76 |
| 61 | methyl [(diphenylmethyl)thio]acetate | 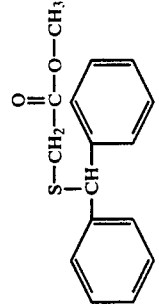 | N | C 70.56 H 5.92 S 11.77 | C 70.59 H 5.96 S 11.70 | oil |
| 62 | 2-(diphenylmethoxy)-N-hydroxyacetamide | 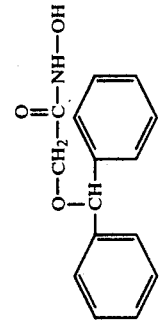 | Y | C 70.02 H 5.88 N 5.44 | C 69.95 H 5.89 N 5.42 | 98–100 |
| 63 | 1,1-dimethyl-1-ethylammonium diphenylmethoxyacetate | 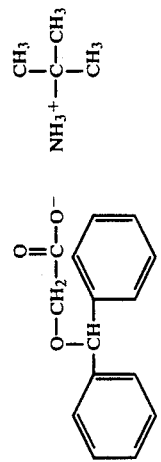 | I | C 72.35 H 7.99 N 4.44 | C 72.32 H 7.99 N 4.44 | 156–160 |
| 64 | ethyl [(triphenylmethyl)thio]acetate | 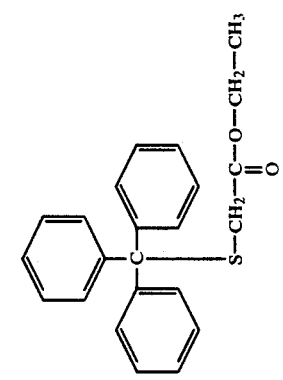 | BB | C 76.21 H 6.12 S 8.85 | C 76.22 H 6.13 S 8.83 | 89–91 |

| | | | | |
|---|---|---|---|---|
| 65 | ethyl [diphenyl(4-methoxyphenyl)-methylthio]acetate | 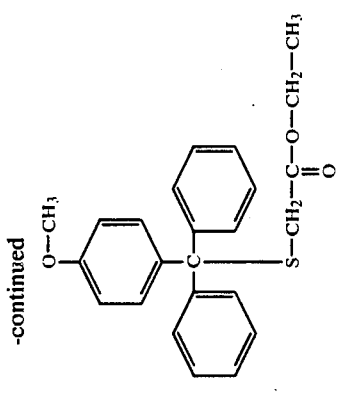 | BB | C 73.44 73.46<br>H 6.16 6.19<br>S 8.17 8.14 | 91-93 |
| 66 | ammonium diphenylmethoxyacetate | 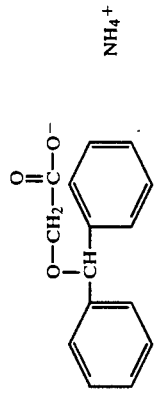 | I | C 69.48 69.35<br>H 6.61 6.64<br>N 5.40 5.38 | 141-149 |
| 67 | triphenylmethylammonium diphenylmethoxyacetate | 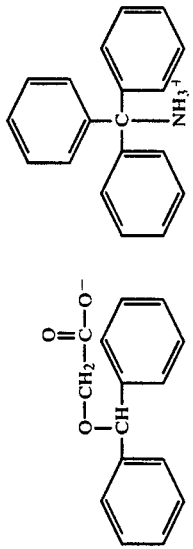 | I | C 81.41 81.40<br>H 6.23 6.28<br>N 2.79 2.77 | 110-113 |
| 68 | morpholinium diphenylmethoxyacetate | 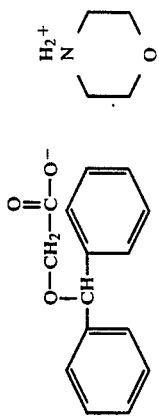 | I | C 69.28 69.25<br>H 7.04 6.97<br>N 4.25 4.24 | 148-151 |
| 69 | 2-hydroxyethylammonium diphenyl-methoxyacetate | 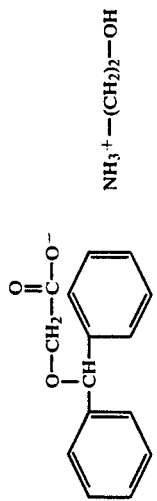 | I | C 67.31 67.19<br>H 6.98 7.04<br>N 4.62 4.61 | 118-120 |

| | | | | | |
|---|---|---|---|---|---|
| 70 | bis-2-hydroxyethylammonium diphenyl-methoxyacetate | 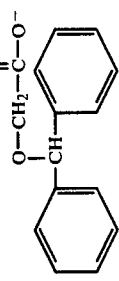 HO—(CH$_2$)$_2$—NH$_3^+$—(CH$_2$)$_2$—OH | I | C 65.69 64.85<br>H 7.25 7.03<br>N 4.03 4.18 | 115–117 |
| 71 | dicyclohexylammonium diphenyl-methoxyacetate | 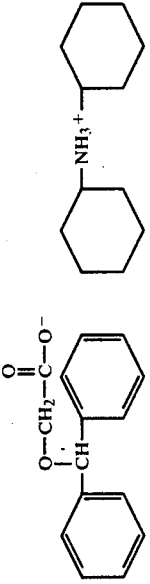 | I | C 76.56 76.59<br>H 8.80 8.81<br>N 3.31 3.31 | 149–151 |
| 72 | methyl phenyl[4-(trifluoromethyl)phenyl]-methoxyacetate | 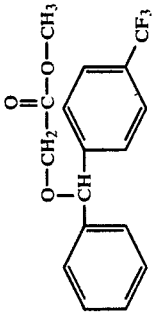 | B | C 62.96 62.93<br>H 4.66 4.66<br>F 17.58 | oil |

| | | | | | |
|---|---|---|---|---|---|
| 73 | ethyl phenyl[3-(trifluoromethyl)phenyl]methoxyacetate | 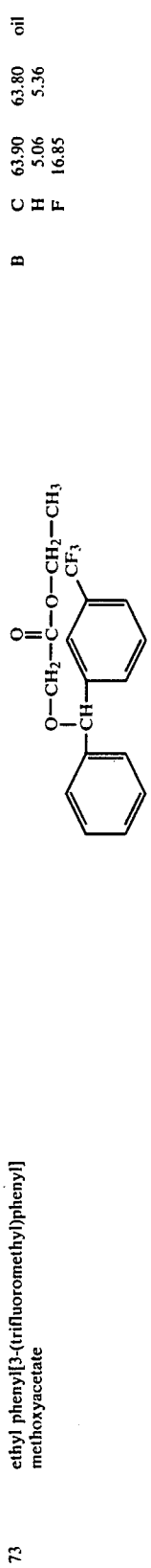 | B | C 63.90 63.80<br>H 5.06 5.36<br>F 16.85 | oil |
| 74 | 2-diphenylmethoxyethanethioamide | 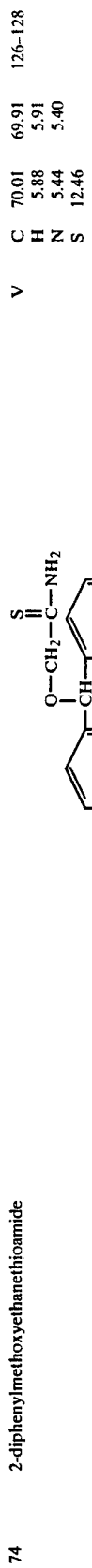 | V | C 70.01 69.91<br>H 5.88 5.91<br>N 5.44 5.40<br>S 12.46 | 126–128 |
| 75 | 2-propylammonium diphenylmethoxyacetate | 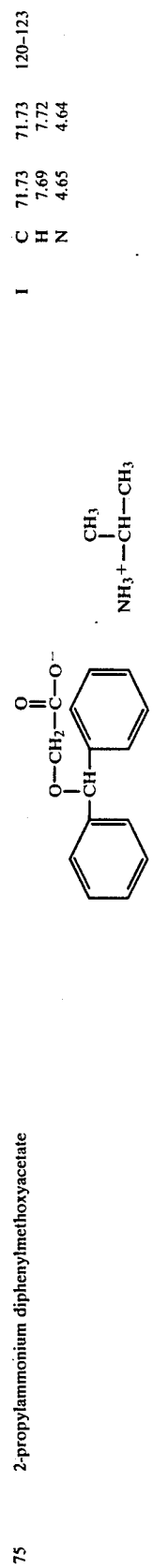 | I | C 71.73 71.73<br>H 7.69 7.72<br>N 4.65 4.64 | 120–123 |
| 76 | 1,1-dimethylethyl phenyl[3-(trifluoromethyl)phenyl]methoxyacetate | 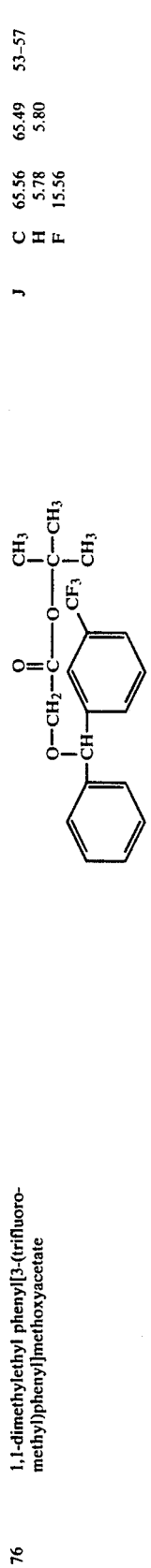 | J | C 65.56 65.49<br>H 5.78 5.80<br>F 15.56 | 53–57 |
| 77 | 1,1-dimethylethyl phenyl[2-(trifluoromethyl)phenyl]methoxyacetate | 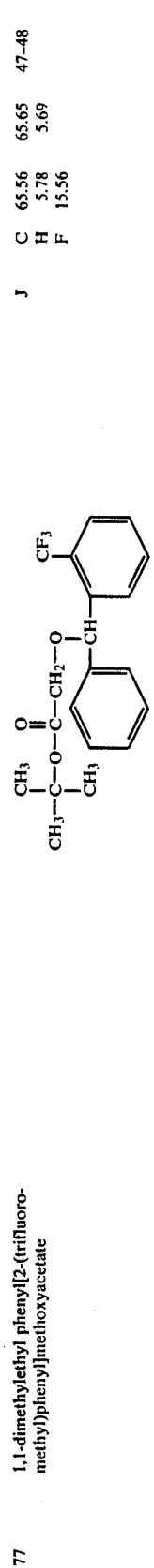 | J | C 65.56 65.65<br>H 5.78 5.69<br>F 15.56 | 47–48 |
| 78 | methyl bis[3-(trifluoromethyl)phenyl]methoxyacetate | 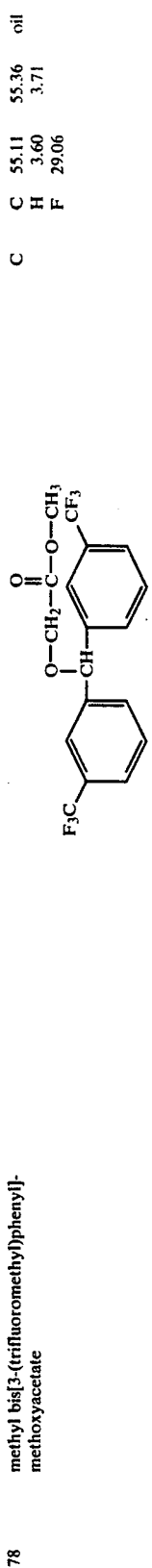 | C | C 55.11 55.36<br>H 3.60 3.71<br>F 29.06 | oil |

| | | | | |
|---|---|---|---|---|
| 79 | 1,1-dimethylethyl bis[4-(dimethylamino)-phenyl]methoxyacetate | 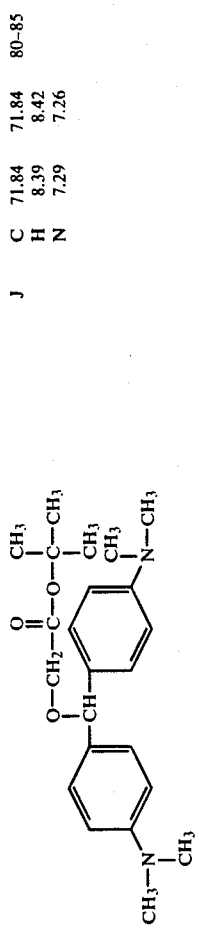 | J | C 71.84 71.84<br>H 8.39 8.42<br>N 7.29 7.26 | 80–85 |
| 80 | 1-butylammonium diphenylmethoxyacetate | 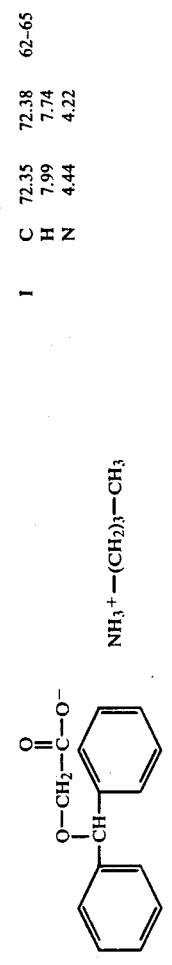 | I | C 72.35 72.38<br>H 7.99 7.74<br>N 4.44 4.22 | 62–65 |
| 81 | 2,2,2-trichloroethyl diphenylmethoxy-acetate | 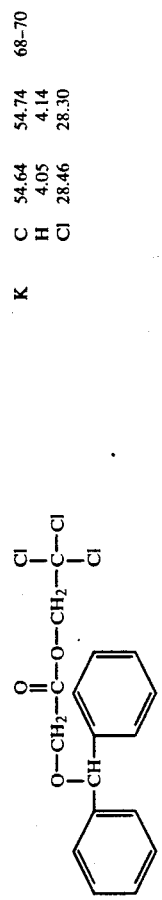 | K | C 54.64 54.74<br>H 4.05 4.14<br>Cl 28.46 28.30 | 68–70 |
| 82 | 2-methoxy-2-oxoethyl diphenylmethoxy-acetate | 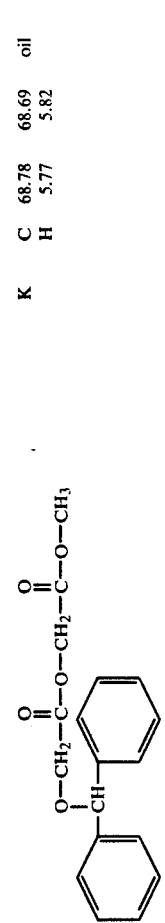 | K | C 68.78 68.69<br>H 5.77 5.82 | oil |
| 83 | (2,2-dimethyl-1,3-dioxolan-4-yl)methyl diphenylmethoxyacetate | 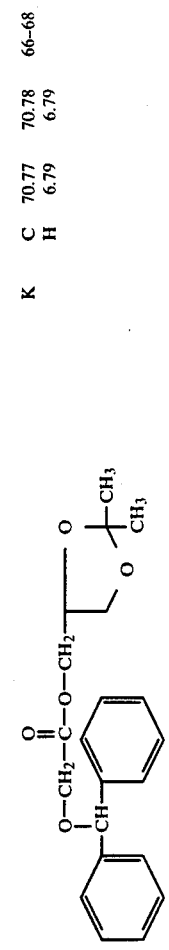 | K | C 70.77 70.78<br>H 6.79 6.79 | 66–68 |
| 84 | 1,1-dimethylethyl-2-hydroxyethylammonium diphenylmethoxyacetate | 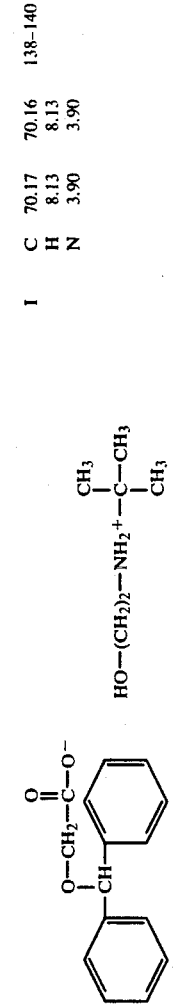 | I | C 70.17 70.16<br>H 8.13 8.13<br>N 3.90 3.90 | 138–140 |

| | | | | | |
|---|---|---|---|---|---|
| 85 | 2-chloroethyl diphenylmethoxyacetate |  | K | C 67.00 H 5.62 Cl 11.63 | 66.94 5.64 11.61 oil |
| 86 | diphenylmethoxyacetonitrile |  | T | C 80.69 H 5.87 N 6.27 | 80.65 5.93 6.26 34–36 |
| 87 | 1,1-dimethylethyl bis[3-(trifluoromethyl)phenyl]methoxyacetate | 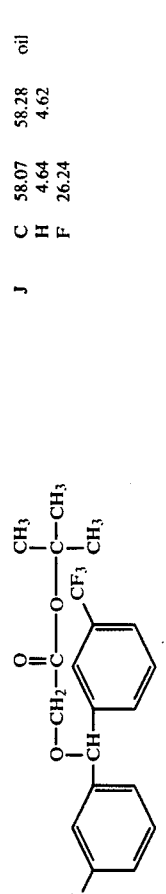 | J | C 58.07 H 4.64 F 26.24 | 58.28 4.62 oil |
| 88 | 1,3-benzodioxol-5-ylmethyl diphenylmethoxyacetate |  | K | C 73.39 H 5.36 | 73.40 5.40 oil |
| 89 | 1,3-benzodioxol-5-yl diphenylmethoxyacetate | 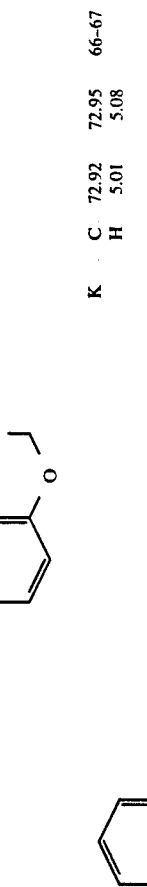 | K | C 72.92 H 5.01 | 72.95 5.08 66–67 |
| 90 | diphenylmethoxyacetyl 2,2-dimethylhydrazide | 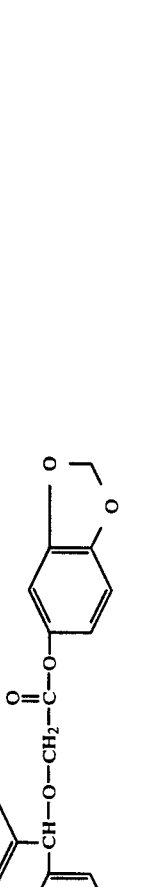 | K | C 71.81 H 7.09 N 9.85 | 71.83 7.11 9.85 119–120 |

-continued

| | | | | | |
|---|---|---|---|---|---|
| 91 | 1,1-dimethylethyl phenyl(3-pyridinyl)-methoxyacetate |  | J | C 72.22 H 7.07 N 4.68 | 72.20 7.08 4.64 | 54-56 |
| 92 | carboethoxymethyl [phenyl-3-(trifluoromethyl)phenylmethoxy]-acetate |  | K | C 60.61 H 4.83 F 14.38 | 60.97 4.87 | oil |
| 93 | methyl (3,5-dichlorophenyl)phenyl-methoxyacetate |  | A | C 59.10 H 4.34 Cl 21.80 | 59.11 4.34 21.78 | 75-78 |
| 94 | methyl phenyl(3-pyridinyl)methoxy-acetate |  | C | C 70.02 H 5.88 N 5.44 | 68.64 5.85 5.14 | oil |
| 95 | 2-(diphenylmethoxy)-N-(1,1-dimethyl-2-hydroxyethyl)acetamide | 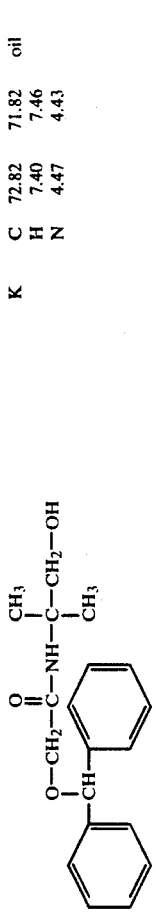 | K | C 72.82 H 7.40 N 4.47 | 71.82 7.46 4.43 | oil |
| 96 | methyl bis(4-fluorophenyl)-methoxyacetate |  | A | C 65.75 H 4.83 F 13.00 | 65.30 4.75 | oil |

| | | | | | |
|---|---|---|---|---|---|
| 97 | methyl phenyl(2-pyridinyl)methoxy-acetate | 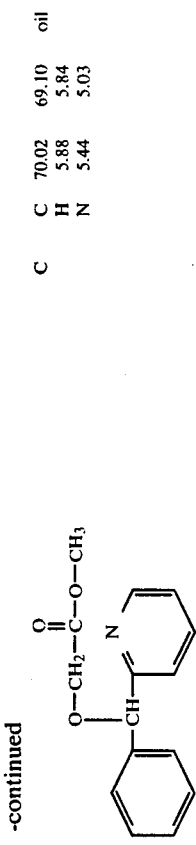 | C | C 70.02 69.10<br>H 5.88 5.84<br>N 5.44 5.03 | oil |
| 98 | carbomethoxymethyl (3,5-dichloro-phenyl)phenylmethoxyacetate | 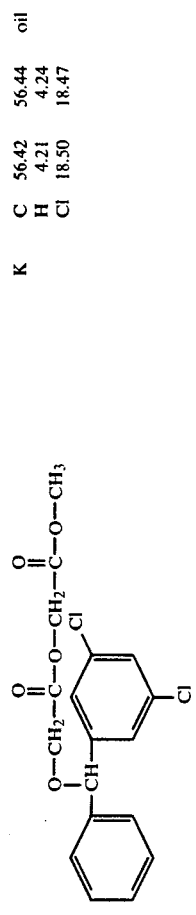 | K | C 56.42 56.44<br>H 4.21 4.24<br>Cl 18.50 18.47 | oil |
| 99 | cyclopropylmethyl diphenylmethoxy-acetate | 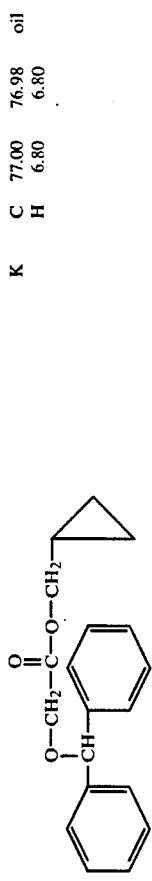 | K | C 77.00 76.98<br>H 6.80 6.80 | oil |
| 100 | 1-methyl-2,2,2-trifluoroethyl diphenyl-methoxyacetate |  | K | C 63.90 63.90<br>H 5.06 5.07<br>F 16.85 | oil |
| 101 | 3-(trifluoromethyl)benzyl diphenylmethoxyacetate | 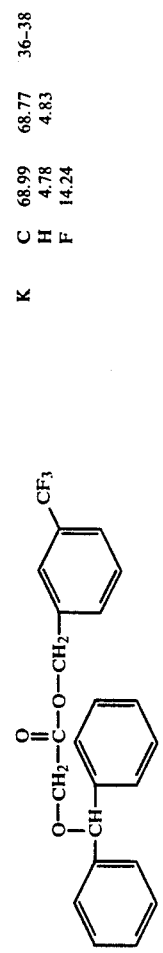 | K | C 68.99 68.77<br>H 4.78 4.83<br>F 14.24 | 36–38 |
| 102 | 2-oxiranylmethyl diphenylmethoxy-acetate | 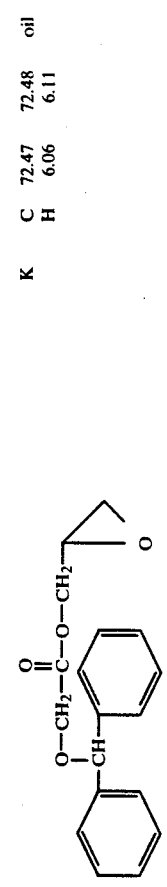 | K | C 72.47 72.48<br>H 6.06 6.11 | oil |

-continued

| | | | | | |
|---|---|---|---|---|---|
| 103 | 2-cyanoethyl diphenylmethoxyacetate | 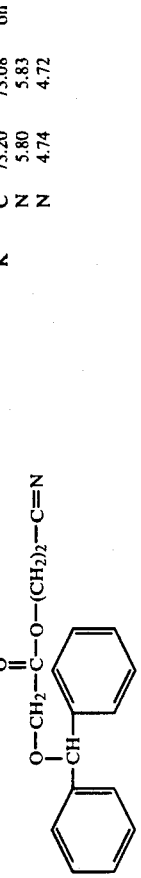 | K | C 73.20 73.08<br>H 5.80 5.83<br>N 4.74 4.72 | oil |
| 104 | diphenylmethoxyacetyl 2-(3-fluorophenyl)hydrazide | 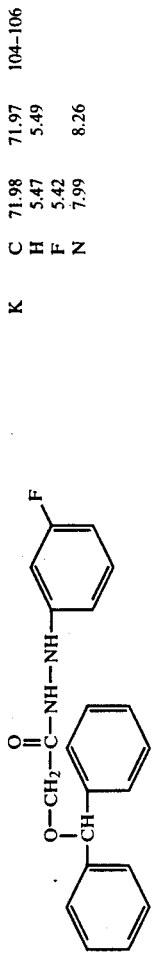 | K | C 71.98 71.97<br>H 5.47 5.49<br>F 5.42<br>N 7.99 8.26 | 104–106 |
| 105 | 1,4-bis[(disphenylmethoxy)acetyl]-piperazine | 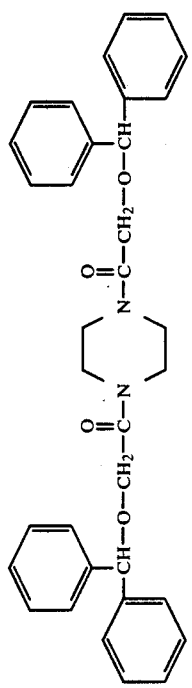 | AA | C 76.38 76.24<br>H 6.41 6.47<br>N 5.24 5.18 | 180–182 |
| 106 | 2-thienylmethyl diphenylmethoxy-acetate | 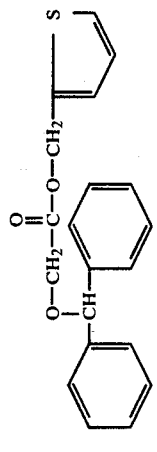 | K | C 70.98 70.93<br>H 5.36 5.43<br>S 9.48 9.48 | 52–55 |
| 107 | 2,2,3,3,3-pentafluoropropyl diphenyl-methoxyacetate | 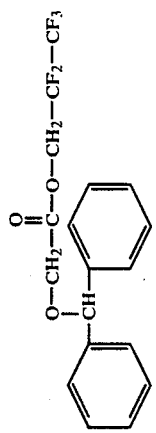 | K | C 57.76 57.79<br>H 4.04 4.06<br>F 25.38 | oil |
| 108 | 2,2,3,3,4,4,4-heptafluorobutyl diphenylmethoxyacetate | 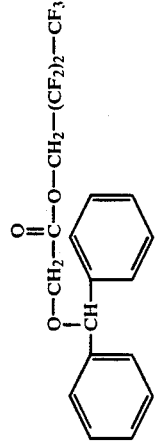 | K | C 53.78 53.64<br>H 3.56 3.70<br>F 31.34 | oil |

| | | | | |
|---|---|---|---|---|
| 109 | pipcrazinium diphenylmethoxyacetate | 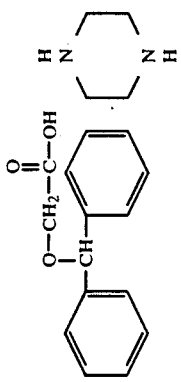 | I | C 69.49 69.23<br>H 7.37 7.44<br>N 8.53 8.48 | 154-155 |
| 110 | methyl phenyl(4-pyridinyl)methoxy-acetate | 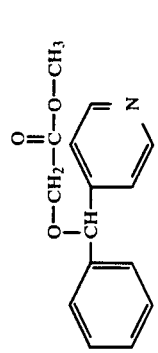 | C | C 70.02 69.87<br>H 5.88 5.94<br>N 5.44 5.39 | oil |
| 111 | methyl [2,4-bis(trifluoromethyl)-phenyl]phenylmethoxyacetate | 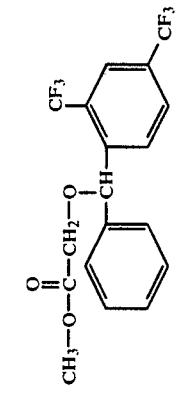 | C | C 55.11 55.34<br>H 3.60 3.72<br>F 29.06 | oil |
| 112 | 2-hydroxy-1-propylammonium diphenyl-methoxyacetate | 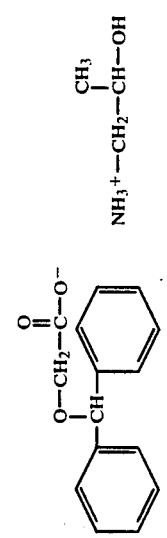 | I | C 68.12 68.14<br>H 7.30 7.34<br>N 4.41 4.38 | 118-120 |
| 113 | 2-amino-1,1-dimethyl-1-ethaneammonium diphenylmethoxyacetate | 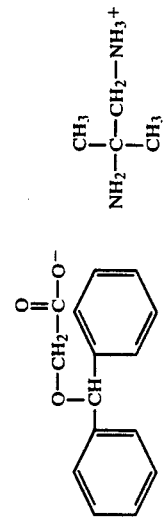 | I | C 69.06 68.98<br>H 7.93 7.97<br>N 8.48 8.44 | 117-119 |
| 114 | 3-hydroxy-1-propylammonium diphenylmethoxyacetate | 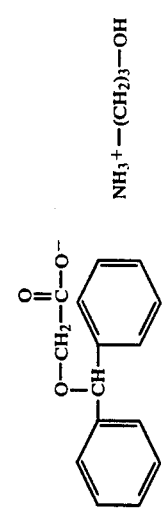 | I | C 68.12 68.04<br>H 7.30 7.30<br>N 4.41 4.39 | 69-71 |

| | | | | | |
|---|---|---|---|---|---|
| 115 | 2-cyano-1-ethylammonium diphenylmethoxyacetate | 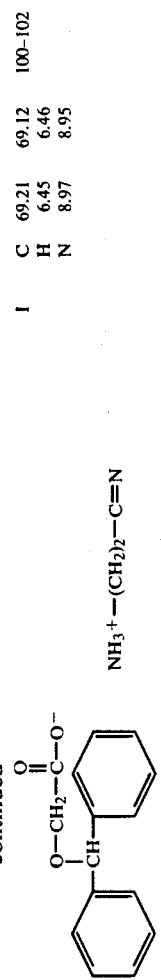 | I | C 69.21 H 6.45 N 8.97 | 69.12 6.46 8.95 | 100–102 |
| 116 | 5-hydroxy-1-pentylammonium diphenylmethoxyacetate | 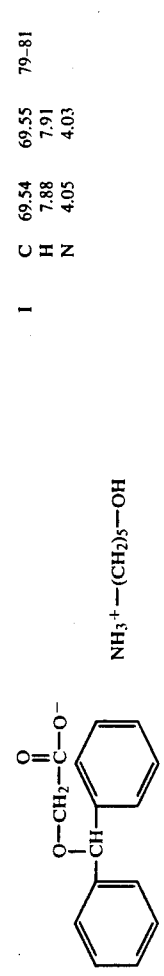 | I | C 69.54 H 7.88 N 4.05 | 69.55 7.91 4.03 | 79–81 |
| 117 | diphenylmethyl diphenylmethoxyacetate | 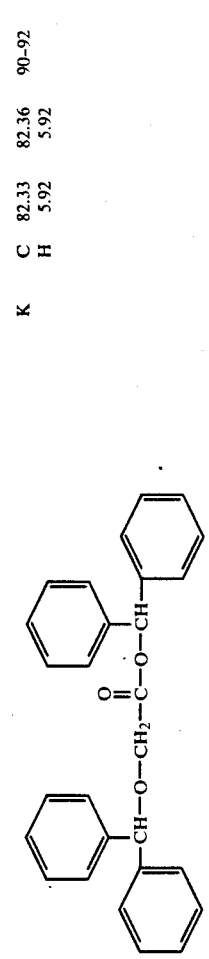 | K | C 82.33 H 5.92 | 82.36 5.92 | 90–92 |
| 118 | methyl (2-furanyl)phenylmethoxyacetate·0.2H₂O |  | C | C 67.30 H 5.81 | 67.43 5.68 | oil |
| 119 | dichloromethyldiphenylmethoxymethyl ketone |  | CC | C 62.15 H 4.56 Cl 22.93 | 62.16 4.58 22.92 | 37–39 |
| 120 | methyl [3-(trifluoromethyl)phenyl]-[4-(trifluoromethyl)phenyl]methoxyacetate |  | C | C 55.11 H 3.60 F 29.06 | 54.94 3.47 | oil |

| | | | | |
|---|---|---|---|---|
| 121 | methyl (2-methylphenyl)phenyl-methoxyacetate |  | A | C 75.53 76.00 H 6.71 7.10 | oil |
| 122 | benzyl phenyl[3-(trifluoromethyl)-phenyl]methoxyacetate | 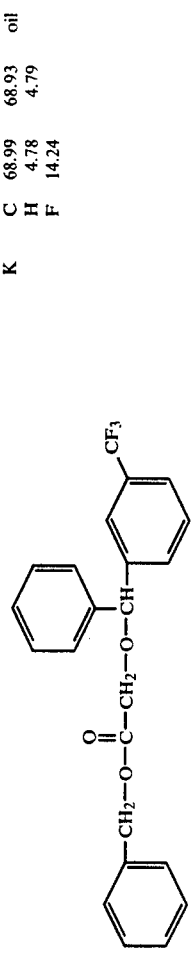 | K | C 68.99 68.93 H 4.78 4.79 F 14.24 | oil |
| 123 | 2-[phenyl[3-(trifluoromethyl)phenyl]-methoxy]acetamide |  | S | C 62.13 62.15 H 4.56 4.56 F 18.43 4.52 N 4.53 | 91–93 |
| 124 | 1,1-dimethyl-2-hydroxy-1-propylammonium diphenyl-methoxyacetate | 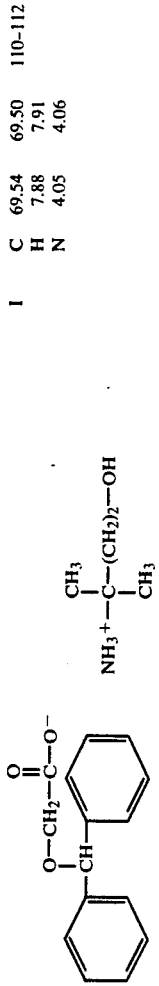 | I | C 69.54 69.50 H 7.88 7.91 N 4.05 4.06 | 110–112 |
| 125 | 1,1-bis(hydroxymethyl)-1-ethyl-ammonium diphenylmethoxyacetate | 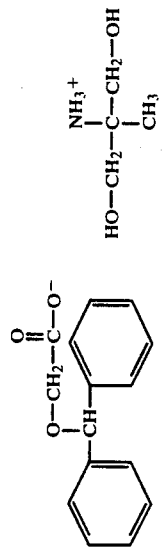 | I | C 65.69 65.73 H 7.25 7.29 N 4.03 4.04 | 133–135 |
| 126 | methyl phenyl(2-thienyl)methoxyacetate |  | C | C 64.10 64.00 H 5.38 5.37 S 12.22 12.25 | oil |

| | | | |
|---|---|---|---|
| 127 | (methylthio)methyl diphenylmethoxyacetate | 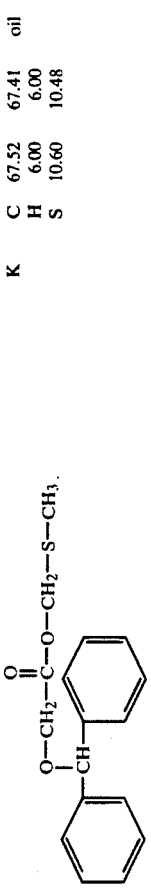 | K | C 67.52 67.41<br>H 6.00 6.00<br>S 10.60 10.48 | oil |
| 128 | methyl bis(3-fluorophenyl)methoxy-acetate |  | A | C 65.75 66.10<br>H 4.83 4.92<br>F 13.00 | oil |
| 129 | butyl diphenylmethoxyacetate | 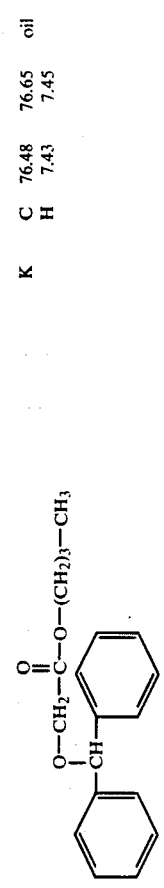 | K | C 76.48 76.65<br>H 7.43 7.45 | oil |
| 130 | dodecyl diphenylmethoxyacetate | 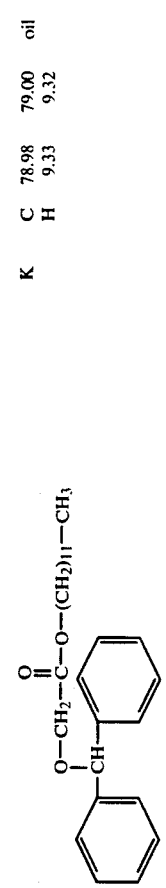 | K | C 78.98 79.00<br>H 9.33 9.32 | oil |
| 131 | [5-(hydroxymethyl)-2-furanyl]methyl diphenylmethoxyacetate·0.5H$_2$O | 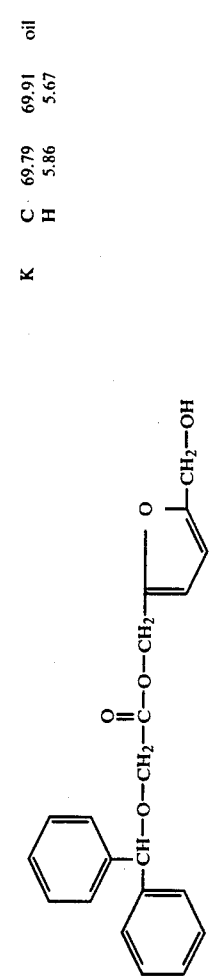 | K | C 69.79 69.91<br>H 5.86 5.67 | oil |
| 132 | diphenylmethoxyacetyl 2-(2,2,2-trifluoroethyl)hydrazide | 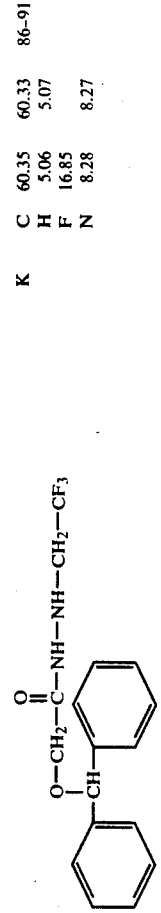 | K | C 60.35 60.33<br>H 5.06 5.07<br>F 16.85<br>N 8.28 8.27 | 86–91 |

| | | | | | |
|---|---|---|---|---|---|
| 133 | dimethyl 1-[2-[(diphenylmethoxy)acetyl]-hydrazono]ethylphosphonate | 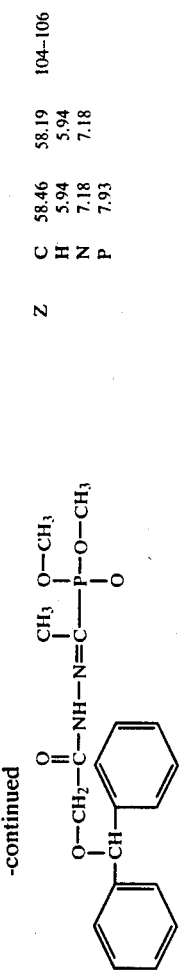 | N | C 58.46<br>H 5.94<br>N 7.18<br>P 7.93 | 58.19<br>5.94<br>7.18 | 104–106 |
| 134 | 2,2,2-trifluoroethyl phenyl[3-(trifluoro-methyl)phenyl]methoxyacetate | 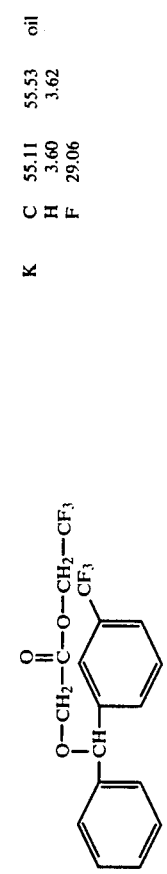 | K | C 55.11<br>H 3.60<br>F 29.06 | 55.53<br>3.62 | oil |
| 135 | methyl [(4-chloro-3-nitrophenyl)phenyl-methoxy]acetate |  | C | C 57.24<br>H 4.20<br>Cl 10.56<br>N 4.17 | 57.49<br>4.19<br>4.08 | oil |
| 136 | methyl [(2,3,4,5,6-pentafluorophenyl)-phenylmethoxy]acetate | 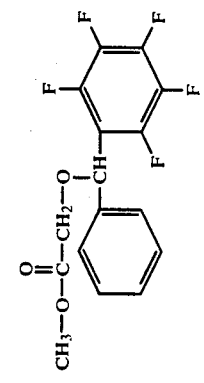 | C | C 55.50<br>H 3.20<br>F 27.44 | 55.83<br>3.27 | oil |
| 137 | methyl [phenyl(3-thienyl)methoxy]-acetate |  | C | C 64.10<br>H 5.38<br>S 12.22 | 64.10<br>5.40<br>12.30 | oil |
| 138 | methyl [phenyl(2-thiazolyl)methoxy]-acetate |  | C | C 59.30<br>H 4.98<br>N 5.32<br>S 12.18 | 59.25<br>5.03<br>5.28 | oil |

| | | | | |
|---|---|---|---|---|
| 139 | 1,1-dimethyl-2-hydroxyethylammonium phenyl[3-(trifluoromethyl)phenyl]-methoxyacetate |  | I | C 60.14 60.15<br>H 6.06 6.12<br>F 14.27<br>N 3.51 3.50 | 87-90 |
| 140 | 2-(diphenylmethoxy)-N-(1,1-dimethyl-2-hydroxyethyl)acetamide compound with 4-methylbenzenesulfonic acid | 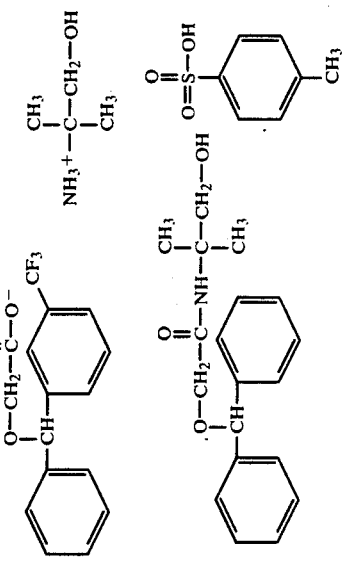 | X | C 64.31 64.28<br>H 6.43 6.39<br>N 2.88 2.87<br>S 6.60 | 186-187 |

| # | Name | Structure | | Analysis | | mp |
|---|---|---|---|---|---|---|
| 141 | DL-3-methyl-1-hydroxy-2-butyl-ammonium diphenylmethoxyacetate | 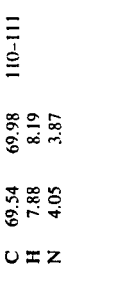 | I | C 69.54<br>H 7.88<br>N 4.05 | 69.98<br>8.19<br>3.87 | 110–111 |
| 142 | L-1-hydroxy-3-methyl-2-pentyl-ammonium diphenylmethoxyacetate | 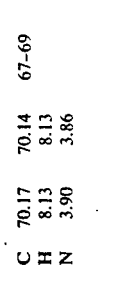 | I | C 70.17<br>H 8.13<br>N 3.90 | 70.14<br>8.13<br>3.86 | 67–69 |
| 143 | 1-hydroxy-4-methyl-2-pentyl-ammonium diphenylmethoxyacetate | 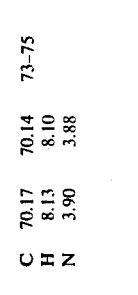 | I | C 70.17<br>H 8.13<br>N 3.90 | 70.14<br>8.10<br>3.88 | 73–75 |
| 144 | methyl (2,4-dichlorophenyl)phenyl-methoxyacetate | 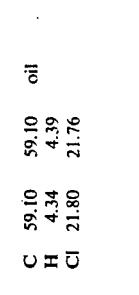 | C | C 59.10<br>H 4.34<br>Cl 21.80 | 59.10<br>4.39<br>21.76 | oil |
| 145 | methyl (3-chlorophenyl)phenylmethoxy-acetate | 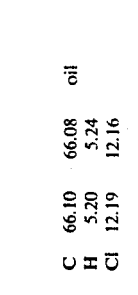 | D | C 66.10<br>H 5.20<br>Cl 12.19 | 66.08<br>5.24<br>12.16 | oil |
| 146 | 2-propynyl diphenylmethoxyacetate | 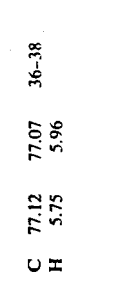 | K | C 77.12<br>H 5.75 | 77.07<br>5.96 | 36–38 |

-continued
| | | | | | |
|---|---|---|---|---|---|
| 147 | N-(1,1-dimethylethyl)-2-(diphenyl-methoxy)acetamide |  | K | C 76.74 H 7.80 N 4.71 | 76.73 7.88 4.61 | 66-70 |
| 148 | methyl bis(2-pyridinyl)methoxy-acetate |  | C | C 65.11 H 5.46 N 10.85 | 65.13 5.53 10.87 | oil |
| 149 | 2-propenyl diphenylmethoxyacetate | 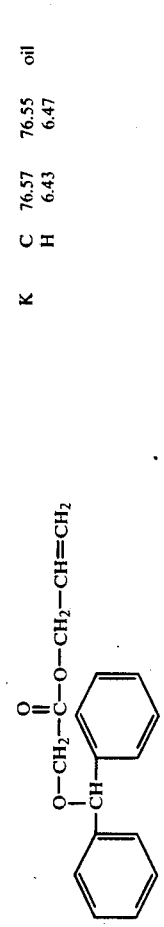 | K | C 76.57 H 6.43 | 76.55 6.47 | oil |
| 150 | 2-methyl-2-butylammonium diphenyl-methoxyacetate | 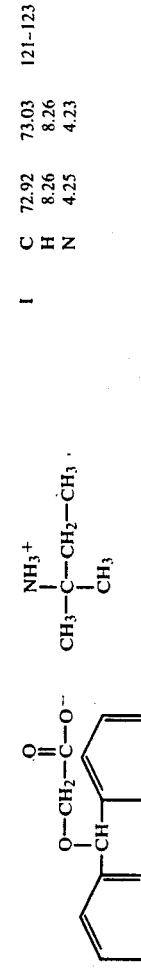 | I | C 72.92 H 8.26 N 4.25 | 73.03 8.26 4.23 | 121-123 |
| 151 | 3-pentylammonium diphenylmethoxy-acetate | 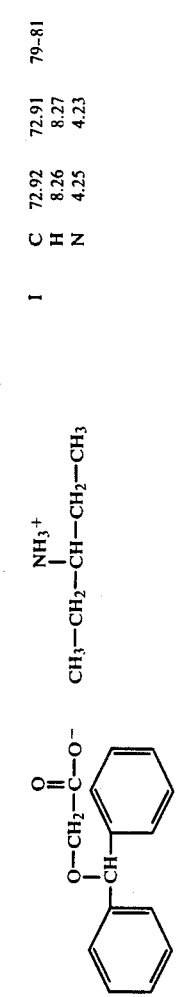 | I | C 72.92 H 8.26 N 4.25 | 72.91 8.27 4.23 | 79-81 |
| 152 | 2-butylammonium diphenylmethoxy-acetate | 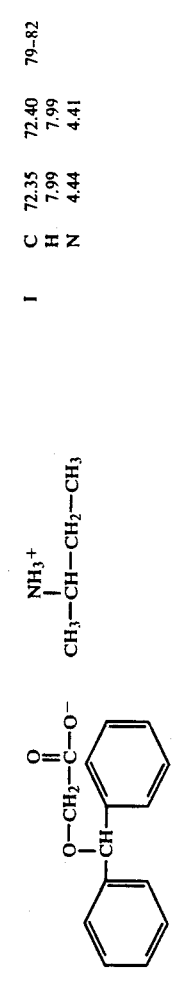 | I | C 72.35 H 7.99 N 4.44 | 72.40 7.99 4.41 | 79-82 |

| No. | Name | Structure | | Analysis | Found | Calc. | mp |
|---|---|---|---|---|---|---|---|
| 153 | 2,2-dimethyl-1-propylammonium diphenylmethoxyacetate | 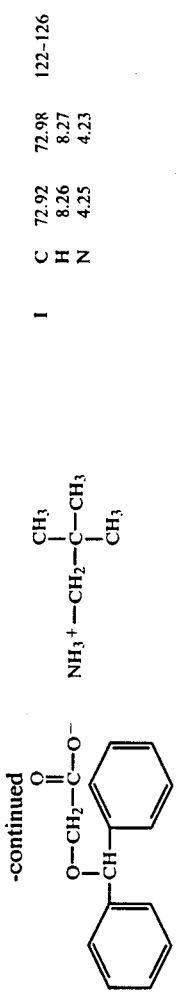 | I | C<br>H<br>N | 72.92<br>8.26<br>4.25 | 72.98<br>8.27<br>4.23 | 122–126 |
| 154 | 3-methyl-2-butylammonium diphenylmethoxyacetate | 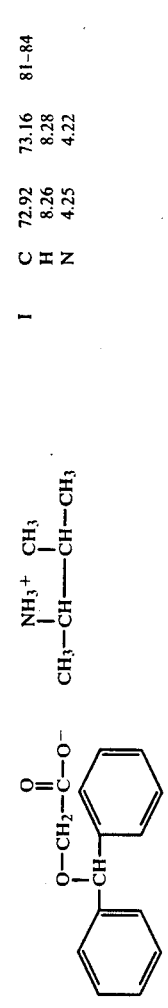 | I | C<br>H<br>N | 72.92<br>8.26<br>4.25 | 73.16<br>8.28<br>4.22 | 81–84 |
| 155 | 2-(2-hydroxyethyl)-1-ethylammonium diphenylmethoxyacetate | 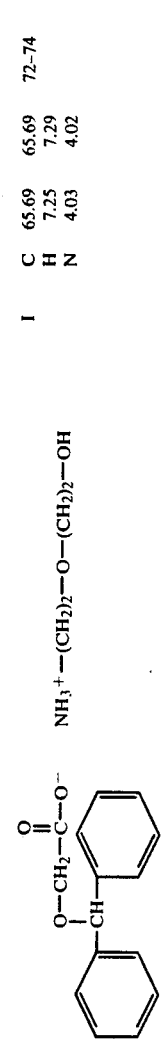 | I | C<br>H<br>N | 65.69<br>7.25<br>4.03 | 65.69<br>7.29<br>4.02 | 72–74 |
| 156 | O-benzyldiphenylmethoxymethylacetoxamine | 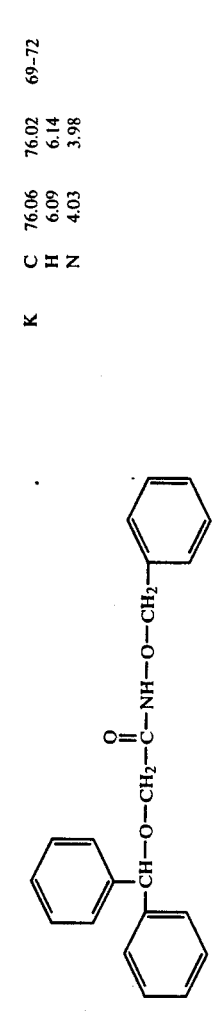 | K | C<br>H<br>N | 76.06<br>6.09<br>4.03 | 76.02<br>6.14<br>3.98 | 69–72 |
| 157 | methyl 4-chlorophenyl[3-(trifluoromethyl)phenyl]methoxyacetate | 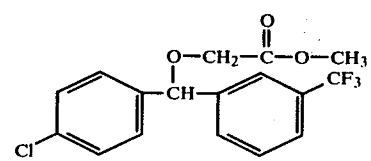 | D | C<br>H<br>Cl<br>F | 56.92<br>3.93<br>9.88<br>15.89 | 56.89<br>4.04<br>9.89<br> | oil |
| 158 | N-(1,1-dimethylethyl)-2-phenyl-[3-(trifluoromethyl)phenyl]methoxyacetamide | 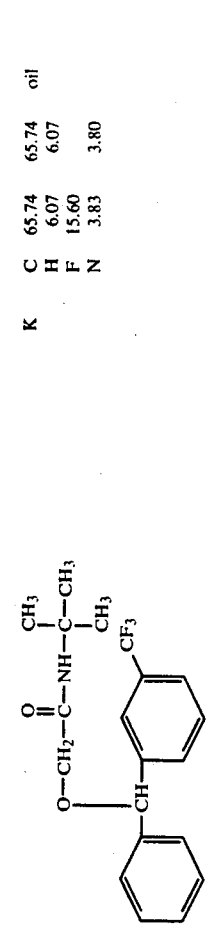 | K | C<br>H<br>F<br>N | 65.74<br>6.07<br>15.60<br>3.83 | 65.74<br>6.07<br><br>3.80 | oil |

-continued

| | | | | | |
|---|---|---|---|---|---|
| 159 | 2,3-dihydroxy-1-propylammonium diphenylmethoxyacetate | 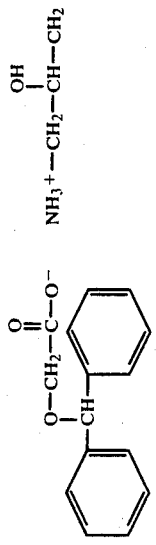 | I | C 64.85<br>H 6.95<br>N 4.20 | 64.81<br>6.96<br>4.22 | 115-119 |
| 160 | 1,1,1,3,3,3-hexafluoro-2-propyl diphenylmethoxyacetate |  | K | C 55.11<br>H 3.60<br>F 29.06 | 55.65<br>3.57 | oil |
| 161 | 1,1,1,3,3,3-hexafluoro-2-propyl phenyl[3-(trifluoromethyl)phenyl]-methoxyacetate | 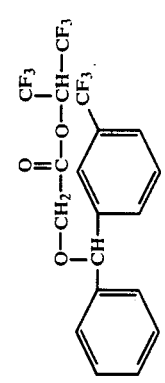 | K | C 49.58<br>H 2.85<br>F 37.15 | 50.07<br>2.86 | oil |
| 162 | propyl phenyl[3-(trifluoromethyl)-phenyl]methoxyacetate | 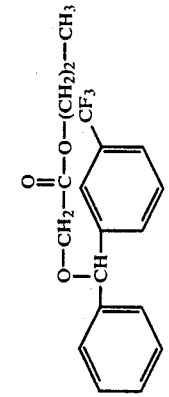 | K | C 64.77<br>H 5.44<br>F 16.18 | 64.63<br>5.39 | oil |
| 163 | butyl phenyl[3-(trifluoromethyl)-phenyl]methoxyacetate | 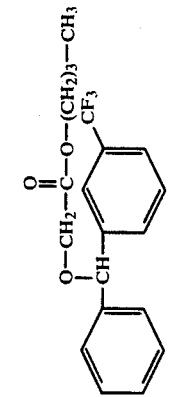 | K | C 65.56<br>H 5.78<br>F 15.56 | 65.57<br>5.77 | oil |
| 164 | ethyl bis(2-thienyl)methoxyacetate | 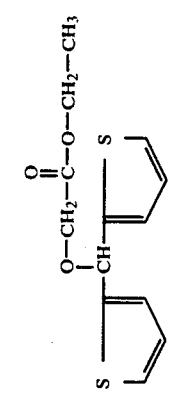 | D | C 55.29<br>H 5.00<br>S 22.71 | 55.39<br>5.03<br>22.75 | oil |

| | | | | |
|---|---|---|---|---|
| 165 | 3-furanylmethyl diphenylmethoxyacetate 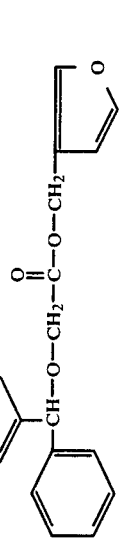 | K | C 74.52 74.50<br>H 5.63 5.67 | 48–50 |
| 166 | 1,1-dicyano-2-(diphenylmethoxy)ethyl diphenylmethoxyacetate 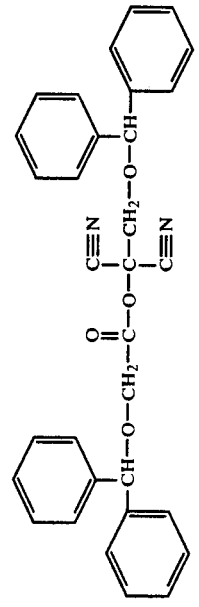 | Q | C 76.48 76.44<br>H 5.21 5.26<br>N 5.57 5.55 | 84–87 |
| 167 | methyl phenyl[4-(N-oxide)pyridinyl]-methoxyacetate.0.6H$_2$O 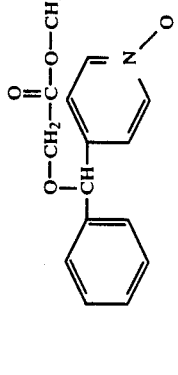 | M | C 63.42 63.26<br>H 5.75 5.65<br>N 4.93 4.62 | 91–94 |
| 168 | phenyl[4-(trifluoromethyl)phenyl]-methoxyacetyl hydrazide 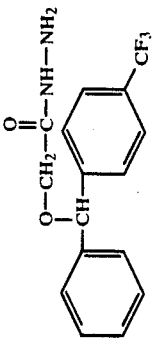 | W | C 59.26 59.32<br>H 4.66 4.74<br>F 17.58<br>N 8.64 8.53 | oil |
| 169 | diphenylmethoxyacetaldehyde oxime .0.25H$_2$O 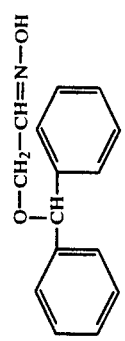 | R | C 73.30 73.38<br>H 6.36 6.62<br>N 5.70 6.09 | 96–102 |

-continued
| | | | | | |
|---|---|---|---|---|---|
| 170 | 2-[(diphenylmethoxy)methyl]-4,5-dihydro-4,4-dimethyloxazole .0.6H$_2$O | 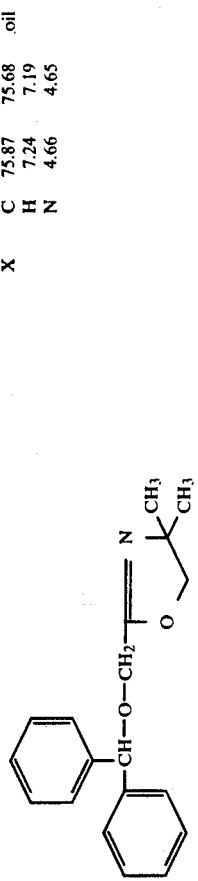 | X | C 75.87 75.68<br>H 7.24 7.19<br>N 4.66 4.65 | oil |
| 171 | methyl bis(2,3,4,5,6-pentafluoro-phenyl)methoxyacetate | 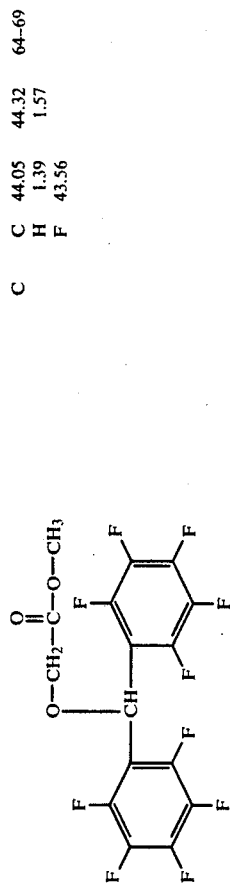 | C | C 44.05 44.32<br>H 1.39 1.57<br>F 43.56 | 64–69 |
| 172 | 4-methylbenzyl diphenylmethoxyacetate | 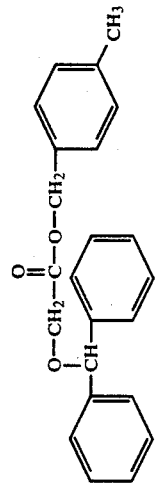 | K | C 79.74 79.67<br>H 6.40 6.48 | 59 |
| 173 | 3-chlorobenzyl diphenylmethoxyacetate | 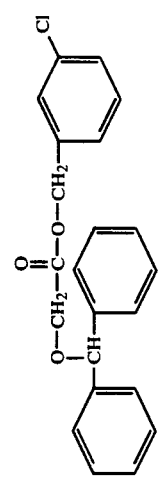 | K | C 72.03 72.06<br>H 5.22 5.26<br>Cl 9.66 | 64–66 |
| 174 | 4-methoxybenzyl diphenylmethoxyacetate | 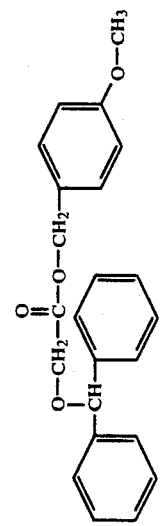 | K | C 76.22 76.55<br>H 6.12 6.42 | 45 |

| | | | | |
|---|---|---|---|---|
| 175 | 4-nitrobenzyl diphenylmethoxyacetate | 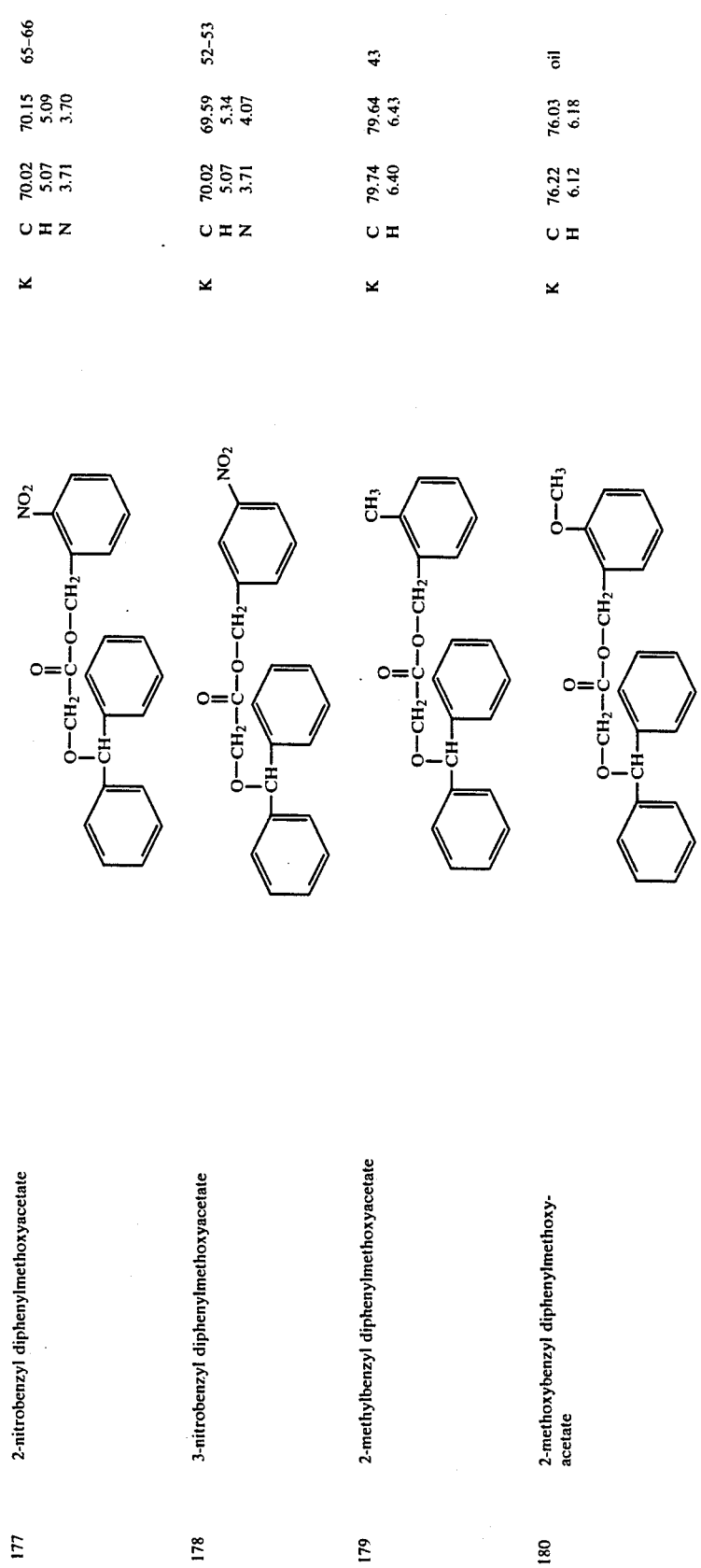 | K | C 70.02 70.02<br>H 5.07 5.13<br>N 3.71 3.71 | 81 |
| 176 | 3-methylbenzyl diphenylmethoxyacetate | | K | C 79.74 79.81<br>H 6.40 6.52 | 58–59 |
| 177 | 2-nitrobenzyl diphenylmethoxyacetate | | K | C 70.02 70.15<br>H 5.07 5.09<br>N 3.71 3.70 | 65–66 |
| 178 | 3-nitrobenzyl diphenylmethoxyacetate | | K | C 70.02 69.59<br>H 5.07 5.34<br>N 3.71 4.07 | 52–53 |
| 179 | 2-methylbenzyl diphenylmethoxyacetate | | K | C 79.74 79.64<br>H 6.40 6.43 | 43 |
| 180 | 2-methoxybenzyl diphenylmethoxy-acetate | | K | C 76.22 76.03<br>H 6.12 6.18 | oil |

-continued
| | | | | | |
|---|---|---|---|---|---|
| 181 | 2-chlorobenzyl diphenylmethoxy-acetate | 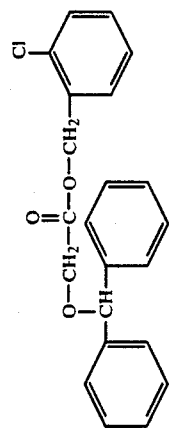 | K | C 71.03 H 5.22 Cl 9.66 | 71.95 5.29 oil |
| 182 | 3-methoxybenzyl diphenylmethoxy-acetate | 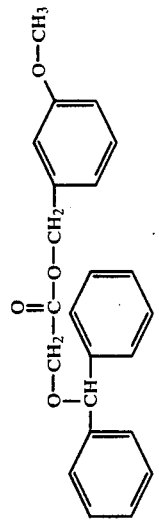 | K | C 76.22 H 6.12 | 76.19 6.15 25 |
| 183 | (2-methylphenyl)phenylmethoxyacetic acid | 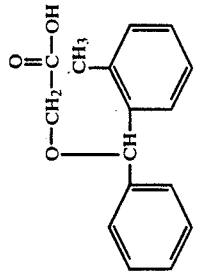 | H | C 74.98 H 6.29 | 75.03 6.33 105 |
| 184 | (2,6-dimethylphenyl)phenylmethoxyacetic acid | 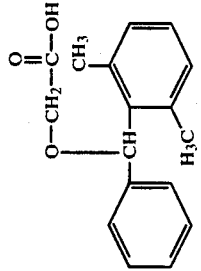 | H | C 75.53 H 6.71 | 75.45 6.71 111–112 |
| 185 | 2,6-dimethylphenyl)(2-methylphenyl)-methoxyacetic acid | 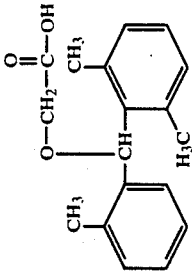 | H | C 76.03 H 7.09 | 75.94 7.13 103–104 |

-continued
| | | | | | |
|---|---|---|---|---|---|
| 186 | bis(2-methylphenyl)methoxyacetic acid |  | H | C 75.53 H 6.71 | 75.40 6.75 | 99-101 |
| 187 | 4-nitrophenyl diphenylmethoxyacetate | 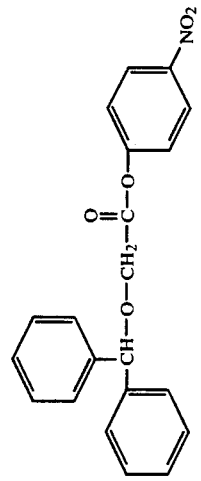 | L | C 69.41 H 4.72 N 3.85 | 69.37 4.74 3.79 | 72-75 |
| 188 | 2-chlorophenyl diphenylmethoxyacetate | 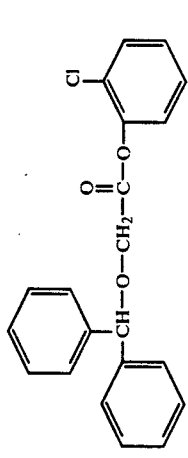 | L | C 71.49 H 4.86 Cl 10.05 | 71.57 4.92 10.11 | 85-87 |
| 189 | 3-chlorophenyl diphenylmethoxyacetate | 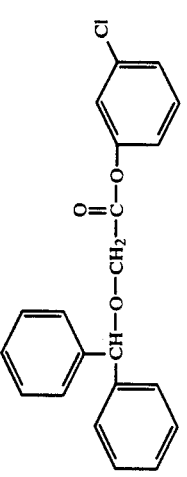 | L | C 71.49 H 4.86 Cl 10.05 | 71.57 4.92 10.11 | 92-94 |
| 190 | 2-nitrophenyl diphenylmethoxyacetate | 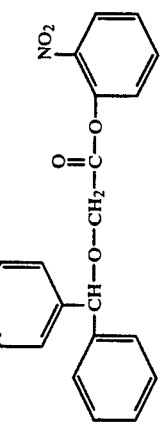 | L | C 69.41 H 4.72 N 3.85 | 69.46 4.74 3.84 | 92-91 |

| | | | | | |
|---|---|---|---|---|---|
| 191 | 3-methoxyphenyl diphenylmethoxyacetate | 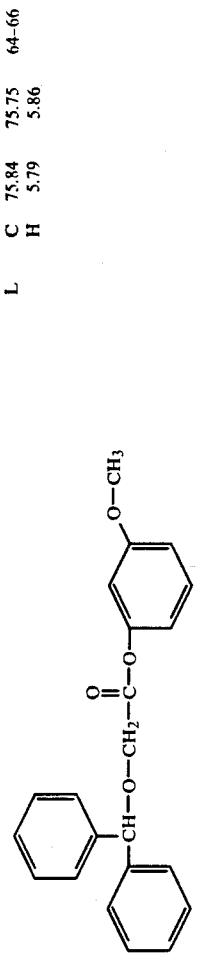 | C<br>H | 75.84<br>5.79 | 75.75  64–66<br>5.86 |
| 192 | 4-methoxyphenyl diphenylmethoxyacetate | 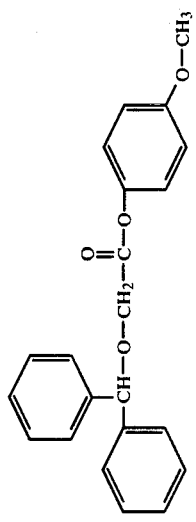 | C<br>H | 75.84<br>5.79 | 75.62  59–61<br>5.87 |
| 193 | 3-methylphenyl diphenylmethoxyacetate | 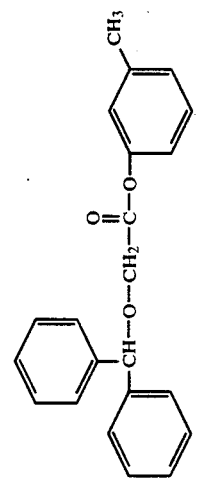 | C<br>H | 79.50<br>6.07 | 79.53  56<br>6.14 |
| 194 | 2-methylphenyl diphenylmethoxyacetate | 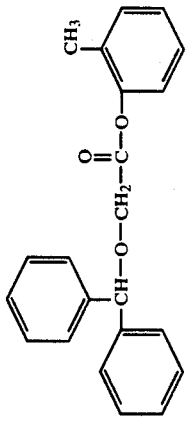 | C<br>H | 79.50<br>6.07 | 79.42  86–87<br>6.08 |
| 195 | 2-methoxyphenyl diphenylmethoxyacetate | 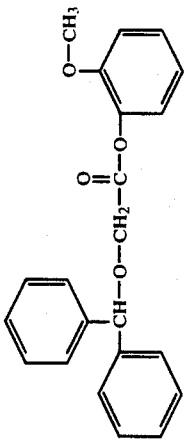 | C<br>H | 75.84<br>5.79 | 75.72  89–91<br>5.82 |

| | | | | | |
|---|---|---|---|---|---|
| 196 | 4-methylphenyl diphenylmethoxyacetate | | L | C 79.50 79.22<br>H 6.07 6.12 | 67-68 |
| 197 | S-propyl diphenylmethoxyethanethioate | | L | C 71.95 72.03<br>H 6.71 6.75<br>S 10.67 10.61 | 32-34 |
| 198 | 4-chlorophenyl diphenylmethoxyacetate | | L | C 71.49 71.60<br>H 4.86 4.90<br>Cl 10.05 10.06 | 75-76 |
| 199 | 2-(diphenylmethoxy)pentanoic acid | | H | C 76.03 75.92<br>H 7.09 7.09 | oil |
| 200 | 1-methylethyl 2-(diphenylmethoxy)-pentanoate | | K | C 77.27 77.12<br>H 8.03 8.03 | oil |

| | | | | | |
|---|---|---|---|---|---|
| 201 | ethyl 2-(diphenylmethoxy)pentanoate | 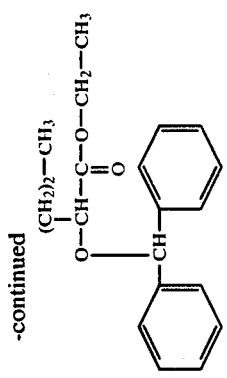 | C | C 76.89 H 7.74 | 76.33 7.59 | oil |
| 202 | 3-trifluoromethylphenyl diphenylmethoxyacetate | 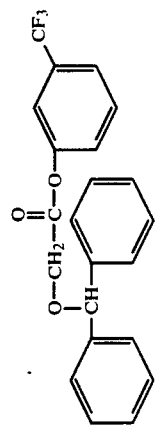 | L | C 68.39 H 4.44 F 14.75 | 68.79 4.59 | 53–55 |
| 203 | 4-fluorobenzyl diphenylmethoxyacetate | 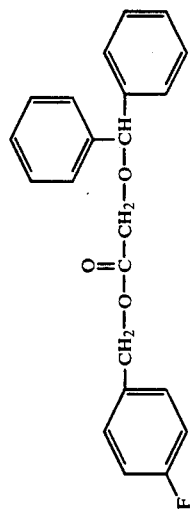 | L | C 75.41 H 5.47 F 5.42 | 75.36 5.48 | 62–64 |
| 204 | phenyl[3-(trifluoromethyl)phenyl]-methoxyacetic acid | 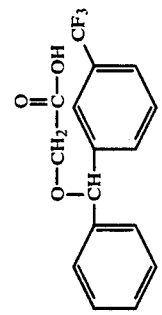 | H | C 61.94 H 4.22 F 18.37 | 61.63 4.26 | 82–85 |
| 205 | ethyl 2-(2,2,2-trifluoro-1,1-diphenyl-ethoxy)acetate | 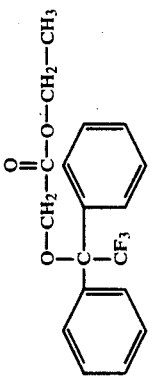 | E | C 63.90 H 5.06 F 16.85 | 63.53 5.03 | oil |
| 206 | S-ethyl 2-[(phenyl)(3-trifluorophenyl)-methoxy]ethanethioate | 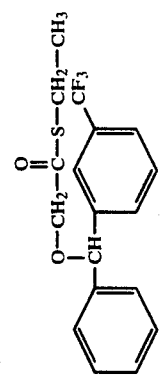 | K | C 61.00 H 4.84 F 16.08 S 9.05 | 61.25 4.89 | oil |

| | | | | |
|---|---|---|---|---|
| 207 | 4-chlorobenzyl [bis(2,6-dimethylphenyl)]methoxyacetate | 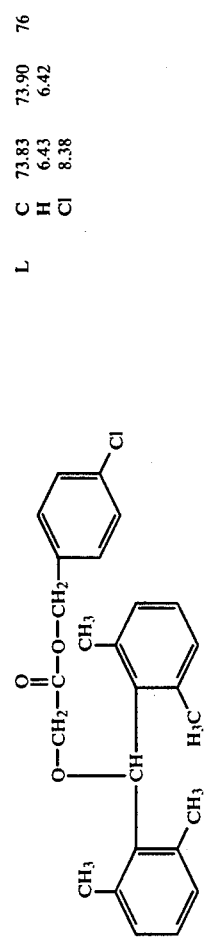 | L | C 73.83 73.90<br>H 6.43 6.42<br>Cl 8.38 | 76 |
| 208 | 3-(trifluoromethyl)benzyl 2-bis(2,6-dimethylphenyl)-methoxyacetate | 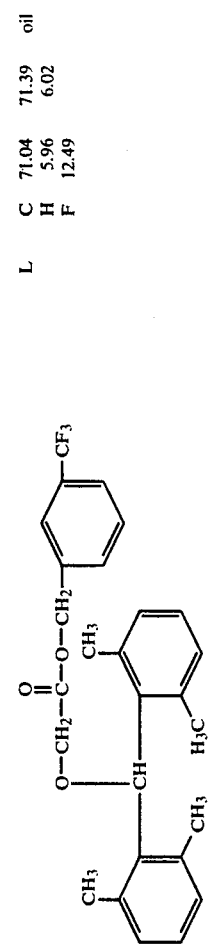 | L | C 71.04 71.39<br>H 5.96 6.02<br>F 12.49 | oil |
| 209 | 1-cyanoethyl 2-diphenylmethoxyacetate | 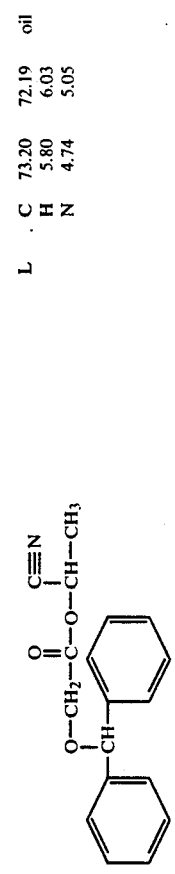 | L | C 73.20 72.19<br>H 5.80 6.03<br>N 4.74 5.05 | oil |
| 210 | 1,1-dimethylethyl 2-(cyclopropyl)-phenylmethoxyacetate |  | J | C 73.25 72.99<br>H 8.45 8.47 | oil |
| 211 | 1,1-dimethylethyl (4-methoxyphenyl)-cyclopropylmethoxyacetate | 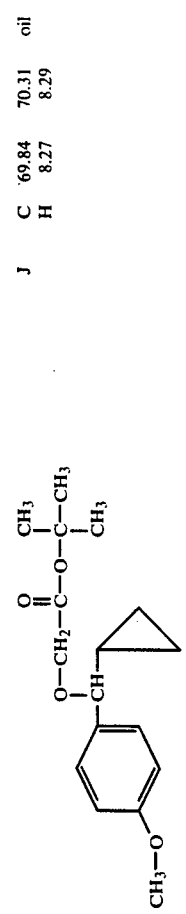 | J | C 69.84 70.31<br>H 8.27 8.29 | oil |

| | | | |
|---|---|---|---|
| 212 | methyl bis(2,6-dimethylphenyl)-methoxyacetate | 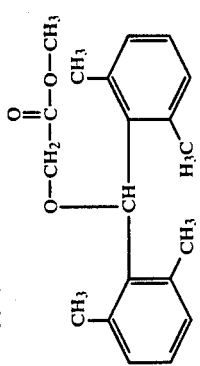 | E C 76.89 76.61 72<br>H 7.74 7.80 |

| | | | | | |
|---|---|---|---|---|---|
| 213 | propyl bis(2,6-dimethylphenyl)-methoxyacetate | 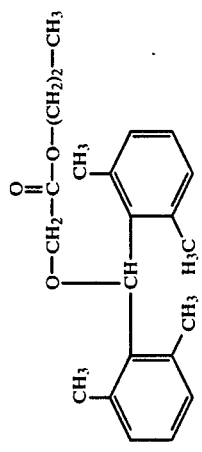 | L | C 77.61 77.68<br>H 8.29 8.59 | oil |
| 214 | 2,2,2-trichloroethyl bis(2,6-dimethylphenyl)-methoxyacetate | 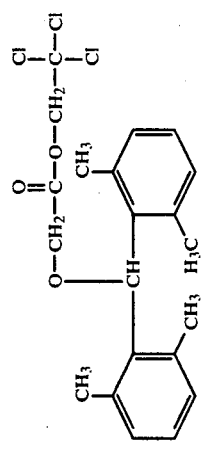 | L | C 58.69 58.73<br>H 5.39 5.54<br>Cl 24.75 24.54 | 56–57 |
| 215 | 3-nitrophenyl bis(2,6-dimethylphenyl)-methoxyacetate | 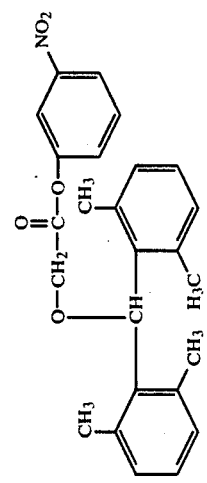 | L | C 71.58 71.33<br>H 6.01 6.32<br>N 3.34 3.54 | 128–130 |
| 216 | 3-pyridinylmethyl bis(2,6-dimethylphenyl)methoxyacetate | 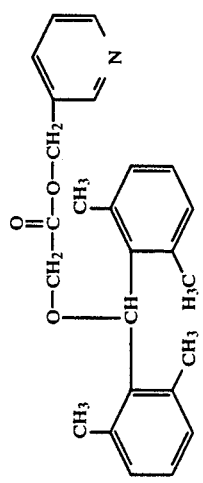 | L | C 77.09 76.77<br>H 6.99 7.05<br>N 3.60 3.95 | 85–88 |
| 217 | 2,2,2-trifluoroethyl bis(2,6-dimethylphenyl)methoxyacetate | 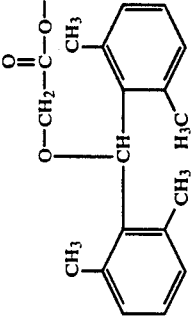 | L | C 66.30 66.63<br>H 6.09 6.35<br>F 14.98 | 57–60 |

-continued
| | | | | | |
|---|---|---|---|---|---|
| 218 | benzyl bis-(2,6-dimethylphenyl)-methoxyacetate | 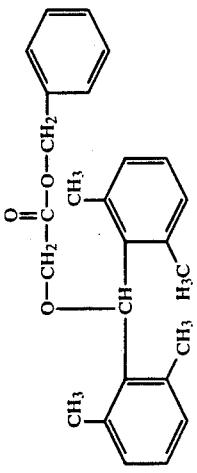 | L | C 80.38 80.16<br>H 7.26 7.21 | 75–77 |
| 219 | 4-fluorobenzyl bis(2,6-dimethylphenyl)-methoxyacetate | 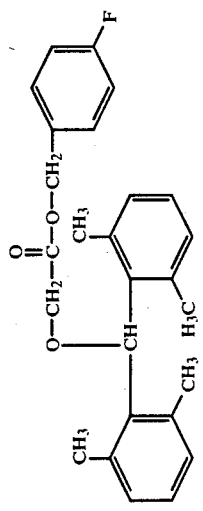 | L | C 76.82 76.68<br>H 6.70 6.72<br>F 4.67 | 82–85 |
| 220 | S-phenyl bis(2,6-dimethylphenyl)-methoxyethanethioate | 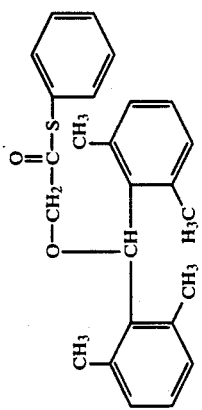 | L | C 76.89 76.83<br>H 6.71 6.75<br>S 8.21 8.31 | 98–100 |
| 221 | methyl (4-chlorophenyl)phenyl-methoxyacetate | 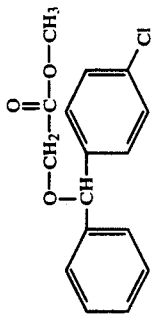 | E | C 66.10 66.10<br>H 5.20 5.13<br>Cl 12.19 | oil |
| 222 | (2,2-dimethyl-1,3-dioxolan-4-yl)methyl bis(2,6-dimethylphenyl)methoxyacetate | 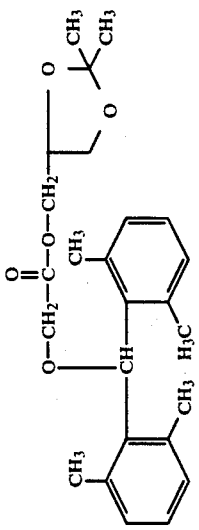 | L | C 72.79 72.64<br>H 7.82 7.89 | 51–55 |

-continued

| | | | | | |
|---|---|---|---|---|---|
| 223 | propyl (4-chlorophenyl)phenyl-methoxyacetate | 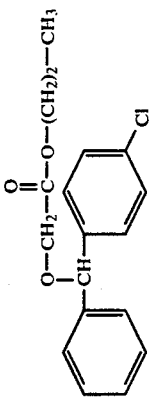 | L | C 67.82 67.87<br>H 6.01 6.05<br>Cl 11.12 | oil |
| 224 | 2,2,2-trichloroethyl (4-chlorophenyl)-phenylmethoxyacetate | 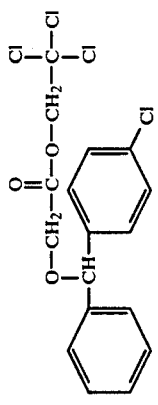 | L | C 50.03 50.15<br>H 3.46 3.41<br>Cl 34.75 | 76–79 |
| 225 | ethyl bis(2,4,6-trimethylphenyl)-methoxyacetate | 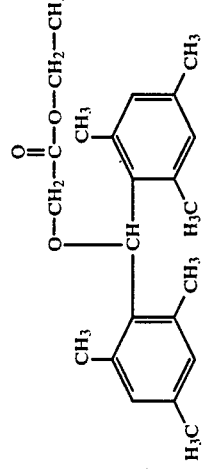 | E | C 77.93 77.90<br>H 8.53 8.59 | 70–71 |
| 226 | 3-pyridinylmethyl (4-chlorophenyl)-phenylmethoxyacetate | 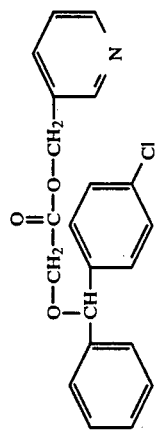 | L | C 68.57 68.24<br>H 4.93 4.99<br>Cl 9.64<br>N 3.81 3.80 | oil |
| 227 | benzyl (4-chlorophenyl)phenyl-methoxyacetate | 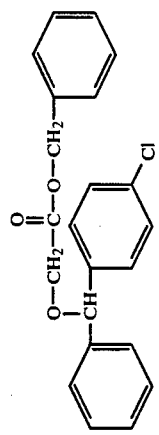 | L | C 72.03 72.11<br>H 5.22 5.24<br>Cl 9.66 | oil |
| 228 | 4-fluorobenzyl (4-chlorophenyl)-phenylmethoxyacetate | 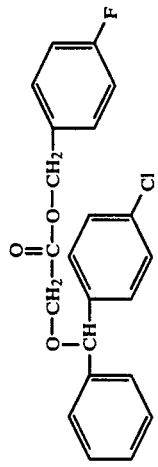 | L | C 68.66 68.62<br>H 4.71 4.71<br>Cl 9.21 | oil |

-continued

| | | | | |
|---|---|---|---|---|
| 229 | S-phenyl (4-chlorophenyl)-phenylmethoxyethanethioate |  | L | C 68.38 68.23<br>H 4.65 4.67<br>Cl 9.61<br>S 8.69 8.61 | 77-78 |
| 230 | 2,2,2-trifluoroethyl (4-chlorophenyl)-phenylmethoxyacetate |  | L | C 56.92 57.02<br>H 3.93 3.98<br>Cl 9.88<br>F 15.89 | oil |
| 231 | S-(1-methylethyl) (4-chlorophenyl)-phenylmethoxyethanethioate |  | L | C 64.56 64.66<br>H 5.72 5.84<br>Cl 10.59<br>S 9.58 9.85 | oil |
| 232 | S-ethyl (4-chlorophenyl)-phenylmethoxyethanethioate |  | L | C 63.64 63.60<br>H 5.34 5.37<br>Cl 11.05<br>S 10.00 10.41 | oil |
| 233 | ammonium phenyl[3-(trifluoromethyl)-phenyl]methoxyacetate |  | I | C 58.71 58.79<br>H 4.93 4.96<br>F 17.41<br>N 4.28 4.17 | 127-128 |
| 234 | bis(2,4,6-trimethylphenyl)methoxy-acetic acid | 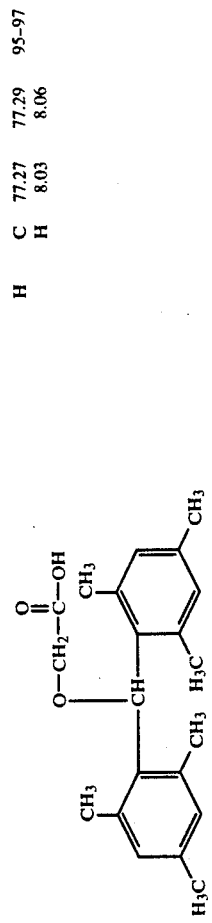 | H | C 77.27 77.29<br>H 8.03 8.06 | 95-97 |

| | | | | | |
|---|---|---|---|---|---|
| 235 | ethyl cyclopropylphenyl-methoxyacetate |  | F | C 71.77 71.70<br>H 7.74 7.77 | oil |
| 236 | 2-propylammonium phenyl[3-(trifluoromethyl)phenyl]methoxy-acetate monohydrate | | I | C 58.91 61.31<br>H 6.24 5.63<br>F 14.71<br>N 3.62 2.73 | oil |
| 237 | (2,2-dimethyl-1,3-dioxolan-4-yl)methyl(4-chlorophenyl)phenyl-methoxyacetate | | L | C 64.53 64.47<br>H 5.93 6.04<br>Cl 9.07 | oil |
| 238 | 1-methyl-2-propynyl bis(2,6-dimethyl-phenyl)methoxyacetate | | L | C 78.83 78.87<br>H 7.48 7.54 | oil |
| 239 | ethyl dicyclopropylmethoxyacetate | | F | C 66.64 66.42<br>H 9.15 9.10 | 87 @ 1.00t |

| | | | | | |
|---|---|---|---|---|---|
| 240 | butyl (4-chlorophenyl)phenylmethoxy-acetate | 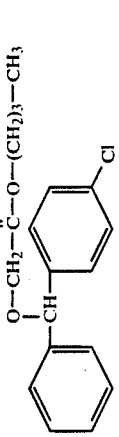 | L | C 68.57 H 6.36 Cl 10.65 | 68.47 6.38 oil |
| 241 | ethyl cyclopropyl(4-methoxyphenyl)-methoxyacetate | 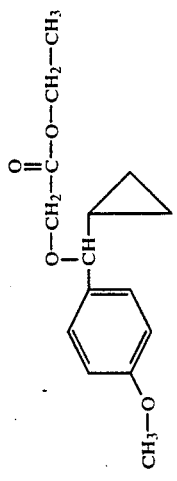 | F | C 68.16 H 7.63 | 68.08 7.62 oil |
| 242 | bis-(2,6-diethylphenyl)methoxy acetic acid | 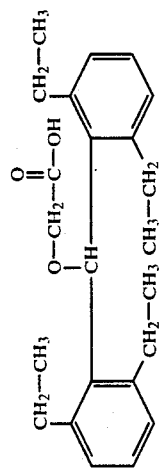 | H | C 77.93 H 8.53 | 78.04 8.59 118–120 |
| 243 | 1,1-dimethyl-2-propynyl diphenylmethoxyacetate | 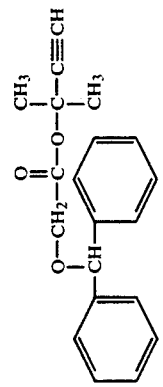 | L | C 77.90 H 6.54 | 77.83 6.55 55–57 |
| 244 | triphenylmethylammonium phenyl[3-(trifluoromethyl)phenyl]-methoxyacetate monohydrate | 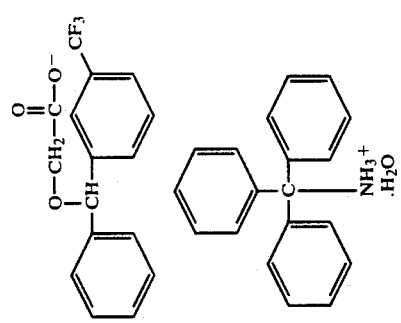 | I | C 71.54 H 5.49 F 9.70 N 2.38 | 70.06 5.09 2.79 117–121 |

| | | | | | |
|---|---|---|---|---|---|
| 245 | (2,2-dimethyl-1,3-dioxolan-4-yl)methyl phenyl[3-(trifluoromethyl)phenyl]-methoxyacetate | 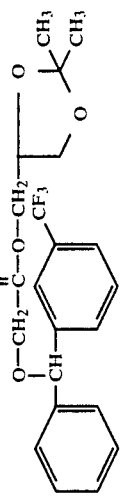 | L | C 62.26 62.17<br>H 5.46 5.69<br>F 13.43 | oil |
| 246 | 2-methoxyethyl phenyl[3-(trifluoromethyl)phenyl]methoxyacetate | 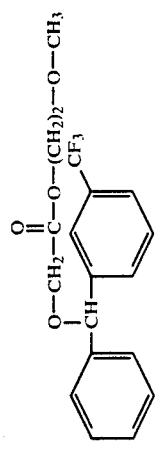 | L | C 61.95 62.06<br>H 5.20 5.19<br>F 15.47 | oil |
| 247 | 1-butylammonium phenyl[3-(trifluoromethyl)phenyl]methoxyacetate | 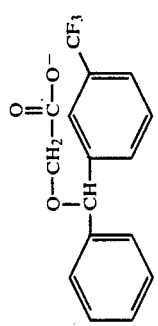 | I | C 62.65 57.77<br>H 6.31 5.68<br>F 14.87<br>N 3.65 2.70 | 320 |
| 248 | bis(3,5-dimethylphenyl)methoxy-acetic acid | 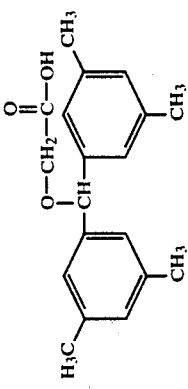 | H | C 76.48 76.48<br>H 7.43 7.43 | 112–115 |
| 249 | ethyl bis(3,5-dimethylphenyl)-methoxyacetate | 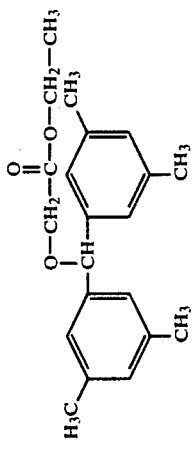 | E | C 77.27 77.59<br>H 8.03 8.21 | oil |

| | | | | | |
|---|---|---|---|---|---|
| 250 | (3,5-dichlorophenyl)phenylmethoxy-acetic acid | 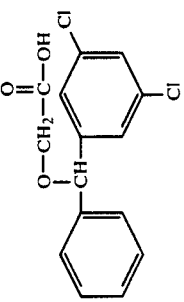 | H | C 57.90 H 3.89 Cl 22.79 | 57.80 3.91 22.72 | 108–110 |
| 251 | 2,3-dihydroxy-1-propylammonium phenyl[3-(trifluoromethyl)phenyl]-methoxyacetate | 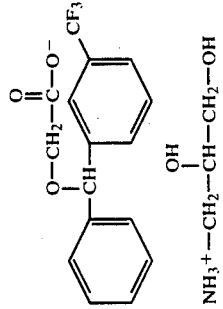 | I | C 56.86 H 5.52 F 14.20 N 3.49 | 55.44 5.69 — 3.37 | oil |
| 252 | 1-methylethyl (4-chlorophenyl)-phenylmethoxyacetate | 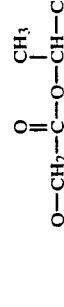 | L | C 67.82 H 6.01 Cl 11.12 | 67.74 6.02 11.09 | oil |
| 253 | 1-methylpropyl (4-chlorophenyl)-phenylmethoxyacetate | 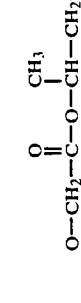 | L | C 68.57 H 6.36 Cl 10.65 | 68.46 6.40 10.58 | oil |
| 254 | propyl (3,5-dichlorophenyl)-phenylmethoxyacetate | 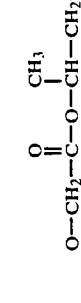 | L | C 61.20 H 5.14 Cl 20.07 | 61.35 5.14 | oil |

| | | | | |
|---|---|---|---|---|
| 255 | 2-(diphenylmethoxy)-N-phenyl-acetamide | 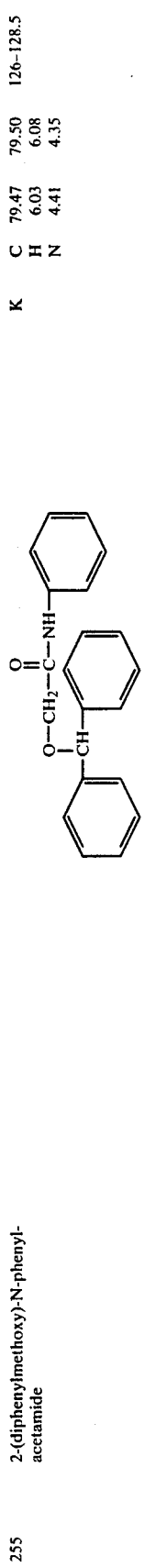 | K | C 79.47 79.50<br>H 6.03 6.08<br>N 4.41 4.35 | 126–128.5 |
| 256 | 1-cyano-1-methylethyl (3,5-dichloro-phenyl)phenylmethoxyacetate | 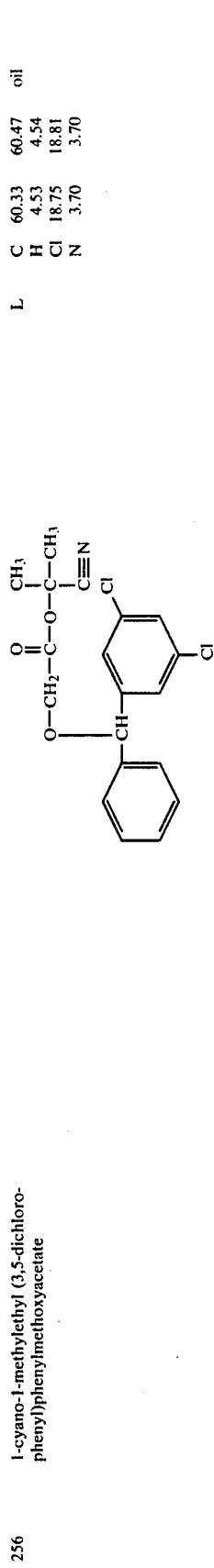 | L | C 60.33 60.47<br>H 4.53 4.54<br>Cl 18.75 18.81<br>N 3.70 3.70 | oil |
| 257 | 4-fluorobenzyl (3,5-dichlorophenyl)-phenylmethoxyacetate | 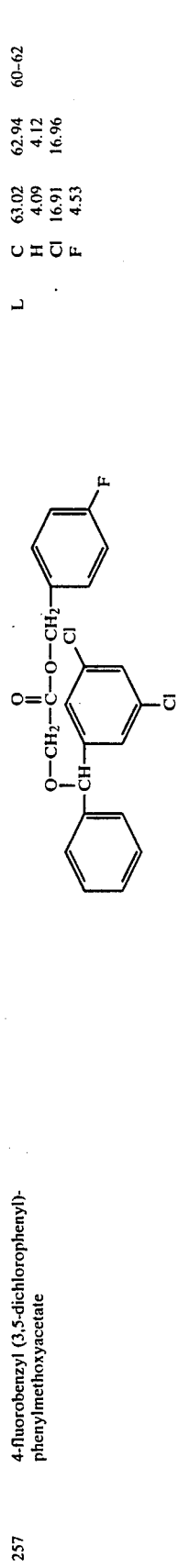 | L | C 63.02 62.94<br>H 4.09 4.12<br>Cl 16.91 16.96<br>F 4.53 | 60–62 |
| 258 | 2,2,2-trichloroethyl (3,5-dichloro-phenyl)phenylmethoxyacetate | 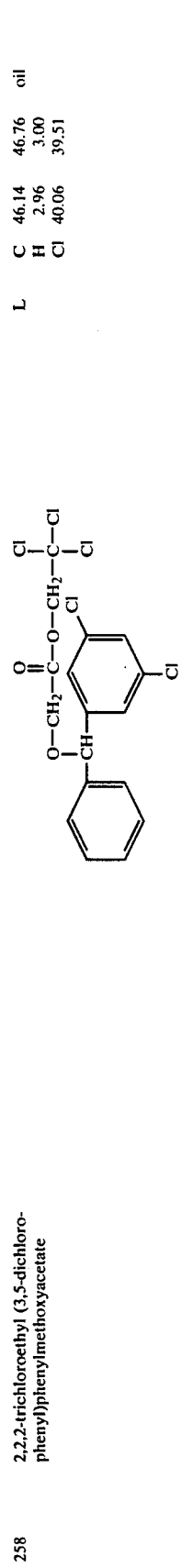 | L | C 46.14 46.76<br>H 2.96 3.00<br>Cl 40.06 39.51 | oil |
| 259 | ethyl (3,5-dichlorophenyl)-phenylmethoxyacetate | 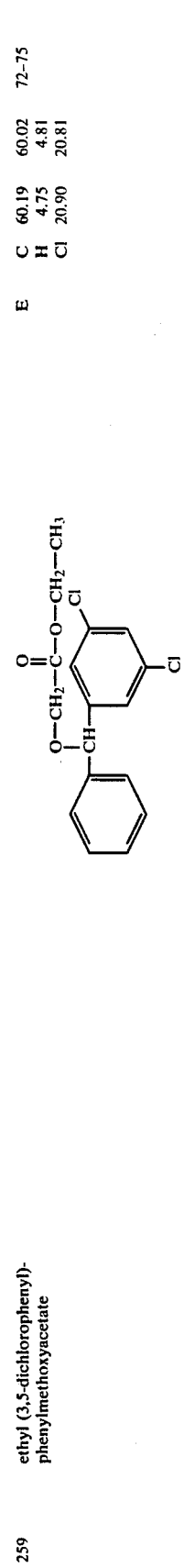 | E | C 60.19 60.02<br>H 4.75 4.81<br>Cl 20.90 20.81 | 72–75 |

| | | | | |
|---|---|---|---|---|
| 260 | [2-chloro-5-(trifluoromethyl)-phenyl]phenylmethoxy acetic acid |  | H | C 55.75 55.82 125-130<br>H 3.51 3.54<br>Cl 10.28 10.36<br>F 16.54 |
| 261 | phenyl bis(2,6-dimethylphenyl)-methoxyacetate | 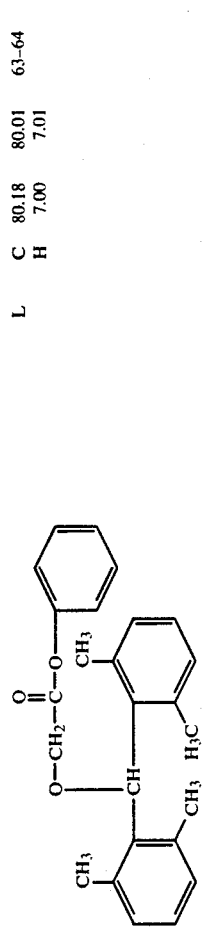 | L | C 80.18 80.01 63-64<br>H 7.00 7.01 |
| 262 | 4-chlorophenyl bis(2,6-dimethyl-phenyl)methoxyacetate | 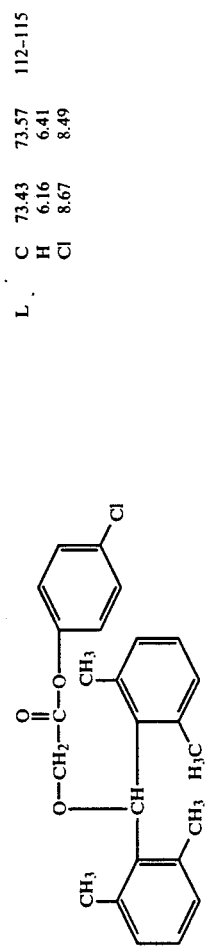 | L | C 73.43 73.57 112-115<br>H 6.16 6.41<br>Cl 8.67 8.49 |
| 263 | ethyl 1,1-diphenylethoxy-acetate |  | E | C 76.03 76.16 oil<br>H 7.09 7.12 |
| 264 | 1-ethyl-2-propynyl (4-chloro-phenyl)phenylmethoxyacetate |  | L | C 70.07 70.08 oil<br>H 5.59 5.59<br>Cl 10.34 10.14 |

| | | | | |
|---|---|---|---|---|
| 265 | phenyl (4-chlorophenyl)phenyl-methoxyacetate | 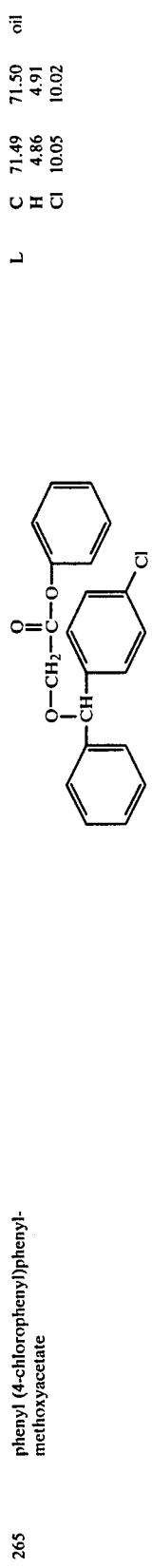 | L | C 71.49 71.50<br>H 4.86 4.91<br>Cl 10.05 10.02 | oil |
| 266 | 2-propynyl (4-chlorophenyl)-phenylmethoxyacetate | 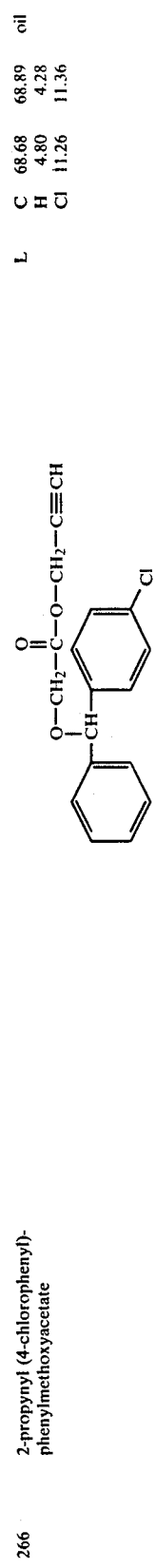 | L | C 68.68 68.89<br>H 4.80 4.28<br>Cl 11.26 11.36 | oil |
| 267 | methyl bis(2-chlorophenyl)-methoxyacetate | 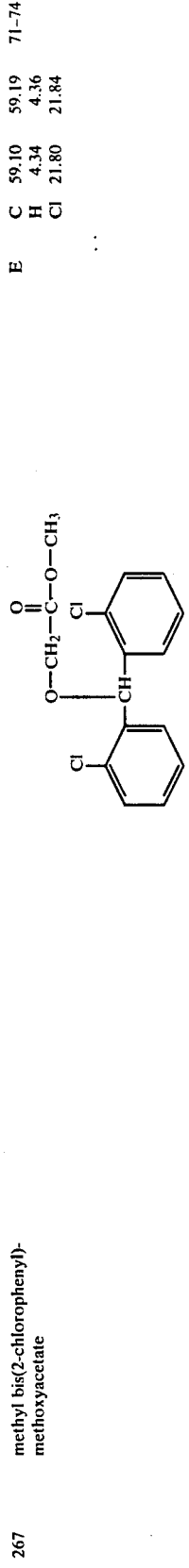 | E | C 59.10 59.19<br>H 4.34 4.36<br>Cl 21.80 21.84 | 71-74 |
| 268 | 4-chlorophenyl (4-chlorophenyl)-phenylmethoxyacetate | 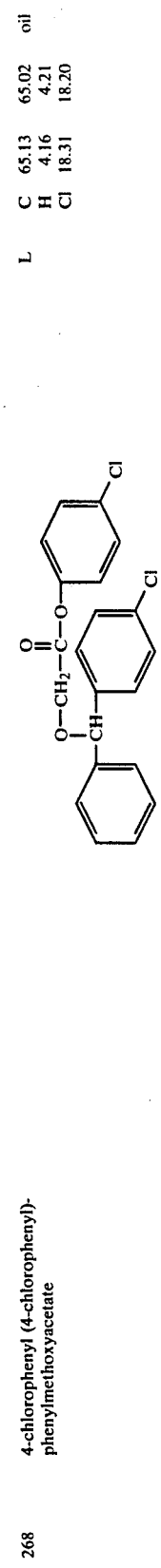 | L | C 65.13 65.02<br>H 4.16 4.21<br>Cl 18.31 18.20 | oil |
| 269 | 2-propynyl [2-chloro-5-(trifluoro-methyl)phenyl]phenylmethoxyacetate | 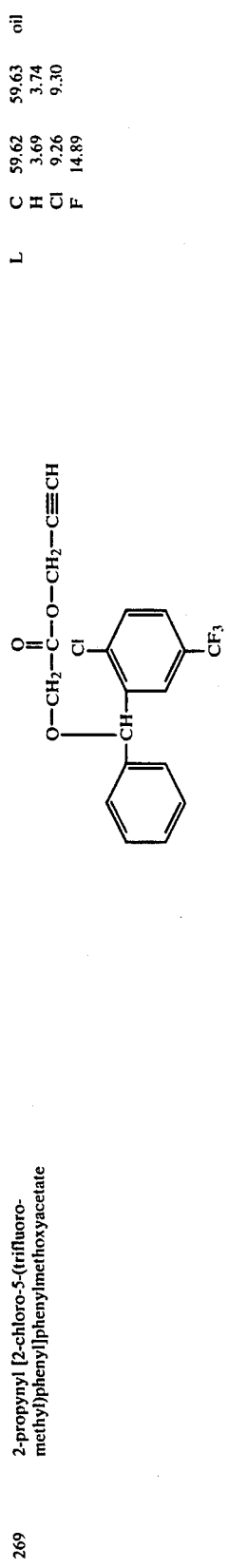 | L | C 59.62 59.63<br>H 3.69 3.74<br>Cl 9.26 9.30<br>F 14.89 | oil |

-continued

| | | | | | |
|---|---|---|---|---|---|
| 270 | 2-propenyl [2-chloro-5-(trifluoromethyl)phenyl]phenylmethoxyacetate | 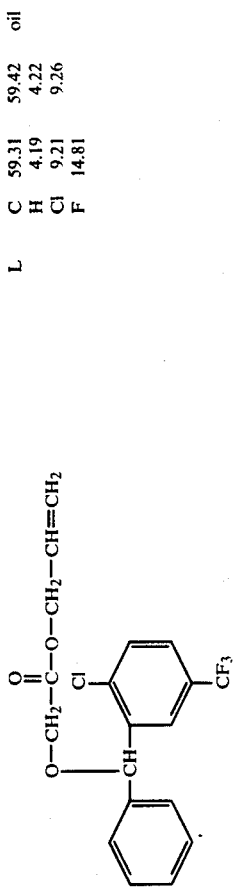 | L | C 59.31<br>H 4.19<br>Cl 9.21<br>F 14.81 | 59.42<br>4.22<br>9.26 | oil |
| 271 | 1-cyano-1-methylethyl [2-chloro-5-(trifluoromethyl)phenyl]phenylmethoxyacetate |  | L | C 58.33<br>H 4.16<br>Cl 8.61<br>F 13.84<br>N 3.40 | 58.53<br>4.19<br>8.76 | 95–96 |
| 272 | 1-ethyl-2-propynyl [2-chloro-5-(trifluoromethyl)phenyl]phenylmethoxyacetate | 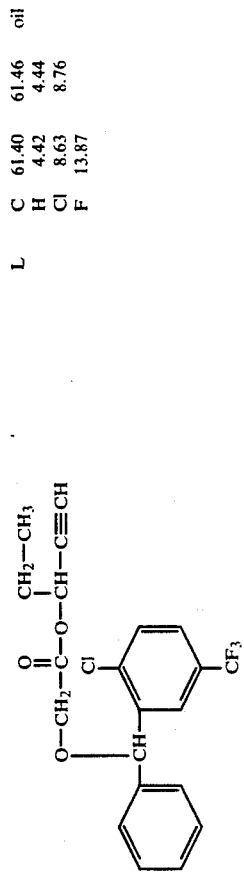 | L | C 61.40<br>H 4.42<br>Cl 8.63<br>F 13.87 | 61.46<br>4.44<br>8.76 | oil |
| 273 | methyl (2,6-dimethylphenyl)(2-methylphenyl)methoxyacetate |  | E | C 76.48<br>H 7.43 | 76.58<br>7.46 | oil |

| | | | | |
|---|---|---|---|---|
| 274 | methyl bis(2-methylphenyl)-methoxyacetate | 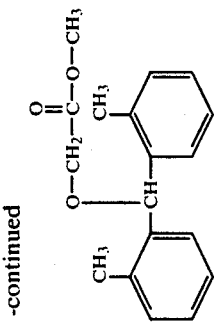 | E | C 76.03 75.89<br>H 7.09 7.10<br>110-115 |
| 275 | phenyl [2-chloro-5-(trifluoromethyl)phenyl]phenylmethoxyacetate | 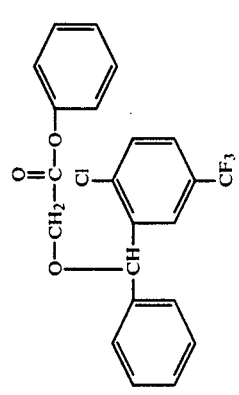 | L | C 62.79 62.90<br>H 3.83 3.84<br>Cl 8.42 8.49<br>F 13.54<br>oil |
| 276 | 4-chlorophenyl [2-chloro-5-(trifluoromethyl)phenyl]phenylmethoxyacetate | 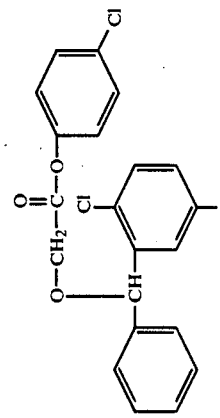 | L | C 58.04 58.11<br>H 3.32 3.33<br>Cl 15.57 15.58<br>F 12.52<br>oil |
| 277 | methyl (2,6-dimethylphenyl)-phenylmethoxyacetate | 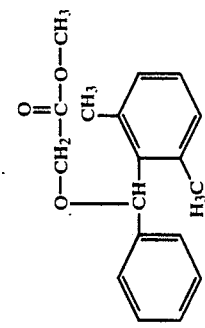 | E | C 76.03 76.12<br>H 7.09 7.10<br>64-66 |
| 278 | ethyl (4-chlorophenyl)-cyclopropylmethoxyacetate | 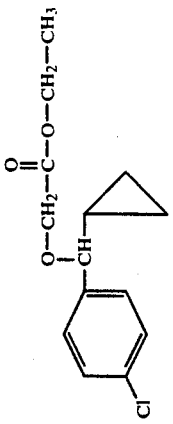 | F | C 62.57 62.61<br>H 6.38 6.41<br>Cl 13.19 13.26<br>oil |

-continued

| | | | | | | |
|---|---|---|---|---|---|---|
| 279 | ethyl cyclobutylphenylmethoxyacetate | | F | C 72.55 72.36 H 8.12 8.14 | | oil |
| 280 | {[bis(2,6-dimethylphenyl)methyl]thio}-acetic acid | | H | C 72.57 72.46 H 7.05 7.07 S 10.20 10.13 | | 146–147 |
| 281 | ethyl {[(4-chlorophenyl)phenylmethyl]-thio}acetate | | L | C 63.64 63.70 H 5.34 5.35 Cl 11.05 11.11 S 10.00 9.91 | | oil |
| 282 | ethyl {[bis(2,6-dimethylphenyl)methyl]-thio}acetate | | L | C 73.64 73.74 H 7.65 7.67 S 9.36 9.27 | | 68–69 |
| 283 | 2-(diphenylmethyl)thiopropane-nitrile | | DD | C 75.85 75.88 H 5.97 6.00 N 5.53 5.53 S 12.66 12.58 | | 160–163 @ 0.20t |
| 284 | (diphenylmethyl)thioacetonitrile | | DD | C 75.27 75.30 H 5.47 5.51 N 5.85 5.82 S 13.40 13.36 | | 77–78 |

BIOLOGICAL EVALUATION

Effective weed control coupled with low crop injury is a result of treatment of a plant locus with a combination of herbicide compound and antidote compound. By application to the "plant locus" is meant application to the plant growing medium, such as to soil, as well as to the seeds, emerging seedlings, roots, stems, leaves, or other plant parts.

The phrase "combination of herbicide compound and antidote compound" embraces various methods of treatment. For example, the soil of a plant locus may be treated with a "tank-mix" composition containing a mixture of the herbicide and the antidote which is "in combination". Or, the soil may be treated with the herbicide and antidote compounds separately so that the "combination" is made on, or in, the soil. After such treatments of the soil, with a mixture of herbicide and antidote, or by separate or sequential application of the herbicide and antidote to the soil, the herbicide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The granule may be applied to a furrow which is prepared for receipt of the crop seed and the herbicide may be applied to the plant locus either before or after in-furrow placement of the antidote-containing granule so that the herbicide and antidote form a "combination". Crop seed may be treated or coated with the antidote compound either while the crop seed is in-furrow just after seeding or, more commonly, the crop seed may be treated or coated with antidote prior to seeding into a furrow. The herbicide may be applied to the soil plant locus before or after seeding and a "combination" is made when both herbicide and antidote-coated seed are in the soil. Also contemplated as a "combination" is a commercially-convenient association or presentation of herbicide and antidote. For example, the herbicide and antidote components in concentrated form may be contained in separate containers, but such containers may be presented for sale or sold together as a "combination". Or, the herbicide and antidote components in concentrated form may be in a mixture in a single container as a "combination". Either such "combination" may be diluted or mixed with adjuvants suitable for soil applications. Another example of a commercially-presented combination is a container of antidote-coated crop seed sold, or presented for sale, along with a container of herbicide material. These containers may, or may not, be physically attached to each other, but nonetheless constitute a "combination of herbicide and antidote" when intended for use ultimately in the same plant locus.

The amount of antidote employed in the methods and compositions of the invention will vary depending upon the particular herbicide with which the antidote is employed, the rate of application of the herbicide, the particular crop to be protected, and the manner of application to the plant locus. In each instance the amount of antidote employed is a "safening-effective amount", that is, an amount which reduces, or protects against, crop injury that otherwise would result from the presence of the herbicide. The amount of antidote employed will be less than an amount that will substantially injure the crop plant.

The antidote can be applied to the crop plant locus in a mixture with the selected herbicide. For example, where the crop seed is first planted, a suitable mixture of antidote and herbicide, whether in a homogeneous liquid, emulsion, suspension or solid form, can be applied to the surface of, or incorporated in, the soil in which the seed has been planted. Or, the herbicide-antidote mixture may be applied to the soil, and then the seed thereafter "drilled" into or below the soil layer containing the herbicide-antidote mixture. The herbicide will reduce or eliminate the presence of undesirable weed plants. Where the herbicide would by itself injure the crop seedlings, the presence of the antidote will reduce or eliminate the injury to the crop seed caused by the herbicide. It is not essential that the application of herbicide and the antidote to the plant locus be made using the selected herbicide and antidote in the form of a mixture or composition. The herbicide and the antidote may be applied to the plant locus in a sequential manner. For example, the antidote may be first applied to the plant locus and thereafter the herbicide is applied. Or, the herbicide may be first applied to the plant locus and thereafter the antidote is applied.

The ratio of herbicide to antidote may vary depending upon the crop to be protected, weed to be inhibited, herbicide and antidote used, etc., but normally a herbicide-to-antidote ratio ranging from 1:25-to-50:1 (preferably 1:5-to-30:1) parts by weight may be employed. As indicated above, the antidote may be applied to the plant locus in a mixture, i.e., a mixture of a herbicidally-effective amount of herbicide and a safening-effective amount of an antidote, or applied sequentially, i.e., the plant locus may be treated with an effective amount of the herbicide followed by a treatment with the antidote or vice versa. In general, effective herbicidal amounts are in the range of about 0.1 to about 12 kilograms/hectare. The preferred range of rate of application is from about 0.4 to about 10 Kg/ha. Preferably, antidote application rates range from about 0.5 Kg/ha down to about 0.05 Kg/ha. It will be appreciated that at times, amounts either below or above these ranges will be necessary to obtain the best results. The selection of the herbicide to inhibit the emergence and growth of weeds depends upon the species of weeds to be controlled and the crop to be protected.

The application of the antidote can be made directly to the seed before planting. In this practice, a quantity of crop seed is first coated with the antidote. The coated seed is thereafter planted. The herbicide may be applied to the soil before or after the coated seed is planted.

Evaluations of safening activity of the antidote compounds of this invention were carried out using the specific procedures of Examples 286–290 in greenhouse testing. Measurements of biological response as reported in Tables II–VII were made in the following manner. A visual comparison was made between a crop plant treated with herbicide alone and crop plant having no herbicide or antidote treatment an ("untreated control"). A number was assigned to this visual comparison indicating the percent injury or inhibition to the herbicide-alone treated crop plant (column "WO" in Tables II–VII indicating herbicide "without" antidote). Also, a visual comparison was made between the crop plant treated with herbicide + antidote combination and the crop plant having no herbicide or antidote treatment (the untreated control). A number was assigned to this visual comparison indicating the percent injury or inhibition to the herbicide + antidote treated crop plant (column "W" in Tables II–VII indicating herbicide "with" antidote). Where treatments involved weed plant species, observations of response to herbicide or herbicide+antidote were similarly recorded. The degree of reduction of herbicide injury provided by an antidote compound is indicated by the magnitude that the plant inhibition number of column "WO" exceeds the corresponding number of column "W". Also reported in Tables II–VII are data showing "safening effect" for the herbicide+antidote combinations calculated from the plant inhibition numbers, the formula for calculation of which is shown below.

Summarized below is key information for interpreting data reported in Tables II–VII:

| Herbicide No. | Name |
|---|---|
| 1 | ethyl dipropylthiocarbamate (EPTC); |
| 2 | 2,3,3-trichloroallyl-diisopropylthiolcarbamate (triallate); |
| 3 | 2-chloro-4-ethylamino-6-isopropylamino-sym-triazine (atrazine); |
| 4 | 2-chloro-2'-(1,1-dimethylethyl)-6'-methyl-N-(methoxymethyl)acetanilide; |
| 5 | 1-(3,4-dichlorophenyl)-3,3-dimethylurea; |
| 6 | 2-chloro-2',6'-diethyl-N-(methoxymethyl)-acetanilide (alachlor); |
| 7 | dimethylamine salt of 2-methoxy-3,6-dichlorobenzoic acid; |
| 8 | α,α,α-trifluoro-2,6-dinitro-N,N-dipropyl-p-toluidine (trifluralin); |
| 9 | 2-chloro-N-(isobutoxymethyl)-2',6'-acetoxylidide; |
| 10 | 2-chloro-2',6'-diethyl-N-(butoxymethyl)-acetanilide (butachlor); |
| 11 | 2-chloro-N-(ethoxymethyl)-6'-ethyl-o-acetotoluidide (acetochlor); |
| 12 | 2-chloro-N-(2,6-dimethyl-1-cyclohexen-1-yl)-N-(2-ethoxyethyl)acetamide; |
| 13 | 2-chloro-4-(isopropylamino)-6-[N-ethyl-N-(2-methylpropenyl)amino]sym-triazine; |
| 14 | 2-chloro-N-(2-methoxy-1-methylethyl)-6'-ethyl-o-acetotoluidide (metolachlor); |
| 15 | 2-chloro-2'-methyl-6'-methoxy-N-(isopropoxy methyl)acetanilide; |
| 16 | 2-chloro-N-(2,6-dimethyl-1-cyclohexen-1-yl)-N-(1H-pyrazol-1-ylmethyl)acetamide; |
| 17 | 2-chloro-6'-trifluoromethyl-N-(isopropoxy methyl)acetanilide; |
| 18 | 2-chloro-2'-methyl-6'-trifluoromethyl-N-(ethoxymethyl)acetanilide; |
| 19 | 2-chloro-2'-trifluoromethyl-6-methyl-N-(propoxymethyl)acetanilide; |
| 20 | 2-chloro-2'-methyl-6'-trifluoromethyl-N-(isopropoxymethyl)acetanilide; |
| 21 | 2-chloro-2'-(3-methylbutoxy)-6'-methyl-N-(methyl)acetanilide; |
| 22 | 2-chloro-2'-isobutoxy-6'-methyl-N-(propoxymethyl)acetanilide; |
| 23 | 2-chloro-2'-methyl-6'-propoxy-N-(methyl)acetanilide; |
| 24 | 2-chloro-2'-butoxy-6'-methyl-N-(methyl)acetanilide; |
| 25 | 2-chloro-2'-propoxy-6'-methyl-N-(ethoxymethyl)acetanilide; |
| 26 | 2-chloro-2'-butoxy-6'-ethyl-N-(methyl)acetanilide; |
| 27 | α-chloro-N-(ethoxymethyl)-N-[2-methyl-1-(1-methylethyl)-1-propenyl]acetamide; |

-continued

| Herbicide No. | Name |
|---|---|
| 28 | 2-chloro-2',6'-dimethyl-N-(1-pyrazolyl-methyl)acetanilide; |
| 29 | 2-chloro-2'-methoxy-3',6'-dimethyl-N-(1-methylethoxymethyl)acetanilide; |
| 30 | 2-chloro-2'-ethyl-6'-(2-methylpropoxy)-N-(ethoxymethyl)acetanilide; |
| 31 | 2-chloro-2'-methyl-6'-(1-methylbutoxy)-N-(methyl)acetanilide; |
| 32 | 2-chloro-2'-ethyl-6'-(1-methylpropyl)-N-(methyl)acetanilide; |
| 33 | 2-chloro-N-{[4-methoxy-6-methyl-1,3,5-triazin-2-yl)amino]carbonyl}benzenesulfonamide; |
| 34 | 2-chloro-N-[1-(2-chloro-6-fluorophenyl)-2-methyl-1-propen-1-yl]-N-(2-propenyl)-acetamide; |
| 35 | 2-chloro-1-(3'-ethoxy-4'-nitrophenoxy)-4-trifluoromethylbenzene (oxyfluorofen); |
| 36 | S-4-chlorobenzyl diethylthiocarbamate (benthiocarb); |
| 37 | 2-chloro-2',6'-diethyl-N-(2-propoxyethyl)-acetanilide (pretilachlor); |
| 38 | methyl 2-[{{[(4,6-dimethoxy-2-pyrimidinyl)-amino]carbonyl}amino]sulfonyl}methyl]benzoate (DPX-5384). |

Antidote No. = Compound in corresponding Example No.
Rate = Kilograms/hectare (Kg/ha).
W = % Plant Inhibition caused by combination of herbicide and antidote.
WO = % Plant Inhibition caused by herbicide alone.
Data reported in parentheses = % Safening Effect $$( \underline{\quad} ) = \frac{WO - W}{WO} \times 100$$

EXAMPLE 285

The following procedure shows interaction between herbicide and antidote when both are incorporated in a soil cover layer before emergence of crop and weed species Containers were filled and compacted with a fumigated silt loam top soil to a depth of about 1.3 cm from the top of the container. A first container was designated as an untreated control, a second container was designated as a herbicide control, and a third container was designated as a herbicide+antidote test container. Each of the containers was seeded with a crop species. A measured amount of herbicide dispersed or dissolved in acetone was applied to a measured quantity of soil. To this same quantity of soil treated with herbicide, there was added a measured amount of antidote dispersed or dissolved in acetone. The quantity of soil treated with the herbicide and antidote was thoroughly mixed to incorporate the herbicide and antidote in the soil uniformly. The seed bed in the third container of soil was covered with the soil treated with the herbicide and antidote and the container was leveled. For each test series, the seed beds of the first and second containers were likewise covered by soil layers. The cover layer of the first container was not treated with herbicide or antidote. The cover layer of the second container had a measured quantity of herbicide alone incorporated therein. The containers were then placed on a bench in a greenhouse and sub-irrigated as required for the duration of the test. Plant response was observed about three weeks after initial treatment. Results are reported in Table II.

TABLE II

% PLANT INHIBITION AND % SAFENING EFFECT ( )

| HERBICIDE NO. | RATE | ANTIDOTE NO. | RATE | RICE W | RICE WO | SORGHUM GRAIN W | SORGHUM GRAIN WO | WHEAT W | WHEAT WO | CORN W | CORN WO | COTTON W | COTTON WO | SOYBEAN W | SOYBEAN WO | HEMP SESBANIA W | HEMP SESBANIA WO | VELVET LEAF W | VELVET LEAF WO |
|---|---|---|---|---|---|---|---|---|---|---|---|---|---|---|---|---|---|---|---|
| 27 | 0.14 | 1 | 8.96 | 0 (100) | 25 | 10 (83) | 60 | 20 (50) | 40 | 0 (100) | 25 | | | | | | | | |
| 27 | 0.56 | 1 | 8.96 | 75 | 90 | 70 (26) | 95 | 45 (47) | 85 | 15 (70) | 50 | | | | | | | | |
| 27 | 2.24 | 1 | 8.96 | 100 (16) | 98 | 99 (0) | 99 | 90 (9) | 99 | 35 (56) | 80 | | | | | | | | |
| 3 | 0.56 | 1 | 8.96 | 30 (0) | 40 | | | 40 (20) | 50 | | | 50 (0) | 10 | 50 (0) | 30 | | | | |
| 3 | 2.24 | 1 | 8.96 | 70 (25) | 80 | | | 98 (0) | 95 | | | 20 (77) | 20 | 90 (0) | 90 | | | | |
| 3 | 8.96 | 1 | 8.96 | 98 (12) | 98 | | | 100 (0) | 99 | | | 85 (13) | 98 | 99 (0) | 99 | | | | |
| 4 | 0.14 | 1 | 8.96 | 0 (100) | 30 | 0 (100) | 25 | 10 (60) | 25 | 0 (100) | 15 | | | | | | | | |
| 4 | 0.56 | 1 | 8.96 | 75 (0) | 70 | 65 (23) | 85 | 45 (30) | 65 | 30 (45) | 55 | | | | | | | | |
| 4 | 2.24 | 1 | 8.96 | 80 (19) | 99 | 80 (18) | 98 | 75 (23) | 98 | 30 (64) | 85 | | | | | | | | |
| 12 | 0.14 | 1 | 8.96 | 0 (100) | 20 | 15 (70) | 50 | 10 (60) | 25 | 10 (50) | 20 | | | | | | | | |
| 12 | 0.56 | 1 | 8.96 | 70 (0) | 50 | 60 (29) | 85 | 60 (14) | 70 | 25 (64) | 70 | | | | | | | | |
| 12 | 2.24 | 1 | 8.96 | 95 (0) | 90 | 98 (2) | 100 | 85 (0) | 80 | 75 (6) | 80 | | | | | | | | |
| 13 | 0.56 | 1 | 8.96 | 10 (66) | 30 | 25 (66) | 75 | 30 (0) | 20 | 0 (100) | 70 | 10 | 0 | | | | | | |
| 13 | 2.24 | 1 | 8.96 | 15 (21) | 40 | 98 (1) | 99 | 40 (0) | 45 | 50 (41) | 85 | 10 (0) | 20 | | | | | | |
| 13 | 8.96 | 1 | 8.96 | 65 (62) | 55 | 98 (2) | 100 | 80 (11) | 98 | 75 (23) | 98 | 15 (50) | 45 | | | | | | |
| 16 | 0.14 | 1 | 8.96 | 0 (0) | 60 | 25 (66) | 75 | 0 (18) | 20 | 0 (100) | 70 | | | | | 20 (50) | 40 | | |
| 16 | 0.56 | 1 | 8.96 | 75 (100) | 95 | 98 (1) | 99 | 70 (29) | 99 | 50 (41) | 85 | | | | | 65 (13) | 75 | | |
| 16 | 2.24 | 1 | 8.96 | 100 (21) | 100 | 98 (2) | 100 | 80 (20) | 100 | 75 (23) | 98 | | | | | 100 (0) | 98 | | |
| 17 | 0.28 | 1 | 8.96 | 50 (37) | 80 | 0 (100) | 65 | 0 (100) | 15 | 0 (0) | 0 | | | | | | | | |
| 17 | 1.12 | 1 | 8.96 | 65 (34) | 99 | 15 (84) | 98 | 35 (36) | 55 | 10 (0) | 0 | | | | | | | | |
| 17 | 4.48 | 1 | 8.96 | 98 (2) | 100 | 60 (40) | 100 | 98 (18) | 98 | 10 (33) | 15 | | | | | | | | |
| 18 | 0.28 | 1 | 8.96 | 65 (31) | 95 | 30 (68) | 95 | 55 (21) | 70 | 0 (0) | 0 | | | | | | | | |
| 18 | 1.12 | 1 | 8.96 | 100 (0) | 100 | 55 (43) | 98 | 70 (28) | 98 | 0 (100) | 10 | | | | | | | | |
| 18 | 4.48 | 1 | 8.96 | 100 (0) | 100 | 90 (9) | 99 | 85 (14) | 99 | 0 (100) | 30 | | | | | | | | |

TABLE II-continued

| HERBICIDE NO. | RATE | ANTIDOTE NO. | RATE | % PLANT INHIBITION AND % SAFENING EFFECT () | | | | | | | | | | | | | | |
|---|---|---|---|---|---|---|---|---|---|---|---|---|---|---|---|---|---|---|
| | | | | RICE | | SORGHUM GRAIN | | WHEAT | | CORN | | COTTON | | SOYBEAN | | HEMP SESBANIA | | VELVET LEAF | |
| | | | | W | WO | W | WO | W | WO | W | WO | W | WO | W | WO | W | WO | W | WO |
| 19 | 0.28 | 1 | 8.96 | 50 (41) | 85 | 20 (77) | 90 | 30 (25) | 40 | 20 (0) | 20 | | | | | | | | |
| 19 | 1.12 | 1 | 8.96 | 85 (10) | 95 | 75 (24) | 99 | 75 (0) | 70 | 25 (37) | 40 | | | | | | | | |
| 19 | 4.48 | 1 | 8.96 | 100 (0) | 100 | 97 (2) | 99 | 85 (10) | 95 | 25 (58) | 60 | | | | | | | | |
| 20 | 0.28 | 1 | 8.96 | 80 (11) | 90 | 95 (5) | 100 | 60 (29) | 85 | 40 (50) | 80 | | | | | | | | |
| 20 | 1.12 | 1 | 8.96 | 96 (2) | 98 | 85 (15) | 100 | 75 (16) | 90 | 75 (21) | 95 | | | | | | | | |
| 20 | 4.48 | 1 | 8.96 | 100 (0) | 100 | 100 (0) | 100 | 85 (14) | 99 | 95 (4) | 99 | | | | | | | | |
| 21 | 0.28 | 1 | 8.96 | 70 (12) | 80 | 60 (33) | 90 | 50 (41) | 85 | 0 (100) | 40 | | | | | | | | |
| 21 | 1.12 | 1 | 8.96 | 80 (5) | 85 | 90 (5) | 95 | 100 (0) | 90 | 35 (58) | 85 | | | | | | | | |
| 21 | 4.48 | 1 | 8.96 | 98 (2) | 100 | 100 (0) | 100 | 90 (2) | 92 | 85 (13) | 98 | | | | | | | | |
| 22 | 0.28 | 1 | 8.96 | 55 (21) | 70 | 15 (83) | 90 | 40 (42) | 70 | 0 (100) | 45 | | | | | | | | |
| 22 | 1.12 | 1 | 8.96 | 80 (11) | 90 | 60 (36) | 95 | 80 (11) | 90 | 25 (66) | 75 | | | | | | | | |
| 22 | 4.48 | 1 | 8.96 | 100 (0) | 100 | 75 (25) | 100 | 98 (0) | 98 | 75 (23) | 98 | | | | | | | | |
| 23 | 0.28 | 1 | 8.96 | 45 (25) | 60 | 70 (22) | 90 | 50 (0) | 45 | 0 (100) | 20 | | | | | | | | |
| 23 | 1.12 | 1 | 8.96 | 80 (0) | 80 | 95 (0) | 95 | 80 (0) | 70 | 20 (73) | 75 | | | | | | | | |
| 23 | 4.48 | 1 | 8.96 | 95 (5) | 100 | 100 (0) | 100 | 100 (0) | 98 | 75 (21) | 95 | | | | | | | | |
| 24 | 0.14 | 1 | 8.96 | 60 (14) | 70 | 95 (4) | 99 | 10 (84) | 65 | 20 (20) | 25 | | | | | | | | |
| 24 | 0.14 | 1 | 8.96 | 0 (100) | 45 | 95 (0) | 95 | 40 (38) | 65 | 10 (80) | 50 | | | | | | | | |
| 24 | 0.56 | 1 | 8.96 | 30 (60) | 75 | 100 (0) | 98 | 80 (11) | 90 | 50 (44) | 90 | | | | | | | | |
| 24 | 0.56 | 1 | 8.96 | 70 (22) | 90 | 100 (0) | 100 | 75 (11) | 85 | 40 (55) | 90 | | | | | | | | |
| 24 | 2.24 | 1 | 8.96 | 95 (3) | 98 | 100 (0) | 100 | 95 (0) | 95 | 90 (9) | 99 | | | | | | | | |
| 24 | 2.24 | 1 | 8.96 | 70 (17) | 85 | 100 (0) | 98 | 90 (8) | 98 | 90 (8) | 98 | | | | | | | | |
| 25 | 0.28 | 1 | 8.96 | 80 (0) | 80 | 15 (84) | 98 | 30 (33) | 45 | 20 (71) | 70 | | | | | | | | |
| 25 | 1.12 | 1 | 8.96 | 85 (13) | 98 | 40 (59) | 98 | 60 (14) | 70 | 45 (47) | 85 | | | | | | | | |
| 25 | 4.48 | 1 | 8.96 | 100 (0) | 100 | 98 (2) | 100 | 85 (15) | 100 | 75 (23) | 98 | | | | | | | | |

TABLE II-continued

| | | | | % PLANT INHIBITION AND % SAFENING EFFECT () | | | | | | | | | | | | | |
|---|---|---|---|---|---|---|---|---|---|---|---|---|---|---|---|---|---|
| HERBICIDE | | ANTIDOTE | | RICE | | SORGHUM GRAIN | | WHEAT | | CORN | | COTTON | | SOYBEAN | | HEMP SESBANIA | VELVET LEAF |
| NO. | RATE | NO. | RATE | W | WO | W | WO | W | WO | W | WO | W | WO | W | WO | W WO | W WO |
| 26 | 0.28 | 1 | 8.96 | 70 (22) | 90 | 70 (28) | 98 | 60 (25) | 80 | 0 (100) | 20 | | | | | | |
| 26 | 1.12 | 1 | 8.96 | 75 (21) | 95 | 75 (25) | 100 | 65 (31) | 95 | 0 (100) | 80 | | | | | | |
| 26 | 4.48 | 1 | 8.96 | 85 (14) | 99 | 90 (10) | 100 | 100 (0) | 100 | 65 (27) | 90 | | | | | | |
| 29 | 0.28 | 1 | 8.96 | 65 (0) | 55 | 0 (100) | 20 | 35 (12) | 40 | 0 (0) | 0 | | | | | | |
| 29 | 1.12 | 1 | 8.96 | 70 (17) | 85 | 20 (66) | 60 | 35 (41) | 60 | 0 (100) | 15 | | | | | | |
| 29 | 4.48 | 1 | 8.96 | 85 (10) | 95 | 25 (70) | 85 | 60 (20) | 75 | 10 (66) | 30 | | | | | | |
| 30 | 0.28 | 1 | 8.96 | 30 (62) | 80 | 10 (88) | 90 | 35 (61) | 90 | 0 (100) | 60 | | | | | | |
| 30 | 1.12 | 1 | 8.96 | 90 (7) | 97 | 35 (63) | 97 | 80 (17) | 97 | 40 (57) | 95 | | | | | | |
| 30 | 4.48 | 1 | 8.96 | 100 (0) | 100 | 90 (9) | 99 | 100 (0) | 100 | 80 (19) | 99 | | | | | | |
| 31 | 0.14 | 1 | 8.96 | 20 (0) | 10 | 40 (55) | 90 | 10 (83) | 60 | 0 (100) | 25 | | | | | | |
| 31 | 0.56 | 1 | 8.96 | 90 (0) | 70 | 100 (0) | 100 | 75 (11) | 85 | 50 (16) | 60 | | | | | | |
| 31 | 2.24 | 1 | 8.96 | 98 (0) | 97 | 100 (0) | 100 | 90 (0) | 90 | 98 (0) | 95 | | | | | | |
| 32 | 0.14 | 1 | 8.96 | 0 (0) | 0 | 20 (0) | 70 | 0 (100) | 30 | 0 (100) | 20 | | | | | | |
| 32 | 0.56 | 1 | 8.96 | 30 (40) | 50 | 98 (71) | 100 | 50 (0) | 30 | 0 (100) | 40 | | | | | | |
| 32 | 2.24 | 1 | 8.96 | 90 (0) | 90 | 100 (2) | 100 | 50 (0) | 70 | 90 (0) | 50 | | | | | | |
| 2 | 0.56 | 1 | 8.96 | | | | 75 | 75 (28) | 95 | | | | | | | | |
| 2 | 0.56 | 1 | 8.96 | | | | 90 | 90 (21) | 98 | | | | | | | | |
| 2 | 0.56 | 2 | 8.96 | | | | 98 | 98 (8) | 95 | | | | | | | | |
| 2 | 0.56 | 3 | 8.96 | | | | 95 | 95 (0) | 95 | | | | | | | | |
| 2 | 0.56 | 4 | 8.96 | | | | 80 | 80 (20) | 100 | | | | | | | | |
| 2 | 0.56 | 5 | 8.96 | | | | 75 | 75 (25) | 95 | | | | | | | | |
| 2 | 0.56 | 6 | 8.96 | | | | 95 | 95 (0) | 100 | | | | | | | | |
| 2 | 0.56 | 7 | 8.96 | | | | 90 | 90 (10) | 100 | | | | | | | | |
| 2 | 0.56 | 8 | 8.96 | | | | | (10) | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 2 | 0.56 | 9 | 8.96 | | | | | 95 (5) | 100 | | | | | | | | | | |
| 2 | 0.56 | 10 | 8.96 | | | | | 80 (15) | 95 | | | | | | | | | | |
| 2 | 0.56 | 11 | 8.96 | | | | | 45 (54) | 98 | | | | | | | | | | |
| 2 | 0.56 | 12 | 8.96 | | | | | 80 (20) | 100 | | | | | | | | | | |
| 2 | 0.56 | 13 | 8.96 | | | | | 100 (0) | 95 | | | | | | | | | | |
| 2 | 0.56 | 14 | 8.96 | | | | | 95 (0) | 95 | | | | | | | | | | |
| 2 | 0.56 | 15 | 8.96 | | | | | 90 (10) | 100 | | | | | | | | | | |
| 2 | 0.56 | 16 | 8.96 | | | | | 100 (0) | 100 | | | | | | | | | | |
| 2 | 0.56 | 17 | 8.96 | | | | | 80 (15) | 95 | | | | | | | | | | |
| 2 | 0.56 | 18 | 8.96 | | | | | 80 (15) | 95 | | | | | | | | | | |
| 2 | 0.56 | 19 | 8.96 | | | | | 80 (11) | 90 | | | | | | | | | | |
| 2 | 0.56 | 20 | 8.96 | | | | | 65 (27) | 90 | | | | | | | | | | |
| 2 | 0.56 | 21 | 8.96 | | | | | 100 (0) | 100 | | | | | | | | | | |
| 2 | 0.56 | 22 | 8.96 | | | | | 100 (0) | 90 | | | | | | | | | | |
| 2 | 0.56 | 23 | 8.96 | | | | | 60 (33) | 90 | | | | | | | | | | |
| 3 | 6.72 | 1 | 8.96 | 45 | 45 | | | | | | | | | 85 | 80 | | | | |
| 3 | 4.48 | 3 | 8.96 | 85 | 80 | | | | | | | | | 55 (0) | 90 | | | | |
| 3 | 4.48 | 4 | 8.96 | 90 | 80 | | | | | | | | | 75 (38) | 75 | | | | |
| 3 | 4.48 | 5 | 8.96 | 80 (0) | 80 | | | | | | | | | 85 (0) | 75 | | | | |
| 3 | 4.48 | 6 | 8.96 | 100 (0) | 85 | | | | | | | | | 100 (0) | 90 | | | | |
| 3 | 4.48 | 7 | 8.96 | 100 (0) | 90 | | | | | | | | | 95 (0) | 85 | | | | |
| 3 | 4.48 | 8 | 8.96 | 100 (0) | 90 | | | | | | | | | 90 (0) | 85 | | | | |
| 3 | 4.48 | 9 | 8.96 | 90 (0) | 90 | | | | | | | | | 80 (5) | 85 | | | | |
| 3 | 4.48 | 10 | 8.96 | 95 (0) | 80 | | | | | | | | | 95 (0) | 85 | | | | |

TABLE II-continued

% PLANT INHIBITION AND % SAFENING EFFECT ()

| HERBICIDE NO. | RATE | ANTIDOTE NO. | RATE | RICE W | RICE WO | SORGHUM GRAIN W | SORGHUM GRAIN WO | WHEAT W | WHEAT WO | CORN W | CORN WO | COTTON W | COTTON WO | SOYBEAN W | SOYBEAN WO | HEMP SESBANIA W | HEMP SESBANIA WO | VELVET LEAF W | VELVET LEAF WO |
|---|---|---|---|---|---|---|---|---|---|---|---|---|---|---|---|---|---|---|---|
| 3 | 4.48 | 11 | 8.96 | 40 (50) | 80 | | | | | | | | | 60 (29) | 85 | | | | |
| 3 | 4.48 | 12 | 8.96 | 100 (0) | 85 | | | | | | | | | 98 (0) | 75 | | | | |
| 3 | 4.48 | 13 | 8.96 | 35 (56) | 80 | | | | | | | | | 40 (50) | 80 | | | | |
| 3 | 4.48 | 14 | 8.96 | 55 (31) | 80 | | | | | | | | | 90 (0) | 80 | | | | |
| 3 | 4.48 | 15 | 8.96 | 95 (0) | 90 | | | | | | | | | 40 (33) | 60 | | | | |
| 3 | 4.48 | 16 | 8.96 | 95 (0) | 95 | | | | | | | | | 95 (0) | 85 | | | | |
| 3 | 4.48 | 17 | 8.96 | 85 (0) | 80 | | | | | | | | | 80 (5) | 95 | | | | |
| 3 | 4.48 | 18 | 8.96 | 90 (0) | 90 | | | | | | | | | 90 (5) | 95 | | | | |
| 3 | 4.48 | 19 | 8.96 | 85 (0) | 95 | | | | | | | | | 80 (11) | 90 | | | | |
| 3 | 4.48 | 20 | 8.96 | 100 (10) | 95 | | | | | | | | | 100 (0) | 90 | | | | |
| 3 | 4.48 | 21 | 8.96 | 45 (0) | 90 | | | | | | | | | 90 (0) | 90 | | | | |
| 3 | 4.48 | 22 | 8.96 | 100 (50) | 100 | | | | | | | | | 90 (10) | 100 | | | | |
| 3 | 4.48 | 23 | 8.96 | 100 (0) | 100 | | | | | | | | | 100 (0) | 100 | | | | |
| 6 | 2.24 | 1 | 8.96 | | | 55 (38) | 90 | 75 (23) | 98 | | | | | | | | | | |
| 6 | 2.24 | 1 | 8.96 | 85 (15) | 100 | 70 (28) | 98 | 55 (31) | 80 | | | | | | | | | | |
| 6 | 2.24 | 2 | 8.96 | 98 (1) | 99 | 98 (0) | 98 | 70 (17) | 85 | | | | | | | | | | |
| 6 | 2.24 | 3 | 8.96 | | | 10 (87) | 80 | 90 (0) | 90 | | | | | | | | | | |
| 6 | 2.24 | 4 | 8.96 | | | 40 (38) | 65 | 25 (66) | 75 | | | | | | | | | | |
| 6 | 2.24 | 5 | 8.96 | | | 45 (30) | 65 | 65 (13) | 75 | | | | | | | | | | |
| 6 | 2.24 | 6 | 8.96 | | | 25 (73) | 95 | 30 (62) | 80 | | | | | | | | | | |
| 6 | 2.24 | 7 | 8.96 | | | 40 (60) | 100 | 35 (63) | 95 | | | | | | | | | | |
| 6 | 2.24 | 8 | 8.96 | | | 30 (70) | 100 | 70 (26) | 95 | | | | | | | | | | |
| 6 | 2.24 | 9 | 8.96 | | | 15 (85) | 100 | 85 (10) | 95 | | | | | | | | | | |
| 6 | 2.24 | 10 | 8.96 | | | 50 (33) | 75 | 40 (50) | 80 | | | | | | | | | | |

TABLE II-continued

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 6 | 2.24 | 11 | 8.96 | | | 30 | 80 | 90 (0) | 85 | | | | | | | | | | |
| 6 | 2.24 | 12 | 8.96 | | | 70 | 99 | 50 (62) | 99 | | | | | | | | | | |
| 6 | 2.24 | 13 | 8.96 | | | 20 | 85 | 80 (29) | 90 | | | | | | | | | | |
| 6 | 2.24 | 14 | 8.96 | | | 10 | 85 | 90 (76) | 90 | | | | | | | | | | |
| 6 | 2.24 | 15 | 8.96 | | | 25 | 95 | 70 (88) | 85 | | | | | | | | | | |
| 6 | 2.24 | 16 | 8.96 | | | 15 | 95 | 90 (73) | 90 | | | | | | | | | | |
| 6 | 2.24 | 17 | 8.96 | | | 25 | 85 | 60 (84) | 90 | | | | | | | | | | |
| 6 | 2.24 | 18 | 8.96 | | | 80 | 85 | 65 (70) | 90 | | | | | | | | | | |
| 6 | 2.24 | 19 | 8.96 | | | 35 | 70 | 55 (5) | 80 | | | | | | | | | | |
| 6 | 2.24 | 20 | 8.96 | | | 35 | 70 | 35 (50) | 80 | | | | | | | | | | |
| 6 | 2.24 | 21 | 8.96 | | | 55 | 75 | 55 (50) | 90 | | | | | | | | | | |
| 6 | 2.24 | 22 | 8.96 | | | 40 | 90 | 100 (26) | 85 | | | | | | | | | | |
| 6 | 2.24 | 23 | 8.96 | | | 45 | 95 | 95 (55) | 100 | | | | | | | | | | |
| 10 | 6.72 | 1 | 8.96 | 60 | 80 | | | (52) | | | | | | | | | | | |
| 10 | 6.72 | 1 | 8.96 | 40 | 85 | 60 | 75 | 45 (43) | 80 | | | | | | | | | | |
| 10 | 6.72 | 2 | 8.96 | 45 | 85 | 80 | 80 | 50 (37) | 80 | | | | | | | | | | |
| 10 | 4.48 | 3 | 8.96 | 75 | 60 | | (0) | | | | | | | | | | | | |
| 10 | 4.48 | 4 | 8.96 | 65 | 75 | | (13) | | | | | | | | | | | | |
| 10 | 4.48 | 5 | 8.96 | 65 | 75 | | (13) | | | | | | | | | | | | |
| 10 | 4.48 | 6 | 8.96 | 30 | 80 | | (62) | | | | | | | | | | | | |
| 10 | 4.48 | 7 | 8.96 | 45 | 95 | | (52) | | | | | | | | | | | | |
| 10 | 4.48 | 8 | 8.96 | 60 | 95 | | (36) | | | | | | | | | | | | |
| 10 | 4.48 | 9 | 8.96 | 50 | 95 | | (47) | | | | | | | | | | | | |
| 10 | 4.48 | 10 | 8.96 | 60 | 90 | | (33) | | | | | | | | | | | | |

TABLE II-continued

| HERBICIDE | | ANTIDOTE | | \% PLANT INHIBITION AND % SAFENING EFFECT () | | | | | | | | | | | | |
|---|---|---|---|---|---|---|---|---|---|---|---|---|---|---|---|---|
| | | | | RICE | | SORGHUM GRAIN | | WHEAT | | CORN | | COTTON | | SOYBEAN | HEMP SESBANIA | VELVET LEAF |
| NO. | RATE | NO. | RATE | W | WO | W | WO | W | WO | W | WO | W | WO | W   WO | W   WO | W   WO |
| 10 | 4.48 | 11 | 8.96 | 35 (61) | 90 | | | | | | | | | | | |
| 10 | 4.48 | 12 | 8.96 | 10 (89) | 99 | | | | | | | | | | | |
| 10 | 4.48 | 13 | 8.96 | 40 (55) | 90 | | | | | | | | | | | |
| 10 | 4.48 | 14 | 8.96 | 40 (55) | 90 | | | | | | | | | | | |
| 10 | 4.48 | 15 | 8.96 | 80 (15) | 95 | | | | | | | | | | | |
| 10 | 4.48 | 16 | 8.96 | 40 (52) | 85 | | | | | | | | | | | |
| 10 | 4.48 | 17 | 8.96 | 90 (5) | 95 | | | | | | | | | | | |
| 10 | 4.48 | 18 | 8.96 | 60 (36) | 95 | | | | | | | | | | | |
| 10 | 4.48 | 19 | 8.96 | 100 (0) | 90 | | | | | | | | | | | |
| 10 | 4.48 | 20 | 8.96 | 70 (22) | 90 | | | | | | | | | | | |
| 10 | 4.48 | 21 | 8.96 | 50 (44) | 90 | | | | | | | | | | | |
| 10 | 4.48 | 22 | 8.96 | 55 (42) | 95 | | | | | | | | | | | |
| 10 | 4.48 | 23 | 8.96 | 70 (26) | 95 | | | | | | | | | | | |
| 15 | 1.12 | 1 | 8.96 | | | | | | | 30 (64) | 85 | | | | | |
| 15 | 2.24 | 3 | 8.96 | | | | | | | 60 (25) | 80 | | | | | |
| 15 | 2.24 | 4 | 8.96 | | | | | | | 55 (26) | 75 | | | | | |
| 15 | 2.24 | 5 | 8.96 | | | | | | | 40 (26) | 75 | | | | | |
| 15 | 2.24 | 6 | 8.96 | | | | | | | 60 (46) | 80 | | | | | |
| 15 | 2.24 | 7 | 8.96 | | | | | | | 90 (25) | 90 | | | | | |
| 15 | 2.24 | 8 | 8.96 | | | | | | | 40 (0) | 90 | | | | | |
| 15 | 2.24 | 9 | 8.96 | | | | | | | 15 (55) | 90 | | | | | |
| 15 | 2.24 | 10 | 8.96 | | | | | | | 30 (83) | 90 | | | | | |
| 15 | 2.24 | 11 | 8.96 | | | | | | | 40 (66) | 95 | | | | | |
| 15 | 2.24 | 12 | 8.96 | | | | | | | 10 (57) | 90 | | | | | |
| 15 | 2.24 | | | | | | | | | (88) | | | | | | |

TABLE II-continued

% PLANT INHIBITION AND % SAFENING EFFECT ( )

| HERBICIDE NO. | RATE | ANTIDOTE NO. | RATE | RICE W | RICE WO | SORGHUM GRAIN W | SORGHUM GRAIN WO | WHEAT W | WHEAT WO | CORN W | CORN WO | COTTON W | COTTON WO | SOYBEAN W | SOYBEAN WO | HEMP SESBANIA W | HEMP SESBANIA WO | VELVET LEAF W | VELVET LEAF WO |
|---|---|---|---|---|---|---|---|---|---|---|---|---|---|---|---|---|---|---|---|
| 15 | 2.24 | 13 | 8.96 | | | | | | | 80 (0) | 80 | | | | | | | | |
| 15 | 2.24 | 14 | 8.96 | | | | | | | 30 (62) | 80 | | | | | | | | |
| 15 | 2.24 | 15 | 8.96 | | | | | | | 20 (76) | 85 | | | | | | | | |
| 15 | 2.24 | 16 | 8.96 | | | | | | | 20 (77) | 90 | | | | | | | | |
| 15 | 2.24 | 17 | 8.96 | | | | | | | 20 (77) | 90 | | | | | | | | |
| 15 | 2.24 | 18 | 8.96 | | | | | | | 90 (0) | 90 | | | | | | | | |
| 15 | 2.24 | 19 | 8.96 | | | | | | | 65 (27) | 90 | | | | | | | | |
| 15 | 2.24 | 20 | 8.96 | | | | | | | 70 (22) | 90 | | | | | | | | |
| 15 | 2.24 | 21 | 8.96 | | | | | | | 85 (5) | 95 | | | | | | | | |
| 15 | 2.24 | 22 | 8.96 | | | | | | | 90 (5) | 100 | | | | | | | | |
| 15 | 2.24 | 23 | 8.96 | | | | | | | 40 (60) | | | | | | | | | |
| 3 | 4.48 | 44 | 8.96 | 98 (0) | 96 | | | 80 (17) | 97 | | | | | | | | | | |
| 3 | 4.48 | 46 | 8.96 | 80 (16) | 96 | | | 90 (7) | 97 | | | | | | | | | | |
| 3 | 4.48 | 47 | 8.96 | 60 (0) | 40 | | | | | | | | | | | | | | |
| 3 | 2.24 | 48 | 8.96 | 30 (0) | 20 | | | | | | | 100 (0) | 100 | 100 | 100 | | | | |
| 3 | 4.48 | 48 | 8.96 | 50 (0) | 40 | | | | | | | 100 (0) | 100 | 97 (3) | 100 | | | | |
| 3 | 4.48 | 48 | 8.96 | 10 (0) | 40 | | | | | | | | | 85 (5) | 90 | | | | |
| 3 | 6.72 | 48 | 8.96 | 50 (75) | 70 | | | | | | | | | 85 (0) | 80 | 95 (0) | 90 | | 90 |
| 3 | 8.96 | 48 | 8.96 | 50 (28) | 80 | | | | | | | | | 97 (0) | 85 | 98 (0) | 95 | | 95 |
| 6 | 0.56 | 50 | 8.96 | 60 (25) | | | | 60 (0) | 60 | | | | | 50 (44) | 90 | 20 (66) | 60 | 95 (0) | 98 |
| 6 | 1.12 | 50 | 8.96 | | | | | 50 (37) | 80 | | | | | 90 (5) | 95 | 60 (0) | 60 | 99 (0) | 99 |
| 6 | 2.24 | 50 | 8.96 | | | | | 80 (11) | 90 | | | | | 98 (0) | 98 | 50 (44) | 90 | 98 (4) | 98 |
| 6 | 4.48 | 50 | 8.96 | | | | | 95 (0) | 90 | | | | | | | 70 (22) | 90 | 97 (0) | 100 |
| 2 | 0.56 | 37 | 8.96 | 90 (8) | 98 | 50 (48) | 98 | 90 (0) | 90 | | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 2 | 0.56 | 38 | 8.96 | 90 | 90 | 50 (44) | 90 | 80 (18) | 98 | | | | | | | | | | |
| 2 | 0.56 | 39 | 8.96 | 100 | 98 (0) | 50 (48) | 98 | 98 (0) | 95 | | | | | | | | | | |
| 2 | 0.56 | 40 | 8.96 | 75 | 95 | 80 (5) | 85 | 97 (0) | 97 | | | | | | | | | | |
| 2 | 0.56 | 41 | 8.96 | 90 | 98 (21) | 20 (79) | 97 100 | 100 (0) | 100 | | | | | | | | | | |
| 2 | 0.56 | 42 | 8.96 | 70 | 96 (8) | 10 (88) | 85 | 98 (1) | 99 | | | | | | | | | | |
| 2 | 0.56 | 43 | 8.96 | 75 | 97 (27) | 10 (87) | 80 | 99 (1) | 100 | | | | | | | | | | |
| 2 | 0.56 | 44 | 8.96 | 97 | 97 (22) | 40 (58) | 97 | 98 (2) | 100 | | | | | | | | | | |
| 2 | 0.56 | 45 | 8.96 | | 85 (0) | | | 98 (0) | 90 | | | | | | | | | | |
| 2 | 0.56 | 46 | 8.96 | 99 | 97 (0) | 60 (38) | 97 | 98 (2) | 100 | | | | | | | | | | |
| 2 | 0.56 | 47 | 8.96 | 100 | 97 (0) | 90 (0) | 85 100 | 100 (2) | 90 | | | | | | | | | | |
| 2 | 0.56 | 48 | 8.96 | 85 | 85 (0) | 60 (33) | 90 | 80 (0) | 99 | | | | | | | | | | |
| 2 | 0.56 | 49 | 8.96 | | | | | 95 (19) | 95 | | | | | | | | | | |
| 2 | 0.56 | 50 | 8.96 | | | | | 98 (0) | 95 | | | | | | | | | | |
| 2 | 0.56 | 51 | 8.96 | | | | | 98 (0) | 90 | | | | | | | | | | |
| 2 | 0.56 | 52 | 8.96 | | | | | 85 (0) | 90 | | | | | | | | | | |
| 2 | 0.56 | 53 | 8.96 | | | | | 97 (5) | 90 | | | | | | | | | | |
| 2 | 0.56 | 54 | 8.96 | | | | | 40 (0) | 95 | | | | | | | | | | |
| 2 | 0.56 | 55 | 8.96 | | | | | 90 (57) | 90 | | | | | | | | | | |
| 2 | 0.56 | 56 | 8.96 | | | | | 95 (0) | 100 | | | | | | | | | | |
| 2 | 0.56 | 57 | 8.96 | | | | | 98 (5) | 95 | | | | | | | | | | |
| 2 | 0.56 | 58 | 8.96 | | | | | 98 (0) | 95 | | | | | | | | | | |
| 2 | 0.56 | 59 | 8.96 | | | | | 70 (26) | 95 | | | | | | | | | | |
| 2 | 0.56 | 60 | 8.96 | | | | | 55 (42) | 95 | | | | | | | | | | |
| 2 | 0.56 | 61 | 8.96 | | | | | 75 (21) | 95 | | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 2 | 0.56 | 62 | 8.96 | | | | | 90 | 95 | | | | | | | | | | |
| 2 | 0.56 | 63 | 8.96 | | | | | 90 (5) | 80 | | | | | | | | | | |
| 2 | 0.56 | 64 | 8.96 | | | | | 85 (0) | 90 | | | | | | | | | | |
| 2 | 0.56 | 65 | 8.96 | | | | | 90 (5) | 90 | | | | | | | | | | |
| 2 | 0.56 | 66 | 8.96 | | | | | 75 (16) | 90 | | | | | | | | | | |
| 2 | 0.56 | 67 | 8.96 | | | | | 75 (16) | 90 | | | | | | | | | | |
| 2 | 0.56 | 68 | 8.96 | | | | | 90 (5) | 95 | | | | | | | | | | |
| 2 | 0.56 | 69 | 8.96 | | | | | 80 (15) | 95 | | | | | | | | | | |
| 2 | 0.56 | 70 | 8.96 | | | | | 95 (0) | 95 | | | | | | | | | | |
| 2 | 0.56 | 71 | 8.96 | | | | | 100 (0) | 100 | | | | | | | | | | |
| 2 | 0.56 | 72 | 8.96 | | | | | 80 (20) | 100 | | | | | | | | | | |
| 2 | 0.56 | 73 | 8.96 | | | | | 90 (5) | 95 | | | | | | | | | | |
| 2 | 0.56 | 74 | 8.96 | | | | | 75 (21) | 95 | | | | | | | | | | |
| 2 | 0.56 | 75 | 8.96 | | | | | 100 (0) | 95 | | | | | | | | | | |
| 2 | 0.56 | 76 | 8.96 | | | | | 100 (0) | 95 | | | | | | | | | | |
| 2 | 0.56 | 77 | 8.96 | | | | | 90 (5) | 95 | | | | | | | | | | |
| 2 | 0.56 | 78 | 8.96 | | | | | 95 (5) | 100 | | | | | | | | | | |
| 2 | 0.56 | 79 | 8.96 | | | | | 100 (5) | 100 | | | | | | | | | | |
| 2 | 0.56 | 80 | 8.96 | | | | | 95 (0) | 100 | | | | | | | | | | |
| 2 | 0.56 | 81 | 8.96 | | | | | 100 (5) | 100 | | | | | | | | | | |
| 2 | 0.56 | 82 | 8.96 | | | | | 100 (0) | 100 | | | | | | | | | | |
| 2 | 0.56 | 83 | 8.96 | | | | | 100 (0) | 100 | | | | | | | | | | |
| 2 | 0.56 | 84 | 8.96 | | | | | 95 (5) | 100 | | | | | | | | | | |
| 2 | 0.56 | 85 | 8.96 | | | | | 90 (10) | 100 | | | | | | | | | | |

TABLE II-continued

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 2 | 0.56 | 86 | 8.96 | | | | | 90 | (5) | 95 | | | | | | | | | |
| 2 | 0.56 | 87 | 8.96 | | | | | 95 | (5) | 100 | | | | | | | | | |
| 2 | 0.56 | 88 | 8.96 | | | | | 90 | (5) | 100 | | | | | | | | | |
| 2 | 0.56 | 89 | 8.96 | | | | | 95 | (10) | 100 | | | | | | | | | |
| 2 | 0.56 | 90 | 8.96 | | | | | 75 | (5) | 100 | | | | | | | | | |
| 2 | 0.56 | 91 | 8.96 | | | | | 100 | (25) | 100 | | | | | | | | | |
| 2 | 0.56 | 92 | 8.96 | | | | | 95 | (0) | 100 | | | | | | | | | |
| 2 | 0.56 | 93 | 8.96 | | | | | 90 | (5) | 100 | | | | | | | | | |
| 2 | 0.56 | 94 | 8.96 | | | | | 90 | (10) | 95 | | | | | | | | | |
| 2 | 0.56 | 95 | 8.96 | | | | | 100 | (5) | 95 | | | | | | | | | |
| 2 | 0.56 | 96 | 8.96 | | | | | 90 | (0) | 100 | | | | | | | | | |
| 2 | 0.56 | 97 | 8.96 | | | | | 90 | (10) | 100 | | | | | | | | | |
| 2 | 0.56 | 98 | 8.96 | | | | | 85 | (15) | 95 | | | | | | | | | |
| 2 | 0.56 | 99 | 8.96 | | | | | 90 | (5) | 95 | | | | | | | | | |
| 2 | 0.56 | 100 | 8.96 | | | | | 85 | (10) | 95 | | | | | | | | | |
| 2 | 0.56 | 101 | 8.96 | | | | | 90 | (5) | 95 | | | | | | | | | |
| 2 | 0.56 | 102 | 8.96 | | | | | 90 | (5) | 95 | | | | | | | | | |
| 2 | 0.56 | 103 | 8.96 | | | | | 85 | (10) | 95 | | | | | | | | | |
| 2 | 0.56 | 104 | 8.96 | | | | | 90 | (5) | 95 | | | | | | | | | |
| 2 | 0.56 | 105 | 8.96 | | | | | 95 | (0) | 95 | | | | | | | | | |
| 2 | 0.56 | 106 | 8.96 | | | | | 95 | (0) | 95 | | | | | | | | | |
| 2 | 0.56 | 107 | 8.96 | | | | | 80 | (15) | 95 | | | | | | | | | |
| 2 | 0.56 | 108 | 8.96 | | | | | 90 | (5) | 95 | | | | | | | | | |
| 2 | 0.56 | 109 | 8.96 | | | | | 65 | (31) | 95 | | | | | | | | | |
| 2 | 0.56 | | 8.96 | | | | | 85 | (10) | 95 | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 2 | 0.56 | 110 | 8.96 | | | | | 90 | | 95 | | | | | | | | | |
| 2 | 0.56 | 111 | 8.96 | | | | | 85 | (5) | 95 | | | | | | | | | |
| 2 | 0.56 | 112 | 8.96 | | | | | 90 | (10) | 80 | | | | | | | | | |
| 2 | 0.56 | 113 | 8.96 | | | | | 75 | (0) | 80 | | | | | | | | | |
| 2 | 0.56 | 114 | 8.96 | | | | | 75 | (6) | 80 | | | | | | | | | |
| 2 | 0.56 | 115 | 8.96 | | | | | 70 | (6) | 80 | | | | | | | | | |
| 2 | 0.56 | 116 | 8.96 | | | | | 75 | (12) | 80 | | | | | | | | | |
| 2 | 0.56 | 117 | 8.96 | | | | | 100 | (6) | 95 | | | | | | | | | |
| 2 | 0.56 | 118 | 8.96 | | | | | 80 | (0) | 95 | | | | | | | | | |
| 2 | 0.56 | 119 | 8.96 | | | | | 95 | (15) | 95 | | | | | | | | | |
| 2 | 0.56 | 120 | 8.96 | | | | | 70 | (0) | 90 | | | | | | | | | |
| 2 | 0.56 | 121 | 8.96 | | | | | 90 | (22) | 90 | | | | | | | | | |
| 2 | 0.56 | 122 | 8.96 | | | | | 45 | (0) | 90 | | | | | | | | | |
| 2 | 0.56 | 123 | 8.96 | | | | | 80 | (50) | 90 | | | | | | | | | |
| 2 | 0.56 | 124 | 8.96 | | | | | 80 | (11) | 90 | | | | | | | | | |
| 2 | 0.56 | 125 | 8.96 | | | | | 90 | (11) | 90 | | | | | | | | | |
| 2 | 0.56 | 126 | 8.96 | | | | | 90 | (0) | 95 | | | | | | | | | |
| 2 | 0.56 | 127 | 8.96 | | | | | 85 | (5) | 95 | | | | | | | | | |
| 2 | 0.56 | 128 | 8.96 | | | | | 75 | (10) | 95 | | | | | | | | | |
| 2 | 0.56 | 129 | 8.96 | | | | | 75 | (21) | 95 | | | | | | | | | |
| 2 | 0.56 | 130 | 8.96 | | | | | 95 | (21) | 95 | | | | | | | | | |
| 2 | 0.56 | 131 | 8.96 | | | | | 90 | (0) | 95 | | | | | | | | | |
| 2 | 0.56 | 132 | 8.96 | | | | | 85 | (5) | 95 | | | | | | | | | |
| 2 | 0.56 | 133 | 8.96 | | | | | 90 | (10) | 95 | | | | | | | | | |
| | | | | | | | | | (5) | | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 2 | 0.56 | 134 | 8.96 | | | | | 35 (61) | 90 | | | | | | | | | | |
| 2 | 0.56 | 135 | 8.96 | | | | | 90 (0) | 90 | | | | | | | | | | |
| 2 | 0.56 | 136 | 8.96 | | | | | 95 (0) | 90 | | | | | | | | | | |
| 2 | 0.56 | 137 | 8.96 | | | | | 90 (0) | 90 | | | | | | | | | | |
| 2 | 0.56 | 138 | 8.96 | | | | | 70 (22) | 90 | | | | | | | | | | |
| 2 | 0.56 | 139 | 8.96 | | | | | 80 (5) | 85 | | | | | | | | | | |
| 2 | 0.56 | 140 | 8.96 | | | | | 90 (0) | 85 | | | | | | | | | | |
| 2 | 0.56 | 141 | 8.96 | | | | | 75 (21) | 95 | | | | | | | | | | |
| 2 | 0.56 | 142 | 8.96 | | | | | 70 (26) | 95 | | | | | | | | | | |
| 2 | 0.56 | 143 | 8.96 | | | | | 90 (5) | 85 | | | | | | | | | | |
| 2 | 0.56 | 144 | 8.96 | | | | | 40 (52) | 85 | | | | | | | | | | |
| 2 | 0.56 | 145 | 8.96 | | | | | 40 (52) | 85 | | | | | | | | | | |
| 2 | 0.56 | 146 | 8.96 | | | | | 45 (47) | 85 | | | | | | | | | | |
| 2 | 0.56 | 147 | 8.96 | | | | | 85 (0) | 85 | | | | | | | | | | |
| 2 | 0.56 | 148 | 8.96 | | | | | 65 (23) | 85 | | | | | | | | | | |
| 2 | 0.56 | 149 | 8.96 | | | | | 40 (50) | 80 | | | | | | | | | | |
| 2 | 0.56 | 150 | 8.96 | | | | | 100 (0) | 90 | | | | | | | | | | |
| 2 | 0.56 | 151 | 8.96 | | | | | 90 (5) | 95 | | | | | | | | | | |
| 2 | 0.56 | 152 | 8.96 | | | | | 90 (5) | 95 | | | | | | | | | | |
| 2 | 0.56 | 153 | 8.96 | | | | | 85 (10) | 95 | | | | | | | | | | |
| 2 | 0.56 | 154 | 8.96 | | | | | 100 (0) | 95 | | | | | | | | | | |
| 2 | 0.56 | 155 | 8.96 | | | | | 85 (10) | 95 | | | | | | | | | | |
| 2 | 0.56 | 156 | 8.96 | | | | | 85 (10) | 95 | | | | | | | | | | |
| 2 | 0.56 | 157 | 8.96 | | | | | 65 (31) | 95 | | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | | CORN | | COTTON | | SOYBEAN | | HEMP SESBANIA | | VELVET LEAF | |
|---|---|---|---|---|---|---|---|---|---|---|---|---|---|---|---|---|---|---|---|---|
| NO. | RATE | NO. | RATE | W | WO | W | WO | W | | WO | W | WO | W | WO | W | WO | W | WO | W | WO |
| 2 | 0.56 | 158 | 8.96 | | | | | 95 | | 90 | | | | | | | | | | |
| 2 | 0.56 | 159 | 8.96 | | | | | 80 | (0) | 90 | | | | | | | | | | |
| 2 | 0.56 | 160 | 8.96 | | | | | 80 | (11) | 90 | | | | | | | | | | |
| 2 | 0.56 | 161 | 8.96 | | | | | 80 | (11) | 90 | | | | | | | | | | |
| 2 | 0.56 | 162 | 8.96 | | | | | 80 | (11) | 90 | | | | | | | | | | |
| 2 | 0.56 | 163 | 8.96 | | | | | 70 | (22) | 90 | | | | | | | | | | |
| 2 | 0.56 | 164 | 8.96 | | | | | 80 | (11) | 90 | | | | | | | | | | |
| 2 | 0.56 | 165 | 8.96 | | | | | 80 | (5) | 85 | | | | | | | | | | |
| 2 | 0.56 | 166 | 8.96 | | | | | 75 | (11) | 85 | | | | | | | | | | |
| 2 | 0.56 | 167 | 8.96 | | | | | 90 | (0) | 90 | | | | | | | | | | |
| 2 | 0.56 | 168 | 8.96 | | | | | 90 | (5) | 95 | | | | | | | | | | |
| 2 | 0.56 | 169 | 8.96 | | | | | 90 | (5) | 95 | | | | | | | | | | |
| 2 | 0.56 | 170 | 8.96 | | | | | 85 | (5) | 90 | | | | | | | | | | |
| 2 | 0.56 | 171 | 8.96 | | | | | 100 | (0) | 90 | | | | | | | | | | |
| 2 | 0.56 | 172 | 8.96 | | | | | 100 | (0) | 90 | | | | | | | | | | |
| 2 | 0.56 | 173 | 8.96 | | | | | 90 | (5) | 95 | | | | | | | | | | |
| 2 | 0.56 | 174 | 8.96 | | | | | 40 | (57) | 95 | | | | | | | | | | |
| 2 | 0.56 | 175 | 8.96 | | | | | 80 | (15) | 95 | | | | | | | | | | |
| 2 | 0.56 | 176 | 8.96 | | | | | 80 | (11) | 95 | | | | | | | | | | |
| 2 | 0.56 | 177 | 8.96 | | | | | 100 | (0) | 90 | | | | | | | | | | |
| 2 | 0.56 | 178 | 8.96 | | | | | 85 | (5) | 90 | | | | | | | | | | |
| 2 | 0.56 | 179 | 8.96 | | | | | 80 | (11) | 90 | | | | | | | | | | |
| 2 | 0.56 | 180 | 8.96 | | | | | 95 | (0) | 90 | | | | | | | | | | |
| 2 | 0.56 | 181 | 8.96 | | | | | 75 | (16) | 90 | | | | | | | | | | |
| 2 | 0.56 | | 8.96 | | | | | 95 | (0) | 90 | | | | | | | | | | |

TABLE II-continued

% PLANT INHIBITION AND % SAFENING EFFECT ()

| HERBICIDE NO. | RATE | ANTIDOTE NO. | RATE | RICE W | RICE WO | SORGHUM GRAIN W | SORGHUM GRAIN WO | WHEAT W | WHEAT WO | CORN W | CORN WO | COTTON W | COTTON WO | SOYBEAN W | SOYBEAN WO | HEMP SESBANIA W | HEMP SESBANIA WO | VELVET LEAF W | VELVET LEAF WO |
|---|---|---|---|---|---|---|---|---|---|---|---|---|---|---|---|---|---|---|---|
| 2 | 0.56 | 182 | 8.96 | | | | | 85 (15) | 100 | | | | | | | | | | |
| 2 | 0.56 | 183 | 8.96 | | | | | 90 (10) | 100 | | | | | | | | | | |
| 2 | 0.56 | 184 | 8.96 | | | | | 100 (0) | 100 | | | | | | | | | | |
| 2 | 0.56 | 185 | 8.96 | | | | | 100 (0) | 95 | | | | | | | | | | |
| 2 | 0.56 | 186 | 8.96 | | | | | 100 (0) | 95 | | | | | | | | | | |
| 2 | 0.56 | 187 | 8.96 | | | | | 80 (11) | 90 | | | | | | | | | | |
| 2 | 0.56 | 188 | 8.96 | | | | | 80 (11) | 90 | | | | | | | | | | |
| 2 | 0.56 | 189 | 8.96 | | | | | 65 (27) | 90 | | | | | | | | | | |
| 2 | 0.56 | 190 | 8.96 | | | | | 95 (0) | 95 | | | | | | | | | | |
| 2 | 0.56 | 191 | 8.96 | | | | | 70 (26) | 95 | | | | | | | | | | |
| 2 | 0.56 | 192 | 8.96 | | | | | 75 (21) | 95 | | | | | | | | | | |
| 2 | 0.56 | 193 | 8.96 | | | | | 70 (30) | 100 | | | | | | | | | | |
| 2 | 0.56 | 194 | 8.96 | | | | | 95 (5) | 100 | | | | | | | | | | |
| 2 | 0.56 | 195 | 8.96 | | | | | 90 (10) | 100 | | | | | | | | | | |
| 2 | 0.56 | 196 | 8.96 | | | | | 85 (15) | 100 | | | | | | | | | | |
| 2 | 0.56 | 197 | 8.96 | | | | | 95 (0) | 95 | | | | | | | | | | |
| 2 | 0.56 | 198 | 8.96 | | | | | 80 (15) | 95 | | | | | | | | | | |
| 2 | 0.56 | 199 | 8.96 | | | | | 100 (0) | 75 | | | | | | | | | | |
| 2 | 0.56 | 200 | 8.96 | | | | | 80 (15) | 95 | | | | | | | | | | |
| 2 | 0.56 | 201 | 8.96 | | | | | 75 (0) | 70 | | | | | | | | | | |
| 2 | 0.56 | 202 | 0.28 | | | | | 85 (5) | 90 | | | | | | | | | | |
| 3 | 6.72 | 45 | 8.96 | 85 (0) | 70 | | | | | | | | | 95 (0) | 85 | | | | |
| 3 | 4.48 | 49 | 8.96 | 45 (0) | 30 | | | | | | | | | 80 (0) | 65 | | | | |
| 3 | 4.48 | 50 | 8.96 | 40 (0) | 30 | | | | | | | | | 60 (7) | 65 | | | | |

TABLE II-continued
% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 3 | 6.72 | 51 | 8.96 | 60 (0) | 50 | | | | | | | | | 95 | (0) | 95 | | | |
| 3 | 6.72 | 52 | 8.96 | 75 (0) | 50 | | | | | | | | | 99 | (0) | 95 | | | |
| 3 | 6.72 | 53 | 8.96 | 10 (0) | 50 | | | | | | | | | 97 | (0) | 95 | | | |
| 3 | 6.72 | 54 | 8.96 | 90 (80) | 80 | | | | | | | | | 95 | (0) | 90 | | | |
| 3 | 6.72 | 55 | 8.96 | 90 (0) | 85 | | | | | | | | | 98 | (0) | 90 | | | |
| 3 | 6.72 | 56 | 8.96 | 100 (0) | 100 | | | | | | | | | 100 | (0) | 100 | | | |
| 3 | 4.48 | 57 | 8.96 | 100 (0) | 100 | | | | | | | | | 100 | (0) | 100 | | | |
| 3 | 4.48 | 58 | 8.96 | 90 (0) | 100 | | | | | | | | | 100 | (0) | 100 | | | |
| 3 | 4.48 | 59 | 8.96 | 100 (10) | 100 | | | | | | | | | 100 | (0) | 100 | | | |
| 3 | 4.48 | 60 | 8.96 | 100 (0) | 100 | | | | | | | | | 100 | (0) | 100 | | | |
| 3 | 4.48 | 61 | 8.96 | 95 (5) | 100 | | | | | | | | | 95 | (5) | 100 | | | |
| 3 | 4.48 | 62 | 8.96 | 100 (0) | 100 | | | | | | | | | 90 | (10) | 100 | | | |
| 3 | 4.48 | 63 | 8.96 | 95 (3) | 98 | | | | | | | | | 100 | (0) | 100 | | | |
| 3 | 4.48 | 64 | 8.96 | 100 (0) | 90 | | | | | | | | | 90 | (8) | 98 | | | |
| 3 | 4.48 | 65 | 8.96 | 95 (0) | 90 | | | | | | | | | 100 | (0) | 90 | | | |
| 3 | 4.48 | 66 | 8.96 | 95 (0) | 90 | | | | | | | | | 90 | (0) | 90 | | | |
| 3 | 4.48 | 67 | 8.96 | 80 (11) | 90 | | | | | | | | | 80 | (11) | 90 | | | |
| 3 | 4.48 | 68 | 8.96 | 70 (0) | 60 | | | | | | | | | 90 | (0) | 70 | | | |
| 3 | 4.48 | 69 | 8.96 | 80 (0) | 60 | | | | | | | | | 80 | (0) | 70 | | | |
| 3 | 4.48 | 70 | 8.96 | 80 (0) | 60 | | | | | | | | | 75 | (0) | 70 | | | |
| 3 | 4.48 | 71 | 8.96 | 90 (0) | 80 | | | | | | | | | 90 | (0) | 75 | | | |
| 3 | 4.48 | 72 | 8.96 | 75 (16) | 90 | | | | | | | | | 75 | (6) | 80 | | | |
| 3 | 4.48 | 73 | 8.96 | 95 (0) | 75 | | | | | | | | | 100 | (0) | 70 | | | |
| 3 | 4.48 | 74 | 8.96 | 85 (0) | 85 | | | | | | | | | 90 | (0) | 90 | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 3 | 4.48 | 75 | 8.96 | 90 | 85 | | | | | | | | | 90 | 90 | | | | |
| 3 | 4.48 | 76 | 8.96 | 100 | (0) 85 | | | | | | | | | 100 | (0) 90 | | | | |
| 3 | 4.48 | 77 | 8.96 | 100 | (0) 85 | | | | | | | | | 100 | (0) 90 | | | | |
| 3 | 4.48 | 78 | 8.96 | 95 | (0) 90 | | | | | | | | | 95 | (0) 85 | | | | |
| 3 | 4.48 | 79 | 8.96 | 95 | (0) 90 | | | | | | | | | 95 | (0) 85 | | | | |
| 3 | 4.48 | 80 | 8.96 | 100 | (0) 90 | | | | | | | | | 25 | (70) 85 | | | | |
| 3 | 4.48 | 81 | 8.96 | 90 | (0) 90 | | | | | | | | | 30 | (64) 85 | | | | |
| 3 | 4.48 | 82 | 8.96 | 80 | (11) 90 | | | | | | | | | 60 | (29) 85 | | | | |
| 3 | 4.48 | 83 | 8.96 | 60 | (33) 90 | | | | | | | | | 60 | (29) 85 | | | | |
| 3 | 4.48 | 84 | 8.96 | 70 | (22) 90 | | | | | | | | | 40 | (52) 85 | | | | |
| 3 | 4.48 | 85 | 8.96 | 90 | (0) 80 | | | | | | | | | 100 | (0) 85 | | | | |
| 3 | 4.48 | 86 | 8.96 | 95 | (0) 90 | | | | | | | | | 75 | (0) 60 | | | | |
| 3 | 4.48 | 87 | 8.96 | 100 | (0) 70 | | | | | | | | | 30 | (0) 60 | | | | |
| 3 | 4.48 | 88 | 8.96 | 85 | (0) 70 | | | | | | | | | 35 | (50) 60 | | | | |
| 3 | 4.48 | 89 | 8.96 | 95 | (0) 95 | | | | | | | | | 100 | (41) 95 | | | | |
| 3 | 4.48 | 90 | 8.96 | 95 | (0) 95 | | | | | | | | | 85 | (0) 95 | | | | |
| 3 | 4.48 | 91 | 8.96 | 80 | (15) 95 | | | | | | | | | 90 | (10) 95 | | | | |
| 3 | 4.48 | 92 | 8.96 | 95 | (0) 80 | | | | | | | | | 100 | (5) 85 | | | | |
| 3 | 4.48 | 93 | 8.96 | 80 | (0) 80 | | | | | | | | | 90 | (0) 90 | | | | |
| 3 | 4.48 | 94 | 8.96 | 85 | (0) 80 | | | | | | | | | 90 | (0) 90 | | | | |
| 3 | 4.48 | 95 | 8.96 | 90 | (0) 90 | | | | | | | | | 95 | (0) 90 | | | | |
| 3 | 4.48 | 96 | 8.96 | 95 | (0) 90 | | | | | | | | | 90 | (0) 90 | | | | |
| 3 | 4.48 | 97 | 8.96 | 100 | (0) 90 | | | | | | | | | 100 | (0) 90 | | | | |
| 3 | 4.48 | 98 | 8.96 | 95 | (0) 90 | | | | | | | | | 90 | (0) 90 | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 3 | 4.48 | 99 | 8.96 | 85 | (0) | | 80 | | | | | | | 85 | (0) | 85 | | | |
| 3 | 4.48 | 100 | 8.96 | 85 | (0) | | 80 | | | | | | | 90 | (0) | 85 | | | |
| 3 | 4.48 | 101 | 8.96 | 95 | (0) | | 80 | | | | | | | 90 | (0) | 85 | | | |
| 3 | 4.48 | 102 | 8.96 | 90 | (0) | | 80 | | | | | | | 95 | (0) | 85 | | | |
| 3 | 4.48 | 103 | 8.96 | 95 | (0) | | 80 | | | | | | | 85 | (0) | 85 | | | |
| 3 | 4.48 | 104 | 8.96 | 90 | (0) | | 80 | | | | | | | 95 | (0) | 85 | | | |
| 3 | 4.48 | 105 | 8.96 | 90 | (0) | | 80 | | | | | | | 85 | (0) | 85 | | | |
| 3 | 4.48 | 106 | 8.96 | 90 | (0) | | 80 | | | | | | | 95 | (0) | 90 | | | |
| 3 | 4.48 | 107 | 8.96 | 95 | (0) | | 80 | | | | | | | 90 | (0) | 90 | | | |
| 3 | 4.48 | 108 | 8.96 | 90 | (0) | | 90 | | | | | | | 70 | (30) | 100 | | | |
| 3 | 4.48 | 109 | 8.96 | 90 | (0) | | 80 | | | | | | | 100 | (0) | 95 | | | |
| 3 | 4.48 | 110 | 8.96 | 95 | (0) | | 80 | | | | | | | 80 | (15) | 95 | | | |
| 3 | 4.48 | 111 | 8.96 | 90 | (0) | | 90 | | | | | | | 65 | (35) | 100 | | | |
| 3 | 4.48 | 112 | 8.96 | 75 | (6) | | 80 | | | | | | | 45 | (47) | 85 | | | |
| 3 | 4.48 | 113 | 8.96 | 80 | (0) | | 80 | | | | | | | 75 | (11) | 85 | | | |
| 3 | 4.48 | 114 | 8.96 | 90 | (0) | | 80 | | | | | | | 65 | (23) | 85 | | | |
| 3 | 4.48 | 115 | 8.96 | 95 | (0) | | 80 | | | | | | | 95 | (0) | 85 | | | |
| 3 | 4.48 | 116 | 8.96 | 90 | (0) | | 80 | | | | | | | 85 | (0) | 85 | | | |
| 3 | 4.48 | 117 | 8.96 | 90 | (0) | | 80 | | | | | | | 95 | (0) | 80 | | | |
| 3 | 4.48 | 118 | 8.96 | 90 | (0) | | 80 | | | | | | | 100 | (0) | 80 | | | |
| 3 | 4.48 | 119 | 8.96 | 80 | (0) | | 80 | | | | | | | 90 | (0) | 85 | | | |
| 3 | 4.48 | 120 | 8.96 | 95 | (0) | | 80 | | | | | | | 65 | (18) | 80 | | | |
| 3 | 4.48 | 121 | 8.96 | 80 | (11) | | 90 | | | | | | | 85 | (0) | 80 | | | |
| 3 | 4.48 | 122 | 8.96 | 100 | (0) | | 90 | | | | | | | 100 | (0) | 80 | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 3 | 4.48 | 123 | 8.96 | 95 | 90 | | | | | | | | | 80 | 80 | | | | |
| 3 | 4.48 | 124 | 8.96 | 85 | (0) 90 | | | | | | | | | 85 | (0) 80 | | | | |
| 3 | 4.48 | 125 | 8.96 | 95 | (5) 80 | | | | | | | | | 90 | (0) 85 | | | | |
| 3 | 4.48 | 126 | 8.96 | 80 | (0) 90 | | | | | | | | | 80 | (11) 90 | | | | |
| 3 | 4.48 | 127 | 8.96 | 95 | (11) 90 | | | | | | | | | 100 | (0) 90 | | | | |
| 3 | 4.48 | 128 | 8.96 | 90 | (0) 90 | | | | | | | | | 95 | (0) 90 | | | | |
| 3 | 4.48 | 129 | 8.96 | 90 | (0) 90 | | | | | | | | | 85 | (5) 90 | | | | |
| 3 | 4.48 | 130 | 8.96 | 90 | (0) 90 | | | | | | | | | 95 | (0) 90 | | | | |
| 3 | 4.48 | 131 | 8.96 | 95 | (0) 90 | | | | | | | | | 90 | (0) 90 | | | | |
| 3 | 4.48 | 132 | 8.96 | 95 | (0) 90 | | | | | | | | | 80 | (0) 80 | | | | |
| 3 | 4.48 | 133 | 8.96 | 95 | (0) 90 | | | | | | | | | 90 | (11) 80 | | | | |
| 3 | 4.48 | 134 | 8.96 | 80 | (11) 80 | | | | | | | | | 90 | (0) 90 | | | | |
| 3 | 4.48 | 135 | 8.96 | 90 | (0) 80 | | | | | | | | | 100 | (0) 80 | | | | |
| 3 | 4.48 | 136 | 8.96 | 90 | (0) 80 | | | | | | | | | 45 | (47) 85 | | | | |
| 3 | 4.48 | 137 | 8.96 | 75 | (6) 85 | | | | | | | | | 90 | (0) 85 | | | | |
| 3 | 4.48 | 138 | 8.96 | 90 | (0) 85 | | | | | | | | | 80 | (5) 85 | | | | |
| 3 | 4.48 | 139 | 8.96 | 90 | (0) 90 | | | | | | | | | 80 | (0) 75 | | | | |
| 3 | 4.48 | 140 | 8.96 | 90 | (0) 90 | | | | | | | | | 60 | (20) 75 | | | | |
| 3 | 4.48 | 141 | 8.96 | 95 | (0) 90 | | | | | | | | | 90 | (0) 90 | | | | |
| 3 | 4.48 | 142 | 8.96 | 85 | (5) 90 | | | | | | | | | 100 | (0) 90 | | | | |
| 3 | 4.48 | 143 | 8.96 | 95 | (0) 85 | | | | | | | | | 100 | (0) 90 | | | | |
| 3 | 4.48 | 144 | 8.96 | 90 | (0) 85 | | | | | | | | | 95 | (0) 80 | | | | |
| 3 | 4.48 | 145 | 8.96 | 80 | (5) 85 | | | | | | | | | 85 | (0) 80 | | | | |
| 3 | 4.48 | 146 | 8.96 | 95 | (0) 85 | | | | | | | | | 100 | (0) 80 | | | | |

TABLE II-continued

% PLANT INHIBITION AND % SAFENING EFFECT ()

| HERBICIDE NO. | RATE | ANTIDOTE NO. | RATE | RICE W | RICE WO | SORGHUM GRAIN W | SORGHUM GRAIN WO | WHEAT W | WHEAT WO | CORN W | CORN WO | COTTON W | COTTON WO | SOYBEAN W | SOYBEAN WO | HEMP SESBANIA W | HEMP SESBANIA WO | VELVET LEAF W | VELVET LEAF WO |
|---|---|---|---|---|---|---|---|---|---|---|---|---|---|---|---|---|---|---|---|
| 3 | 4.48 | 147 | 8.96 | 95 | 85 | | | | | | | | | 95 | 80 | | | | |
| 3 | 4.48 | 148 | 8.96 | 70 | (0) 85 | | | | | | | | | 90 | (0) 80 | | | | |
| 3 | 4.48 | 149 | 8.96 | 90 | (17) 80 | | | | | | | | | 85 | (0) 85 | | | | |
| 3 | 4.48 | 150 | 8.96 | 95 | (0) 90 | | | | | | | | | 90 | (0) 85 | | | | |
| 3 | 4.48 | 151 | 8.96 | 95 | (0) 90 | | | | | | | | | 95 | (0) 95 | | | | |
| 3 | 4.48 | 152 | 8.96 | 95 | (0) 90 | | | | | | | | | 100 | (0) 95 | | | | |
| 3 | 4.48 | 153 | 8.96 | 95 | (0) 90 | | | | | | | | | 100 | (0) 95 | | | | |
| 3 | 4.48 | 154 | 8.96 | 90 | (0) 90 | | | | | | | | | 80 | (11) 90 | | | | |
| 3 | 4.48 | 155 | 8.96 | 95 | (0) 90 | | | | | | | | | 95 | (0) 95 | | | | |
| 3 | 4.48 | 156 | 8.96 | 90 | (0) 90 | | | | | | | | | 100 | (0) 95 | | | | |
| 3 | 4.48 | 157 | 8.96 | 95 | (0) 90 | | | | | | | | | 95 | (0) 95 | | | | |
| 3 | 4.48 | 158 | 8.96 | 90 | (5) 95 | | | | | | | | | 90 | (0) 90 | | | | |
| 3 | 4.48 | 159 | 8.96 | 95 | (0) 95 | | | | | | | | | 95 | (0) 90 | | | | |
| 3 | 4.48 | 160 | 8.96 | 95 | (0) 95 | | | | | | | | | 95 | (0) 90 | | | | |
| 3 | 4.48 | 161 | 8.96 | 100 | (0) 95 | | | | | | | | | 100 | (0) 90 | | | | |
| 3 | 4.48 | 162 | 8.96 | 95 | (0) 95 | | | | | | | | | 85 | (5) 90 | | | | |
| 3 | 4.48 | 163 | 8.96 | 90 | (5) 90 | | | | | | | | | 85 | (5) 90 | | | | |
| 3 | 4.48 | 164 | 8.96 | 65 | (27) 85 | | | | | | | | | 95 | (0) 95 | | | | |
| 3 | 4.48 | 165 | 8.96 | 95 | (0) 90 | | | | | | | | | 100 | (0) 90 | | | | |
| 3 | 4.48 | 166 | 8.96 | 95 | (0) 90 | | | | | | | | | 100 | (0) 90 | | | | |
| 3 | 4.48 | 167 | 8.96 | 100 | (0) 90 | | | | | | | | | 95 | (0) 90 | | | | |
| 3 | 4.48 | 168 | 8.96 | 100 | (0) 90 | | | | | | | | | 85 | (5) 90 | | | | |
| 3 | 4.48 | 169 | 8.96 | 75 | (16) 90 | | | | | | | | | 70 | (22) 90 | | | | |
| 3 | 4.48 | 170 | 8.96 | 75 | (16) 90 | | | | | | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 3 | 4.48 | 171 | 8.96 | 80 | 90 | | | | | | | | | 80 (11) | 90 | | | | |
| 3 | 4.48 | 172 | 8.96 | 35 (11) | 85 | | | | | | | | | 100 (0) | 75 | | | | |
| 3 | 4.48 | 173 | 8.96 | 95 (58) | 85 | | | | | | | | | 85 (10) | 95 | | | | |
| 3 | 4.48 | 174 | 8.96 | 90 (0) | 85 | | | | | | | | | 95 (0) | 95 | | | | |
| 3 | 4.48 | 175 | 8.96 | 85 (5) | 85 | | | | | | | | | 80 (0) | 90 | | | | |
| 3 | 4.48 | 176 | 8.96 | 90 (0) | 90 | | | | | | | | | 100 (11) | 95 | | | | |
| 3 | 4.48 | 177 | 8.96 | 95 (0) | 85 | | | | | | | | | 100 (0) | 90 | | | | |
| 3 | 4.48 | 178 | 8.96 | 90 (0) | 90 | | | | | | | | | 95 (0) | 90 | | | | |
| 3 | 4.48 | 179 | 8.96 | 90 (0) | 90 | | | | | | | | | 85 (0) | 90 | | | | |
| 3 | 4.48 | 180 | 8.96 | 85 (5) | 90 | | | | | | | | | 85 (5) | 90 | | | | |
| 3 | 4.48 | 181 | 8.96 | 95 (0) | 90 | | | | | | | | | 100 (0) | 90 | | | | |
| 3 | 4.48 | 182 | 8.96 | 90 (0) | 85 | | | | | | | | | 95 (0) | 90 | | | | |
| 3 | 4.48 | 183 | 8.96 | 65 (23) | 85 | | | | | | | | | 90 (0) | 90 | | | | |
| 3 | 4.48 | 184 | 8.96 | 90 (0) | 90 | | | | | | | | | 85 (5) | 75 | | | | |
| 3 | 4.48 | 185 | 8.96 | 70 (17) | 85 | | | | | | | | | 60 (0) | 80 | | | | |
| 3 | 4.48 | 186 | 8.96 | 100 (0) | 100 | | | | | | | | | 95 (25) | 90 | | | | |
| 3 | 4.48 | 187 | 8.96 | 100 (0) | 100 | | | | | | | | | 100 (0) | 100 | | | | |
| 3 | 4.48 | 188 | 8.96 | 100 (0) | 100 | | | | | | | | | 100 (0) | 100 | | | | |
| 3 | 4.48 | 189 | 8.96 | 100 (0) | 100 | | | | | | | | | 100 (0) | 100 | | | | |
| 3 | 4.48 | 190 | 8.96 | 100 (0) | 100 | | | | | | | | | 100 (0) | 100 | | | | |
| 3 | 4.48 | 191 | 8.96 | 95 (5) | 100 | | | | | | | | | 95 (5) | 100 | | | | |
| 3 | 4.48 | 192 | 8.96 | 100 (0) | 100 | | | | | | | | | 100 (0) | 100 | | | | |
| 3 | 4.48 | 193 | 8.96 | 100 (0) | 95 | | | | | | | | | 100 (0) | 95 | | | | |
| 3 | 4.48 | 194 | 8.96 | 100 (0) | 95 | | | | | | | | | 100 (0) | 95 | | | | |

TABLE II-continued

% PLANT INHIBITION AND % SAFENING EFFECT ()

| HERBICIDE NO. | RATE | ANTIDOTE NO. | RATE | RICE W | WO | SORGHUM GRAIN W | WO | WHEAT W | WO | CORN W | WO | COTTON W | WO | SOYBEAN W | WO | HEMP SESBANIA W | WO | VELVET LEAF W | WO |
|---|---|---|---|---|---|---|---|---|---|---|---|---|---|---|---|---|---|---|---|
| 3 | 4.48 | 195 | 8.96 | 100 | 95 | | | | | | | | | 100 (0) | 95 | | | | |
| 3 | 4.48 | 196 | 8.96 | 100 | (0) 100 | | | | | | | | | 95 (0) | 95 | | | | |
| 3 | 4.48 | 197 | 8.96 | 100 | (0) 100 | | | | | | | | | 95 (0) | 95 | | | | |
| 3 | 4.48 | 198 | 8.96 | 100 | (0) 95 | | | | | | | | | 100 (0) | 95 | | | | |
| 3 | 4.48 | 199 | 8.96 | 95 | (0) 60 | | | | | | | | | 95 (0) | 80 | | | | |
| 3 | 6.72 | 200 | 8.96 | 80 | (0) 80 | | | | | | | | | 80 (15) | 95 | | | | |
| 3 | 4.48 | 201 | 8.96 | 60 | (7) 65 | | | | | | | | | 80 (0) | 75 | | | | |
| 3 | 6.72 | 202 | 0.28 | 50 | (47) 95 | | | | | | | | | 55 (38) | 90 | | | | |
| 6 | 2.24 | 37 | 8.96 | 85 | (5) 90 | 70 (26) | 95 | 70 (12) | 80 | | | | | | | | | | |
| 6 | 2.24 | 38 | 8.96 | 90 | (10) 100 | 75 (23) | 98 | 90 (0) | 80 | | | | | | | | | | |
| 6 | 2.24 | 39 | 8.96 | 100 | (0) 99 | 99 (0) | 98 | 90 (0) | 85 | | | | | | | | | | |
| 6 | 2.24 | 40 | 8.96 | 95 | (2) 97 | 97 (0) | 95 | 80 (0) | 75 | | | | | | | | | | |
| 6 | 2.24 | 41 | 8.96 | 90 | (6) 96 | 65 (34) | 99 | 80 (11) | 90 | | | | | | | | | | |
| 6 | 2.24 | 42 | 8.96 | 100 | (0) 100 | 30 (69) | 99 | 70 (12) | 80 | | | | | | | | | | |
| 6 | 2.24 | 43 | 8.96 | 98 | (0) 98 | 35 (64) | 98 | 60 (29) | 85 | | | | | | | | | | |
| 6 | 2.24 | 44 | 8.96 | 90 | (0) 99 | 70 (27) | 97 | 85 (14) | 99 | | | | | | | | | | |
| 6 | 2.24 | 45 | 8.96 | | (9) | 50 (44) | 90 | 60 (33) | 90 | | | | | | | | | | |
| 6 | 2.24 | 46 | 8.96 | 100 | (0) 99 | 80 (17) | 97 | 95 (4) | 99 | | | | | | | | | | |
| 6 | 2.24 | 47 | 8.96 | 100 | (0) 99 | 95 (4) | 99 | 100 (0) | 98 | | | | | | | | | | |
| 6 | 2.24 | 48 | 8.96 | 99 | (0) 99 | 70 (27) | 96 | 75 (16) | 90 | | | | | | | | | | |
| 6 | 2.24 | 49 | 8.96 | | | 99 (0) | 99 | 55 (31) | 80 | | | | | | | | | | |
| 6 | 2.24 | 50 | 8.96 | | | 98 (1) | 99 | 70 (12) | 80 | | | | | | | | | | |
| 6 | 2.24 | 51 | 8.96 | | | 60 (38) | 98 | 80 (11) | 90 | | | | | | | | | | |
| 6 | 2.24 | 52 | 8.96 | | | 70 (28) | 98 | 90 (0) | 90 | | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 6 | 2.24 | 53 | 8.96 | | | 90 | 98 (8) | 80 (11) | 90 | | | | | | | | | | | |
| 6 | 2.24 | 54 | 8.96 | | | 50 | 60 (16) | 40 (38) | 65 | | | | | | | | | | | |
| 6 | 2.24 | 55 | 8.96 | | | 80 | 75 (0) | 60 (25) | 80 | | | | | | | | | | | |
| 6 | 2.24 | 56 | 8.96 | | | 30 | 100 (70) | 80 (0) | 80 | | | | | | | | | | | |
| 6 | 2.24 | 57 | 8.96 | | | 40 | 95 (57) | 80 (5) | 85 | | | | | | | | | | | |
| 6 | 2.24 | 58 | 8.96 | | | 98 | 95 (0) | 90 (0) | 85 | | | | | | | | | | | |
| 6 | 2.24 | 59 | 8.96 | | | 30 | 95 (68) | 25 (70) | 85 | | | | | | | | | | | |
| 6 | 2.24 | 60 | 8.96 | | | 20 | 95 (78) | 30 (64) | 85 | | | | | | | | | | | |
| 6 | 2.24 | 61 | 8.96 | | | 25 | 95 (73) | 35 (58) | 85 | | | | | | | | | | | |
| 6 | 2.24 | 62 | 8.96 | | | 0 | 95 (100) | 35 (58) | 85 | | | | | | | | | | | |
| 6 | 2.24 | 63 | 8.96 | | | 45 | 90 (50) | 60 (20) | 75 | | | | | | | | | | | |
| 6 | 2.24 | 64 | 8.96 | | | 75 | 80 (6) | 50 (33) | 75 | | | | | | | | | | | |
| 6 | 2.24 | 65 | 8.96 | | | 98 | 80 (0) | 80 (0) | 75 | | | | | | | | | | | |
| 6 | 2.24 | 66 | 8.96 | | | 20 | 80 (75) | 30 (60) | 75 | | | | | | | | | | | |
| 6 | 2.24 | 67 | 8.96 | | | 35 | 80 (56) | 55 (26) | 75 | | | | | | | | | | | |
| 6 | 2.24 | 68 | 8.96 | | | 45 | 95 (52) | 90 (0) | 75 | | | | | | | | | | | |
| 6 | 2.24 | 69 | 8.96 | | | 70 | 95 (26) | 50 (33) | 75 | | | | | | | | | | | |
| 6 | 2.24 | 70 | 8.96 | | | 80 | 95 (15) | 75 (0) | 75 | | | | | | | | | | | |
| 6 | 2.24 | 71 | 8.96 | | | 35 | 65 (46) | 45 (40) | 75 | | | | | | | | | | | |
| 6 | 2.24 | 72 | 8.96 | | | 20 | 85 (76) | 55 (26) | 75 | | | | | | | | | | | |
| 6 | 2.24 | 73 | 8.96 | | | 30 | 75 (60) | 35 (58) | 85 | | | | | | | | | | | |
| 6 | 2.24 | 74 | 8.96 | | | 30 | 95 (68) | 60 (25) | 80 | | | | | | | | | | | |
| 6 | 2.24 | 75 | 8.96 | | | 20 | 95 (78) | 60 (25) | 80 | | | | | | | | | | | |
| 6 | 2.24 | 76 | 8.96 | | | 35 | 95 (63) | 65 (18) | 80 | | | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 6 | 2.24 | 77 | 8.96 | | | 80 (15) | 95 | 70 (12) | 80 | | | | | | | | | | |
| 6 | 2.24 | 78 | 8.96 | | | 20 (77) | 90 | 60 (29) | 85 | | | | | | | | | | |
| 6 | 2.24 | 79 | 8.96 | | | 95 (0) | 90 | 90 (0) | 85 | | | | | | | | | | |
| 6 | 2.24 | 80 | 8.96 | | | 30 (70) | 100 | 90 (5) | 95 | | | | | | | | | | |
| 6 | 2.24 | 81 | 8.96 | | | 20 (80) | 100 | 85 (10) | 95 | | | | | | | | | | |
| 6 | 2.24 | 82 | 8.96 | | | 15 (85) | 100 | 40 (57) | 95 | | | | | | | | | | |
| 6 | 2.24 | 83 | 8.96 | | | 35 (65) | 100 | 80 (15) | 95 | | | | | | | | | | |
| 6 | 2.24 | 84 | 8.96 | | | 35 (65) | 100 | 60 (36) | 95 | | | | | | | | | | |
| 6 | 2.24 | 85 | 8.96 | | | 45 (55) | 100 | 90 (5) | 95 | | | | | | | | | | |
| 6 | 2.24 | 86 | 8.96 | | | 10 (86) | 75 | 55 (31) | 80 | | | | | | | | | | |
| 6 | 2.24 | 87 | 8.96 | | | 70 (26) | 95 | 80 (5) | 85 | | | | | | | | | | |
| 6 | 2.24 | 88 | 8.96 | | | 30 (68) | 95 | 60 (33) | 90 | | | | | | | | | | |
| 6 | 2.24 | 89 | 8.96 | | | 40 (57) | 95 | 95 (0) | 90 | | | | | | | | | | |
| 6 | 2.24 | 90 | 8.96 | | | 25 (73) | 95 | 75 (16) | 90 | | | | | | | | | | |
| 6 | 2.24 | 91 | 8.96 | | | 70 (26) | 95 | 90 (0) | 90 | | | | | | | | | | |
| 6 | 2.24 | 92 | 8.96 | | | 20 (78) | 95 | 75 (16) | 90 | | | | | | | | | | |
| 6 | 2.24 | 93 | 8.96 | | | 35 (65) | 100 | 70 (22) | 90 | | | | | | | | | | |
| 6 | 2.24 | 94 | 8.96 | | | 95 (5) | 100 | 70 (6) | 75 | | | | | | | | | | |
| 6 | 2.24 | 95 | 8.96 | | | 80 (20) | 100 | 95 (0) | 75 | | | | | | | | | | |
| 6 | 2.24 | 96 | 8.96 | | | 45 (52) | 95 | 55 (31) | 80 | | | | | | | | | | |
| 6 | 2.24 | 97 | 8.96 | | | 60 (36) | 95 | 70 (12) | 80 | | | | | | | | | | |
| 6 | 2.24 | 98 | 8.96 | | | 20 (75) | 80 | 75 (0) | 70 | | | | | | | | | | |
| 6 | 2.24 | 99 | 8.96 | | | 30 (64) | 85 | 90 (0) | 90 | | | | | | | | | | |
| 6 | 2.24 | 100 | 8.96 | | | 30 (64) | 85 | 95 (0) | 90 | | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 6 | 2.24 | 101 | 8.96 | | | 35 (58) | 85 | 95 (0) | 90 | | | | | | | | | | |
| 6 | 2.24 | 102 | 8.96 | | | 30 (64) | 85 | 80 (11) | 90 | | | | | | | | | | |
| 6 | 2.24 | 103 | 8.96 | | | 20 (76) | 85 | 95 (0) | 90 | | | | | | | | | | |
| 6 | 2.24 | 104 | 8.96 | | | 30 (64) | 85 | 90 (0) | 90 | | | | | | | | | | |
| 6 | 2.24 | 105 | 8.96 | | | 100 (0) | 85 | 90 (0) | 90 | | | | | | | | | | |
| 6 | 2.24 | 106 | 8.96 | | | 40 (57) | 95 | 35 (56) | 80 | | | | | | | | | | |
| 6 | 2.24 | 107 | 8.96 | | | 40 (57) | 95 | 100 (0) | 80 | | | | | | | | | | |
| 6 | 2.24 | 108 | 8.96 | | | 30 (53) | 65 | 70 (0) | 60 | | | | | | | | | | |
| 6 | 2.24 | 109 | 8.96 | | | 25 (73) | 95 | 90 (0) | 85 | | | | | | | | | | |
| 6 | 2.24 | 110 | 8.96 | | | 95 (0) | 95 | 75 (11) | 85 | | | | | | | | | | |
| 6 | 2.24 | 111 | 8.96 | | | 55 (15) | 65 | 30 (50) | 60 | | | | | | | | | | |
| 6 | 2.24 | 112 | 8.96 | | | 55 (38) | 90 | 45 (40) | 75 | | | | | | | | | | |
| 6 | 2.24 | 113 | 8.96 | | | 80 (11) | 90 | 55 (26) | 75 | | | | | | | | | | |
| 6 | 2.24 | 114 | 8.96 | | | 70 (22) | 90 | 70 (6) | 75 | | | | | | | | | | |
| 6 | 2.24 | 115 | 8.96 | | | 30 (66) | 90 | 60 (20) | 75 | | | | | | | | | | |
| 6 | 2.24 | 116 | 8.96 | | | 35 (61) | 90 | 45 (40) | 75 | | | | | | | | | | |
| 6 | 2.24 | 117 | 8.96 | | | 50 (37) | 80 | 80 (0) | 75 | | | | | | | | | | |
| 6 | 2.24 | 118 | 8.96 | | | 95 (0) | 80 | 80 (0) | 85 | | | | | | | | | | |
| 6 | 2.24 | 119 | 8.96 | | | 100 (0) | 90 | 90 (0) | 90 | | | | | | | | | | |
| 6 | 2.24 | 120 | 8.96 | | | 55 (38) | 90 | 85 (5) | 90 | | | | | | | | | | |
| 6 | 2.24 | 121 | 8.96 | | | 80 (11) | 90 | 85 (5) | 90 | | | | | | | | | | |
| 6 | 2.24 | 122 | 8.96 | | | 30 (66) | 90 | 80 (11) | 90 | | | | | | | | | | |
| 6 | 2.24 | 123 | 8.96 | | | 55 (38) | 90 | 40 (55) | 90 | | | | | | | | | | |
| 6 | 2.24 | 124 | 8.96 | | | 55 (38) | 90 | 70 (22) | 90 | | | | | | | | | | |

TABLE II-continued

% PLANT INHIBITION AND % SAFENING EFFECT ()

| HERBICIDE NO. | RATE | ANTIDOTE NO. | RATE | RICE W | RICE WO | SORGHUM GRAIN W | SORGHUM GRAIN WO | WHEAT W | WHEAT WO | CORN W | CORN WO | COTTON W | COTTON WO | SOYBEAN W | SOYBEAN WO | HEMP SESBANIA W | HEMP SESBANIA WO | VELVET LEAF W | VELVET LEAF WO |
|---|---|---|---|---|---|---|---|---|---|---|---|---|---|---|---|---|---|---|---|
| 6 | 2.24 | 125 | 8.96 | | | 35 (61) | 90 | 80 (20) | 100 | | | | | | | | | | |
| 6 | 2.24 | 126 | 8.96 | | | 50 (47) | 95 | 90 | 85 | | | | | | | | | | |
| 6 | 2.24 | 127 | 8.96 | | | 60 (36) | 95 | 95 | 85 | | | | | | | | | | |
| 6 | 2.24 | 128 | 8.96 | | | 40 (57) | 95 | 70 (17) | 85 | | | | | | | | | | |
| 6 | 2.24 | 129 | 8.96 | | | 50 (47) | 95 | 80 (5) | 85 | | | | | | | | | | |
| 6 | 2.24 | 130 | 8.96 | | | 80 (15) | 95 | 65 (23) | 85 | | | | | | | | | | |
| 6 | 2.24 | 131 | 8.96 | | | 35 (63) | 95 | 80 (5) | 85 | | | | | | | | | | |
| 6 | 2.24 | 132 | 8.96 | | | 30 (68) | 95 | 75 (11) | 85 | | | | | | | | | | |
| 6 | 2.24 | 133 | 8.96 | | | 95 (0) | 90 | 100 (0) | 85 | | | | | | | | | | |
| 6 | 2.24 | 134 | 8.96 | | | 55 (38) | 90 | 95 (0) | 85 | | | | | | | | | | |
| 6 | 2.24 | 135 | 8.96 | | | 55 (38) | 95 | 95 (0) | 85 | | | | | | | | | | |
| 6 | 2.24 | 136 | 8.96 | | | 40 (57) | 95 | 90 (5) | 95 | | | | | | | | | | |
| 6 | 2.24 | 137 | 8.96 | | | 95 (0) | 95 | 90 (5) | 95 | | | | | | | | | | |
| 6 | 2.24 | 138 | 8.96 | | | 90 (5) | 95 | 70 (26) | 75 | | | | | | | | | | |
| 6 | 2.24 | 139 | 8.96 | | | 70 (17) | 85 | 70 (6) | 75 | | | | | | | | | | |
| 6 | 2.24 | 140 | 8.96 | | | 65 (23) | 85 | 80 (0) | 80 | | | | | | | | | | |
| 6 | 2.24 | 141 | 8.96 | | | 70 (12) | 80 | 95 (0) | 80 | | | | | | | | | | |
| 6 | 2.24 | 142 | 8.96 | | | 80 (0) | 80 | 70 (12) | 80 | | | | | | | | | | |
| 6 | 2.24 | 143 | 8.96 | | | 80 (0) | 80 | 60 (25) | 80 | | | | | | | | | | |
| 6 | 2.24 | 144 | 8.96 | | | 60 (25) | 80 | 30 (62) | 80 | | | | | | | | | | |
| 6 | 2.24 | 145 | 8.96 | | | 20 (75) | 80 | 70 (12) | 80 | | | | | | | | | | |
| 6 | 2.24 | 146 | 8.96 | | | 70 (12) | 80 | 50 (37) | 80 | | | | | | | | | | |
| 6 | 2.24 | 147 | 8.96 | | | 90 (0) | 80 | 80 (0) | 80 | | | | | | | | | | |
| 6 | 2.24 | 148 | 8.96 | | | 95 (0) | 80 | 65 (18) | 80 | | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 6 | 2.24 | 149 | 8.96 | | | 50 (44) | 90 | 85 (5) | 90 | | | | | | | | | | |
| 6 | 2.24 | 150 | 8.96 | | | 45 (50) | 90 | 90 (0) | 90 | | | | | | | | | | |
| 6 | 2.24 | 151 | 8.96 | | | 75 (11) | 85 | 90 (0) | 90 | | | | | | | | | | |
| 6 | 2.24 | 152 | 8.96 | | | 80 (5) | 85 | 90 (0) | 90 | | | | | | | | | | |
| 6 | 2.24 | 153 | 8.96 | | | 75 (11) | 85 | 80 (11) | 90 | | | | | | | | | | |
| 6 | 2.24 | 154 | 8.96 | | | 10 (88) | 90 | 60 (29) | 85 | | | | | | | | | | |
| 6 | 2.24 | 155 | 8.96 | | | 75 (11) | 85 | 75 (16) | 90 | | | | | | | | | | |
| 6 | 2.24 | 156 | 8.96 | | | 80 (5) | 85 | 95 (0) | 90 | | | | | | | | | | |
| 6 | 2.24 | 157 | 8.96 | | | 50 (41) | 85 | 75 (16) | 80 | | | | | | | | | | |
| 6 | 2.24 | 158 | 8.96 | | | 85 (0) | 70 | 80 (0) | 80 | | | | | | | | | | |
| 6 | 2.24 | 159 | 8.96 | | | 30 (57) | 70 | 70 (12) | 80 | | | | | | | | | | |
| 6 | 2.24 | 160 | 8.96 | | | 0 (57) | 70 | 70 (12) | 80 | | | | | | | | | | |
| 6 | 2.24 | 161 | 8.96 | | | 40 (42) | 70 | 45 (43) | 80 | | | | | | | | | | |
| 6 | 2.24 | 162 | 8.96 | | | 45 (35) | 70 | 40 (50) | 80 | | | | | | | | | | |
| 6 | 2.24 | 163 | 8.96 | | | 45 (35) | 70 | 70 (12) | 70 | | | | | | | | | | |
| 6 | 2.24 | 164 | 8.96 | | | 80 (11) | 90 | 65 (7) | 85 | | | | | | | | | | |
| 6 | 2.24 | 165 | 8.96 | | | 35 (63) | 95 | 25 (70) | 85 | | | | | | | | | | |
| 6 | 2.24 | 166 | 8.96 | | | 35 (61) | 90 | 70 (22) | 90 | | | | | | | | | | |
| 6 | 2.24 | 167 | 8.96 | | | 95 (0) | 90 | 100 (0) | 85 | | | | | | | | | | |
| 6 | 2.24 | 168 | 8.96 | | | 10 (88) | 90 | 80 (5) | 85 | | | | | | | | | | |
| 6 | 2.24 | 169 | 8.96 | | | 35 (61) | 90 | 55 (38) | 90 | | | | | | | | | | |
| 6 | 2.24 | 170 | 8.96 | | | 50 (44) | 90 | 65 (27) | 90 | | | | | | | | | | |
| 6 | 2.24 | 171 | 8.96 | | | 35 (61) | 90 | 100 (0) | 90 | | | | | | | | | | |
| 6 | 2.24 | 172 | 8.96 | | | 20 (77) | 90 | 50 (37) | 80 | | | | | | | | | | |

TABLE II-continued

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 6 | 2.24 | 173 | 8.96 | | | 35 (56) | 80 | 20 (76) | 85 | | | | | | | | | | |
| 6 | 2.24 | 174 | 8.96 | | | 30 (62) | 80 | 30 (64) | 85 | | | | | | | | | | |
| 6 | 2.24 | 175 | 8.96 | | | 35 (53) | 75 | 40 (11) | 45 | | | | | | | | | | |
| 6 | 2.24 | 176 | 8.96 | | | 45 (43) | 80 | 40 (52) | 85 | | | | | | | | | | |
| 6 | 2.24 | 177 | 8.96 | | | 35 (53) | 75 | 50 (0) | 45 | | | | | | | | | | |
| 6 | 2.24 | 178 | 8.96 | | | 35 (53) | 75 | 35 (22) | 45 | | | | | | | | | | |
| 6 | 2.24 | 179 | 8.96 | | | 35 (53) | 75 | 65 (0) | 45 | | | | | | | | | | |
| 6 | 2.24 | 180 | 8.96 | | | 35 (53) | 75 | 65 (0) | 45 | | | | | | | | | | |
| 6 | 2.24 | 181 | 8.96 | | | 0 (100) | 75 | 80 (0) | 45 | | | | | | | | | | |
| 6 | 2.24 | 182 | 8.96 | | | 25 (68) | 80 | 100 (0) | 100 | | | | | | | | | | |
| 6 | 2.24 | 183 | 8.96 | | | 40 (50) | 80 | 100 (0) | 100 | | | | | | | | | | |
| 6 | 2.24 | 184 | 8.96 | | | 60 (7) | 65 | 95 (0) | 75 | | | | | | | | | | |
| 6 | 2.24 | 185 | 8.96 | | | 55 (38) | 90 | 90 (0) | 75 | | | | | | | | | | |
| 6 | 2.24 | 186 | 8.96 | | | 40 (38) | 65 | 85 (5) | 90 | | | | | | | | | | |
| 6 | 2.24 | 187 | 8.96 | | | 30 (66) | 90 | 85 (0) | 85 | | | | | | | | | | |
| 6 | 2.24 | 188 | 8.96 | | | 70 (26) | 95 | 90 (10) | 100 | | | | | | | | | | |
| 6 | 2.24 | 189 | 8.96 | | | 50 (47) | 95 | 75 (25) | 100 | | | | | | | | | | |
| 6 | 2.24 | 190 | 8.96 | | | 35 (63) | 95 | 55 (26) | 75 | | | | | | | | | | |
| 6 | 2.24 | 191 | 8.96 | | | 30 (68) | 95 | 90 (0) | 75 | | | | | | | | | | |
| 6 | 2.24 | 192 | 8.96 | | | 40 (57) | 95 | 65 (13) | 75 | | | | | | | | | | |
| 6 | 2.24 | 193 | 8.96 | | | 45 (55) | 100 | 100 (0) | 90 | | | | | | | | | | |
| 6 | 2.24 | 194 | 8.96 | | | 45 (55) | 100 | 90 (0) | 90 | | | | | | | | | | |
| 6 | 2.24 | 195 | 8.96 | | | 50 (50) | 100 | 85 (5) | 90 | | | | | | | | | | |
| 6 | 2.24 | 196 | 8.96 | | | 35 (63) | 95 | 70 (26) | 95 | | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 6 | 2.24 | 197 | 8.96 | | | 60 (36) | 95 | 70 (22) | 90 | | | | | | | | | | |
| 6 | 2.24 | 198 | 8.96 | | | 35 (63) | 95 | 95 (0) | 95 | | | | | | | | | | |
| 6 | 2.24 | 199 | 8.96 | | | 80 (20) | 100 | 70 (0) | 65 | | | | | | | | | | |
| 6 | 2.24 | 200 | 8.96 | | | 75 (0) | 75 | 50 (33) | 75 | | | | | | | | | | |
| 6 | 2.24 | 201 | 8.96 | | | 40 (55) | 90 | 0 (100) | 65 | | | | | | | | | | |
| 6 | 2.24 | 202 | 0.28 | | | 0 (100) | 85 | 15 (82) | 85 | | | | | | | | | | |
| 10 | 6.72 | 37 | 8.96 | 50 | 90 | 70 (22) | 90 | 70 (12) | 80 | | | | | | | | | | |
| 10 | 6.72 | 38 | 8.96 | 45 | 85 | 60 (20) | 75 | 80 (0) | 80 | | | | | | | | | | |
| 10 | 6.72 | 39 | 8.96 | 90 (47) | 85 | 70 (20) | 80 | 90 (0) | 80 | | | | | | | | | | |
| 10 | 6.72 | 40 | 8.96 | 50 (0) | 90 | 85 (12) | 80 | 95 (0) | 95 | | | | | | | | | | |
| 10 | 6.72 | 41 | 8.96 | 90 (44) | 90 | 60 (0) | 95 | 80 (0) | 85 | | | | | | | | | | |
| 10 | 6.72 | 42 | 8.96 | 90 (0) | 90 | 40 (36) | 80 | 50 (5) | 75 | | | | | | | | | | |
| 10 | 6.72 | 43 | 8.96 | 97 (0) | 95 | 60 (50) | 75 | 80 (33) | 80 | | | | | | | | | | |
| 10 | 6.72 | 44 | 8.96 | 10 (89) | 95 | 50 (20) | 95 | 60 (0) | 97 | | | | | | | | | | |
| 10 | 6.72 | 45 | 8.96 | 55 (15) | 65 | 50 (47) | | | | | | | | | | | | | |
| 10 | 6.72 | 46 | 8.96 | 90 (5) | 95 | 60 (36) | 95 | 75 (22) | 97 | | | | | | | | | | |
| 10 | 6.72 | 47 | 8.96 | 90 (0) | 90 | 85 (5) | 90 | 95 (0) | 95 | | | | | | | | | | |
| 10 | 6.72 | 48 | 8.96 | 65 (0) | 95 | 65 (32) | 97 | 50 (41) | 85 | | | | | | | | | | |
| 10 | 6.72 | 49 | 8.96 | 90 (31) | 95 | | | | | | | | | | | | | | |
| 10 | 6.72 | 50 | 8.96 | 95 (5) | 95 | | | | | | | | | | | | | | |
| 10 | 6.72 | 51 | 8.96 | 75 (0) | 80 | | | | | | | | | | | | | | |
| 10 | 6.72 | 52 | 8.96 | 70 (6) | 80 | | | | | | | | | | | | | | |
| 10 | 6.72 | 53 | 8.96 | 70 (12) | 80 | | | | | | | | | | | | | | |
| 10 | 6.72 | 54 | 8.96 | 75 (6) | 80 | | | | | | | | | | | | | | |

TABLE II-continued

% PLANT INHIBITION AND % SAFENING EFFECT ()

| HERBICIDE | | ANTIDOTE | | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO | W |
| 10 | 6.72 | 55 | 8.96 | 20 | 80 | | | | | | | | | | | | | | | |
| 10 | 6.72 | 56 | 8.96 | 50 | (75) 98 | | | | | | | | | | | | | | | |
| 10 | 4.48 | 57 | 8.96 | 65 | (48) 95 | | | | | | | | | | | | | | | |
| 10 | 4.48 | 58 | 8.96 | 98 | (31) 95 | | | | | | | | | | | | | | | |
| 10 | 4.48 | 59 | 8.96 | 65 | (0) 95 | | | | | | | | | | | | | | | |
| 10 | 4.48 | 60 | 8.96 | 70 | (31) 95 | | | | | | | | | | | | | | | |
| 10 | 4.48 | 61 | 8.96 | 55 | (26) 95 | | | | | | | | | | | | | | | |
| 10 | 4.48 | 62 | 8.96 | 60 | (42) 95 | | | | | | | | | | | | | | | |
| 10 | 4.48 | 63 | 8.96 | 45 | (36) 90 | | | | | | | | | | | | | | | |
| 10 | 4.48 | 64 | 8.96 | 60 | (50) 90 | | | | | | | | | | | | | | | |
| 10 | 4.48 | 65 | 8.96 | 90 | (33) 90 | | | | | | | | | | | | | | | |
| 10 | 4.48 | 66 | 8.96 | 50 | (0) 90 | | | | | | | | | | | | | | | |
| 10 | 4.48 | 67 | 8.96 | 45 | (44) 90 | | | | | | | | | | | | | | | |
| 10 | 4.48 | 68 | 8.96 | 100 | (50) 90 | | | | | | | | | | | | | | | |
| 10 | 4.48 | 69 | 8.96 | 50 | (0) 90 | | | | | | | | | | | | | | | |
| 10 | 4.48 | 70 | 8.96 | 60 | (44) 90 | | | | | | | | | | | | | | | |
| 10 | 4.48 | 71 | 8.96 | 55 | (33) 75 | | | | | | | | | | | | | | | |
| 10 | 4.48 | 72 | 8.96 | 80 | (26) 90 | | | | | | | | | | | | | | | |
| 10 | 4.48 | 73 | 8.96 | 55 | (11) 80 | | | | | | | | | | | | | | | |
| 10 | 4.48 | 74 | 8.96 | 60 | (31) 80 | | | | | | | | | | | | | | | |
| 10 | 4.48 | 75 | 8.96 | 40 | (25) 80 | | | | | | | | | | | | | | | |
| 10 | 4.48 | 76 | 8.96 | 75 | (50) 80 | | | | | | | | | | | | | | | |
| 10 | 4.48 | 77 | 8.96 | 60 | (6) 80 | | | | | | | | | | | | | | | |
| 10 | 4.48 | 78 | 8.96 | 95 | (25) 90 | | | | | | | | | | | | | | | |
| | | | | | (0) | | | | | | | | | | | | | | | |

TABLE II-continued

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 10 | 4.48 | 79 | 8.96 | 95 (0) | 90 | | | | | | | | | | | | | | |
| 10 | 4.48 | 80 | 8.96 | 35 (63) | 95 | | | | | | | | | | | | | | |
| 10 | 4.48 | 81 | 8.96 | 80 (15) | 95 | | | | | | | | | | | | | | |
| 10 | 4.48 | 82 | 8.96 | 70 (26) | 95 | | | | | | | | | | | | | | |
| 10 | 4.48 | 83 | 8.96 | 80 (15) | 95 | | | | | | | | | | | | | | |
| 10 | 4.48 | 84 | 8.96 | 95 (0) | 95 | | | | | | | | | | | | | | |
| 10 | 4.48 | 85 | 8.96 | 85 (10) | 95 | | | | | | | | | | | | | | |
| 10 | 4.48 | 96985 | 8.96 | 80 (11) | 90 | | | | | | | | | | | | | | |
| 10 | 4.48 | 96994 | 8.96 | 95 (0) | 95 | | | | | | | | | | | | | | |
| 10 | 4.48 | 96997 | 8.96 | 90 (0) | 90 | | | | | | | | | | | | | | |
| 10 | 4.48 | 89 | 8.96 | 85 (5) | 90 | | | | | | | | | | | | | | |
| 10 | 4.48 | 90 | 8.96 | 85 (0) | 85 | | | | | | | | | | | | | | |
| 10 | 4.48 | 91 | 8.96 | 85 (0) | 85 | | | | | | | | | | | | | | |
| 10 | 4.48 | 92 | 8.96 | 90 (0) | 85 | | | | | | | | | | | | | | |
| 10 | 4.48 | 93 | 8.96 | 45 (50) | 90 | | | | | | | | | | | | | | |
| 10 | 4.48 | 94 | 8.96 | 95 (0) | 85 | | | | | | | | | | | | | | |
| 10 | 4.48 | 95 | 8.96 | 90 (0) | 85 | | | | | | | | | | | | | | |
| 10 | 4.48 | 96 | 8.96 | 80 (11) | 90 | | | | | | | | | | | | | | |
| 10 | 4.48 | 97 | 8.96 | 90 (0) | 90 | | | | | | | | | | | | | | |
| 10 | 4.48 | 98 | 8.96 | 90 (0) | 80 | | | | | | | | | | | | | | |
| 10 | 4.48 | 99 | 8.96 | 90 (5) | 95 | | | | | | | | | | | | | | |
| 10 | 4.48 | 100 | 8.96 | 50 (47) | 95 | | | | | | | | | | | | | | |
| 10 | 4.48 | 101 | 8.96 | 75 (21) | 95 | | | | | | | | | | | | | | |
| 10 | 4.48 | 102 | 8.96 | 80 (15) | 95 | | | | | | | | | | | | | | |

TABLE II-continued

% PLANT INHIBITION AND % SAFENING EFFECT ()

| HERBICIDE | | ANTIDOTE | | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 10 | 4.48 | 103 | 8.96 | 75 | (21) 95 | | | | | | | | | | | | | | |
| 10 | 4.48 | 104 | 8.96 | 60 | (36) 95 | | | | | | | | | | | | | | |
| 10 | 4.48 | 105 | 8.96 | 100 | (0) 95 | | | | | | | | | | | | | | |
| 10 | 4.48 | 106 | 8.96 | 50 | (37) 80 | | | | | | | | | | | | | | |
| 10 | 4.48 | 107 | 8.96 | 75 | (6) 80 | | | | | | | | | | | | | | |
| 10 | 4.48 | 108 | 8.96 | 70 | (12) 80 | | | | | | | | | | | | | | |
| 10 | 4.48 | 109 | 8.96 | 100 | (0) 90 | | | | | | | | | | | | | | |
| 10 | 4.48 | 110 | 8.96 | 85 | (5) 90 | | | | | | | | | | | | | | |
| 10 | 4.48 | 111 | 8.96 | 65 | (18) 80 | | | | | | | | | | | | | | |
| 10 | 4.48 | 112 | 8.96 | 85 | (5) 90 | | | | | | | | | | | | | | |
| 10 | 4.48 | 113 | 8.96 | 60 | (33) 90 | | | | | | | | | | | | | | |
| 10 | 4.48 | 114 | 8.96 | 60 | (33) 90 | | | | | | | | | | | | | | |
| 10 | 4.48 | 115 | 8.96 | 70 | (22) 90 | | | | | | | | | | | | | | |
| 10 | 4.48 | 116 | 8.96 | 85 | (5) 80 | | | | | | | | | | | | | | |
| 10 | 4.48 | 117 | 8.96 | 90 | (0) 80 | | | | | | | | | | | | | | |
| 10 | 4.48 | 118 | 8.96 | 95 | (0) 80 | | | | | | | | | | | | | | |
| 10 | 4.48 | 119 | 8.96 | 90 | (0) 80 | | | | | | | | | | | | | | |
| 10 | 4.48 | 120 | 8.96 | 80 | (15) 95 | | | | | | | | | | | | | | |
| 10 | 4.48 | 121 | 8.96 | 80 | (15) 95 | | | | | | | | | | | | | | |
| 10 | 4.48 | 122 | 8.96 | 85 | (10) 95 | | | | | | | | | | | | | | |
| 10 | 4.48 | 123 | 8.96 | 90 | (5) 95 | | | | | | | | | | | | | | |
| 10 | 4.48 | 124 | 8.96 | 90 | (5) 95 | | | | | | | | | | | | | | |
| 10 | 4.48 | 125 | 8.96 | 85 | (10) 95 | | | | | | | | | | | | | | |
| 10 | 4.48 | 126 | 8.96 | 75 | (16) 90 | | | | | | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 10 | 4.48 | 127 | 8.96 | 90 | 90 | | | | | | | | | | | | | | |
| 10 | 4.48 | 128 | 8.96 | 85 | (0) 90 | | | | | | | | | | | | | | |
| 10 | 4.48 | 129 | 8.96 | 85 | (5) 90 | | | | | | | | | | | | | | |
| 10 | 4.48 | 130 | 8.96 | 90 | (5) 90 | | | | | | | | | | | | | | |
| 10 | 4.48 | 131 | 8.96 | 80 | (0) 90 | | | | | | | | | | | | | | |
| 10 | 4.48 | 132 | 8.96 | 65 | (11) 90 | | | | | | | | | | | | | | |
| 10 | 4.48 | 133 | 8.96 | 90 | (27) 90 | | | | | | | | | | | | | | |
| 10 | 4.48 | 134 | 8.96 | 60 | (0) 90 | | | | | | | | | | | | | | |
| 10 | 4.48 | 135 | 8.96 | 90 | (33) 90 | | | | | | | | | | | | | | |
| 10 | 4.48 | 136 | 8.96 | 90 | (0) 90 | | | | | | | | | | | | | | |
| 10 | 4.48 | 137 | 8.96 | 55 | (0) 90 | | | | | | | | | | | | | | |
| 10 | 4.48 | 138 | 8.96 | 80 | (38) 80 | | | | | | | | | | | | | | |
| 10 | 4.48 | 139 | 8.96 | 90 | (11) 80 | | | | | | | | | | | | | | |
| 10 | 4.48 | 140 | 8.96 | 90 | (0) 85 | | | | | | | | | | | | | | |
| 10 | 4.48 | 141 | 8.96 | 90 | (0) 85 | | | | | | | | | | | | | | |
| 10 | 4.48 | 142 | 8.96 | 45 | (47) 85 | | | | | | | | | | | | | | |
| 10 | 4.48 | 143 | 8.96 | 65 | (23) 85 | | | | | | | | | | | | | | |
| 10 | 4.48 | 144 | 8.96 | 85 | (5) 90 | | | | | | | | | | | | | | |
| 10 | 4.48 | 145 | 8.96 | 60 | (33) 90 | | | | | | | | | | | | | | |
| 10 | 4.48 | 146 | 8.96 | 80 | (11) 90 | | | | | | | | | | | | | | |
| 10 | 4.48 | 147 | 8.96 | 95 | (0) 90 | | | | | | | | | | | | | | |
| 10 | 4.48 | 148 | 8.96 | 95 | (0) 90 | | | | | | | | | | | | | | |
| 10 | 4.48 | 149 | 8.96 | 65 | (27) 90 | | | | | | | | | | | | | | |
| 10 | 4.48 | 150 | 8.96 | 90 | (0) 85 | | | | | | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 10 | 4.48 | 151 | 8.96 | 65 (31) | 95 | | | | | | | | | | | | | | |
| 10 | 4.48 | 152 | 8.96 | 95 (0) | 95 | | | | | | | | | | | | | | |
| 10 | 4.48 | 153 | 8.96 | 90 (5) | 95 | | | | | | | | | | | | | | |
| 10 | 4.48 | 154 | 8.96 | 70 (22) | 90 | | | | | | | | | | | | | | |
| 10 | 4.48 | 155 | 8.96 | 75 (21) | 95 | | | | | | | | | | | | | | |
| 10 | 4.48 | 156 | 8.96 | 80 (15) | 95 | | | | | | | | | | | | | | |
| 10 | 4.48 | 157 | 8.96 | 90 (5) | 95 | | | | | | | | | | | | | | |
| 10 | 4.48 | 158 | 8.96 | 100 (0) | 90 | | | | | | | | | | | | | | |
| 10 | 4.48 | 159 | 8.96 | 80 (11) | 90 | | | | | | | | | | | | | | |
| 10 | 4.48 | 160 | 8.96 | 80 (11) | 90 | | | | | | | | | | | | | | |
| 10 | 4.48 | 161 | 8.96 | 80 (11) | 90 | | | | | | | | | | | | | | |
| 10 | 4.48 | 162 | 8.96 | 95 (0) | 90 | | | | | | | | | | | | | | |
| 10 | 4.48 | 163 | 8.96 | 90 (0) | 85 | | | | | | | | | | | | | | |
| 10 | 4.48 | 164 | 8.96 | 95 (0) | 90 | | | | | | | | | | | | | | |
| 10 | 4.48 | 165 | 8.96 | 90 (0) | 90 | | | | | | | | | | | | | | |
| 10 | 4.48 | 166 | 8.96 | 75 (16) | 90 | | | | | | | | | | | | | | |
| 10 | 4.48 | 167 | 8.96 | 95 (0) | 90 | | | | | | | | | | | | | | |
| 10 | 4.48 | 168 | 8.96 | 90 (0) | 90 | | | | | | | | | | | | | | |
| 10 | 4.48 | 169 | 8.96 | 90 (0) | 90 | | | | | | | | | | | | | | |
| 10 | 4.48 | 170 | 8.96 | 70 (22) | 90 | | | | | | | | | | | | | | |
| 10 | 4.48 | 171 | 8.96 | 85 (5) | 90 | | | | | | | | | | | | | | |
| 10 | 4.48 | 172 | 8.96 | 90 (0) | 90 | | | | | | | | | | | | | | |
| 10 | 4.48 | 173 | 8.96 | 90 (0) | 80 | | | | | | | | | | | | | | |
| 10 | 4.48 | 174 | 8.96 | 75 (6) | 80 | | | | | | | | | | | | | | |

TABLE II-continued
% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 10 | 4.48 | 175 | 8.96 | 75 | 90 | | | | | | | | | | | | | | |
| 10 | 4.48 | 176 | 8.96 | 90 | 80 | | | | | | | | | | | | | | |
| | | | | (16) | | | | | | | | | | | | | | | |
| 10 | 4.48 | 177 | 8.96 | 75 | 90 | | | | | | | | | | | | | | |
| | | | | (0) | | | | | | | | | | | | | | | |
| 10 | 4.48 | 178 | 8.96 | 65 | 90 | | | | | | | | | | | | | | |
| | | | | (16) | | | | | | | | | | | | | | | |
| 10 | 4.48 | 179 | 8.96 | 80 | 90 | | | | | | | | | | | | | | |
| | | | | (27) | | | | | | | | | | | | | | | |
| 10 | 4.48 | 180 | 8.96 | 80 | 90 | | | | | | | | | | | | | | |
| | | | | (11) | | | | | | | | | | | | | | | |
| 10 | 4.48 | 181 | 8.96 | 85 | 90 | | | | | | | | | | | | | | |
| | | | | (11) | | | | | | | | | | | | | | | |
| 10 | 4.48 | 182 | 8.96 | 80 | 90 | | | | | | | | | | | | | | |
| | | | | (5) | | | | | | | | | | | | | | | |
| 10 | 4.48 | 183 | 8.96 | 75 | 90 | | | | | | | | | | | | | | |
| | | | | (11) | | | | | | | | | | | | | | | |
| 10 | 4.48 | 184 | 8.96 | 90 | 90 | | | | | | | | | | | | | | |
| | | | | (16) | | | | | | | | | | | | | | | |
| 10 | 4.48 | 185 | 8.96 | 45 | 80 | | | | | | | | | | | | | | |
| | | | | (0) | | | | | | | | | | | | | | | |
| 10 | 4.48 | 186 | 8.96 | 90 | 75 | | | | | | | | | | | | | | |
| | | | | (43) | | | | | | | | | | | | | | | |
| 10 | 4.48 | 187 | 8.96 | 75 | 95 | | | | | | | | | | | | | | |
| | | | | (0) | | | | | | | | | | | | | | | |
| 10 | 4.48 | 188 | 8.96 | 75 | 95 | | | | | | | | | | | | | | |
| | | | | (21) | | | | | | | | | | | | | | | |
| 10 | 4.48 | 189 | 8.96 | 80 | 95 | | | | | | | | | | | | | | |
| | | | | (21) | | | | | | | | | | | | | | | |
| 10 | 4.48 | 190 | 8.96 | 90 | 95 | | | | | | | | | | | | | | |
| | | | | (15) | | | | | | | | | | | | | | | |
| 10 | 4.48 | 191 | 8.96 | 95 | 95 | | | | | | | | | | | | | | |
| | | | | (5) | | | | | | | | | | | | | | | |
| 10 | 4.48 | 192 | 8.96 | 80 | 95 | | | | | | | | | | | | | | |
| | | | | (0) | | | | | | | | | | | | | | | |
| 10 | 4.48 | 193 | 8.96 | 80 | 95 | | | | | | | | | | | | | | |
| | | | | (15) | | | | | | | | | | | | | | | |
| 10 | 4.48 | 194 | 8.96 | 90 | 95 | | | | | | | | | | | | | | |
| | | | | (15) | | | | | | | | | | | | | | | |
| 10 | 4.48 | 195 | 8.96 | 80 | 95 | | | | | | | | | | | | | | |
| | | | | (5) | | | | | | | | | | | | | | | |
| 10 | 4.48 | 196 | 8.96 | 70 | 100 | | | | | | | | | | | | | | |
| | | | | (15) | | | | | | | | | | | | | | | |
| 10 | 4.48 | 197 | 8.96 | 80 | 100 | | | | | | | | | | | | | | |
| | | | | (30) | | | | | | | | | | | | | | | |
| 10 | 4.48 | 198 | 8.96 | 90 | 100 | | | | | | | | | | | | | | |
| | | | | (20) | | | | | | | | | | | | | | | |
| | | | | (10) | | | | | | | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 10 | 4.48 | 199 | 8.96 | 95 | 70 | | | | | | | | | | | | | | |
| 10 | 4.48 | 200 | 8.96 | 90 (0) | 90 | | | | | | | | | | | | | | |
| 10 | 4.48 | 201 | 8.96 | 75 (0) | 80 | | | | | | | | | | | | | | |
| 10 | 4.48 | 202 | 0.28 | 0 (6) | 90 | | | | | | | | | | | | | | |
| 10 | 4.48 | 202 | 8.96 | 0 (100) | | | | | | | | | | | | | | | |
| 15 | 1.12 | 45 | 8.96 | | | | | | | 60 | 75 | | | | | | | | |
| 15 | 1.12 | 49 | 8.96 | | | | | | | 80 (20) | 85 | | | | | | | | |
| 15 | 1.12 | 50 | 8.96 | | | | | | | 85 (5) | 85 | | | | | | | | |
| 15 | 1.12 | 51 | 8.96 | | | | | | | 75 (0) | 70 | | | | | | | | |
| 15 | 1.12 | 52 | 8.96 | | | | | | | 80 (0) | 70 | | | | | | | | |
| 15 | 1.12 | 53 | 8.96 | | | | | | | 50 (0) | 70 | | | | | | | | |
| 15 | 1.12 | 54 | 8.96 | | | | | | | 85 (28) | 85 | | | | | | | | |
| 15 | 1.12 | 55 | 8.96 | | | | | | | 30 (0) | 90 | | | | | | | | |
| 15 | 1.12 | 56 | 8.96 | | | | | | | 30 (66) | 90 | | | | | | | | |
| 15 | 1.12 | 57 | 8.96 | | | | | | | 80 (66) | 90 | | | | | | | | |
| 15 | 1.12 | 58 | 8.96 | | | | | | | 95 (11) | 90 | | | | | | | | |
| 15 | 1.12 | 59 | 8.96 | | | | | | | 20 (0) | 90 | | | | | | | | |
| 15 | 1.12 | 60 | 8.96 | | | | | | | 65 (77) | 90 | | | | | | | | |
| 15 | 1.12 | 61 | 8.96 | | | | | | | 75 (27) | 90 | | | | | | | | |
| 15 | 1.12 | 62 | 8.96 | | | | | | | 30 (16) | 90 | | | | | | | | |
| 15 | 1.12 | 63 | 8.96 | | | | | | | 30 (66) | 90 | | | | | | | | |
| 15 | 2.24 | 64 | 8.96 | | | | | | | 95 (66) | 90 | | | | | | | | |
| 15 | 2.24 | 65 | 8.96 | | | | | | | 95 (0) | 90 | | | | | | | | |
| 15 | 2.24 | 66 | 8.96 | | | | | | | 50 (0) | 90 | | | | | | | | |
| 15 | 2.24 | 67 | 8.96 | | | | | | | 50 (44) | 90 | | | | | | | | |
| 15 | 2.24 | | 8.96 | | | | | | | 50 (44) | | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 15 | 2.24 | 68 | 8.96 | | | | | | | 40 | 85 | | | | | | | | |
| 15 | 2.24 | 69 | 8.96 | | | | | | | 45 (52) | 85 | | | | | | | | |
| 15 | 2.24 | 70 | 8.96 | | | | | | | 35 (47) | 85 | | | | | | | | |
| 15 | 2.24 | 71 | 8.96 | | | | | | | 25 (58) | 75 | | | | | | | | |
| 15 | 2.24 | 72 | 8.96 | | | | | | | 65 (66) | 75 | | | | | | | | |
| 15 | 2.24 | 73 | 8.96 | | | | | | | 35 (13) | 75 | | | | | | | | |
| 15 | 2.24 | 74 | 8.96 | | | | | | | 80 (53) | 80 | | | | | | | | |
| 15 | 2.24 | 75 | 8.96 | | | | | | | 75 (0) | 80 | | | | | | | | |
| 15 | 2.24 | 76 | 8.96 | | | | | | | 25 (6) | 80 | | | | | | | | |
| 15 | 2.24 | 77 | 8.96 | | | | | | | 70 (68) | 80 | | | | | | | | |
| 15 | 2.24 | 78 | 8.96 | | | | | | | 65 (12) | 90 | | | | | | | | |
| 15 | 2.24 | 79 | 8.96 | | | | | | | 90 (27) | 90 | | | | | | | | |
| 15 | 2.24 | 80 | 8.96 | | | | | | | 40 (0) | 90 | | | | | | | | |
| 15 | 2.24 | 81 | 8.96 | | | | | | | 20 (55) | 90 | | | | | | | | |
| 15 | 2.24 | 82 | 8.96 | | | | | | | 75 (77) | 90 | | | | | | | | |
| 15 | 2.24 | 83 | 8.96 | | | | | | | 10 (16) | 90 | | | | | | | | |
| 15 | 2.24 | 84 | 8.96 | | | | | | | 45 (88) | 90 | | | | | | | | |
| 15 | 2.24 | 85 | 8.96 | | | | | | | 40 (50) | 90 | | | | | | | | |
| 15 | 2.24 | 86 | 8.96 | | | | | | | 90 (55) | 90 | | | | | | | | |
| 15 | 2.24 | 87 | 8.96 | | | | | | | 80 (0) | 85 | | | | | | | | |
| 15 | 2.24 | 88 | 8.96 | | | | | | | 65 (5) | 90 | | | | | | | | |
| 15 | 2.24 | 89 | 8.96 | | | | | | | 70 (27) | 90 | | | | | | | | |
| 15 | 2.24 | 90 | 8.96 | | | | | | | 60 (22) | 90 | | | | | | | | |
| 15 | 2.24 | 91 | 8.96 | | | | | | | 95 (33) | 90 | | | | | | | | |
| 15 | 2.24 | 91 | 8.96 | | | | | | | (0) | 90 | | | | | | | | |

TABLE II-continued

% PLANT INHIBITION AND % SAFENING EFFECT ()

| HERBICIDE NO. | RATE | ANTIDOTE NO. | RATE | RICE W | RICE WO | SORGHUM GRAIN W | SORGHUM GRAIN WO | WHEAT W | WHEAT WO | CORN W | CORN WO | COTTON W | COTTON WO | SOYBEAN W | SOYBEAN WO | HEMP SESBANIA W | HEMP SESBANIA WO | VELVET LEAF W | VELVET LEAF WO |
|---|---|---|---|---|---|---|---|---|---|---|---|---|---|---|---|---|---|---|---|
| 15 | 2.24 | 92 | 8.96 | | | | | | | 90 | 90 | | | | | | | | |
| 15 | 2.24 | 93 | 8.96 | | | | | | | 45 (0) | 90 | | | | | | | | |
| 15 | 2.24 | 94 | 8.96 | | | | | | | 80 (50) | 90 | | | | | | | | |
| 15 | 2.24 | 95 | 8.96 | | | | | | | 45 (11) | 90 | | | | | | | | |
| 15 | 2.24 | 96 | 8.96 | | | | | | | 60 (50) | 75 | | | | | | | | |
| 15 | 2.24 | 97 | 8.96 | | | | | | | 90 (20) | 75 | | | | | | | | |
| 15 | 2.24 | 98 | 8.96 | | | | | | | 70 (0) | 80 | | | | | | | | |
| 15 | 2.24 | 99 | 8.96 | | | | | | | 20 (12) | 90 | | | | | | | | |
| 15 | 2.24 | 100 | 8.96 | | | | | | | 50 (77) | 90 | | | | | | | | |
| 15 | 2.24 | 101 | 8.96 | | | | | | | 45 (44) | 90 | | | | | | | | |
| 15 | 2.24 | 102 | 8.96 | | | | | | | 85 (50) | 90 | | | | | | | | |
| 15 | 2.24 | 103 | 8.96 | | | | | | | 15 (5) | 90 | | | | | | | | |
| 15 | 2.24 | 104 | 8.96 | | | | | | | 50 (83) | 90 | | | | | | | | |
| 15 | 2.24 | 105 | 8.96 | | | | | | | 90 (44) | 90 | | | | | | | | |
| 15 | 2.24 | 106 | 8.96 | | | | | | | 80 (0) | 90 | | | | | | | | |
| 15 | 2.24 | 107 | 8.96 | | | | | | | 85 (11) | 90 | | | | | | | | |
| 15 | 2.24 | 108 | 8.96 | | | | | | | 50 (5) | 80 | | | | | | | | |
| 15 | 2.24 | 109 | 8.96 | | | | | | | 65 (37) | 95 | | | | | | | | |
| 15 | 2.24 | 110 | 8.96 | | | | | | | 85 (31) | 95 | | | | | | | | |
| 15 | 2.24 | 111 | 8.96 | | | | | | | 70 (10) | 80 | | | | | | | | |
| 15 | 2.24 | 112 | 8.96 | | | | | | | 35 (12) | 90 | | | | | | | | |
| 15 | 2.24 | 113 | 8.96 | | | | | | | 65 (61) | 90 | | | | | | | | |
| 15 | 2.24 | 114 | 8.96 | | | | | | | 50 (27) | 90 | | | | | | | | |
| 15 | 2.24 | 115 | 8.96 | | | | | | | 50 (44) | 90 | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 15 | 2.24 | 116 | 8.96 | | | | | | | 85 | 90 | | | | | | | | |
| 15 | 2.24 | 117 | 8.96 | | | | | | | 90 (5) | 90 | | | | | | | | |
| 15 | 2.24 | 118 | 8.96 | | | | | | | 90 (0) | 90 | | | | | | | | |
| 15 | 2.24 | 119 | 8.96 | | | | | | | 90 (0) | 90 | | | | | | | | |
| 15 | 2.24 | 120 | 8.96 | | | | | | | 70 (22) | 95 | | | | | | | | |
| 15 | 2.24 | 121 | 8.96 | | | | | | | 60 (36) | 95 | | | | | | | | |
| 15 | 2.24 | 122 | 8.96 | | | | | | | 90 (5) | 95 | | | | | | | | |
| 15 | 2.24 | 123 | 8.96 | | | | | | | 90 (5) | 95 | | | | | | | | |
| 15 | 2.24 | 124 | 8.96 | | | | | | | 55 (42) | 95 | | | | | | | | |
| 15 | 2.24 | 125 | 8.96 | | | | | | | 85 (10) | 90 | | | | | | | | |
| 15 | 2.24 | 126 | 8.96 | | | | | | | 40 (55) | 90 | | | | | | | | |
| 15 | 2.24 | 127 | 8.96 | | | | | | | 45 (50) | 90 | | | | | | | | |
| 15 | 2.24 | 128 | 8.96 | | | | | | | 75 (16) | 90 | | | | | | | | |
| 15 | 2.24 | 129 | 8.96 | | | | | | | 65 (27) | 90 | | | | | | | | |
| 15 | 2.24 | 130 | 8.96 | | | | | | | 30 (66) | 90 | | | | | | | | |
| 15 | 2.24 | 131 | 8.96 | | | | | | | 85 (5) | 90 | | | | | | | | |
| 15 | 2.24 | 132 | 8.96 | | | | | | | 80 (11) | 90 | | | | | | | | |
| 15 | 2.24 | 133 | 8.96 | | | | | | | 40 (55) | 90 | | | | | | | | |
| 15 | 2.24 | 134 | 8.96 | | | | | | | 95 (0) | 90 | | | | | | | | |
| 15 | 2.24 | 135 | 8.96 | | | | | | | 70 (22) | 90 | | | | | | | | |
| 15 | 2.24 | 136 | 8.96 | | | | | | | 90 (0) | 90 | | | | | | | | |
| 15 | 2.24 | 137 | 8.96 | | | | | | | 65 (27) | 90 | | | | | | | | |
| 15 | 2.24 | 138 | 8.96 | | | | | | | 90 (0) | 90 | | | | | | | | |
| 15 | 2.24 | 139 | 8.96 | | | | | | | 80 (11) | 90 | | | | | | | | |
| 15 | 2.24 | | 8.96 | | | | | | | 90 (0) | 80 | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 15 | 2.24 | 140 | 8.96 | | | | | | | 80 (0) | 80 | | | | | | | | |
| 15 | 2.24 | 141 | 8.96 | | | | | | | 80 (0) | 80 | | | | | | | | |
| 15 | 2.24 | 142 | 8.96 | | | | | | | 60 (25) | 80 | | | | | | | | |
| 15 | 2.24 | 143 | 8.96 | | | | | | | 25 (68) | 80 | | | | | | | | |
| 15 | 2.24 | 144 | 8.96 | | | | | | | 50 (44) | 90 | | | | | | | | |
| 15 | 2.24 | 145 | 8.96 | | | | | | | 70 (22) | 90 | | | | | | | | |
| 15 | 2.24 | 146 | 8.96 | | | | | | | 30 (66) | 90 | | | | | | | | |
| 15 | 2.24 | 147 | 8.96 | | | | | | | 80 (11) | 90 | | | | | | | | |
| 15 | 2.24 | 148 | 8.96 | | | | | | | 95 (0) | 90 | | | | | | | | |
| 15 | 2.24 | 149 | 8.96 | | | | | | | 65 (31) | 95 | | | | | | | | |
| 15 | 2.24 | 150 | 8.96 | | | | | | | 45 (50) | 90 | | | | | | | | |
| 15 | 2.24 | 151 | 8.96 | | | | | | | 30 (66) | 90 | | | | | | | | |
| 15 | 2.24 | 152 | 8.96 | | | | | | | 80 (11) | 90 | | | | | | | | |
| 15 | 2.24 | 153 | 8.96 | | | | | | | 75 (16) | 90 | | | | | | | | |
| 15 | 2.24 | 154 | 8.96 | | | | | | | 60 (36) | 95 | | | | | | | | |
| 15 | 2.24 | 155 | 8.96 | | | | | | | 40 (55) | 90 | | | | | | | | |
| 15 | 2.24 | 156 | 8.96 | | | | | | | 80 (11) | 90 | | | | | | | | |
| 15 | 2.24 | 157 | 8.96 | | | | | | | 75 (16) | 90 | | | | | | | | |
| 15 | 2.24 | 158 | 8.96 | | | | | | | 90 (0) | 90 | | | | | | | | |
| 15 | 2.24 | 159 | 8.96 | | | | | | | 50 (44) | 90 | | | | | | | | |
| 15 | 2.24 | 160 | 8.96 | | | | | | | 30 (66) | 90 | | | | | | | | |
| 15 | 2.24 | 161 | 8.96 | | | | | | | 65 (27) | 90 | | | | | | | | |
| 15 | 2.24 | 162 | 8.96 | | | | | | | 75 (16) | 90 | | | | | | | | |
| 15 | 2.24 | 163 | 8.96 | | | | | | | 65 (27) | 90 | | | | | | | | |

TABLE II-continued

% PLANT INHIBITION AND % SAFENING EFFECT ()

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 15 | 2.24 | 164 | 8.96 | | | | | | | 80 (11) | 90 | | | | | | | | |
| 15 | 2.24 | 165 | 8.96 | | | | | | | 50 (44) | 90 | | | | | | | | |
| 15 | 2.24 | 166 | 8.96 | | | | | | | 65 (23) | 85 | | | | | | | | |
| 15 | 2.24 | 167 | 8.96 | | | | | | | 90 (5) | 95 | | | | | | | | |
| 15 | 2.24 | 168 | 8.96 | | | | | | | 75 (21) | 95 | | | | | | | | |
| 15 | 2.24 | 169 | 8.96 | | | | | | | 45 (47) | 85 | | | | | | | | |
| 15 | 2.24 | 170 | 8.96 | | | | | | | 60 (29) | 85 | | | | | | | | |
| 15 | 2.24 | 171 | 8.96 | | | | | | | 95 (0) | 85 | | | | | | | | |
| 15 | 2.24 | 172 | 8.96 | | | | | | | 35 (56) | 80 | | | | | | | | |
| 15 | 2.24 | 173 | 8.96 | | | | | | | 45 (43) | 80 | | | | | | | | |
| 15 | 2.24 | 174 | 8.96 | | | | | | | 20 (75) | 80 | | | | | | | | |
| 15 | 2.24 | 175 | 8.96 | | | | | | | 25 (68) | 80 | | | | | | | | |
| 15 | 2.24 | 176 | 8.96 | | | | | | | 40 (50) | 80 | | | | | | | | |
| 15 | 2.24 | 177 | 8.96 | | | | | | | 45 (43) | 80 | | | | | | | | |
| 15 | 2.24 | 178 | 8.96 | | | | | | | 35 (56) | 80 | | | | | | | | |
| 15 | 2.24 | 179 | 8.96 | | | | | | | 45 (43) | 80 | | | | | | | | |
| 15 | 2.24 | 180 | 8.96 | | | | | | | 25 (68) | 80 | | | | | | | | |
| 15 | 2.24 | 181 | 8.96 | | | | | | | 65 (18) | 80 | | | | | | | | |
| 15 | 2.24 | 182 | 8.96 | | | | | | | 35 (56) | 80 | | | | | | | | |
| 15 | 2.24 | 183 | 8.96 | | | | | | | 50 (37) | 80 | | | | | | | | |
| 15 | 2.24 | 184 | 8.96 | | | | | | | 60 (29) | 85 | | | | | | | | |
| 15 | 2.24 | 185 | 8.96 | | | | | | | 65 (23) | 85 | | | | | | | | |
| 15 | 2.24 | 186 | 8.96 | | | | | | | 60 (36) | 95 | | | | | | | | |
| 15 | 2.24 | 187 | 8.96 | | | | | | | 50 (47) | 95 | | | | | | | | |

TABLE II-continued

| HERBICIDE | | ANTIDOTE | | RICE | | SORGHUM GRAIN | | WHEAT | | CORN | | COTTON | | SOYBEAN | | HEMP SESBANIA | | VELVET LEAF | |
|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO |
| 15 | 2.24 | 188 | 8.96 | | | | | | | 75 | (25) | 100 | | | | | | | |
| 15 | 2.24 | 189 | 8.96 | | | | | | | 60 | (40) | 100 | | | | | | | |
| 15 | 2.24 | 190 | 8.96 | | | | | | | 80 | (15) | 95 | | | | | | | |
| 15 | 2.24 | 191 | 8.96 | | | | | | | 70 | (26) | 95 | | | | | | | |
| 15 | 2.24 | 192 | 8.96 | | | | | | | 60 | (36) | 95 | | | | | | | |
| 15 | 2.24 | 193 | 8.96 | | | | | | | 70 | (26) | 95 | | | | | | | |
| 15 | 2.24 | 194 | 8.96 | | | | | | | 50 | (47) | 95 | | | | | | | |
| 15 | 2.24 | 195 | 8.96 | | | | | | | 45 | (52) | 95 | | | | | | | |
| 15 | 2.24 | 197 | 8.96 | | | | | | | 50 | (50) | 100 | | | | | | | |
| 15 | 2.24 | 198 | 8.96 | | | | | | | 0 | (100) | 95 | | | | | | | |
| 15 | 2.24 | 199 | 8.96 | | | | | | | 90 | (5) | 95 | | | | | | | |
| 15 | 2.24 | 200 | 8.96 | | | | | | | 50 | (47) | 95 | | | | | | | |
| 15 | 2.24 | 201 | 8.96 | | | | | | | 80 | (11) | 90 | | | | | | | |
| 15 | 2.24 | 202 | 0.28 | | | | | | | 30 | (68) | 95 | | | | | | | |

EXAMPLE 286

The following procedure shows interaction between a herbicide and antidote when the antidote is applied in a soil furrow containing crop seed and the herbicide is incorporated in a soil cover layer. Containers were filled and compacted with fumigated silt loam soil to a depth of about 1.3 cm from the top of the container. A first container was designated as an untreated control, a second container was designated as a herbicide control, and a third container was designated as a herbicide + antidote test container. Each container was seeded with crop seed in marked furrows. Antidote compound, dissolved in acetone, was applied directly to the seeded furrows of the third container. Antidote application rate was 0.55 mg active compound per inch of furrow (0.22 mg/cm). This rate was comparable to a plot application rate of 0.28 kilogram per hectare (kg/ha), based on 76 cm (30") spaced-apart furrows. Then, each of the second and third containers was filled and leveled with a cover layer of soil having incorporated therein the selected herbicide at a pre-determined concentration. The first container was filled and leveled with soil containing no herbicide. The containers were then placed on a bench in a greenhouse and sub-irrigated as required for the duration of the test. Plant response was observed about three weeks after initial treatment. Results are reported in Table III.

TABLE III

% PLANT INHIBITION AND % SAFENING EFFECT ( )

| HERBICIDE NO. | RATE | ANTIDOTE NO. | RATE | SORGHUM GRAIN W | WO | WHEAT W | WO | RICE W | WO | SOYBEAN W | WO | CORN W | WO |
|---|---|---|---|---|---|---|---|---|---|---|---|---|---|
| 2 | 0.56 | 1 | 0.28 | | | 70 (26) | 95 | | | | | | |
| 2 | 0.56 | 24 | 0.28 | | | 90 (10) | 100 | | | | | | |
| 2 | 0.56 | 25 | 0.28 | | | 95 (0) | 95 | | | | | | |
| 2 | 0.56 | 26 | 0.28 | | | 95 (0) | 95 | | | | | | |
| 2 | 0.56 | 27 | 0.28 | | | 85 (10) | 95 | | | | | | |
| 2 | 0.56 | 28 | 0.28 | | | 90 (5) | 95 | | | | | | |
| 2 | 0.56 | 29 | 0.28 | | | 95 (0) | 95 | | | | | | |
| 2 | 0.56 | 30 | 0.28 | | | 100 (0) | 100 | | | | | | |
| 2 | 0.56 | 31 | 0.28 | | | 95 (5) | 100 | | | | | | |
| 2 | 0.56 | 32 | 0.28 | | | 85 (10) | 95 | | | | | | |
| 2 | 0.56 | 33 | 0.28 | | | 80 (15) | 95 | | | | | | |
| 2 | 0.56 | 34 | 0.28 | | | 90 (10) | 100 | | | | | | |
| 2 | 0.56 | 35 | 0.28 | | | 85 (10) | 95 | | | | | | |
| 2 | 0.56 | 36 | 0.28 | | | 85 (15) | 100 | | | | | | |
| 3 | 6.72 | 1 | 0.28 | | | | | 95 (5) | 100 | 100 (0) | 95 | | |
| 3 | 6.72 | 24 | 0.28 | | | | | 100 (0) | 100 | 100 (0) | 100 | | |
| 3 | 6.72 | 25 | 0.28 | | | | | 100 (0) | 100 | 100 (0) | 100 | | |
| 3 | 4.48 | 26 | 0.28 | | | | | 90 (0) | 90 | 70 (6) | 75 | | |
| 3 | 4.48 | 27 | 0.28 | | | | | 100 (0) | 95 | | | | |
| 3 | 4.48 | 27 | 0.28 | | | | | | | 85 (10) | 95 | | |
| 3 | 4.48 | 28 | 0.28 | | | | | 60 (7) | 65 | 95 (0) | 90 | | |
| 3 | 4.48 | 29 | 0.28 | | | | | 90 (0) | 80 | 95 (0) | 95 | | |
| 3 | 6.72 | 30 | 0.28 | | | | | 60 (14) | 70 | 40 (52) | 85 | | |
| 3 | 6.72 | 31 | 0.28 | | | | | 70 (17) | 85 | 70 (22) | 90 | | |
| 3 | 6.72 | 32 | 0.28 | | | | | | | 40 (52) | 85 | | |
| 3 | 6.72 | 33 | 0.28 | | | | | | | 85 (0) | 85 | | |
| 3 | 6.72 | 34 | 0.28 | | | | | | | 85 (0) | 85 | | |
| 3 | 6.72 | 35 | 0.28 | | | | | | | 60 (25) | 80 | | |
| 3 | 4.48 | 36 | 0.28 | | | | | | | 40 (55) | 90 | | |
| 6 | 2.24 | 1 | 0.28 | 20 (78) | 95 | 20 (75) | 80 | | | | | | |

TABLE III-continued

| | | | | % PLANT INHIBITION AND % SAFENING EFFECT ( ) | | | | | | | | | |
|---|---|---|---|---|---|---|---|---|---|---|---|---|---|
| HERBICIDE | | ANTIDOTE | | SORGHUM GRAIN | | WHEAT | | RICE | | SOYBEAN | | CORN | |
| NO. | RATE | NO. | RATE | W | WO | W | WO | W | WO | W | WO | W | WO |
| 6 | 2.24 | 24 | 0.28 | 45 (52) | 95 | 90 (5) | 95 | | | | | | |
| 6 | 2.24 | 25 | 0.28 | 0 (100) | 95 | 45 (47) | 85 | | | | | | |
| 6 | 2.24 | 26 | 0.28 | 65 (31) | 95 | 70 (6) | 75 | | | | | | |
| 6 | 2.24 | 27 | 0.28 | 10 (90) | 100 | 40 (42) | 70 | | | | | | |
| 6 | 2.24 | 28 | 0.28 | 100 (0) | 100 | 85 (10) | 95 | | | | | | |
| 6 | 2.24 | 29 | 0.28 | 40 (60) | 100 | 80 (20) | 100 | | | | | | |
| 6 | 2.24 | 30 | 0.28 | 95 (5) | 100 | 30 (57) | 70 | | | | | | |
| 6 | 2.24 | 31 | 0.28 | 100 (0) | 100 | 60 (25) | 80 | | | | | | |
| 6 | 2.24 | 32 | 0.28 | 30 (70) | 100 | 95 (5) | 100 | | | | | | |
| 6 | 2.24 | 33 | 0.28 | 10 (89) | 95 | 20 (73) | 75 | | | | | | |
| 6 | 2.24 | 34 | 0.28 | 50 (50) | 100 | 70 (26) | 95 | | | | | | |
| 6 | 2.24 | 35 | 0.28 | 15 (84) | 95 | 35 (53) | 75 | | | | | | |
| 6 | 2.24 | 36 | 0.28 | 70 (30) | 100 | 90 (10) | 100 | | | | | | |
| 10 | 4.48 | 1 | 0.28 | | | | | 0 (100) | 95 | | | | |
| 10 | 4.48 | 24 | 0.28 | | | | | 50 (47) | 95 | | | | |
| 10 | 4.48 | 25 | 0.28 | | | | | 40 (60) | 100 | | | | |
| 10 | 4.48 | 26 | 0.28 | | | | | 5 (94) | 95 | | | | |
| 10 | 4.48 | 27 | 0.28 | | | | | 10 (88) | 85 | | | | |
| 10 | 4.48 | 28 | 0.28 | | | | | 35 (65) | 100 | | | | |
| 10 | 4.48 | 29 | 0.28 | | | | | 35 (63) | 95 | | | | |
| 10 | 4.48 | 30 | 0.28 | | | | | 40 (57) | 95 | | | | |
| 10 | 4.48 | 31 | 0.28 | | | | | 70 (22) | 90 | | | | |
| 10 | 4.48 | 32 | 0.28 | | | | | 40 (50) | 80 | | | | |
| 10 | 4.48 | 33 | 0.28 | | | | | 20 (66) | 60 | | | | |
| 10 | 4.48 | 34 | 0.28 | | | | | 10 (88) | 90 | | | | |
| 10 | 4.48 | 35 | 0.28 | | | | | 25 (73) | 95 | | | | |
| 10 | 4.48 | 36 | 0.28 | | | | | 55 (42) | 95 | | | | |
| 15 | 2.24 | 1 | 0.28 | | | | | | | 80 (0) | 55 | 20 (78) | 95 |
| 15 | 2.24 | 24 | 0.28 | | | | | | | | | 85 (15) | 100 |
| 15 | 2.24 | 25 | 0.28 | | | | | | | | | 80 (15) | 95 |
| 15 | 2.24 | 26 | 0.28 | | | | | | | 40 (11) | 45 | 70 (26) | 95 |
| 15 | 2.24 | 27 | 0.28 | | | | | | | 70 (0) | 40 | 30 (68) | 95 |
| 15 | 2.24 | 28 | 0.28 | | | | | | | 55 (0) | 50 | 95 (0) | 95 |
| 15 | 2.24 | 29 | 0.28 | | | | | | | 30 (57) | 70 | 10 (89) | 95 |
| 15 | 2.24 | 30 | 0.28 | | | | | | | 90 (0) | 85 | 95 (0) | 95 |
| 15 | 2.24 | 31 | 0.28 | | | | | | | 70 (0) | 65 | 95 (0) | 95 |
| 15 | 2.24 | 32 | 0.28 | | | | | | | 20 (73) | 75 | 20 (78) | 95 |
| 15 | 2.24 | 33 | 0.28 | | | | | | | 90 (0) | 80 | 50 (47) | 95 |
| 15 | 2.24 | 34 | 0.28 | | | | | | | 30 | 70 | 10 | 90 |

TABLE III-continued

| HERBICIDE | | ANTIDOTE | | SORGHUM GRAIN | | WHEAT | | RICE | | SOYBEAN | | CORN | |
|---|---|---|---|---|---|---|---|---|---|---|---|---|---|
| NO. | RATE | NO. | RATE | W | WO | W | WO | W | WO | W | WO | W | WO |
| 15 | 2.24 | 35 | 0.28 | | | | | | | 20 (57) (63) | 55 | 5 (88) (95) | 100 |
| 15 | 2.24 | 36 | 0.28 | | | | | | | 40 (52) | 85 | 30 (68) | 95 |
| 2 | 0.56 | 203 | 0.28 | | | 95 (0) | 95 | | | | | | |
| 2 | 0.56 | 204 | 0.28 | | | 95 (5) | 100 | | | | | | |
| 2 | 0.56 | 205 | 0.28 | | | 90 (10) | 100 | | | | | | |
| 2 | 0.56 | 206 | 0.28 | | | 80 (15) | 95 | | | | | | |
| 2 | 0.56 | 207 | 0.28 | | | 95 (0) | 95 | | | | | | |
| 2 | 0.56 | 208 | 0.28 | | | 85 (10) | 95 | | | | | | |
| 2 | 0.56 | 209 | 0.28 | | | 90 (5) | 95 | | | | | | |
| 2 | 0.56 | 210 | 0.28 | | | 45 (55) | 100 | | | | | | |
| 2 | 0.56 | 211 | 0.28 | | | 10 (90) | 100 | | | | | | |
| 2 | 0.56 | 212 | 0.28 | | | 75 (21) | 95 | | | | | | |
| 2 | 0.56 | 213 | 0.28 | | | 60 (36) | 95 | | | | | | |
| 2 | 0.56 | 214 | 0.28 | | | 95 (5) | 100 | | | | | | |
| 2 | 0.56 | 215 | 0.28 | | | 100 (0) | 100 | | | | | | |
| 2 | 0.56 | 216 | 0.28 | | | 95 (5) | 100 | | | | | | |
| 2 | 0.56 | 217 | 0.28 | | | 95 (5) | 100 | | | | | | |
| 2 | 0.56 | 218 | 0.28 | | | 95 (5) | 100 | | | | | | |
| 2 | 0.56 | 219 | 0.28 | | | 95 (5) | 100 | | | | | | |
| 2 | 0.56 | 220 | 0.28 | | | 100 (0) | 95 | | | | | | |
| 2 | 0.56 | 221 | 0.28 | | | 80 (20) | 100 | | | | | | |
| 2 | 0.56 | 222 | 0.28 | | | 100 (0) | 100 | | | | | | |
| 2 | 0.56 | 223 | 0.28 | | | 95 (0) | 95 | | | | | | |
| 2 | 0.56 | 224 | 0.28 | | | 95 (0) | 95 | | | | | | |
| 2 | 0.56 | 225 | 0.28 | | | 95 (5) | 100 | | | | | | |
| 2 | 0.56 | 226 | 0.28 | | | 95 (5) | 100 | | | | | | |
| 2 | 0.56 | 227 | 0.28 | | | 95 (5) | 100 | | | | | | |
| 2 | 0.56 | 228 | 0.28 | | | 95 (5) | 100 | | | | | | |
| 2 | 0.56 | 229 | 0.28 | | | 85 (15) | 100 | | | | | | |
| 2 | 0.56 | 230 | 0.28 | | | 80 (15) | 95 | | | | | | |
| 2 | 0.56 | 231 | 0.28 | | | 90 (5) | 95 | | | | | | |
| 2 | 0.56 | 232 | 0.28 | | | 95 (0) | 95 | | | | | | |
| 2 | 0.56 | 233 | 0.28 | | | 80 (11) | 90 | | | | | | |
| 2 | 0.56 | 234 | 0.28 | | | 90 (0) | 90 | | | | | | |
| 2 | 0.56 | 235 | 0.28 | | | 100 (0) | 100 | | | | | | |
| 2 | 0.56 | 236 | 0.28 | | | 95 (5) | 100 | | | | | | |
| 2 | 0.56 | 237 | 0.28 | | | 75 (25) | 100 | | | | | | |
| 2 | 0.56 | 238 | 0.28 | | | 95 (5) | 100 | | | | | | |

TABLE III-continued

| | | | | % PLANT INHIBITION AND % SAFENING EFFECT ( ) | | | | | | | | | |
|---|---|---|---|---|---|---|---|---|---|---|---|---|---|
| HERBICIDE | | ANTIDOTE | | SORGHUM GRAIN | | WHEAT | | RICE | | SOYBEAN | | CORN | |
| NO. | RATE | NO. | RATE | W | WO | W | WO | W | WO | W | WO | W | WO |
| 2 | 0.56 | 239 | 0.28 | | | 100 (0) | 95 | | | | | | |
| 2 | 0.56 | 240 | 0.28 | | | 90 (5) | 95 | | | | | | |
| 2 | 0.56 | 241 | 0.28 | | | 100 (0) | 95 | | | | | | |
| 2 | 0.56 | 242 | 0.28 | | | 100 (0) | 95 | | | | | | |
| 2 | 0.56 | 243 | 0.28 | | | 90 (5) | 95 | | | | | | |
| 2 | 0.56 | 244 | 0.28 | | | 95 (0) | 95 | | | | | | |
| 2 | 0.56 | 245 | 0.28 | | | 95 (5) | 100 | | | | | | |
| 2 | 0.56 | 246 | 0.28 | | | 85 (15) | 100 | | | | | | |
| 2 | 0.56 | 247 | 0.28 | | | 85 (15) | 100 | | | | | | |
| 2 | 0.56 | 248 | 0.28 | | | 100 (0) | 95 | | | | | | |
| 2 | 0.56 | 249 | 0.28 | | | 85 (10) | 95 | | | | | | |
| 2 | 0.56 | 250 | 0.28 | | | 100 (0) | 95 | | | | | | |
| 2 | 0.56 | 251 | 0.28 | | | 75 (21) | 95 | | | | | | |
| 2 | 0.56 | 252 | 0.28 | | | 70 (30) | 100 | | | | | | |
| 2 | 0.56 | 253 | 0.28 | | | 65 (35) | 100 | | | | | | |
| 2 | 0.56 | 254 | 0.28 | | | 95 (0) | 95 | | | | | | |
| 2 | 0.56 | 255 | 0.28 | | | 70 (26) | 95 | | | | | | |
| 2 | 0.56 | 256 | 0.28 | | | 75 (21) | 95 | | | | | | |
| 2 | 0.56 | 257 | 0.28 | | | 90 (5) | 95 | | | | | | |
| 2 | 0.56 | 258 | 0.28 | | | 90 (10) | 100 | | | | | | |
| 2 | 0.56 | 259 | 0.28 | | | 90 (5) | 95 | | | | | | |
| 2 | 0.56 | 260 | 0.28 | | | 85 (5) | 90 | | | | | | |
| 2 | 0.56 | 261 | 0.28 | | | 85 (10) | 95 | | | | | | |
| 2 | 0.56 | 262 | 0.28 | | | 80 (15) | 95 | | | | | | |
| 2 | 0.56 | 263 | 0.28 | | | 85 (15) | 100 | | | | | | |
| 2 | 0.56 | 264 | 0.28 | | | 75 (25) | 100 | | | | | | |
| 2 | 0.56 | 265 | 0.28 | | | 80 (20) | 100 | | | | | | |
| 2 | 0.56 | 266 | 0.28 | | | 80 (20) | 100 | | | | | | |
| 2 | 0.56 | 267 | 0.28 | | | 80 (20) | 100 | | | | | | |
| 2 | 0.56 | 268 | 0.28 | | | 80 (20) | 100 | | | | | | |
| 2 | 0.56 | 269 | 0.28 | | | 60 (40) | 100 | | | | | | |
| 2 | 0.56 | 270 | 0.28 | | | 75 (21) | 95 | | | | | | |
| 2 | 0.56 | 271 | 0.28 | | | 65 (31) | 95 | | | | | | |
| 2 | 0.56 | 272 | 0.28 | | | 75 (21) | 95 | | | | | | |
| 2 | 0.56 | 273 | 0.28 | | | 35 (63) | 95 | | | | | | |
| 2 | 0.56 | 274 | 0.28 | | | 90 (5) | 95 | | | | | | |
| 2 | 0.56 | 275 | 0.28 | | | 60 (36) | 95 | | | | | | |
| 2 | 0.56 | 276 | 0.28 | | | 70 (26) | 95 | | | | | | |
| 2 | 0.56 | 277 | 0.28 | | | 90 | 95 | | | | | | |

TABLE III-continued

| | | | | % PLANT INHIBITION AND % SAFENING EFFECT ( ) | | | | | | | | | |
|---|---|---|---|---|---|---|---|---|---|---|---|---|---|
| HERBICIDE | | ANTIDOTE | | SORGHUM GRAIN | | WHEAT | | RICE | | SOYBEAN | | CORN | |
| NO. | RATE | NO. | RATE | W | WO | W | WO | W | WO | W | WO | W | WO |
| 2 | 0.56 | 278 | 0.28 | | | 75 (5) | 95 | | | | | | |
| 2 | 0.56 | 279 | 0.28 | | | 70 (21) | 95 | | | | | | |
| 2 | 0.56 | 280 | 0.28 | | | 100 (26) | 95 | | | | | | |
| 2 | 0.56 | 281 | 0.28 | | | 70 (0) | 95 | | | | | | |
| 2 | 0.56 | 282 | 0.28 | | | 80 (26) | 100 | | | | | | |
| 2 | 0.56 | 283 | 0.28 | | | 80 (20) | 100 | | | | | | |
| 3 | 6.72 | 203 | 0.28 | | | | | 90 (0) | 85 | 95 (0) | 90 | | |
| 3 | 6.72 | 204 | 0.28 | | | | | 65 (31) | 95 | 70 (26) | 95 | | |
| 3 | 4.48 | 205 | 0.28 | | | | | 100 (0) | 100 | 60 (36) | 95 | | |
| 3 | 4.48 | 206 | 0.28 | | | | | 70 (0) | 65 | 90 (0) | 90 | | |
| 3 | 4.48 | 207 | 0.28 | | | | | 70 (12) | 80 | 75 (16) | 90 | | |
| 3 | 4.48 | 208 | 0.28 | | | | | 95 (0) | 95 | 95 (0) | 90 | | |
| 3 | 4.48 | 209 | 0.28 | | | | | 65 (0) | 60 | 70 (26) | 95 | | |
| 3 | 4.48 | 210 | 0.28 | | | | | 70 (6) | 75 | 95 (0) | 95 | | |
| 3 | 4.48 | 211 | 0.28 | | | | | 95 (0) | 80 | 100 (0) | 95 | | |
| 3 | 6.72 | 212 | 0.28 | | | | | 40 (46) | 75 | 100 (0) | 80 | | |
| 3 | 6.72 | 213 | 0.28 | | | | | 40 (42) | 70 | 40 (55) | 90 | | |
| 3 | 6.72 | 214 | 0.28 | | | | | 45 (47) | 85 | 45 (43) | 80 | | |
| 3 | 6.72 | 215 | 0.28 | | | | | 45 (47) | 85 | 70 (12) | 80 | | |
| 3 | 6.72 | 216 | 0.28 | | | | | 60 (29) | 85 | 50 (37) | 80 | | |
| 3 | 6.72 | 217 | 0.28 | | | | | 80 (0) | 70 | 50 (41) | 85 | | |
| 3 | 6.72 | 218 | 0.28 | | | | | 50 (28) | 70 | 55 (35) | 85 | | |
| 3 | 6.72 | 219 | 0.28 | | | | | 40 (42) | 70 | 15 (82) | 85 | | |
| 3 | 6.72 | 220 | 0.28 | | | | | 70 (22) | 90 | 75 (21) | 95 | | |
| 3 | 6.72 | 221 | 0.28 | | | | | | | 90 (0) | 85 | | |
| 3 | 6.72 | 222 | 0.28 | | | | | | | 95 (0) | 85 | | |
| 3 | 6.72 | 223 | 0.28 | | | | | | | 95 (5) | 100 | | |
| 3 | 6.72 | 224 | 0.28 | | | | | | | 60 (40) | 100 | | |
| 3 | 6.72 | 225 | 0.28 | | | | | | | 85 (0) | 85 | | |
| 3 | 6.72 | 226 | 0.28 | | | | | | | 100 (0) | 85 | | |
| 3 | 6.72 | 227 | 0.28 | | | | | | | 30 (64) | 85 | | |
| 3 | 6.72 | 228 | 0.28 | | | | | | | 95 (0) | 85 | | |
| 3 | 6.72 | 229 | 0.28 | | | | | | | 75 (11) | 85 | | |
| 3 | 6.72 | 230 | 0.28 | | | | | | | 45 (10) | 50 | | |
| 3 | 6.72 | 231 | 0.28 | | | | | | | 85 (0) | 80 | | |
| 3 | 6.72 | 232 | 0.28 | | | | | | | 85 (0) | 80 | | |
| 3 | 6.72 | 233 | 0.28 | | | | | | | 10 (83) | 60 | | |
| 3 | 6.72 | 234 | 0.28 | | | | | | | 50 (16) | 60 | | |

TABLE III-continued

| | | | | % PLANT INHIBITION AND % SAFENING EFFECT ( ) | | | | | | | | | |
|---|---|---|---|---|---|---|---|---|---|---|---|---|---|
| HERBICIDE | | ANTIDOTE | | SORGHUM GRAIN | | WHEAT | | RICE | | SOYBEAN | | CORN | |
| NO. | RATE | NO. | RATE | W | WO | W | WO | W | WO | W | WO | W | WO |
| 3 | 6.72 | 235 | 0.28 | | | | | | | 80 (0) | 80 | | |
| 3 | 6.72 | 236 | 0.28 | | | | | | | 75 (6) | 80 | | |
| 3 | 6.72 | 237 | 0.28 | | | | | | | 75 (11) | 85 | | |
| 3 | 6.72 | 238 | 0.28 | | | | | | | 85 (0) | 85 | | |
| 3 | 6.72 | 239 | 0.28 | | | | | | | 90 (0) | 80 | | |
| 3 | 6.72 | 240 | 0.28 | | | | | | | 75 (6) | 80 | | |
| 3 | 6.72 | 241 | 0.28 | | | | | | | 70 (7) | 75 | | |
| 3 | 6.72 | 242 | 0.28 | | | | | | | 20 (73) | 75 | | |
| 3 | 6.72 | 243 | 0.28 | | | | | | | 95 (0) | 95 | | |
| 3 | 6.72 | 244 | 0.28 | | | | | | | 100 (0) | 95 | | |
| 3 | 6.72 | 245 | 0.28 | | | | | | | 70 (30) | 100 | | |
| 3 | 6.72 | 246 | 0.28 | | | | | | | 75 (25) | 100 | | |
| 3 | 6.72 | 247 | 0.28 | | | | | | | 100 (0) | 100 | | |
| 3 | 6.72 | 248 | 0.28 | | | | | | | 100 (0) | 100 | | |
| 3 | 4.48 | 249 | 0.28 | | | | | | | 20 (78) | 95 | | |
| 3 | 4.48 | 250 | 0.28 | | | | | | | 100 (0) | 100 | | |
| 3 | 4.48 | 251 | 0.28 | | | | | | | 100 (0) | 100 | | |
| 3 | 4.48 | 252 | 0.28 | | | | | | | 100 (0) | 100 | | |
| 3 | 4.48 | 253 | 0.28 | | | | | | | 100 (0) | 100 | | |
| 3 | 4.48 | 254 | 0.28 | | | | | | | 75 (16) | 90 | | |
| 3 | 4.48 | 255 | 0.28 | | | | | | | 100 (0) | 95 | | |
| 3 | 4.48 | 256 | 0.28 | | | | | | | 95 (0) | 95 | | |
| 3 | 4.48 | 257 | 0.28 | | | | | | | 95 (0) | 95 | | |
| 3 | 4.48 | 258 | 0.28 | | | | | | | 100 (0) | 100 | | |
| 3 | 4.48 | 259 | 0.28 | | | | | | | 95 (5) | 100 | | |
| 3 | 4.48 | 260 | 0.28 | | | | | | | 95 (0) | 85 | | |
| 3 | 4.48 | 261 | 0.28 | | | | | | | 20 (73) | 75 | | |
| 3 | 4.48 | 262 | 0.28 | | | | | | | 70 (6) | 75 | | |
| 3 | 4.48 | 263 | 0.28 | | | | | | | 70 (22) | 90 | | |
| 3 | 4.48 | 264 | 0.28 | | | | | | | 15 (83) | 90 | | |
| 3 | 4.48 | 265 | 0.28 | | | | | | | 25 (72) | 90 | | |
| 3 | 4.48 | 266 | 0.28 | | | | | | | 30 (66) | 90 | | |
| 6 | 2.24 | 203 | 0.28 | 30 (66) | | 90 | | 50 (41) | 85 | | | | |
| 6 | 2.24 | 204 | 0.28 | 10 (88) | | 90 | | | | | | | |
| 6 | 2.24 | 204 | 0.28 | | | | 30 | 66 (66) | 90 | | | | |
| 6 | 2.24 | 205 | 0.28 | 20 (76) | | 85 | 10 | (85) | 70 | | | | |
| 6 | 2.24 | 206 | 0.28 | 10 (90) | | 100 | 65 | (31) | 95 | | | | |
| 6 | 2.24 | 207 | 0.28 | 100 (0) | | 100 | 40 | (42) | 70 | | | | |
| 6 | 2.24 | 208 | 0.28 | 95 | | 100 | 75 | | 80 | | | | |

TABLE III-continued

% PLANT INHIBITION AND % SAFENING EFFECT ( )

| HERBICIDE | | ANTIDOTE | | SORGHUM GRAIN | | WHEAT | | RICE | | SOYBEAN | | CORN | |
|---|---|---|---|---|---|---|---|---|---|---|---|---|---|
| NO. | RATE | NO. | RATE | W | WO | W | WO | W | WO | W | WO | W | WO |
| 6 | 2.24 | 209 | 0.28 | 0 (5) | 100 | 35 (6) | 90 | | | | | | |
| 6 | 2.24 | 210 | 0.28 | 85 (100) | 100 | 95 (61) | 95 | | | | | | |
| 6 | 2.24 | 211 | 0.28 | 100 (15) | 100 | 90 (0) | 100 | | | | | | |
| 6 | 2.24 | 212 | 0.28 | 65 (0) | 95 | 70 (10) | 95 | | | | | | |
| 6 | 2.24 | 213 | 0.28 | 50 (31) | 95 | 95 (26) | 90 | | | | | | |
| 6 | 2.24 | 214 | 0.28 | 90 (47) | 100 | 50 (0) | 95 | | | | | | |
| 6 | 2.24 | 215 | 0.28 | 95 (10) | 100 | 70 (47) | 95 | | | | | | |
| 6 | 2.24 | 216 | 0.28 | 90 (5) | 100 | 70 (26) | 95 | | | | | | |
| 6 | 2.24 | 217 | 0.28 | 80 (10) | 100 | 60 (26) | 70 | | | | | | |
| 6 | 2.24 | 218 | 0.28 | 100 (20) | 100 | 60 (14) | 70 | | | | | | |
| 6 | 2.24 | 219 | 0.28 | 100 (0) | 100 | 50 (14) | 70 | | | | | | |
| 6 | 2.24 | 220 | 0.28 | 95 (0) | 100 | 50 (28) | 90 | | | | | | |
| 6 | 2.24 | 221 | 0.28 | 10 (5) | 100 | 50 (44) | 90 | | | | | | |
| 6 | 2.24 | 222 | 0.28 | 40 (90) | 100 | 65 (44) | 90 | | | | | | |
| 6 | 2.24 | 223 | 0.28 | 10 (60) | 100 | 40 (27) | 90 | | | | | | |
| 6 | 2.24 | 224 | 0.28 | 20 (90) | 100 | 30 (55) | 90 | | | | | | |
| 6 | 2.24 | 225 | 0.28 | 95 (80) | 100 | 85 (66) | 95 | | | | | | |
| 6 | 2.24 | 226 | 0.28 | 60 (5) | 100 | 80 (10) | 95 | | | | | | |
| 6 | 2.24 | 227 | 0.28 | 50 (40) | 100 | 80 (15) | 95 | | | | | | |
| 6 | 2.24 | 228 | 0.28 | 35 (50) | 100 | 70 (15) | 95 | | | | | | |
| 6 | 2.24 | 229 | 0.28 | 50 (65) | 100 | 60 (26) | 95 | | | | | | |
| 6 | 2.24 | 230 | 0.28 | 5 (50) | 100 | 0 (36) | 80 | | | | | | |
| 6 | 2.24 | 231 | 0.28 | 30 (95) | 95 | 10 (100) | 70 | | | | | | |
| 6 | 2.24 | 232 | 0.28 | 20 (68) | 95 | 30 (85) | 70 | | | | | | |
| 6 | 2.24 | 233 | 0.28 | 60 (78) | 95 | 75 (57) | 85 | | | | | | |
| 6 | 2.24 | 234 | 0.28 | 95 (36) | 95 | 45 (11) | 85 | | | | | | |
| 6 | 2.24 | 235 | 0.28 | 65 (0) | 95 | 95 (47) | 85 | | | | | | |
| 6 | 2.24 | 236 | 0.28 | 60 (31) | 95 | 45 (0) | 85 | | | | | | |
| 6 | 2.24 | 237 | 0.28 | 10 (36) | 100 | 40 (47) | 60 | | | | | | |
| 6 | 2.24 | 238 | 0.28 | 90 (90) | 100 | 25 (33) | 60 | | | | | | |
| 6 | 2.24 | 239 | 0.28 | 85 (10) | 95 | 80 (58) | 75 | | | | | | |
| 6 | 2.24 | 240 | 0.28 | 25 (10) | 95 | 25 (0) | 75 | | | | | | |
| 6 | 2.24 | 241 | 0.28 | 95 (73) | 100 | (66) | | | | | | | |
| 6 | 2.24 | 241 | 0.28 | (5) | | 85 (0) | 85 | | | | | | |
| 6 | 2.24 | 242 | 0.28 | | | 70 (17) | 85 | | | | | | |
| 6 | 2.24 | 242 | 0.28 | 100 (0) | 100 | | | | | | | | |
| 6 | 2.24 | 243 | 0.28 | 5 (94) | 85 | 45 (30) | 65 | | | | | | |
| 6 | 2.24 | 244 | 0.28 | 45 (55) | 100 | 85 (10) | 95 | | | | | | |

TABLE III-continued

| | | | | % PLANT INHIBITION AND % SAFENING EFFECT ( ) | | | | | | | | | |
|---|---|---|---|---|---|---|---|---|---|---|---|---|---|
| HERBICIDE | | ANTIDOTE | | SORGHUM GRAIN | | WHEAT | | RICE | | SOYBEAN | | CORN | |
| NO. | RATE | NO. | RATE | W | WO | W | WO | W | WO | W | WO | W | WO |
| 6 | 2.24 | 245 | 0.28 | 35 (65) | 100 | 50 (47) | 95 | | | | | | |
| 6 | 2.24 | 246 | 0.28 | 20 (80) | 100 | 85 (10) | 95 | | | | | | |
| 6 | 2.24 | 247 | 0.28 | 35 (65) | 100 | 95 (0) | 90 | | | | | | |
| 6 | 2.24 | 248 | 0.28 | 100 (0) | 100 | 70 (0) | 60 | | | | | | |
| 6 | 2.24 | 249 | 0.28 | 100 (0) | 100 | 50 (28) | 70 | | | | | | |
| 6 | 2.24 | 250 | 0.28 | 65 (35) | 100 | 70 (22) | 90 | | | | | | |
| 6 | 2.24 | 251 | 0.28 | 55 (45) | 100 | 25 (72) | 90 | | | | | | |
| 6 | 2.24 | 252 | 0.28 | 40 (60) | 100 | 40 (57) | 95 | | | | | | |
| 6 | 2.24 | 253 | 0.28 | 35 (65) | 100 | 60 (36) | 95 | | | | | | |
| 6 | 2.24 | 254 | 0.28 | 60 (40) | 100 | 45 (47) | 85 | | | | | | |
| 6 | 2.24 | 255 | 0.28 | 60 (40) | 100 | 85 (10) | 95 | | | | | | |
| 6 | 2.24 | 256 | 0.28 | 60 (40) | 100 | 60 (36) | 95 | | | | | | |
| 6 | 2.24 | 257 | 0.28 | 65 (35) | 100 | 50 (47) | 95 | | | | | | |
| 6 | 2.24 | 258 | 0.28 | 80 (20) | 100 | 55 (42) | 95 | | | | | | |
| 6 | 2.24 | 259 | 0.28 | 60 (40) | 100 | 85 (10) | 95 | | | | | | |
| 6 | 2.24 | 260 | 0.28 | 45 (55) | 100 | 95 (0) | 95 | | | | | | |
| 6 | 2.24 | 261 | 0.28 | 100 (0) | 100 | 95 (5) | 100 | | | | | | |
| 6 | 2.24 | 262 | 0.28 | 100 (0) | 100 | 95 (5) | 100 | | | | | | |
| 6 | 2.24 | 263 | 0.28 | 70 (30) | 100 | 90 (10) | 100 | | | | | | |
| 6 | 2.24 | 264 | 0.28 | 40 (60) | 100 | 90 (10) | 100 | | | | | | |
| 6 | 2.24 | 265 | 0.28 | 70 (30) | 100 | 95 (5) | 100 | | | | | | |
| 6 | 2.24 | 266 | 0.28 | 40 (60) | 100 | 85 (15) | 100 | | | | | | |
| 6 | 2.24 | 267 | 0.28 | 50 (50) | 100 | 85 (15) | 100 | | | | | | |
| 6 | 2.24 | 268 | 0.28 | 65 (35) | 100 | 90 (10) | 100 | | | | | | |
| 6 | 2.24 | 269 | 0.28 | 60 (40) | 100 | 65 (35) | 100 | | | | | | |
| 6 | 2.24 | 270 | 0.28 | 65 (35) | 100 | 80 (20) | 100 | | | | | | |
| 6 | 2.24 | 271 | 0.28 | 5 (94) | 95 | 35 (65) | 100 | | | | | | |
| 6 | 2.24 | 272 | 0.28 | 30 (68) | 95 | 55 (45) | 100 | | | | | | |
| 6 | 2.24 | 273 | 0.28 | 60 (36) | 95 | 75 (25) | 100 | | | | | | |
| 6 | 2.24 | 274 | 0.28 | 80 (20) | 100 | 40 (57) | 95 | | | | | | |
| 6 | 2.24 | 275 | 0.28 | 65 (35) | 100 | 40 (57) | 95 | | | | | | |
| 6 | 2.24 | 276 | 0.28 | 35 (65) | 100 | 60 (36) | 95 | | | | | | |
| 6 | 2.24 | 277 | 0.28 | 85 (10) | 95 | 65 (27) | 90 | | | | | | |
| 6 | 2.24 | 278 | 0.28 | 30 (70) | 100 | 65 (18) | 80 | | | | | | |
| 6 | 2.24 | 279 | 0.28 | 50 (44) | 90 | 65 (18) | 80 | | | | | | |
| 6 | 2.24 | 280 | 0.28 | 95 (0) | 95 | | | | | | | | |
| 6 | 2.24 | 281 | 0.28 | 35 (63) | 95 | 20 (55) | 45 | | | | | | |
| 6 | 2.24 | 282 | 0.28 | 100 (0) | 95 | 90 (10) | 100 | | | | | | |
| 6 | 2.24 | 283 | 0.28 | 95 | 95 | 85 | 70 | | | | | | |

TABLE III-continued

| HERBICIDE | | ANTIDOTE | | % PLANT INHIBITION AND % SAFENING EFFECT ( ) | | | | | | | | | |
|---|---|---|---|---|---|---|---|---|---|---|---|---|---|
| | | | | SORGHUM GRAIN | | WHEAT | | RICE | | SOYBEAN | | CORN | |
| NO. | RATE | NO. | RATE | W | WO | W | WO | W | WO | W | WO | W | WO |
| 6 | 2.24 | 284 | 0.28 | 95 (0) (5) | 100 | (0) | | | | | | | |
| 10 | 4.48 | 203 | 0.28 | | | | | 20 (78) | 95 | | | | |
| 10 | 4.48 | 204 | 0.28 | | | | | 60 (29) | 85 | | | | |
| 10 | 4.48 | 205 | 0.28 | | | | | 45 (52) | 95 | | | | |
| 10 | 4.48 | 206 | 0.28 | | | | | 60 (40) | 100 | | | | |
| 10 | 4.48 | 207 | 0.28 | | | | | 80 (15) | 95 | | | | |
| 10 | 4.48 | 208 | 0.28 | | | | | 60 (29) | 85 | | | | |
| 10 | 4.48 | 209 | 0.28 | | | | | 35 (63) | 95 | | | | |
| 10 | 4.48 | 210 | 0.28 | | | | | 100 (0) | 95 | | | | |
| 10 | 4.48 | 211 | 0.28 | | | | | 100 (0) | 100 | | | | |
| 10 | 4.48 | 212 | 0.28 | | | | | 30 (62) | 80 | | | | |
| 10 | 4.48 | 213 | 0.28 | | | | | 75 (0) | 65 | | | | |
| 10 | 4.48 | 214 | 0.28 | | | | | 45 (50) | 90 | | | | |
| 10 | 4.48 | 215 | 0.28 | | | | | 50 (44) | 90 | | | | |
| 10 | 4.48 | 216 | 0.28 | | | | | 40 (55) | 90 | | | | |
| 10 | 4.48 | 217 | 0.28 | | | | | 40 (57) | 95 | | | | |
| 10 | 4.48 | 218 | 0.28 | | | | | 55 (42) | 95 | | | | |
| 10 | 4.48 | 219 | 0.28 | | | | | 50 (47) | 95 | | | | |
| 10 | 4.48 | 220 | 0.28 | | | | | 75 (16) | 90 | | | | |
| 10 | 4.48 | 221 | 0.28 | | | | | 40 (55) | 90 | | | | |
| 10 | 4.48 | 222 | 0.28 | | | | | 50 (44) | 90 | | | | |
| 10 | 4.48 | 223 | 0.28 | | | | | 40 (55) | 90 | | | | |
| 10 | 4.48 | 224 | 0.28 | | | | | 20 (77) | 90 | | | | |
| 10 | 4.48 | 225 | 0.28 | | | | | 70 (22) | 90 | | | | |
| 10 | 4.48 | 226 | 0.28 | | | | | 20 (77) | 90 | | | | |
| 10 | 4.48 | 227 | 0.28 | | | | | 30 (66) | 90 | | | | |
| 10 | 4.48 | 228 | 0.28 | | | | | 20 (77) | 90 | | | | |
| 10 | 4.48 | 229 | 0.28 | | | | | 40 (55) | 90 | | | | |
| 10 | 4.48 | 230 | 0.28 | | | | | 20 (76) | 85 | | | | |
| 10 | 4.48 | 231 | 0.28 | | | | | 40 (52) | 85 | | | | |
| 10 | 4.48 | 232 | 0.28 | | | | | 20 (76) | 85 | | | | |
| 10 | 4.48 | 233 | 0.28 | | | | | 40 (50) | 80 | | | | |
| 10 | 4.48 | 234 | 0.28 | | | | | 60 (25) | 80 | | | | |
| 10 | 4.48 | 235 | 0.28 | | | | | 50 (44) | 90 | | | | |
| 10 | 4.48 | 236 | 0.28 | | | | | 45 (50) | 90 | | | | |
| 10 | 4.48 | 237 | 0.28 | | | | | 15 (82) | 85 | | | | |
| 10 | 4.48 | 238 | 0.28 | | | | | 15 (82) | 85 | | | | |
| 10 | 4.48 | 239 | 0.28 | | | | | 80 (15) | 95 | | | | |

TABLE III-continued

| | | | | % PLANT INHIBITION AND % SAFENING EFFECT ( ) | | | | | | | | | | |
|---|---|---|---|---|---|---|---|---|---|---|---|---|---|---|
| HERBICIDE | | ANTIDOTE | | SORGHUM GRAIN | | WHEAT | | RICE | | SOYBEAN | | CORN | | |
| NO. | RATE | NO. | RATE | W | WO | W | WO | W | WO | W | WO | W | WO | |
| 10 | 4.48 | 240 | 0.28 | | | | | 30 | 95 | | | | | |
| | | | | | | | | (68) | | | | | | |
| 10 | 4.48 | 241 | 0.28 | | | | | 75 | 75 | | | | | |
| | | | | | | | | (0) | | | | | | |
| 10 | 4.48 | 242 | 0.28 | | | | | 55 | 75 | | | | | |
| | | | | | | | | (26) | | | | | | |
| 10 | 4.48 | 243 | 0.28 | | | | | 10 | 65 | | | | | |
| | | | | | | | | (84) | | | | | | |
| 10 | 4.48 | 244 | 0.28 | | | | | 45 | 95 | | | | | |
| | | | | | | | | (52) | | | | | | |
| 10 | 4.48 | 245 | 0.28 | | | | | 50 | 90 | | | | | |
| | | | | | | | | (44) | | | | | | |
| 10 | 4.48 | 246 | 0.28 | | | | | 45 | 90 | | | | | |
| | | | | | | | | (50) | | | | | | |
| 10 | 4.48 | 247 | 0.28 | | | | | 55 | 95 | | | | | |
| | | | | | | | | (42) | | | | | | |
| 10 | 4.48 | 248 | 0.28 | | | | | 50 | 65 | | | | | |
| | | | | | | | | (23) | | | | | | |
| 10 | 4.48 | 249 | 0.28 | | | | | 85 | 95 | | | | | |
| | | | | | | | | (10) | | | | | | |
| 10 | 4.48 | 250 | 0.28 | | | | | 95 | 90 | | | | | |
| | | | | | | | | (0) | | | | | | |
| 10 | 4.48 | 251 | 0.28 | | | | | 80 | 90 | | | | | |
| | | | | | | | | (11) | | | | | | |
| 10 | 4.48 | 252 | 0.28 | | | | | 35 | 60 | | | | | |
| | | | | | | | | (41) | | | | | | |
| 10 | 4.48 | 253 | 0.28 | | | | | 15 | 60 | | | | | |
| | | | | | | | | (75) | | | | | | |
| 10 | 4.48 | 254 | 0.28 | | | | | 55 | 95 | | | | | |
| | | | | | | | | (42) | | | | | | |
| 10 | 4.48 | 255 | 0.28 | | | | | 65 | 95 | | | | | |
| | | | | | | | | (31) | | | | | | |
| 10 | 4.48 | 256 | 0.28 | | | | | 75 | 95 | | | | | |
| | | | | | | | | (21) | | | | | | |
| 10 | 4.48 | 257 | 0.28 | | | | | 75 | 95 | | | | | |
| | | | | | | | | (21) | | | | | | |
| 10 | 4.48 | 258 | 0.28 | | | | | 95 | 100 | | | | | |
| | | | | | | | | (5) | | | | | | |
| 10 | 4.48 | 259 | 0.28 | | | | | 65 | 95 | | | | | |
| | | | | | | | | (31) | | | | | | |
| 10 | 4.48 | 260 | 0.28 | | | | | 70 | 95 | | | | | |
| | | | | | | | | (26) | | | | | | |
| 10 | 4.48 | 261 | 0.28 | | | | | 55 | 95 | | | | | |
| | | | | | | | | (42) | | | | | | |
| 10 | 4.48 | 262 | 0.28 | | | | | 55 | 95 | | | | | |
| | | | | | | | | (42) | | | | | | |
| 10 | 4.48 | 263 | 0.28 | | | | | 55 | 95 | | | | | |
| | | | | | | | | (42) | | | | | | |
| 10 | 4.48 | 264 | 0.28 | | | | | 40 | 95 | | | | | |
| | | | | | | | | (57) | | | | | | |
| 10 | 4.48 | 265 | 0.28 | | | | | 50 | 95 | | | | | |
| | | | | | | | | (47) | | | | | | |
| 10 | 4.48 | 266 | 0.28 | | | | | 50 | 95 | | | | | |
| | | | | | | | | (47) | | | | | | |
| 10 | 4.48 | 267 | 0.28 | | | | | 55 | 95 | | | | | |
| | | | | | | | | (42) | | | | | | |
| 10 | 4.48 | 268 | 0.28 | | | | | 65 | 95 | | | | | |
| | | | | | | | | (31) | | | | | | |
| 10 | 4.48 | 269 | 0.28 | | | | | 55 | 95 | | | | | |
| | | | | | | | | (42) | | | | | | |
| 10 | 4.48 | 270 | 0.28 | | | | | 55 | 95 | | | | | |
| | | | | | | | | (42) | | | | | | |
| 10 | 4.48 | 271 | 0.28 | | | | | 65 | 95 | | | | | |
| | | | | | | | | (31) | | | | | | |
| 10 | 4.48 | 272 | 0.28 | | | | | 65 | 95 | | | | | |
| | | | | | | | | (31) | | | | | | |
| 10 | 4.48 | 273 | 0.28 | | | | | 70 | 95 | | | | | |
| | | | | | | | | (26) | | | | | | |
| 10 | 4.48 | 274 | 0.28 | | | | | 65 | 95 | | | | | |
| | | | | | | | | (31) | | | | | | |
| 10 | 4.48 | 275 | 0.28 | | | | | 40 | 95 | | | | | |
| | | | | | | | | (57) | | | | | | |
| 10 | 4.48 | 276 | 0.28 | | | | | 50 | 95 | | | | | |
| | | | | | | | | (47) | | | | | | |
| 10 | 4.48 | 277 | 0.28 | | | | | 50 | 90 | | | | | |
| | | | | | | | | (44) | | | | | | |
| 10 | 4.48 | 278 | 0.28 | | | | | 70 | 100 | | | | | |

TABLE III-continued

% PLANT INHIBITION AND % SAFENING EFFECT ( )

| HERBICIDE NO | RATE | ANTIDOTE NO | RATE | SORGHUM GRAIN W | WO | WHEAT W | WO | RICE W | WO | SOYBEAN W | WO | CORN W | WO |
|---|---|---|---|---|---|---|---|---|---|---|---|---|---|
| 10 | 4.48 | 279 | 0.28 | | | | | 45 (30) | 95 | | | | |
| 10 | 4.48 | 280 | 0.28 | | | | | 50 (52) | 70 | | | | |
| 10 | 4.48 | 281 | 0.28 | | | | | 65 (28) | 85 | | | | |
| 10 | 4.48 | 282 | 0.28 | | | | | 90 (23) | 95 | | | | |
| 10 | 4.48 | 283 | 0.28 | | | | | 95 (5) | 95 (0) | | | | |
| 15 | 2.24 | 203 | 0.28 | | | | | | | | | 40 (57) | 95 |
| 15 | 2.24 | 203 | 0.28 | | | | | | | 40 (33) | 60 | 40 (0) | 85 |
| 15 | 2.24 | 204 | 0.28 | | | | | | | 55 (0) | 40 | 85 (0) | 85 |
| 15 | 2.24 | 205 | 0.28 | | | | | | | 15 (72) | 55 | 20 (77) | 90 |
| 15 | 2.24 | 206 | 0.28 | | | | | | | 20 (60) | 50 | 50 (47) | 95 |
| 15 | 2.24 | 207 | 0.28 | | | | | | | 50 (0) | 45 | 80 (15) | 95 |
| 15 | 2.24 | 208 | 0.28 | | | | | | | 30 (40) | 50 | 95 (0) | 95 |
| 15 | 2.24 | 209 | 0.28 | | | | | | | 20 (60) | 50 | 0 (100) | 90 |
| 15 | 2.24 | 210 | 0.28 | | | | | | | 30 (57) | 70 | 70 (26) | 90 |
| 15 | 2.24 | 211 | 0.28 | | | | | | | 80 (0) | 60 | 60 (33) | 90 |
| 15 | 2.24 | 212 | 0.28 | | | | | | | 60 (25) | 80 | 20 (75) | 80 |
| 15 | 2.24 | 213 | 0.28 | | | | | | | 40 (50) | 80 | 10 (89) | 95 |
| 15 | 2.24 | 214 | 0.28 | | | | | | | 70 (0) | 70 | 95 (0) | 95 |
| 15 | 2.24 | 215 | 0.28 | | | | | | | 70 (0) | 70 | 95 (0) | 95 |
| 15 | 2.24 | 216 | 0.28 | | | | | | | 70 (0) | 70 | 95 (0) | 95 |
| 15 | 2.24 | 217 | 0.28 | | | | | | | 70 (17) | 85 | 75 (21) | 95 |
| 15 | 2.24 | 218 | 0.28 | | | | | | | 85 (0) | 85 | 95 (0) | 95 |
| 15 | 2.24 | 219 | 0.28 | | | | | | | 85 (0) | 85 | 95 (0) | 95 |
| 15 | 2.24 | 220 | 0.28 | | | | | | | 85 (5) | 90 | 95 (0) | 95 |
| 15 | 2.24 | 221 | 0.28 | | | | | | | 80 (0) | 70 | 50 (47) | 95 |
| 15 | 2.24 | 222 | 0.28 | | | | | | | 85 (0) | 70 | 95 (0) | 95 |
| 15 | 2.24 | 223 | 0.28 | | | | | | | 95 (0) | 70 | 85 (10) | 95 |
| 15 | 2.24 | 224 | 0.28 | | | | | | | 90 (0) | 70 | 60 (36) | 90 |
| 15 | 2.24 | 225 | 0.28 | | | | | | | 75 (0) | 70 | 90 (0) | 90 |
| 15 | 2.24 | 226 | 0.28 | | | | | | | 70 (0) | 70 | 60 (33) | 90 |
| 15 | 2.24 | 227 | 0.28 | | | | | | | 30 (57) | 70 | 40 (55) | 90 |
| 15 | 2.24 | 228 | 0.28 | | | | | | | 30 (57) | 70 | 40 (55) | 90 |
| 15 | 2.24 | 229 | 0.28 | | | | | | | 20 (71) | 70 | 10 (88) | 85 |
| 15 | 2.24 | 230 | 0.28 | | | | | | | 20 (71) | 70 | 10 (88) | 95 |
| 15 | 2.24 | 231 | 0.28 | | | | | | | 20 (69) | 65 | 50 (47) | 95 |
| 15 | 2.24 | 232 | 0.28 | | | | | | | 10 (84) | 65 | 30 (68) | 95 |
| 15 | 2.24 | 233 | 0.28 | | | | | | | 15 (72) | 55 | 95 (0) | 95 |
| 15 | 2.24 | 234 | 0.28 | | | | | | | 40 (27) | 55 | 90 (5) | 95 |

TABLE III-continued

% PLANT INHIBITION AND % SAFENING EFFECT ( )

| HERBICIDE | | ANTIDOTE | | SORGHUM GRAIN | | WHEAT | | RICE | | SOYBEAN | | CORN | |
|---|---|---|---|---|---|---|---|---|---|---|---|---|---|
| NO. | RATE | NO. | RATE | W | WO | W | WO | W | WO | W | WO | W | WO |
| 15 | 2.24 | 235 | 0.28 | | | | | | | 60 (0) | 45 | 55 (31) | 80 |
| 15 | 2.24 | 236 | 0.28 | | | | | | | 70 (0) | 45 | 30 (62) | 80 |
| 15 | 2.24 | 237 | 0.28 | | | | | | | | | 30 (50) | 60 |
| 15 | 2.24 | 237 | 0.28 | | | | | | | 65 (0) | 45 | | |
| 15 | 2.24 | 238 | 0.28 | | | | | | | 80 (0) | 45 | 100 (0) | 95 |
| 15 | 2.24 | 239 | 0.28 | | | | | | | 15 (72) | 55 | 80 (20) | 100 |
| 15 | 2.24 | 240 | 0.28 | | | | | | | 20 (63) | 55 | 50 (50) | 100 |
| 15 | 2.24 | 241 | 0.28 | | | | | | | 25 (54) | 55 | 60 (29) | 85 |
| 15 | 2.24 | 242 | 0.28 | | | | | | | 45 (18) | 55 | 70 (17) | 85 |
| 15 | 2.24 | 243 | 0.28 | | | | | | | | | 25 (68) | 80 |
| 15 | 2.24 | 244 | 0.28 | | | | | | | 15 (66) | 45 | 65 (35) | 100 |
| 15 | 2.24 | 245 | 0.28 | | | | | | | 0 (100) | 40 | 45 (43) | 80 |
| 15 | 2.24 | 246 | 0.28 | | | | | | | 35 (12) | 40 | 65 (18) | 80 |
| 15 | 2.24 | 247 | 0.28 | | | | | | | 55 (0) | 50 | 45 (52) | 95 |
| 15 | 2.24 | 248 | 0.28 | | | | | | | | | 80 (20) | 100 |
| 15 | 2.24 | 248 | 0.28 | | | | | | | 85 (0) | 45 | | |
| 15 | 2.24 | 249 | 0.28 | | | | | | | 15 (66) | 45 | 95 (5) | 100 |
| 15 | 2.24 | 250 | 0.28 | | | | | | | 90 (0) | 75 | 15 (83) | 90 |
| 15 | 2.24 | 251 | 0.28 | | | | | | | 65 (13) | 75 | 20 (77) | 90 |
| 15 | 2.24 | 252 | 0.28 | | | | | | | 10 (80) | 50 | 20 (80) | 100 |
| 15 | 2.24 | 253 | 0.28 | | | | | | | 40 (20) | 50 | 15 (85) | 100 |
| 15 | 2.24 | 254 | 0.28 | | | | | | | 35 (41) | 60 | 95 (0) | 95 |
| 15 | 2.24 | 255 | 0.28 | | | | | | | 5 (88) | 45 | 75 (21) | 95 |
| 15 | 2.24 | 256 | 0.28 | | | | | | | 15 (66) | 45 | 90 (5) | 95 |
| 15 | 2.24 | 257 | 0.28 | | | | | | | 90 (0) | 45 | 100 (0) | 95 |
| 15 | 2.24 | 258 | 0.28 | | | | | | | 60 (7) | 65 | 95 (5) | 100 |
| 15 | 2.24 | 259 | 0.28 | | | | | | | 95 (0) | 50 | 90 (5) | 95 |
| 15 | 2.24 | 260 | 0.28 | | | | | | | 55 (31) | 80 | 90 (5) | 95 |
| 15 | 2.24 | 261 | 0.28 | | | | | | | 85 (0) | 75 | 95 (5) | 100 |
| 15 | 2.24 | 262 | 0.28 | | | | | | | 70 (6) | 75 | 100 (0) | 100 |
| 15 | 2.24 | 263 | 0.28 | | | | | | | 55 (35) | 85 | 55 (42) | 95 |
| 15 | 2.24 | 264 | 0.28 | | | | | | | 45 (47) | 85 | 30 (68) | 95 |
| 15 | 2.24 | 265 | 0.28 | | | | | | | 55 (35) | 85 | 55 (42) | 95 |
| 15 | 2.24 | 266 | 0.28 | | | | | | | 90 (0) | 85 | 55 (42) | 95 |
| 15 | 2.24 | 267 | 0.28 | | | | | | | 95 (0) | 90 | 90 (5) | 95 |
| 15 | 2.24 | 268 | 0.28 | | | | | | | 65 (27) | 90 | 95 (0) | 95 |
| 15 | 2.24 | 269 | 0.28 | | | | | | | 80 (11) | 90 | 90 (5) | 95 |
| 15 | 2.24 | 270 | 0.28 | | | | | | | 50 (44) | 90 | 95 (5) | 100 |
| 15 | 2.24 | 271 | 0.28 | | | | | | | 75 | 80 | 40 | 80 |

TABLE III-continued

| HERBICIDE | | ANTIDOTE | | SORGHUM GRAIN | | WHEAT | | RICE | | SOYBEAN | | | CORN | | |
|---|---|---|---|---|---|---|---|---|---|---|---|---|---|---|---|
| NO. | RATE | NO. | RATE | W | WO | W | WO | W | WO | W | (safening) | WO | W | (safening) | WO |
| 15 | 2.24 | 272 | 0.28 | | | | | | | 40 | (6) | 80 | 55 | (50) | 80 |
| 15 | 2.24 | 273 | 0.28 | | | | | | | 20 | (50) | 80 | 65 | (31) | 80 |
| 15 | 2.24 | 274 | 0.28 | | | | | | | 55 | (75) | 90 | 30 | (18) | 80 |
| 15 | 2.24 | 275 | 0.28 | | | | | | | 50 | (38) | 90 | 35 | (62) | 80 |
| 15 | 2.24 | 276 | 0.28 | | | | | | | 40 | (44) | 90 | 15 | (56) | 80 |
| 15 | 2.24 | 277 | 0.28 | | | | | | | 85 | (55) | 90 | 75 | (81) | 100 |
| 15 | 2.24 | 278 | 0.28 | | | | | | | 75 | (5) | 80 | 50 | (25) | 95 |
| 15 | 2.24 | 279 | 0.28 | | | | | | | 45 | (6) | 85 | 65 | (47) | 95 |
| 15 | 2.24 | 280 | 0.28 | | | | | | | 40 | (47) | 50 | 85 | (31) | 80 |
| 15 | 2.24 | 281 | 0.28 | | | | | | | 45 | (20) | 50 | 65 | (0) | 95 |
| 15 | 2.24 | 282 | 0.28 | | | | | | | 95 | (10) | 80 | 90 | (31) | 95 |
| 15 | 2.24 | 283 | 0.28 | | | | | | | 60 | (0) | 80 (25) | 95 | (5) | 95 (0) |

EXAMPLE 287

The procedure of Example 285 was followed to determine the interaction between herbicide and antidote when both are incorporated in a soil cover layer before emergence of the crop species. In this series of tests, however, all containers were seeded with at least one weed species in addition to crop seed. Results are reported in Table IV.

TABLE IV

| HERBICIDE NO. | RATE | ANTIDOTE NO. | RATE | SOYBEAN W | WO | RICE W | WO | HEMP SESBANIA W | WO | VELVET LEAF W | WO | SORGHUM GRAIN W | WO | WHEAT W | WO | GREEN FOXTAIL W | WO | CORN W | WO | BARNYARD GRASS W | WO | RED RICE W | WO | SHATTER CANE W | WO |
|---|---|---|---|---|---|---|---|---|---|---|---|---|---|---|---|---|---|---|---|---|---|---|---|---|---|
| 3 | 1.12 | 11 | 8.96 | 30 | 35 (14) | 10 | 40 (75) | 99 | 99 (0) | 50 | 90 (44) | | | | | | | | | | | | | | |
| 3 | 2.24 | 11 | 8.96 | 50 | 60 (16) | 50 | 75 (33) | 99 | 100 (1) | 99 | 99 (0) | | | | | | | | | | | | | | |
| 3 | 4.48 | 11 | 8.96 | 95 | 90 (0) | 99 | 80 (0) | 100 | 100 (0) | 100 | 100 (0) | | | | | | | | | | | | | | |
| 3 | 6.72 | 11 | 8.96 | 100 | 95 (0) | 100 | 95 (0) | 100 | 100 (0) | 100 | 100 (0) | | | | | | | | | | | | | | |
| 3 | 1.12 | 13 | 8.96 | 95 | 50 (0) | 70 | 30 (0) | 100 | 100 (0) | 85 | 40 (0) | | | | | | | | | | | | | | |
| 3 | 2.24 | 13 | 8.96 | 99 | 60 (0) | 40 | 30 (0) | 99 | 99 (0) | 30 | 70 (57) | | | | | | | | | | | | | | |
| 3 | 4.48 | 13 | 8.96 | 100 | 80 (0) | 75 | 70 (0) | 99 | 99 (0) | 99 | 100 (1) | | | | | | | | | | | | | | |
| 3 | 6.72 | 13 | 8.96 | 99 | 100 (1) | 80 | 100 (20) | 99 | 100 (1) | 90 | 100 (10) | | | | | | | | | | | | | | |
| 3 | 1.12 | 21 | 8.96 | 90 | 60 (0) | 50 | 45 (0) | 100 | 80 (0) | 85 | 60 (0) | | | | | | | | | | | | | | |
| 3 | 2.24 | 21 | 8.96 | 95 | 60 (0) | 30 | 60 (50) | 100 | 100 (0) | 100 | 90 (0) | | | | | | | | | | | | | | |
| 3 | 4.48 | 21 | 8.96 | 95 | 70 (0) | 30 | 85 (64) | 100 | 100 (0) | 95 | 100 (5) | | | | | | | | | | | | | | |
| 3 | 6.72 | 21 | 8.96 | 90 | 90 (0) | 70 | 75 (6) | 100 | 100 (0) | 100 | 100 (0) | | | | | | | | | | | | | | |
| 3 | 2.24 | 30 | 2.24 | 10 | 60 (83) | | | | | 90 | 100 (10) | | | | | | | | | | | | | | |
| 3 | 2.24 | 30 | 8.96 | 10 | 60 (83) | | | | | 100 | 100 (0) | | | | | | | | | | | | | | |
| 3 | 6.72 | 30 | 2.24 | 95 | 90 (0) | | | | | 100 | 100 (0) | | | | | | | | | | | | | | |
| 3 | 6.72 | 30 | 8.96 | 75 | 90 (16) | | | | | 100 | 100 (0) | | | | | | | | | | | | | | |
| 3 | 2.24 | 32 | 2.24 | 70 | 80 (12) | | | | | 100 | 100 (0) | | | | | | | | | | | | | | |
| 3 | 2.24 | 32 | 8.96 | 80 | 80 (0) | | | | | 100 | 100 (0) | | | | | | | | | | | | | | |
| 3 | 6.72 | 32 | 2.24 | 95 | 95 (0) | | | | | 100 | 100 (0) | | | | | | | | | | | | | | |
| 3 | 6.72 | 32 | 8.96 | 90 | 95 (5) | | | | | 100 | 100 (0) | | | | | | | | | | | | | | |
| 6 | 0.56 | 1 | 2.24 | | | | | | | | | 60 | 58 (0) | 5 | 28 (82) | | | | | | | | | | |
| 6 | 0.56 | 1 | 2.24 | | | | | | | | | 30 | 85 (64) | 15 | 30 (50) | 85 | 90 (5) | | | | | | | | |
| 6 | 0.56 | 1 | 2.24 | | | | | | | | | 0 | 50 (100) | 30 | 40 (25) | 98 | 98 (0) | | | | | | | | |
| 6 | 0.56 | 1 | 8.96 | | | | | | | | | | | | | | | | | | | | | | |

TABLE IV-continued

| HERBICIDE NO. | RATE | ANTIDOTE NO. | RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 6 | 0.56 | 1 | 8.96 | | | | | | | | | 5 (94) | 85 | 20 (33) | 30 | 85 (5) | 90 | | | | | | | | |
| 6 | 0.56 | 1 | 8.96 | | | | | | | | | | | 5 (82) | 28 | | | | | | | | | | |
| 6 | 0.56 | 1 | 8.96 | | | | | | | | | 20 (65) | 58 | | | | | | | | | | | | |
| 6 | 1.12 | 1 | 8.96 | | | | | | | | | 10 (85) | 70 | 30 (40) | 50 | (0) | 99 | | | | | | | | |
| 6 | 2.24 | 1 | 2.24 | | | | | | | | | 75 (14) | 88 | | | | | | | | | | | | |
| 6 | 2.24 | 1 | 2.24 | | | | | | | | | 45 (52) | 95 | 35 (30) | 50 | (0) | 95 | | | | | | | | |
| 6 | 2.24 | 1 | 2.24 | | | | | | | | | | | 5 (87) | 40 | | | | | | | | | | |
| 6 | 2.24 | 1 | 8.96 | | | | | | | | | 60 (31) | 88 | | | | | | | | | | | | |
| 6 | 2.24 | 1 | 8.96 | | | | | | | | | | | 15 (62) | 40 | | | | | | | | | | |
| 6 | 2.24 | 1 | 8.96 | | | | | | | | | 15 (84) | 95 | 30 (57) | 70 | 98 (1) | 99 | | | | | | | | |
| 6 | 2.24 | 1 | 8.96 | | | | | | | | | 40 (57) | 95 | 45 (10) | 50 | 100 (0) | 95 | | | | | | | | |
| 6 | 4.48 | 1 | 8.96 | | | | | | | | | 75 (23) | 98 | 70 (12) | 80 | 100 (0) | 99 | | | | | | | | |
| 6 | 0.56 | 3 | 2.24 | | | | | | | | | 15 (74) | 58 | | | | | | | | | | | | |
| 6 | 0.56 | 3 | 2.24 | | | | | | | | | | | 0 (100) | 28 | | | | | | | | | | |
| 6 | 0.56 | 3 | 8.96 | | | | | | | | | 0 (100) | 60 | 10 (83) | 60 | 100 (0) | 100 | | | | | | | | |
| 6 | 0.56 | 3 | 8.96 | | | | | | | | | | | 0 (100) | 28 | | | | | | | | | | |
| 6 | 0.56 | 3 | 8.96 | | | | | | | | | 5 (91) | 58 | | | | | | | | | | | | |
| 6 | 1.12 | 3 | 8.96 | | | | | | | | | 0 (100) | 90 | 0 (100) | 80 | 100 (0) | 100 | | | | | | | | |
| 6 | 2.24 | 3 | 0.56 | | | | | | | | | 80 (15) | 95 | 40 (45) | 73 | | | | | | | | | | |
| 6 | 2.24 | 3 | 2.24 | | | | | | | | | 25 (73) | 95 | 40 (45) | 73 | | | | | | | | | | |
| 6 | 2.24 | 3 | 2.24 | | | | | | | | | 80 (9) | 88 | | | | | | | | | | | | |
| 6 | 2.24 | 3 | 2.24 | | | | | | | | | 35 (63) | 95 | 20 (50) | 40 | | | | | | | | | | |
| 6 | 2.24 | 3 | 4.48 | | | | | | | | | | | 70 (4) | 73 | | | | | | | | | | |
| 6 | 2.24 | 3 | 8.96 | | | | | | | | | 15 (83) | 90 | 35 (56) | 80 | 100 (0) | 100 | | | | | | | | |

TABLE IV-continued

| | | | | % PLANT INHIBITION AND % SAFENING EFFECT ( ) | | | | | | | | | | | | | | | | | | | | | | | | |
|---|---|---|---|---|---|---|---|---|---|---|---|---|---|---|---|---|---|---|---|---|---|---|---|---|---|---|---|---|
| HERBICIDE | | ANTIDOTE | | SOYBEAN | | RICE | | HEMP SESBANIA | | VELVET LEAF | | SORGHUM GRAIN | | WHEAT | | GREEN FOXTAIL | | CORN | | BARNYARD GRASS | | RED RICE | | SHATTER CANE | |
| NO. | RATE | NO. | RATE | W | WO | W | WO | W | WO | W | WO | W | WO | W | WO | W | WO | W | WO | W | WO | W | WO | W | WO |
| 6 | 2.24 | 3 | 8.96 | | | | | | | | | | | 10 | 40 (75) | | | | | | | | | | |
| 6 | 2.24 | 3 | 8.96 | | | | | | | | | 25 | 88 (71) | | | | | | | | | | | | |
| 6 | 4.48 | 3 | 8.96 | | | | | | | | | 10 | 100 (90) | 75 | 90 (16) | 100 | 100 (0) | | | | | | | | |
| 6 | 0.56 | 4 | 2.24 | | | | | | | | | 5 | 48 (89) | | | | | | | | | | | | |
| 6 | 0.56 | 4 | 8.96 | | | | | | | | | 5 | 48 (89) | | | | | | | | | | | | |
| 6 | 0.56 | 4 | 8.96 | | | | | | | | | 10 | 65 (84) | 25 | 60 (58) | 99 | 99 (0) | | | | | | | | |
| 6 | 1.12 | 4 | 8.96 | | | | | | | | | 20 | 90 (77) | 25 | 70 (64) | 100 | 99 (0) | | | | | | | | |
| 6 | 2.24 | 4 | 2.24 | | | | | | | | | 10 | 83 (87) | | | | | | | | | | | | |
| 6 | 2.24 | 4 | 8.96 | | | | | | | | | 5 | 83 (93) | | | | | | | | | | | | |
| 6 | 2.24 | 4 | 8.96 | | | | | | | | | 40 | 98 (59) | 50 | 85 (41) | 100 | 99 (0) | | | | | | | | |
| 6 | 4.48 | 4 | 8.96 | | | | | | | | | 50 | 99 (49) | 70 | 85 (17) | 100 | 99 (0) | | | | | | | | |
| 6 | 0.56 | 6 | 8.96 | | | | | | | | | 0 | 20 (100) | 30 | 75 (60) | 75 | 50 (0) | | | | | | | | |
| 6 | 1.12 | 6 | 8.96 | | | | | | | | | 0 | 30 (100) | 40 | 70 (42) | 90 | 80 (0) | | | | | | | | |
| 6 | 2.24 | 6 | 8.96 | | | | | | | | | 10 | 50 (80) | 40 | 50 (20) | 99 | 95 (0) | | | | | | | | |
| 6 | 4.48 | 6 | 8.96 | | | | | | | | | 20 | 80 (75) | 60 | 70 (0) | 100 | 95 (14) | | | | | | | | |
| 6 | 0.56 | 7 | 2.24 | | | | | | | | | 35 | 58 (39) | 15 | 28 (46) | | | | | | | | | | |
| 6 | 0.56 | 7 | 2.24 | | | | | | | | | 0 | 90 (100) | 80 | 40 (0) | 80 | 50 (0) | | | | | | | | |
| 6 | 0.56 | 7 | 8.96 | | | | | | | | | | | 5 | 28 (82) | | | | | | | | | | |
| 6 | 0.56 | 7 | 8.96 | | | | | | | | | 10 | 58 (82) | | | | | | | | | | | | |
| 6 | 1.12 | 7 | 8.96 | | | | | | | | | 0 | 90 (100) | 60 | 60 (0) | 70 | 70 (0) | | | | | | | | |
| 6 | 2.24 | 7 | 2.24 | | | | | | | | | 85 | 88 (3) | | | | | | | | | | | | |
| 6 | 2.24 | 7 | 2.24 | | | | | | | | | | | 25 | 40 (37) | | | | | | | | | | |
| 6 | 2.24 | 7 | 8.96 | | | | | | | | | | | 30 | 40 (25) | | | | | | | | | | |

TABLE IV-continued

| HERBICIDE NO. | RATE | ANTIDOTE NO. | RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 6 | 2.24 | 7 | 8.96 | | | | | | | | | 5 | 99 (94) | 95 | 85 (0) | 100 | 75 (0) | | | | | | | | |
| 6 | 2.24 | 7 | 8.96 | | | | | | | | | 35 | 88 (60) | | | | | | | | | | | | |
| 6 | 4.48 | 7 | 8.96 | | | | | | | | | 10 | 99 (89) | 90 | 90 (0) | 95 | 99 (4) | | | | | | | | |
| 6 | 0.56 | 8 | 8.96 | | | | | | | | | 0 | 90 (100) | 80 | 40 (0) | 20 | 50 (60) | | | | | | | | |
| 6 | 1.12 | 8 | 8.96 | | | | | | | | | 0 | 90 (100) | 90 | 60 (0) | 70 | 70 (0) | | | | | | | | |
| 6 | 2.24 | 8 | 8.96 | | | | | | | | | 0 | 99 (100) | 90 | 85 (0) | 90 | 75 (0) | | | | | | | | |
| 6 | 4.48 | 8 | 8.96 | | | | | | | | | 20 | 99 (79) | 85 | 90 (0) | 99 | 99 (0) | | | | | | | | |
| 6 | 0.56 | 9 | 2.24 | | | | | | | | | 45 | 58 (22) | | | | | | | | | | | | |
| 6 | 0.56 | 9 | 2.24 | | | | | | | | | | | 5 | 28 (82) | | | | | | | | | | |
| 6 | 0.56 | 9 | 8.96 | | | | | | | | | 25 | 58 (56) | | | | | | | | | | | | |
| 6 | 0.56 | 9 | 8.96 | | | | | | | | | 0 | 90 (100) | 50 | 70 (28) | 95 | 50 (0) | | | | | | | | |
| 6 | 0.56 | 9 | 8.96 | | | | | | | | | | | 10 | 28 (64) | | | | | | | | | | |
| 6 | 1.12 | 9 | 8.96 | | | | | | | | | 0 | 95 (100) | 70 | 80 (12) | 80 | 80 (0) | | | | | | | | |
| 6 | 2.24 | 9 | 2.24 | | | | | | | | | 80 | 88 (9) | | | | | | | | | | | | |
| 6 | 2.24 | 9 | 2.24 | | | | | | | | | | | 30 | 40 (25) | | | | | | | | | | |
| 6 | 2.24 | 9 | 8.96 | | | | | | | | | 70 | 88 (20) | 90 | 80 (0) | 100 | 100 (0) | | | | | | | | |
| 6 | 2.24 | 9 | 8.96 | | | | | | | | | 10 | 100 (90) | 20 | 40 (50) | | | | | | | | | | |
| 6 | 4.48 | 9 | 8.96 | | | | | | | | | 30 | 100 (70) | 95 | 100 (5) | 100 | 99 (0) | | | | | | | | |
| 6 | 0.56 | 10 | 2.24 | | | | | | | | | 35 | 88 (60) | | | | | | | | | | | | |
| 6 | 0.56 | 10 | 2.24 | | | | | | | | | | | 15 | 48 (68) | | | | | | | | | | |
| 6 | 0.56 | 10 | 8.96 | | | | | | | | | 0 | 90 (100) | 40 | 70 (42) | 90 | 50 (0) | | | | | | | | |
| 6 | 0.56 | 10 | 8.96 | | | | | | | | | | | 15 | 48 (68) | | | | | | | | | | |
| 6 | 0.56 | 10 | 8.96 | | | | | | | | | 5 | 88 (94) | | | | | | | | | | | | |

TABLE IV-continued

| HERBICIDE NO. | RATE | ANTIDOTE NO. | RATE | SOYBEAN W | WO | RICE W | WO | HEMP SESBANIA W | WO | VELVET LEAF W | WO | SORGHUM GRAIN W | WO | WHEAT W | WO | GREEN FOXTAIL W | WO | CORN W | WO | BARNYARD GRASS W | WO | RED RICE W | WO | SHATTER CANE W | WO |
|---|---|---|---|---|---|---|---|---|---|---|---|---|---|---|---|---|---|---|---|---|---|---|---|---|---|
| 6 | 1.12 | 10 | 8.96 | | | | | | | | | 0 | 95 (100) | 60 | 80 (25) | 90 | 80 (0) | | | | | | | | |
| 6 | 2.24 | 10 | 2.24 | | | | | | | | | 65 | 98 (33) | | | | | | | | | | | | |
| 6 | 2.24 | 10 | 2.24 | | | | | | | | | | | 70 | 75 (6) | | | | | | | | | | |
| 6 | 2.24 | 10 | 8.96 | | | | | | | | | 25 | 98 (74) | | | | | | | | | | | | |
| 6 | 2.24 | 10 | 8.96 | | | | | | | | | 20 | 100 (80) | 60 | 80 (25) | 100 | 100 (0) | | | | | | | | |
| 6 | 2.24 | 10 | 8.96 | | | | | | | | | | | 60 | 75 (20) | | | | | | | | | | |
| 6 | 4.48 | 10 | 8.96 | | | | | | | | | 25 | 100 (75) | 90 | 100 (10) | 100 | 99 (0) | | | | | | | | |
| 6 | 0.56 | 11 | 8.96 | | | | | | | | | 0 | 35 (100) | 40 | 60 (33) | 40 | 80 (50) | | | | | | | | |
| 6 | 1.12 | 11 | 8.96 | | | | | | | | | 10 | 85 (88) | 80 | 70 (0) | 90 | 90 (0) | | | | | | | | |
| 6 | 2.24 | 11 | 8.96 | | | | | | | | | 10 | 90 (88) | 80 | 90 (11) | 100 | 99 (0) | | | | | | | | |
| 6 | 4.48 | 11 | 8.96 | | | | | | | | | 50 | 99 (49) | 90 | 90 (0) | 100 | 100 (0) | | | | | | | | |
| 6 | 0.56 | 12 | 2.24 | | | | | | | | | 30 | 58 (48) | 10 | 28 (64) | | | | | | | | | | |
| 6 | 0.56 | 12 | 2.24 | | | | | | | | | | | 20 | 28 (28) | | | | | | | | | | |
| 6 | 0.56 | 12 | 8.96 | | | | | | | | | 0 | 58 (100) | | | | | | | | | | | | |
| 6 | 0.56 | 12 | 8.96 | | | | | | | | | 10 | 60 (83) | 40 | 50 (20) | 50 | 70 (28) | | | | | | | | |
| 6 | 1.12 | 12 | 8.96 | | | | | | | | | 20 | 60 (66) | 70 | 50 (0) | 95 | 80 (0) | | | | | | | | |
| 6 | 2.24 | 12 | 2.24 | | | | | | | | | 55 | 88 (37) | | | | | | | | | | | | |
| 6 | 2.24 | 12 | 8.96 | | | | | | | | | | | 10 | 40 (75) | | | | | | | | | | |
| 6 | 2.24 | 12 | 8.96 | | | | | | | | | | | 10 | 40 (75) | | | | | | | | | | |
| 6 | 2.24 | 12 | 8.96 | | | | | | | | | 25 | 80 (68) | 70 | 85 (17) | 80 | 95 (15) | | | | | | | | |
| 6 | 2.24 | 12 | 8.96 | | | | | | | | | 25 | 88 (71) | | | | | | | | | | | | |
| 6 | 4.48 | 12 | 8.96 | | | | | | | | | 30 | 90 (66) | 90 | 95 (5) | 100 | 100 (0) | | | | | | | | |
| 6 | 0.56 | 13 | 8.96 | | | | | | | | | 30 | 90 (66) | 30 | 40 (25) | 99 | 90 (0) | | | | | | | | |

TABLE IV-continued

% PLANT INHIBITION AND % SAFENING EFFECT ( )

| HERBICIDE NO. | RATE | ANTIDOTE NO. | RATE | SOYBEAN W | WO | RICE W | WO | HEMP SESBANIA W | WO | VELVET LEAF W | WO | SORGHUM GRAIN W | WO | WHEAT W | WO | GREEN FOXTAIL W | WO | CORN W | WO | BARNYARD GRASS W | WO | RED RICE W | WO | SHATTER CANE W | WO |
|---|---|---|---|---|---|---|---|---|---|---|---|---|---|---|---|---|---|---|---|---|---|---|---|---|---|
| 6 | 1.12 | 13 | 8.96 | | | | | | | | | 40 | 99 (59) | 40 | 60 (33) | 80 | 90 (11) | | | | | | | | |
| 6 | 2.24 | 13 | 8.96 | | | | | | | | | 80 | 99 (19) | 70 | 75 (6) | 99 | 95 (0) | | | | | | | | |
| 6 | 4.48 | 13 | 8.96 | | | | | | | | | 90 | (0) | 85 | 95 (10) | 100 | 95 (0) | | | | | | | | |
| 6 | 0.56 | 14 | 2.24 | | | | | | | | | | | 10 | 28 (64) | | | | | | | | | | |
| 6 | 0.56 | 14 | 2.24 | | | | | | | | | 40 | 58 (31) | | | | | | | | | | | | |
| 6 | 0.56 | 14 | 8.96 | | | | | | | | | 0 | 58 (100) | | | | | | | | | | | | |
| 6 | 0.56 | 14 | 8.96 | | | | | | | | | 10 | 90 (88) | 50 | 40 (0) | 80 | 90 (11) | | | | | | | | |
| 6 | 0.56 | 14 | 8.96 | | | | | | | | | | | 15 | 28 (46) | | | | | | | | | | |
| 6 | 1.12 | 14 | 8.96 | | | | | | | | | 35 | 99 (64) | 60 | 60 (0) | 95 | 90 (0) | | | | | | | | |
| 6 | 2.24 | 14 | 2.24 | | | | | | | | | 50 | 88 (43) | | | | | | | | | | | | |
| 6 | 2.24 | 14 | 2.24 | | | | | | | | | | | 20 | 40 (50) | | | | | | | | | | |
| 6 | 2.24 | 14 | 8.96 | | | | | | | | | 50 | 99 (49) | 90 | 75 (0) | 100 | 95 (0) | | | | | | | | |
| 6 | 2.24 | 14 | 8.96 | | | | | | | | | 45 | 88 (48) | | | | | | | | | | | | |
| 6 | 2.24 | 14 | 8.96 | | | | | | | | | | | 15 | 40 (62) | | | | | | | | | | |
| 6 | 4.48 | 14 | 8.96 | | | | | | | | | 50 | 90 (44) | 90 | 95 (5) | 99 | 95 (0) | | | | | | | | |
| 6 | 0.56 | 15 | 8.96 | | | | | | | | | 10 | 95 (89) | 50 | 70 (28) | 80 | 70 (0) | | | | | | | | |
| 6 | 1.12 | 15 | 8.96 | | | | | | | | | 60 | 95 (36) | 60 | 90 (33) | 100 | 80 (0) | | | | | | | | |
| 6 | 2.24 | 15 | 8.96 | | | | | | | | | 25 | 95 (73) | 70 | 99 (29) | 100 | 99 (0) | | | | | | | | |
| 6 | 4.48 | 15 | 8.96 | | | | | | | | | 55 | 100 (45) | 100 | 100 (0) | 100 | 99 (0) | | | | | | | | |
| 6 | 0.56 | 16 | 2.24 | | | | | | | | | | | 5 | 28 (82) | | | | | | | | | | |
| 6 | 0.56 | 16 | 2.24 | | | | | | | | | 10 | 58 (82) | | | | | | | | | | | | |
| 6 | 0.56 | 16 | 8.96 | | | | | | | | | | | 20 | 28 (28) | | | | | | | | | | |
| 6 | 0.56 | 16 | 8.96 | | | | | | | | | 10 | 58 (82) | | | | | | | | | | | | |
| 6 | 0.56 | 16 | 8.96 | | | | | | | | | 10 | 80 (87) | 30 | 50 (40) | 80 | 80 (0) | | | | | | | | |

TABLE IV-continued

% PLANT INHIBITION AND % SAFENING EFFECT ( )

| HERBICIDE NO. | HERBICIDE RATE | ANTIDOTE NO. | ANTIDOTE RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 6 | 1.12 | 16 | 8.96 | | | | | | | | | 30 | 80 (62) | 50 | 70 (28) | 90 | 95 (5) | | | | | | | | |
| 6 | 2.24 | 16 | 2.24 | | | | | | | | | 60 | 88 (31) | | | | | | | | | | | | |
| 6 | 2.24 | 16 | 2.24 | | | | | | | | | | | 25 | 40 (37) | | | | | | | | | | |
| 6 | 2.24 | 16 | 8.96 | | | | | | | | | 15 | 88 (82) | | | | | | | | | | | | |
| 6 | 2.24 | 16 | 8.96 | | | | | | | | | 40 | 95 (57) | 50 | 80 (37) | 90 | 95 (5) | | | | | | | | |
| 6 | 2.24 | 16 | 8.96 | | | | | | | | | | | 5 | 40 (87) | | | | | | | | | | |
| 6 | 4.48 | 16 | 8.96 | | | | | | | | | 60 | 100 (40) | 90 | 90 (0) | 95 | 99 (5) | | | | | | | | |
| 6 | 0.56 | 17 | 8.96 | | | | | | | | | 0 | 70 (100) | 10 | 45 (77) | 99 | 95 (0) | | | | | | | | |
| 6 | 1.12 | 17 | 8.96 | | | | | | | | | 10 | 80 (87) | 30 | 60 (50) | 99 | 95 (0) | | | | | | | | |
| 6 | 2.24 | 17 | 8.96 | | | | | | | | | 30 | 90 (66) | 40 | 80 (50) | 100 | 100 (0) | | | | | | | | |
| 6 | 4.48 | 17 | 8.96 | | | | | | | | | 40 | 95 (57) | 80 | 90 (50) | 100 | 100 (0) | | | | | | | | |
| 6 | 0.56 | 19 | 2.24 | | | | | | | | | 25 | 48 (47) | | (11) | | | | | | | | | | |
| 6 | 0.56 | 19 | 8.96 | | | | | | | | | 5 | 48 (89) | | | | | | | | | | | | |
| 6 | 2.24 | 19 | 2.24 | | | | | | | | | 30 | 83 (63) | | | | | | | | | | | | |
| 6 | 2.24 | 19 | 8.96 | | | | | | | | | 10 | 83 (87) | | | | | | | | | | | | |
| 6 | 0.56 | 20 | 2.24 | | | | | | | | | 10 | 48 (79) | | | | | | | | | | | | |
| 6 | 0.56 | 20 | 8.96 | | | | | | | | | 50 | 95 (47) | 30 | 50 (40) | 95 | 95 (0) | | | | | | | | |
| 6 | 0.56 | 20 | 8.96 | | | | | | | | | 10 | 48 (79) | | | | | | | | | | | | |
| 6 | 1.12 | 20 | 8.96 | | | | | | | | | 50 | 100 (50) | 40 | 80 (50) | 95 | 100 (5) | | | | | | | | |
| 6 | 2.24 | 20 | 2.24 | | | | | | | | | 35 | 83 (57) | | | | | | | | | | | | |
| 6 | 2.24 | 20 | 8.96 | | | | | | | | | 10 | 83 (87) | | | | | | | | | | | | |
| 6 | 2.24 | 20 | 2.24 | | | | | | | | | 50 | 100 (50) | 50 | 90 (44) | 99 | 100 (1) | | | | | | | | |
| 6 | 4.48 | 20 | 8.96 | | | | | | | | | 85 | 100 (15) | 80 | 95 (15) | 100 | 100 (0) | | | | | | | | |
| 6 | 0.56 | 22 | 2.24 | | | | | | | | | | | 5 | 20 (75) | | | | | | | | | | |

TABLE IV-continued

| | | | | | | | | % PLANT INHIBITION AND % SAFENING EFFECT ( ) | | | | | | | | | | | | | | | |
|---|---|---|---|---|---|---|---|---|---|---|---|---|---|---|---|---|---|---|---|---|---|---|---|
| HERBICIDE NO. | HERBICIDE RATE | ANTIDOTE NO. | ANTIDOTE RATE | SOYBEAN | | RICE | | HEMP SESBANIA | | VELVET LEAF | | SORGHUM GRAIN | | WHEAT | | GREEN FOXTAIL | | CORN | | BARNYARD GRASS | | RED RICE | | SHATTER CANE |
| | | | | W | WO | W | WO | W | WO | W | WO | W | WO | W | WO | W | WO | W | WO | W | WO | W | WO | W | WO |
| 6 | 0.56 | 22 | 8.96 | | | | | | | | | 0 | 95 (100) | 55 | 80 (31) | 85 | 35 (0) | | | | | | | | |
| 6 | 0.56 | 22 | 8.96 | | | | | | | | | | | 10 | 20 (50) | | | | | | | | | | |
| 6 | 1.12 | 22 | 8.96 | | | | | | | | | 50 | 100 (50) | 60 | 70 (14) | 80 | 75 (0) | | | | | | | | |
| 6 | 2.24 | 22 | 0.56 | | | | | | | | | 90 | 93 (3) | | | | | | | | | | | | |
| 6 | 2.24 | 22 | 2.24 | | | | | | | | | 95 | 93 (0) | | | | | | | | | | | | |
| 6 | 2.24 | 22 | 2.24 | | | | | | | | | | | 30 | 55 (45) | | | | | | | | | | |
| 6 | 2.24 | 22 | 8.96 | | | | | | | | | 75 | 95 (21) | 80 | 100 (20) | 95 | 90 (0) | | | | | | | | |
| 6 | 2.24 | 22 | 8.96 | | | | | | | | | | | 35 | 55 (36) | | | | | | | | | | |
| 6 | 2.24 | 22 | 8.96 | | | | | | | | | 65 | 93 (30) | | | | | | | | | | | | |
| 6 | 4.48 | 22 | 8.96 | | | | | | | | | 90 | 100 (10) | | | | | | | | | | | | |
| 6 | 0.56 | 23 | 2.24 | | | | | | | | | 45 | 70 (35) | 0 | 10 (100) | 95 | 95 (0) | | | | | | | | |
| 6 | 0.56 | 23 | 2.24 | | | | | | | | | | | 55 | 60 (8) | | | | | | | | | | |
| 6 | 0.56 | 23 | 2.24 | | | | | | | | | | | 50 | 40 (0) | 95 | 100 (0) | | | | | | | | |
| 6 | 0.56 | 23 | 2.24 | | | | | | | | | | | 15 | 45 (66) | 100 | 100 (0) | | | | | | | | |
| 6 | 0.56 | 23 | 2.24 | | | | | | | | | 95 | (0) | 20 | 40 (50) | 90 | 95 (5) | | | | | | | | |
| 6 | 0.56 | 23 | 2.24 | | | | | | | | | 55 | 85 (35) | 5 | 30 (83) | 90 | 90 (0) | | | | | | | | |
| 6 | 0.56 | 23 | 2.24 | | | | | | | | | | | 25 | 25 (0) | 100 | 100 (0) | | | | | | | | |
| 6 | 0.56 | 23 | 2.24 | | | | | | | | | | | 35 | 20 (0) | 90 | 100 (0) | | | | | | | | |
| 6 | 0.56 | 23 | 2.24 | | | | | | | | | 65 | 90 (27) | 30 | 35 (14) | 95 | 95 (0) | | | | | | | | |
| 6 | 0.56 | 23 | 2.24 | | | | | | | | | | | 40 | 40 (0) | 100 | 100 (0) | | | | | | | | |
| 6 | 0.56 | 23 | 2.24 | | | | | | | | | | | 85 | 85 (0) | 100 | 100 (0) | | | | | | | | |
| 6 | 0.56 | 23 | 2.24 | | | | | | | | | 25 | 90 (72) | 20 | 35 (42) | 90 | 95 (5) | | | | | | | | |
| 6 | 0.56 | 23 | 2.24 | | | | | | | | | | | 60 | 90 (33) | 100 | 100 (0) | | | | | | | | |
| 6 | 0.56 | 23 | 2.24 | | | | | | | | | 35 | 75 (53) | 10 | 30 (66) | 95 | 95 (0) | | | | | | | | |

TABLE IV-continued

% PLANT INHIBITION AND % SAFENING EFFECT ( )

| HERBICIDE NO. | RATE | ANTIDOTE NO. | RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 6 | 0.56 | 23 | 2.24 | | | | | | | | | | | 0 | 10 (100) | 100 | 100 (0) | | | | | | | | |
| 6 | 0.56 | 23 | 2.24 | | | | | | | | | 40 | 80 (50) | 20 | 35 (42) | 90 | 100 (10) | | | | | | | | |
| 6 | 0.56 | 23 | 2.24 | | | | | | | | | 15 | 10 (0) | 0 | 0 (0) | 90 | 95 (5) | | | | | | | | |
| 6 | 0.56 | 23 | 2.24 | | | | | | | | | 50 | 90 (44) | 10 | 20 (50) | 95 | 95 (0) | | | | | | | | |
| 6 | 0.56 | 23 | 2.24 | | | | | | | | | 35 | 95 (63) | 5 | 50 (90) | 100 | 100 (0) | | | | | | | | |
| 6 | 0.56 | 23 | 2.24 | | | | | | | | | | | 60 | 80 (25) | 100 | 100 (0) | | | | | | | | |
| 6 | 0.56 | 23 | 2.24 | | | | | | | | | 5 | 100 (95) | 15 | 40 (62) | 90 | 100 (10) | | | | | | | | |
| 6 | 0.56 | 23 | 2.24 | | | | | | | | | | | 40 | 90 (55) | 100 | 100 (0) | | | | | | | | |
| 6 | 0.56 | 23 | 2.24 | | | | | | | | | | | 10 | 35 (71) | 100 | 100 (0) | | | | | | | | |
| 6 | 0.56 | 23 | 2.24 | | | | | | | | | | | 0 | 65 (100) | 100 | 100 (0) | | | | | | | | |
| 6 | 0.56 | 23 | 2.24 | | | | | | | | | 75 | 100 (25) | 15 | 65 (76) | 95 | 100 (5) | | | | | | | | |
| 6 | 0.56 | 23 | 2.24 | | | | | | | | | | | 0 | 35 (100) | 90 | 100 (10) | | | | | | | | |
| 6 | 0.56 | 23 | 2.24 | | | | | | | | | 35 | 100 (65) | 45 | 20 (0) | 95 | 100 (0) | | | | | | | | |
| 6 | 0.56 | 23 | 2.24 | | | | | | | | | | | 65 | 80 (18) | 100 | 100 (0) | | | | | | | | |
| 6 | 0.56 | 23 | 2.24 | | | | | | | | | 15 | 100 (85) | 45 | 45 (0) | 95 | 95 (0) | | | | | | | | |
| 6 | 0.56 | 23 | 2.24 | | | | | | | | | 60 | 100 (40) | 85 | 60 (0) | 100 | 100 (0) | | | | | | | | |
| 6 | 0.56 | 23 | 2.24 | | | | | | | | | 75 | 95 (21) | 10 | 35 (71) | 100 | 100 (0) | | | | | | | | |
| 6 | 0.56 | 23 | 2.24 | | | | | | | | | | | 50 | 95 (47) | 100 | 100 (0) | | | | | | | | |
| 6 | 0.56 | 23 | 2.24 | | | | | | | | | 60 | 100 (40) | 55 | 40 (0) | 95 | 95 (0) | | | | | | | | |
| 6 | 0.56 | 23 | 2.24 | | | | | | | | | | | 5 | 30 (83) | 90 | 95 (5) | | | | | | | | |
| 6 | 0.56 | 23 | 2.24 | | | | | | | | | 25 | 100 (75) | 0 | 75 (100) | 100 | 100 (0) | | | | | | | | |
| 6 | 0.56 | 23 | 2.24 | | | | | | | | | | | 45 | 80 (43) | 100 | 100 (0) | | | | | | | | |
| 6 | 0.56 | 23 | 2.24 | | | | | | | | | | | 60 | 50 (0) | 95 | 100 (0) | | | | | | | | |
| 6 | 0.56 | 23 | 2.24 | | | | | | | | | 10 | 75 (86) | 10 | 35 (71) | 95 | 95 (0) | | | | | | | | |

TABLE IV-continued

% PLANT INHIBITION AND % SAFENING EFFECT ( )

| HERBICIDE NO. | HERBICIDE RATE | ANTIDOTE NO. | ANTIDOTE RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 6 | 0.56 | 23 | 2.24 | | | | | | | | | | | 20 | 25 (20) | 100 | 100 (0) | | | | | | | | |
| 6 | 0.56 | 23 | 2.24 | | | | | | | | | | | 15 | 75 (80) | 100 | 100 (0) | | | | | | | | |
| 6 | 0.56 | 23 | 2.24 | | | | | | | | | 45 | 100 (55) | 15 | 50 (70) | 100 | 100 (0) | | | | | | | | |
| 6 | 0.56 | 23 | 2.24 | | | | | | | | | 40 | 58 (31) | | | | | | | | | | | | |
| 6 | 0.56 | 23 | 2.24 | | | | | | | | | | | 5 | 28 (82) | | | | | | | | | | |
| 6 | 0.56 | 23 | 2.24 | | | | | | | | | 25 | 100 (75) | 20 | 60 (66) | 95 | 100 (5) | | | | | | | | |
| 6 | 0.56 | 23 | 2.24 | | | | | | | | | 35 | 100 (65) | 35 | 80 (56) | 100 | 95 (0) | | | | | | | | |
| 6 | 0.56 | 23 | 2.24 | | | | | | | | | 40 | 95 (57) | 50 | 70 (28) | 95 | 100 (5) | | | | | | | | |
| 6 | 0.56 | 23 | 2.24 | | | | | | | | | 30 | 100 (70) | 45 | 75 (40) | 95 | 100 (5) | | | | | | | | |
| 6 | 0.56 | 23 | 2.24 | | | | | | | | | 35 | 95 (63) | 5 | 60 (91) | 95 | 100 (5) | | | | | | | | |
| 6 | 0.56 | 23 | 2.24 | | | | | | | | | 55 | 100 (45) | 50 | 65 (23) | 100 | 95 (0) | | | | | | | | |
| 6 | 0.56 | 23 | 8.96 | | | | | | | | | | | 10 | 75 (86) | 95 | 100 (5) | | | | | | | | |
| 6 | 0.56 | 23 | 8.96 | | | | | | | | | 0 | 100 (100) | 20 | 50 (60) | 100 | 100 (0) | | | | | | | | |
| 6 | 0.56 | 23 | 8.96 | | | | | | | | | | | 30 | 50 (40) | 100 | 95 (5) | | | | | | | | |
| 6 | 0.56 | 23 | 8.96 | | | | | | | | | | | 20 | 25 (20) | 100 | 100 (0) | | | | | | | | |
| 6 | 0.56 | 23 | 8.96 | | | | | | | | | | | 55 | 80 (31) | 100 | 100 (0) | | | | | | | | |
| 6 | 0.56 | 23 | 8.96 | | | | | | | | | 25 | 100 (75) | 0 | 75 (100) | 100 | 100 (0) | | | | | | | | |
| 6 | 0.56 | 23 | 8.96 | | | | | | | | | 5 | 75 (93) | 0 | 35 (100) | 90 | 95 (5) | | | | | | | | |
| 6 | 0.56 | 23 | 8.96 | | | | | | | | | | | 40 | 95 (57) | 100 | 100 (0) | | | | | | | | |
| 6 | 0.56 | 23 | 8.96 | | | | | | | | | 10 | 80 (87) | 0 | 35 (100) | 95 | 100 (5) | | | | | | | | |
| 6 | 0.56 | 23 | 8.96 | | | | | | | | | 10 | 95 (89) | 30 | 35 (14) | 100 | 100 (0) | | | | | | | | |
| 6 | 0.56 | 23 | 8.96 | | | | | | | | | | | 0 | 65 (100) | 100 | 100 (0) | | | | | | | | |
| 6 | 0.56 | 23 | 8.96 | | | | | | | | | 15 | 100 (85) | 25 | 80 (68) | 100 | 95 (0) | | | | | | | | |
| 6 | 0.56 | 23 | 8.96 | | | | | | | | | | | 15 | 20 (25) | 95 | 100 (5) | | | | | | | | |

TABLE IV-continued

% PLANT INHIBITION AND % SAFENING EFFECT ( )

| HERBICIDE NO. | RATE | ANTIDOTE NO. | RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 6 | 0.56 | 23 | 8.96 | | | | | | | | | 15 | 100 (85) | 0 | 60 (100) | 100 | 100 (0) | | | | | | | | |
| 6 | 0.56 | 23 | 8.96 | | | | | | | | | 10 | 100 (90) | 20 | 45 (55) | 95 | 95 (0) | | | | | | | | |
| 6 | 0.56 | 23 | 8.96 | | | | | | | | | 15 | 100 (85) | 5 | 40 (87) | 85 | 95 (10) | | | | | | | | |
| 6 | 0.56 | 23 | 8.96 | | | | | | | | | 0 | 100 (100) | 10 | 65 (84) | 100 | 100 (0) | | | | | | | | |
| 6 | 0.56 | 23 | 8.96 | | | | | | | | | 10 | 10 (0) | 0 | 0 (0) | 95 | 95 (0) | | | | | | | | |
| 6 | 0.56 | 23 | 8.96 | | | | | | | | | | | 10 | 35 (71) | 85 | 100 (15) | | | | | | | | |
| 6 | 0.56 | 23 | 8.96 | | | | | | | | | | | 0 | 35 (100) | 95 | 100 (5) | | | | | | | | |
| 6 | 0.56 | 23 | 8.96 | | | | | | | | | | | 15 | 30 (50) | 85 | 95 (10) | | | | | | | | |
| 6 | 0.56 | 23 | 8.96 | | | | | | | | | 20 | 100 (80) | 5 | 40 (87) | 90 | 100 (10) | | | | | | | | |
| 6 | 0.56 | 23 | 8.96 | | | | | | | | | | | 15 | 80 (81) | 100 | 100 (0) | | | | | | | | |
| 6 | 0.56 | 23 | 8.96 | | | | | | | | | 10 | 95 (89) | 25 | 40 (37) | 95 | 95 (0) | | | | | | | | |
| 6 | 0.56 | 23 | 8.96 | | | | | | | | | | | 40 | 90 (55) | 100 | 100 (0) | | | | | | | | |
| 6 | 0.56 | 23 | 8.96 | | | | | | | | | 60 | 90 (33) | 5 | 20 (75) | 95 | 95 (0) | | | | | | | | |
| 6 | 0.56 | 23 | 8.96 | | | | | | | | | 10 | 95 (89) | 5 | 50 (90) | 100 | 100 (0) | | | | | | | | |
| 6 | 0.56 | 23 | 8.96 | | | | | | | | | 30 | 90 (66) | 15 | 35 (57) | 90 | 95 (5) | | | | | | | | |
| 6 | 0.56 | 23 | 8.96 | | | | | | | | | 30 | 75 (60) | 25 | 30 (16) | 95 | 95 (0) | | | | | | | | |
| 6 | 0.56 | 23 | 8.96 | | | | | | | | | | | 55 | 90 (38) | 100 | 100 (0) | | | | | | | | |
| 6 | 0.56 | 23 | 8.96 | | | | | | | | | | | 35 | 40 (12) | 95 | 100 (5) | | | | | | | | |
| 6 | 0.56 | 23 | 8.96 | | | | | | | | | 55 | 90 (38) | 0 | 25 (100) | 100 | 100 (0) | | | | | | | | |
| 6 | 0.56 | 23 | 8.96 | | | | | | | | | | | 25 | 75 (66) | 80 | 85 (5) | | | | | | | | |
| 6 | 0.56 | 23 | 8.96 | | | | | | | | | | | 70 | 85 (17) | 100 | 100 (0) | | | | | | | | |
| 6 | 0.56 | 23 | 8.96 | | | | | | | | | 20 | 90 (77) | 5 | 40 (87) | 100 | 100 (0) | | | | | | | | |
| 6 | 0.56 | 23 | 8.96 | | | | | | | | | | | 0 | 35 (100) | 100 | 95 (0) | | | | | | | | |
| 6 | 0.56 | 23 | 8.96 | | | | | | | | | 50 | 70 (28) | 0 | 10 (100) | 95 | 95 (0) | | | | | | | | |

TABLE IV-continued

% PLANT INHIBITION AND % SAFENING EFFECT ( )

| HERBICIDE NO. | RATE | ANTIDOTE NO. | RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 6 | 0.56 | 23 | 8.96 | | | | | | | | | 0 | 85 (100) | 0 (100) | 20 | 100 (0) | 100 | | | | | | | | |
| 6 | 0.56 | 23 | 8.96 | | | | | | | | | | | 25 (16) | 30 | 95 (0) | 90 | | | | | | | | |
| 6 | 0.56 | 23 | 8.96 | | | | | | | | | | | 15 (66) | 45 | 100 (0) | 100 | | | | | | | | |
| 6 | 0.56 | 23 | 8.96 | | | | | | | | | | | 0 (100) | 10 | 95 (5) | 100 | | | | | | | | |
| 6 | 0.56 | 23 | 8.96 | | | | | | | | | | | 60 (0) | 60 | 80 (20) | 100 | | | | | | | | |
| 6 | 0.56 | 23 | 8.96 | | | | | | | | | 15 (74) | 58 | 35 (53) | 75 | 100 (0) | 100 | | | | | | | | |
| 6 | 0.56 | 23 | 8.96 | | | | | | | | | 15 (85) | 100 | 10 (85) | 70 | 95 (5) | 100 | | | | | | | | |
| 6 | 0.56 | 23 | 8.96 | | | | | | | | | 35 (63) | 95 | 35 (56) | 80 | 100 (0) | 100 | | | | | | | | |
| 6 | 0.56 | 23 | 8.96 | | | | | | | | | 30 (70) | 100 | 25 (58) | 60 | 95 (5) | 95 | | | | | | | | |
| 6 | 0.56 | 23 | 8.96 | | | | | | | | | 45 (52) | 95 | 45 (47) | 85 | 100 (0) | 100 | | | | | | | | |
| 6 | 0.56 | 23 | 8.96 | | | | | | | | | 15 (85) | 100 | 45 (25) | 60 | 95 (5) | 100 | | | | | | | | |
| 6 | 0.56 | 23 | 8.96 | | | | | | | | | 20 (80) | 100 | 30 (53) | 65 | 95 (0) | 95 | | | | | | | | |
| 6 | 1.12 | 23 | 8.96 | | | | | | | | | | | 20 (28) | 28 | 100 (0) | 100 | | | | | | | | |
| 6 | 2.24 | 23 | 2.24 | | | | | | | | | 90 (0) | 90 | 30 (64) | 85 | 100 (0) | 100 | | | | | | | | |
| 6 | 2.24 | 23 | 2.24 | | | | | | | | | 90 (10) | 100 | 50 (0) | 50 | 90 (10) | 100 | | | | | | | | |
| 6 | 2.24 | 23 | 2.24 | | | | | | | | | | | 90 (0) | 80 | 100 (0) | 100 | | | | | | | | |
| 6 | 2.24 | 23 | 2.24 | | | | | | | | | | | 50 (37) | 80 | 100 (0) | 100 | | | | | | | | |
| 6 | 2.24 | 23 | 2.24 | | | | | | | | | | | 45 (47) | 85 | 100 (0) | 100 | | | | | | | | |
| 6 | 2.24 | 23 | 2.24 | | | | | | | | | | | 60 (20) | 75 | 100 (0) | 100 | | | | | | | | |
| 6 | 2.24 | 23 | 2.24 | | | | | | | | | 85 (10) | 95 | 30 (40) | 50 | 100 (0) | 95 | | | | | | | | |
| 6 | 2.24 | 23 | 2.24 | | | | | | | | | | | 75 (6) | 80 | 100 (0) | 100 | | | | | | | | |
| 6 | 2.24 | 23 | 2.24 | | | | | | | | | 80 (15) | 95 | 5 (90) | 50 | 100 (0) | 100 | | | | | | | | |
| 6 | 2.24 | 23 | 2.24 | | | | | | | | | | | 65 (0) | 55 | 95 (0) | 95 | | | | | | | | |
| 6 | 2.24 | 23 | 2.24 | | | | | | | | | 85 (5) | 90 | 15 (80) | 75 | 100 (0) | 100 | | | | | | | | |

TABLE IV-continued

% PLANT INHIBITION AND % SAFENING EFFECT ()

| HERBICIDE RATE | ANTIDOTE NO. | ANTIDOTE RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|
| 6 | 23 | 2.24 | | | | | | | | | | | 90 | 95 (5) | 100 | 100 (90) | | | | | | | | |
| 6 | 23 | 2.24 | | | | | | | | | 80 | 100 (20) | 35 | 55 (36) | 100 | 100 (0) | | | | | | | | |
| 6 | 23 | 2.24 | | | | | | | | | | | 85 | 95 (10) | 100 | 100 (0) | | | | | | | | |
| 6 | 23 | 2.24 | | | | | | | | | | | 70 | 55 (0) | 100 | 100 (0) | | | | | | | | |
| 6 | 23 | 2.24 | | | | | | | | | 40 | 80 (50) | 0 | 0 (0) | 95 | 100 (5) | | | | | | | | |
| 6 | 23 | 2.24 | | | | | | | | | 75 | 100 (25) | 25 | 60 (58) | 100 | 100 (0) | | | | | | | | |
| 6 | 23 | 2.24 | | | | | | | | | 85 | 100 (15) | 55 | 95 (42) | 100 | 100 (0) | | | | | | | | |
| 6 | 23 | 2.24 | | | | | | | | | 95 | 100 (5) | 50 | 60 (16) | 100 | 100 (5) | | | | | | | | |
| 6 | 23 | 2.24 | | | | | | | | | | | 90 | 95 (5) | 100 | 100 (0) | | | | | | | | |
| 6 | 23 | 2.24 | | | | | | | | | 75 | 95 (21) | 60 | 65 (7) | 85 | 95 (10) | | | | | | | | |
| 6 | 23 | 2.24 | | | | | | | | | 80 | 100 (20) | 80 | 90 (11) | 100 | 100 (0) | | | | | | | | |
| 6 | 23 | 2.24 | | | | | | | | | | | 30 | 75 (60) | 100 | 100 (0) | | | | | | | | |
| 6 | 23 | 2.24 | | | | | | | | | | | 100 | 95 (0) | 100 | 100 (0) | | | | | | | | |
| 6 | 23 | 2.24 | | | | | | | | | 55 | 100 (45) | 10 | 80 (87) | 100 | 100 (0) | | | | | | | | |
| 6 | 23 | 2.24 | | | | | | | | | 90 | 100 (10) | 50 | 70 (28) | 100 | 100 (0) | | | | | | | | |
| 6 | 23 | 2.24 | | | | | | | | | | | 85 | 95 (10) | 100 | 100 (0) | | | | | | | | |
| 6 | 23 | 2.24 | | | | | | | | | | | 70 | 50 (0) | 100 | 100 (0) | | | | | | | | |
| 6 | 23 | 2.24 | | | | | | | | | 60 | 100 (40) | 35 | 65 (46) | 100 | 100 (0) | | | | | | | | |
| 6 | 23 | 2.24 | | | | | | | | | | | 85 | 95 (10) | 100 | 100 (0) | | | | | | | | |
| 6 | 23 | 2.24 | | | | | | | | | 80 | 100 (20) | 65 | 75 (13) | 100 | 100 (0) | | | | | | | | |
| 6 | 23 | 2.24 | | | | | | | | | 75 | 100 (25) | 50 | 75 (33) | 100 | 100 (0) | | | | | | | | |
| 6 | 23 | 2.24 | | | | | | | | | | | 30 | 65 (53) | 100 | 100 (0) | | | | | | | | |
| 6 | 23 | 2.24 | | | | | | | | | 15 | 95 (84) | 65 | 60 (0) | 100 | 100 (0) | | | | | | | | |
| 6 | 23 | 2.24 | | | | | | | | | 85 | 100 (15) | 80 | 90 (11) | 100 | 100 (0) | | | | | | | | |

TABLE IV-continued

% PLANT INHIBITION AND % SAFENING EFFECT ( )

| HERBICIDE NO. | HERBICIDE RATE | ANTIDOTE NO. | ANTIDOTE RATE | SOYBEAN | | RICE | | HEMP SESBANIA | | VELVET LEAF | | SORGHUM GRAIN | | WHEAT | | GREEN FOXTAIL | | CORN | | BARNYARD GRASS | | RED RICE | | SHATTER CANE | |
|---|---|---|---|---|---|---|---|---|---|---|---|---|---|---|---|---|---|---|---|---|---|---|---|---|---|
| | | | | W | WO | W | WO | W | WO | W | WO | W | WO | W | WO | W | WO | W | WO | W | WO | W | WO | W | WO |
| 6 | 2.24 | 23 | 2.24 | | | | | | | | | | | 80 | 95 (15) | 100 | 100 (0) | | | | | | | | |
| 6 | 2.24 | 23 | 2.24 | | | | | | | | | 100 | 100 (0) | 75 | 100 (25) | 100 | 100 (0) | | | | | | | | |
| 6 | 2.24 | 23 | 2.24 | | | | | | | | | | | 75 | 95 (21) | 100 | 100 (0) | | | | | | | | |
| 6 | 2.24 | 23 | 2.24 | | | | | | | | | | | 60 | 60 (0) | 100 | 100 (0) | | | | | | | | |
| 6 | 2.24 | 23 | 2.24 | | | | | | | | | | | 60 | 95 (36) | 100 | 100 (0) | | | | | | | | |
| 6 | 2.24 | 23 | 2.24 | | | | | | | | | 50 | 100 (50) | 70 | 90 (22) | 100 | 100 (0) | | | | | | | | |
| 6 | 2.24 | 23 | 2.24 | | | | | | | | | | | 75 | 90 (16) | 100 | 100 (0) | | | | | | | | |
| 6 | 2.24 | 23 | 2.24 | | | | | | | | | 60 | 100 (40) | 65 | 90 (27) | 100 | 100 (0) | | | | | | | | |
| 6 | 2.24 | 23 | 2.24 | | | | | | | | | | | 40 | 40 (0) | 100 | 100 (0) | | | | | | | | |
| 6 | 2.24 | 23 | 2.24 | | | | | | | | | 70 | 100 (30) | 45 | 90 (50) | 100 | 100 (0) | | | | | | | | |
| 6 | 2.24 | 23 | 2.24 | | | | | | | | | 80 | 100 (20) | 50 | 80 (37) | 100 | 100 (0) | | | | | | | | |
| 6 | 2.24 | 23 | 2.24 | | | | | | | | | 85 | 100 (15) | 85 | 90 (5) | 100 | 100 (0) | | | | | | | | |
| 6 | 2.24 | 23 | 2.24 | | | | | | | | | 70 | 88 (20) | | | 100 | 100 (0) | | | | | | | | |
| 6 | 2.24 | 23 | 2.24 | | | | | | | | | 85 | 100 (15) | 65 | 70 (7) | 100 | 100 (0) | | | | | | | | |
| 6 | 2.24 | 23 | 2.24 | | | | | | | | | 55 | 100 (45) | 50 | 95 (45) | 95 | 100 (5) | | | | | | | | |
| 6 | 2.24 | 23 | 8.96 | | | | | | | | | 10 | 95 (89) | 10 | 60 (47) | 100 | 100 (0) | | | | | | | | |
| 6 | 2.24 | 23 | 8.96 | | | | | | | | | | | 15 | 60 (83) | 100 | 100 (0) | | | | | | | | |
| 6 | 2.24 | 23 | 8.96 | | | | | | | | | | | 95 | 95 (0) | 100 | 100 (0) | | | | | | | | |
| 6 | 2.24 | 23 | 8.96 | | | | | | | | | | | 75 | 90 (16) | 100 | 100 (0) | | | | | | | | |
| 6 | 2.24 | 23 | 8.96 | | | | | | | | | 45 | 100 (55) | 50 | 90 (44) | 100 | 100 (0) | | | | | | | | |
| 6 | 2.24 | 23 | 8.96 | | | | | | | | | | | 85 | 95 (10) | 100 | 100 (0) | | | | | | | | |
| 6 | 2.24 | 23 | 8.96 | | | | | | | | | | | 70 | 95 (26) | 100 | 100 (0) | | | | | | | | |
| 6 | 2.24 | 23 | 8.96 | | | | | | | | | 70 | 100 (30) | 40 | 90 (55) | 100 | 100 (0) | | | | | | | | |
| 6 | 2.24 | 23 | 8.96 | | | | | | | | | 35 | 100 (65) | 5 | 60 (91) | 100 | 100 (0) | | | | | | | | |

TABLE IV-continued

% PLANT INHIBITION AND % SAFENING EFFECT ( )

| HERBICIDE NO. | RATE | ANTIDOTE NO. | RATE | SOYBEAN W | WO | RICE W | WO | HEMP SESBANIA W | WO | VELVET LEAF W | WO | SORGHUM GRAIN W | WO | WHEAT W | WO | GREEN FOXTAIL W | WO | CORN W | WO | BARNYARD GRASS W | WO | RED RICE W | WO | SHATTER CANE W | WO |
|---|---|---|---|---|---|---|---|---|---|---|---|---|---|---|---|---|---|---|---|---|---|---|---|---|---|
| 6 | 2.24 | 23 | 8.96 | | | | | | | | | 45 | 100 (55) | 70 | 100 (30) | 100 | 100 (0) | | | | | | | | |
| 6 | 2.24 | 23 | 8.96 | | | | | | | | | 35 | 100 (65) | 45 | 65 (30) | 100 | 100 (0) | | | | | | | | |
| 6 | 2.24 | 23 | 8.96 | | | | | | | | | | | 60 | 95 (36) | 100 | 100 (0) | | | | | | | | |
| 6 | 2.24 | 23 | 8.96 | | | | | | | | | | | 60 | 95 (36) | 100 | 100 (0) | | | | | | | | |
| 6 | 2.24 | 23 | 8.96 | | | | | | | | | 35 | 100 (65) | 50 | 75 (33) | 95 | 95 (0) | | | | | | | | |
| 6 | 2.24 | 23 | 8.96 | | | | | | | | | | | 35 | 65 (46) | 100 | 100 (0) | | | | | | | | |
| 6 | 2.24 | 23 | 8.96 | | | | | | | | | 45 | 80 (43) | 5 | 0 (0) | 95 | 100 (5) | | | | | | | | |
| 6 | 2.24 | 23 | 8.96 | | | | | | | | | 60 | 100 (40) | 55 | 75 (26) | 100 | 100 (0) | | | | | | | | |
| 6 | 2.24 | 23 | 8.96 | | | | | | | | | 50 | 100 (50) | 50 | 70 (28) | 100 | 100 (0) | | | | | | | | |
| 6 | 2.24 | 23 | 8.96 | | | | | | | | | 5 | 100 (95) | 35 | 80 (56) | 100 | 100 (0) | | | | | | | | |
| 6 | 2.24 | 23 | 8.96 | | | | | | | | | 80 | 95 (15) | 100 | 100 (0) | | | | | | | | | | |
| 6 | 2.24 | 23 | 8.96 | | | | | | | | | 35 | 100 (65) | 45 | 90 (50) | 100 | 100 (0) | | | | | | | | |
| 6 | 2.24 | 23 | 8.96 | | | | | | | | | 60 | 95 (36) | 50 | 80 (37) | 100 | 100 (0) | | | | | | | | |
| 6 | 2.24 | 23 | 8.96 | | | | | | | | | | | 40 | 75 (46) | 100 | 100 (0) | | | | | | | | |
| 6 | 2.24 | 23 | 8.96 | | | | | | | | | | | 60 | 95 (36) | 100 | 100 (5) | | | | | | | | |
| 6 | 2.24 | 23 | 8.96 | | | | | | | | | | | 25 | 50 (50) | 100 | 100 (0) | | | | | | | | |
| 6 | 2.24 | 23 | 8.96 | | | | | | | | | 70 | 100 (30) | 70 | 95 (26) | 100 | 100 (0) | | | | | | | | |
| 6 | 2.24 | 23 | 8.96 | | | | | | | | | 60 | 100 (40) | 55 | 60 (8) | 100 | 100 (0) | | | | | | | | |
| 6 | 2.24 | 23 | 8.96 | | | | | | | | | 20 | 100 (80) | 35 | 55 (36) | 95 | 100 (5) | | | | | | | | |
| 6 | 2.24 | 23 | 8.96 | | | | | | | | | 50 | 100 (50) | 35 | 50 (30) | 95 | 100 (5) | | | | | | | | |
| 6 | 2.24 | 23 | 8.96 | | | | | | | | | 55 | 95 (42) | 50 | 55 (9) | 100 | 100 (0) | | | | | | | | |
| 6 | 2.24 | 23 | 8.96 | | | | | | | | | | | 90 | 95 (5) | 100 | 100 (0) | | | | | | | | |
| 6 | 2.24 | 23 | 8.96 | | | | | | | | | | | 35 | 75 (53) | 100 | 100 (0) | | | | | | | | |
| 6 | 2.24 | 23 | 8.96 | | | | | | | | | 60 | 95 (36) | 30 | 65 (53) | 100 | 95 (0) | | | | | | | | |

TABLE IV-continued
% PLANT INHIBITION AND % SAFENING EFFECT ( )

| HERBICIDE NO. | HERBICIDE RATE | ANTIDOTE NO. | ANTIDOTE RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 6 | 2.24 | 23 | 8.96 | | | | | | | | | | | 95 | 95 (0) | 100 | 100 (0) | | | | | | | | |
| 6 | 2.24 | 23 | 8.96 | | | | | | | | | | | 45 | 80 (43) | 100 | 100 (0) | | | | | | | | |
| 6 | 2.24 | 23 | 8.96 | | | | | | | | | | | 55 | 50 (0) | 100 | 100 (0) | | | | | | | | |
| 6 | 2.24 | 23 | 8.96 | | | | | | | | | 35 | 95 (63) | 45 | 50 (10) | 100 | 95 (0) | | | | | | | | |
| 6 | 2.24 | 23 | 8.96 | | | | | | | | | | | 20 | 85 (76) | 100 | 100 (0) | | | | | | | | |
| 6 | 2.24 | 23 | 8.96 | | | | | | | | | | | 60 | 80 (25) | 100 | 100 (0) | | | | | | | | |
| 6 | 2.24 | 23 | 8.96 | | | | | | | | | | | 40 | 80 (50) | 100 | 100 (0) | | | | | | | | |
| 6 | 2.24 | 23 | 8.96 | | | | | | | | | 80 | 90 (11) | 20 | 75 (73) | 95 | 100 (5) | | | | | | | | |
| 6 | 2.24 | 23 | 8.96 | | | | | | | | | | | 25 | 55 (54) | 100 | 100 (0) | | | | | | | | |
| 6 | 2.24 | 23 | 8.96 | | | | | | | | | 45 | 100 (55) | 65 | 80 (18) | 100 | 100 (0) | | | | | | | | |
| 6 | 2.24 | 23 | 8.96 | | | | | | | | | 25 | 100 (75) | 50 | 90 (44) | 100 | 100 (0) | | | | | | | | |
| 6 | 2.24 | 23 | 8.96 | | | | | | | | | 30 | 88 (65) | | | | | | | | | | | | |
| 6 | 2.24 | 23 | 8.96 | | | | | | | | | 40 | 100 (60) | 40 | 40 (0) | 100 | 100 (0) | | | | | | | | |
| 6 | 2.24 | 23 | 8.96 | | | | | | | | | 10 | 100 (90) | 55 | 90 (38) | 100 | 100 (0) | | | | | | | | |
| 6 | 2.24 | 23 | 8.96 | | | | | | | | | 25 | 100 (75) | 60 | 70 (14) | 100 | 100 (0) | | | | | | | | |
| 6 | 2.24 | 23 | 8.96 | | | | | | | | | 15 | 100 (85) | 40 | 90 (55) | 100 | 100 (0) | | | | | | | | |
| 6 | 2.24 | 23 | 8.96 | | | | | | | | | 60 | 95 (36) | 50 | 95 (47) | 100 | 100 (0) | | | | | | | | |
| 6 | 4.48 | 23 | 8.96 | | | | | | | | | | | 70 | 100 (30) | 100 | 100 (0) | | | | | | | | |
| 6 | 0.56 | 24 | 2.24 | | | | | | | | | | | 15 | 30 (50) | 90 | 95 (5) | | | | | | | | |
| 6 | 0.56 | 24 | 2.24 | | | | | | | | | 10 | 10 (0) | 25 | 0 (0) | 85 | 85 (0) | | | | | | | | |
| 6 | 0.56 | 24 | 2.24 | | | | | | | | | | | 30 | 20 (0) | 100 | 100 (0) | | | | | | | | |
| 6 | 0.56 | 24 | 8.96 | | | | | | | | | | | 10 | 30 (66) | 95 | 95 (0) | | | | | | | | |
| 6 | 0.56 | 24 | 8.96 | | | | | | | | | 0 | 10 (100) | 10 | 0 (0) | 85 | 85 (10) | | | | | | | | |
| 6 | 0.56 | 24 | 8.96 | | | | | | | | | | | 15 | 20 (25) | 95 | 95 (10) | | | | | | | | |

TABLE IV-continued

| HERBICIDE NO. | HERBICIDE RATE | ANTIDOTE NO. | ANTIDOTE RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 6 | 2.24 | 24 | 0.56 | | | | | | | | | 95 | 93 (0) | | | | | | | | | | | | |
| 6 | 2.24 | 24 | 2.24 | | | | | | | | | | | 30 | 50 (40) | 95 | 100 (5) | | | | | | | | |
| 6 | 2.24 | 24 | 2.24 | | | | | | | | | 10 | 80 (87) | 0 | 0 (0) | 95 | 100 (5) | | | | | | | | |
| 6 | 2.24 | 24 | 2.24 | | | | | | | | | | | 40 | 55 (27) | | | | | | | | | | |
| 6 | 2.24 | 24 | 2.24 | | | | | | | | | 70 | 93 (24) | | | | | | | | | | | | |
| 6 | 2.24 | 24 | 8.96 | | | | | | | | | | | 35 | 50 (30) | 95 | 100 (5) | | | | | | | | |
| 6 | 2.24 | 24 | 8.96 | | | | | | | | | 15 | 80 (81) | 0 | 0 (0) | 90 | 100 (10) | | | | | | | | |
| 6 | 2.24 | 24 | 8.96 | | | | | | | | | | | 15 | 55 (72) | | | | | | | | | | |
| 6 | 2.24 | 24 | 8.96 | | | | | | | | | 35 | 93 (62) | | | | | | | | | | | | |
| 6 | 0.56 | 25 | 2.24 | | | | | | | | | 20 | 80 (75) | 0 | 35 (100) | 100 | 100 (0) | | | | | | | | |
| 6 | 0.56 | 25 | 8.96 | | | | | | | | | 10 | 80 (87) | 0 | 35 (100) | 100 | 100 (0) | | | | | | | | |
| 6 | 2.24 | 25 | 2.24 | | | | | | | | | 70 | 100 (30) | 10 | 60 (83) | 100 | 100 (0) | | | | | | | | |
| 6 | 2.24 | 25 | 8.96 | | | | | | | | | 25 | 100 (75) | 20 | 60 (66) | 100 | 100 (0) | | | | | | | | |
| 6 | 0.56 | 27 | 2.24 | | | | | | | | | 50 | 100 (50) | 60 | 80 (25) | 100 | 100 (0) | | | | | | | | |
| 6 | 0.56 | 27 | 8.96 | | | | | | | | | 15 | 100 (85) | 25 | 80 (68) | 100 | 95 (0) | | | | | | | | |
| 6 | 2.24 | 27 | 2.24 | | | | | | | | | 15 | 100 (85) | 80 | 90 (11) | 100 | 100 (0) | | | | | | | | |
| 6 | 2.24 | 27 | 8.96 | | | | | | | | | 5 | 100 (95) | 30 | 90 (66) | 100 | 100 (0) | | | | | | | | |
| 6 | 0.56 | 28 | 2.24 | | | | | | | | | | | 10 | 20 (50) | | | | | | | | | | |
| 6 | 0.56 | 28 | 8.96 | | | | | | | | | | | 15 | 20 (25) | | | | | | | | | | |
| 6 | 2.24 | 28 | 0.56 | | | | | | | | | | | | | | | | | | | | | | |
| 6 | 2.24 | 28 | 2.24 | | | | | | | | | 75 | 93 (19) | | | | | | | | | | | | |
| 6 | 2.24 | 28 | 2.24 | | | | | | | | | 75 | 93 (19) | 30 | 55 (45) | | | | | | | | | | |
| 6 | 2.24 | 28 | 8.96 | | | | | | | | | 30 | 93 (67) | | | | | | | | | | | | |
| 6 | 2.24 | 28 | 8.96 | | | | | | | | | | | 40 | 55 (27) | | | | | | | | | | |

TABLE IV-continued

% PLANT INHIBITION AND % SAFENING EFFECT ( )

| HERBICIDE NO. | RATE | ANTIDOTE NO. | RATE | SOYBEAN W | WO | RICE W | WO | HEMP SESBANIA W | WO | VELVET LEAF W | WO | SORGHUM GRAIN W | WO | WHEAT W | WO | GREEN FOXTAIL W | WO | CORN W | WO | BARNYARD GRASS W | WO | RED RICE W | WO | SHATTER CANE W | WO |
|---|---|---|---|---|---|---|---|---|---|---|---|---|---|---|---|---|---|---|---|---|---|---|---|---|---|
| 6 | 0.56 | 29 | 2.24 | | | | | | | | | 60 | 100 (40) | 15 | 75 (80) | 100 | 100 (0) | | | | | | | | |
| 6 | 0.56 | 29 | 8.96 | | | | | | | | | 35 | 100 (65) | 85 | 75 (0) | 100 | 100 (0) | | | | | | | | |
| 6 | 2.24 | 29 | 2.24 | | | | | | | | | 70 | 100 (30) | 95 | 100 (5) | 100 | 100 (0) | | | | | | | | |
| 6 | 2.24 | 29 | 8.96 | | | | | | | | | 80 | 100 (20) | 50 | 100 (50) | 100 | 100 (0) | | | | | | | | |
| 6 | 0.56 | 30 | 2.24 | | | | | | | | | | | 15 | 20 (25) | | | | | | | | | | |
| 6 | 0.56 | 30 | 8.96 | | | | | | | | | | | 35 | 75 (53) | 100 | 100 (0) | | | | | | | | |
| 6 | 2.24 | 30 | 8.96 | | | | | | | | | | | 30 | 20 (0) | | | | | | | | | | |
| 6 | 0.56 | 30 | 8.96 | | | | | | | | | | | 25 | 75 (66) | 100 | 100 (0) | | | | | | | | |
| 6 | 2.24 | 30 | 0.56 | | | | | | | | | 85 | 93 (8) | | | | | | | | | | | | |
| 6 | 2.24 | 30 | 2.24 | | | | | | | | | 55 | 93 (40) | | | | | | | | | | | | |
| 6 | 2.24 | 30 | 2.24 | | | | | | | | | | | 60 | 90 (33) | 100 | 100 (0) | | | | | | | | |
| 6 | 2.24 | 30 | 2.24 | | | | | | | | | | | 50 | 55 (9) | | | | | | | | | | |
| 6 | 2.24 | 30 | 8.96 | | | | | | | | | | | 75 | 90 (16) | 100 | 100 (0) | | | | | | | | |
| 6 | 2.24 | 30 | 8.96 | | | | | | | | | | | 30 | 55 (45) | | | | | | | | | | |
| 6 | 2.24 | 30 | 8.96 | | | | | | | | | 45 | 93 (51) | | | | | | | | | | | | |
| 6 | 0.56 | 31 | 2.24 | | | | | | | | | | | 20 | 20 (0) | | | | | | | | | | |
| 6 | 0.56 | 31 | 8.96 | | | | | | | | | | | 25 | 20 (0) | | | | | | | | | | |
| 6 | 2.24 | 31 | 0.56 | | | | | | | | | 95 | 93 (0) | | | | | | | | | | | | |
| 6 | 2.24 | 31 | 2.24 | | | | | | | | | | | 45 | 55 (18) | | | | | | | | | | |
| 6 | 2.24 | 31 | 2.24 | | | | | | | | | 85 | 93 (8) | | | | | | | | | | | | |
| 6 | 2.24 | 31 | 8.96 | | | | | | | | | 80 | 93 (13) | | | | | | | | | | | | |
| 6 | 2.24 | 31 | 8.96 | | | | | | | | | | | 25 | 55 (54) | | | | | | | | | | |
| 6 | 0.56 | 32 | 2.24 | | | | | | | | | 5 | 95 (94) | | | 90 | 100 (10) | | | | | | | | |
| 6 | 0.56 | 32 | 8.96 | | | | | | | | | 5 | 95 (94) | | | 100 | 100 (0) | | | | | | | | |

TABLE IV-continued

| | | | | | | | | | | | | | | | | | | | | | | | |
|---|---|---|---|---|---|---|---|---|---|---|---|---|---|---|---|---|---|---|---|---|---|---|---|
| HERBICIDE | | ANTIDOTE | | SOYBEAN | | RICE | | HEMP SESBANIA | | VELVET LEAF | | SORGHUM GRAIN | | WHEAT | | GREEN FOXTAIL | | CORN | | BARNYARD GRASS | | RED RICE | | SHATTER CANE |
| NO. | RATE | NO. | RATE | W | WO | W | WO | W | WO | W | WO | W | WO | W | WO | W | WO | W | WO | W | WO | W | WO | W | WO |
| 6 | 2.24 | 32 | 2.24 | | | | | | | | | | | 70 | 80 (12) | 100 | 100 (0) | | | | | | | | |
| 6 | 2.24 | 32 | 2.24 | | | | | | | | | 50 | 95 (47) | | | 100 | 100 (0) | | | | | | | | |
| 6 | 2.24 | 32 | 8.96 | | | | | | | | | 20 | 95 (78) | | | 100 | 100 (0) | | | | | | | | |
| 6 | 2.24 | 32 | 8.96 | | | | | | | | | | | 65 | 80 (18) | 100 | 100 (0) | | | | | | | | |
| 6 | 0.56 | 33 | 2.24 | | | | | | | | | | | 30 | 48 (37) | | | | | | | | | | |
| 6 | 0.56 | 33 | 2.24 | | | | | | | | | 25 | 90 (72) | | | 95 | 100 (5) | | | | | | | | |
| 6 | 0.56 | 33 | 2.24 | | | | | | | | | 25 | 88 (71) | | | | | | | | | | | | |
| 6 | 0.56 | 33 | 8.96 | | | | | | | | | | | 5 | 48 (89) | | | | | | | | | | |
| 6 | 0.56 | 33 | 8.96 | | | | | | | | | 20 | 88 (77) | | | 90 | 100 (10) | | | | | | | | |
| 6 | 0.56 | 33 | 8.96 | | | | | | | | | 25 | 90 (72) | | | 100 | 100 (0) | | | | | | | | |
| 6 | 2.24 | 33 | 2.24 | | | | | | | | | 35 | 95 (63) | | | | | | | | | | | | |
| 6 | 2.24 | 33 | 2.24 | | | | | | | | | | | 70 | 75 (6) | | | | | | | | | | |
| 6 | 2.24 | 33 | 2.24 | | | | | | | | | 50 | 98 (48) | | | | | | | | | | | | |
| 6 | 2.24 | 33 | 8.96 | | | | | | | | | | | 50 | 75 (33) | 100 | 100 (0) | | | | | | | | |
| 6 | 2.24 | 33 | 8.96 | | | | | | | | | 20 | 95 (78) | | | | | | | | | | | | |
| 6 | 2.24 | 33 | 8.96 | | | | | | | | | 20 | 98 (79) | | | 95 | 100 (5) | | | | | | | | |
| 6 | 0.56 | 34 | 2.24 | | | | | | | | | 20 | 90 (77) | | | | | | | | | | | | |
| 6 | 0.56 | 34 | 2.24 | | | | | | | | | 20 | 88 (77) | 5 | 48 (89) | | | | | | | | | | |
| 6 | 0.56 | 34 | 8.96 | | | | | | | | | 0 | 88 (100) | | | | | | | | | | | | |
| 6 | 0.56 | 34 | 8.96 | | | | | | | | | 0 | 90 (100) | 35 | 48 (27) | 90 | 100 (10) | | | | | | | | |
| 6 | 2.24 | 34 | 2.24 | | | | | | | | | 70 | 98 (28) | | | | | | | | | | | | |
| 6 | 2.24 | 34 | 2.24 | | | | | | | | | | | 40 | 75 (46) | | | | | | | | | | |

TABLE IV-continued

% PLANT INHIBITION AND % SAFENING EFFECT ( )

| HERBICIDE NO. | RATE | ANTIDOTE NO. | RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 6 | 2.24 | 34 | 2.24 | | | | | | | | | 40 | 95 (57) | | | 100 | 100 (0) | | | | | | | | |
| 6 | 2.24 | 34 | 8.96 | | | | | | | | | 45 | 95 (52) | | | 100 | 100 (0) | | | | | | | | |
| 6 | 8.96 | 34 | 8.96 | | | | | | | | | | | 30 | 75 (60) | | | | | | | | | | |
| 6 | 8.96 | 34 | 2.24 | | | | | | | | | 25 | 98 (74) | | | | | | | | | | | | |
| 6 | 0.56 | 35 | 2.24 | | | | | | | | | | | 5 | 25 (80) | 100 | 100 (0) | | | | | | | | |
| 6 | 0.56 | 35 | 8.96 | | | | | | | | | 20 | 85 (76) | | | 95 | 100 (5) | | | | | | | | |
| 6 | 0.56 | 35 | 8.96 | | | | | | | | | | | 20 | 45 (55) | 100 | 100 (0) | | | | | | | | |
| 6 | 0.56 | 35 | 8.96 | | | | | | | | | | | 5 | 45 (88) | 100 | 100 (0) | | | | | | | | |
| 6 | 0.56 | 35 | 8.96 | | | | | | | | | 0 | 85 (100) | | | 95 | 100 (5) | | | | | | | | |
| 6 | 2.24 | 35 | 2.24 | | | | | | | | | | | 15 | 25 (40) | 100 | 100 (0) | | | | | | | | |
| 6 | 2.24 | 35 | 2.24 | | | | | | | | | | | 75 | 75 (0) | 100 | 100 (0) | | | | | | | | |
| 6 | 2.24 | 35 | 8.96 | | | | | | | | | 35 | 95 (63) | | | 100 | 100 (0) | | | | | | | | |
| 6 | 2.24 | 35 | 8.96 | | | | | | | | | | | 40 | 80 (50) | 100 | 100 (0) | | | | | | | | |
| 6 | 2.24 | 35 | 8.96 | | | | | | | | | | | 30 | 80 (62) | 100 | 100 (0) | | | | | | | | |
| 6 | 2.24 | 35 | 8.96 | | | | | | | | | 10 | 95 (89) | | | 100 | 100 (0) | | | | | | | | |
| 6 | 2.24 | 35 | 8.96 | | | | | | | | | | | 15 | 75 (80) | 100 | 100 (0) | | | | | | | | |
| 9 | 0.28 | 1 | 8.96 | | | 20 | 20 (0) | | | | | 0 | 50 (100) | 0 | 10 (100) | | | 0 | 0 (0) | | | | | | |
| 9 | 1.12 | 1 | 8.96 | | | 50 | 50 (0) | | | | | 30 | 60 (50) | 10 | 40 (75) | | | 25 | 20 (0) | | | | | | |
| 9 | 4.48 | 1 | 8.96 | | | 60 | 70 (14) | | | | | 35 | 90 (61) | 50 | 75 (33) | | | 25 | 60 (58) | | | | | | |
| 9 | 0.28 | 9 | 8.96 | | | 10 | 20 (50) | | | | | 15 | 50 (70) | 0 | 10 (100) | | | 10 | 0 (0) | | | | | | |
| 9 | 1.12 | 9 | 8.96 | | | 50 | 50 (0) | | | | | 50 | 60 (16) | 10 | 40 (75) | | | 20 | 20 (0) | | | | | | |
| 9 | 4.48 | 9 | 8.96 | | | 70 | 70 (0) | | | | | 75 | 90 (16) | 80 | 75 (0) | | | 20 | 60 (66) | | | | | | |
| 9 | 0.28 | 11 | 8.96 | | | 40 | 20 (0) | | | | | 35 | 50 (30) | 20 | 10 (0) | | | 10 | 0 (0) | | | | | | |
| 9 | 1.12 | 11 | 8.96 | | | 50 | 50 (0) | | | | | 25 | 60 (58) | 20 | 40 (50) | | | 20 | 20 (0) | | | | | | |

TABLE IV-continued

| | | | | | | | | | | | | | | | | | | | | | | |
|---|---|---|---|---|---|---|---|---|---|---|---|---|---|---|---|---|---|---|---|---|---|---|
| | | | | | | | % PLANT INHIBITION AND % SAFENING EFFECT ( ) | | | | | | | | | | | | | | | |
| HERBICIDE | | ANTIDOTE | | SOYBEAN | | RICE | | HEMP SESBANIA | | VELVET LEAF | | SORGHUM GRAIN | | WHEAT | | GREEN FOXTAIL | | CORN | | BARNYARD GRASS | | RED RICE | SHATTER CANE |
| NO. | RATE | NO. | RATE | W | WO | W | WO | W | WO | W | WO | W | WO | W | WO | W | WO | W | WO | W | WO | W WO | W WO |
| 9 | 4.48 | 11 | 8.96 | | | 60 | 70 (14) | | | | | 75 | 90 (16) | 80 | 75 (0) | | | 10 | 60 (83) | | | | |
| 10 | 1.12 | 1 | 2.24 | | | 10 | 55 (81) | | | | | | | | | | | | | 100 | 100 (0) | | |
| 10 | 1.12 | 1 | 2.24 | | | 35 | 50 (30) | | | | | | | | | | | | | 100 | 100 (0) | | |
| 10 | 1.12 | 1 | 2.24 | | | 25 | 40 (37) | | | | | | | | | | | | | 95 | 100 (5) | | |
| 10 | 1.12 | 1 | 2.24 | | | 85 | 55 (0) | | | | | | | | | | | | | 100 | 100 (0) | | |
| 10 | 1.12 | 1 | 2.24 | | | 5 | 65 (92) | | | | | | | | | | | | | 100 | 100 (0) | | |
| 10 | 1.12 | 1 | 2.24 | | | 35 | 65 (46) | | | | | | | | | | | | | 100 | 100 (0) | | |
| 10 | 1.12 | 1 | 2.24 | | | 85 | 75 (0) | | | | | | | | | | | | | 100 | 100 (0) | | |
| 10 | 1.12 | 1 | 2.24 | | | 20 | 45 (55) | | | | | | | | | | | | | 95 | 100 (5) | | |
| 10 | 1.12 | 1 | 2.24 | | | 25 | 85 (70) | | | | | | | | | | | | | 95 | 100 (5) | | |
| 10 | 1.12 | 1 | 2.24 | | | 25 | 70 (64) | | | | | | | | | | | | | 100 | 100 (0) | | |
| 10 | 1.12 | 1 | 2.24 | | | 30 | 43 (30) | | | | | | | | | | | | | | | | |
| 10 | 1.12 | 1 | 2.24 | | | 20 | 18 (0) | | | | | | | | | | | | | 75 | 99 (24) | | |
| 10 | 1.12 | 1 | 8.96 | | | 0 | 30 (100) | | | | | | | | | | | | | 75 | 100 (25) | | |
| 10 | 1.12 | 1 | 8.96 | | | 15 | 18 (16) | | | | | | | | | | | | | 100 | 100 (0) | | |
| 10 | 1.12 | 1 | 8.96 | | | 0 | 70 (100) | | | | | | | | | | | | | 100 | 100 (0) | | |
| 10 | 1.12 | 1 | 8.96 | | | 35 | 75 (53) | | | | | | | | | | | | | 70 | 98 (28) | | |
| 10 | 1.12 | 1 | 8.96 | | | 10 | 85 (88) | | | | | | | | | | | | | 20 | 100 (80) | | |
| 10 | 1.12 | 1 | 8.96 | | | 0 | 30 (100) | | | | | | | | | | | | | 100 | 100 (0) | | |
| 10 | 1.12 | 1 | 8.96 | | | 30 | 60 (50) | | | | | | | | | | | | | 100 | 100 (0) | | |
| 10 | 1.12 | 1 | 8.96 | | | 10 | 65 (84) | | | | | | | | | | | | | | | | |
| 10 | 1.12 | 1 | 8.96 | | | 10 | 30 (66) | | | | | | | | | | | | | | | | |
| 10 | 1.12 | 1 | 8.96 | | | 10 | 43 (76) | | | | | | | | | | | | | | | | |
| 10 | 1.12 | 1 | 8.96 | | | 25 | 60 (58) | | | | | | | | | | | | | 100 | 100 (0) | | |

TABLE IV-continued

% PLANT INHIBITION AND % SAFENING EFFECT ( )

| HERBICIDE NO. | RATE | ANTIDOTE NO. | RATE | SOYBEAN W | WO | RICE W | WO | HEMP SESBANIA W | WO | VELVET LEAF W | WO | SORGHUM GRAIN W | WO | WHEAT W | WO | GREEN FOXTAIL W | WO | CORN W | WO | BARNYARD GRASS W | WO | RED RICE W | WO | SHATTER CANE W | WO |
|---|---|---|---|---|---|---|---|---|---|---|---|---|---|---|---|---|---|---|---|---|---|---|---|---|---|
| 10 | 1.12 | 1 | 8.96 | | | 5 | 50 (90) | | | | | | | | | | | | | 100 | 100 (0) | | | | |
| 10 | 1.12 | 1 | 8.96 | | | 0 | 45 (100) | | | | | | | | | | | | | 85 | 100 (15) | | | | |
| 10 | 1.12 | 1 | 8.96 | | | 20 | 20 (0) | | | | | | | | | | | | | 90 | 95 (5) | | | | |
| 10 | 1.12 | 1 | 8.96 | | | 20 | 70 (71) | | | | | | | | | | | | | 85 | 100 (15) | | | | |
| 10 | 1.12 | 1 | 8.96 | | | 10 | 35 (71) | | | | | | | | | | | | | 99 | 99 (0) | | | | |
| 10 | 1.12 | 1 | 8.96 | | | 20 | 55 (63) | | | | | | | | | | | | | 80 | 100 (20) | | | | |
| 10 | 1.12 | 1 | 8.96 | | | 5 | 40 (87) | | | | | | | | | | | | | 80 | 100 (20) | | | | |
| 10 | 1.12 | 1 | 8.96 | | | 15 | 65 (76) | | | | | | | | | | | | | 100 | 100 (0) | | | | |
| 10 | 1.12 | 1 | 8.96 | | | 5 | 55 (90) | | | | | | | | | | | | | 100 | 100 (0) | | | | |
| 10 | 2.24 | 1 | 8.96 | | | 10 | 50 (80) | | | | | | | | | | | | | 100 | 100 (0) | | | | |
| 10 | 2.24 | 1 | 8.96 | | | 15 | 50 (70) | | | | | | | | | | | | | 99 | 99 (0) | | | | |
| 10 | 2.24 | 1 | 8.96 | | | 40 | 70 (42) | | | | | | | | | | | | | 30 | 95 (68) | | | | |
| 10 | 2.24 | 1 | 8.96 | | | 20 | 50 (60) | | | | | | | | | | | | | 90 | 99 (9) | | | | |
| 10 | 2.24 | 1 | 8.96 | | | 10 | 80 (87) | | | | | | | | | | | | | 80 | 100 (20) | | | | |
| 10 | 2.24 | 1 | 8.96 | | | 0 | 60 (100) | | | | | | | | | | | | | 100 | 100 (0) | | | | |
| 10 | 2.24 | 1 | 8.96 | | | 15 | 45 (66) | | | | | | | | | | | | | 99 | 99 (0) | | | | |
| 10 | 2.24 | 1 | 8.96 | | | 35 | 60 (41) | | | | | | | | | | | | | 100 | 100 (0) | | | | |
| 10 | 2.24 | 1 | 8.96 | | | 20 | 50 (60) | | | | | | | | | | | | | 95 | 98 (3) | | | | |
| 10 | 2.24 | 1 | 8.96 | | | 0 | 70 (100) | | | | | | | | | | | | | 100 | 100 (0) | | | | |
| 10 | 4.48 | 1 | 2.24 | | | 35 | 90 (61) | | | | | | | | | | | | | 100 | 100 (0) | | | | |
| 10 | 4.48 | 1 | 2.24 | | | 40 | 80 (50) | | | | | | | | | | | | | 100 | 100 (0) | | | | |
| 10 | 4.48 | 1 | 2.24 | | | 60 | 85 (29) | | | | | | | | | | | | | 100 | 100 (0) | | | | |
| 10 | 4.48 | 1 | 2.24 | | | 40 | 80 (50) | | | | | | | | | | | | | 100 | 100 (0) | | | | |
| 10 | 4.48 | 1 | 2.24 | | | 55 | 95 (42) | | | | | | | | | | | | | 100 | 100 (0) | | | | |

TABLE IV-continued

| HERBICIDE | | ANTIDOTE | | SOYBEAN | | RICE | | HEMP SESBANIA | | VELVET LEAF | | SORGHUM GRAIN | | WHEAT | | GREEN FOXTAIL | | CORN | | BARNYARD GRASS | | RED RICE | | SHATTER CANE | |
|---|---|---|---|---|---|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO | W | WO | W | WO | W | WO |
| 10 | 4.48 | 1 | 2.24 | | | 15 | 80 (81) | | | | | | | | | | | | | 100 | 100 (0) | | | | |
| 10 | 4.48 | 1 | 2.24 | | | 40 | 67 (40) | | | | | | | | | | | | | | | | | | |
| 10 | 4.48 | 1 | 2.24 | | | 30 | 58 (48) | | | | | | | | | | | | | 100 | 100 (0) | | | | |
| 10 | 4.48 | 1 | 2.24 | | | 35 | 95 (63) | | | | | | | | | | | | | 100 | 100 (0) | | | | |
| 10 | 4.48 | 1 | 2.24 | | | 15 | 85 (82) | | | | | | | | | | | | | 100 | 100 (0) | | | | |
| 10 | 4.48 | 1 | 2.24 | | | 40 | 90 (55) | | | | | | | | | | | | | 100 | 100 (0) | | | | |
| 10 | 4.48 | 1 | 2.24 | | | 95 | 90 (0) | | | | | | | | | | | | | 100 | 100 (0) | | | | |
| 10 | 4.48 | 1 | 8.96 | | | 30 | 85 (64) | | | | | | | | | | | | | 100 | 100 (0) | | | | |
| 10 | 4.48 | 1 | 8.96 | | | 15 | 95 (84) | | | | | | | | | | | | | 100 | 100 (0) | | | | |
| 10 | 4.48 | 1 | 8.96 | | | 10 | 67 (85) | | | | | | | | | | | | | 99 | 99 (0) | | | | |
| 10 | 4.48 | 1 | 8.96 | | | 30 | 65 (53) | | | | | | | | | | | | | 35 | 100 (65) | | | | |
| 10 | 4.48 | 1 | 8.96 | | | 5 | 58 (91) | | | | | | | | | | | | | 100 | 100 (0) | | | | |
| 10 | 4.48 | 1 | 8.96 | | | 65 | 100 (35) | | | | | | | | | | | | | 100 | 100 (0) | | | | |
| 10 | 4.48 | 1 | 8.96 | | | 20 | 90 (77) | | | | | | | | | | | | | 100 | 100 (0) | | | | |
| 10 | 4.48 | 1 | 8.96 | | | 50 | 75 (33) | | | | | | | | | | | | | 100 | 100 (0) | | | | |
| 10 | 4.48 | 1 | 8.96 | | | 35 | 90 (61) | | | | | | | | | | | | | 100 | 100 (0) | | | | |
| 10 | 4.48 | 1 | 8.96 | | | 15 | 75 (80) | | | | | | | | | | | | | 100 | 100 (0) | | | | |
| 10 | 4.48 | 1 | 8.96 | | | 10 | 85 (88) | | | | | | | | | | | | | 100 | 100 (0) | | | | |
| 10 | 4.48 | 1 | 8.96 | | | 60 | 80 (25) | | | | | | | | | | | | | 100 | 100 (0) | | | | |
| 10 | 4.48 | 1 | 8.96 | | | 20 | 80 (75) | | | | | | | | | | | | | 100 | 100 (0) | | | | |
| 10 | 4.48 | 1 | 8.96 | | | 15 | 70 (78) | | | | | | | | | | | | | 99 | 100 (1) | | | | |
| 10 | 4.48 | 1 | 8.96 | | | 20 | 80 (75) | | | | | | | | | | | | | 100 | 100 (0) | | | | |
| 10 | 4.48 | 1 | 8.96 | | | 25 | 80 (68) | | | | | | | | | | | | | 100 | 100 (0) | | | | |
| 10 | 4.48 | 1 | 8.96 | | | 25 | 75 (66) | | | | | | | | | | | | | 99 | 99 (0) | | | | |

TABLE IV-continued

% PLANT INHIBITION AND % SAFENING EFFECT ( )

| HERBICIDE NO. | RATE | ANTIDOTE NO. | RATE | SOYBEAN W | WO | RICE W | WO | HEMP SESBANIA W | WO | VELVET LEAF W | WO | SORGHUM GRAIN W | WO | WHEAT W | WO | GREEN FOXTAIL W | WO | CORN W | WO | BARNYARD GRASS W | WO | RED RICE W | WO | SHATTER CANE W | WO |
|---|---|---|---|---|---|---|---|---|---|---|---|---|---|---|---|---|---|---|---|---|---|---|---|---|---|
| 10 | 4.48 | 1 | 8.96 | 90 | | | 95 (5) | | | | | | | | | | | | | | 100 | 100 (0) | | | | |
| 10 | 4.48 | 1 | 8.96 | 35 | | | 75 (53) | | | | | | | | | | | | | | 100 | 99 (0) | | | | |
| 10 | 4.48 | 1 | 8.96 | 20 | | | 80 (75) | | | | | | | | | | | | | | 100 | 100 (0) | | | | |
| 10 | 4.48 | 1 | 8.96 | 50 | | | 80 (37) | | | | | | | | | | | | | | 100 | 100 (0) | | | | |
| 10 | 4.48 | 1 | 8.96 | 60 | | | 90 (33) | | | | | | | | | | | | | | 100 | 100 (0) | | | | |
| 10 | 6.72 | 1 | 8.96 | 20 | | | 95 (78) | | | | | | | | | | | | | | 100 | 100 (0) | | | | |
| 10 | 6.72 | 1 | 8.96 | 35 | | | 80 (56) | | | | | | | | | | | | | | 100 | 100 (0) | | | | |
| 10 | 6.72 | 1 | 8.96 | 30 | | | 95 (68) | | | | | | | | | | | | | | 100 | 100 (0) | | | | |
| 10 | 6.72 | 1 | 8.96 | 30 | | | 95 (68) | | | | | | | | | | | | | | 100 | 100 (0) | | | | |
| 10 | 6.72 | 1 | 8.96 | 25 | | | 85 (70) | | | | | | | | | | | | | | 100 | 100 (0) | | | | |
| 10 | 6.72 | 1 | 8.96 | 40 | | | 90 (55) | | | | | | | | | | | | | | 100 | 100 (0) | | | | |
| 10 | 6.72 | 1 | 8.96 | 15 | | | 95 (84) | | | | | | | | | | | | | | 100 | 100 (0) | | | | |
| 10 | 6.72 | 1 | 8.96 | 75 | | | 70 (0) | | | | | | | | | | | | | | 75 | 100 (25) | | | | |
| 10 | 6.72 | 1 | 8.96 | 30 | | | 80 (62) | | | | | | | | | | | | | | 100 | 99 (0) | | | | |
| 10 | 6.72 | 1 | 8.96 | 75 | | | 90 (16) | | | | | | | | | | | | | | 100 | 100 (0) | | | | |
| 10 | 8.96 | 1 | 8.96 | 35 | | | 90 (61) | | | | | | | | | | | | | | 100 | 100 (0) | | | | |
| 10 | 8.96 | 1 | 8.96 | 35 | | | 98 (64) | | | | | | | | | | | | | | 100 | 100 (0) | | | | |
| 10 | 1.12 | 3 | 2.24 | 10 | | | 43 (76) | | | | | | | | | | | | | | | | | | | |
| 10 | 1.12 | 3 | 2.24 | 20 | | | 18 (0) | | | | | | | | | | | | | | | | | | | |
| 10 | 1.12 | 3 | 8.96 | 0 | | | 18 (100) | | | | | | | | | | | | | | | | | | | |
| 10 | 1.12 | 3 | 8.96 | 15 | | | 43 (65) | | | | | | | | | | | | | | 100 | 100 (0) | | | | |
| 10 | 4.48 | 3 | 0.56 | 50 | | | 80 (37) | | | | | | | | | | | | | | 100 | 100 (0) | | | | |
| 10 | 4.48 | 3 | 2.24 | 25 | | | 80 (68) | | | | | | | | | | | | | | | | | | | |
| 10 | 4.48 | 3 | 2.24 | 25 | | | 58 (56) | | | | | | | | | | | | | | | | | | | |

TABLE IV-continued

% PLANT INHIBITION AND % SAFENING EFFECT ( )

| HERBICIDE | | ANTIDOTE | | SOYBEAN | | RICE | | HEMP SESBANIA | | VELVET LEAF | | SORGHUM GRAIN | | WHEAT | | GREEN FOXTAIL | | CORN | | BARNYARD GRASS | | RED RICE | | SHATTER CANE | |
|---|---|---|---|---|---|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO | W | WO | W | WO | W | WO |
| 10 | 4.48 | 3 | 2.24 | | | 25 | 67 (62) | | | | | | | | | | | | | | | | | | | |
| 10 | 4.48 | 3 | 4.48 | | | 30 | 80 (62) | | | | | | | | | | | | | 100 | 100 (0) | | | | |
| 10 | 4.48 | 3 | 8.96 | | | 0 | 58 (100) | | | | | | | | | | | | | | | | | | |
| 10 | 4.48 | 3 | 8.96 | | | 10 | 67 (85) | | | | | | | | | | | | | | | | | | |
| 10 | 1.12 | 4 | 2.24 | | | 10 | 13 (23) | | | | | | | | | | | | | | | | | | |
| 10 | 1.12 | 4 | 8.96 | | | 15 | 13 (0) | | | | | | | | | | | | | | | | | | |
| 10 | 3.36 | 4 | 2.24 | | | 65 | 72 (9) | | | | | | | | | | | | | | | | | | |
| 10 | 3.36 | 4 | 8.96 | | | 25 | 72 (65) | | | | | | | | | | | | | | | | | | |
| 10 | 4.48 | 4 | 2.24 | | | 20 | 40 (50) | | | | | | | | | | | | | | | | | | |
| 10 | 4.48 | 4 | 8.96 | | | 25 | 40 (37) | | | | | | | | | | | | | | | | | | |
| 10 | 6.72 | 4 | 2.24 | | | 80 | 95 (15) | | | | | | | | | | | | | 99 | 100 (1) | | | | |
| 10 | 6.72 | 4 | 8.96 | | | 60 | 95 (36) | | | | | | | | | | | | | 100 | 100 (0) | | | | |
| 10 | 1.12 | 6 | 8.96 | | | 0 | 30 (100) | | | | | | | | | | | | | 100 | 100 (0) | | | | |
| 10 | 2.24 | 6 | 8.96 | | | 0 | 50 (100) | | | | | | | | | | | | | 100 | 100 (0) | | | | |
| 10 | 4.48 | 6 | 8.96 | | | 10 | 80 (87) | | | | | | | | | | | | | | | | | | |
| 10 | 6.72 | 6 | 8.96 | | | 10 | 95 (89) | | | | | | | | | | | | | | | | | | |
| 10 | 1.12 | 7 | 2.24 | | | 15 | 43 (65) | | | | | | | | | | | | | | | | | | |
| 10 | 1.12 | 7 | 8.96 | | | 15 | 18 (16) | | | | | | | | | | | | | | | | | | |
| 10 | 1.12 | 7 | 8.96 | | | 30 | 43 (30) | | | | | | | | | | | | | 99 | 100 (1) | | | | |
| 10 | 1.12 | 7 | 8.96 | | | 15 | 18 (16) | | | | | | | | | | | | | 100 | 100 (0) | | | | |
| 10 | 1.12 | 7 | 8.96 | | | 0 | 30 (100) | | | | | | | | | | | | | | | | | | |
| 10 | 2.24 | 7 | 8.96 | | | 10 | 50 (80) | | | | | | | | | | | | | | | | | | |
| 10 | 4.48 | 7 | 2.24 | | | 40 | 58 (31) | | | | | | | | | | | | | | | | | | |
| 10 | 4.48 | 7 | 2.24 | | | 45 | 67 (32) | | | | | | | | | | | | | | | | | | |

TABLE IV-continued

% PLANT INHIBITION AND % SAFENING EFFECT ( )

| HERBICIDE NO. | RATE | ANTIDOTE NO. | RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 10 | 4.48 | 7 | 8.96 | | | 15 | 58 (74) | | | | | | | | | | | | | 100 | 100 (0) | | | | |
| 10 | 4.48 | 7 | 8.96 | | | 25 | 80 (68) | | | | | | | | | | | | | | | | | | |
| 10 | 4.48 | 7 | 8.96 | | | 25 | 67 (62) | | | | | | | | | | | | | 100 | 100 (0) | | | | |
| 10 | 6.72 | 7 | 8.96 | | | 60 | 95 (36) | | | | | | | | | | | | | | | | | | |
| 10 | 1.12 | 9 | 2.24 | | | 25 | 43 (41) | | | | | | | | | | | | | | | | | | |
| 10 | 1.12 | 9 | 2.24 | | | 20 | 18 (0) | | | | | | | | | | | | | 80 | 100 (20) | | | | |
| 10 | 1.12 | 9 | 8.96 | | | 30 | 30 (0) | | | | | | | | | | | | | | | | | | |
| 10 | 1.12 | 9 | 8.96 | | | 35 | 43 (18) | | | | | | | | | | | | | 100 | 100 (0) | | | | |
| 10 | 1.12 | 9 | 8.96 | | | 15 | 18 (16) | | | | | | | | | | | | | | | | | | |
| 10 | 2.24 | 9 | 8.96 | | | 10 | 50 (80) | | | | | | | | | | | | | | | | | | |
| 10 | 4.48 | 9 | 2.24 | | | 25 | 67 (62) | | | | | | | | | | | | | | | | | | |
| 10 | 4.48 | 9 | 8.96 | | | 15 | 58 (74) | | | | | | | | | | | | | | | | | | |
| 10 | 4.48 | 9 | 8.96 | | | 25 | 67 (62) | | | | | | | | | | | | | | | | | | |
| 10 | 4.48 | 9 | 8.96 | | | 15 | 58 (74) | | | | | | | | | | | | | 100 | 100 (0) | | | | |
| 10 | 6.72 | 9 | 8.96 | | | 20 | 80 (75) | | | | | | | | | | | | | 100 | 100 (0) | | | | |
| 10 | 6.72 | 9 | 8.96 | | | 20 | 95 (78) | | | | | | | | | | | | | | | | | | |
| 10 | 3.36 | 10 | 2.24 | | | 45 | 87 (48) | | | | | | | | | | | | | | | | | | |
| 10 | 3.36 | 10 | 8.96 | | | 45 | 87 (48) | | | | | | | | | | | | | | | | | | |
| 10 | 6.72 | 10 | 2.24 | | | 70 | 90 (22) | | | | | | | | | | | | | | | | | | |
| 10 | 6.72 | 10 | 8.96 | | | 45 | 90 (50) | | | | | | | | | | | | | | | | | | |
| 10 | 1.12 | 11 | 8.96 | | | 10 | 30 (66) | | | | | | | | | | | | | 100 | 100 (0) | | | | |
| 10 | 2.24 | 11 | 8.96 | | | 40 | 50 (20) | | | | | | | | | | | | | 100 | 100 (0) | | | | |
| 10 | 4.48 | 11 | 8.96 | | | 50 | 80 (37) | | | | | | | | | | | | | 100 | 100 (0) | | | | |
| 10 | 6.72 | 11 | 8.96 | | | 75 | 95 (21) | | | | | | | | | | | | | 100 | 100 (0) | | | | |

TABLE IV-continued

% PLANT INHIBITION AND % SAFENING EFFECT ( )

| HERBICIDE | | ANTIDOTE | | SOYBEAN | | RICE | | HEMP SESBANIA | | VELVET LEAF | | SORGHUM GRAIN | | WHEAT | | GREEN FOXTAIL | | CORN | | BARNYARD GRASS | | RED RICE | | SHATTER CANE | |
|---|---|---|---|---|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO | W | WO | W | WO | W | WO |
| 10 | 1.12 | 12 | 2.24 | | | 5 | 18 (72) | | | | | | | | | | | | | | | | | | |
| 10 | 1.12 | 12 | 2.24 | | | 20 | 43 (53) | | | | | | | | | | | | | | | | | | |
| 10 | 1.12 | 12 | 8.96 | | | 0 | 30 (100) | | | | | | | | | | | | | | | | | | |
| 10 | 1.12 | 12 | 8.96 | | | 15 | 18 (16) | | | | | | | | | | | | 100 | 100 (0) | | | | |
| 10 | 1.12 | 12 | 8.96 | | | 15 | 43 (65) | | | | | | | | | | | | | | | | | | |
| 10 | 2.24 | 12 | 2.24 | | | 0 | 50 (100) | | | | | | | | | | | | 100 | 100 (0) | | | | |
| 10 | 4.48 | 12 | 2.24 | | | 25 | 58 (56) | | | | | | | | | | | | | | | | | | |
| 10 | 4.48 | 12 | 8.96 | | | 10 | 67 (85) | | | | | | | | | | | | | | | | | | |
| 10 | 4.48 | 12 | 8.96 | | | 0 | 58 (100) | | | | | | | | | | | | 100 | 100 (0) | | | | |
| 10 | 4.48 | 12 | 8.96 | | | 30 | 80 (62) | | | | | | | | | | | | 100 | 100 (0) | | | | |
| 10 | 6.72 | 12 | 8.96 | | | 30 | 67 (55) | | | | | | | | | | | | 70 | 100 (30) | | | | |
| 10 | 1.12 | 13 | 8.96 | | | 50 | 95 (47) | | | | | | | | | | | | 95 | 100 (5) | | | | |
| 10 | 2.24 | 13 | 8.96 | | | 10 | 70 (85) | | | | | | | | | | | | 100 | 100 (0) | | | | |
| 10 | 4.48 | 13 | 8.96 | | | 20 | 80 (75) | | | | | | | | | | | | 100 | 100 (0) | | | | |
| 10 | 6.72 | 13 | 8.96 | | | 30 | 90 (62) | | | | | | | | | | | | | | | | | | |
| 10 | 1.12 | 14 | 2.24 | | | 50 | 43 (44) | | | | | | | | | | | | 100 | 100 (0) | | | | |
| 10 | 1.12 | 14 | 2.24 | | | 10 | 18 (76) | | | | | | | | | | | | | | | | | | |
| 10 | 1.12 | 14 | 8.96 | | | 0 | 70 (100) | | | | | | | | | | | | | | | | | | |
| 10 | 1.12 | 14 | 8.96 | | | 15 | 43 (78) | | | | | | | | | | | | | | | | | | |
| 10 | 1.12 | 14 | 8.96 | | | 0 | 18 (100) | | | | | | | | | | | | 100 | 100 (0) | | | | |
| 10 | 2.24 | 14 | 8.96 | | | 10 | 80 (44) | | | | | | | | | | | | | | | | | | |
| 10 | 4.48 | 14 | 2.24 | | | 40 | 58 (50) | | | | | | | | | | | | | | | | | | |
| 10 | 4.48 | 14 | 2.24 | | | 5 | 67 (91) | | | | | | | | | | | | 100 | 100 (0) | | | | |
| 10 | 4.48 | 14 | 2.24 | | | 30 | 67 (55) | | | | | | | | | | | | | | | | | | |

TABLE IV-continued

| HERBICIDE | | ANTIDOTE | | SOYBEAN | | RICE | | HEMP SESBANIA | | VELVET LEAF | | SORGHUM GRAIN | | WHEAT | | GREEN FOXTAIL | | CORN | | BARNYARD GRASS | | RED RICE | | SHATTER CANE | |
|---|---|---|---|---|---|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO | W | WO | W | WO | W | WO |
| 10 | 4.48 | 14 | 8.96 | | | 5 | 58 (91) | | | | | | | | | | | | | 100 | 100 (0) | | | | |
| 10 | 4.48 | 14 | 8.96 | | | 60 | 80 (25) | | | | | | | | | | | | | | | | | | |
| 10 | 4.48 | 14 | 8.96 | | | 45 | 67 (32) | | | | | | | | | | | | | | | | | | |
| 10 | 6.72 | 14 | 8.96 | | | 70 | 90 (22) | | | | | | | | | | | | | 100 | 100 (0) | | | | |
| 10 | 1.12 | 16 | 2.24 | | | 20 | 43 (53) | | | | | | | | | | | | | | | | | | |
| 10 | 1.12 | 16 | 2.24 | | | 5 | 18 (72) | | | | | | | | | | | | | | | | | | |
| 10 | 1.12 | 16 | 8.96 | | | 25 | 43 (41) | | | | | | | | | | | | | | | | | | |
| 10 | 1.12 | 16 | 8.96 | | | 25 | 18 (0) | | | | | | | | | | | | | | | | | | |
| 10 | 1.12 | 16 | 8.96 | | | 0 | 70 (100) | | | | | | | | | | | | | 70 | 100 (30) | | | | |
| 10 | 2.24 | 16 | 8.96 | | | 0 | 80 (100) | | | | | | | | | | | | | 90 | 100 (10) | | | | |
| 10 | 4.48 | 16 | 2.24 | | | 55 | 67 (17) | | | | | | | | | | | | | | | | | | |
| 10 | 4.48 | 16 | 2.24 | | | 15 | 58 (74) | | | | | | | | | | | | | | | | | | |
| 10 | 4.48 | 16 | 8.96 | | | 25 | 58 (56) | | | | | | | | | | | | | | | | | | |
| 10 | 4.48 | 16 | 8.96 | | | 30 | 67 (55) | | | | | | | | | | | | | 100 | 100 (0) | | | | |
| 10 | 6.72 | 16 | 8.96 | | | 10 | 80 (87) | | | | | | | | | | | | | 100 | 100 (0) | | | | |
| 10 | 6.72 | 16 | 8.96 | | | 30 | 90 (66) | | | | | | | | | | | | | | | | | | |
| 10 | 1.12 | 19 | 2.24 | | | 5 | 13 (61) | | | | | | | | | | | | | | | | | | |
| 10 | 1.12 | 19 | 8.96 | | | 10 | 13 (23) | | | | | | | | | | | | | | | | | | |
| 10 | 3.36 | 19 | 2.24 | | | 45 | 72 (37) | | | | | | | | | | | | | | | | | | |
| 10 | 3.36 | 19 | 8.96 | | | 5 | 72 (93) | | | | | | | | | | | | | | | | | | |
| 10 | 4.48 | 19 | 2.24 | | | 15 | 40 (62) | | | | | | | | | | | | | | | | | | |
| 10 | 4.48 | 19 | 8.96 | | | 15 | 40 (62) | | | | | | | | | | | | | | | | | | |
| 10 | 6.72 | 19 | 2.24 | | | 70 | 95 (26) | | | | | | | | | | | | | | | | | | |
| 10 | 6.72 | 19 | 8.96 | | | 20 | 95 (78) | | | | | | | | | | | | | | | | | | |

TABLE IV-continued

| | | | | % PLANT INHIBITION AND % SAFENING EFFECT () | | | | | | | | | | | | | | | | | |
|---|---|---|---|---|---|---|---|---|---|---|---|---|---|---|---|---|---|---|---|---|---|
| HERBICIDE | | ANTIDOTE | | SOYBEAN | | RICE | | HEMP SESBANIA | | VELVET LEAF | | SORGHUM GRAIN | | WHEAT | | GREEN FOXTAIL | | CORN | | BARNYARD GRASS | | RED RICE | | SHATTER CANE |
| NO. | RATE | NO. | RATE | W | WO | W | WO | W | WO | W | WO | W | WO | W | WO | W | WO | W | WO | W | WO | W | WO | W | WO |
| 10 | 1.12 | 20 | 2.24 | | | 5 | 13 (61) | | | | | | | | | | | | | | | | | | |
| 10 | 1.12 | 20 | 8.96 | | | 5 | 13 (61) | | | | | | | | | | | | | | | | | | |
| 10 | 3.36 | 20 | 2.24 | | | 80 | 72 (0) | | | | | | | | | | | | | | | | | | |
| 10 | 3.36 | 20 | 8.96 | | | 65 | 72 (9) | | | | | | | | | | | | | | | | | | |
| 10 | 4.48 | 20 | 2.24 | | | 5 | 40 (87) | | | | | | | | | | | | | | | | | | |
| 10 | 4.48 | 20 | 8.96 | | | 40 | 40 (0) | | | | | | | | | | | | | | | | | | |
| 10 | 6.72 | 20 | 2.24 | | | 80 | 95 (15) | | | | | | | | | | | | | | | | | | |
| 10 | 6.72 | 20 | 8.96 | | | 60 | 95 (36) | | | | | | | | | | | | | | | | | | |
| 10 | 1.12 | 21 | 8.96 | | | 0 | 60 (100) | | | | | | | | | | | | | 80 | 100 (20) | | | | |
| 10 | 2.24 | 21 | 8.96 | | | 0 | 70 (100) | | | | | | | | | | | | | 100 | 95 (0) | | | | |
| 10 | 4.48 | 21 | 8.96 | | | 10 | 100 (90) | | | | | | | | | | | | | 90 | 100 (10) | | | | |
| 10 | 6.72 | 21 | 8.96 | | | 0 | 70 (100) | | | | | | | | | | | | | 100 | 100 (0) | | | | |
| 10 | 1.12 | 22 | 2.24 | | | 23 | 30 (23) | | | | | | | | | | | | | 100 | 100 (0) | | | | |
| 10 | 1.12 | 22 | 8.96 | | | 0 | 60 (100) | | | | | | | | | | | | | 90 | 100 (10) | | | | |
| 10 | 1.12 | 22 | 0.56 | | | 20 | 30 (33) | | | | | | | | | | | | | 85 | 100 (15) | | | | |
| 10 | 2.24 | 22 | 8.96 | | | 10 | 70 (85) | | | | | | | | | | | | | 95 | 95 (0) | | | | |
| 10 | 3.36 | 22 | 2.24 | | | 25 | 63 (60) | | | | | | | | | | | | | | | | | | |
| 10 | 3.36 | 22 | 8.96 | | | 15 | 63 (76) | | | | | | | | | | | | | | | | | | |
| 10 | 4.48 | 22 | 0.56 | | | 55 | 48 (0) | | | | | | | | | | | | | | | | | | |
| 10 | 4.48 | 22 | 2.24 | | | 20 | 48 (58) | | | | | | | | | | | | | 100 | 98 (0) | | | | |
| 10 | 4.48 | 22 | 2.24 | | | 25 | 53 (52) | | | | | | | | | | | | | 100 | 98 (0) | | | | |
| 10 | 4.48 | 22 | 8.96 | | | 13 | 53 (75) | | | | | | | | | | | | | | | | | | |
| 10 | 4.48 | 22 | 8.96 | | | 0 | 48 (100) | | | | | | | | | | | | | 100 | 100 (0) | | | | |
| 10 | 4.48 | 22 | 8.96 | | | 20 | 100 (80) | | | | | | | | | | | | | | | | | | |

TABLE IV-continued

% PLANT INHIBITION AND % SAFENING EFFECT ( )

| HERBICIDE | | ANTIDOTE | | SOYBEAN | | RICE | | HEMP SESBANIA | | VELVET LEAF | | SORGHUM GRAIN | | WHEAT | | GREEN FOXTAIL | | CORN | | BARNYARD GRASS | | RED RICE | | SHATTER CANE | |
|---|---|---|---|---|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO | W | WO | W | WO | W | WO |
| 10 | 6.72 | 22 | 2.24 | | | 70 | 88 (20) | | | | | | | | | | | | | | | | | | |
| 10 | 6.72 | 22 | 8.96 | | | 10 | 88 (88) | | | | | | | | | | | | | | | | | | |
| 10 | 6.72 | 22 | 8.96 | | | 0 | 70 (100) | | | | | | | | | | | | | 100 | 100 (0) | | | | |
| 10 | 1.12 | 23 | 2.24 | | | 25 | 43 (41) | | | | | | | | | | | | | | | | | | |
| 10 | 1.12 | 23 | 2.24 | | | 20 | 18 (0) | | | | | | | | | | | | | | | | | | |
| 10 | 1.12 | 23 | 8.96 | | | 25 | 43 (41) | | | | | | | | | | | | | | | | | | |
| 10 | 1.12 | 23 | 8.96 | | | 10 | 18 (44) | | | | | | | | | | | | | | | | | | |
| 10 | 4.48 | 23 | 2.24 | | | 60 | 67 (10) | | | | | | | | | | | | | | | | | | |
| 10 | 4.48 | 23 | 2.24 | | | 35 | 58 (39) | | | | | | | | | | | | | | | | | | |
| 10 | 4.48 | 23 | 8.96 | | | 25 | 58 (56) | | | | | | | | | | | | | | | | | | |
| 10 | 4.48 | 23 | 8.96 | | | 20 | 67 (70) | | | | | | | | | | | | | | | | | | |
| 10 | 1.12 | 24 | 0.56 | | | 20 | 30 (33) | | | | | | | | | | | | | 95 | 100 (5) | | | | |
| 10 | 1.12 | 24 | 0.56 | | | 10 | 35 (71) | | | | | | | | | | | | | 100 | 100 (0) | | | | |
| 10 | 1.12 | 24 | 0.56 | | | 35 | 70 (50) | | | | | | | | | | | | | 100 | 100 (0) | | | | |
| 10 | 1.12 | 24 | 0.56 | | | 5 | 50 (90) | | | | | | | | | | | | | 100 | 100 (0) | | | | |
| 10 | 1.12 | 24 | 0.56 | | | 40 | 50 (20) | | | | | | | | | | | | | 95 | 95 (0) | | | | |
| 10 | 1.12 | 24 | 0.56 | | | 0 | 25 (100) | | | | | | | | | | | | | 100 | 100 (0) | | | | |
| 10 | 1.12 | 24 | 0.56 | | | 5 | 25 (80) | | | | | | | | | | | | | 100 | 100 (0) | | | | |
| 10 | 1.12 | 24 | 0.56 | | | 25 | 10 (0) | | | | | | | | | | | | | 95 | 100 (5) | | | | |
| 10 | 1.12 | 24 | 0.56 | | | 0 | 35 (100) | | | | | | | | | | | | | 100 | 100 (0) | | | | |
| 10 | 1.12 | 24 | 0.56 | | | 5 | 15 (66) | | | | | | | | | | | | | 100 | 100 (0) | | | | |
| 10 | 1.12 | 24 | 0.56 | | | 10 | 40 (75) | | | | | | | | | | | | | 100 | 100 (0) | | | | |
| 10 | 1.12 | 24 | 2.24 | | | 5 | 30 (83) | | | | | | | | | | | | | 95 | 100 (5) | | | | |
| 10 | 1.12 | 24 | 2.24 | | | 13 | 30 (56) | | | | | | | | | | | | | 100 | 100 (0) | | | | |

TABLE IV-continued

| | | | | % PLANT INHIBITION AND % SAFENING EFFECT ( ) | | | | | | | | | | | | | | | | |
|---|---|---|---|---|---|---|---|---|---|---|---|---|---|---|---|---|---|---|---|---|
| HERBICIDE | | ANTIDOTE | | SOYBEAN | | RICE | | HEMP SESBANIA | | VELVET LEAF | | SORGHUM GRAIN | | WHEAT | | GREEN FOXTAIL | | CORN | | BARNYARD GRASS | | RED RICE | | SHATTER CANE |
| NO. | RATE | NO. | RATE | W | WO | W | WO | W | WO | W | WO | W | WO | W | WO | W | WO | W | WO | W | WO | W | WO | W | WO |
| 10 | 1.12 | 24 | 2.24 | | | 10 | 35 (71) | | | | | | | | | | | | | 100 | 100 (0) | | | | |
| 10 | 1.12 | 24 | 2.24 | | | 60 | 50 (0) | | | | | | | | | | | | | 100 | 100 (0) | | | | |
| 10 | 1.12 | 24 | 2.24 | | | 0 | 45 (100) | | | | | | | | | | | | | 90 | 100 (10) | | | | |
| 10 | 1.12 | 24 | 2.24 | | | 20 | 35 (42) | | | | | | | | | | | | | 100 | 100 (0) | | | | |
| 10 | 1.12 | 24 | 2.24 | | | 5 | 15 (66) | | | | | | | | | | | | | 100 | 100 (0) | | | | |
| 10 | 1.12 | 24 | 2.24 | | | 20 | 50 (60) | | | | | | | | | | | | | 95 | 100 (5) | | | | |
| 10 | 1.12 | 24 | 2.24 | | | 0 | 10 (100) | | | | | | | | | | | | | 100 | 100 (0) | | | | |
| 10 | 1.12 | 24 | 2.24 | | | 15 | 25 (40) | | | | | | | | | | | | | 100 | 100 (0) | | | | |
| 10 | 1.12 | 24 | 2.24 | | | 20 | 70 (71) | | | | | | | | | | | | | 95 | 100 (5) | | | | |
| 10 | 1.12 | 24 | 2.24 | | | 0 | 43 (100) | | | | | | | | | | | | | | | | | | |
| 10 | 1.12 | 24 | 8.96 | | | 20 | 40 (50) | | | | | | | | | | | | | 95 | 100 (5) | | | | |
| 10 | 1.12 | 24 | 8.96 | | | 15 | 25 (40) | | | | | | | | | | | | | 95 | 95 (0) | | | | |
| 10 | 1.12 | 24 | 8.96 | | | 5 | 45 (88) | | | | | | | | | | | | | 90 | 100 (10) | | | | |
| 10 | 1.12 | 24 | 8.96 | | | 25 | 35 (28) | | | | | | | | | | | | | 90 | 100 (10) | | | | |
| 10 | 1.12 | 24 | 8.96 | | | 45 | 30 (0) | | | | | | | | | | | | | 90 | 100 (10) | | | | |
| 10 | 1.12 | 24 | 8.96 | | | 18 | 30 (40) | | | | | | | | | | | | | 100 | 100 (0) | | | | |
| 10 | 1.12 | 24 | 8.96 | | | 30 | 50 (40) | | | | | | | | | | | | | 100 | 100 (0) | | | | |
| 10 | 1.12 | 24 | 8.96 | | | 10 | 10 (0) | | | | | | | | | | | | | 90 | 100 (10) | | | | |
| 10 | 1.12 | 24 | 8.96 | | | 15 | 25 (40) | | | | | | | | | | | | | 40 | 95 (57) | | | | |
| 10 | 1.12 | 24 | 8.96 | | | 35 | 35 (0) | | | | | | | | | | | | | 95 | 100 (5) | | | | |
| 10 | 1.12 | 24 | 8.96 | | | 35 | 40 (12) | | | | | | | | | | | | | 90 | 100 (10) | | | | |
| 10 | 1.12 | 24 | 8.96 | | | 15 | 25 (40) | | | | | | | | | | | | | 90 | 100 (10) | | | | |
| 10 | 1.12 | 24 | 8.96 | | | 15 | 15 (0) | | | | | | | | | | | | | 95 | 100 (5) | | | | |
| 10 | 1.12 | 24 | 8.96 | | | 20 | 50 (60) | | | | | | | | | | | | | 95 | 100 (5) | | | | |

TABLE IV-continued

% PLANT INHIBITION AND % SAFFENING EFFECT ( )

| HERBICIDE NO. | RATE | ANTIDOTE NO. | RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 10 | 1.12 | 24 | 8.96 | | | 20 | 43 (53) | | | | | | | | | | | | | | | | | | |
| 10 | 1.12 | 24 | 8.96 | | | 25 | 70 (64) | | | | | | | | | | | | | 90 | 100 (10) | | | | |
| 10 | 3.36 | 24 | 2.24 | | | 5 | 63 (92) | | | | | | | | | | | | | | | | | | |
| 10 | 3.36 | 24 | 2.24 | | | 15 | 72 (79) | | | | | | | | | | | | | | | | | | |
| 10 | 3.36 | 24 | 8.96 | | | 0 | 72 (100) | | | | | | | | | | | | | | | | | | |
| 10 | 3.36 | 24 | 8.96 | | | 10 | 63 (84) | | | | | | | | | | | | | | | | | | |
| 10 | 4.48 | 24 | 0.56 | | | 30 | 80 (62) | | | | | | | | | | | | | 100 | 100 (0) | | | | |
| 10 | 4.48 | 24 | 0.56 | | | 40 | 95 (57) | | | | | | | | | | | | | 100 | 100 (0) | | | | |
| 10 | 4.48 | 24 | 0.56 | | | 10 | 80 (87) | | | | | | | | | | | | | 100 | 100 (0) | | | | |
| 10 | 4.48 | 24 | 0.56 | | | 50 | 90 (44) | | | | | | | | | | | | | 100 | 100 (0) | | | | |
| 10 | 4.48 | 24 | 0.56 | | | 70 | 85 (17) | | | | | | | | | | | | | 100 | 100 (0) | | | | |
| 10 | 4.48 | 24 | 0.56 | | | 40 | 80 (50) | | | | | | | | | | | | | 100 | 100 (0) | | | | |
| 10 | 4.48 | 24 | 0.56 | | | 40 | 95 (57) | | | | | | | | | | | | | 100 | 100 (0) | | | | |
| 10 | 4.48 | 24 | 0.56 | | | 0 | 90 (100) | | | | | | | | | | | | | 100 | 100 (0) | | | | |
| 10 | 4.48 | 24 | 0.56 | | | 35 | 48 (27) | | | | | | | | | | | | | 100 | 100 (0) | | | | |
| 10 | 4.48 | 24 | 0.56 | | | 70 | 80 (12) | | | | | | | | | | | | | 100 | 100 (0) | | | | |
| 10 | 4.48 | 24 | 0.56 | | | 60 | 80 (25) | | | | | | | | | | | | | 100 | 100 (0) | | | | |
| 10 | 4.48 | 24 | 0.56 | | | 25 | 65 (61) | | | | | | | | | | | | | 100 | 100 (0) | | | | |
| 10 | 4.48 | 24 | 0.56 | | | 60 | 80 (25) | | | | | | | | | | | | | 100 | 100 (0) | | | | |
| 10 | 4.48 | 24 | 0.56 | | | 25 | 90 (72) | | | | | | | | | | | | | 100 | 100 (0) | | | | |
| 10 | 4.48 | 24 | 0.56 | | | 35 | 60 (41) | | | | | | | | | | | | | 100 | 100 (0) | | | | |
| 10 | 4.48 | 24 | 2.24 | | | 40 | 85 (52) | | | | | | | | | | | | | 100 | 100 (0) | | | | |
| 10 | 4.48 | 24 | 2.24 | | | 40 | 95 (57) | | | | | | | | | | | | | 100 | 100 (0) | | | | |
| 10 | 4.48 | 24 | 2.24 | | | 25 | 80 (68) | | | | | | | | | | | | | 100 | 100 (0) | | | | |

TABLE IV-continued

% PLANT INHIBITION AND % SAFENING EFFECT ( )

| HERBICIDE NO. | RATE | ANTIDOTE NO. | RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 10 | 4.48 | 24 | 2.24 | | | 5 | 85 (94) | | | | | | | | | | | | | 100 | 100 (0) | | | | |
| 10 | 4.48 | 24 | 2.24 | | | 30 | 53 (43) | | | | | | | | | | | | | 100 | 98 (0) | | | | |
| 10 | 4.48 | 24 | 2.24 | | | 5 | 80 (93) | | | | | | | | | | | | | 100 | 100 (0) | | | | |
| 10 | 4.48 | 24 | 2.24 | | | 50 | 90 (44) | | | | | | | | | | | | | 100 | 100 (0) | | | | |
| 10 | 4.48 | 24 | 2.24 | | | 10 | 67 (85) | | | | | | | | | | | | | | | | | | |
| 10 | 4.48 | 24 | 2.24 | | | 60 | 90 (33) | | | | | | | | | | | | | 100 | 100 (0) | | | | |
| 10 | 4.48 | 24 | 2.24 | | | 15 | 90 (83) | | | | | | | | | | | | | 100 | 100 (0) | | | | |
| 10 | 4.48 | 24 | 2.24 | | | 30 | 80 (62) | | | | | | | | | | | | | 100 | 100 (0) | | | | |
| 10 | 4.48 | 24 | 2.24 | | | 10 | 80 (87) | | | | | | | | | | | | | 100 | 100 (0) | | | | |
| 10 | 4.48 | 24 | 2.24 | | | 20 | 80 (75) | | | | | | | | | | | | | 100 | 100 (0) | | | | |
| 10 | 4.48 | 24 | 2.24 | | | 10 | 48 (79) | | | | | | | | | | | | | | | | | | |
| 10 | 4.48 | 24 | 2.24 | | | 5 | 60 (91) | | | | | | | | | | | | | 100 | 100 (0) | | | | |
| 10 | 4.48 | 24 | 2.24 | | | 45 | 80 (43) | | | | | | | | | | | | | 100 | 100 (0) | | | | |
| 10 | 4.48 | 24 | 2.24 | | | 35 | 95 (63) | | | | | | | | | | | | | 100 | 100 (0) | | | | |
| 10 | 4.48 | 24 | 2.24 | | | 25 | 65 (61) | | | | | | | | | | | | | 100 | 100 (0) | | | | |
| 10 | 4.48 | 24 | 4.48 | | | 10 | 80 (87) | | | | | | | | | | | | | 95 | 100 (5) | | | | |
| 10 | 4.48 | 24 | 8.96 | | | 15 | 80 (81) | | | | | | | | | | | | | 100 | 100 (0) | | | | |
| 10 | 4.48 | 24 | 8.96 | | | 45 | 80 (43) | | | | | | | | | | | | | 100 | 100 (0) | | | | |
| 10 | 4.48 | 24 | 8.96 | | | 60 | 85 (29) | | | | | | | | | | | | | 100 | 100 (0) | | | | |
| 10 | 4.48 | 24 | 8.96 | | | 10 | 85 (88) | | | | | | | | | | | | | 100 | 100 (0) | | | | |
| 10 | 4.48 | 24 | 8.96 | | | 30 | 95 (68) | | | | | | | | | | | | | 100 | 100 (0) | | | | |
| 10 | 4.48 | 24 | 8.96 | | | 25 | 53 (52) | | | | | | | | | | | | | 100 | 98 (0) | | | | |
| 10 | 4.48 | 24 | 8.96 | | | 40 | 65 (38) | | | | | | | | | | | | | 100 | 100 (0) | | | | |
| 10 | 4.48 | 24 | 8.96 | | | 10 | 80 (87) | | | | | | | | | | | | | 100 | 100 (0) | | | | |

TABLE IV-continued

% PLANT INHIBITION AND % SAFENING EFFECT ()

| HERBICIDE | | ANTIDOTE | | SOYBEAN | | RICE | | HEMP SESBANIA | | VELVET LEAF | | SORGHUM GRAIN | | WHEAT | | GREEN FOXTAIL | | CORN | | BARNYARD GRASS | | RED RICE | | SHATTER CANE | |
|---|---|---|---|---|---|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO | W | WO | W | WO | W | WO |
| 10 | 4.48 | 24 | 8.96 | | | 25 | 90 (72) | | | | | | | | | | | | | 100 | 100 (0) | | | | |
| 10 | 4.48 | 24 | 8.96 | | | 35 | 95 (63) | | | | | | | | | | | | | 95 | 100 (5) | | | | |
| 10 | 4.48 | 24 | 8.96 | | | 30 | 80 (62) | | | | | | | | | | | | | 100 | 100 (0) | | | | |
| 10 | 4.48 | 24 | 8.96 | | | 0 | 60 (100) | | | | | | | | | | | | | 100 | 100 (0) | | | | |
| 10 | 4.48 | 24 | 8.96 | | | 55 | 90 (38) | | | | | | | | | | | | | 100 | 100 (0) | | | | |
| 10 | 4.48 | 24 | 8.96 | | | 30 | 80 (62) | | | | | | | | | | | | | 100 | 100 (0) | | | | |
| 10 | 4.48 | 24 | 8.96 | | | 20 | 48 (58) | | | | | | | | | | | | | | | | | | |
| 10 | 4.48 | 24 | 8.96 | | | 35 | 90 (61) | | | | | | | | | | | | | 100 | 100 (0) | | | | |
| 10 | 4.48 | 24 | 8.96 | | | 0 | 67 (100) | | | | | | | | | | | | | | | | | | |
| 10 | 6.72 | 24 | 2.24 | | | 30 | 88 (65) | | | | | | | | | | | | | | | | | | |
| 10 | 6.72 | 24 | 2.24 | | | 25 | 95 (73) | | | | | | | | | | | | | | | | | | |
| 10 | 6.72 | 24 | 8.96 | | | 15 | 95 (84) | | | | | | | | | | | | | | | | | | |
| 10 | 6.72 | 24 | 8.96 | | | 5 | 88 (94) | | | | | | | | | | | | | | | | | | |
| 10 | 1.12 | 25 | 2.24 | | | 25 | 70 (64) | | | | | | | | | | | | | 100 | 100 (0) | | | | |
| 10 | 1.12 | 25 | 8.96 | | | 10 | 70 (85) | | | | | | | | | | | | | 50 | 100 (50) | | | | |
| 10 | 4.48 | 25 | 2.24 | | | 35 | 90 (61) | | | | | | | | | | | | | 100 | 100 (0) | | | | |
| 10 | 4.48 | 25 | 8.96 | | | 15 | 90 (83) | | | | | | | | | | | | | 100 | 100 (0) | | | | |
| 10 | 1.12 | 26 | 2.24 | | | 5 | 55 (90) | | | | | | | | | | | | | 100 | 100 (0) | | | | |
| 10 | 1.12 | 26 | 8.96 | | | 20 | 55 (63) | | | | | | | | | | | | | 95 | 100 (5) | | | | |
| 10 | 4.48 | 26 | 2.24 | | | 10 | 80 (87) | | | | | | | | | | | | | 100 | 100 (0) | | | | |
| 10 | 4.48 | 26 | 8.96 | | | 10 | 80 (87) | | | | | | | | | | | | | 100 | 100 (0) | | | | |
| 10 | 1.12 | 27 | 2.24 | | | 20 | 55 (63) | | | | | | | | | | | | | 100 | 100 (0) | | | | |
| 10 | 1.12 | 27 | 8.96 | | | 25 | 55 (54) | | | | | | | | | | | | | 85 | 100 (15) | | | | |
| 10 | 4.48 | 27 | 2.24 | | | 20 | 80 (75) | | | | | | | | | | | | | 100 | 100 (0) | | | | |

TABLE IV-continued

% PLANT INHIBITION AND % SAFENING EFFECT ( )

| HERBICIDE NO. | RATE | ANTIDOTE NO. | RATE | SOYBEAN W | WO | RICE W | WO | HEMP SESBANIA W | WO | VELVET LEAF W | WO | SORGHUM GRAIN W | WO | WHEAT W | WO | GREEN FOXTAIL W | WO | CORN W | WO | BARNYARD GRASS W | WO | RED RICE W | WO | SHATTER CANE W | WO |
|---|---|---|---|---|---|---|---|---|---|---|---|---|---|---|---|---|---|---|---|---|---|---|---|---|---|
| 10 | 4.48 | 27 | 8.96 | | | 5 | 80 (93) | | | | | | | | | | | | | 100 | 100 (0) | | | | |
| 10 | 1.12 | 28 | 2.24 | | | 10 | 45 (77) | | | | | | | | | | | | | 100 | 100 (0) | | | | |
| 10 | 1.12 | 28 | 8.96 | | | 15 | 45 (66) | | | | | | | | | | | | | 100 | 100 (0) | | | | |
| 10 | 3.36 | 28 | 2.24 | | | 5 | 63 (92) | | | | | | | | | | | | | | | | | | |
| 10 | 3.36 | 28 | 8.96 | | | 5 | 63 (92) | | | | | | | | | | | | | | | | | | |
| 10 | 4.48 | 28 | 0.56 | | | 20 | 48 (58) | | | | | | | | | | | | | | | | | | |
| 10 | 4.48 | 28 | 2.24 | | | 20 | 95 (78) | | | | | | | | | | | | | 100 | 100 (0) | | | | |
| 10 | 4.48 | 28 | 2.24 | | | 10 | 48 (79) | | | | | | | | | | | | | | | | | | |
| 10 | 4.48 | 28 | 8.96 | | | 20 | 48 (58) | | | | | | | | | | | | | | | | | | |
| 10 | 4.48 | 28 | 8.96 | | | 25 | 95 (73) | | | | | | | | | | | | | 100 | 100 (0) | | | | |
| 10 | 6.72 | 28 | 2.24 | | | 30 | 88 (65) | | | | | | | | | | | | | | | | | | |
| 10 | 6.72 | 28 | 8.96 | | | 15 | 88 (82) | | | | | | | | | | | | | | | | | | |
| 10 | 1.12 | 29 | 2.24 | | | 15 | 45 (66) | | | | | | | | | | | | | 100 | 100 (0) | | | | |
| 10 | 1.12 | 29 | 8.96 | | | 75 | 0 | | | | | | | | | | | | | 100 | 100 (0) | | | | |
| 10 | 4.48 | 29 | 2.24 | | | 30 | 95 (68) | | | | | | | | | | | | | 100 | 100 (0) | | | | |
| 10 | 4.48 | 29 | 8.96 | | | 45 | 95 (52) | | | | | | | | | | | | | 100 | 100 (0) | | | | |
| 10 | 1.12 | 30 | 2.24 | | | 25 | 60 (58) | | | | | | | | | | | | | 100 | 100 (0) | | | | |
| 10 | 1.12 | 30 | 8.96 | | | 40 | 60 (33) | | | | | | | | | | | | | 100 | 100 (0) | | | | |
| 10 | 3.36 | 30 | 2.24 | | | 20 | 63 (68) | | | | | | | | | | | | | | | | | | |
| 10 | 3.36 | 30 | 8.96 | | | 20 | 63 (68) | | | | | | | | | | | | | | | | | | |
| 10 | 4.48 | 30 | 0.56 | | | 25 | 48 (47) | | | | | | | | | | | | | | | | | | |
| 10 | 4.48 | 30 | 2.24 | | | 30 | 80 (62) | | | | | | | | | | | | | 100 | 100 (0) | | | | |
| 10 | 4.48 | 30 | 2.24 | | | 20 | 48 (58) | | | | | | | | | | | | | | | | | | |
| 10 | 4.48 | 30 | 8.96 | | | 10 | 48 (79) | | | | | | | | | | | | | | | | | | |

TABLE IV-continued

% PLANT INHIBITION AND % SAFENING EFFECT ( )

| HERBICIDE NO. | RATE | ANTIDOTE NO. | RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 10 | 4.48 | 30 | 8.96 | 60 | | 80 (25) | | | | | | | | | | | | | | 100 | 100 (0) | | | | |
| 10 | 6.72 | 30 | 2.24 | 15 | | 88 (82) | | | | | | | | | | | | | | | | | | | |
| 10 | 6.72 | 30 | 8.96 | 15 | | 88 (82) | | | | | | | | | | | | | | | | | | | |
| 10 | 3.36 | 31 | 2.24 | 5 | | 63 (92) | | | | | | | | | | | | | | | | | | | |
| 10 | 3.36 | 31 | 8.96 | 10 | | 63 (84) | | | | | | | | | | | | | | | | | | | |
| 10 | 4.48 | 31 | 0.56 | 20 | | 48 (58) | | | | | | | | | | | | | | | | | | | |
| 10 | 4.48 | 31 | 2.24 | 20 | | 48 (58) | | | | | | | | | | | | | | | | | | | |
| 10 | 4.48 | 31 | 8.96 | 25 | | 48 (47) | | | | | | | | | | | | | | | | | | | |
| 10 | 6.72 | 31 | 2.24 | 20 | | 88 (77) | | | | | | | | | | | | | | | | | | | |
| 10 | 6.72 | 31 | 8.96 | 10 | | 88 (88) | | | | | | | | | | | | | | | | | | | |
| 10 | 1.12 | 32 | 2.24 | 35 | | 60 (41) | | | | | | | | | | | | | | 100 | 100 (0) | | | | |
| 10 | 1.12 | 32 | 8.96 | 65 | | 60 (0) | | | | | | | | | | | | | | 100 | 100 (0) | | | | |
| 10 | 4.48 | 32 | 2.24 | 40 | | 85 (52) | | | | | | | | | | | | | | 100 | 100 (0) | | | | |
| 10 | 4.48 | 32 | 8.96 | 35 | | 85 (58) | | | | | | | | | | | | | | 100 | 100 (0) | | | | |
| 10 | 1.12 | 33 | 2.24 | 10 | | 45 (77) | | | | | | | | | | | | | | 100 | 100 (0) | | | | |
| 10 | 1.12 | 33 | 8.96 | 5 | | 45 (88) | | | | | | | | | | | | | | 95 | 100 (5) | | | | |
| 10 | 3.36 | 33 | 2.24 | 45 | | 87 (48) | | | | | | | | | | | | | | | | | | | |
| 10 | 3.36 | 33 | 8.96 | 20 | | 87 (77) | | | | | | | | | | | | | | | | | | | |
| 10 | 4.48 | 33 | 2.24 | 25 | | 55 (54) | | | | | | | | | | | | | | 100 | 100 (0) | | | | |
| 10 | 4.48 | 33 | 8.96 | 60 | | 55 (0) | | | | | | | | | | | | | | 100 | 100 (0) | | | | |
| 10 | 6.72 | 33 | 2.24 | 80 | | 90 (11) | | | | | | | | | | | | | | | | | | | |
| 10 | 6.72 | 33 | 8.96 | 55 | | 90 (38) | | | | | | | | | | | | | | | | | | | |
| 10 | 1.12 | 34 | 2.24 | 15 | | 45 (66) | | | | | | | | | | | | | | 100 | 100 (0) | | | | |
| 10 | 1.12 | 34 | 8.96 | 10 | | 45 (77) | | | | | | | | | | | | | | 100 | 100 (0) | | | | |

TABLE IV-continued

% PLANT INHIBITION AND % SAFENING EFFECT ( )

| HERBICIDE NO. | HERBICIDE RATE | ANTIDOTE NO. | ANTIDOTE RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 10 | 3.36 | 34 | 2.24 | | | 25 | 87 (71) | | | | | | | | | | | | | | | | | | | |
| 10 | 3.36 | 34 | 8.96 | | | 10 | 87 (88) | | | | | | | | | | | | | | | | | | | |
| 10 | 4.48 | 34 | 2.24 | | | 10 | 55 (81) | | | | | | | | | | | | | | | | | | | |
| 10 | 4.48 | 34 | 8.96 | | | 20 | 55 (63) | | | | | | | | | | | | | | | | | | | |
| 10 | 6.72 | 34 | 2.24 | | | 70 | 90 (22) | | | | | | | | | | | | | | | | | | | |
| 10 | 6.72 | 34 | 8.96 | | | 5 | 90 (94) | | | | | | | | | | | | | | | | | | | |
| 10 | 1.12 | 35 | 2.24 | | | 35 | 95 (63) | | | | | | | | | | | | | | 100 | 100 (0) | | | | |
| 10 | 1.12 | 35 | 8.96 | | | 15 | 95 (84) | | | | | | | | | | | | | | 100 | 100 (0) | | | | |
| 10 | 4.48 | 35 | 2.24 | | | 20 | 95 (78) | | | | | | | | | | | | | | 100 | 100 (0) | | | | |
| 10 | 4.48 | 35 | 8.96 | | | 30 | 95 (68) | | | | | | | | | | | | | | 100 | 100 (0) | | | | |
| 10 | 1.12 | 36 | 0.56 | | | 5 | 15 (66) | | | | | | | | | | | | | | 100 | 100 (0) | | | | |
| 10 | 1.12 | 36 | 2.24 | | | 40 | 50 (20) | | | | | | | | | | | | | | 100 | 100 (0) | | | | |
| 10 | 1.12 | 36 | 8.96 | | | 5 | 15 (66) | | | | | | | | | | | | | | 100 | 100 (0) | | | | |
| 10 | 1.12 | 36 | 8.96 | | | 90 | 50 (0) | | | | | | | | | | | | | | 95 | 100 (5) | | | | |
| 10 | 1.12 | 36 | 0.56 | | | 5 | 15 (66) | | | | | | | | | | | | | | 100 | 100 (0) | | | | |
| 10 | 1.12 | 36 | 2.24 | | | 20 | 50 (60) | | | | | | | | | | | | | | 95 | 100 (5) | | | | |
| 10 | 4.48 | 36 | 0.56 | | | 30 | 65 (53) | | | | | | | | | | | | | | 100 | 100 (0) | | | | |
| 10 | 4.48 | 36 | 0.56 | | | 80 | 85 (5) | | | | | | | | | | | | | | 100 | 100 (0) | | | | |
| 10 | 4.48 | 36 | 2.24 | | | 30 | 65 (53) | | | | | | | | | | | | | | 100 | 100 (0) | | | | |
| 10 | 4.48 | 36 | 2.24 | | | 85 | 85 (0) | | | | | | | | | | | | | | 100 | 100 (0) | | | | |
| 10 | 4.48 | 36 | 8.96 | | | 5 | 65 (92) | | | | | | | | | | | | | | 100 | 100 (0) | | | | |
| 10 | 4.48 | 36 | 8.96 | | | 50 | 85 (41) | | | | | | | | | | | | | | 100 | 100 (0) | | | | |
| 11 | 1.12 | 1 | 8.96 | 0 | 15 (100) | | | | | | | | | | | | | | | | 90 | 85 (0) | | 95 (5) | | |
| 11 | 2.24 | 1 | 8.96 | 0 | 20 (100) | | | | | | | | | | | | | | | | 90 | 95 (5) | | | | |

TABLE IV-continued

% PLANT INHIBITION AND % SAFEENING EFFECT ()

| HERBICIDE NO. | HERBICIDE RATE | ANTIDOTE NO. | ANTIDOTE RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 11 | 2.24 | 1 | 8.96 | 15 | 17 (11) | | | | | | | | | | | | | | | | | 97 | 90 (0) | | |
| 11 | 4.48 | 1 | 8.96 | 10 | 35 (71) | | | | | | | | | | | | | | | | | 95 | 100 (5) | | |
| 11 | 4.48 | 1 | 8.96 | 15 | 45 (66) | | | | | | | | | | | | | | | | | 97 | 100 (3) | | |
| 11 | 6.72 | 1 | 8.96 | 37 | 30 (0) | | | | | | | | | | | | | | | | | 99 | 100 (1) | | |
| 11 | 8.96 | 1 | 8.96 | 47 | 35 (0) | | | | | | | | | | | | | | | | | 99 | 100 (1) | | |
| 11 | 1.12 | 9 | 8.96 | 40 | 15 (0) | | | | | | | | | | | | | | | | | 75 | 85 (11) | | |
| 11 | 2.24 | 9 | 8.96 | 0 | 20 (0) | | | | | | | | | | | | | | | | | 85 | 95 (10) | | |
| 11 | 2.24 | 9 | 8.96 | 13 | 17 (100) | | | | | | | | | | | | | | | | | 85 | 90 (5) | | |
| 11 | 4.48 | 9 | 8.96 | 40 | 45 (23) | | | | | | | | | | | | | | | | | 97 | 100 (3) | | |
| 11 | 4.48 | 9 | 8.96 | 10 | 35 (11) | | | | | | | | | | | | | | | | | 80 | 100 (20) | | |
| 11 | 6.72 | 9 | 8.96 | 20 | 30 (71) | | | | | | | | | | | | | | | | | 95 | 100 (5) | | |
| 11 | 8.96 | 9 | 8.96 | 60 | 35 (33) | | | | | | | | | | | | | | | | | 99 | 100 (1) | | |
| 11 | 1.12 | 10 | 2.24 | 40 | 50 (0) | | | | | | | 80 | 99 (19) | | | | | 40 | 50 (20) | | | | | | |
| 11 | 3.36 | 10 | 2.24 | 40 | 60 (20) | | | | | | | 90 | 100 (10) | | | | | 40 | 75 (46) | | | | | | |
| 11 | 6.72 | 10 | 2.24 | 60 | 80 (33) | | | | | | | 95 | 100 (5) | | | | | 75 | 95 (21) | | | | | | |
| 11 | 1.12 | 11 | 2.24 | 35 | 50 (25) | | | | | | | 85 | 99 (14) | | | | | 15 | 50 (70) | | | | | | |
| 11 | 1.12 | 11 | 8.96 | 30 | 15 (30) | | | | | | | | | | | | | | | 90 | 85 (0) | | | |
| 11 | 2.24 | 11 | 8.96 | 80 | 20 (0) | | | | | | | | | | | | | | | 95 | 95 (0) | | | |
| 11 | 3.36 | 11 | 2.24 | 65 | 60 (0) | | | | | | | 99 | 100 (1) | | | | | 70 | 75 (6) | | | | | | |
| 11 | 4.48 | 11 | 8.96 | 10 | 35 (71) | | | | | | | | | | | | | | | 100 | 100 (0) | | | |
| 11 | 6.72 | 11 | 2.24 | 90 | 80 (0) | | | | | | | 100 | 100 (0) | | | | | 70 | 95 (26) | | | | | | |
| 11 | 2.24 | 23 | 2.24 | 10 | 40 (75) | | | | | | | | | | | | | 10 | 60 (83) | 100 | 95 (0) | 90 | 85 (0) | 95 | 95 (0) |
| 11 | 2.24 | 23 | 8.96 | 0 | 40 (100) | | | | | | | | | | | | | 10 | 60 (83) | 100 | 95 (0) | 95 | 95 (0) | 70 | 95 (26) |
| 11 | 8.96 | 23 | 2.24 | 15 | 55 (72) | | | | | | | | | | | | | 40 | 75 (46) | 100 | 100 (0) | | 100 (0) | 100 | 100 (0) |

TABLE IV-continued

| HERBICIDE NO. | HERBICIDE RATE | ANTIDOTE NO. | ANTIDOTE RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 11 | 8.96 | 23 | 8.96 | 30 | 55 (45) | | | | | | | | | | | | | 20 | 75 (73) | 100 | 100 (0) | 95 | 100 | 95 | 100 (5) |
| 15 | 0.56 | 1 | 2.24 | | | | | | | | | | | 5 | 10 (50) | | | | | | | | | | |
| 15 | 0.56 | 1 | 8.96 | | | | | | | | | | | | | 95 | 100 (5) | 10 | 55 (81) | | | | | | |
| 15 | 0.56 | 1 | 8.96 | | | | | | | | | | | 35 | 10 (0) | | | | | | | | | | |
| 15 | 0.56 | 1 | 8.96 | | | | | | | | | | | | | 100 | 100 (0) | 0 | 55 (100) | | | | | | |
| 15 | 2.24 | 1 | 2.24 | | | | | | | | | | | | | 100 | 100 (0) | 30 | 95 (68) | | | | | | |
| 15 | 2.24 | 1 | 2.24 | | | | | | | | | | | 45 | 50 (10) | | | | | | | | | | |
| 15 | 2.24 | 1 | 8.96 | | | | | | | | | | | | | 100 | 100 (0) | 10 | 95 (89) | | | | | | |
| 15 | 2.24 | 1 | 8.96 | | | | | | | | | | | 25 | 50 (50) | | | | | | | | | | |
| 15 | 0.56 | 3 | 2.24 | | | | | | | | | | | 15 | 10 (0) | | | | | | | | | | |
| 15 | 0.56 | 3 | 0.56 | | | | | | | | | | | 5 | 10 (50) | | | | | | | | | | |
| 15 | 0.56 | 3 | 2.24 | | | | | | | | | | | 30 | 50 (40) | | | | | | | | | | |
| 15 | 2.24 | 3 | 8.96 | | | | | | | | | | | 55 | 50 (0) | | | | | | | | | | |
| 15 | 0.56 | 4 | 2.24 | | | | | | | | | | | 5 | 18 (72) | | | | | | | | | | |
| 15 | 0.56 | 4 | 8.96 | | | | | | | | | | | 0 | 18 (100) | | | | | | | | | | |
| 15 | 2.24 | 4 | 2.24 | | | | | | | | | | | 30 | 73 (58) | | | | | | | | | | |
| 15 | 2.24 | 4 | 8.96 | | | | | | | | | | | 55 | 73 (24) | | | | | | | | | | |
| 15 | 0.56 | 7 | 0.56 | 35 | 38 (7) | | | | | | | | | 95 | 10 (0) | | | | | | | | | | |
| 15 | 0.56 | 7 | 0.56 | 40 | 60 (33) | | | | | | | | | 5 | 10 (50) | | | | | | | | | | |
| 15 | 2.24 | 7 | 2.24 | 5 | 38 (86) | | | | | | | | | | | | | | | 100 | 100 (0) | | | | |
| 15 | 2.24 | 7 | 2.24 | | | | | | | | | | | 65 | 60 (0) | | | | | 100 | 100 (0) | | | | |
| 15 | 2.24 | 7 | 2.24 | | | | | | | | | | | | | | | | | 100 | 100 (0) | | | | |
| 15 | 2.24 | 7 | 2.24 | 30 | 60 (50) | | | | | | | | | | | | | | | 100 | 100 (0) | | | | |
| 15 | 2.24 | 7 | 8.96 | | | | | | | | | | | | | | | | | | | | | | |

TABLE IV-continued

% PLANT INHIBITION AND % SAFENING EFFECT ( )

| HERBICIDE NO. | RATE | ANTIDOTE NO. | RATE | SOYBEAN W | WO | RICE W | WO | HEMP SESBANIA W | WO | VELVET LEAF W | WO | SORGHUM GRAIN W | WO | WHEAT W | WO | GREEN FOXTAIL W | WO | CORN W | WO | BARNYARD GRASS W | WO | RED RICE W | WO | SHATTER CANE W | WO |
|---|---|---|---|---|---|---|---|---|---|---|---|---|---|---|---|---|---|---|---|---|---|---|---|---|---|
| 15 | 2.24 | 7 | 8.96 | | | | | | | | | | | 30 | 50 (40) | | | | | | | | | | |
| 15 | 2.24 | 7 | 8.96 | 15 | 60 (75) | | | | | | | | | | | | | | | | | | | | |
| 15 | 2.24 | 7 | 8.96 | 10 | 38 (73) | | | | | | | | | | | | | | | | | | | | |
| 15 | 0.28 | 8 | 8.96 | | | | | | | | | | | | | 99 | 90 (0) | 0 | 30 (100) | 100 | 100 (0) | | | | |
| 15 | 0.56 | 8 | 2.24 | | | | | | | | | | | | | 95 | 95 (0) | 0 | 85 (100) | 100 | 100 (0) | | | | |
| 15 | 0.56 | 8 | 8.96 | | | | | | | | | | | | | 99 | 99 (0) | 0 | 80 (100) | 95 | 95 (0) | | | | |
| 15 | 0.56 | 8 | 8.96 | | | | | | | | | | | | | 99 | 99 (0) | 0 | 45 (100) | 100 | 100 (0) | | | | |
| 15 | 1.12 | 8 | 8.96 | | | | | | | | | | | | | 100 | 95 (0) | 5 | 85 (94) | 95 | 80 (0) | | | | |
| 15 | 2.24 | 8 | 0.56 | 55 | 60 (8) | | | | | | | | | | | 100 | 95 (0) | 0 | 60 (100) | 100 | 100 (0) | | | | |
| 15 | 2.24 | 8 | 0.56 | 5 | 38 (86) | | | | | | | | | | | | | | | 100 | 100 (0) | | | | |
| 15 | 2.24 | 8 | 2.24 | 10 | 38 (73) | | | | | | | | | | | | | | | 100 | 100 (0) | | | | |
| 15 | 2.24 | 8 | 2.24 | 35 | 60 (41) | | | | | | | | | | | 100 | 100 (0) | 90 | 85 (0) | 100 | 100 (0) | | | | |
| 15 | 2.24 | 8 | 2.24 | | | | | | | | | | | | | 100 | 100 (0) | 10 | 75 (86) | 100 | 100 (0) | | | | |
| 15 | 2.24 | 8 | 8.96 | 45 | 60 (25) | | | | | | | | | | | | | | | 100 | 100 (0) | | | | |
| 15 | 2.24 | 8 | 8.96 | 5 | 38 (86) | | | | | | | | | | | 100 | 100 (0) | 65 | 85 (23) | 100 | 100 (0) | | | | |
| 15 | 2.24 | 8 | 8.96 | | | | | | | | | | | | | 99 | 90 (0) | 0 | 30 (100) | 100 | 95 (0) | | | | |
| 15 | 0.28 | 9 | 2.24 | | | | | | | | | | | 5 | 10 (50) | | | | | | | | | | |
| 15 | 0.56 | 9 | 8.96 | | | | | | | | | | | 10 | 10 (0) | | | | | | | | | | |
| 15 | 0.56 | 9 | 8.96 | | | | | | | | | | | | | 99 | | 10 | 45 (77) | 100 | 100 (0) | | | | |
| 15 | 1.12 | 9 | 8.96 | | | | | | | | | | | | | 100 | 95 (0) | 35 | 60 (41) | 100 | 100 (0) | | | | |
| 15 | 2.24 | 9 | 2.24 | | | | | | | | | | | 75 | 50 (0) | | | | | | | | | | |
| 15 | 2.24 | 9 | 8.96 | | | | | | | | | | | | | 100 | 100 (0) | 50 | 75 (33) | 100 | 100 (0) | | | | |

TABLE IV-continued

| HERBICIDE NO. | HERBICIDE RATE | ANTIDOTE NO. | ANTIDOTE RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 15 | 2.24 | 9 | 8.96 | | | | | | | | | | | 60 | 50 (0) | | | | | | | | | | |
| 15 | 4.48 | 9 | 0.56 | 70 | 65 (0) | | | | | | | | | | | | | | | | | | | | |
| 15 | 4.48 | 9 | 2.24 | 75 | 60 (0) | | | | | | | | | | | | | | | | | | | | |
| 15 | 4.48 | 9 | 8.96 | 55 | 65 (15) | | | | | | | | | | | | | | | | | | | | |
| 15 | 0.28 | 10 | 8.96 | | | | | | | | | | | | | 99 | 99 (0) | 0 | 50 (100) | 100 | 98 (0) | | | | |
| 15 | 0.56 | 10 | 2.24 | | | | | | | | | | | 0 | 13 (100) | | | | | 100 | 98 (0) | | | | |
| 15 | 0.56 | 10 | 8.96 | | | | | | | | | | | 5 | 13 (61) | 99 | 99 (0) | 0 | 70 (100) | 100 | 98 (0) | | | | |
| 15 | 0.56 | 10 | 8.96 | | | | | | | | | | | | | | | | | | | | | | |
| 15 | 1.12 | 10 | 2.24 | 30 | 50 (40) | | | | | | | 100 | 100 (0) | | | | | | | | | | | | |
| 15 | 1.12 | 10 | 8.96 | | | | | | | | | 99 | 100 (1) | | | 99 | 99 (0) | 60 | 99 (39) | 99 | 100 (1) | | | | |
| 15 | 2.24 | 10 | 2.24 | | | | | | | | | 100 | 100 (90) | 25 | 55 (54) | 100 | 100 (0) | 0 | 90 (100) | 100 | 100 (0) | | | | |
| 15 | 2.24 | 10 | 8.96 | | | | | | | | | | | 5 | 55 (90) | 100 | 100 (0) | 0 | 90 (100) | 100 | 100 (0) | | | | |
| 15 | 2.24 | 10 | 8.96 | | | | | | | | | | | | | | | 0 | 90 (100) | | | | | | |
| 15 | 3.36 | 10 | 2.24 | 75 | 60 (0) | | | | | | | | | | | 99 | 99 (0) | 95 | 99 (4) | 99 | 100 (1) | | | | |
| 15 | 6.72 | 10 | 8.96 | 85 | 80 (0) | | | | | | | | | | | | | 99 | 99 (0) | | | | | | |
| 15 | 0.28 | 11 | 8.96 | | | | | | | | | | | | | 100 | 100 (0) | 0 | 50 (100) | 100 | 100 (0) | | | | |
| 15 | 0.56 | 11 | 8.96 | | | | | | | | | | | | | | | 15 | 70 (78) | | | | | | |
| 15 | 1.12 | 11 | 2.24 | 30 | 50 (40) | | | | | | | 99 | 100 (1) | | | 100 | 100 (0) | 50 | 99 (49) | 100 | 100 (0) | | | | |
| 15 | 1.12 | 11 | 8.96 | | | | | | | | | | | | | | | 50 | 90 (44) | 100 | 100 (0) | | | | |
| 15 | 2.24 | 11 | 8.96 | | | | | | | | | 100 | 100 (0) | | | 100 | 100 (0) | 60 | 90 (33) | 100 | 100 (0) | | | | |
| 15 | 3.36 | 11 | 2.24 | 70 | 60 (0) | | | | | | | 100 | 100 (0) | | | 100 | 100 (0) | 95 | 99 (4) | 100 | 100 (0) | | | | |
| 15 | 6.72 | 11 | 2.24 | 90 | 80 (0) | | | | | | | | | | | | | 95 | 99 (4) | | | | | | |
| 15 | 0.28 | 12 | 8.96 | | | | | | | | | | | | | 99 | 99 (0) | | | 100 | 100 (0) | | | | |
| 15 | 0.56 | 12 | 2.24 | | | | | | | | | | | 0 | 10 (100) | | | 0 | 50 (100) | | | | | | |

TABLE IV-continued

% PLANT INHIBITION AND % SAFENING EFFECT ()

| HERBICIDE NO. | RATE | ANTIDOTE NO. | RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 15 | 0.56 | 12 | 8.96 | | | | | | | | | | | 0 | 10 (100) | 99 | 99 (0) | 30 | 70 (57) | 100 | 100 (0) | | | | |
| 15 | 0.56 | 12 | 8.96 | | | | | | | | | | | | | 99 | 100 (1) | 10 | 90 (88) | 100 | 100 (0) | | | | |
| 15 | 1.12 | 12 | 8.96 | | | | | | | | | | | | | | | | | | | | | | |
| 15 | 2.24 | 12 | 2.24 | | | | | | | | | | | 45 | 50 (10) | | | | | | | | | | |
| 15 | 2.24 | 12 | 8.96 | | | | | | | | | | | 20 | 50 (60) | | | | | | | | | | |
| 15 | 2.24 | 12 | 8.96 | | | | | | | | | | | | | 100 | 100 (0) | 40 | 90 (55) | 100 | 100 (0) | | | | |
| 15 | 0.28 | 14 | 8.96 | | | | | | | | | | | | | 99 | 99 (0) | 0 | 40 (100) | 80 | 95 (15) | | | | |
| 15 | 0.56 | 14 | 2.24 | | | | | | | | | | | 10 | 10 (0) | | | | | | | | | | |
| 15 | 0.56 | 14 | 8.96 | | | | | | | | | | | 10 | 10 (0) | | | | | | | | | | |
| 15 | 0.56 | 14 | 8.96 | | | | | | | | | | | | | 99 | 99 (0) | 20 | 60 (66) | 90 | 95 (5) | | | | |
| 15 | 1.12 | 14 | 8.96 | | | | | | | | | | | | | 99 | 100 (1) | 40 | 70 (42) | 99 | 99 (0) | | | | |
| 15 | 2.24 | 14 | 2.24 | | | | | | | | | | | 30 | 50 (40) | | | | | | | | | | |
| 15 | 2.24 | 14 | 8.96 | | | | | | | | | | | | | 100 | 100 (0) | 50 | 90 (44) | 100 | 100 (0) | | | | |
| 15 | 2.24 | 14 | 8.96 | | | | | | | | | | | 15 | 50 (70) | | | | | | | | | | |
| 15 | 0.28 | 15 | 8.96 | | | | | | | | | | | | | 99 | 99 (0) | 0 | 40 (100) | 75 | 95 (21) | | | | |
| 15 | 0.56 | 15 | 8.96 | | | | | | | | | | | | | 99 | 99 (0) | 10 | 60 (83) | 99 | 95 (0) | | | | |
| 15 | 1.12 | 15 | 8.96 | | | | | | | | | | | | | 100 | 100 (0) | 30 | 70 (57) | 100 | 99 (0) | | | | |
| 15 | 2.24 | 15 | 8.96 | | | | | | | | | | | | | 100 | 100 (0) | 60 | 90 (33) | 100 | 100 (0) | | | | |
| 15 | 0.28 | 16 | 8.96 | | | | | | | | | | | | | 99 | 99 (0) | 0 | 40 (100) | 95 | 95 (0) | | | | |
| 15 | 0.56 | 16 | 2.24 | | | | | | | | | | | 5 | 10 (50) | | | | | | | | | | |
| 15 | 0.56 | 16 | 8.96 | | | | | | | | | | | 5 | 10 (50) | | | | | | | | | | |
| 15 | 0.56 | 16 | 8.96 | | | | | | | | | | | | | 100 | 99 (0) | 0 | 60 (100) | 70 | 95 (26) | | | | |
| 15 | 1.12 | 16 | 8.96 | | | | | | | | | | | | | 99 | 100 (1) | 10 | 70 (85) | 100 | 99 (0) | | | | |
| 15 | 2.24 | 16 | 2.24 | | | | | | | | | | | 30 | 50 (40) | | | | | | | | | | |

TABLE IV-continued

% PLANT INHIBITION AND % SAFENING EFFECT ( )

| HERBICIDE NO. | RATE | ANTIDOTE NO. | RATE | SOYBEAN W | WO | RICE W | WO | HEMP SESBANIA W | WO | VELVET LEAF W | WO | SORGHUM GRAIN W | WO | WHEAT W | WO | GREEN FOXTAIL W | WO | CORN W | WO | BARNYARD GRASS W | WO | RED RICE W | WO | SHATTER CANE W | WO |
|---|---|---|---|---|---|---|---|---|---|---|---|---|---|---|---|---|---|---|---|---|---|---|---|---|---|
| 15 | 2.24 | 16 | 8.96 | | | | | | | | | | | 25 (50) | 50 | | | | | | | | | | |
| 15 | 2.24 | 16 | 8.96 | | | | | | | | | | | | | 100 (0) | 100 | 20 (77) | 90 | 100 (5) | 100 | | | | |
| 15 | 0.28 | 17 | 8.96 | | | | | | | | | | | | | 99 (0) | 90 | 5 (83) | 30 | 75 (16) | 90 | | | | |
| 15 | 0.56 | 17 | 8.96 | | | | | | | | | | | | | 99 (0) | 95 | 20 (33) | 30 | 95 (0) | 80 | | | | |
| 15 | 1.12 | 17 | 8.96 | | | | | | | | | | | | | 99 (0) | 99 | 30 (60) | 75 | 80 (11) | 90 | | | | |
| 15 | 2.24 | 17 | 8.96 | | | | | | | | | | | | | 99 (0) | 99 | 40 (58) | 97 | 95 (0) | 95 | | | | |
| 15 | 0.56 | 19 | 2.24 | | | | | | | | | | | 20 (0) | 18 | | | | | | | | | | |
| 15 | 0.56 | 19 | 8.96 | | | | | | | | | | | 5 (72) | 18 | | | | | | | | | | |
| 15 | 2.24 | 19 | 2.24 | | | | | | | | | | | 35 (52) | 73 | | | | | | | | | | |
| 15 | 2.24 | 19 | 8.96 | | | | | | | | | | | 10 (86) | 73 | | | | | | | | | | |
| 15 | 0.56 | 20 | 2.24 | | | | | | | | | | | 15 (16) | 18 | | | | | | | | | | |
| 15 | 0.56 | 20 | 8.96 | | | | | | | | | | | 5 (72) | 18 | | | | | | | | | | |
| 15 | 2.24 | 20 | 2.24 | | | | | | | | | | | 25 (65) | 73 | | | | | | | | | | |
| 15 | 2.24 | 20 | 8.96 | | | | | | | | | | | 45 (38) | 73 | | | | | | | | | | |
| 15 | 0.56 | 22 | 2.24 | | | | | | | | | | | 35 (30) | 50 | | | | | | | | | | |
| 15 | 0.56 | 22 | 8.96 | | | | | | | | | | | 30 (40) | 50 | | | | | | | | | | |
| 15 | 2.24 | 22 | 2.24 | | | | | | | | | | | 45 (48) | 88 | | | | | | | | | | |
| 15 | 2.24 | 22 | 8.96 | | | | | | | | | | | 85 (3) | 88 | | | | | | | | | | |
| 15 | 0.28 | 23 | 8.96 | | | | | | | | | | | | | 100 (0) | 100 | 10 (88) | 90 | 95 | 100 (5) | | | | |
| 15 | 0.56 | 23 | 2.24 | | | | | | | | | | | 10 (0) | 10 | | | | | | | | | | |
| 15 | 0.56 | 23 | 8.96 | | | | | | | | | | | | | 100 (0) | 100 | 0 (100) | 85 | 100 | 100 (0) | | | | |
| 15 | 1.12 | 23 | 8.96 | | | | | | | | | | | 10 (0) | 10 | | | | | | | | | | |
| 15 | 2.24 | 23 | 8.96 | | | | | | | | | | | | | 100 (0) | 100 | 35 (56) | 80 | 100 | 95 (0) | | | | |
| 15 | 2.24 | 23 | 2.24 | | | | | | | | | | | 65 (0) | 50 | | | | | | | | | | |

TABLE IV-continued

% PLANT INHIBITION AND % SAFENING EFFECT ()

| HERBICIDE NO. | RATE | ANTIDOTE NO. | RATE | SOYBEAN W | SOYBEAN WO | RICE W | RICE WO | HEMP SESBANIA W | HEMP SESBANIA WO | VELVET LEAF W | VELVET LEAF WO | SORGHUM GRAIN W | SORGHUM GRAIN WO | WHEAT W | WHEAT WO | GREEN FOXTAIL W | GREEN FOXTAIL WO | CORN W | CORN WO | BARNYARD GRASS W | BARNYARD GRASS WO | RED RICE W | RED RICE WO | SHATTER CANE W | SHATTER CANE WO |
|---|---|---|---|---|---|---|---|---|---|---|---|---|---|---|---|---|---|---|---|---|---|---|---|---|---|
| 15 | 2.24 | 23 | 8.96 | | | | | | | | | | | | | 100 | 100 (0) | 35 | 75 (53) | 100 | 100 (0) | | | | |
| 15 | 2.24 | 24 | 8.96 | | | | | | | | | | | 35 | 50 (30) | | | | | | | | | | |
| 15 | 0.56 | 24 | 8.96 | | | | | | | | | | | 30 | 50 (40) | | | | | | | | | | |
| 15 | 0.56 | 24 | 2.24 | | | | | | | | | | | 15 | 50 (70) | | | | | | | | | | |
| 15 | 2.24 | 24 | 2.24 | | | | | | | | | | | 75 | 88 (114) | | | | | | | | | | |
| 15 | 2.24 | 24 | 8.96 | | | | | | | | | | | 45 | 88 (48) | | | | | | | | | | |
| 15 | 0.56 | 27 | 2.24 | | | | | | | | | | | | | 100 | 100 (0) | 40 | 85 (52) | 100 | 100 (0) | | | | |
| 15 | 0.56 | 27 | 8.96 | | | | | | | | | | | | | 100 | 100 (0) | 10 | 85 (88) | 100 | 100 (0) | | | | |
| 15 | 2.24 | 27 | 2.24 | | | | | | | | | | | | | 100 | 100 (0) | 80 | 95 (15) | 100 | 100 (0) | | | | |
| 15 | 2.24 | 27 | 8.96 | | | | | | | | | | | | | 100 | 100 (0) | 60 | 95 (36) | 100 | 100 (0) | | | | |
| 15 | 0.56 | 28 | 2.24 | | | | | | | | | | | 15 | 50 (50) | | | | | | | | | | |
| 15 | 0.56 | 28 | 8.96 | | | | | | | | | | | 15 | 50 (70) | | | | | | | | | | |
| 15 | 2.24 | 28 | 2.24 | | | | | | | | | | | 60 | 88 (31) | | | | | | | | | | |
| 15 | 2.24 | 28 | 8.96 | | | | | | | | | | | 80 | 88 (9) | | | | | | | | | | |
| 15 | 0.56 | 29 | 2.24 | | | | | | | | | | | | | 95 | 100 (5) | 35 | 60 (41) | 95 | 100 (5) | | | | |
| 15 | 0.56 | 29 | 8.96 | | | | | | | | | | | | | 95 | 100 (5) | 10 | 60 (83) | 100 | 100 (0) | | | | |
| 15 | 2.24 | 29 | 2.24 | 45 | 75 (40) | | | | | | | | | | | 100 | 100 (0) | 45 | 90 (50) | 100 | 100 (0) | | | | |
| 15 | 2.24 | 29 | 8.96 | 45 | 75 (40) | | | | | | | | | | | 100 | 100 (0) | | | 100 | 100 (0) | | | | |
| 15 | 2.24 | 29 | 2.24 | 75 | 80 (6) | | | | | | | | | | | 100 | 100 (0) | 35 | 90 (61) | 100 | 100 (0) | | | | |
| 15 | 6.72 | 29 | 2.24 | 35 | 80 (56) | | | | | | | | | | | 100 | 100 (0) | | | 100 | 100 (0) | | | | |
| 15 | 6.72 | 29 | 8.96 | | | | | | | | | | | 30 | 50 (40) | 100 | 100 (0) | | | 100 | 100 (0) | | | | |
| 15 | 0.56 | 30 | 2.24 | | | | | | | | | | | 15 | 50 (70) | | | | | | | | | | |
| 15 | 0.56 | 30 | 8.96 | | | | | | | | | | | | | | | | | | | | | | |

TABLE IV-continued

| HERBICIDE | | ANTIDOTE | | SOYBEAN | | RICE | | HEMP SESBANIA | | VELVET LEAF | | SORGHUM GRAIN | | WHEAT | | GREEN FOXTAIL | | CORN | | BARNYARD GRASS | | RED RICE | | SHATTER CANE | |
|---|---|---|---|---|---|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO | W | WO | W | WO | W | WO |
| 15 | 2.24 | 30 | 2.24 | | | | | | | | | | | 80 | 88 (9) | | | | | | | | | | |
| 15 | 2.24 | 30 | 8.96 | | | | | | | | | | | 65 | 88 (26) | | | | | | | | | | |
| 15 | 0.56 | 31 | 2.24 | | | | | | | | | | | 45 | 50 (10) | | | | | | | | | | |
| 15 | 0.56 | 31 | 8.96 | | | | | | | | | | | 45 | 50 (10) | | | | | | | | | | |
| 15 | 2.24 | 31 | 2.24 | | | | | | | | | | | 90 | 88 (0) | | | | | | | | | | |
| 15 | 2.24 | 31 | 8.96 | | | | | | | | | | | 80 | 88 (9) | | | | | | | | | | |
| 15 | 0.56 | 32 | 2.24 | | | | | | | | | | | | | | | | | | | | | | |
| 15 | 0.56 | 32 | 8.96 | | | | | | | | | | | | | | | | | | | | | | |
| 15 | 1.12 | 32 | 2.24 | 40 | 55 (27) | | | | | | | | | | | | | | | | | | | | |
| 15 | 1.12 | 32 | 8.96 | 5 | 55 (90) | | | | | | | | | | | | | | | | | | | | |
| 15 | 2.24 | 32 | 2.24 | 50 | 85 (41) | | | | | | | | | | | | | | | | | | | | |
| 15 | 2.24 | 32 | 8.96 | | | | | | | | | | | | | | | | | | | | | | |
| 15 | 2.24 | 32 | 2.24 | | | | | | | | | | | | | | | | | | | | | | |
| 15 | 2.24 | 32 | 8.96 | 35 | 85 (58) | | | | | | | | | | | | | | | | | | | | |
| 15 | 0.56 | 33 | 0.56 | | | | | | | | | | | 75 | 50 (0) | 100 | 100 (0) | 15 | 65 (76) | 100 | 100 (0) | | | | |
| 15 | 0.56 | 33 | 2.24 | | | | | | | | | | | | | | | 10 | 65 (84) | 100 | 100 (0) | | | | |
| 15 | 0.56 | 33 | 2.24 | | | | | | | | | | | 40 | 50 (20) | 100 | 100 (0) | | | 100 | 95 (0) | | | | |
| 15 | 0.56 | 33 | 8.96 | | | | | | | | | | | 10 | 13 (23) | 100 | 100 (0) | 55 | 75 (26) | 95 | 95 (0) | | | | |
| 15 | 0.56 | 33 | 2.24 | | | | | | | | | | | 30 | 50 (40) | 100 | 100 (0) | 15 | 75 (80) | 100 | 100 (0) | | | | |
| 15 | 0.56 | 33 | 8.96 | | | | | | | | | | | 0 | 13 (100) | | | 5 | 25 (80) | 95 | 100 (5) | | | | |
| 15 | 0.56 | 33 | 0.56 | | | | | | | | | | | 75 | 75 (0) | 100 | 100 (0) | | | | | | | | |
| 15 | 2.24 | 33 | 2.24 | | | | | | | | | | | 30 | 55 (45) | | | 5 | 25 (80) | 100 | 100 (0) | | | | |
| 15 | 2.24 | 33 | 2.24 | | | | | | | | | | | | | | | 30 | 95 (68) | 100 | 100 (0) | | | | |

TABLE IV-continued

% PLANT INHIBITION AND % SAFENING EFFECT ( )

| HERBICIDE NO. | RATE | ANTIDOTE NO. | RATE | SOYBEAN W | WO | RICE W | WO | HEMP SESBANIA W | WO | VELVET LEAF W | WO | SORGHUM GRAIN W | WO | WHEAT W | WO | GREEN FOXTAIL W | WO | CORN W | WO | BARNYARD GRASS W | WO | RED RICE W | WO | SHATTER CANE W | WO |
|---|---|---|---|---|---|---|---|---|---|---|---|---|---|---|---|---|---|---|---|---|---|---|---|---|---|
| 15 | 2.24 | 33 | 2.24 | | | | | | | | | | | 50 | 75 (33) | 100 | 100 (0) | 10 | 95 (89) | | | | | | |
| 15 | 2.24 | 33 | 8.96 | | | | | | | | | | | | | 100 | 100 (0) | | | | | | | | |
| 15 | 2.24 | 33 | 8.96 | | | | | | | | | | | 55 | 75 (26) | 100 | 100 (0) | | | | | | | | |
| 15 | 2.24 | 33 | 8.96 | | | | | | | | | | | 20 | 55 (63) | | | | | | | | | | |
| 15 | 0.56 | 34 | 2.24 | | | | | | | | | | | 5 | 13 (61) | | | | | | | | | | |
| 15 | 0.56 | 34 | 2.24 | | | | | | | | | | | | | | | 5 | 25 (80) | 100 | 100 (0) | | | | |
| 15 | 0.56 | 34 | 8.96 | | | | | | | | | | | | | | | 10 | 25 (60) | 95 | 100 (5) | | | | |
| 15 | 0.56 | 34 | 8.96 | | | | | | | | | | | 5 | 13 (61) | | | | | | | | | | |
| 15 | 2.24 | 34 | 2.24 | 10 | 35 (71) | | | | | | | | | 15 | 55 (72) | | | 45 | 95 (52) | 100 | 100 (0) | | | | |
| 15 | 2.24 | 34 | 2.24 | | | | | | | | | | | 10 | 55 (81) | | | 10 | 95 (89) | 100 | 100 (0) | | | | |
| 15 | 2.24 | 34 | 8.96 | 25 | 35 (28) | | | | | | | | | | | | | | | 100 | 100 (0) | | | | |
| 15 | 2.24 | 34 | 2.24 | 20 | 45 (55) | | | | | | | | | | | | | 10 | 25 (60) | 100 | 100 (0) | | | | |
| 15 | 4.48 | 34 | 8.96 | 15 | 45 (66) | | | | | | | | | | | | | 0 | 25 (100) | 100 | 100 (0) | | | | |
| 15 | 4.48 | 34 | 2.24 | | | | | | | | | | | | | | | 70 | 95 (26) | 100 | 100 (0) | | | | |
| 15 | 0.56 | 34 | 8.96 | | | | | | | | | | | | | | | 10 | 95 (89) | 100 | 100 (0) | | | | |
| 15 | 0.56 | 35 | 2.24 | | | | | | | | | | | | | | | 5 | 10 (50) | 100 | 100 (0) | | | | |
| 15 | 2.24 | 35 | 8.96 | | | | | | | | | | | | | | | 5 | 10 (50) | 100 | 100 (0) | | | | |
| 15 | 2.24 | 35 | 2.24 | | | | | | | | | | | | | | | 0 | 10 (100) | 100 | 100 (0) | | | | |
| 15 | 0.56 | 36 | 8.96 | | | | | | | | | | | | | | | | | 100 | 100 (0) | | | | |
| 15 | 0.56 | 36 | 0.56 | | | | | | | | | | | | | | | | | 100 | 100 (0) | | | | |
| 15 | 0.56 | 36 | 2.24 | | | | | | | | | | | | | | | | | 100 | 100 (0) | | | | |
| 15 | 0.56 | 36 | 8.96 | | | | | | | | | | | | | | | | | 100 | 100 (0) | | | | |
| 15 | 1.12 | 36 | 0.56 | 60 | 70 (14) | | | | | | | | | | | | | | | 95 | 95 (0) | | | | |

TABLE IV-continued

| | | | | | | | | | % PLANT INHIBITION AND % SAFENING EFFECT ( ) | | | | | | | | | | | | | |
|---|---|---|---|---|---|---|---|---|---|---|---|---|---|---|---|---|---|---|---|---|---|---|
| HERBICIDE | | ANTIDOTE | | SOYBEAN | | RICE | | HEMP SESBANIA | | VELVET LEAF | | SORGHUM GRAIN | | WHEAT | | GREEN FOXTAIL | | CORN | | BARNYARD GRASS | | RED RICE | | SHATTER CANE |
| NO. | RATE | NO. | RATE | W | WO | W | WO | W | WO | W | WO | W | WO | W | WO | W | WO | W | WO | W | WO | W | WO | W | WO |
| 15 | 1.12 | 36 | 2.24 | 70 | 70 (0) | | | | | | | | | | | | | | | 95 | 95 (0) | | | | |
| 15 | 1.12 | 35 | 8.96 | 80 | 70 (0) | | | | | | | | | | | | | | | 95 | 95 (0) | | | | |
| 15 | 2.24 | 36 | 0.56 | | | | | | | | | | | | | | | 55 | 45 (0) | 100 | 100 (0) | | | | |
| 15 | 2.24 | 36 | 2.24 | | | | | | | | | | | | | | | 40 | 45 (11) | 100 | 100 (0) | | | | |
| 15 | 2.24 | 36 | 8.96 | | | | | | | | | | | | | | | 10 | 45 (77) | 100 | 100 (0) | | | | |
| 15 | 4.48 | 36 | 0.56 | 55 | 90 (38) | | | | | | | | | | | | | | | 100 | 100 (0) | | | | |
| 15 | 4.48 | 36 | 2.24 | 40 | 90 (55) | | | | | | | | | | | | | | | 100 | 100 (0) | | | | |
| 15 | 4.48 | 36 | 8.96 | 15 | 90 (83) | | | | | | | | | | | | | | | 100 | 100 (0) | | | | |
| 18 | 1.12 | 10 | 2.24 | 10 | 25 (60) | | | | | | | 90 | 100 (10) | | | | | 0 | 20 (100) | | | | | | |
| 18 | 3.36 | 10 | 2.24 | 10 | 30 (66) | | | | | | | 99 | 100 (1) | | | | | 0 | 40 (100) | | | | | | |
| 18 | 6.72 | 10 | 2.24 | 20 | 40 (50) | | | | | | | 95 | 100 (5) | | | | | 20 | 60 (66) | | | | | | |
| 18 | 1.12 | 11 | 2.24 | 20 | 25 (20) | | | | | | | 80 | 100 (20) | | | | | 0 | 20 (100) | | | | | | |
| 18 | 3.36 | 11 | 2.24 | 20 | 30 (33) | | | | | | | 90 | 100 (10) | | | | | 0 | 40 (100) | | | | | | |
| 18 | 6.72 | 11 | 2.24 | 30 | 40 (25) | | | | | | | 100 | 100 (0) | | | | | 20 | 60 (66) | | | | | | |
| 33 | 0.02 | 1 | 8.96 | | | 40 | 80 (50) | | | | | 50 | 40 (0) | 0 | 10 (100) | | | 60 | 80 (25) | | | | | | |
| 33 | 0.07 | 1 | 8.96 | | | 50 | 90 (44) | | | | | 45 | 60 (25) | 0 | 10 (100) | | | 90 | 95 (5) | | | | | | |
| 33 | 0.28 | 1 | 8.96 | | | 80 | 98 (18) | | | | | 65 | 70 (7) | 10 | 30 (66) | | | 99 | 99 (0) | | | | | | |

EXAMPLE 288

The following procedure was used to determine the interaction between a herbicide and antidote when the herbicide is topically applied to the soil surface and the antidote is applied to crop seed. Crop plant seed was treated with the antidote either by contacting the seed with antidote in powder form or by contacting the seed with a solution or suspension of antidote compound dissolved or suspended in a suitable solvent, typically methylene chloride or toluene. Relative amounts of antidote compound and seed were used to provide an antidote-on-seed concentration, on a percent weight/weight basis, of 0.13 wt. %. Containers were filled and compacted with fumigated silt loam type soil to a depth of about 1.3 cm from the top of the container. A first container was designated as an untreated control, a second container was designated as a herbicide control, and a third container was designated as a herbicide + antidote test container. Untreated crop seed was placed in the first and second containers. Antidote-treated crop seed was placed in the third container. Then, each of the second and third containers was filled and leveled with a cover layer of soil having incorporated therein the selected herbicide at a pre-determined concentration. The first container was filled and leveled with soil containing no herbicide. All containers were given about 0.6 cm of overhead water to simulate an activating rainfall. The containers were placed on a greenhouse bench and sub-irrigated as required for the duration of the test. Plant response was observed about three weeks after initial treatment. Results are set forth in Table V. Herbicide rate is given in kg/ha and antidote rate is given in percent weight/weight of antidote/seed.

TABLE V

| HERBICIDE (kg/ha) | | ANTIDOTE wt. % | | % PLANT INHIBITION AND % SAFENING EFFECT ( ) | | | | | |
|---|---|---|---|---|---|---|---|---|---|
| | | | | JOHNSON GRASS | | GREEN FOXTAIL | | SORGHUM GRAIN | |
| NO. | RATE | NO. | RATE | W | WO | W | WO | W | WO |
| 6 | 0.28 | 11 | 0.13 | 75 (16) | 90 | 97 (0) | 97 | 23 (67) | 70 |
| 6 | 1.12 | 11 | 0.13 | 95 (4) | 99 | 99 (0) | 99 | 45 (47) | 85 |
| 6 | 4.48 | 11 | 0.13 | 100 (0) | 100 | 100 (0) | 100 | 65 (32) | 97 |
| 11 | 0.28 | 11 | 0.13 | 99 (0) | 99 | 100 (0) | 99 | 60 (36) | 95 |
| 11 | 1.12 | 11 | 0.13 | 100 (0) | 100 | 100 (0) | 100 | 82 (11) | 93 |
| 11 | 4.48 | 11 | 0.13 | 100 (0) | 100 | 100 (0) | 100 | 92 (8) | 100 |
| 18 | 0.28 | 11 | 0.13 | 70 (6) | 75 | 90 (9) | 99 | 28 (61) | 73 |
| 18 | 1.12 | 11 | 0.13 | 100 (0) | 99 | 99 (0) | 99 | 70 (27) | 97 |
| 18 | 4.48 | 11 | 0.13 | 100 (0) | 99 | 100 (0) | 99 | 93 (6) | 99 |
| 34 | 0.28 | 11 | 0.13 | 30 (40) | 50 | 95 (0) | 60 | 0 (100) | 5 |
| 34 | 1.12 | 11 | 0.13 | 40 (33) | 60 | 99 (0) | 95 | 17 (0) | 13 |
| 34 | 4.48 | 11 | 0.13 | 80 (11) | 90 | 99 (0) | 99 | 20 (33) | 30 |

EXAMPLE 289

The procedure of Example 285 was followed to determine the interaction between herbicide and antidote when both are incorporated in a soil cover layer before emergence of the crop species. In this series of tests, however, all containers were seeded with several weed species in addition to crop seed. Results are reported in Table VI.

TABLE VI

% Plant Inhibition and % Safening Effect ( )

| HERBICIDE NO. | RATE | ANTIDOTE NO. | RATE | WHEAT W | WHEAT ( ) | WHEAT WO | SORGHUM GRAIN W | SORGHUM GRAIN ( ) | SORGHUM GRAIN WO | CORN W | CORN ( ) | CORN WO | SOYBEAN W | SOYBEAN ( ) | SOYBEAN WO | GREEN FOXTAIL W | GREEN FOXTAIL ( ) | GREEN FOXTAIL WO | DOWNY BROME W | DOWNY BROME ( ) | DOWNY BROME WO | WILD OATS W | WILD OATS ( ) | WILD OATS WO | BARNYARD GRASS W | BARNYARD GRASS WO | RICE W | RICE WO |
|---|---|---|---|---|---|---|---|---|---|---|---|---|---|---|---|---|---|---|---|---|---|---|---|---|---|---|---|---|
| 1 | 2.24 | 1 | 1.12 | 65 |   | 50 | 99 |   | 99 | 0 | (0) | 0 | 30 | (0) | 15 |   |   |   |   |   |   |   |   |   |   |   |   |   |
| 1 | 11.20 | 1 | 1.12 | 95 | (0) | 95 | 99 | (0) | 99 | 0 | (0) | 0 | 45 | (0) | 50 |   |   |   |   |   |   |   |   |   |   |   |   |   |
| 1 | 2.24 | 10 | 1.12 | 53 | (0) | 50 | 97 | (0) | 99 | 0 | (0) | 0 | 10 | (10) | 15 |   |   |   |   |   |   |   |   |   |   |   |   |   |
| 1 | 11.20 | 10 | 1.12 | 100 | (0) | 95 | 99 | (2) | 99 | 0 | (0) | 0 | 15 | (33) | 50 |   |   |   |   |   |   |   |   |   |   |   |   |   |
| 1 | 2.24 | 11 | 1.12 | 85 | (0) | 50 | 99 | (0) | 99 | 0 | (0) | 0 | 15 | (70) | 15 |   |   |   |   |   |   |   |   |   |   |   |   |   |
| 1 | 11.20 | 11 | 1.12 | 99 | (0) | 95 | 99 | (0) | 99 | 0 | (0) | 0 | 20 | (60) | 50 |   |   |   |   |   |   |   |   |   |   |   |   |   |
| 5 | 1.12 | 1 | 1.12 | 35 | (0) | 30 | 55 | (24) | 73 | 10 | (0) | 15 | 33 | (17) | 40 |   |   |   |   |   |   |   |   |   |   |   |   |   |
| 5 | 6.72 | 1 | 1.12 | 73 | (12) | 83 | 75 | (22) | 97 | 25 | (0) | 75 | 77 | (3) | 80 |   |   |   |   |   |   |   |   |   |   |   |   |   |
| 5 | 1.12 | 10 | 1.12 | 47 | (0) | 30 | 60 | (17) | 73 | 15 | (40) | 15 | 23 | (42) | 40 |   |   |   |   |   |   |   |   |   |   |   |   |   |
| 5 | 6.72 | 10 | 1.12 | 77 | (7) | 83 | 95 | (2) | 97 | 55 | (0) | 75 | 95 | (0) | 80 |   |   |   |   |   |   |   |   |   |   |   |   |   |
| 5 | 1.12 | 11 | 1.12 | 45 | (0) | 30 | 30 | (58) | 73 | 40 | (26) | 15 | 25 | (37) | 40 |   |   |   |   |   |   |   |   |   |   |   |   |   |
| 5 | 6.72 | 11 | 1.12 | 90 | (0) | 83 | 87 | (10) | 97 | 50 | (33) | 75 | 70 | (12) | 80 |   |   |   |   |   |   |   |   |   |   |   |   |   |
| 6 | 0.84 | 23 | 0.14 | 95 | (0) | 85 |   |   |   |   |   |   |   |   |   | 100 | (0) | 100 | 80 | (5) | 85 | 80 | (0) | 90 |   |   |   |   |
| 6 | 0.84 | 23 | 0.14 | 15 | (64) | 42 |   |   |   |   |   |   |   |   |   | 100 | (0) | 100 | 90 | (0) | 90 | 90 | (16) | 75 |   |   |   |   |
| 6 | 0.84 | 23 | 0.14 | 55 | (29) | 78 |   |   |   |   |   |   |   |   |   | 95 | (0) | 95 | 100 | (0) | 95 | 100 | (0) | 100 |   |   |   |   |
| 6 | 0.84 | 23 | 0.14 | 18 | (48) | 35 |   |   |   |   |   |   |   |   |   | 100 | (0) | 100 | 100 | (0) | 90 | 90 | (0) | 90 |   |   |   |   |
| 6 | 0.84 | 23 | 0.14 | 78 | (0) | 50 |   |   |   |   |   |   |   |   |   | 100 | (0) | 100 | 100 | (0) | 95 | 100 | (5) | 95 |   |   |   |   |
| 6 | 0.84 | 23 | 0.14 | 73 | (2) | 75 |   |   |   |   |   |   |   |   |   | 100 | (0) | 100 | 95 | (0) | 98 | 95 | (0) | 98 |   |   |   |   |
| 6 | 0.84 | 23 | 0.28 | 65 | (0) | 30 |   |   |   |   |   |   |   |   |   | 95 | (0) | 95 | 100 | (0) | 90 | 85 | (0) | 80 |   |   |   |   |
| 6 | 0.84 | 23 | 0.56 | 15 | (64) | 42 |   |   |   |   |   |   |   |   |   | 100 | (0) | 100 | 95 | (0) | 90 | 90 | (5) | 70 |   |   |   |   |
| 6 | 0.84 | 23 | 0.56 | 45 | (42) | 78 |   |   |   |   |   |   |   |   |   | 95 | (0) | 95 | 100 | (0) | 95 | 100 | (22) | 100 |   |   |   |   |
| 6 | 0.84 | 23 | 0.56 | 65 | (23) | 85 |   |   |   |   |   |   |   |   |   | 100 | (0) | 100 | 95 | (0) | 85 | 80 | (0) | 95 |   |   |   |   |
| 6 | 0.84 | 23 | 0.56 | 33 | (5) | 35 |   |   |   |   |   |   |   |   |   | 100 | (0) | 100 | 100 | (0) | 90 | 90 | (27) | 65 |   |   |   |   |
| 6 | 0.84 | 23 | 0.56 | 18 | (64) | 50 |   |   |   |   |   |   |   |   |   | 100 | (0) | 100 | 100 | (0) | 95 | 100 | (2) | 98 |   |   |   |   |

TABLE VI-continued

% PLANT INHIBITION AND % SAFENING EFFECT ( )

| HERBICIDE NO. | RATE | ANTIDOTE NO. | RATE | WHEAT W | WHEAT WO | SORGHUM GRAIN W | SORGHUM GRAIN WO | CORN W | CORN WO | SOYBEAN W | SOYBEAN WO | GREEN FOXTAIL W | GREEN FOXTAIL WO | DOWNY BROME W | DOWNY BROME WO | WILD OATS W | WILD OATS WO | BARNYARD GRASS W | BARNYARD GRASS WO | RICE W | RICE WO |
|---|---|---|---|---|---|---|---|---|---|---|---|---|---|---|---|---|---|---|---|---|---|
| 6 | 0.84 | 23 | 0.56 | 85 | 75 |  |  |  |  |  |  | 100 | 100 (0) | 95 | 98 (3) | 95 | 95 (0) |  |  |  |  |
| 6 | 0.84 | 23 | 0.84 | 45 | 30 (0) |  |  |  |  |  |  | 100 (0) | 95 | 95 | 90 (0) | 70 | 85 (17) |  |  |  |  |
| 6 | 0.84 | 23 | 2.24 | 65 | 85 (0) |  |  |  |  |  |  | 100 (0) | 100 | 90 | 85 (0) | 70 | 80 (12) |  |  |  |  |
| 6 | 0.84 | 23 | 2.24 | 42 | 42 (23) |  |  |  |  |  |  | 100 (0) | 100 | 90 | 90 (0) | 50 | 90 (44) |  |  |  |  |
| 6 | 0.84 | 23 | 2.24 | 48 | 75 (0) |  |  |  |  |  |  | 100 (0) | 98 | 98 | 98 (0) | 95 | 100 (0) |  |  |  |  |
| 6 | 0.84 | 23 | 2.24 | 43 | 50 (36) |  |  |  |  |  |  | 95 (0) | 100 | 100 | 95 (0) | 90 | 100 (10) |  |  |  |  |
| 6 | 0.84 | 23 | 2.24 | 35 | 78 (14) |  |  |  |  |  |  | 100 (0) | 95 | 95 | 95 (0) | 95 | 90 (5) |  |  |  |  |
| 6 | 0.84 | 23 | 2.24 | 15 | 35 (55) |  |  |  |  |  |  | 100 (0) | 100 | 95 | 90 (0) | 60 | 85 (33) |  |  |  |  |
| 6 | 0.84 | 23 | 2.24 | 15 | 30 (57) |  |  |  |  |  |  | 95 (0) | 95 | 95 | 90 (0) | 50 | 100 (41) |  |  |  |  |
| 6 | 1.68 | 23 | 0.14 | 90 | 90 (50) |  |  |  |  |  |  | 100 (0) | 100 | 100 | 100 (0) | 100 | 100 (0) |  |  |  |  |
| 6 | 1.68 | 23 | 0.14 | 90 | 73 (0) |  |  |  |  |  |  | 100 (0) | 100 | 95 | 95 (5) | 90 | 100 (0) |  |  |  |  |
| 6 | 1.68 | 23 | 0.14 | 40 | 75 (0) |  |  |  |  |  |  | 100 (0) | 100 | 100 | 100 (0) | 90 | 100 (10) |  |  |  |  |
| 6 | 1.68 | 23 | 0.14 | 55 | 55 (46) |  |  |  |  |  |  | 100 (0) | 100 | 95 | 95 (5) | 90 | 95 (5) |  |  |  |  |
| 6 | 1.68 | 23 | 0.14 | 83 | 90 (0) |  |  |  |  |  |  | 100 (0) | 100 | 95 | 85 (5) | 95 | 100 (0) |  |  |  |  |
| 6 | 1.68 | 23 | 0.14 | 80 | 85 (7) |  |  |  |  |  |  | 100 (0) | 100 | 95 | 95 (0) | 90 | 90 (0) |  |  |  |  |
| 6 | 1.68 | 23 | 0.14 | 92 | 82 (5) |  |  |  |  |  |  | 100 (0) | 100 | 90 | 85 (0) | 100 | 90 (0) |  |  |  |  |
| 6 | 1.68 | 23 | 0.56 | 95 | 85 (0) |  |  |  |  |  |  | 95 (5) | 95 | 100 | 100 (0) | 95 | 90 (0) |  |  |  |  |
| 6 | 1.68 | 23 | 0.56 | 65 | 73 (0) |  |  |  |  |  |  | 100 (0) | 100 | 100 | 100 (0) | 95 | 100 (5) |  |  |  |  |
| 6 | 1.68 | 23 | 0.56 | 88 | 90 (10) |  |  |  |  |  |  | 100 (0) | 100 | 95 | 85 (0) | 90 | 90 (0) |  |  |  |  |
| 6 | 1.68 | 23 | 0.56 | 35 | 75 (2) |  |  |  |  |  |  | 100 (0) | 100 | 100 | 95 (0) | 100 | 100 (0) |  |  |  |  |
| 6 | 1.68 | 23 | 0.56 | 70 | 55 (53) |  |  |  |  |  |  | 100 (0) | 100 | 95 | 95 (0) | 90 | 95 (10) |  |  |  |  |
| 6 | 1.68 | 23 | 0.56 | 80 | 90 (0) |  |  |  |  |  |  | 100 (0) | 100 | 95 | 95 (5) | 90 | 100 (5) |  |  |  |  |
| 6 | 1.68 | 23 | 0.84 | 58 | 82 (11) |  |  |  |  |  |  | 100 (0) | 100 | 78 | 95 (17) | 90 | 90 (0) |  |  |  |  |
| 6 | 1.68 | 23 | 2.24 | 63 | 90 (29) |  |  |  |  |  |  | 100 (0) | 100 | 100 | 100 (0) | 95 | 100 (5) |  |  |  |  |
| 6 | 1.68 | 23 |  |  | (30) |  |  |  |  |  |  | (0) |  |  | (0) |  | (5) |  |  |  |  |

TABLE VI-continued

% PLANT INHIBITION AND % SAFENING EFFECT ( )

| HERBICIDE | | ANTIDOTE | | WHEAT | | SORGHUM GRAIN | | CORN | | SOYBEAN | | GREEN FOXTAIL | | DOWNY BROME | | WILD OATS | | BARNYARD GRASS | | RICE | |
|---|---|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO | W | WO |
| 6 | 1.68 | 23 | 2.24 | 80 | 85 | | | | | | | 100 | 100 | 90 | 85 | 95 | 90 | | | | |
| 6 | 1.68 | 23 | 2.24 | 15 | (5) 75 | | | | | | | 100 (0) | 100 | 100 (0) | 100 | 80 (0) | 100 | | | | |
| 6 | 1.68 | 23 | 2.24 | 95 | (80) 90 | | | | | | | 100 (0) | 100 | 98 (0) | 100 | 100 (20) | 100 | | | | |
| 6 | 1.68 | 23 | 2.24 | 15 | (0) 55 | | | | | | | 100 (0) | 100 | 90 (2) | 95 | 80 (0) | 95 | | | | |
| 6 | 1.68 | 23 | 2.24 | 30 | (72) 82 | | | | | | | 95 (0) | 95 | 95 (5) | 95 | 65 (15) | 90 | | | | |
| 6 | 1.68 | 23 | 2.24 | 45 | (63) 73 | | | | | | | 100 (5) | 95 | 100 (0) | 95 | 100 (27) | 100 | | | | |
| 6 | 1.68 | 23 | 0.14 | 88 | (38) 95 | | | | | | | 100 (0) | 100 | 100 (0) | 100 | 100 (0) | 100 | | | | |
| 6 | 3.36 | 23 | 0.14 | 88 | (7) 80 | | | | | | | 100 (0) | 100 | 95 (0) | 95 | 95 (0) | 95 | | | | |
| 6 | 3.36 | 23 | 0.14 | 50 | (0) 100 | | | | | | | 100 (0) | 100 | 100 (0) | 100 | 100 (5) | 100 | | | | |
| 6 | 3.36 | 23 | 0.14 | 95 | (50) 97 | | | | | | | 100 (0) | 100 | 100 (0) | 100 | 95 (0) | 100 | | | | |
| 6 | 3.36 | 23 | 0.14 | 90 | (2) 100 | | | | | | | 100 (0) | 100 | 95 (0) | 95 | 100 (5) | 100 | | | | |
| 6 | 3.36 | 23 | 0.14 | 95 | (10) 90 | | | | | | | 100 (0) | 100 | 100 (0) | 100 | 98 (2) | 95 | | | | |
| 6 | 3.36 | 23 | 0.28 | 90 | (0) 83 | | | | | | | 100 (0) | 100 | 95 (0) | 95 | 90 (5) | 100 | | | | |
| 6 | 3.36 | 23 | 0.56 | 90 | (0) 97 | | | | | | | 100 (0) | 100 | 100 (0) | 100 | 100 (0) | 100 | | | | |
| 6 | 3.36 | 23 | 0.56 | 98 | (0) 95 | | | | | | | 100 (0) | 100 | 100 (0) | 100 | 100 (5) | 100 | | | | |
| 6 | 3.36 | 23 | 0.56 | 90 | (5) 80 | | | | | | | 100 (0) | 100 | 100 (0) | 100 | 95 (0) | 95 | | | | |
| 6 | 3.36 | 23 | 0.56 | 80 | (0) 100 | | | | | | | 100 (0) | 100 | 100 (0) | 100 | 100 (0) | 100 | | | | |
| 6 | 3.36 | 23 | 0.56 | 90 | (10) 90 | | | | | | | 100 (0) | 100 | 100 (10) | 100 | 95 (0) | 100 | | | | |
| 6 | 3.36 | 23 | 0.56 | 98 | (0) 100 | | | | | | | 100 (0) | 100 | 100 (0) | 100 | 100 (0) | 100 | | | | |
| 6 | 3.36 | 23 | 0.84 | 75 | (25) 83 | | | | | | | 100 (0) | 100 | 95 (0) | 95 | 95 (0) | 95 | | | | |
| 6 | 3.36 | 23 | 2.24 | 88 | (0) 90 | | | | | | | 95 (0) | 100 | 100 (0) | 100 | 100 (0) | 100 | | | | |
| 6 | 3.36 | 23 | 2.24 | 0 | (100) 100 | | | | | | | 0 (0) | 100 | 0 (0) | 100 | 0 (0) | 100 | | | | |
| 6 | 3.36 | 23 | 2.24 | 82 | (1) 83 | | | | | | | 95 (100) | 100 | 95 (100) | 100 | 95 (100) | 95 | | | | |
| 6 | 3.36 | 23 | 2.24 | 78 | (2) 80 | | | | | | | 100 (5) | 100 | 100 (0) | 95 | 82 (0) | 95 | | | | |
| 6 | 3.36 | 23 | 2.24 | 98 | (0) 97 | | | | | | | 100 (0) | 100 | 100 (0) | 100 | 100 (13) | 100 | | | | |
| 6 | 3.36 | 23 | 2.24 | | (0) | | | | | | | (0) | | (0) | | (0) | | | | | |

TABLE VI-continued

% PLANT INHIBITION AND % SAFENING EFFECT ( )

| HERBICIDE | | ANTIDOTE | | WHEAT | | SORGHUM GRAIN | | CORN | | SOYBEAN | | GREEN FOXTAIL | | DOWNY BROME | | WILD OATS | | BARNYARD GRASS | | RICE | |
|---|---|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO | W | WO |
| 6 | 3.36 | 23 | 2.24 | 50 | 100 | | | | | | | 100 | 100 | 98 | 100 | 98 | 100 | | | |
| 6 | 3.36 | 23 | 2.24 | 90 | 95 (50) | | | | | | | 100 (0) | 100 | 100 (2) | 100 | 100 (2) | 100 | | | |
| 6 | 3.36 | 23 | 2.24 | 95 | 100 (5) | | | | | | | 100 (0) | 100 | 95 (0) | 95 | 95 (0) | 100 | | | |
| 6 | 0.84 | 25 | 0.14 | 75 | 78 (5) | | | | | | | 95 (0) | 95 | 95 (5) | 95 | 100 (5) | 100 | | | |
| 6 | 0.84 | 25 | 0.56 | 50 | 78 (3) | | | | | | | 100 (0) | 95 | 95 (0) | 95 | 95 (0) | 100 | | | |
| 6 | 0.84 | 25 | 2.24 | 25 | 78 (35) | | | | | | | 95 (0) | 95 | 95 (0) | 95 | 80 (5) | 100 | | | |
| 6 | 1.68 | 25 | 0.14 | 80 | 73 (67) | | | | | | | 100 (0) | 95 | 95 (0) | 95 | 100 (20) | 100 | | | |
| 6 | 1.68 | 25 | 0.56 | 65 | 73 (0) | | | | | | | 100 (0) | 95 | 100 (0) | 95 | 95 (0) | 100 | | | |
| 6 | 1.68 | 25 | 2.24 | 48 | 73 (10) | | | | | | | 95 (0) | 100 | 100 (0) | 100 | 100 (5) | 100 | | | |
| 6 | 3.36 | 25 | 0.14 | 90 | 95 (34) | | | | | | | 95 (5) | 100 | 100 (0) | 100 | 100 (0) | 100 | | | |
| 6 | 3.36 | 25 | 0.56 | 90 | 95 (5) | | | | | | | 95 (5) | 100 | 100 (0) | 100 | 100 (0) | 100 | | | |
| 6 | 3.36 | 25 | 2.24 | 78 | 95 (5) | | | | | | | 100 (0) | 100 | 100 (0) | 100 | 95 (5) | 100 | | | |
| 7 | 0.56 | 1 | 1.12 | 25 | 20 (17) | 25 | 77 | 25 (67) | 40 | 95 (5) | 100 | | | | | | | | | |
| 7 | 2.24 | 1 | 1.12 | 70 | 60 (0) | 35 | 77 | 35 (54) | 40 | 100 (0) | 100 | | | | | | | | | |
| 7 | 0.56 | 10 | 1.12 | 37 | 20 (0) | 20 | 77 | 15 (12) | 40 | 100 (0) | 100 | | | | | | | | | |
| 7 | 2.24 | 10 | 1.12 | 68 | 60 (0) | 60 | 77 | 15 (62) | 40 | 100 (0) | 100 | | | | | | | | | |
| 7 | 0.56 | 11 | 1.12 | 35 | 20 (0) | 17 | 77 | 0 (22) | 40 | 100 (0) | 100 | | | | | | | | | |
| 7 | 2.24 | 11 | 1.12 | 83 | 60 (0) | 70 | 77 | 13 (77) | 40 | 100 (0) | 100 | | | | | | | | | |
| 8 | 0.56 | 1 | 1.12 | 100 | 100 (0) | 100 | 100 | 95 (9) | 40 | 10 (83) | 60 | | | | | | | | | |
| 8 | 2.24 | 1 | 1.12 | 100 | 100 (0) | 100 | 100 | 99 (3) | 98 | 83 (2) | 85 | | | | | | | | | |
| 8 | 0.56 | 10 | 1.12 | 97 | 100 (0) | 100 | 100 | 55 (1) | 100 | 70 (0) | 60 | | | | | | | | | |
| 8 | 2.24 | 10 | 1.12 | 100 | 100 (3) | 100 | 100 | 99 (43) | 98 | 95 (0) | 85 | | | | | | | | | |
| 8 | 0.56 | 11 | 1.12 | 95 | 100 (0) | 100 | 100 | 75 (1) | 100 | 63 (0) | 60 | | | | | | | | | |
| 8 | 2.24 | 11 | 1.12 | 100 | 100 (5) | 100 | 100 | 99 (23) | 98 | 85 (0) | 85 | | | | | | | | | |
| 8 | | | | | (0) | | | (1) | 100 | (0) | | | | | | | | | | |

TABLE VI-continued
% PLANT INHIBITION AND % SAFENING EFFECT ( )

| HERBICIDE NO. | HERBICIDE RATE | ANTIDOTE NO. | ANTIDOTE RATE | WHEAT W | WHEAT WO | SORGHUM GRAIN W | SORGHUM GRAIN WO | CORN W | CORN WO | SOYBEAN W | SOYBEAN WO | GREEN FOXTAIL W | GREEN FOXTAIL WO | DOWNY BROME W | DOWNY BROME WO | WILD OATS W | WILD OATS WO | BARNYARD GRASS W | BARNYARD GRASS WO | RICE W | RICE WO |
|---|---|---|---|---|---|---|---|---|---|---|---|---|---|---|---|---|---|---|---|---|---|
| 10 | 1.68 | 1 | 0.84 | | | | | | | | | | | | | | | 98 | 99 | 48 (40) | 80 |
| 10 | 1.68 | 1 | 1.68 | | | | | | | | | | | | | | | 85 (1) | 99 | 15 (81) | 80 |
| 10 | 1.68 | 1 | 3.36 | | | | | | | | | | | | | | | 95 (14) | 99 | 20 (75) | 80 |
| 10 | 3.36 | 1 | 0.84 | | | | | | | | | | | | | | | 100 (4) | 100 | 75 (24) | 99 |
| 10 | 3.36 | 1 | 1.68 | | | | | | | | | | | | | | | 100 (0) | 100 | 65 (34) | 99 |
| 10 | 3.36 | 1 | 3.36 | | | | | | | | | | | | | | | 100 (0) | 100 | 53 (46) | 99 |
| 10 | 6.72 | 1 | 0.84 | | | | | | | | | | | | | | | 100 (0) | 100 | 98 (2) | 100 |
| 10 | 6.72 | 1 | 1.68 | | | | | | | | | | | | | | | 100 (0) | 100 | 80 (20) | 100 |
| 10 | 6.72 | 1 | 3.36 | | | | | | | | | | | | | | | 100 (0) | 100 | 88 (12) | 100 |
| 11 | 1.12 | 1 | 1.12 | 65 | 45 (0) | 99 | 99 | 5 (75) | 20 | 65 | 43 | | | | | | | | | | |
| 11 | 3.36 | 1 | 1.12 | 55 | 75 (26) | 100 | 95 | 17 (66) | 50 | 45 (0) | 65 | | | | | | | | | | |
| 11 | 4.48 | 1 | 2.24 | | | | | | | 25 (30) | 45 | | | | | | | | | | |
| 11 | 4.48 | 1 | 8.96 | | | | | | | 60 (44) | 45 | | | | | | | | | | |
| 11 | 8.96 | 1 | 2.24 | | | | | | | 30 (0) | 65 | | | | | | | | | | |
| 11 | 8.96 | 1 | 8.96 | | | | | | | 70 (53) | 65 | | | | | | | | | | |
| 11 | 1.12 | 10 | 1.12 | 57 | 45 (0) | 85 | 99 | 12 (40) | 20 | | | | | | | | | | | | |
| 11 | 3.36 | 10 | 1.12 | 45 | 75 (40) | 75 | 95 | 5 (90) | 50 | 30 (33) | 45 | | | | | | | | | | |
| 11 | 4.48 | 10 | 2.24 | | | | | | | 40 (11) | 45 | | | | | | | | | | |
| 11 | 4.48 | 10 | 8.96 | | | | | | | 60 (7) | 65 | | | | | | | | | | |
| 11 | 8.96 | 10 | 2.24 | | | | | | | 50 (23) | 65 | | | | | | | | | | |
| 11 | 8.96 | 10 | 8.96 | | | | | | | | | | | | | | | | | | |
| 11 | 1.12 | 11 | 1.12 | 40 | 45 (11) | 87 | 99 | 5 (75) | 20 | 50 (0) | 43 | | | | | | | | | | |
| 11 | 3.36 | 11 | 1.12 | 70 | 75 (6) | 99 | 95 | 22 (56) | 50 | 63 (3) | 65 | | | | | | | | | | |
| 11 | 4.48 | 11 | 2.24 | | | | | | | 50 (0) | 45 | | | | | | | | | | |

TABLE VI-continued

% PLANT INHIBITION AND % SAFENING EFFECT ()

| HERBICIDE NO. | HERBICIDE RATE | ANTIDOTE NO. | ANTIDOTE RATE | WHEAT W | WHEAT WO | SORGHUM GRAIN W | SORGHUM GRAIN WO | CORN W | CORN WO | SOYBEAN W | SOYBEAN WO | GREEN FOXTAIL W | GREEN FOXTAIL WO | DOWNY BROME W | DOWNY BROME WO | WILD OATS W | WILD OATS WO | BARNYARD GRASS W | BARNYARD GRASS WO | RICE W | RICE WO |
|---|---|---|---|---|---|---|---|---|---|---|---|---|---|---|---|---|---|---|---|---|---|
| 11 | 4.48 | 11 | 8.96 | | | | | | | 45 | 45 | | | | | | | | | | |
| 11 | 8.96 | 11 | 2.24 | | | | | | | 65 | (0) 65 | | | | | | | | | | |
| 11 | 8.96 | 11 | 8.96 | | | | | | | 75 | (0) 65 | | | | | | | | | | |
| 35 | 0.28 | 1 | 1.12 | 87 | 97 (10) | 100 | 100 (0) | 85 (5) | 90 | 53 | (0) 37 | | | | | | | | | | |
| 35 | 1.12 | 1 | 1.12 | 93 | 100 (7) | 100 | 100 (0) | 95 (0) | 95 | 93 | (0) 87 | | | | | | | | | | |
| 35 | 0.28 | 10 | 1.12 | 90 | 97 (7) | 99 | 100 (1) | 70 (22) | 90 | 90 | (0) 37 | | | | | | | | | | |
| 35 | 1.12 | 10 | 1.12 | 100 | 100 (0) | 100 | 100 (0) | 97 (0) | 95 | 90 | (0) 87 | | | | | | | | | | |
| 35 | 0.28 | 11 | 1.12 | 99 | 97 (0) | 100 | 100 (0) | 90 (0) | 90 | 57 | (0) 37 | | | | | | | | | | |
| 35 | 1.12 | 11 | 1.12 | 100 | 100 (0) | 100 | 100 (0) | 97 (0) | 95 | 83 | (0) 87 | | | | | | | | | | |
| 35 | 1.12 | 1 | 1.12 | 50 | 75 (33) | 77 | 87 (11) | 60 (0) | 55 | 55 | (4) 60 | | | | | | | | | | |
| 35 | 5.60 | 1 | 1.12 | 97 | 95 (0) | 99 | 97 (0) | 75 (9) | 83 | 98 | (8) 90 | | | | | | | | | | |
| 35 | 1.12 | 10 | 1.12 | 55 | 75 (26) | 83 | 87 (4) | 55 (0) | 55 | 90 | (0) 60 | | | | | | | | | | |
| 35 | 5.60 | 10 | 1.12 | 97 | 95 (0) | 99 | 97 (0) | 83 (0) | 83 | 95 | (0) 90 | | | | | | | | | | |
| 35 | 1.12 | 11 | 1.12 | 73 | 75 (2) | 93 | 87 (0) | 60 (0) | 55 | 55 | (8) 60 | | | | | | | | | | |
| 35 | 5.60 | 11 | 1.12 | 95 | 95 (0) | 99 | 97 (0) | 83 (0) | 83 | 98 | (0) 90 | | | | | | | | | | |
| 35 | 1.12 | 1 | 1.12 | 40 | 30 (0) | 90 | 70 (0) | 60 (0) | 60 | 53 | (0) 45 | | | | | | | | | | |
| 35 | 2.24 | 1 | 2.24 | | | | | | | 40 | (0) 40 | | | | | | | | | | |
| 15 | 2.24 | 1 | 8.96 | | | | | | | 50 | (0) 40 | | | | | | | | | | |
| 15 | 3.36 | 1 | 1.12 | 55 | 60 (8) | 93 | 99 (6) | 83 (0) | 60 | 57 | (0) 55 | | | | | | | | | | |
| 15 | 4.48 | 1 | 2.24 | | | | | | | 30 | (45) 55 | | | | | | | | | | |
| 15 | 4.48 | 1 | 8.96 | | | | | | | 10 | (81) 55 | | | | | | | | | | |
| 15 | 1.12 | 10 | 1.12 | 43 | 30 (0) | 99 | 70 (0) | 60 (0) | 60 | 57 | (0) 45 | | | | | | | | | | |
| 15 | 2.24 | 10 | 2.24 | | | | | | | 30 | (25) 40 | | | | | | | | | | |
| 15 | 2.24 | 10 | 8.96 | | | | | | | 20 | (50) 40 | | | | | | | | | | |

TABLE VI-continued

% PLANT INHIBITION AND % SAFENING EFFECT ( )

| HERBICIDE NO. | RATE | ANTIDOTE NO. | RATE | WHEAT W | WO | SORGHUM GRAIN W | WO | CORN W | WO | SOYBEAN W | WO | GREEN FOXTAIL W | WO | DOWNY BROME W | WO | WILD OATS W | WO | BARNYARD GRASS W | WO | RICE W | WO |
|---|---|---|---|---|---|---|---|---|---|---|---|---|---|---|---|---|---|---|---|---|---|
| 15 | 3.36 | 10 | 1.12 | 65 | 60 (0) | 97 | 99 (2) | 75 | 60 (0) | 60 | 55 | | | | | | | | | | |
| 15 | 4.48 | 10 | 2.24 | | | | | | | 50 | 55 (9) | | | | | | | | | | |
| 15 | 4.48 | 10 | 8.96 | 43 | 30 (0) | 95 | 70 (0) | 40 | 60 (33) | 40 | 55 (27) | | | | | | | | | | |
| 15 | 1.12 | 11 | 1.12 | | | | | | | 83 | 45 (0) | | | | | | | | | | |
| 15 | 2.24 | 11 | 2.24 | | | | | | | 20 | 40 (50) | | | | | | | | | | |
| 15 | 2.24 | 11 | 8.96 | 30 | 60 (50) | 99 | 99 (0) | 73 | 60 (0) | 20 | 40 (50) | | | | | | | | | | |
| 15 | 3.36 | 11 | 1.12 | | | | | | | 55 | 55 (0) | | | | | | | | | | |
| 15 | 4.48 | 11 | 2.24 | | | | | | | 40 | 55 (27) | | | | | | | | | | |
| 15 | 4.48 | 11 | 8.96 | | | | | | | 65 | 55 (0) | | | | | | | | | | |
| 18 | 1.12 | 1 | 1.12 | 63 | 50 (0) | 97 | 99 (2) | 0 | 5 (100) | 73 | 20 (0) | | | | | | | | | | |
| 18 | 3.36 | 1 | 1.12 | 80 | 75 (0) | 95 | 99 (4) | 30 | 23 (0) | 63 | 25 (0) | | | | | | | | | | |
| 18 | 1.12 | 10 | 1.12 | 45 | 50 (0) | 90 | 99 (9) | 0 | 5 (100) | 25 | 20 (0) | | | | | | | | | | |
| 18 | 3.36 | 10 | 1.12 | 50 | 75 (10) | 93 | 99 (6) | 10 | 23 (56) | 70 | 25 (0) | | | | | | | | | | |
| 18 | 1.12 | 11 | 1.12 | 83 | 50 (33) | 97 | 99 (2) | 20 | 5 (0) | 60 | 20 (0) | | | | | | | | | | |
| 18 | 3.36 | 11 | 1.12 | 80 | 75 (0) | 100 | 99 (0) | 53 | 23 (0) | 85 | 25 (0) | | | | | | | | | | |
| 28 | 1.12 | 1 | 1.12 | 60 | 30 (0) | 99 | 97 (0) | 35 | 80 (56) | 65 | 55 (0) | | | | | | | | | | |
| 28 | 3.36 | 1 | 1.12 | 63 | 87 (27) | 98 | 95 (0) | 50 | 95 (47) | 63 | 55 (0) | | | | | | | | | | |
| 28 | 1.12 | 10 | 1.12 | 35 | 30 (0) | 100 | 97 (0) | 45 | 80 (43) | 67 | 83 (24) | | | | | | | | | | |
| 28 | 3.36 | 10 | 1.12 | 83 | 87 (0) | 100 | 95 (0) | 99 | 95 (0) | 100 | 55 (0) | | | | | | | | | | |
| 28 | 1.12 | 11 | 1.12 | 37 | 30 (4) | 83 | 97 (0) | 40 | 80 (50) | 55 | 83 (0) | | | | | | | | | | |
| 28 | 3.36 | 11 | 1.12 | 80 | 87 (0) | 99 | 95 (14) | 99 | 95 (0) | 75 | 83 (9) | | | | | | | | | | |

EXAMPLE 290

The following procedure shows interaction between herbicide and antidote when applied together as a mixture before emergence of the crop and weed species. Containers were filled and compacted with fumigated silt loam top soil to a depth of about 1.3 cm from the top of the container. A first container was designated as an untreated control, a second container was designated as a herbicide control, and a third container was designated as a herbicide+antidote test container. Each of the containers was seeded with both crop plant and weed species. The herbicide and the herbicide+antidote test mixture were applied to the seeded containers either by a procedure of topical application to a soil layer placed over the seed bed followed by watering to achieve incorporation, or by a procedure of incorporation into soil and then placement of the treated soil into the container over the seed bed. The containers were then placed on a greenhouse bench, and sub-irrigated as required for the duration of the test. Plant response was observed about three weeks after initial treatment. Results are reported in Table VII.

TABLE VII

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W WO | SHATTER CANE W WO | CRAB-GRASS W WO | PIG-WEED W WO | PROSO MILLET W WO | RICE W WO | BARNYARD GRASS W WO | SORGHUM W WO | SOYBEAN W WO |
|---|---|---|---|---|---|---|---|---|---|---|---|---|---|---|---|---|---|---|---|---|---|
| 6 | 2.24 | 1 | 1.12 | 88 | 95 (7) | | | 78 | 100 (22) | | | | | | | | | | | | |
| 6 | 2.24 | 1 | 1.12 | 72 | 70 (0) | | | 70 | 98 (28) | | | | | | | | | | | | |
| 6 | 2.24 | 1 | 1.12 | 55 | 70 (21) | | | 80 | 98 (18) | | | | | | | | | | | | |
| 6 | 2.24 | 1 | 2.24 | 90 | 95 (5) | | | 60 | 100 (40) | | | | | | | | | | | | |
| 6 | 2.24 | 1 | 4.48 | 72 | 95 (24) | | | 55 | 100 (45) | | | | | | | | | | | | |
| 6 | 2.24 | 1 | 4.48 | 60 | 70 (14) | | | 55 | 98 (43) | | | | | | | | | | | | |
| 6 | 2.24 | 1 | 8.96 | 52 | 70 (25) | | | 30 | 98 (69) | | | | | | | | | | | | |
| 6 | 2.24 | 1 | 8.96 | 82 | 95 (13) | | | 20 | 100 (80) | | | | | | | | | | | | |
| 6 | 2.24 | 2 | 1.12 | 70 | 62 (0) | | | 90 | 100 (10) | | | | | | | | | | | | |
| 6 | 2.24 | 2 | 2.24 | 58 | 70 (17) | | | 92 | 98 (6) | | | | | | | | | | | | |
| 6 | 2.24 | 2 | 2.24 | 68 | 62 (0) | | | 80 | 100 (20) | | | | | | | | | | | | |
| 6 | 2.24 | 2 | 4.48 | 52 | 62 (16) | | | 80 | 100 (20) | | | | | | | | | | | | |
| 6 | 2.24 | 2 | 8.96 | 60 | 62 (3) | | | 70 | 100 (30) | | | | | | | | | | | | |
| 6 | 2.24 | 3 | 1.12 | 45 | 62 (27) | | | 68 | 100 (32) | | | | | | | | | | | | |
| 6 | 2.24 | 3 | 1.12 | 65 | 80 (18) | | | 65 | 92 (29) | | | | | | | | | | | | |
| 6 | 2.24 | 3 | 2.24 | 62 | 80 (22) | | | 50 | 92 (45) | | | | | | | | | | | | |
| 6 | 2.24 | 3 | 2.24 | 60 | 62 (3) | | | 55 | 100 (45) | | | | | | | | | | | | |
| 6 | 2.24 | 3 | 4.48 | 70 | 80 (12) | | | 20 | 92 (78) | | | | | | | | | | | | |
| 6 | 2.24 | 3 | 4.48 | 70 | 62 (0) | | | 35 | 100 (65) | | | | | | | | | | | | |
| 6 | 2.24 | 3 | 8.96 | 62 | 62 (0) | | | 20 | 100 (80) | | | | | | | | | | | | |
| 6 | 2.24 | 3 | 8.96 | 48 | 80 (40) | | | 30 | 92 (67) | | | | | | | | | | | | |
| 6 | 0.14 | 4 | 0.14 | 20 | 33 (39) | 40 | 55 (27) | | | 40 | 25 (57) | 15 | 35 (0) | | | | | | | | |
| 6 | 0.14 | 4 | 0.56 | 15 | 33 (54) | 50 | 55 (9) | | | 33 | 25 (14) | 30 | 35 (0) | | | | | | | | |
| 6 | 0.14 | 4 | 2.24 | 25 | 33 (24) | 35 | 55 (36) | | | 35 | 25 (28) | 25 | 35 (0) | | | | | | | | |

TABLE VII-continued

| | | | | % PLANT INHIBITION AND % SAFENING EFFECT ( ) | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| HERBICIDE | | ANTIDOTE | | WHEAT | | DOWNEY BROME | | SORGHUM GRAIN | | GREEN FOXTAIL | | WILD OATS | | JOHNSON GRASS | | SHATTER CANE | | CRAB GRASS | | PIG- WEED | | PROSO MILLET | | RICE | | BARNYARD GRASS | | SORGHUM | | SOYBEAN | |
| NO. | RATE | NO. | RATE | W | WO | W | WO | W | WO | W | WO | W | WO | W | WO | W | WO | W | WO | W | WO | W | WO | W | WO | W | WO | W | WO | W | WO |
| 6 | 0.56 | 4 | 0.14 | 30 | 43 (30) | 40 | 65 (38) | | | 93 | 50 (4) | 43 | 45 (0) | | | | | | | | | | | | | | | | | | |
| 6 | 0.56 | 4 | 0.56 | 57 | 43 (0) | 70 | 65 (0) | | | 55 | 50 (0) | 70 | 45 (0) | | | | | | | | | | | | | | | | | | |
| 6 | 0.56 | 4 | 2.24 | 50 | 43 (0) | 65 | 65 (0) | | | 65 | 50 (0) | 60 | 45 (0) | | | | | | | | | | | | | | | | | | |
| 6 | 2.24 | 4 | 0.14 | 83 | 80 (0) | 90 | 75 (0) | | | 99 | 90 (0) | 85 | 85 (0) | | | | | | | | | | | | | | | | | | |
| 6 | 2.24 | 4 | 0.56 | 57 | 80 (28) | 83 | 75 (0) | | | 95 | 90 (0) | 50 | 85 (41) | | | | | | | | | | | | | | | | | | |
| 6 | 2.24 | 4 | 1.12 | 80 | 95 (15) | | | 62 | 100 (38) | | | | | | | | | | | | | | | | | | | | | | | |
| 6 | 2.24 | 4 | 2.24 | 75 | 95 (21) | | | 45 | 100 (55) | | | | | | | | | | | | | | | | | | | | | | | |
| 6 | 2.24 | 4 | 2.24 | 75 | 80 (6) | 93 | 75 (0) | 28 | 100 (72) | 95 | 90 (0) | 70 | 85 (17) | | | | | | | | | | | | | | | | | | |
| 6 | 2.24 | 4 | 4.48 | 70 | 95 (26) | | | 10 | 100 (90) | | | | | | | | | | | | | | | | | | | | | | | |
| 6 | 2.24 | 4 | 8.96 | 65 | 95 (31) | | | 62 | 100 (38) | | | | | | | | | | | | | | | | | | | | | | | |
| 6 | 2.24 | 5 | 1.12 | 75 | 95 (21) | | | 40 | 100 (60) | | | | | | | | | | | | | | | | | | | | | | | |
| 6 | 2.24 | 5 | 2.24 | 75 | 95 (21) | | | 30 | 100 (70) | | | | | | | | | | | | | | | | | | | | | | | |
| 6 | 2.24 | 5 | 4.48 | 45 | 95 (52) | | | 40 | 100 (60) | | | | | | | | | | | | | | | | | | | | | | | |
| 6 | 2.24 | 5 | 8.96 | 35 | 95 (63) | | | | | | | | | | | | | | | | | | | | | | | | | | | |
| 6 | 0.03 | 6 | 0.03 | | | | | 0 | 13 (100) | 80 | 85 (5) | | | 0 | 5 (100) | 0 | 5 (100) | 78 | 83 (6) | 68 | 83 (18) | 100 | 100 (0) | | | | | | | | |
| 6 | 0.03 | 6 | 0.14 | | | | | 0 | 13 (100) | 80 | 85 (5) | | | 0 | 5 (100) | 0 | 5 (100) | 75 | 83 (9) | 70 | 83 (15) | 100 | 100 (0) | | | | | | | | |
| 6 | 0.03 | 6 | 0.56 | | | | | 0 | 13 (100) | 80 | 85 (5) | | | 5 | 5 (0) | 0 | 5 (100) | 85 | 83 (0) | 85 | 83 (0) | 100 | 100 (0) | | | | | | | | |
| 6 | 0.03 | 6 | 2.24 | | | | | 0 | 13 (100) | 78 | 85 (8) | | | 0 | 5 (100) | 0 | 5 (100) | 80 | 83 (3) | 80 | 83 (3) | 100 | 100 (0) | | | | | | | | |
| 6 | 0.14 | 6 | 0.03 | | | | | 0 | 25 (100) | 90 | 93 (3) | | | 10 | 45 (77) | 15 | 55 (72) | 90 | 93 (3) | 70 | 90 (22) | 100 | 100 (0) | | | | | | | | |
| 6 | 0.14 | 6 | 0.14 | | | | | 17 | 45 (62) | 87 | 95 (8) | | | 8 | 45 (82) | 5 | 55 (90) | 65 | 45 (0) | 90 | 90 (0) | 100 | 100 (0) | | | 85 | 99 (14) | | | | |
| 6 | 0.14 | 6 | 0.56 | | | | | 0 | 25 (100) | 93 | 93 (0) | | | 15 | 45 (66) | 13 | 55 (76) | 93 | 93 (0) | 100 | 90 (0) | 100 | 100 (0) | | | | | | | | |
| 6 | 0.14 | 6 | 0.56 | | | | | 5 | 45 (88) | 95 | 95 (0) | | | | | | | 73 | 45 (0) | | | 100 | 100 (0) | | | 75 | 99 (24) | | | | |
| 6 | 0.14 | 6 | 0.56 | | | | | 0 | 25 (100) | 93 | 93 (0) | | | 15 | 45 (66) | 13 | 55 (76) | 93 | 93 (0) | 100 | 90 (0) | 100 | 100 (0) | | | | | | | | |
| 6 | 0.14 | 6 | 2.24 | | | | | 5 | 25 (80) | 95 | 93 (0) | | | 13 | 45 (71) | 10 | 55 (81) | 97 | 93 (0) | 100 | 90 (0) | 100 | 100 (0) | | | | | | | | |

TABLE VII-continued

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB-GRASS W | WO | PIG-WEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|---|
| 6 | 0.14 | 6 | 2.24 | | | | | 0 (100) | 45 | 85 (10) | 95 | | | 99 | | | | 57 (0) | 45 | | | | | | | 50 (49) | 99 | | | | |
| 6 | 0.56 | 6 | 0.03 | | | | | 50 (9) | 55 | 98 (0) | 98 | | | 99 | | | 92 | 99 (0) | 98 | 99 (1) | 100 | 100 (0) | 100 | | | | | | | | |
| 6 | 0.56 | 6 | 0.14 | | | | | 55 (0) | 50 | 93 (2) | 95 | | | | | | | 70 (22) | 90 | | | | | | | 85 (14) | 99 | | | | |
| 6 | 0.56 | 6 | 0.56 | | | | | 40 (27) | 55 | 97 (1) | 98 | | | 80 (18) | 98 | | 92 | 98 (0) | 98 | 100 (0) | 100 | 100 (0) | 100 | | | | | | | | |
| 6 | 0.56 | 6 | 2.24 | | | | | 10 (80) | 50 | 95 (0) | 95 | | | | | | | 85 (5) | 90 | | | | | | | 87 (12) | 99 | | | | |
| 6 | 0.56 | 6 | 2.24 | | | | | 15 (72) | 55 | 98 (0) | 98 | | | 75 (23) | 98 | | 92 | 98 (0) | 98 | 95 (5) | 100 | 100 (0) | 100 | | | | | | | | |
| 6 | 0.56 | 6 | 2.24 | | | | | 20 (60) | 50 | 99 (0) | 99 | | | | | | | 87 (3) | 90 | | | | | | | 90 (9) | 99 | | | | |
| 6 | 0.56 | 6 | 2.24 | | | | | 50 (9) | 55 | 97 (1) | 98 | | | 85 (13) | 99 | 75 | 92 | 99 (0) | 98 | 100 (0) | 100 | 100 (0) | 100 | | | | | | | | |
| 6 | 2.24 | 6 | 0.03 | | | | | 75 (6) | 80 | 100 (0) | 100 | | | 99 (0) | 99 | 98 | 98 | 100 (0) | 100 | 100 (0) | 100 | 100 (0) | 100 | | | 100 (0) | 100 | | | | |
| 6 | 2.24 | 6 | 0.14 | | | | | 83 (0) | 80 | 100 (0) | 100 | | | 99 (0) | 99 | 98 | 98 | 100 (0) | 100 | 100 (0) | 100 | 100 (0) | 100 | | | 100 (0) | 100 | | | | |
| 6 | 2.24 | 6 | 0.14 | | | | | 90 (6) | 96 | 99 (0) | 99 | | | | | 97 | | 99 (0) | 97 | | | | | | | | | | | | |
| 6 | 2.24 | 6 | 0.56 | | | | | 65 (32) | 96 | 95 (4) | 99 | | | | | 90 | 98 | 83 (14) | 97 | | | | | | | | | | | | |
| 6 | 2.24 | 6 | 0.56 | | | | | 78 (2) | 80 | 99 (1) | 100 | | | 99 (0) | 99 | 99 | 98 | 100 (0) | 100 | 100 (0) | 100 | 100 (0) | 100 | | | 100 (0) | 100 | | | | |
| 6 | 2.24 | 6 | 2.24 | | | | | 63 (21) | 80 | 98 (2) | 100 | | | 99 (1) | 100 | 99 | 98 | 100 (0) | 100 | 100 (0) | 100 | 100 (0) | 100 | | | | | | | | |
| 6 | 2.24 | 6 | 2.24 | | | | | 40 (58) | 96 | 99 (0) | 99 | | | | | 99 | 99 | 99 (0) | 97 | | | | | | | | | | | | |
| 6 | 4.48 | 6 | 0.03 | | | | | 94 (0) | 94 | 100 (0) | 100 | | | 100 (0) | 100 | 100 | 99 | 100 (0) | 100 | 100 (0) | 100 | 100 (0) | 100 | | | | | | | | |
| 6 | 4.48 | 6 | 0.14 | | | | | 90 (5) | 99 | 100 (0) | 100 | | | 95 (5) | 100 | 100 | 99 | 100 (0) | 100 | 100 (0) | 100 | 100 (0) | 100 | | | | | | | | |
| 6 | 4.48 | 6 | 0.56 | | | | | 78 (9) | 99 | 100 (0) | 100 | | | 99 (1) | 100 | 99 | 99 | 100 (0) | 100 | 100 (0) | 100 | 100 (0) | 100 | | | | | | | | |
| 6 | 4.48 | 6 | 2.24 | | | | | 83 (16) | 99 | 99 (1) | 100 | | | 100 (0) | 100 | 99 | 99 | 100 (0) | 100 | 100 (0) | 100 | 100 (0) | 100 | | | | | | | | |
| 6 | 0.03 | 7 | 0.03 | | | | | 0 (100) | 5 | 90 (3) | 93 | | | 3 (40) | 5 | 5 | 8 | 93 (0) | 93 | 48 (0) | 45 | | | | | | | | | | |
| 6 | 0.03 | 7 | 0.14 | | | | | 5 (0) | 5 | 90 (3) | 93 | | | 3 (40) | 5 | 3 | 8 | 93 (0) | 93 | 40 (11) | 45 | | | | | | | | | | |
| 6 | 0.03 | 7 | 0.56 | | | | | 5 (0) | 5 | 93 (0) | 93 | | | 5 (0) | 5 | 0 | 8 | 93 (0) | 93 | 40 (11) | 45 | | | | | | | | | | |
| 6 | 0.03 | 7 | 2.24 | | | | | 0 (100) | 5 | 95 (0) | 93 | | | 0 (100) | 5 | 3 | 8 | 93 (0) | 93 | 40 (11) | 45 | | | | | | | | | | |
| 6 | 0.14 | 7 | 0.03 | | | | | 43 (21) | 55 | 97 (0) | 95 | | | 63 (0) | 45 | 60 | 50 | 98 (0) | 95 | 40 (31) | 58 | | | | | | | | | | |

TABLE VII-continued

% PLANT INHIBITION AND % SAFENING EFFECT ( )

| HERBICIDE NO. | HERBICIDE RATE | ANTIDOTE NO. | ANTIDOTE RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRAB-GRASS W | CRAB-GRASS WO | PIG-WEED W | PIG-WEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|---|
| 6 | 0.14 | 7 | 0.14 | | | | | 45 (18) | 55 | 95 | 95 (0) | | | 40 | 45 (11) | 53 | 50 (0) | 97 (0) | 95 | 45 (22) | 58 | | | | | 80 (19) | 99 | | | | |
| 6 | 0.14 | 7 | 0.14 | | | | | 0 (100) | 45 | 65 | 95 (31) | | | | | | | 45 (0) | 45 | | | | | | | | | | | | |
| 6 | 0.14 | 7 | 0.56 | | | | | 10 (77) | 45 | 87 | 95 (8) | | | | | | | 67 (0) | 45 | | | | | | | 85 (14) | 99 | | | | |
| 6 | 0.14 | 7 | 0.56 | | | | | 40 (27) | 55 | 95 | 95 (0) | | | 40 | 45 (11) | 30 | 50 (40) | 97 (0) | 95 | 40 (31) | 58 | | | | | | | | | | |
| 6 | 0.14 | 7 | 2.24 | | | | | 25 (44) | 45 | 95 | 95 (0) | | | | | | | 55 (0) | 45 | | | | | | | 57 (42) | 99 | | | | |
| 6 | 0.14 | 7 | 2.24 | | | | | 20 (63) | 55 | 93 | 95 (2) | | | 15 | 45 (66) | 20 | 50 (60) | 97 (0) | 95 | 43 (25) | 58 | | | | | | | | | | |
| 6 | 0.56 | 7 | 0.03 | | | | | 65 (10) | 73 | 94 | 97 (3) | | | 85 | 93 (8) | 97 | 83 (0) | 98 (0) | 97 | 65 (0) | 60 | | | | | | | | | | |
| 6 | 0.56 | 7 | 0.14 | | | | | 70 (4) | 73 | 97 | 97 (0) | | | 84 | 93 (9) | 78 | 83 (6) | 97 (0) | 97 | 65 (0) | 60 | | | | | | | | | | |
| 6 | 0.56 | 7 | 0.14 | | | | | 30 (40) | 50 | 90 | 95 (5) | | | | | | | 70 (22) | 90 | | | | | | | 99 (0) | 99 | | | | |
| 6 | 0.56 | 7 | 0.56 | | | | | 25 (50) | 50 | 95 | 95 (0) | | | | | | | 80 (11) | 90 | | | | | | | 99 (0) | 99 | | | | |
| 6 | 0.56 | 7 | 0.56 | | | | | 65 (10) | 73 | 97 | 97 (0) | | | 83 | 93 (10) | 75 | 83 (9) | 97 (0) | 97 | 65 (8) | 95 | | | | | | | | | | |
| 6 | 0.56 | 7 | 2.24 | | | | | 25 (50) | 50 | 99 | 95 (0) | | | | | | | 85 (5) | 90 | | | | | | | 99 (0) | 99 | | | | |
| 6 | 0.56 | 7 | 2.24 | | | | | 50 (31) | 73 | 95 | 97 (2) | | | 65 (30) | 93 | 65 | 83 (21) | 94 (3) | 97 | 55 (0) | 95 | | | | | | | | | | |
| 6 | 2.24 | 7 | 0.03 | | | | | 97 (0) | 90 | 97 | 98 (1) | | | 95 (3) | 98 | 99 | 99 (0) | 98 (2) | 100 | 95 (0) | 95 | | | | | | | | | | |
| 6 | 2.24 | 7 | 0.14 | | | | | 98 (0) | 90 | 98 | 98 (0) | | | 99 (0) | 98 | 99 | 99 (0) | 99 (0) | 100 | 98 (0) | 95 | | | | | | | | | | |
| 6 | 2.24 | 7 | 0.14 | | | | | 45 (53) | 96 | 99 | 99 (0) | | | | | | | 99 (0) | 97 | | | | | | | 100 (0) | 100 | | | | |
| 6 | 2.24 | 7 | 0.56 | | | | | 88 (2) | 90 | 98 | 98 (0) | | | 94 (4) | 98 | 97 | 99 (0) | 99 (1) | 100 | 93 (2) | 95 | | | | | | | | | | |
| 6 | 2.24 | 7 | 0.56 | | | | | 77 (19) | 96 | 100 | 99 (0) | | | | | | | 100 (0) | 97 | | | | | | | 99 (0) | 100 | | | | |
| 6 | 2.24 | 7 | 2.24 | | | | | 83 (7) | 90 | 98 | 98 (0) | | | 99 (0) | 98 | 88 | 95 (7) | 97 (3) | 100 | 85 (10) | 95 | | | | | | | | | | |
| 6 | 2.24 | 7 | 2.24 | | | | | 53 (44) | 96 | 99 | 99 (0) | | | | | | | 97 (0) | 97 | | | | | | | 97 | 100 | | | | |
| 6 | 4.48 | 7 | 0.03 | | | | | 99 (0) | 99 | 99 | 99 (0) | | | 98 (1) | 99 | 99 | 99 (0) | 99 (0) | 99 | 98 (0) | 98 | | | | | | | | | | |
| 6 | 4.48 | 7 | 0.14 | | | | | 99 (0) | 99 | 99 | 99 (0) | | | 99 (0) | 99 | 99 | 99 (0) | 100 (0) | 99 | 97 (1) | 98 | | | | | | | | | | |
| 6 | 4.48 | 7 | 0.56 | | | | | 98 (0) | 99 | 98 | 99 (1) | | | 99 (0) | 99 | 99 | 99 (0) | 100 (0) | 99 | 94 (4) | 98 | | | | | | | | | | |
| 6 | 4.48 | 7 | 2.24 | | | | | 97 (2) | 99 | 99 | 99 (0) | | | 99 (0) | 99 | 99 | 99 (0) | 99 (0) | 99 | 93 (5) | 98 | | | | | | | | | | |

TABLE VII-continued

% PLANT INHIBITION AND % SAFENING EFFECT ( )

| HERBICIDE NO. | RATE | ANTIDOTE NO. | RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRAB-GRASS W | CRAB-GRASS WO | PIG-WEED W | PIG-WEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|
| 6 | 0.14 | 8 | 0.14 | | | | | 5 (88) | 45 | 77 (18) | 95 | | | | | | | 47 (0) | 45 | | | | | | | 77 (22) | 99 | | | | |
| 6 | 0.14 | 8 | 0.56 | | | | | 0 (100) | 45 | 93 (2) | 95 | | | | | | | 47 (0) | 45 | | | | | | | 50 (49) | 99 | | | | |
| 6 | 0.14 | 8 | 2.24 | | | | | 7 (84) | 45 | 85 (10) | 95 | | | | | | | 70 (0) | 45 | | | | | | | 75 (24) | 99 | | | | |
| 6 | 0.56 | 8 | 0.14 | | | | | 37 (26) | 50 | 95 (0) | 95 | | | | | | | 80 (11) | 90 | | | | | | | 97 (2) | 99 | | | | |
| 6 | 0.56 | 8 | 0.56 | | | | | 20 (60) | 50 | 93 (2) | 95 | | | | | | | 80 (11) | 90 | | | | | | | 85 (14) | 99 | | | | |
| 6 | 0.56 | 8 | 2.24 | | | | | 43 (14) | 50 | 99 (0) | 99 | | | | | | | 95 (0) | 90 | | | | | | | 97 (2) | 99 | | | | |
| 6 | 2.24 | 8 | 0.14 | | | | | 65 (32) | 96 | 99 (0) | 99 | | | | | | | 99 (0) | 97 | | | | | | | 99 (1) | 100 | | | | |
| 6 | 2.24 | 8 | 0.56 | | | | | 80 (16) | 96 | 99 (0) | 99 | | | | | | | 99 (0) | 97 | | | | | | | 100 (0) | 100 | | | | |
| 6 | 2.24 | 8 | 1.12 | 62 (22) | 80 | | | 75 (18) | 92 | | | | | | | | | | | | | | | | | | | | | | |
| 6 | 2.24 | 8 | 2.24 | 58 (27) | 80 | | | 40 (58) | 96 | 99 (0) | 99 | | | | | | | 99 (0) | 97 | | | | | | | 99 (1) | 100 | | | | |
| 6 | 2.24 | 8 | 4.48 | 55 (31) | 80 | | | 70 (23) | 92 | | | | | | | | | | | | | | | | | | | | | | |
| 6 | 2.24 | 8 | 8.96 | 45 (43) | 80 | | | 60 (34) | 92 | | | | | | | | | | | | | | | | | | | | | | |
| 6 | 2.24 | 9 | 0.03 | | | | | 40 (56) | 92 | | | | | | | | | | | | | | | | | | | | | | |
| 6 | 0.03 | 9 | 0.14 | | | | | 10 (0) | 5 | 90 (3) | 93 | | | 5 (0) | 5 | 5 (0) | 8 | 90 (3) | 93 | 45 (0) | 45 | | | | | | | | | | |
| 6 | 0.03 | 9 | 0.56 | | | | | 0 (100) | 5 | 93 (0) | 93 | | | 5 (0) | 5 | 5 (37) | 8 | 93 (3) | 93 | 40 (11) | 45 | | | | | | | | | | |
| 6 | 0.03 | 9 | 2.24 | | | | | 0 (100) | 5 | 90 (3) | 93 | | | 0 (100) | 5 | 3 (62) | 8 | 90 (3) | 93 | 35 (22) | 45 | | | | | | | | | | |
| 6 | 0.03 | 9 | 0.03 | | | | | 0 (100) | 5 | 93 (3) | 93 | | | 0 (100) | 5 | 0 (100) | 8 | 90 (3) | 93 | 45 (0) | 45 | | | | | | | | | | |
| 6 | 0.14 | 9 | 0.03 | | | | | 45 (18) | 55 | 93 (2) | 95 | | | 33 (26) | 45 | 50 (0) | 50 | 95 (0) | 95 | 65 (0) | 58 | | | | | | | | | | |
| 6 | 0.14 | 9 | 0.14 | | | | | 5 (88) | 45 | 95 (0) | 95 | | | | | | | 50 (0) | 45 | | | | | | | 95 | 99 (4) | | | | |
| 6 | 0.14 | 9 | 0.14 | | | | | 30 (45) | 55 | 97 (0) | 95 | | | 25 (44) | 45 | 40 (20) | 50 | 97 (0) | 95 | 45 (22) | 58 | | | | | | | | | | |
| 6 | 0.14 | 9 | 0.56 | | | | | 10 (55) | 55 | 97 (0) | 95 | | | 15 (66) | 45 | 18 (64) | 50 | 98 (0) | 95 | 60 (0) | 58 | | | | | | | | | | |
| 6 | 0.14 | 9 | 0.56 | | | | | 7 (81) | 45 | 87 (8) | 95 | | | | | | | 77 (0) | 45 | | | | | | | 63 (36) | 99 | | | | |
| 6 | 0.14 | 9 | 2.24 | | | | | 20 (63) | 55 | 93 (2) | 95 | | | 25 (44) | 45 | 18 (64) | 50 | 97 (0) | 95 | 65 (0) | 58 | | | | | | | | | | |
| 6 | 0.14 | 9 | 2.24 | | | | | 10 (77) | 45 | 75 (21) | 95 | | | | | | | 40 (11) | 45 | | | | | | | | | | | | |

TABLE VII-continued

% PLANT INHIBITION AND % SAFENING EFFECT ( )

| HERBICIDE NO. | HERBICIDE RATE | ANTIDOTE NO. | ANTIDOTE RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRAB GRASS W | CRAB GRASS WO | PIG-WEED W | PIG-WEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|---|
| 6 | 0.56 | 9 | 0.03 | | | | | 55 | 73 (24) | 95 | 97 (2) | | | 58 | 93 (37) | 68 | 83 (18) | 97 | 97 (0) | 75 | 60 (0) | | | | | | | | | | |
| 6 | 0.56 | 9 | 0.14 | | | | | 45 | 73 (38) | 97 | 97 (0) | | | 50 | 93 (46) | 65 | 83 (21) | 97 | 90 (0) | 80 | 60 (0) | | | | | 97 | 99 (2) | | | | |
| 6 | 0.56 | 9 | 0.14 | | | | | 23 | 50 (54) | 95 | 95 (0) | | | | | | | 73 | 90 (18) | | | | | | | 99 | 99 (0) | | | | |
| 6 | 0.56 | 9 | 0.56 | | | | | 17 | 50 (66) | 95 | 95 (0) | | | | | | | 95 | 90 (90) | | | | | | | | | | | | |
| 6 | 0.56 | 9 | 0.56 | | | | | 30 | 73 (58) | 98 | 97 (0) | | | 83 | 93 (24) | 55 | 83 (0) | 97 | 97 (0) | 65 | 60 (0) | | | | | 95 | 99 (4) | | | | |
| 6 | 0.56 | 9 | 2.24 | | | | | 10 | 50 (80) | 95 | 95 (0) | | | | | | | 67 | 90 (25) | | | | | | | | | | | | |
| 6 | 2.24 | 9 | 0.03 | | | | | 93 | 90 (0) | 97 | 98 (1) | | | 95 | 98 (3) | 98 | 95 (0) | 98 | 100 (2) | 94 | 95 (1) | | | | | 99 | 100 (1) | | | | |
| 6 | 2.24 | 9 | 0.14 | | | | | 83 | 96 (13) | 99 | 99 (0) | | | | | | | 99 | 97 (0) | | | | | | | | | | | | |
| 6 | 2.24 | 9 | 0.14 | | | | | 93 | 90 (0) | 98 | 98 (0) | | | 94 | 98 (4) | 98 | 95 (0) | 98 | 100 (2) | 90 | 95 (5) | | | | | | | | | | |
| 6 | 2.24 | 9 | 0.56 | | | | | 90 | 90 (0) | 99 | 98 (0) | | | 99 | 99 (0) | 98 | 95 (0) | 98 | 100 (2) | 80 | 95 (15) | | | | | | | | | | |
| 6 | 2.24 | 9 | 0.56 | | | | | 35 | 96 (63) | 99 | 99 (0) | | | | | | | 93 | 97 (4) | | | | | | | | | | | | |
| 6 | 2.24 | 9 | 2.24 | | | | | 83 | 90 (7) | 99 | 98 (0) | | | 97 | 98 (1) | 97 | 95 (0) | 99 | 100 (1) | 85 | 95 (10) | | | | | 100 | 100 (0) | | | | |
| 6 | 4.48 | 9 | 0.03 | | | | | 43 | 96 (55) | 100 | 99 (0) | | | | | | | 97 | 97 (0) | | | | | | | | | | | | |
| 6 | 4.48 | 9 | 0.14 | | | | | 99 | 99 (0) | 97 | 99 (2) | | | 99 | 99 (0) | 99 | 99 (0) | 99 | 99 (0) | 98 | 98 (0) | | | | | | | | | | |
| 6 | 4.48 | 9 | 0.56 | | | | | 93 | 99 (6) | 99 | 99 (0) | | | 98 | 99 (1) | 98 | 99 (1) | 99 | 99 (0) | 97 | 98 (1) | | | | | | | | | | |
| 6 | 4.48 | 9 | 2.24 | | | | | 97 | 99 (2) | 99 | 99 (0) | | | 100 | 99 (0) | 99 | 99 (1) | 99 | 99 (0) | 95 | 98 (3) | | | | | | | | | | |
| 6 | 0.14 | 10 | 0.14 | | | | | 94 | 99 (5) | 100 | 99 (0) | | | 98 | 99 (1) | 97 | 97 (2) | 99 | 99 (0) | 100 | 98 (0) | | | | | | | | | | |
| 6 | 0.14 | 10 | 0.56 | | | | | 10 | 45 (77) | 90 | 95 (5) | | | | | | | 65 | 45 (0) | | | | | | | 95 | 99 (14) | | | | |
| 6 | 0.14 | 10 | 2.24 | | | | | 13 | 45 (71) | 90 | 95 (5) | | | | | | | 50 | 45 (0) | | | | | | | 50 | 99 (49) | | | | |
| 6 | 0.56 | 10 | 0.14 | | | | | 10 | 45 (77) | 98 | 95 (5) | | | | | | | 55 | 45 (0) | | | | | | | 57 | 99 (42) | | | | |
| 6 | 0.56 | 10 | 0.56 | | | | | 25 | 50 (50) | 99 | 95 (0) | | | | | | | 77 | 90 (14) | | | | | | | 95 | 99 (4) | | | | |
| 6 | 0.56 | 10 | 2.24 | | | | | 33 | 50 (34) | 97 | 95 (0) | | | | | | | 75 | 90 (16) | | | | | | | 99 | 99 (0) | | | | |
| 6 | 2.24 | 10 | 0.14 | | | | | 13 | 50 (74) | 90 | 95 (5) | | | | | | | 93 | 90 (0) | | | | | | | 83 | 99 (16) | | | | |
| 6 | 2.24 | 10 | 0.14 | | | | | 77 | 96 (19) | 100 | 99 (0) | | | | | | | 100 | 97 (0) | | | | | | | 97 | 100 (3) | | | | |

TABLE VII-continued

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB GRASS W | WO | PIG-WEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|---|
| 10 | 1.12 | 1 | 0.56 | | | | | | | | | | | | | | | | | | | | | 10 15 (33) | | 85 | 80 (0) |  |  |  |  |
| 10 | 1.12 | 1 | 0.56 | | | | | | | | | | | | | | | | | | | | | 25 50 (50) | | 90 | 80 (0) |  |  |  |  |
| 10 | 1.12 | 1 | 1.12 | | | | | | | | | | | | | | | | | | | | | 0 15 (100) | | 95 | 80 (0) |  |  |  |  |
| 10 | 1.12 | 1 | 1.12 | | | | | | | | | | | | | | | | | | | | | 30 50 (40) | | 90 | 80 (0) |  |  |  |  |
| 10 | 1.12 | 1 | 2.24 | | | | | | | | | | | | | | | | | | | | | 35 50 (30) | | 90 | 80 (0) |  |  |  |  |
| 10 | 1.12 | 1 | 2.24 | | | | | | | | | | | | | | | | | | | | | 15 15 (0) | | 75 | 80 (6) |  |  |  |  |
| 10 | 1.12 | 1 | 3.36 | | | | | | | | | | | | | | | | | | | | | 10 15 (33) | | 85 | 80 (0) |  |  |  |  |
| 10 | 1.12 | 1 | 3.36 | | | | | | | | | | | | | | | | | | | | | 20 50 (60) | | 90 | 80 (0) |  |  |  |  |
| 10 | 1.68 | 1 | 0.14 | | | | | | | | | | | | | | | | | | | | | 20 45 (55) | | 100 | 100 (0) |  |  |  |  |
| 10 | 1.68 | 1 | 0.56 | | | | | | | | | | | | | | | | | | | | | 15 45 (66) | | 100 | 100 (0) |  |  |  |  |
| 10 | 1.68 | 1 | 0.84 | | | | | | | | | | | | | | | | | | | | | 10 45 (77) | | 100 | 100 (0) |  |  |  |  |
| 10 | 1.68 | 1 | 0.84 | | | | | | | | | | | | | | | | | | | | | 10 17 (41) | | 100 | 100 (0) |  |  |  |  |
| 10 | 1.68 | 1 | 0.84 | | | | | | | | | | | | | | | | | | | | | 10 5 (0) | | 85 | 81 (0) |  |  |  |  |
| 10 | 1.68 | 1 | 0.84 | | | | | | | | | | | | | | | | | | | | | 58 72 (19) | | 100 | 100 (0) |  |  |  |  |
| 10 | 1.68 | 1 | 0.84 | | | | | | | | | | | | | | | | | | | | | 0 0 (0) | | 75 | 60 (0) |  |  |  |  |
| 10 | 1.68 | 1 | 0.84 | | | | | | | | | | | | | | | | | | | | | 0 30 (100) | | 100 | 97 (0) |  |  |  |  |
| 10 | 1.68 | 1 | 0.84 | | | | | | | | | | | | | | | | | | | | | 45 78 (42) | | 98 | 100 (2) |  |  |  |  |
| 10 | 1.68 | 1 | 0.84 | | | | | | | | | | | | | | | | | | | | | 35 75 (53) | | 100 | 100 (0) |  |  |  |  |
| 10 | 1.68 | 1 | 0.84 | | | | | | | | | | | | | | | | | | | | | 13 55 (76) | | 87 | 100 (13) |  |  |  |  |
| 10 | 1.68 | 1 | 1.68 | | | | | | | | | | | | | | | | | | | | | 8 17 (52) | | 95 | 100 (5) |  |  |  |  |
| 10 | 1.68 | 1 | 1.68 | | | | | | | | | | | | | | | | | | | | | 15 45 (66) | | 100 | 100 (0) |  |  |  |  |
| 10 | 1.68 | 1 | 1.68 | | | | | | | | | | | | | | | | | | | | | 15 30 (50) | | 90 | 97 (7) |  |  |  |  |
| 10 | 1.68 | 1 | 1.68 | | | | | | | | | | | | | | | | | | | | | 0 0 (0) | | 65 | 60 (0) |  |  |  |  |
| 10 | 1.68 | 1 | 1.68 | | | | | | | | | | | | | | | | | | | | | 38 78 (51) | | 100 | 100 (0) |  |  |  |  |

TABLE VII-continued

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB-GRASS W | WO | PIG-WEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|---|
| 10 | 1.68 | 1 | 1.68 | | | | | | | | | | | | | | | | | | | | | 23 55 (58) | | 85 100 (15) | | | | | |
| 10 | 1.68 | 1 | 1.68 | | | | | | | | | | | | | | | | | | | | | 50 72 (30) | | 100 100 (0) | | | | | |
| 10 | 1.68 | 1 | 1.68 | | | | | | | | | | | | | | | | | | | | | 47 75 (37) | | 100 100 (0) | | | | | |
| 10 | 1.68 | 1 | 1.68 | | | | | | | | | | | | | | | | | | | | | 17 5 (0) | | 95 81 (0) | | | | | |
| 10 | 1.68 | 1 | 2.24 | | | | | | | | | | | | | | | | | | | | | 10 45 (77) | | 100 100 (0) | | | | | |
| 10 | 1.68 | 1 | 3.36 | | | | | | | | | | | | | | | | | | | | | 0 17 (100) | | 100 100 (0) | | | | | |
| 10 | 1.68 | 1 | 3.36 | | | | | | | | | | | | | | | | | | | | | 8 45 (82) | | 100 100 (0) | | | | | |
| 10 | 1.68 | 1 | 3.36 | | | | | | | | | | | | | | | | | | | | | 25 78 (67) | | 100 100 (0) | | | | | |
| 10 | 1.68 | 1 | 3.36 | | | | | | | | | | | | | | | | | | | | | 50 72 (30) | | 100 100 (0) | | | | | |
| 10 | 1.68 | 1 | 3.36 | | | | | | | | | | | | | | | | | | | | | 35 75 (53) | | 99 100 (0) | | | | | |
| 10 | 1.68 | 1 | 3.36 | | | | | | | | | | | | | | | | | | | | | 45 5 (0) | | 70 81 (1) | | | | | |
| 10 | 1.68 | 1 | 3.36 | | | | | | | | | | | | | | | | | | | | | 30 55 (45) | | 88 100 (13) | | | | | |
| 10 | 1.68 | 1 | 3.36 | | | | | | | | | | | | | | | | | | | | | 20 30 (33) | | 95 97 (12) | | | | | |
| 10 | 1.68 | 1 | 3.36 | | | | | | | | | | | | | | | | | | | | | 0 0 (0) | | 35 60 (2) | | | | | |
| 10 | 2.24 | 1 | 0.56 | | | | | | | | | | | | | | | | | | | | | 10 25 (60) | | 95 100 (41) | | | | | |
| 10 | 2.24 | 1 | 0.56 | | | | | | | | | | | | | | | | | | | | | 45 65 (30) | | 100 90 (5) | | | | | |
| 10 | 2.24 | 1 | 1.12 | | | | | | | | | | | | | | | | | | | | | 15 25 (40) | | 80 100 (0) | | | | | |
| 10 | 2.24 | 1 | 1.12 | | | | | | | | | | | | | | | | | | | | | 35 65 (46) | | 100 90 (20) | | | | | |
| 10 | 2.24 | 1 | 2.24 | | | | | | | | | | | | | | | | | | | | | 30 65 (53) | | 100 90 (0) | | | | | |
| 10 | 2.24 | 1 | 2.24 | | | | | | | | | | | | | | | | | | | | | 10 25 (60) | | 90 100 (10) | | | | | |
| 10 | 2.24 | 1 | 3.36 | | | | | | | | | | | | | | | | | | | | | 5 25 (80) | | | | | | | |
| 10 | 2.24 | 1 | 3.36 | | | | | | | | | | | | | | | | | | | | | 25 65 (61) | | | | | | | |
| 10 | 2.24 | 1 | 0.14 | | | | | | | | | | | | | | | | | | | | | 35 63 (44) | | 100 100 (0) | | | | | |
| 10 | 3.36 | 1 | 0.56 | | | | | | | | | | | | | | | | | | | | | 40 63 (36) | | | | | | | |

TABLE VII-continued

| | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | % PLANT INHIBITION AND % SAFENING EFFECT ( ) | | | | | | | | | | | | | | | | | |
| HERBICIDE | | ANTIDOTE | | WHEAT | | DOWNEY BROME | | SORGHUM GRAIN | | GREEN FOXTAIL | | WILD OATS | | JOHNSON GRASS | | SHATTER CANE | | CRAB-GRASS | | PIG-WEED | | PROSO MILLET | | RICE | | BARNYARD GRASS | | SORGHUM | | SOYBEAN | |
| NO. | RATE | NO. | RATE | W | WO | W | WO | W | WO | W | WO | W | WO | W | WO | W | WO | W | WO | W | WO | W | WO | W | WO | W | WO | W | WO | W | WO |
| 10 | 3.36 | 1 | 0.84 | | | | | | | | | | | | | | | | | | | | | 5 | 60 (91) | 100 | 100 (0) | | | | |
| 10 | 3.36 | 1 | 0.84 | | | | | | | | | | | | | | | | | | | | | 25 | 72 (65) | 100 | 100 (0) | | | | |
| 10 | 3.36 | 1 | 0.84 | | | | | | | | | | | | | | | | | | | | | 15 | 20 (25) | 90 | 100 (10) | | | | |
| 10 | 3.36 | 1 | 0.84 | | | | | | | | | | | | | | | | | | | | | 80 | 88 (9) | 100 | 100 (0) | | | | |
| 10 | 3.36 | 1 | 0.84 | | | | | | | | | | | | | | | | | | | | | 48 | 90 (46) | 99 | 100 (1) | | | | |
| 10 | 3.36 | 1 | 0.84 | | | | | | | | | | | | | | | | | | | | | 78 | 86 (9) | 100 | 100 (0) | | | | |
| 10 | 3.36 | 1 | 0.84 | | | | | | | | | | | | | | | | | | | | | 68 | 60 (0) | 100 | 100 (0) | | | | |
| 10 | 3.36 | 1 | 0.84 | | | | | | | | | | | | | | | | | | | | | 5 | 25 (80) | 99 | 95 (0) | | | | |
| 10 | 3.36 | 1 | 1.68 | | | | | | | | | | | | | | | | | | | | | 18 | 55 (67) | 97 | 99 (2) | | | | |
| 10 | 3.36 | 1 | 1.68 | | | | | | | | | | | | | | | | | | | | | 10 | 60 (83) | 100 | 100 (0) | | | | |
| 10 | 3.36 | 1 | 1.68 | | | | | | | | | | | | | | | | | | | | | 23 | 72 (68) | 100 | 100 (0) | | | | |
| 10 | 3.36 | 1 | 1.68 | | | | | | | | | | | | | | | | | | | | | 30 | 90 (66) | 87 | 100 (13) | | | | |
| 10 | 3.36 | 1 | 1.68 | | | | | | | | | | | | | | | | | | | | | 20 | 20 (0) | 80 | 100 (20) | | | | |
| 10 | 3.36 | 1 | 1.68 | | | | | | | | | | | | | | | | | | | | | 25 | 25 (0) | 98 | 95 (0) | | | | |
| 10 | 3.36 | 1 | 1.68 | | | | | | | | | | | | | | | | | | | | | 68 | 88 (22) | 100 | 100 (0) | | | | |
| 10 | 3.36 | 1 | 1.68 | | | | | | | | | | | | | | | | | | | | | 17 | 55 (69) | 99 | 99 (0) | | | | |
| 10 | 3.36 | 1 | 2.24 | | | | | | | | | | | | | | | | | | | | | 48 | 86 (44) | 100 | 100 (0) | | | | |
| 10 | 3.36 | 1 | 3.36 | | | | | | | | | | | | | | | | | | | | | 25 | 60 (58) | 97 | 100 (3) | | | | |
| 10 | 3.36 | 1 | 3.36 | | | | | | | | | | | | | | | | | | | | | 8 | 63 (87) | 100 | 100 (0) | | | | |
| 10 | 3.36 | 1 | 3.36 | | | | | | | | | | | | | | | | | | | | | 10 | 60 (83) | 100 | 100 (0) | | | | |
| 10 | 3.36 | 1 | 3.36 | | | | | | | | | | | | | | | | | | | | | 8 | 72 (88) | 100 | 100 (0) | | | | |
| 10 | 3.36 | 1 | 3.36 | | | | | | | | | | | | | | | | | | | | | 0 | 20 (100) | 60 | 100 (40) | | | | |
| 10 | 3.36 | 1 | 3.36 | | | | | | | | | | | | | | | | | | | | | 23 | 60 (61) | 99 | 100 (1) | | | | |
| 10 | 3.36 | 1 | 3.36 | | | | | | | | | | | | | | | | | | | | | 30 | 55 (45) | 97 | 99 (2) | | | | |

TABLE VII-continued

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB GRASS W | WO | PIG-WEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|---|
| 10 | 3.36 | 1 | 3.36 | | | | | | | | | | | | | | | | | | | | | 15 | 90 (83) | 85 | 100 (15) | | | | |
| 10 | 3.36 | 1 | 3.36 | | | | | | | | | | | | | | | | | | | | | 23 | 25 (8) | 98 | 95 (0) | | | | |
| 10 | 3.36 | 1 | 3.36 | | | | | | | | | | | | | | | | | | | | | 38 | 86 (55) | 100 | 100 (0) | | | | |
| 10 | 3.36 | 1 | 3.36 | | | | | | | | | | | | | | | | | | | | | 58 | 88 (34) | 100 | 100 (0) | | | | |
| 10 | 3.36 | 1 | 0.56 | | | | | | | | | | | | | | | | | | | | | 30 | 45 (33) | 90 | 100 (10) | | | | |
| 10 | 3.36 | 1 | 0.56 | | | | | | | | | | | | | | | | | | | | | 70 | 80 (12) | 100 | 100 (0) | | | | |
| 10 | 3.36 | 1 | 1.12 | | | | | | | | | | | | | | | | | | | | | 60 | 80 (25) | 90 | 100 (10) | | | | |
| 10 | 4.48 | 1 | 1.12 | | | | | | | | | | | | | | | | | | | | | 48 | 82 (41) | | | | | | |
| 10 | 4.48 | 1 | 1.12 | | | | | | | | | | | | | | | | | | | | | 95 | 98 (3) | | | | | | |
| 10 | 4.48 | 1 | 2.24 | | | | | | | | | | | | | | | | | | | | | 25 | 45 (44) | 100 | 100 (0) | | | | |
| 10 | 4.48 | 1 | 2.24 | | | | | | | | | | | | | | | | | | | | | 20 | 45 (55) | 100 | 100 (0) | | | | |
| 10 | 4.48 | 1 | 2.24 | | | | | | | | | | | | | | | | | | | | | 45 | 82 (45) | | | | | | |
| 10 | 4.48 | 1 | 2.24 | | | | | | | | | | | | | | | | | | | | | 55 | 80 (31) | 100 | 100 (0) | | | | |
| 10 | 4.48 | 1 | 3.36 | | | | | | | | | | | | | | | | | | | | | 55 | 98 (43) | | | | | | |
| 10 | 4.48 | 1 | 3.36 | | | | | | | | | | | | | | | | | | | | | 50 | 80 (37) | 100 | 100 (0) | | | | |
| 10 | 4.48 | 1 | 4.48 | | | | | | | | | | | | | | | | | | | | | 15 | 45 (66) | 100 | 100 (0) | | | | |
| 10 | 4.48 | 1 | 4.48 | | | | | | | | | | | | | | | | | | | | | 40 | 82 (51) | | | | | | |
| 10 | 4.48 | 1 | 8.96 | | | | | | | | | | | | | | | | | | | | | 68 | 98 (30) | | | | | | |
| 10 | 4.48 | 1 | 8.96 | | | | | | | | | | | | | | | | | | | | | 50 | 98 (48) | | | | | | |
| 10 | 6.72 | 1 | 0.14 | | | | | | | | | | | | | | | | | | | | | 38 | 82 (53) | | | | | | |
| 10 | 6.72 | 1 | 0.56 | | | | | | | | | | | | | | | | | | | | | 88 | 88 (0) | 100 | 100 (0) | | | | |
| 10 | 6.72 | 1 | 0.56 | | | | | | | | | | | | | | | | | | | | | 68 | 88 (22) | 100 | 100 (0) | | | | |
| 10 | 6.72 | 1 | 0.56 | | | | | | | | | | | | | | | | | | | | | 40 | 70 (42) | 100 | 100 (0) | | | | |
| 10 | 6.72 | 1 | 0.56 | | | | | | | | | | | | | | | | | | | | | 70 | 90 (22) | 100 | 100 (0) | | | | |

TABLE VII-continued

% PLANT INHIBITION AND % SAFENING EFFECT ( )

| HERBICIDE NO. | RATE | ANTIDOTE NO. | ANTIDOTE RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRAB GRASS W | CRAB GRASS WO | PIG- WEED W | PIG- WEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|---|
| 10 | 6.72 | 1 | 0.84 | | | | | | | | | | | | | | | | | | | | | 28 | 88 (68) | 100 | 100 (0) | | | | |
| 10 | 6.72 | 1 | 0.84 | | | | | | | | | | | | | | | | | | | | | 55 | 85 (35) | 100 | 100 (0) | | | | |
| 10 | 6.72 | 1 | 0.84 | | | | | | | | | | | | | | | | | | | | | 25 | 67 (62) | 97 | 97 (0) | | | | |
| 10 | 6.72 | 1 | 0.84 | | | | | | | | | | | | | | | | | | | | | 90 | 98 (8) | 100 | 100 (0) | | | | |
| 10 | 6.72 | 1 | 0.84 | | | | | | | | | | | | | | | | | | | | | 40 | 27 (0) | 99 | 97 (0) | | | | |
| 10 | 6.72 | 1 | 0.84 | | | | | | | | | | | | | | | | | | | | | 70 | 77 (9) | 100 | 100 (0) | | | | |
| 10 | 6.72 | 1 | 0.84 | | | | | | | | | | | | | | | | | | | | | 27 | 93 (70) | 100 | 100 (0) | | | | |
| 10 | 6.72 | 1 | 0.84 | | | | | | | | | | | | | | | | | | | | | 88 | 95 (7) | 100 | 100 (0) | | | | |
| 10 | 6.72 | 1 | 1.12 | | | | | | | | | | | | | | | | | | | | | 25 | 55 (54) | 90 | 100 (10) | | | | |
| 10 | 6.72 | 1 | 1.12 | | | | | | | | | | | | | | | | | | | | | 65 | 90 (27) | 100 | 100 (0) | | | | |
| 10 | 6.72 | 1 | 1.68 | | | | | | | | | | | | | | | | | | | | | 20 | 70 (71) | 100 | 100 (0) | | | | |
| 10 | 6.72 | 1 | 1.68 | | | | | | | | | | | | | | | | | | | | | 25 | 85 (70) | 100 | 100 (0) | | | | |
| 10 | 6.72 | 1 | 1.68 | | | | | | | | | | | | | | | | | | | | | 38 | 88 (56) | 100 | 100 (0) | | | | |
| 10 | 6.72 | 1 | 1.68 | | | | | | | | | | | | | | | | | | | | | 37 | 27 (0) | 95 | 97 (2) | | | | |
| 10 | 6.72 | 1 | 1.68 | | | | | | | | | | | | | | | | | | | | | 78 | 95 (17) | 100 | 100 (0) | | | | |
| 10 | 6.72 | 1 | 1.68 | | | | | | | | | | | | | | | | | | | | | 37 | 67 (44) | 97 | 97 (0) | | | | |
| 10 | 6.72 | 1 | 1.68 | | | | | | | | | | | | | | | | | | | | | 45 | 93 (51) | 95 | 100 (5) | | | | |
| 10 | 6.72 | 1 | 1.68 | | | | | | | | | | | | | | | | | | | | | 88 | 98 (10) | 100 | 100 (0) | | | | |
| 10 | 6.72 | 1 | 1.68 | | | | | | | | | | | | | | | | | | | | | 30 | 55 (45) | 95 | 100 (5) | | | | |
| 10 | 6.72 | 1 | 2.24 | | | | | | | | | | | | | | | | | | | | | 45 | 77 (41) | 100 | 100 (0) | | | | |
| 10 | 6.72 | 1 | 2.24 | | | | | | | | | | | | | | | | | | | | | 15 | 88 (82) | 100 | 100 (0) | | | | |
| 10 | 6.72 | 1 | 2.24 | | | | | | | | | | | | | | | | | | | | | 45 | 90 (50) | 100 | 100 (0) | | | | |
| 10 | 6.72 | 1 | 3.36 | | | | | | | | | | | | | | | | | | | | | 45 | 70 (35) | 100 | 100 (0) | | | | |
| 10 | 6.72 | 1 | 3.36 | | | | | | | | | | | | | | | | | | | | | 10 | 88 (88) | 100 | 100 (0) | | | | |

TABLE VII-continued

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB-GRASS W | WO | PIG-WEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|---|
| 10 | 6.72 | 1 | 3.36 | | | | | | | | | | | | | | | | | | | | | 10 | 85 (88) | 100 | 100 (0) | | | | |
| 10 | 6.72 | 1 | 3.36 | | | | | | | | | | | | | | | | | | | | | 75 | 98 (23) | 100 | 100 (0) | | | | |
| 10 | 6.72 | 1 | 3.36 | | | | | | | | | | | | | | | | | | | | | 33 | 27 (0) | 99 | 97 (0) | | | | |
| 10 | 6.72 | 1 | 3.36 | | | | | | | | | | | | | | | | | | | | | 20 | 55 (63) | 85 | 100 (15) | | | | |
| 10 | 6.72 | 1 | 3.36 | | | | | | | | | | | | | | | | | | | | | 55 | 77 (28) | 99 | 100 (1) | | | | |
| 10 | 6.72 | 1 | 3.36 | | | | | | | | | | | | | | | | | | | | | 68 | 93 (26) | 93 | 100 (7) | | | | |
| 10 | 6.72 | 1 | 3.36 | | | | | | | | | | | | | | | | | | | | | 13 | 67 (80) | 99 | 97 (0) | | | | |
| 10 | 6.72 | 1 | 3.36 | | | | | | | | | | | | | | | | | | | | | 85 | 95 (10) | 100 | 100 (0) | | | | |
| 10 | 6.72 | 1 | 3.36 | | | | | | | | | | | | | | | | | | | | | 60 | 90 (33) | 100 | 100 (0) | | | | |
| 10 | 4.48 | 2 | 1.12 | | | | | | | | | | | | | | | | | | | | | 15 | 70 (78) | 100 | 100 (0) | | | | |
| 10 | 4.48 | 2 | 1.12 | | | | | | | | | | | | | | | | | | | | | 78 | 82 (4) | | | | | | |
| 10 | 4.48 | 2 | 2.24 | | | | | | | | | | | | | | | | | | | | | 78 | 55 (0) | | | | | | |
| 10 | 4.48 | 2 | 2.24 | | | | | | | | | | | | | | | | | | | | | 82 | 55 (0) | | | | | | |
| 10 | 4.48 | 2 | 4.48 | | | | | | | | | | | | | | | | | | | | | 68 | 82 (17) | | | | | | |
| 10 | 4.48 | 2 | 4.48 | | | | | | | | | | | | | | | | | | | | | 45 | 55 (18) | | | | | | |
| 10 | 4.48 | 2 | 8.96 | | | | | | | | | | | | | | | | | | | | | 50 | 82 (39) | | | | | | |
| 10 | 4.48 | 2 | 8.96 | | | | | | | | | | | | | | | | | | | | | 45 | 82 (45) | | | | | | |
| 10 | 4.48 | 3 | 1.12 | | | | | | | | | | | | | | | | | | | | | 70 | 55 (0) | | | | | | |
| 10 | 4.48 | 3 | 1.12 | | | | | | | | | | | | | | | | | | | | | 38 | 82 (53) | | | | | | |
| 10 | 4.48 | 3 | 1.12 | | | | | | | | | | | | | | | | | | | | | 50 | 82 (39) | | | | | | |
| 10 | 4.48 | 3 | 2.24 | | | | | | | | | | | | | | | | | | | | | 78 | 55 (0) | | | | | | |
| 10 | 4.48 | 3 | 2.24 | | | | | | | | | | | | | | | | | | | | | 20 | 55 (63) | | | | | | |
| 10 | 4.48 | 3 | 2.24 | | | | | | | | | | | | | | | | | | | | | 35 | 82 (57) | | | | | | |
| 10 | 4.48 | 3 | 2.24 | | | | | | | | | | | | | | | | | | | | | 52 | 82 (36) | | | | | | |

TABLE VII-continued

% PLANT INHIBITION AND % SAFENING EFFECT ( )

| HERBICIDE NO. | HERBICIDE RATE | ANTIDOTE NO. | ANTIDOTE RATE | WHEAT W | WHEAT WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRABGRASS W | WO | PIGWEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|---|
| 10 | 4.48 | 3 | 4.48 | | | | | | | | | | | | | | | | | | | | | 40 | 55 (27) | | | | | | |
| 10 | 4.48 | 3 | 4.48 | | | | | | | | | | | | | | | | | | | | | 48 | 82 (41) | | | | | | |
| 10 | 4.48 | 3 | 4.48 | | | | | | | | | | | | | | | | | | | | | 25 | 82 (69) | | | | | | |
| 10 | 4.48 | 3 | 8.96 | | | | | | | | | | | | | | | | | | | | | 25 | 82 (69) | | | | | | |
| 10 | 4.48 | 3 | 8.96 | | | | | | | | | | | | | | | | | | | | | 20 | 82 (75) | | | | | | |
| 10 | 4.48 | 3 | 8.96 | | | | | | | | | | | | | | | | | | | | | 18 | 55 (67) | | | | | | |
| 10 | 4.48 | 4 | 1.12 | | | | | | | | | | | | | | | | | | | | | 95 | 98 (3) | | | | | | |
| 10 | 4.48 | 4 | 2.24 | | | | | | | | | | | | | | | | | | | | | 85 | 98 (13) | | | | | | |
| 10 | 4.48 | 4 | 4.48 | | | | | | | | | | | | | | | | | | | | | 75 | 98 (23) | | | | | | |
| 10 | 4.48 | 4 | 8.96 | | | | | | | | | | | | | | | | | | | | | 80 | 98 (18) | | | | | | |
| 10 | 4.48 | 5 | 1.12 | | | | | | | | | | | | | | | | | | | | | 45 | 98 (54) | | | | | | |
| 10 | 4.48 | 5 | 2.24 | | | | | | | | | | | | | | | | | | | | | 50 | 98 (48) | | | | | | |
| 10 | 4.48 | 5 | 4.48 | | | | | | | | | | | | | | | | | | | | | 52 | 98 (46) | | | | | | |
| 10 | 4.48 | 5 | 8.96 | | | | | | | | | | | | | | | | | | | | | 60 | 98 (38) | | | | | | |
| 10 | 1.68 | 6 | 0.84 | | | | | | | | | | | | | | | | | | | | | 5 | 30 (83) | 90 | 97 (7) | | | | |
| 10 | 1.68 | 6 | 1.68 | | | | | | | | | | | | | | | | | | | | | 13 | 30 (56) | 92 | 97 (5) | | | | |
| 10 | 1.68 | 6 | 3.36 | | | | | | | | | | | | | | | | | | | | | 17 | 30 (43) | 97 | 97 (0) | | | | |
| 10 | 3.36 | 6 | 0.84 | | | | | | | | | | | | | | | | | | | | | 23 | 55 (58) | 95 | 99 (4) | | | | |
| 10 | 3.36 | 6 | 1.68 | | | | | | | | | | | | | | | | | | | | | 15 | 55 (72) | 97 | 99 (2) | | | | |
| 10 | 3.36 | 6 | 3.36 | | | | | | | | | | | | | | | | | | | | | 40 | 55 (27) | 97 | 99 (2) | | | | |
| 10 | 6.72 | 6 | 0.84 | | | | | | | | | | | | | | | | | | | | | 33 | 67 (50) | 100 | 97 (0) | | | | |
| 10 | 6.72 | 6 | 1.68 | | | | | | | | | | | | | | | | | | | | | 25 | 67 (62) | 99 | 97 (0) | | | | |
| 10 | 6.72 | 6 | 3.36 | | | | | | | | | | | | | | | | | | | | | 10 | 67 (85) | 100 | 97 (0) | | | | |
| 10 | 4.48 | 8 | 1.12 | | | | | | | | | | | | | | | | | | | | | 48 | 82 (41) | | | | | | |

TABLE VII-continued

% PLANT INHIBITION AND % SAFENING EFFECT ( )

| HERBICIDE NO. | RATE | ANTIDOTE NO. | RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRAB GRASS W | CRAB GRASS WO | PIG-WEED W | PIG-WEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|
| 10 | 4.48 | 8 | 2.24 | | | | | | | | | | | | | | | | | | | | | 30 (63) | 82 | | | | | | |
| 10 | 4.48 | 8 | 4.48 | | | | | | | | | | | | | | | | | | | | | 35 (57) | 82 | | | | | | |
| 10 | 4.48 | 8 | 8.96 | | | | | | | | | | | | | | | | | | | | | 30 (63) | 82 | | | | | | |
| 10 | 4.48 | 10 | 1.12 | | | | | | | | | | | | | | | | | | | | | 50 (39) | 82 | | | | | | |
| 10 | 4.48 | 10 | 1.12 | | | | | | | | | | | | | | | | | | | | | 70 (0) | 55 | | | | | | |
| 10 | 4.48 | 10 | 2.24 | | | | | | | | | | | | | | | | | | | | | 45 (45) | 82 | | | | | | |
| 10 | 4.48 | 10 | 2.24 | | | | | | | | | | | | | | | | | | | | | 52 (5) | 55 | | | | | | |
| 10 | 4.48 | 10 | 4.48 | | | | | | | | | | | | | | | | | | | | | 35 (57) | 82 | | | | | | |
| 10 | 4.48 | 10 | 4.48 | | | | | | | | | | | | | | | | | | | | | 78 (0) | 55 | | | | | | |
| 10 | 4.48 | 10 | 8.96 | | | | | | | | | | | | | | | | | | | | | 45 (18) | 55 | | | | | | |
| 10 | 4.48 | 10 | 8.96 | | | | | | | | | | | | | | | | | | | | | 40 (51) | 82 | | | | | | |
| 10 | 4.48 | 12 | 1.12 | | | | | | | | | | | | | | | | | | | | | 50 (39) | 82 | | | | | | |
| 10 | 4.48 | 12 | 2.24 | | | | | | | | | | | | | | | | | | | | | 40 (51) | 82 | | | | | | |
| 10 | 4.48 | 12 | 2.24 | | | | | | | | | | | | | | | | | | | | | 18 (78) | 82 | | | | | | |
| 10 | 4.48 | 12 | 4.48 | | | | | | | | | | | | | | | | | | | | | 10 (87) | 82 | | | | | | |
| 10 | 4.48 | 12 | 8.96 | | | | | | | | | | | | | | | | | | | | | 55 (32) | 82 | | | | | | |
| 10 | 4.48 | 13 | 1.12 | | | | | | | | | | | | | | | | | | | | | 62 (24) | 82 | | | | | | |
| 10 | 4.48 | 13 | 1.12 | | | | | | | | | | | | | | | | | | | | | 80 (2) | 82 | | | | | | |
| 10 | 4.48 | 13 | 2.24 | | | | | | | | | | | | | | | | | | | | | 45 (45) | 82 | | | | | | |
| 10 | 4.48 | 13 | 2.24 | | | | | | | | | | | | | | | | | | | | | 12 (85) | 82 | | | | | | |
| 10 | 4.48 | 13 | 4.48 | | | | | | | | | | | | | | | | | | | | | 68 (17) | 82 | | | | | | |
| 10 | 4.48 | 13 | 4.48 | | | | | | | | | | | | | | | | | | | | | 75 (8) | 82 | | | | | | |
| 10 | 4.48 | 13 | 8.96 | | | | | | | | | | | | | | | | | | | | | 35 (57) | 82 | | | | | | |
| 10 | 4.48 | 13 | 8.96 | | | | | | | | | | | | | | | | | | | | | 50 (39) | 82 | | | | | | |
| 10 | 4.48 | 14 | 1.12 | | | | | | | | | | | | | | | | | | | | | | | | | | | | |

TABLE VII-continued

% PLANT INHIBITION AND % SAFENING EFFECT ( )

| HERBICIDE NO. | RATE | ANTIDOTE NO. | RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRAB GRASS W | CRAB GRASS WO | PIG-WEED W | PIG-WEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|---|
| 10 | 4.48 | 14 | 2.24 | | | | | | | | | | | | | | | | | | | | | 30 | 82 (63) | | | | | | |
| 10 | 4.48 | 14 | 4.48 | | | | | | | | | | | | | | | | | | | | | 32 | 82 (60) | | | | | | |
| 10 | 4.48 | 14 | 8.96 | | | | | | | | | | | | | | | | | | | | | 30 | 82 (63) | | | | | | |
| 10 | 4.48 | 15 | 1.12 | | | | | | | | | | | | | | | | | | | | | 95 | 98 (3) | | | | | | |
| 10 | 4.48 | 15 | 2.24 | | | | | | | | | | | | | | | | | | | | | 92 | 98 (6) | | | | | | |
| 10 | 4.48 | 15 | 4.48 | | | | | | | | | | | | | | | | | | | | | 85 | 98 (13) | | | | | | |
| 10 | 4.48 | 15 | 8.96 | | | | | | | | | | | | | | | | | | | | | 85 | 98 (13) | | | | | | |
| 10 | 1.12 | 16 | 0.56 | | | | | | | | | | | | | | | | | | | | | 10 | 15 (33) | 90 | 80 (0) | | | | |
| 10 | 1.12 | 16 | 1.12 | | | | | | | | | | | | | | | | | | | | | 15 | 15 (0) | 80 | 80 (0) | | | | |
| 10 | 1.12 | 16 | 2.24 | | | | | | | | | | | | | | | | | | | | | 15 | 15 (0) | 90 | 80 (0) | | | | |
| 10 | 1.12 | 16 | 3.36 | | | | | | | | | | | | | | | | | | | | | 20 | 15 (0) | 85 | 80 (0) | | | | |
| 10 | 1.68 | 16 | 0.84 | | | | | | | | | | | | | | | | | | | | | 10 | 30 (66) | 95 | 97 (2) | | | | |
| 10 | 1.68 | 16 | 1.68 | | | | | | | | | | | | | | | | | | | | | 8 | 30 (73) | 94 | 97 (3) | | | | |
| 10 | 1.68 | 16 | 3.36 | | | | | | | | | | | | | | | | | | | | | 20 | 30 (33) | 86 | 97 (11) | | | | |
| 10 | 2.24 | 16 | 0.56 | | | | | | | | | | | | | | | | | | | | | 10 | 25 (60) | 90 | 100 (10) | | | | |
| 10 | 2.24 | 16 | 1.12 | | | | | | | | | | | | | | | | | | | | | 15 | 25 (40) | 100 | 100 (0) | | | | |
| 10 | 2.24 | 16 | 2.24 | | | | | | | | | | | | | | | | | | | | | 20 | 25 (20) | 90 | 100 (10) | | | | |
| 10 | 2.24 | 16 | 3.36 | | | | | | | | | | | | | | | | | | | | | 15 | 25 (40) | 95 | 100 (5) | | | | |
| 10 | 3.36 | 16 | 0.84 | | | | | | | | | | | | | | | | | | | | | 15 | 55 (72) | 99 | 99 (0) | | | | |
| 10 | 3.36 | 16 | 1.68 | | | | | | | | | | | | | | | | | | | | | 13 | 55 (76) | 95 | 99 (4) | | | | |
| 10 | 3.36 | 16 | 3.36 | | | | | | | | | | | | | | | | | | | | | 18 | 55 (67) | 96 | 99 (3) | | | | |
| 10 | 4.48 | 16 | 0.56 | | | | | | | | | | | | | | | | | | | | | 35 | 45 (22) | 94 | 100 (5) | | | | |
| 10 | 4.48 | 16 | 1.12 | | | | | | | | | | | | | | | | | | | | | 20 | 45 (55) | 100 | 100 (0) | | | | |
| 10 | 4.48 | 16 | 1.12 | | | | | | | | | | | | | | | | | | | | | 28 | 82 (65) | | | | | | |

TABLE VII-continued

% PLANT INHIBITION AND % SAFENING EFFECT ( )

| HERBICIDE | | ANTIDOTE | | WHEAT | | DOWNEY BROME | | SORGHUM GRAIN | | GREEN FOXTAIL | | WILD OATS | | JOHNSON GRASS | | SHATTER CANE | | CRAB- GRASS | | PIG- WEED | | PROSO MILLET | | RICE | | BARNYARD GRASS | | SORGHUM | | SOYBEAN | |
|---|---|---|---|---|---|---|---|---|---|---|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO | W | WO | W | WO | W | WO | W | WO | W | WO | W | WO |
| 10 | 4.48 | 16 | 2.24 | | | | | | | | | | | | | | | | | | | | | 30 | 82 (63) | | | | | | |
| 10 | 4.48 | 16 | 2.24 | | | | | | | | | | | | | | | | | | | | | 35 | 45 (22) | 100 | 100 (0) | | | | |
| 10 | 4.48 | 16 | 3.36 | | | | | | | | | | | | | | | | | | | | | 30 | 45 (33) | 100 | 100 (0) | | | | |
| 10 | 4.48 | 16 | 4.48 | | | | | | | | | | | | | | | | | | | | | 30 | 82 (63) | | | | | | |
| 10 | 4.48 | 16 | 8.96 | | | | | | | | | | | | | | | | | | | | | 15 | 82 (81) | | | | | | |
| 10 | 6.72 | 16 | 0.56 | | | | | | | | | | | | | | | | | | | | | 30 | 70 (57) | 90 | 100 (10) | | | | |
| 10 | 6.72 | 16 | 0.84 | | | | | | | | | | | | | | | | | | | | | 17 | 67 (74) | 90 | 97 (7) | | | | |
| 10 | 6.72 | 16 | 1.12 | | | | | | | | | | | | | | | | | | | | | 30 | 70 (57) | 100 | 100 (0) | | | | |
| 10 | 6.72 | 16 | 1.68 | | | | | | | | | | | | | | | | | | | | | 20 | 67 (70) | 99 | 97 (0) | | | | |
| 10 | 6.72 | 16 | 2.24 | | | | | | | | | | | | | | | | | | | | | 35 | 70 (50) | 100 | 100 (0) | | | | |
| 10 | 6.72 | 16 | 3.36 | | | | | | | | | | | | | | | | | | | | | 40 | 70 (42) | 90 | 100 (10) | | | | |
| 10 | 6.72 | 16 | 3.36 | | | | | | | | | | | | | | | | | | | | | 20 | 67 (70) | 97 | 97 (0) | | | | |
| 10 | 4.48 | 18 | 1.12 | | | | | | | | | | | | | | | | | | | | | 62 | 98 (36) | | | | | | |
| 10 | 4.48 | 18 | 2.24 | | | | | | | | | | | | | | | | | | | | | 60 | 98 (38) | | | | | | |
| 10 | 4.48 | 18 | 4.48 | | | | | | | | | | | | | | | | | | | | | 50 | 98 (48) | | | | | | |
| 10 | 4.48 | 18 | 8.96 | | | | | | | | | | | | | | | | | | | | | 52 | 98 (46) | | | | | | |
| 10 | 4.48 | 19 | 1.12 | | | | | | | | | | | | | | | | | | | | | 62 | 82 (24) | | | | | | |
| 10 | 4.48 | 19 | 2.24 | | | | | | | | | | | | | | | | | | | | | 48 | 82 (41) | | | | | | |
| 10 | 4.48 | 19 | 4.48 | | | | | | | | | | | | | | | | | | | | | 45 | 82 (45) | | | | | | |
| 10 | 4.48 | 19 | 8.96 | | | | | | | | | | | | | | | | | | | | | 28 | 82 (65) | | | | | | |
| 10 | 4.48 | 20 | 1.12 | | | | | | | | | | | | | | | | | | | | | 65 | 82 (20) | | | | | | |
| 10 | 4.48 | 20 | 2.24 | | | | | | | | | | | | | | | | | | | | | 55 | 82 (32) | | | | | | |
| 10 | 4.48 | 20 | 4.48 | | | | | | | | | | | | | | | | | | | | | 60 | 82 (26) | | | | | | |
| 10 | 4.48 | 20 | 8.96 | | | | | | | | | | | | | | | | | | | | | 55 | 82 (32) | | | | | | |

TABLE VII-continued

% PLANT INHIBITION AND % SAFENING EFFECT ( )

| HERBICIDE NO. | RATE | ANTIDOTE NO. | RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRAB-GRASS W | CRAB-GRASS WO | PIG-WEED W | PIG-WEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|
| 10 | 1.68 | 21 | 0.84 | | | | | | | | | | | | | | | | | | | | | | 0 | 0 (0) | 85 | 60 (0) | | | | |
| 10 | 1.68 | 21 | 1.68 | | | | | | | | | | | | | | | | | | | | | | 0 | 0 (0) | 95 | 60 (0) | | | | |
| 10 | 3.36 | 21 | 0.84 | | | | | | | | | | | | | | | | | | | | | | 10 | 20 (50) | 100 | 100 (0) | | | | |
| 10 | 3.36 | 21 | 1.68 | | | | | | | | | | | | | | | | | | | | | | 10 | 20 (50) | 100 | 100 (0) | | | | |
| 10 | 3.36 | 21 | 3.36 | | | | | | | | | | | | | | | | | | | | | | 10 | 20 (50) | 90 | 100 (10) | | | | |
| 10 | 6.72 | 21 | 0.84 | | | | | | | | | | | | | | | | | | | | | | 20 | 55 (63) | 80 | 100 (20) | | | | |
| 10 | 6.72 | 21 | 1.68 | | | | | | | | | | | | | | | | | | | | | | 10 | 55 (81) | 100 | 100 (0) | | | | |
| 10 | 6.72 | 21 | 3.36 | | | | | | | | | | | | | | | | | | | | | | 25 | 55 (54) | 100 | 100 (0) | | | | |
| 10 | 1.12 | 22 | 0.56 | | | | | | | | | | | | | | | | | | | | | | 35 | 50 (30) | 100 | 80 (0) | | | | |
| 10 | 1.12 | 22 | 1.12 | | | | | | | | | | | | | | | | | | | | | | 20 | 50 (60) | 95 | 80 (0) | | | | |
| 10 | 1.12 | 22 | 2.24 | | | | | | | | | | | | | | | | | | | | | | 35 | 50 (30) | 95 | 80 (0) | | | | |
| 10 | 1.12 | 22 | 3.36 | | | | | | | | | | | | | | | | | | | | | | 25 | 50 (50) | 100 | 80 (0) | | | | |
| 10 | 1.68 | 22 | 0.84 | | | | | | | | | | | | | | | | | | | | | | 0 | 0 (0) | 95 | 60 (0) | | | | |
| 10 | 1.68 | 22 | 1.68 | | | | | | | | | | | | | | | | | | | | | | 0 | 0 (0) | 90 | 60 (0) | | | | |
| 10 | 1.68 | 22 | 3.36 | | | | | | | | | | | | | | | | | | | | | | 0 | 0 (0) | 90 | 60 (0) | | | | |
| 10 | 2.24 | 22 | 0.56 | | | | | | | | | | | | | | | | | | | | | | 40 | 65 (38) | 100 | 90 (0) | | | | |
| 10 | 2.24 | 22 | 1.12 | | | | | | | | | | | | | | | | | | | | | | 30 | 65 (53) | 95 | 90 (0) | | | | |
| 10 | 2.24 | 22 | 2.24 | | | | | | | | | | | | | | | | | | | | | | 30 | 65 (53) | 95 | 90 (0) | | | | |
| 10 | 2.24 | 22 | 3.36 | | | | | | | | | | | | | | | | | | | | | | 20 | 65 (69) | 100 | 90 (0) | | | | |
| 10 | 3.36 | 22 | 0.84 | | | | | | | | | | | | | | | | | | | | | | 0 | 20 (100) | 100 | 100 (0) | | | | |
| 10 | 3.36 | 22 | 1.68 | | | | | | | | | | | | | | | | | | | | | | 0 | 20 (100) | 95 | 100 (5) | | | | |
| 10 | 3.36 | 22 | 3.36 | | | | | | | | | | | | | | | | | | | | | | 15 | 20 (25) | 75 | 100 (25) | | | | |
| 10 | 4.48 | 22 | 0.56 | | | | | | | | | | | | | | | | | | | | | | 55 | 80 (31) | 100 | 100 (0) | | | | |
| 10 | 4.48 | 22 | 1.12 | | | | | | | | | | | | | | | | | | | | | | 50 | 80 (37) | 95 | 100 (5) | | | | |

TABLE VII-continued

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB- GRASS W | WO | PIG- WEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|
| 10 | 4.48 | 22 | 1.12 | | | | | | | | | | | | | | | | | | | | | 20 (63) | 55 | | | | | | |
| 10 | 4.48 | 22 | 2.24 | | | | | | | | | | | | | | | | | | | | | 48 (12) | 55 | 100 (0) | 100 | | | | |
| 10 | 4.48 | 22 | 2.24 | | | | | | | | | | | | | | | | | | | | | 60 (25) | 80 | 100 (0) | 100 | | | | |
| 10 | 4.48 | 22 | 3.36 | | | | | | | | | | | | | | | | | | | | | 50 (37) | 80 | | | | | | |
| 10 | 4.48 | 22 | 4.48 | | | | | | | | | | | | | | | | | | | | | 32 (41) | 55 | | | | | | |
| 10 | 4.48 | 22 | 8.96 | | | | | | | | | | | | | | | | | | | | | 32 (41) | 55 | 100 (0) | 100 | | | | |
| 10 | 6.72 | 22 | 0.56 | | | | | | | | | | | | | | | | | | | | | 70 (22) | 90 | 95 (5) | 100 | | | | |
| 10 | 6.72 | 22 | 0.84 | | | | | | | | | | | | | | | | | | | | | 0 (100) | 55 | 100 (0) | 100 | | | | |
| 10 | 6.72 | 22 | 1.12 | | | | | | | | | | | | | | | | | | | | | 65 (27) | 90 | 90 (10) | 100 | | | | |
| 10 | 6.72 | 22 | 1.68 | | | | | | | | | | | | | | | | | | | | | 0 (100) | 55 | 100 (0) | 100 | | | | |
| 10 | 6.72 | 22 | 2.24 | | | | | | | | | | | | | | | | | | | | | 60 (33) | 90 | 75 (25) | 100 | | | | |
| 10 | 6.72 | 22 | 3.36 | | | | | | | | | | | | | | | | | | | | | 0 (100) | 55 | 100 (0) | 100 | | | | |
| 10 | 6.72 | 22 | 3.36 | | | | | | | | | | | | | | | | | | | | | 55 (38) | 90 | 100 (0) | 100 | | | | |
| 10 | 1.68 | 24 | 0.14 | | | | | | | | | | | | | | | | | | | | | 13 (71) | 45 | 100 (0) | 100 | | | | |
| 10 | 1.68 | 24 | 0.43 | | | | | | | | | | | | | | | | | | | | | 5 (85) | 35 | 100 (0) | 100 | | | | |
| 10 | 1.68 | 24 | 0.56 | | | | | | | | | | | | | | | | | | | | | 5 (88) | 45 | 100 (0) | 100 | | | | |
| 10 | 1.68 | 24 | 0.56 | | | | | | | | | | | | | | | | | | | | | 38 (0) | 37 | 100 (0) | 100 | | | | |
| 10 | 1.68 | 24 | 0.84 | | | | | | | | | | | | | | | | | | | | | 0 (100) | 45 | 98 (2) | 100 | | | | |
| 10 | 1.68 | 24 | 0.84 | | | | | | | | | | | | | | | | | | | | | 20 (65) | 17 | 100 (0) | 100 | | | | |
| 10 | 1.68 | 24 | 0.84 | | | | | | | | | | | | | | | | | | | | | 8 (65) | 23 | 100 (0) | 100 | | | | |
| 10 | 1.68 | 24 | 0.84 | | | | | | | | | | | | | | | | | | | | | 0 (100) | 35 | 100 (0) | 100 | | | | |
| 10 | 1.68 | 24 | 0.84 | | | | | | | | | | | | | | | | | | | | | 5 (93) | 78 | 100 (0) | 100 | | | | |
| 10 | 1.68 | 24 | 0.84 | | | | | | | | | | | | | | | | | | | | | 0 (100) | 8 | 100 (0) | 100 | | | | |
| 10 | 1.68 | 24 | 0.84 | | | | | | | | | | | | | | | | | | | | | 0 (0) | 0 | 100 (0) | 100 | | | | |

TABLE VII-continued

% PLANT INHIBITION AND % SAFENING EFFECT ( )

| HERBICIDE NO. | RATE | ANTIDOTE NO. | RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRABGRASS W | CRABGRASS WO | PIGWEED W | PIGWEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|---|
| 10 | 1.68 | 24 | 0.84 | | | | | | | | | | | | | | | | | | | | | 28 (0) | 23 | 100 (0) | 100 | | | | |
| 10 | 1.68 | 24 | 0.84 | | | | | | | | | | | | | | | | | | | | | 8 (84) | 50 | 100 (0) | 100 | | | | |
| 10 | 1.68 | 24 | 0.84 | | | | | | | | | | | | | | | | | | | | | 0 (100) | 8 | 100 (0) | 100 | | | | |
| 10 | 1.68 | 24 | 0.84 | | | | | | | | | | | | | | | | | | | | | 10 (71) | 35 | 100 (0) | 100 | | | | |
| 10 | 1.68 | 24 | 1.12 | | | | | | | | | | | | | | | | | | | | | 8 (78) | 37 | 98 (2) | 100 | | | | |
| 10 | 1.68 | 24 | 1.68 | | | | | | | | | | | | | | | | | | | | | 8 (52) | 17 | 100 (0) | 100 | | | | |
| 10 | 1.68 | 24 | 1.68 | | | | | | | | | | | | | | | | | | | | | 0 (100) | 35 | 100 (0) | 100 | | | | |
| 10 | 1.68 | 24 | 1.68 | | | | | | | | | | | | | | | | | | | | | 5 (78) | 23 | 100 (0) | 100 | | | | |
| 10 | 1.68 | 24 | 1.68 | | | | | | | | | | | | | | | | | | | | | 10 (77) | 45 | 100 (0) | 100 | | | | |
| 10 | 1.68 | 24 | 1.68 | | | | | | | | | | | | | | | | | | | | | 13 (43) | 23 | 98 (2) | 100 | | | | |
| 10 | 1.68 | 24 | 1.68 | | | | | | | | | | | | | | | | | | | | | 23 (54) | 50 | 100 (0) | 100 | | | | |
| 10 | 1.68 | 24 | 1.68 | | | | | | | | | | | | | | | | | | | | | 10 (87) | 78 | 100 (0) | 100 | | | | |
| 10 | 1.68 | 24 | 1.68 | | | | | | | | | | | | | | | | | | | | | 0 (100) | 8 | 100 (0) | 100 | | | | |
| 10 | 1.68 | 24 | 1.68 | | | | | | | | | | | | | | | | | | | | | 5 (85) | 35 | 100 (0) | 100 | | | | |
| 10 | 1.68 | 24 | 1.68 | | | | | | | | | | | | | | | | | | | | | 0 (0) | 0 | 100 (0) | 100 | | | | |
| 10 | 1.68 | 24 | 2.24 | | | | | | | | | | | | | | | | | | | | | 13 (0) | 8 | 98 (2) | 100 | | | | |
| 10 | 1.68 | 24 | 2.24 | | | | | | | | | | | | | | | | | | | | | 13 (71) | 45 | 100 (0) | 100 | | | | |
| 10 | 1.68 | 24 | 3.36 | | | | | | | | | | | | | | | | | | | | | 55 (0) | 37 | 100 (0) | 100 | | | | |
| 10 | 1.68 | 24 | 3.36 | | | | | | | | | | | | | | | | | | | | | 0 (100) | 35 | 100 (0) | 100 | | | | |
| 10 | 1.68 | 24 | 3.36 | | | | | | | | | | | | | | | | | | | | | 0 (100) | 23 | 100 (0) | 100 | | | | |
| 10 | 1.68 | 24 | 3.36 | | | | | | | | | | | | | | | | | | | | | 5 (88) | 45 | 100 (0) | 100 | | | | |
| 10 | 1.68 | 24 | 3.36 | | | | | | | | | | | | | | | | | | | | | 0 (100) | 17 | 100 (0) | 100 | | | | |
| 10 | 1.68 | 24 | 3.36 | | | | | | | | | | | | | | | | | | | | | 0 (0) | 0 | 100 (0) | 100 | | | | |
| 10 | 1.68 | 24 | 3.36 | | | | | | | | | | | | | | | | | | | | | 5 (37) | 8 | 100 (0) | 100 | | | | |

TABLE VII-continued

% PLANT INHIBITION AND % SAFENING EFFECT ( )

| HERBICIDE NO. | RATE | ANTIDOTE NO. | RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRAB-GRASS W | CRAB-GRASS WO | PIG-WEED W | PIG-WEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|---|
| 10 | 1.68 | 24 | 3.36 | | | | | | | | | | | | | | | | | | | | | 0 (100) | 23 | 100 (0) | 100 | | | | |
| 10 | 1.68 | 24 | 3.36 | | | | | | | | | | | | | | | | | | | | | 5 (37) | 8 | 100 (0) | 100 | | | | |
| 10 | 1.68 | 24 | 3.36 | | | | | | | | | | | | | | | | | | | | | 5 (93) | 78 | 100 (0) | 100 | | | | |
| 10 | 1.68 | 24 | 3.36 | | | | | | | | | | | | | | | | | | | | | 5 (85) | 35 | 100 (0) | 100 | | | | |
| 10 | 1.68 | 24 | 3.36 | | | | | | | | | | | | | | | | | | | | | 20 (60) | 50 | 100 (0) | 100 | | | | |
| 10 | 3.36 | 24 | 0.14 | | | | | | | | | | | | | | | | | | | | | 18 (71) | 63 | 100 (0) | 100 | | | | |
| 10 | 3.36 | 24 | 0.43 | | | | | | | | | | | | | | | | | | | | | 55 (12) | 63 | 100 (0) | 100 | | | | |
| 10 | 3.36 | 24 | 0.56 | | | | | | | | | | | | | | | | | | | | | 13 (79) | 63 | 100 (0) | 100 | | | | |
| 10 | 3.36 | 24 | 0.56 | | | | | | | | | | | | | | | | | | | | | 25 (63) | 68 | 98 (2) | 100 | | | | |
| 10 | 3.36 | 24 | 0.84 | | | | | | | | | | | | | | | | | | | | | 8 (87) | 63 | 100 (0) | 100 | | | | |
| 10 | 3.36 | 24 | 0.84 | | | | | | | | | | | | | | | | | | | | | 23 (70) | 78 | 100 (0) | 100 | | | | |
| 10 | 3.36 | 24 | 0.84 | | | | | | | | | | | | | | | | | | | | | 18 (75) | 72 | 100 (0) | 100 | | | | |
| 10 | 3.36 | 24 | 0.84 | | | | | | | | | | | | | | | | | | | | | 30 (50) | 60 | 100 (0) | 100 | | | | |
| 10 | 3.36 | 24 | 0.84 | | | | | | | | | | | | | | | | | | | | | 10 (80) | 50 | 100 (0) | 100 | | | | |
| 10 | 3.36 | 24 | 0.84 | | | | | | | | | | | | | | | | | | | | | 0 (100) | 23 | 100 (0) | 100 | | | | |
| 10 | 3.36 | 24 | 0.84 | | | | | | | | | | | | | | | | | | | | | 25 (70) | 86 | 100 (0) | 100 | | | | |
| 10 | 3.36 | 24 | 0.84 | | | | | | | | | | | | | | | | | | | | | 10 (0) | 8 | 95 (5) | 100 | | | | |
| 10 | 3.36 | 24 | 0.84 | | | | | | | | | | | | | | | | | | | | | 25 (64) | 70 | 100 (0) | 100 | | | | |
| 10 | 3.36 | 24 | 0.84 | | | | | | | | | | | | | | | | | | | | | 20 (70) | 67 | 95 (5) | 100 | | | | |
| 10 | 3.36 | 24 | 1.12 | | | | | | | | | | | | | | | | | | | | | 5 (85) | 35 | 100 (0) | 100 | | | | |
| 10 | 3.36 | 24 | 1.68 | | | | | | | | | | | | | | | | | | | | | 23 (66) | 68 | 100 (0) | 100 | | | | |
| 10 | 3.36 | 24 | 1.68 | | | | | | | | | | | | | | | | | | | | | 10 (87) | 78 | 95 (5) | 100 | | | | |
| 10 | 3.36 | 24 | 1.68 | | | | | | | | | | | | | | | | | | | | | 5 (92) | 63 | 100 (0) | 100 | | | | |
| 10 | 3.36 | 24 | 1.68 | | | | | | | | | | | | | | | | | | | | | 0 (100) | 60 | 100 (0) | 100 | | | | |

TABLE VII-continued

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB GRASS W | WO | PIG-WEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|---|
| 10 | 3.36 | 24 | 1.68 | | | | | | | | | | | | | | | | | | | | | 13 (81) | 72 | 100 | 100 (0) | | | | |
| 10 | 3.36 | 24 | 1.68 | | | | | | | | | | | | | | | | | | | | | 10 (85) | 70 | 100 | 100 (0) | | | | |
| 10 | 3.36 | 24 | 1.68 | | | | | | | | | | | | | | | | | | | | | 13 (84) | 86 | 100 | 100 (0) | | | | |
| 10 | 3.36 | 24 | 1.68 | | | | | | | | | | | | | | | | | | | | | 0 (100) | 35 | 100 | 100 (0) | | | | |
| 10 | 3.36 | 24 | 1.68 | | | | | | | | | | | | | | | | | | | | | 5 (92) | 67 | 100 | 100 (0) | | | | |
| 10 | 3.36 | 24 | 1.68 | | | | | | | | | | | | | | | | | | | | | 10 (80) | 50 | 100 | 100 (0) | | | | |
| 10 | 3.36 | 24 | 1.68 | | | | | | | | | | | | | | | | | | | | | 10 (0) | 8 | 100 | 100 (0) | | | | |
| 10 | 3.36 | 24 | 2.24 | | | | | | | | | | | | | | | | | | | | | 5 (78) | 23 | 100 | 100 (0) | | | | |
| 10 | 3.36 | 24 | 2.24 | | | | | | | | | | | | | | | | | | | | | 10 (84) | 63 | 100 | 100 (0) | | | | |
| 10 | 3.36 | 24 | 3.36 | | | | | | | | | | | | | | | | | | | | | 15 (77) | 68 | 95 | 100 (5) | | | | |
| 10 | 3.36 | 24 | 3.36 | | | | | | | | | | | | | | | | | | | | | 15 (76) | 63 | 100 | 100 (0) | | | | |
| 10 | 3.36 | 24 | 3.36 | | | | | | | | | | | | | | | | | | | | | 25 (67) | 78 | 100 | 100 (0) | | | | |
| 10 | 3.36 | 24 | 3.36 | | | | | | | | | | | | | | | | | | | | | 5 (93) | 72 | 100 | 100 (0) | | | | |
| 10 | 3.36 | 24 | 3.36 | | | | | | | | | | | | | | | | | | | | | 15 (75) | 60 | 100 | 100 (0) | | | | |
| 10 | 3.36 | 24 | 3.36 | | | | | | | | | | | | | | | | | | | | | 0 (100) | 8 | 100 | 100 (0) | | | | |
| 10 | 3.36 | 24 | 3.36 | | | | | | | | | | | | | | | | | | | | | 20 (60) | 50 | 100 | 100 (0) | | | | |
| 10 | 3.36 | 24 | 3.36 | | | | | | | | | | | | | | | | | | | | | 5 (85) | 35 | 100 | 100 (0) | | | | |
| 10 | 3.36 | 24 | 3.36 | | | | | | | | | | | | | | | | | | | | | 10 (56) | 23 | 100 | 100 (0) | | | | |
| 10 | 3.36 | 24 | 3.36 | | | | | | | | | | | | | | | | | | | | | 35 (47) | 67 | 100 | 100 (0) | | | | |
| 10 | 3.36 | 24 | 3.36 | | | | | | | | | | | | | | | | | | | | | 20 (76) | 86 | 100 | 100 (0) | | | | |
| 10 | 4.48 | 24 | 1.12 | | | | | | | | | | | | | | | | | | | | | 38 (45) | 70 | 100 | 100 (0) | | | | |
| 10 | 4.48 | 24 | 1.12 | | | | | | | | | | | | | | | | | | | | | 50 (39) | 82 | | | | | | |
| 10 | 4.48 | 24 | 1.12 | | | | | | | | | | | | | | | | | | | | | 50 (39) | 82 | | | | | | |
| | | | | | | | | | | | | | | | | | | | | | | | | 35 (57) | 83 | | | | | | |

TABLE VII-continued

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB GRASS W | WO | PIG-WEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|---|
| 10 | 4.48 | 24 | 1.12 | | | | | | | | | | | | | | | | | | | | | 52 | 98 (46) | | | | | | |
| 10 | 4.48 | 24 | 1.12 | | | | | | | | | | | | | | | | | | | | | 28 | 55 (49) | | | | | | |
| 10 | 4.48 | 24 | 2.24 | | | | | | | | | | | | | | | | | | | | | 45 | 83 (45) | | | | | | |
| 10 | 4.48 | 24 | 2.24 | | | | | | | | | | | | | | | | | | | | | 8 | 55 (85) | | | | | | |
| 10 | 4.48 | 24 | 2.24 | | | | | | | | | | | | | | | | | | | | | 48 | 98 (51) | | | | | | |
| 10 | 4.48 | 24 | 2.24 | | | | | | | | | | | | | | | | | | | | | 35 | 82 (57) | | | | | | |
| 10 | 4.48 | 24 | 4.48 | | | | | | | | | | | | | | | | | | | | | 28 | 82 (65) | | | | | | |
| 10 | 4.48 | 24 | 4.48 | | | | | | | | | | | | | | | | | | | | | 25 | 82 (69) | | | | | | |
| 10 | 4.48 | 24 | 4.48 | | | | | | | | | | | | | | | | | | | | | 22 | 83 (73) | | | | | | |
| 10 | 4.48 | 24 | 4.48 | | | | | | | | | | | | | | | | | | | | | 20 | 82 (75) | | | | | | |
| 10 | 4.48 | 24 | 4.48 | | | | | | | | | | | | | | | | | | | | | 18 | 55 (67) | | | | | | |
| 10 | 4.48 | 24 | 8.96 | | | | | | | | | | | | | | | | | | | | | 58 | 98 (40) | | | | | | |
| 10 | 4.48 | 24 | 8.96 | | | | | | | | | | | | | | | | | | | | | 20 | 55 (63) | | | | | | |
| 10 | 4.48 | 24 | 8.96 | | | | | | | | | | | | | | | | | | | | | 10 | 83 (87) | | | | | | |
| 10 | 4.48 | 24 | 8.96 | | | | | | | | | | | | | | | | | | | | | 55 | 98 (43) | | | | | | |
| 10 | 6.72 | 24 | 0.14 | | | | | | | | | | | | | | | | | | | | | 22 | 82 (73) | | | | | | |
| 10 | 6.72 | 24 | 0.43 | | | | | | | | | | | | | | | | | | | | | 15 | 82 (81) | | | | | | |
| 10 | 6.72 | 24 | 0.56 | | | | | | | | | | | | | | | | | | | | | 45 | 88 (48) | 100 | 100 (0) | | | | |
| 10 | 6.72 | 24 | 0.56 | | | | | | | | | | | | | | | | | | | | | 68 | 88 (22) | 100 | 100 (0) | | | | |
| 10 | 6.72 | 24 | 0.84 | | | | | | | | | | | | | | | | | | | | | 25 | 88 (71) | 100 | 100 (0) | | | | |
| 10 | 6.72 | 24 | 0.84 | | | | | | | | | | | | | | | | | | | | | 30 | 82 (63) | 100 | 100 (0) | | | | |
| 10 | 6.72 | 24 | 0.84 | | | | | | | | | | | | | | | | | | | | | 33 | 85 (61) | 100 | 100 (0) | | | | |
| 10 | 6.72 | 24 | 0.84 | | | | | | | | | | | | | | | | | | | | | 55 | 88 (37) | 100 | 100 (0) | | | | |
| 10 | 6.72 | 24 | 0.84 | | | | | | | | | | | | | | | | | | | | | 13 | 88 (85) | 100 | 100 (0) | | | | |

TABLE VII-continued

% PLANT INHIBITION AND % SAFENING EFFECT ( )

| HERBICIDE NO. | HERBICIDE RATE | ANTIDOTE NO. | ANTIDOTE RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRAB-GRASS W | CRAB-GRASS WO | PIG-WEED W | PIG-WEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|---|
| 10 | 6.72 | 24 | 0.84 | | | | | | | | | | | | | | | | | | | | | 35 | 93 (62) | 100 | 100 (0) | | | | |
| 10 | 6.72 | 24 | 0.84 | | | | | | | | | | | | | | | | | | | | | 35 | 67 (47) | 100 | 100 (0) | | | | |
| 10 | 6.72 | 24 | 0.84 | | | | | | | | | | | | | | | | | | | | | 33 | 87 (62) | 100 | 100 (0) | | | | |
| 10 | 6.72 | 24 | 0.84 | | | | | | | | | | | | | | | | | | | | | 25 | 45 (44) | 100 | 100 (0) | | | | |
| 10 | 6.72 | 24 | 0.84 | | | | | | | | | | | | | | | | | | | | | 73 | 98 (25) | 100 | 100 (0) | | | | |
| 10 | 6.72 | 24 | 0.84 | | | | | | | | | | | | | | | | | | | | | 8 | 58 (86) | 100 | 100 (0) | | | | |
| 10 | 6.72 | 24 | 0.84 | | | | | | | | | | | | | | | | | | | | | 23 | 88 (73) | 12 | 100 (88) | | | | |
| 10 | 6.72 | 24 | 1.12 | | | | | | | | | | | | | | | | | | | | | 5 | 70 (92) | 100 | 100 (0) | | | | |
| 10 | 6.72 | 24 | 1.68 | | | | | | | | | | | | | | | | | | | | | 15 | 82 (81) | 100 | 100 (0) | | | | |
| 10 | 6.72 | 24 | 1.68 | | | | | | | | | | | | | | | | | | | | | 40 | 93 (56) | 95 | 100 (5) | | | | |
| 10 | 6.72 | 24 | 1.68 | | | | | | | | | | | | | | | | | | | | | 18 | 85 (78) | 100 | 100 (0) | | | | |
| 10 | 6.72 | 24 | 1.68 | | | | | | | | | | | | | | | | | | | | | 8 | 88 (90) | 100 | 100 (0) | | | | |
| 10 | 6.72 | 24 | 1.68 | | | | | | | | | | | | | | | | | | | | | 20 | 88 (77) | 100 | 100 (0) | | | | |
| 10 | 6.72 | 24 | 1.68 | | | | | | | | | | | | | | | | | | | | | 35 | 87 (59) | 100 | 100 (0) | | | | |
| 10 | 6.72 | 24 | 1.68 | | | | | | | | | | | | | | | | | | | | | 45 | 98 (54) | 100 | 100 (0) | | | | |
| 10 | 6.72 | 24 | 1.68 | | | | | | | | | | | | | | | | | | | | | 10 | 45 (77) | 100 | 100 (0) | | | | |
| 10 | 6.72 | 24 | 1.68 | | | | | | | | | | | | | | | | | | | | | 15 | 70 (78) | 100 | 100 (0) | | | | |
| 10 | 6.72 | 24 | 2.24 | | | | | | | | | | | | | | | | | | | | | 25 | 88 (71) | 100 | 100 (0) | | | | |
| 10 | 6.72 | 24 | 2.24 | | | | | | | | | | | | | | | | | | | | | 28 | 67 (58) | 100 | 100 (0) | | | | |
| 10 | 6.72 | 24 | 3.36 | | | | | | | | | | | | | | | | | | | | | 5 | 58 (91) | 100 | 100 (0) | | | | |
| 10 | 6.72 | 24 | 3.36 | | | | | | | | | | | | | | | | | | | | | 5 | 88 (94) | 100 | 100 (0) | | | | |
| 10 | 6.72 | 24 | | | | | | | | | | | | | | | | | | | | | | 58 | 82 (29) | 100 | 100 (0) | | | | |
| 10 | 6.72 | 24 | | | | | | | | | | | | | | | | | | | | | | 8 | 93 (91) | 100 | 100 (0) | | | | |
| 10 | 6.72 | 24 | | | | | | | | | | | | | | | | | | | | | | 0 | 88 (100) | 100 | 100 (0) | | | | |

TABLE VII-continued

% PLANT INHIBITION AND % SAFENING EFFECT ( )

| HERBICIDE NO. | RATE | ANTIDOTE NO. | RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRAB GRASS W | CRAB GRASS WO | PIG-WEED W | PIG-WEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|---|
| 10 | 6.72 | 24 | 3.36 | | | | | | | | | | | | | | | | | | | | | 8 | 85 (90) | 100 | 100 (0) | | | | |
| 10 | 6.72 | 24 | 3.36 | | | | | | | | | | | | | | | | | | | | | 10 | 88 (88) | 100 | 100 (0) | | | | |
| 10 | 6.72 | 24 | 3.36 | | | | | | | | | | | | | | | | | | | | | 5 | 58 (91) | 100 | 100 (0) | | | | |
| 10 | 6.72 | 24 | 3.36 | | | | | | | | | | | | | | | | | | | | | 33 | 98 (66) | 100 | 100 (0) | | | | |
| 10 | 6.72 | 24 | 3.36 | | | | | | | | | | | | | | | | | | | | | 8 | 67 (88) | 100 | 100 (0) | | | | |
| 10 | 6.72 | 24 | 3.36 | | | | | | | | | | | | | | | | | | | | | 8 | 70 (88) | 100 | 100 (0) | | | | |
| 10 | 6.72 | 24 | 3.36 | | | | | | | | | | | | | | | | | | | | | 30 | 88 (65) | 100 | 100 (0) | | | | |
| 10 | 6.72 | 24 | 3.36 | | | | | | | | | | | | | | | | | | | | | 25 | 87 (71) | 100 | 100 (0) | | | | |
| 10 | 1.68 | 25 | 0.84 | | | | | | | | | | | | | | | | | | | | | 13 | 45 (71) | 100 | 100 (0) | | | | |
| 10 | 1.68 | 25 | 1.68 | | | | | | | | | | | | | | | | | | | | | 25 | 78 (67) | 100 | 100 (0) | | | | |
| 10 | 1.68 | 25 | 3.36 | | | | | | | | | | | | | | | | | | | | | 13 | 78 (83) | 100 | 100 (0) | | | | |
| 10 | 3.36 | 25 | 0.84 | | | | | | | | | | | | | | | | | | | | | 28 | 78 (64) | 100 | 100 (0) | | | | |
| 10 | 3.36 | 25 | 1.68 | | | | | | | | | | | | | | | | | | | | | 58 | 86 (32) | 100 | 100 (24) | | | | |
| 10 | 3.36 | 25 | 3.36 | | | | | | | | | | | | | | | | | | | | | 18 | 86 (79) | 0 | 100 (0) | | | | |
| 10 | 6.72 | 25 | 0.84 | | | | | | | | | | | | | | | | | | | | | 5 | 86 (94) | 100 | 100 (0) | | | | |
| 10 | 6.72 | 25 | 1.68 | | | | | | | | | | | | | | | | | | | | | 95 | 98 (3) | 100 | 100 (0) | | | | |
| 10 | 6.72 | 25 | 3.36 | | | | | | | | | | | | | | | | | | | | | 58 | 98 (40) | 100 | 100 (0) | | | | |
| 10 | 1.68 | 26 | 0.56 | | | | | | | | | | | | | | | | | | | | | 25 | 98 (74) | 100 | 100 (0) | | | | |
| 10 | 1.68 | 26 | 0.84 | | | | | | | | | | | | | | | | | | | | | 28 | 37 (0) | 100 | 100 (0) | | | | |
| 10 | 1.68 | 26 | 1.12 | | | | | | | | | | | | | | | | | | | | | 45 | 78 (42) | 100 | 100 (0) | | | | |
| 10 | 1.68 | 26 | 1.68 | | | | | | | | | | | | | | | | | | | | | 0 | 37 (100) | 100 | 100 (0) | | | | |
| 10 | 1.68 | 26 | 2.24 | | | | | | | | | | | | | | | | | | | | | 38 | 78 (51) | 100 | 100 (0) | | | | |
| 10 | 1.68 | 26 | 3.36 | | | | | | | | | | | | | | | | | | | | | 8 | 37 (78) | 100 | 100 (0) | | | | |
| 10 | 1.68 | 26 | 3.36 | | | | | | | | | | | | | | | | | | | | | 55 | 78 (29) | 100 | 100 (0) | | | | |

TABLE VII-continued

% PLANT INHIBITION AND % SAFENING EFFECT ()

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB GRASS W | WO | PIGWEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|---|
| 10 | 3.36 | 26 | 0.56 | | | | | | | | | | | | | | | | | | | | | 28 | 68 (58) | 100 | 100 (0) | | | | |
| 10 | 3.36 | 26 | 0.84 | | | | | | | | | | | | | | | | | | | | | 53 | 90 (41) | 100 | 100 (0) | | | | |
| 10 | 3.36 | 26 | 1.12 | | | | | | | | | | | | | | | | | | | | | 10 | 68 (85) | 100 | 100 (0) | | | | |
| 10 | 3.36 | 26 | 1.68 | | | | | | | | | | | | | | | | | | | | | 35 | 90 (61) | 100 | 100 (0) | | | | |
| 10 | 3.36 | 26 | 2.24 | | | | | | | | | | | | | | | | | | | | | 30 | 68 (55) | 100 | 100 (0) | | | | |
| 10 | 3.36 | 26 | 3.36 | | | | | | | | | | | | | | | | | | | | | 48 | 90 (46) | 98 | 100 (2) | | | | |
| 10 | 6.72 | 26 | 0.56 | | | | | | | | | | | | | | | | | | | | | 63 | 82 (23) | 95 | 100 (5) | | | | |
| 10 | 6.72 | 26 | 0.84 | | | | | | | | | | | | | | | | | | | | | 43 | 95 (54) | 100 | 100 (0) | | | | |
| 10 | 6.72 | 26 | 1.12 | | | | | | | | | | | | | | | | | | | | | 28 | 82 (65) | 100 | 100 (5) | | | | |
| 10 | 6.72 | 26 | 1.68 | | | | | | | | | | | | | | | | | | | | | 38 | 95 (60) | 100 | 100 (0) | | | | |
| 10 | 6.72 | 26 | 2.24 | | | | | | | | | | | | | | | | | | | | | 23 | 82 (71) | 100 | 100 (0) | | | | |
| 10 | 6.72 | 26 | 3.36 | | | | | | | | | | | | | | | | | | | | | 53 | 95 (44) | 100 | 100 (0) | | | | |
| 10 | 1.68 | 27 | 0.14 | | | | | | | | | | | | | | | | | | | | | 8 | 45 (82) | 100 | 100 (0) | | | | |
| 10 | 1.68 | 27 | 0.56 | | | | | | | | | | | | | | | | | | | | | 13 | 45 (71) | 100 | 100 (0) | | | | |
| 10 | 1.68 | 27 | 0.56 | | | | | | | | | | | | | | | | | | | | | 10 | 37 (72) | 100 | 100 (0) | | | | |
| 10 | 1.68 | 27 | 0.84 | | | | | | | | | | | | | | | | | | | | | 43 | 78 (44) | 100 | 100 (0) | | | | |
| 10 | 1.68 | 27 | 1.12 | | | | | | | | | | | | | | | | | | | | | 23 | 37 (37) | 100 | 100 (0) | | | | |
| 10 | 1.68 | 27 | 1.68 | | | | | | | | | | | | | | | | | | | | | 40 | 78 (48) | 100 | 100 (0) | | | | |
| 10 | 1.68 | 27 | 2.24 | | | | | | | | | | | | | | | | | | | | | 8 | 45 (82) | 100 | 100 (0) | | | | |
| 10 | 1.68 | 27 | 2.24 | | | | | | | | | | | | | | | | | | | | | 8 | 37 (78) | 98 | 100 (2) | | | | |
| 10 | 1.68 | 27 | 3.36 | | | | | | | | | | | | | | | | | | | | | 53 | 78 (32) | 100 | 100 (0) | | | | |
| 10 | 3.36 | 27 | 0.14 | | | | | | | | | | | | | | | | | | | | | 30 | 63 (52) | 100 | 100 (0) | | | | |
| 10 | 3.36 | 27 | 0.56 | | | | | | | | | | | | | | | | | | | | | 18 | 63 (71) | 100 | 100 (0) | | | | |
| 10 | 3.36 | 27 | 0.56 | | | | | | | | | | | | | | | | | | | | | 8 | 68 (88) | 100 | 100 (0) | | | | |

TABLE VII-continued

| HERBICIDE | | ANTIDOTE | | WHEAT | | DOWNEY BROME | | SORGHUM GRAIN | | GREEN FOXTAIL | | WILD OATS | | JOHNSON GRASS | | SHATTER CANE | | CRAB- GRASS | | PIG- WEED | | PROSO MILLET | | RICE | | BARNYARD GRASS | | SORGHUM | | SOYBEAN | |
|---|---|---|---|---|---|---|---|---|---|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO | W | WO | W | WO | W | WO | W | WO | W | WO |
| 10 | 3.36 | 27 | 0.84 | | | | | | | | | | | | | | | | | | | | | 35 (61) | 90 | 100 (0) | 100 | | | | |
| 10 | 3.36 | 27 | 1.12 | | | | | | | | | | | | | | | | | | | | | 10 (85) | 68 | 100 (0) | 100 | | | | |
| 10 | 3.36 | 27 | 1.68 | | | | | | | | | | | | | | | | | | | | | 30 (66) | 90 | 100 (0) | 100 | | | | |
| 10 | 3.36 | 27 | 2.24 | | | | | | | | | | | | | | | | | | | | | 10 (84) | 63 | 100 (0) | 100 | | | | |
| 10 | 3.36 | 27 | 2.24 | | | | | | | | | | | | | | | | | | | | | 23 (66) | 68 | 100 (0) | 100 | | | | |
| 10 | 3.36 | 27 | 3.36 | | | | | | | | | | | | | | | | | | | | | 45 (50) | 90 | 100 (0) | 100 | | | | |
| 10 | 6.72 | 27 | 0.14 | | | | | | | | | | | | | | | | | | | | | 75 (14) | 88 | 100 (0) | 100 | | | | |
| 10 | 6.72 | 27 | 0.56 | | | | | | | | | | | | | | | | | | | | | 30 (65) | 88 | 100 (0) | 100 | | | | |
| 10 | 6.72 | 27 | 0.56 | | | | | | | | | | | | | | | | | | | | | 43 (47) | 82 | 100 (0) | 100 | | | | |
| 10 | 6.72 | 27 | 0.84 | | | | | | | | | | | | | | | | | | | | | 45 (52) | 95 | 100 (0) | 100 | | | | |
| 10 | 6.72 | 27 | 1.12 | | | | | | | | | | | | | | | | | | | | | 5 (93) | 82 | 100 (0) | 100 | | | | |
| 10 | 6.72 | 27 | 1.68 | | | | | | | | | | | | | | | | | | | | | 53 (44) | 95 | 100 (0) | 100 | | | | |
| 10 | 6.72 | 27 | 2.24 | | | | | | | | | | | | | | | | | | | | | 18 (79) | 88 | 100 (0) | 100 | | | | |
| 10 | 6.72 | 27 | 2.24 | | | | | | | | | | | | | | | | | | | | | 18 (78) | 82 | 100 (0) | 100 | | | | |
| 10 | 6.72 | 27 | 3.36 | | | | | | | | | | | | | | | | | | | | | 40 (57) | 95 | 98 (2) | 100 | | | | |
| 10 | 1.68 | 28 | 0.56 | | | | | | | | | | | | | | | | | | | | | 25 (32) | 37 | 98 (2) | 100 | | | | |
| 10 | 1.68 | 28 | 1.12 | | | | | | | | | | | | | | | | | | | | | 0 (100) | 37 | 100 (0) | 100 | | | | |
| 10 | 1.68 | 28 | 2.24 | | | | | | | | | | | | | | | | | | | | | 5 (86) | 37 | 100 (0) | 100 | | | | |
| 10 | 3.36 | 28 | 0.56 | | | | | | | | | | | | | | | | | | | | | 65 (4) | 68 | 100 (0) | 100 | | | | |
| 10 | 3.36 | 28 | 1.12 | | | | | | | | | | | | | | | | | | | | | 20 (70) | 68 | 100 (0) | 100 | | | | |
| 10 | 3.36 | 28 | 2.24 | | | | | | | | | | | | | | | | | | | | | 50 (26) | 68 | 98 (2) | 100 | | | | |
| 10 | 4.48 | 28 | 1.12 | | | | | | | | | | | | | | | | | | | | | 38 (53) | 82 | | | | | | |
| 10 | 4.48 | 28 | 2.24 | | | | | | | | | | | | | | | | | | | | | 22 (73) | 82 | | | | | | |
| 10 | 4.48 | 28 | 4.48 | | | | | | | | | | | | | | | | | | | | | 42 (48) | 82 | | | | | | |

TABLE VII-continued

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB GRASS W | WO | PIG-WEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|---|
| 10 | 4.48 | 28 | 8.96 | | | | | | | | | | | | | | | | | | | | | 15 | 82 (81) | | | | | | |
| 10 | 6.72 | 28 | 0.56 | | | | | | | | | | | | | | | | | | | | | 50 | 82 (39) | 100 | 100 (0) | | | | |
| 10 | 6.72 | 28 | 1.12 | | | | | | | | | | | | | | | | | | | | | 43 | 82 (47) | 100 | 100 (0) | | | | |
| 10 | 6.72 | 28 | 2.24 | | | | | | | | | | | | | | | | | | | | | 20 | 82 (75) | 100 | 100 (0) | | | | |
| 10 | 1.68 | 29 | 0.84 | | | | | | | | | | | | | | | | | | | | | 45 | 78 (42) | 100 | 100 (0) | | | | |
| 10 | 1.68 | 29 | 0.84 | | | | | | | | | | | | | | | | | | | | | 30 | 27 (0) | 100 | 100 (0) | | | | |
| 10 | 1.68 | 29 | 1.68 | | | | | | | | | | | | | | | | | | | | | 15 | 27 (44) | 100 | 100 (0) | | | | |
| 10 | 1.68 | 29 | 1.68 | | | | | | | | | | | | | | | | | | | | | 33 | 78 (57) | 100 | 100 (0) | | | | |
| 10 | 1.68 | 29 | 3.36 | | | | | | | | | | | | | | | | | | | | | 40 | 78 (48) | 100 | 100 (0) | | | | |
| 10 | 1.68 | 29 | 3.36 | | | | | | | | | | | | | | | | | | | | | 23 | 27 (14) | 100 | 100 (0) | | | | |
| 10 | 3.36 | 29 | 0.84 | | | | | | | | | | | | | | | | | | | | | 15 | 33 (54) | 100 | 100 (0) | | | | |
| 10 | 3.36 | 29 | 0.84 | | | | | | | | | | | | | | | | | | | | | 13 | 90 (85) | 100 | 100 (0) | | | | |
| 10 | 3.36 | 29 | 1.68 | | | | | | | | | | | | | | | | | | | | | 8 | 33 (75) | 100 | 100 (0) | | | | |
| 10 | 3.36 | 29 | 1.68 | | | | | | | | | | | | | | | | | | | | | 38 | 90 (57) | 100 | 100 (0) | | | | |
| 10 | 3.36 | 29 | 3.36 | | | | | | | | | | | | | | | | | | | | | 13 | 33 (60) | 100 | 100 (0) | | | | |
| 10 | 3.36 | 29 | 3.36 | | | | | | | | | | | | | | | | | | | | | 33 | 90 (63) | 100 | 100 (0) | | | | |
| 10 | 6.72 | 29 | 0.84 | | | | | | | | | | | | | | | | | | | | | 58 | 95 (38) | 100 | 100 (0) | | | | |
| 10 | 6.72 | 29 | 0.84 | | | | | | | | | | | | | | | | | | | | | 38 | 53 (28) | 100 | 100 (0) | | | | |
| 10 | 6.72 | 29 | 1.68 | | | | | | | | | | | | | | | | | | | | | 48 | 53 (9) | 100 | 100 (0) | | | | |
| 10 | 6.72 | 29 | 1.68 | | | | | | | | | | | | | | | | | | | | | 45 | 95 (52) | 100 | 100 (0) | | | | |
| 10 | 6.72 | 29 | 3.36 | | | | | | | | | | | | | | | | | | | | | 38 | 53 (28) | 100 | 100 (0) | | | | |
| 10 | 6.72 | 29 | 3.36 | | | | | | | | | | | | | | | | | | | | | 68 | 95 (28) | 100 | 100 (0) | | | | |
| 10 | 1.68 | 30 | 0.14 | | | | | | | | | | | | | | | | | | | | | 8 | 45 (82) | 100 | 100 (0) | | | | |
| 10 | 1.68 | 30 | 0.56 | | | | | | | | | | | | | | | | | | | | | 5 | 45 (88) | 100 | 100 (0) | | | | |

TABLE VII-continued

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB-GRASS W | WO | PIG-WEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|---|
| 10 | 1.68 | 30 | 0.84 | | | | | | | | | | | | | | | | | | | | | 35 | 38 (7) | 100 | 100 (0) | | | | |
| 10 | 1.68 | 30 | 0.84 | | | | | | | | | | | | | | | | | | | | | 5 | 23 (78) | 100 | 100 (0) | | | | |
| 10 | 1.68 | 30 | 1.68 | | | | | | | | | | | | | | | | | | | | | 13 | 38 (65) | 100 | 100 (0) | | | | |
| 10 | 1.68 | 30 | 1.68 | | | | | | | | | | | | | | | | | | | | | 8 | 23 (65) | 100 | 100 (0) | | | | |
| 10 | 1.68 | 30 | 2.24 | | | | | | | | | | | | | | | | | | | | | 8 | 45 (82) | 100 | 100 (0) | | | | |
| 10 | 1.68 | 30 | 3.36 | | | | | | | | | | | | | | | | | | | | | 30 | 38 (21) | 100 | 100 (0) | | | | |
| 10 | 1.68 | 30 | 3.36 | | | | | | | | | | | | | | | | | | | | | 15 | 23 (34) | 100 | 100 (0) | | | | |
| 10 | 3.36 | 30 | 0.14 | | | | | | | | | | | | | | | | | | | | | 5 | 63 (92) | 100 | 100 (0) | | | | |
| 10 | 3.36 | 30 | 0.56 | | | | | | | | | | | | | | | | | | | | | 8 | 63 (87) | 100 | 100 (0) | | | | |
| 10 | 3.36 | 30 | 0.84 | | | | | | | | | | | | | | | | | | | | | 15 | 67 (77) | 100 | 100 (0) | | | | |
| 10 | 3.36 | 30 | 0.84 | | | | | | | | | | | | | | | | | | | | | 15 | 68 (77) | 100 | 100 (0) | | | | |
| 10 | 3.36 | 30 | 1.68 | | | | | | | | | | | | | | | | | | | | | 23 | 67 (65) | 100 | 100 (0) | | | | |
| 10 | 3.36 | 30 | 1.68 | | | | | | | | | | | | | | | | | | | | | 28 | 68 (58) | 100 | 100 (0) | | | | |
| 10 | 3.36 | 30 | 2.24 | | | | | | | | | | | | | | | | | | | | | 10 | 63 (84) | 100 | 100 (0) | | | | |
| 10 | 3.36 | 30 | 3.36 | | | | | | | | | | | | | | | | | | | | | 13 | 67 (80) | 100 | 100 (0) | | | | |
| 10 | 3.36 | 30 | 3.36 | | | | | | | | | | | | | | | | | | | | | 0 | 68 (100) | 100 | 100 (0) | | | | |
| 10 | 6.72 | 30 | 0.14 | | | | | | | | | | | | | | | | | | | | | 48 | 88 (45) | 100 | 100 (0) | | | | |
| 10 | 6.72 | 30 | 0.56 | | | | | | | | | | | | | | | | | | | | | 18 | 88 (79) | 100 | 100 (0) | | | | |
| 10 | 6.72 | 30 | 0.84 | | | | | | | | | | | | | | | | | | | | | 73 | 92 (20) | 100 | 100 (0) | | | | |
| 10 | 6.72 | 30 | 0.84 | | | | | | | | | | | | | | | | | | | | | 33 | 88 (62) | 100 | 100 (0) | | | | |
| 10 | 6.72 | 30 | 1.68 | | | | | | | | | | | | | | | | | | | | | 40 | 88 (54) | 100 | 100 (0) | | | | |
| 10 | 6.72 | 30 | 1.68 | | | | | | | | | | | | | | | | | | | | | 40 | 92 (56) | 100 | 100 (0) | | | | |
| 10 | 6.72 | 30 | 2.24 | | | | | | | | | | | | | | | | | | | | | 18 | 88 (79) | 100 | 100 (0) | | | | |
| 10 | 6.72 | 30 | 3.36 | | | | | | | | | | | | | | | | | | | | | 30 | 92 (67) | 100 | 100 (0) | | | | |

TABLE VII-continued

% PLANT INHIBITION AND % SAFENING EFFECT ( )

| HERBICIDE NO. | RATE | ANTIDOTE NO. | RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRAB- GRASS W | CRAB- GRASS WO | PIG- WEED W | PIG- WEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|---|
| 10 | 6.72 | 30 | 3.36 | | | | | | | | | | | | | | | | | | | | | 30 (65) | 88 | 100 | 100 (0) | | | | |
| 10 | 1.68 | 31 | 0.84 | | | | | | | | | | | | | | | | | | | | | 10 (56) | 23 | 100 | 100 (0) | | | | |
| 10 | 1.68 | 31 | 1.68 | | | | | | | | | | | | | | | | | | | | | 8 (65) | 23 | 100 | 100 (0) | | | | |
| 10 | 1.68 | 31 | 3.36 | | | | | | | | | | | | | | | | | | | | | 5 (78) | 23 | 100 | 100 (0) | | | | |
| 10 | 3.36 | 31 | 0.84 | | | | | | | | | | | | | | | | | | | | | 38 (43) | 67 | 100 | 100 (0) | | | | |
| 10 | 3.36 | 31 | 1.68 | | | | | | | | | | | | | | | | | | | | | 13 (80) | 67 | 100 | 100 (0) | | | | |
| 10 | 3.36 | 31 | 3.36 | | | | | | | | | | | | | | | | | | | | | 10 (85) | 67 | 100 | 100 (0) | | | | |
| 10 | 6.72 | 31 | 0.84 | | | | | | | | | | | | | | | | | | | | | 30 (65) | 88 | 100 | 100 (0) | | | | |
| 10 | 6.72 | 31 | 1.68 | | | | | | | | | | | | | | | | | | | | | 25 (71) | 88 | 100 | 100 (0) | | | | |
| 10 | 6.72 | 31 | 3.36 | | | | | | | | | | | | | | | | | | | | | 30 (65) | 88 | 100 | 100 (0) | | | | |
| 10 | 1.68 | 32 | 0.84 | | | | | | | | | | | | | | | | | | | | | 18 (35) | 28 | 100 | 100 (0) | | | | |
| 10 | 1.68 | 32 | 1.68 | | | | | | | | | | | | | | | | | | | | | 23 (17) | 28 | 100 | 100 (0) | | | | |
| 10 | 1.68 | 32 | 3.36 | | | | | | | | | | | | | | | | | | | | | 0 (100) | 28 | 100 | 100 (0) | | | | |
| 10 | 3.36 | 32 | 0.84 | | | | | | | | | | | | | | | | | | | | | 30 (43) | 53 | 100 | 100 (0) | | | | |
| 10 | 3.36 | 32 | 1.68 | | | | | | | | | | | | | | | | | | | | | 15 (71) | 53 | 100 | 100 (0) | | | | |
| 10 | 3.36 | 32 | 3.36 | | | | | | | | | | | | | | | | | | | | | 15 (71) | 53 | 100 | 100 (0) | | | | |
| 10 | 6.72 | 32 | 0.84 | | | | | | | | | | | | | | | | | | | | | 45 (50) | 90 | 100 | 100 (0) | | | | |
| 10 | 6.72 | 32 | 1.68 | | | | | | | | | | | | | | | | | | | | | 33 (63) | 90 | 100 | 100 (0) | | | | |
| 10 | 6.72 | 32 | 3.36 | | | | | | | | | | | | | | | | | | | | | 33 (63) | 90 | 100 | 100 (0) | | | | |
| 10 | 1.68 | 33 | 0.14 | | | | | | | | | | | | | | | | | | | | | 23 (48) | 45 | 100 | 100 (0) | | | | |
| 10 | 1.68 | 33 | 0.56 | | | | | | | | | | | | | | | | | | | | | 18 (60) | 45 | 100 | 100 (0) | | | | |
| 10 | 1.68 | 33 | 0.84 | | | | | | | | | | | | | | | | | | | | | 8 (80) | 42 | 100 | 100 (0) | | | | |
| 10 | 1.68 | 33 | 1.68 | | | | | | | | | | | | | | | | | | | | | 15 (64) | 42 | 100 | 100 (0) | | | | |
| 10 | 1.68 | 33 | 2.24 | | | | | | | | | | | | | | | | | | | | | 5 (88) | 45 | 100 | 100 (0) | | | | |

TABLE VII-continued

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB- GRASS W | WO | PIG- WEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|
| 10 | 1.68 | 33 | 3.36 | | | | | | | | | | | | | | | | | | | | | 5 | 42 (88) | 100 | 100 (0) | | | | |
| 10 | 3.36 | 33 | 0.14 | | | | | | | | | | | | | | | | | | | | | 45 | 63 (28) | 100 | 100 (0) | | | | |
| 10 | 3.36 | 33 | 0.56 | | | | | | | | | | | | | | | | | | | | | 28 | 63 (55) | 100 | 100 (0) | | | | |
| 10 | 3.36 | 33 | 0.84 | | | | | | | | | | | | | | | | | | | | | 13 | 70 (81) | 100 | 100 (0) | | | | |
| 10 | 3.36 | 33 | 1.68 | | | | | | | | | | | | | | | | | | | | | 13 | 70 (81) | 100 | 100 (0) | | | | |
| 10 | 3.36 | 33 | 2.24 | | | | | | | | | | | | | | | | | | | | | 8 | 63 (87) | 100 | 100 (0) | | | | |
| 10 | 3.36 | 33 | 3.36 | | | | | | | | | | | | | | | | | | | | | 18 | 70 (74) | 100 | 100 (0) | | | | |
| 10 | 6.72 | 33 | 0.14 | | | | | | | | | | | | | | | | | | | | | 80 | 88 (9) | 100 | 100 (0) | | | | |
| 10 | 6.72 | 33 | 0.56 | | | | | | | | | | | | | | | | | | | | | 60 | 88 (31) | 100 | 100 (0) | | | | |
| 10 | 6.72 | 33 | 0.84 | | | | | | | | | | | | | | | | | | | | | 40 | 72 (44) | 100 | 100 (0) | | | | |
| 10 | 6.72 | 33 | 1.68 | | | | | | | | | | | | | | | | | | | | | 28 | 72 (61) | 100 | 100 (0) | | | | |
| 10 | 6.72 | 33 | 2.24 | | | | | | | | | | | | | | | | | | | | | 18 | 88 (79) | 100 | 100 (0) | | | | |
| 10 | 6.72 | 33 | 3.36 | | | | | | | | | | | | | | | | | | | | | 13 | 72 (81) | 100 | 100 (0) | | | | |
| 10 | 1.68 | 34 | 0.14 | | | | | | | | | | | | | | | | | | | | | 13 | 45 (71) | 100 | 100 (0) | | | | |
| 10 | 1.68 | 34 | 0.56 | | | | | | | | | | | | | | | | | | | | | 10 | 45 (77) | 100 | 100 (0) | | | | |
| 10 | 1.68 | 34 | 0.84 | | | | | | | | | | | | | | | | | | | | | 10 | 42 (76) | 100 | 100 (0) | | | | |
| 10 | 1.68 | 34 | 1.68 | | | | | | | | | | | | | | | | | | | | | 8 | 42 (80) | 100 | 100 (0) | | | | |
| 10 | 1.68 | 34 | 2.24 | | | | | | | | | | | | | | | | | | | | | 10 | 45 (77) | 100 | 100 (0) | | | | |
| 10 | 1.68 | 34 | 3.36 | | | | | | | | | | | | | | | | | | | | | 8 | 42 (80) | 100 | 100 (0) | | | | |
| 10 | 3.36 | 34 | 0.14 | | | | | | | | | | | | | | | | | | | | | 50 | 63 (20) | 100 | 100 (0) | | | | |
| 10 | 3.36 | 34 | 0.56 | | | | | | | | | | | | | | | | | | | | | 18 | 63 (71) | 100 | 100 (0) | | | | |
| 10 | 3.36 | 34 | 0.84 | | | | | | | | | | | | | | | | | | | | | 28 | 70 (60) | 100 | 100 (0) | | | | |
| 10 | 3.36 | 34 | 1.68 | | | | | | | | | | | | | | | | | | | | | 8 | 70 (88) | 100 | 100 (0) | | | | |
| 10 | 3.36 | 34 | 2.24 | | | | | | | | | | | | | | | | | | | | | 10 | 63 (84) | 100 | 100 (0) | | | | |

TABLE VII-continued

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB- GRASS W | WO | PIG- WEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|---|
| 10 | 3.36 | 34 | 3.36 | | | | | | | | | | | | | | | | | | | | | 8 | 70 (88) | 100 | 100 (0) | | | | |
| 10 | 6.72 | 34 | 0.14 | | | | | | | | | | | | | | | | | | | | | 50 | 88 (43) | 100 | 100 (0) | | | | |
| 10 | 6.72 | 34 | 0.56 | | | | | | | | | | | | | | | | | | | | | 40 | 88 (54) | 100 | 100 (0) | | | | |
| 10 | 6.72 | 34 | 0.84 | | | | | | | | | | | | | | | | | | | | | 30 | 72 (58) | 100 | 100 (0) | | | | |
| 10 | 6.72 | 34 | 1.68 | | | | | | | | | | | | | | | | | | | | | 33 | 72 (54) | 100 | 100 (0) | | | | |
| 10 | 6.72 | 34 | 2.24 | | | | | | | | | | | | | | | | | | | | | 20 | 88 (77) | 100 | 100 (0) | | | | |
| 10 | 6.72 | 34 | 3.36 | | | | | | | | | | | | | | | | | | | | | 13 | 72 (81) | 100 | 100 (0) | | | | |
| 10 | 1.68 | 35 | 0.14 | | | | | | | | | | | | | | | | | | | | | 10 | 45 (77) | 100 | 100 (0) | | | | |
| 10 | 1.68 | 35 | 0.56 | | | | | | | | | | | | | | | | | | | | | 8 | 45 (82) | 100 | 100 (0) | | | | |
| 10 | 1.68 | 35 | 0.84 | | | | | | | | | | | | | | | | | | | | | 15 | 55 (72) | 100 | 100 (0) | | | | |
| 10 | 1.68 | 35 | 1.68 | | | | | | | | | | | | | | | | | | | | | 25 | 55 (54) | 100 | 100 (0) | | | | |
| 10 | 1.68 | 35 | 2.24 | | | | | | | | | | | | | | | | | | | | | 0 | 45 (100) | 98 | 100 (2) | | | | |
| 10 | 1.68 | 35 | 3.36 | | | | | | | | | | | | | | | | | | | | | 8 | 55 (85) | 100 | 100 (0) | | | | |
| 10 | 3.36 | 35 | 0.14 | | | | | | | | | | | | | | | | | | | | | 45 | 63 (28) | 100 | 100 (0) | | | | |
| 10 | 3.36 | 35 | 0.56 | | | | | | | | | | | | | | | | | | | | | 20 | 63 (68) | 100 | 100 (0) | | | | |
| 10 | 3.36 | 35 | 0.84 | | | | | | | | | | | | | | | | | | | | | 40 | 93 (56) | 98 | 100 (2) | | | | |
| 10 | 3.36 | 35 | 1.68 | | | | | | | | | | | | | | | | | | | | | 23 | 93 (75) | 100 | 100 (0) | | | | |
| 10 | 3.36 | 35 | 2.24 | | | | | | | | | | | | | | | | | | | | | 8 | 63 (87) | 100 | 100 (0) | | | | |
| 10 | 3.36 | 35 | 3.36 | | | | | | | | | | | | | | | | | | | | | 23 | 93 (75) | 100 | 100 (0) | | | | |
| 10 | 6.72 | 35 | 0.14 | | | | | | | | | | | | | | | | | | | | | 65 | 88 (26) | 100 | 100 (0) | | | | |
| 10 | 6.72 | 35 | 0.56 | | | | | | | | | | | | | | | | | | | | | 13 | 88 (85) | 100 | 100 (0) | | | | |
| 10 | 6.72 | 35 | 0.84 | | | | | | | | | | | | | | | | | | | | | 40 | 98 (59) | 100 | 100 (0) | | | | |
| 10 | 6.72 | 35 | 1.68 | | | | | | | | | | | | | | | | | | | | | 38 | 98 (61) | 100 | 100 (0) | | | | |
| 10 | 6.72 | 35 | 2.24 | | | | | | | | | | | | | | | | | | | | | 13 | 88 (85) | 100 | 100 (0) | | | | |

TABLE VII-continued

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB GRASS W | WO | PIG- WEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|---|
| 10 | 6.72 | 35 | 3.36 | | | | | | | | | | | | | | | | | | | | | 18 (81) | 98 | 100 (0) | 100 | | | | |
| 10 | 1.68 | 36 | 0.84 | | | | | | | | | | | | | | | | | | | | | 0 (0) | 0 | 100 (0) | 100 | | | | |
| 10 | 1.68 | 36 | 1.68 | | | | | | | | | | | | | | | | | | | | | 0 (0) | 0 | 100 (0) | 100 | | | | |
| 10 | 1.68 | 36 | 3.36 | | | | | | | | | | | | | | | | | | | | | 0 (0) | 0 | 100 (0) | 100 | | | | |
| 10 | 3.36 | 36 | 0.84 | | | | | | | | | | | | | | | | | | | | | 15 (0) | 8 | 100 (0) | 100 | | | | |
| 10 | 3.36 | 36 | 1.68 | | | | | | | | | | | | | | | | | | | | | 15 (0) | 8 | 100 (0) | 100 | | | | |
| 10 | 3.36 | 36 | 3.36 | | | | | | | | | | | | | | | | | | | | | 13 (0) | 8 | 100 (0) | 100 | | | | |
| 10 | 6.72 | 36 | 0.84 | | | | | | | | | | | | | | | | | | | | | 30 (57) | 70 | 100 (0) | 100 | | | | |
| 10 | 6.72 | 36 | 1.68 | | | | | | | | | | | | | | | | | | | | | 35 (50) | 70 | 100 (0) | 100 | | | | |
| 10 | 6.72 | 36 | 3.36 | | | | | | | | | | | | | | | | | | | | | 18 (74) | 70 | 100 (0) | 100 | | | | |
| 11 | 1.12 | 1 | 1.12 | | | | | 80 (19) | 99 | | | | | | | | | | | | | | | | | | | | | | |
| 11 | 1.12 | 1 | 2.24 | | | | | 72 (27) | 99 | | | | | | | | | | | | | | | | | | | | | | |
| 11 | 1.12 | 1 | 4.48 | | | | | 60 (39) | 99 | | | | | | | | | | | | | | | | | | | | | | |
| 11 | 1.12 | 1 | 8.96 | | | | | 52 (47) | 99 | | | | | | | | | | | | | | | | | | | | | | |
| 11 | 1.12 | 4 | 1.12 | | | | | 80 (19) | 99 | | | | | | | | | | | | | | | | | | | | | | |
| 11 | 1.12 | 4 | 2.24 | | | | | 58 (41) | 99 | | | | | | | | | | | | | | | | | | | | | | |
| 11 | 1.12 | 4 | 4.48 | | | | | 45 (54) | 99 | | | | | | | | | | | | | | | | | | | | | | |
| 11 | 1.12 | 4 | 8.96 | | | | | 35 (64) | 99 | | | | | | | | | | | | | | | | | | | | | | |
| 11 | 1.12 | 5 | 1.12 | | | | | 68 (31) | 99 | | | | | | | | | | | | | | | | | | | | | | |
| 11 | 1.12 | 5 | 2.24 | | | | | 42 (57) | 99 | | | | | | | | | | | | | | | | | | | | | | |
| 11 | 1.12 | 5 | 4.48 | | | | | 48 (51) | 99 | | | | | | | | | | | | | | | | | | | | | | |
| 11 | 1.12 | 5 | 8.96 | | | | | | | | | | | | | | | | | | | | | | | | | 42 (57) | 99 | | |
| 11 | 1.12 | 15 | 1.12 | | | | | | | | | | | | | | | | | | | | | | | | | 55 (44) | 99 | | |
| 11 | 1.12 | 15 | 2.24 | | | | | | | | | | | | | | | | | | | | | | | | | 60 (39) | 99 | | |

TABLE VII-continued

% PLANT INHIBITION AND % SAFENING EFFECT ( )

| HERBICIDE | | ANTIDOTE | | WHEAT | | DOWNEY BROME | | SORGHUM GRAIN | | GREEN FOXTAIL | | WILD OATS | | JOHNSON GRASS | | SHATTER CANE | | CRAB-GRASS | | PIG-WEED | | PROSO MILLET | | RICE | | BARNYARD GRASS | | SORGHUM | | SOYBEAN | |
|---|---|---|---|---|---|---|---|---|---|---|---|---|---|---|---|---|---|---|---|---|---|---|---|---|---|---|---|---|---|---|
| NO. | RATE | NO. | RATE | W | WO | W | WO | W | WO | W | WO | W | WO | W | WO | W | WO | W | WO | W | WO | W | WO | W | WO | W | WO | W | WO | W | WO |
| 11 | 1.12 | 15 | 4.48 | | | | | | | | | | | | | | | | | | | | | | | | | 58 | 99 (41) | | |
| 11 | 1.12 | 15 | 8.96 | | | | | | | | | | | | | | | | | | | | | | | | | 55 | 99 (44) | | |
| 11 | 1.12 | 18 | 1.12 | | | | | | | | | | | | | | | | | | | | | | | | | 50 | 99 (49) | | |
| 11 | 1.12 | 18 | 2.24 | | | | | | | | | | | | | | | | | | | | | | | | | 70 | 99 (29) | | |
| 11 | 1.12 | 18 | 4.48 | | | | | | | | | | | | | | | | | | | | | | | | | 50 | 99 (49) | | |
| 11 | 1.12 | 18 | 8.96 | | | | | | | | | | | | | | | | | | | | | | | | | 62 | 99 (37) | | |
| 11 | 1.12 | 23 | 0.14 | | | | | | | | | | | 85 | 85 (0) | 85 | 98 (0) | 90 | 98 (8) | | | | | | | | | | | 20 | 37 (45) |
| 11 | 1.12 | 23 | 0.56 | | | | | | | | | | | 95 | 85 (0) | 90 | 98 (8) | 90 | 98 (8) | | | | | | | | | | | 20 | 37 (45) |
| 11 | 1.12 | 23 | 2.24 | | | | | | | | | | | 95 | 85 (0) | 90 | 98 (8) | 90 | 98 (8) | | | | | | | | | | | 50 | 37 (0) |
| 11 | 2.24 | 23 | 0.14 | | | | | | | | | | | 85 | 95 (10) | 98 | 98 (0) | 98 | 98 (0) | | | | | | | | | | | 53 | 53 (0) |
| 11 | 2.24 | 23 | 0.56 | | | | | | | | | | | 95 | 95 (0) | 90 | 98 (8) | 90 | 98 (8) | | | | | | | | | | | 43 | 53 (0) |
| 11 | 2.24 | 23 | 2.24 | | | | | | | | | | | 95 | 95 (0) | 85 | 98 (13) | 85 | 98 (13) | | | | | | | | | | | 55 | 53 (0) |
| 11 | 4.48 | 23 | 0.14 | | | | | | | | | | | 95 | 95 (0) | 98 | 100 (2) | 98 | 100 (2) | | | | | | | | | | | 63 | 70 (10) |
| 11 | 4.48 | 23 | 0.56 | | | | | | | | | | | 98 | 95 (0) | 98 | 100 (2) | 100 | 100 (0) | | | | | | | | | | | 50 | 70 (28) |
| 11 | 4.48 | 23 | 2.24 | | | | | | | | | | | 98 | 95 (0) | 100 | 100 (0) | 100 | 100 (0) | | | | | | | | | | | 40 | 70 (42) |
| 11 | 1.12 | 29 | 0.14 | | | | | | | | | | | 95 | 95 (0) | 98 | 90 (0) | 98 | 90 (0) | | | | | | | | | | | 20 | 50 (60) |
| 11 | 1.12 | 29 | 0.56 | | | | | | | | | | | 95 | 95 (0) | 98 | 90 (0) | 98 | 90 (0) | | | | | | | | | | | 20 | 50 (60) |
| 11 | 1.12 | 29 | 2.24 | | | | | | | | | | | 95 | 98 (10) | 60 | 90 (33) | 60 | 90 (33) | | | | | | | | | | | 35 | 50 (30) |
| 11 | 2.24 | 29 | 0.14 | | | | | | | | | | | 95 | 98 (3) | 90 | 98 (8) | 90 | 98 (8) | | | | | | | | | | | 30 | 52 (42) |
| 11 | 2.24 | 29 | 0.56 | | | | | | | | | | | 95 | 98 (3) | 95 | 98 (3) | 95 | 98 (3) | | | | | | | | | | | 33 | 52 (36) |
| 11 | 2.24 | 29 | 2.24 | | | | | | | | | | | 95 | 98 (3) | 90 | 98 (8) | 90 | 98 (8) | | | | | | | | | | | 43 | 52 (17) |
| 11 | 4.48 | 29 | 0.14 | | | | | | | | | | | 95 | 98 (3) | 95 | 98 (3) | 95 | 98 (3) | | | | | | | | | | | 48 | 60 (20) |
| 11 | 4.48 | 29 | 0.56 | | | | | | | | | | | 95 | 98 (3) | 95 | 98 (3) | 95 | 98 (3) | | | | | | | | | | | 53 | 60 (11) |
| 11 | 4.48 | 29 | 2.24 | | | | | | | | | | | 100 | 98 (0) | 95 | 98 (3) | 95 | 98 (3) | | | | | | | | | | | 53 | 60 (11) |

TABLE VII-continued

% PLANT INHIBITION AND % SAFENING EFFECT ( )

| HERBICIDE NO. | RATE | ANTIDOTE NO. | RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRAB-GRASS W | CRAB-GRASS WO | PIG-WEED W | PIG-WEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|---|
| 6 | 2.24 | 10 | 0.56 | 50 | 80 (37) | | | 35 | 96 (63) | 99 | 99 (0) | | | | | | | 97 | 97 (0) | | | | | | | 99 | 100 (1) | | | | |
| 6 | 2.24 | 10 | 1.12 | 62 | 62 (0) | | | 30 | 92 (67) | | | | | | | | | | | | | | | | | | | | | | |
| 6 | 2.24 | 10 | 1.12 | 35 | 80 (56) | | | 62 | 100 (38) | | | | | | | | | | | | | | | | | | | | | | |
| 6 | 2.24 | 10 | 2.24 | 45 | 62 (27) | | | 40 | 92 (56) | | | | | | | | | | | | | | | | | | | | | | |
| 6 | 2.24 | 10 | 2.24 | | | | | 58 | 100 (42) | | | | | | | | | | | | | | | | | | | | | | |
| 6 | 2.24 | 10 | 2.24 | 48 | 62 (922) | | | 65 | 96 (32) | 100 | 99 (0) | | | | | | | 99 | 97 (0) | | | | | | | | | | | | |
| 6 | 2.24 | 10 | 4.48 | 35 | 80 (56) | | | 35 | 100 (65) | | | | | | | | | | | | | | | | | | | | | | |
| 6 | 2.24 | 10 | 4.48 | 35 | 62 (43) | | | 25 | 92 (72) | | | | | | | | | | | | | | | | | | | | | | |
| 6 | 2.24 | 10 | 8.96 | 30 | 80 (62) | | | 20 | 100 (80) | | | | | | | | | | | | | | | | | | | | | | |
| 6 | 2.24 | 10 | 8.96 | | | | | 22 | 92 (76) | | | | | | | | | | | | | | | | | | | | | | |
| 6 | 0.03 | 11 | 0.03 | | | | | 5 | 35 (85) | 80 | 78 (0) | | | 48 | 40 (0) | 45 | 43 (0) | 85 | 78 (0) | 88 | 90 (0) | 100 | 100 (0) | | | | | | | | |
| 6 | 0.03 | 11 | 0.14 | | | | | 5 | 35 (85) | 85 | 78 (0) | | | 40 | 40 (0) | 38 | 43 (11) | 85 | 78 (0) | 85 | 90 (5) | 100 | 100 (0) | | | | | | | | |
| 6 | 0.03 | 11 | 0.56 | | | | | 0 | 35 (100) | 80 | 78 (0) | | | 30 | 40 (25) | 33 | 43 (23) | 78 | 78 (0) | 93 | 90 (0) | 100 | 100 (0) | | | | | | | | |
| 6 | 0.14 | 11 | 0.03 | | | | | 55 | 83 (33) | 95 | 90 (0) | | | 80 | 80 (0) | 65 | 83 (21) | 95 | 93 (0) | 98 | 99 (1) | 100 | 100 (0) | | | | | | | | |
| 6 | 0.14 | 11 | 0.14 | | | | | 50 | 42 (0) | 90 | 90 (0) | | | | | | | 97 | 78 (0) | | | | | | | | | | | | |
| 6 | 0.14 | 11 | 0.14 | | | | | 38 | 83 (54) | 95 | 90 (0) | | | 80 | 80 (3) | 48 | 83 (42) | 93 | 93 (0) | 97 | 99 (2) | 100 | 100 (0) | | | 97 | 80 (0) | | | | |
| 6 | 0.14 | 11 | 0.56 | | | | | 35 | 42 (16) | 93 | 90 (0) | | | | | | | 90 | 78 (0) | | | | | | | | | | | | |
| 6 | 0.14 | 11 | 0.56 | | | | | 15 | 83 (81) | 94 | 90 (0) | | | 60 | 80 (25) | 55 | 83 (33) | 94 | 93 (0) | 99 | 99 (0) | 100 | 100 (0) | | | 93 | 80 (0) | | | | |
| 6 | 0.14 | 11 | 2.24 | | | | | 17 | 42 (59) | 95 | 90 (0) | | | | | | | 99 | 78 (0) | | | | | | | | | | | | |
| 6 | 0.14 | 11 | 2.24 | | | | | 28 | 83 (66) | 93 | 90 (0) | | | 50 | 80 (37) | 48 | 83 (42) | 93 | 93 (0) | 99 | 99 (0) | 100 | 100 (0) | | | 97 | 80 (0) | | | | |
| 6 | 0.56 | 11 | 0.03 | | | | | 95 | 98 (3) | 98 | 98 (0) | | | 93 | 97 (4) | 90 | 97 (0) | 94 | 98 (1) | 99 | 100 (1) | 100 | 100 (0) | | | | | | | | |
| 6 | 0.56 | 11 | 0.14 | | | | | 73 | 70 (0) | 92 | 97 (5) | | | 97 | 97 (0) | 97 | 97 (0) | 99 | 93 93 | 99 | 100 (0) | 100 | 100 (0) | | | 99 | 99 (0) | | | | |
| 6 | 0.56 | 11 | 0.14 | | | | | 85 | 98 (13) | 98 | 98 (0) | | | 98 | 97 (0) | 97 | 94 (0) | 98 | 98 (0) | 100 | 100 (0) | 100 | 100 (0) | | | | | | | | |
| 6 | 0.56 | 11 | 0.56 | | | | | 70 | 98 (28) | 98 | 98 (0) | | | 98 | 97 (0) | 88 | 94 (6) | 98 | 98 (0) | 100 | 100 (0) | 100 | 100 (0) | | | | | | | | |

TABLE VII-continued

% PLANT INHIBITION AND % SAFENING EFFECT ( )

| HERBICIDE NO. | HERBICIDE RATE | ANTIDOTE NO. | ANTIDOTE RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRAB GRASS W | CRAB GRASS WO | PIG-WEED W | PIG-WEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|
| 6 | 0.56 | 11 | 0.56 | | | | | 70 | 70 (0) | 92 | 97 (5) | | | | | | | 99 | 93 (0) | | | | | | | 97 | 99 (2) | | | | |
| 6 | 0.56 | 11 | 2.24 | | | | | 52 | 98 (46) | 98 | 98 (0) | | | 98 | 97 (0) | 70 | 94 (25) | 98 | 98 (0) | 100 | 100 (0) | 100 | 100 (0) | | | | | | | | |
| 6 | 0.56 | 11 | 2.24 | | | | | 40 | 70 (42) | 99 | 97 (0) | | | | | | | 99 | 93 (0) | | | | | | | 87 | 99 (12) | | | | |
| 6 | 2.24 | 11 | 0.03 | | | | | 98 | 99 (1) | 98 | 99 (1) | | | 97 | 99 (2) | 92 | 99 (7) | 99 | 99 (0) | 100 | 100 (0) | 100 | 100 (0) | | | | | | | | |
| 6 | 2.24 | 11 | 0.14 | | | | | 99 | 99 (0) | 99 | 99 (0) | | | 99 | 99 (0) | 99 | 99 (0) | 99 | 99 (0) | 100 | 100 (0) | 100 | 100 (0) | | | | | | | | |
| 6 | 2.24 | 11 | 0.14 | | | | | 80 | 88 (9) | 99 | 99 (0) | | | | | | | 99 | 99 (0) | | | | | | | 97 | 99 (2) | | | | |
| 6 | 2.24 | 11 | 0.56 | | | | | 94 | 99 (5) | 100 | 99 (0) | | | 99 | 99 (0) | 99 | 99 (0) | 99 | 99 (0) | 100 | 100 (0) | 100 | 100 (0) | | | | | | | | |
| 6 | 2.24 | 11 | 0.56 | | | | | 75 | 88 (14) | 99 | 99 (0) | | | | | | | 99 | 99 (0) | | | | | | | 99 | 99 (0) | | | | |
| 6 | 2.24 | 11 | 2.24 | | | | | 68 | 88 (22) | 99 | 99 (0) | | | | | | | 99 | 99 (0) | | | | | | | 92 | 99 (7) | | | | |
| 6 | 2.24 | 11 | 2.24 | | | | | 60 | 99 (39) | 99 | 99 (0) | | | 98 | 99 (1) | 94 | 99 (5) | 99 | 99 (0) | 100 | 100 (0) | 100 | 100 (0) | | | | | | | | |
| 6 | 4.48 | 11 | 0.03 | | | | | 97 | 100 (3) | 100 | 100 (0) | | | 99 | 100 (1) | 99 | 100 (1) | 100 | 100 (0) | 100 | 100 (0) | 100 | 100 (0) | | | | | | | | |
| 6 | 4.48 | 11 | 0.14 | | | | | 97 | 100 (3) | 100 | 100 (0) | | | 99 | 100 (1) | 100 | 100 (0) | 99 | 100 (1) | 100 | 100 (0) | 100 | 100 (0) | | | | | | | | |
| 6 | 4.48 | 11 | 0.56 | | | | | 98 | 100 (2) | 99 | 100 (1) | | | 99 | 100 (1) | 99 | 100 (1) | 99 | 100 (1) | 100 | 100 (0) | 100 | 100 (0) | | | | | | | | |
| 6 | 4.48 | 11 | 2.24 | | | | | 80 | 100 (20) | 99 | 100 (1) | | | 99 | 100 (1) | 99 | 100 (1) | 99 | 100 (1) | 100 | 100 (0) | 100 | 100 (0) | | | | | | | | |
| 6 | 2.24 | 12 | 1.12 | 62 | 80 (22) | | | 55 | 92 (40) | | | | | | | | | | | | | | | | | | | | | | |
| 6 | 2.24 | 12 | 2.24 | 55 | 80 (31) | | | 40 | 92 (56) | | | | | | | | | | | | | | | | | | | | | | |
| 6 | 2.24 | 12 | 4.48 | 52 | 80 (35) | | | 35 | 92 (61) | | | | | | | | | | | | | | | | | | | | | | |
| 6 | 2.24 | 12 | 8.96 | 35 | 80 (56) | | | 30 | 92 (67) | | | | | | | | | | | | | | | | | | | | | | |
| 6 | 2.24 | 13 | 1.12 | 65 | 80 (18) | | | 85 | 92 (7) | | | | | | | | | | | | | | | | | | | | | | |
| 6 | 2.24 | 13 | 1.12 | 68 | 70 (2) | | | 100 | 98 (0) | | | | | | | | | | | | | | | | | | | | | | |
| 6 | 2.24 | 13 | 2.24 | 60 | 80 (25) | | | 75 | 92 (18) | | | | | | | | | | | | | | | | | | | | | | |
| 6 | 2.24 | 13 | 2.24 | 68 | 70 (2) | | | 100 | 98 (0) | | | | | | | | | | | | | | | | | | | | | | |
| 6 | 2.24 | 13 | 4.48 | 58 | 80 (27) | | | 60 | 92 (34) | | | | | | | | | | | | | | | | | | | | | | |
| 6 | 2.24 | 13 | 4.48 | 65 | 70 (7) | | | 98 | 98 (0) | | | | | | | | | | | | | | | | | | | | | | |

TABLE VII-continued

% PLANT INHIBITION AND % SAFENING EFFECT ( )

| HERBICIDE NO. | RATE | ANTIDOTE NO. | RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRAB-GRASS W | CRAB-GRASS WO | PIG-WEED W | PIG-WEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|---|
| 6 | 2.24 | 13 | 8.96 | 58 | 80 (27) | | | 55 | 92 (40) | | | | | | | | | | | | | | | | | | | | | | |
| 6 | 2.24 | 13 | 8.96 | 60 | 70 (14) | | | 100 | 98 (0) | | | | | | | | | | | | | | | | | | | | | | |
| 6 | 2.24 | 14 | 1.12 | 55 | 80 (31) | | | 90 | 92 (2) | | | | | | | | | | | | | | | | | | | | | | |
| 6 | 2.24 | 14 | 2.24 | 42 | 80 (47) | | | 60 | 92 (34) | | | | | | | | | | | | | | | | | | | | | | |
| 6 | 2.24 | 14 | 4.48 | 48 | 80 (40) | | | 55 | 92 (40) | | | | | | | | | | | | | | | | | | | | | | |
| 6 | 2.24 | 14 | 8.96 | 45 | 80 (43) | | | 30 | 92 (67) | | | | | | | | | | | | | | | | | | | | | | |
| 6 | 2.24 | 15 | 1.12 | 85 | 95 (10) | | | 60 | 100 (40) | | | | | | | | | | | | | | | | | | | | | | |
| 6 | 2.24 | 15 | 2.24 | 75 | 95 (21) | | | 45 | 100 (55) | | | | | | | | | | | | | | | | | | | | | | |
| 6 | 2.24 | 15 | 4.48 | 68 | 95 (28) | | | 35 | 100 (65) | | | | | | | | | | | | | | | | | | | | | | |
| 6 | 2.24 | 15 | 8.96 | 50 | 95 (47) | | | 55 | 100 (45) | | | | | | | | | | | | | | | | | | | | | | |
| 6 | 2.24 | 16 | 1.12 | 62 | 80 (22) | | | 55 | 92 (40) | | | | | | | | | | | | | | | | | | | | | | |
| 6 | 2.24 | 16 | 2.24 | 50 | 80 (37) | | | 45 | 92 (51) | | | | | | | | | | | | | | | | | | | | | | |
| 6 | 2.24 | 16 | 4.48 | 42 | 80 (47) | | | 30 | 92 (67) | | | | | | | | | | | | | | | | | | | | | | |
| 6 | 2.24 | 16 | 8.96 | 32 | 80 (60) | | | 30 | 92 (67) | | | | | | | | | | | | | | | | | | | | | | |
| 6 | 0.14 | 17 | 0.14 | 30 | 65 (53) | | | 88 | 93 (5) | 67 | 80 (16) | | | | | | | | | | | | | | | 99 | 97 (0) | | | | |
| 6 | 0.14 | 17 | 0.56 | 25 | 65 (61) | | | 95 | 93 (0) | 80 | 80 (0) | | | | | | | | | | | | | | | 100 | 97 (0) | | | | |
| 6 | 0.14 | 17 | 2.24 | 15 | 65 (76) | | | 80 | 93 (13) | 95 | 80 (0) | | | | | | | | | | | | | | | 95 | 97 (2) | | | | |
| 6 | 0.56 | 17 | 0.14 | | | | | 73 | 90 (18) | 97 | 99 (2) | | | | | | | | | | | | | | | 100 | 99 (0) | | | | |
| 6 | 0.56 | 17 | 0.56 | | | | | 73 | 90 (18) | 97 | 99 (2) | | | | | | | | | | | | | | | 99 | 99 (0) | | | | |
| 6 | 0.56 | 17 | 2.24 | | | | | 50 | 90 (44) | 93 | 99 (6) | | | | | | | | | | | | | | | 100 | 99 (0) | | | | |
| 6 | 2.24 | 17 | 0.14 | | | | | 90 | 97 (7) | 99 | 100 (1) | | | | | | | | | | | | | | | | | | | | |
| 6 | 2.24 | 17 | 0.56 | | | | | 85 | 97 (12) | 100 | 100 (0) | | | | | | | | | | | | | | | | | | | | |
| 6 | 2.24 | 17 | 2.24 | | | | | 85 | 97 (12) | 100 | 100 (0) | | | | | | | | | | | | | | | | | | | | |
| 6 | 2.24 | 18 | 1.12 | 50 | 95 (47) | | | 45 | 100 (55) | | | | | | | | | | | | | | | | | | | | | | |

TABLE VII-continued

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB- GRASS W | WO | PIG- WEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|---|
| 6 | 2.24 | 18 | 2.24 | 70 | 95 (26) | | | 45 | 100 (55) | | | | | | | | | | | | | | | | | | | | | | |
| 6 | 2.24 | 18 | 4.48 | 65 | 95 (31) | | | 40 | 100 (60) | | | | | | | | | | | | | | | | | | | | | | |
| 6 | 2.24 | 18 | 8.96 | 45 | 95 (52) | | | 35 | 100 (65) | | | | | | | | | | | | | | | | | | | | | | |
| 6 | 2.24 | 19 | 1.12 | 60 | 80 (25) | 65 | 92 (29) | 50 | 92 (45) | | | | | | | | | | | | | | | | | | | | | | |
| 6 | 2.24 | 19 | 2.24 | 55 | 80 (31) | | | 25 | 92 (72) | | | | | | | | | | | | | | | | | | | | | | |
| 6 | 2.24 | 19 | 4.48 | 52 | 80 (35) | | | 20 | 92 (78) | | | | | | | | | | | | | | | | | | | | | | |
| 6 | 2.24 | 19 | 8.96 | 58 | 80 (27) | | | 48 | 92 (47) | | | | | | | | | | | | | | | | | | | | | | |
| 6 | 2.24 | 20 | 1.12 | 35 | 80 (56) | | | 55 | 92 (40) | | | | | | | | | | | | | | | | | | | | | | |
| 6 | 2.24 | 20 | 2.24 | 60 | 80 (25) | | | 35 | 92 (61) | | | | | | | | | | | | | | | | | | | | | | |
| 6 | 2.24 | 20 | 4.48 | 58 | 80 (27) | | | 10 | 92 (89) | | | | | | | | | | | | | | | | | | | | | | |
| 6 | 2.24 | 20 | 8.96 | 48 | 80 (40) | | | 95 | 100 (5) | | | | | | | | | | | | | | | | | | | | | | |
| 6 | 2.24 | 22 | 1.12 | 35 | 62 (43) | | | 95 | 100 (5) | | | | | | | | | | | | | | | | | | | | | | |
| 6 | 2.24 | 22 | 2.24 | 70 | 62 (0) | | | 80 | 100 (20) | | | | | | | | | | | | | | | | | | | | | | |
| 6 | 2.24 | 22 | 4.48 | 65 | 62 (0) | | | 60 | 100 (40) | | | | | | | | | | | | | | | | | | | | | | |
| 6 | 2.24 | 22 | 8.96 | 72 | 62 (0) | | | | | 30 | 60 (50) | 30 | 60 (50) | | | | | | | | | | | | | | | | | | | |
| 6 | 0.14 | 23 | 0.14 | 10 | 30 (66) | 0 | 35 (100) | | | 90 | (0) | 90 | 98 (8) | | | | | | | | | | | | | | | | | | |
| 6 | 0.14 | 23 | 0.14 | 65 | 70 (7) | 90 | 73 (0) | | | 100 | (0) | 90 | 98 (8) | | | | | | | | | | | | | | | | | | |
| 6 | 0.14 | 23 | 0.14 | 58 | 37 (0) | 60 | 70 (14) | | | 85 | (0) | 85 | 98 (13) | | | | | | | | | | | | | | | | | | |
| 6 | 0.14 | 23 | 0.14 | 20 | 20 (0) | 40 | 60 (33) | | | 85 | (0) | 0 | 45 (100) | | | | | | | | | | | | | | | | | | |
| 6 | 0.14 | 23 | 0.56 | 10 | 30 (66) | 30 | 35 (14) | | | 85 | (0) | 30 | 60 (50) | | | | | | | | | | | | | | | | | | |
| 6 | 0.14 | 23 | 0.56 | 13 | 20 (35) | 35 | 60 (41) | | | 85 | (0) | 70 | 45 (0) | | | | | | | | | | | | | | | | | | |
| 6 | 0.14 | 23 | 0.56 | 60 | 70 (14) | 90 | 73 (0) | | | 90 | (0) | 40 | 98 (59) | | | | | | | | | | | | | | | | | | |
| 6 | 0.14 | 23 | 0.56 | 40 | 37 (0) | 80 | 70 (0) | | | 85 | (11) | 80 | 98 (18) | | | | | | | | | | | | | | | | | | |
| 6 | 0.14 | 23 | 2.24 | 10 | 30 (66) | 0 | 35 (100) | | | 90 | (0) | 20 | 60 (66) | | | | | | | | | | | | | | | | | | |

TABLE VII-continued

% PLANT INHIBITION AND % SAFENING EFFECT ( )

| HERBICIDE NO. | RATE | ANTIDOTE NO. | RATE | WHEAT W | WO | DOWNEY BROME W | WO | SORGHUM GRAIN W | WO | GREEN FOXTAIL W | WO | WILD OATS W | WO | JOHNSON GRASS W | WO | SHATTER CANE W | WO | CRAB-GRASS W | WO | PIG-WEED W | WO | PROSO MILLET W | WO | RICE W | WO | BARNYARD GRASS W | WO | SORGHUM W | WO | SOYBEAN W | WO |
|---|---|---|---|---|---|---|---|---|---|---|---|---|---|---|---|---|---|---|---|---|---|---|---|---|---|---|---|---|---|---|---|
| 6 | 0.14 | 23 | 2.24 | 43 | 37 (0) | 80 | 70 (0) | | | 90 | 85 (0) | 60 | 98 (38) | | | | | | | | | | | | | | | | | | |
| 6 | 0.14 | 23 | 2.24 | 5 | 20 (75) | 35 | 60 (41) | | | 85 | 85 (0) | 0 | 45 (100) | | | | | | | | | | | | | | | | | | |
| 6 | 0.14 | 23 | 2.24 | 45 | 70 (35) | 73 | 73 (0) | | | 80 | 90 (11) | 0 | 98 (100) | | | | | | | | | | | | | | | | | | |
| 6 | 0.56 | 23 | 0.14 | 85 | 70 (0) | 85 | 90 (5) | | | 98 | 85 (0) | 95 100 (5) | | | | | | | | | | | | | | | | | | | |
| 6 | 0.56 | 23 | 0.14 | 15 | 45 (66) | 60 | 90 (33) | | | | | 80 83 (3) | | | | | | | | | | | | | | | | | | | |
| 6 | 0.56 | 23 | 0.14 | 70 | 82 (14) | | | | | | | 100 100 | | | | | | | | | | | | | | | | | | | |
| 6 | 0.56 | 23 | 0.14 | 53 | 50 (0) | 85 | 75 (0) | | | 98 | 90 (0) | 80 75 (0) | | | | | | | | | | | | | | | | | | | |
| 6 | 0.56 | 23 | 0.14 | 98 | 83 (0) | 98 | 95 (0) | | | 98 | 90 (0) | 98 100 (2) | | | | | | | | | | | | | | | | | | | |
| 6 | 0.14 | 23 | 0.14 | 100 | 78 (0) | 100 | 95 (0) | | | 100 | 100 (0) | 100 98 (0) | | | | | | | | | | | | | | | | | | | |
| 6 | 0.56 | 23 | 0.28 | 30 | 15 (0) | 75 | 90 (16) | | | | | 30 78 (61) | | | | | | | | | | | | | | | | | | | |
| 6 | 0.56 | 23 | 0.56 | 60 | 70 (0) | 100 | 90 (0) | | | 98 | 85 (0) | 88 100 (12) | | | | | | | | | | | | | | | | | | | |
| 6 | 0.56 | 23 | 0.56 | 63 | 78 (14) | 90 | 95 (0) | | | 100 | 100 (0) | 95 98 (3) | | | | | | | | | | | | | | | | | | | |
| 6 | 0.56 | 23 | 0.56 | 85 | 82 (0) | | | | | | | 95 100 (5) | | | | | | | | | | | | | | | | | | | |
| 6 | 0.56 | 23 | 0.56 | 20 | 45 (55) | 40 | 90 (55) | | | 95 | 90 (0) | 60 83 (27) | | | | | | | | | | | | | | | | | | | |
| 6 | 0.56 | 23 | 0.56 | 38 | 50 (24) | 90 | 75 (0) | | | 95 | 90 (0) | 60 75 (20) | | | | | | | | | | | | | | | | | | | |
| 6 | 0.56 | 23 | 0.56 | 90 | 83 (0) | 95 | 95 (0) | | | 95 | 90 (0) | 100 100 (0) | | | | | | | | | | | | | | | | | | | |
| 6 | 0.56 | 23 | 2.24 | 78 | 78 (0) | 90 | 95 (5) | | | 100 | 100 (0) | 90 98 (8) | | | | | | | | | | | | | | | | | | | |
| 6 | 0.56 | 23 | 2.24 | 73 | 70 (0) | 85 | 90 (5) | | | 100 | 85 (0) | 75 100 (25) | | | | | | | | | | | | | | | | | | | |
| 6 | 0.56 | 23 | 2.24 | 43 | 50 (14) | 50 | 75 (33) | | | 95 | 90 (0) | 78 75 (0) | | | | | | | | | | | | | | | | | | | |
| 6 | 0.56 | 23 | 2.24 | 0 | 15 (100) | 70 | 90 (22) | | | | | 0 78 (100) | | | | | | | | | | | | | | | | | | | |
| 6 | 0.56 | 23 | 2.24 | 65 | 82 (20) | | | | | | | 95 100 (5) | | | | | | | | | | | | | | | | | | | |
| 6 | 0.56 | 23 | 2.24 | 88 | 83 (0) | 95 | 95 (0) | | | 100 | (0) | 95 100 (5) | | | | | | | | | | | | | | | | | | | |
| 6 | 0.56 | 23 | 2.24 | 15 | 45 (66) | 80 | 90 (11) | | | | | 40 83 (51) | | | | | | | | | | | | | | | | | | | |
| 6 | 0.84 | 23 | 0.14 | 45 | 70 (35) | 90 | 95 (5) | | | 100 | 100 (0) | | | | | | | | | | | | | | | | | | | | |

TABLE VII-continued

| HERBICIDE NO. | RATE | ANTIDOTE NO. | RATE | WHEAT W | WHEAT WO | DOWNEY BROME W | DOWNEY BROME WO | SORGHUM GRAIN W | SORGHUM GRAIN WO | GREEN FOXTAIL W | GREEN FOXTAIL WO | WILD OATS W | WILD OATS WO | JOHNSON GRASS W | JOHNSON GRASS WO | SHATTER CANE W | SHATTER CANE WO | CRAB-GRASS W | CRAB-GRASS WO | PIG-WEED W | PIG-WEED WO | PROSO MILLET W | PROSO MILLET WO | RICE W | RICE WO | BARNYARD GRASS W | BARNYARD GRASS WO | SORGHUM W | SORGHUM WO | SOYBEAN W | SOYBEAN WO |
|---|---|---|---|---|---|---|---|---|---|---|---|---|---|---|---|---|---|---|---|---|---|---|---|---|---|---|---|---|---|---|---|
| 6 | 0.84 | 23 | 0.14 | 30 | 42 (28) | 90 | 90 (0) | | | 100 | 100 (0) | | | | | | | | | | | | | | | | | | | | |
| 6 | 0.84 | 23 | 0.14 | 15 | 41 (63) | 90 | 90 (0) | | | 100 | 100 (0) | | | | | | | | | | | | | | | | | | | | |
| 6 | 0.84 | 23 | 0.14 | 45 | 53 (15) | 75 | 60 (0) | | | 100 | 100 (0) | | | | | | | | | | | | | | | | | | | | |
| 6 | 0.84 | 23 | 0.14 | 98 | 82 (0) | 100 | 98 (0) | | | 100 | 100 (0) | 100 | 100 (0) | | | | | | | | | | | | | | | | | | |
| 6 | 0.84 | 23 | 0.14 | 45 | 35 (0) | 70 | 85 (17) | | | 100 | 100 (0) | | | | | | | | | | | | | | | | | | | | |
| 6 | 0.84 | 23 | 0.14 | 85 | 70 (0) | 85 | 100 (15) | | | 100 | 100 (0) | | | | | | | | | | | | | | | | | | | | |
| 6 | 0.84 | 23 | 0.14 | 30 | 58 (48) | 95 | 95 (0) | | | 100 | 100 (0) | | | | | | | | | | | | | | | | | | | | |
| 6 | 0.84 | 23 | 0.14 | 43 | 15 (0) | 85 | 60 (0) | | | 100 | 100 (0) | | | | | | | | | | | | | | | | | | | | |
| 6 | 0.84 | 23 | 0.14 | 15 | 43 (65) | 80 | 73 (0) | | | 95 | 95 (0) | 50 | 63 (20) | | | | | | | | | | | | | | | | | | |
| 6 | 0.84 | 23 | 0.14 | 10 | 20 (50) | 95 | 60 (0) | | | 100 | 100 (0) | | | | | | | | | | | | | | | | | | | | |
| 6 | 0.84 | 23 | 0.14 | 50 | 48 (0) | 90 | 90 (0) | | | 100 | 100 (0) | | | | | | | | | | | | | | | | | | | | |
| 6 | 0.84 | 23 | 0.14 | 23 | 27 (14) | 100 | 100 (0) | | | 100 | 100 (0) | | | | | | | | | | | | | | | | | | | | |
| 6 | 0.84 | 23 | 0.14 | 30 | 83 (63) | 0 | 98 (100) | | | 100 | 100 (0) | 90 | 100 (10) | | | | | | | | | | | | | | | | | | |
| 6 | 0.84 | 23 | 0.56 | 48 | 58 (17) | 95 | 95 (0) | | | 100 | 100 (0) | | | | | | | | | | | | | | | | | | | | |
| 6 | 0.84 | 23 | 0.56 | 25 | 42 (40) | 60 | 90 (33) | | | 100 | 100 (0) | | | | | | | | | | | | | | | | | | | | |

EXAMPLE 291

The procedure of Example 285 was followed to determine the interaction between various combinations of herbicide and antidotes when incorporated in a soil cover layer before emergence of rice and barnyardgrass. The tested combinations included mixtures of two different antidotes in combination against various herbicides. The combinations of antidotes included an antidote of the invention, i.e., benzhydryl compound TM 1 or v24, and a commercially-known antidote, namely, the compound 4,6-dichloro-2'-phenylpyrimidine (commonly known as "CGA-123407" and designated as "CGA" in Tables VIII-A and VIII-B), which is sold in combination with the herbicide pretilachlor by Ciba-Geigy Corporation, Ardsley, N.Y. The herbicide a compounds tested were butachlor (herbicide TM 10), metolachlor (herbicide TM 14), benthiocarb (herbicide TM 36) and pretilachlor (herbicide TM 37). Results are reported in Tables VIII-A and VIII-B.

TABLE VIII-A

| Herbicide No. | Rate kg/ha | Antidote* No. | Rate kg/ha | % Inhibition Rice | % Inhibition Barnyardgrass |
|---|---|---|---|---|---|
| 37 | 0.83 | — | 0 | 35 | 100 |
| 37 | 0.83 | 1 + CGA | 0.28 + 0.28 | 5 | 90 |
| 37 | 0.83 | 24 + CGA | 0.28 + 0.28 | 10 | 100 |
| 37 | 0.83 | 1 + CGA | 1.12 + 1.12 | 5 | 100 |
| 37 | 0.83 | 24 + CGA | 1.12 + 1.12 | 10 | 100 |
| 37 | 0.83 | 1 + CGA | 4.48 + 4.48 | 10 | 100 |
| 37 | 0.83 | 24 + CGA | 4.48 + 4.48 | 10 | 100 |
| 37 | 3.36 | — | 0 | 65 | 100 |
| 37 | 3.36 | 1 + CGA | 0.28 + 0.28 | 10 | 100 |
| 37 | 3.36 | 24 + CGA | 0.28 + 0.28 | 20 | 100 |
| 37 | 3.36 | 1 + CGA | 1.12 + 1.12 | 5 | 100 |
| 27 | 3.36 | 24 + CGA | 1.12 + 1.12 | 10 | 100 |
| 37 | 3.36 | 1 + CGA | 4.48 + 4.48 | 10 | 100 |
| 37 | 3.36 | 24 + CGA | 4.48 + 4.48 | 30 | 100 |
| 10 | 1.68 | — | 0 | 58 | 100 |
| 10 | 1.68 | 1 + CGA | 0.28 + 0.28 | 15 | 100 |
| 10 | 1.68 | 24 + CGA | 0.28 + 0.28 | 10 | 100 |
| 10 | 1.68 | 1 + CGA | 1.12 + 1.12 | 30 | 100 |
| 10 | 1.68 | 24 + CGA | 1.12 + 1.12 | 10 | 100 |
| 10 | 1.68 | 1 + CGA | 4.48 + 4.48 | 35 | 100 |
| 10 | 1.68 | 1 + CGA | 4.48 + 4.48 | 35 | 100 |
| 10 | 6.72 | — | 0 | 95 | 100 |
| 10 | 6.72 | 1 + CGA | 0.28 + 0.28 | 40 | 100 |
| 10 | 6.72 | 24 + CGA | 0.28 + 0.28 | 35 | 100 |
| 10 | 6.72 | 1 + CGA | 1.12 + 1.12 | 30 | 100 |
| 10 | 6.72 | 24 + CGA | 1.12 + 1.12 | 45 | 100 |
| 10 | 6.72 | 1 + CGA | 4.48 + 4.48 | 60 | 100 |
| 10 | 6.72 | 24 + CGA | 4.48 + 4.48 | 35 | 100 |
| 14 | 0.43 | — | 0 | 58 | 95 |
| 14 | 0.43 | 1 | 0.56 | 30 | 95 |
| 14 | 0.43 | 24 | 0.56 | 10 | 95 |
| 14 | 0.43 | 1 | 2.24 | 45 | 90 |
| 14 | 0.43 | 24 | 2.24 | 25 | 100 |
| 14 | 0.43 | 1 | 8.96 | 50 | 100 |
| 14 | 0.43 | 24 | 8.96 | 35 | 80 |
| 14 | 1.68 | — | 0 | 85 | 100 |
| 14 | 1.68 | 1 | 0.56 | 65 | 100 |
| 14 | 1.68 | 24 | 0.56 | 75 | 100 |
| 14 | 1.68 | 1 | 2.24 | 65 | 100 |
| 14 | 1.68 | 24 | 2.24 | 65 | 100 |
| 14 | 1.68 | 1 | 8.96 | 60 | 100 |
| 14 | 1.68 | 24 | 8.96 | 45 | 100 |
| 36 | 4.48 | — | 0 | 85 | 100 |
| 36 | 4.48 | 1 | 0.56 | 75 | 100 |
| 36 | 4.48 | 24 | 0.56 | 95 | 100 |
| 36 | 4.48 | 1 | 2.24 | 70 | 100 |
| 36 | 4.48 | 24 | 2.24 | 85 | 100 |
| 36 | 4.48 | 1 | 8.96 | 85 | 100 |
| 36 | 4.48 | 24 | 8.96 | 80 | 100 |
| 36 | 8.96 | — | 0 | 97 | 100 |
| 36 | 8.96 | 1 | 0.56 | 95 | 100 |
| 36 | 8.96 | 24 | 0.56 | 80 | 100 |
| 36 | 8.96 | 1 | 2.24 | 95 | 100 |
| 36 | 8.96 | 24 | 2.24 | 95 | 100 |
| 36 | 8.96 | 1 | 8.96 | 90 | 100 |
| 36 | 8.96 | 24 | 8.96 | 90 | 100 |

*CGA = CGA-123407 antidote compound

TABLE VIII-B

| Antidote* No. | Rate kg/ha | Herbicide No. | % Rice Inhibition by Rate of Herbicide (kg/ha) | | | | |
|---|---|---|---|---|---|---|---|
| | | | 0.28 | 0.56 | 1.68 | 3.36 | 6.72 |
| — | 0 | 37 | 25 | 52 | 90 | 92 | 98 |
| 1 + CGA | 0.28 + 0.28 | 37 | 0 | 5 | 0 | 30 | 70 |
| 1 + CGA | 1.12 + 1.12 | 37 | 5 | 15 | 15 | 10 | 10 |
| 1 + CGA | 4.48 + 4.48 | 37 | 5 | 35 | 5 | 25 | 45 |
| — | 0 | 14 | 78 | 95 | 95 | 98 | 100 |
| 1 + CGA | 0.28 + 0.28 | 14 | 30 | 60 | 65 | 95 | 100 |
| 1 + CGA | 1.12 + 1.12 | 14 | 25 | 25 | 95 | 90 | 100 |
| 1 + CGA | 4.48 + 4.48 | 14 | 15 | 20 | 55 | 95 | 95 |
| — | 0 | 10 | 55 | 35 | 83 | 87 | 95 |
| 1 + CGA | 0.28 + 0.28 | 10 | 0 | 35 | 10 | 10 | 60 |
| 1 + CGA | 1.12 + 1.12 | 10 | 35 | 5 | 5 | 50 | 50 |
| 1 + CGA | 4.48 + 4.48 | 10 | 45 | 30 | 5 | 75 | 80 |

*CGA = CGA-123407 Antidote Compound

EXAMPLE 292

The following procedure shows interaction between herbicide and antidote when applied together as a mixture in puddle seeded rice conditions characteristic of Asian rice-growing methods. This test included a tank mixture of butachlor (herbicide TM 10) plus DPX-5384 (herbicide TM 38) plus benzhydryl antidote compound TM 1. The combination of butachlor plus DPX-5384 provides broad spectrum control of the most troublesome weeds found in rice. An untreated control pan, a herbicide control pan and a herbicide antidote test pan were filled with 5 cm of Ray silt loam soil saturated with water and were placed in a greenhouse. Pre-germinated rice seed, previously soaked in water for 24 hours followed by a 24-hour moist incubation period, was sown on to the wet soil surface. Labelle, a long-grain Indica type seed, and S-201, a short-grain Japonica type seed, were used for the test. The rice seed was pressed lightly into the soil to cover the seeds. Two weed species, barnyardgrass (an annual grass) and *Sagittaria pygmaea* (a perennial broadleaf weed) were also seeded into the pans seeded with rice. Barnyardgrass was sown onto the soil in a manner similar to rice seed. *Sagittaria pygmaea* was pressed about 1-2 cm below the soil surface. The tank mixtures were applied to the soil by a track sprayer. The pans were placed in watering trays and the water level was maintained to assure saturated soil conditions throughout the duration of the test. Greenhouse temperature was 27° C. at night and 29° C. in daytime. A tank mix ratio of 2:1 butachlor:antidote TM 1 (1.68/kg/ha:0.84 kg/ha) showed complete rice safening. The tank mixtures containing butachlor+DPX-5384 were also safened with antidote TM 1 to a degree equivalent to butachlor+antidote TM 1 mixtures, along with excellent control of barnyardgrass and *Sagittaria pygmaea* weeds. Results are reported in Table IX.

TABLE IX

| *Herbicide #10 | Rate & #38 | *Antidote #1 | % Plant Inhibition ||||
|---|---|---|---|---|---|---|
| | | | Labelle Rice | S-201 Rice | Barnyard-grass | Sagittaria pygmaea |
| — | — | — | 0 | 0 | — | 0 |
| 0.56 | — | — | 30 | 10 | 70 | 30 |
| 1.68 | — | — | 95 | 90 | 98 | 80 |
| 4.48 | — | — | 100 | 95 | 100 | 90 |
| — | — | 0.28 | 0 | 0 | 0 | 0 |
| — | — | 0.84 | 0 | 0 | 0 | 0 |
| — | — | 2.24 | 0 | 0 | 0 | 0 |
| 0.56 | — | 0.28 | 10 | 10 | 80 | 40 |
| 1.68 | — | 0.84 | 0 | 0 | 90 | 40 |
| 4.48 | — | 2.24 | 60 | 40 | 99 | 90 |
| — | 0.025 | — | 10 | 0 | 10 | 100 |
| — | 0.050 | — | 20 | 0 | 10 | 100 |
| — | 0.025 | 2.24 | 0 | 0 | 10 | 100 |
| — | 0.050 | 2.24 | 10 | 0 | 10 | 100 |
| 0.56 | 0.025 | — | 20 | 0 | 60 | 100 |
| 1.68 | 0.025 | — | 95 | 90 | 90 | 100 |
| 4.48 | 0.025 | — | 98 | 95 | 99 | 100 |
| 0.56 | 0.025 | 0.28 | 0 | 0 | 70 | 100 |
| 1.68 | 0.025 | 0.84 | 20 | 0 | 80 | 100 |
| 4.48 | 0.025 | 2.24 | 50 | 20 | 95 | 100 |
| 0.56 | 0.050 | — | 30 | 10 | 80 | 100 |
| 1.68 | 0.050 | — | 80 | 70 | 90 | 100 |
| 4.48 | 0.050 | — | 100 | 95 | 99 | 100 |
| 0.56 | 0.050 | 0.28 | 20 | 0 | 60 | 100 |
| 1.68 | 0.050 | 0.84 | 20 | 10 | 80 | 100 |
| 4.48 | 0.050 | 2.24 | 20 | 10 | 90 | 100 |

*In kg/ha

The foregoing examples illustrate that the benzhydryl-type antidote compounds of this invention are useful in reducing herbicidal injury to crop plants under greenhouse test conditions.

In field applications, the herbicide, antidote, or a mixture thereof, may be applied to the plant locus without any adjuvants other than a solvent. Usually, the herbicide, antidote, or a mixture thereof, is applied in conjunction with one or more adjuvants in liquid or solid form. Compositions or formulations containing mixtures of an appropriate herbicide and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants. These mixtures may be in the form of particulate solids, granules, pellets, wettable powders, dusts, solutions, aqueous dispersions, or emulsions.

Examples of suitable adjuvants are finely-divided solid carriers and extenders including talcs, clays, pumice, silica, diatomaceous earth, quartz, Fuller's earth, sulfur, powdered cork, powdered wood, walnut flour, chalk, tobacco dust, charcoal, and the like. Typical liquid diluents include Stoddard's solvent, acetone, methylene chloride, alcohols, glycols, ethyl acetate, benzene, and the like. Liquids and wettable powders usually contain as a conditioning agent one or more surface-active agents in amounts sufficient to make a composition readily dispersible in water or in oil. The term "surface-active agent" includes wetting agents, dispersing agents, suspending agents, and emulsifying agents. Typical surface-active agents are mentioned in U.S. Pat. No. 2,547,724.

Compositions of this invention generally contain from about 5 to 95 parts herbicide-and-antidote, about 1 to 50 parts surface-active agent, and about 4 to 94 parts solvent, all parts being by weight based on the total weight of the composition.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

The crop may be protected by treating the crop seed with an effective amount of antidote prior to planting. Generally, smaller amounts of antidote are required to treat such seeds. A weight ratio of as little as 0.6 parts of antidote per 1000 parts of seed may be effective. The amount of antidote utilized in treating the seed may be increased if desired. Generally, however, a weight ratio of antidote-to-seed weight may range from 0.1 to 10.0 parts of antidote per 1000 parts of seed. Since only a very small amount of active antidote is usually required for the seed treatment, the compound preferably is formulated as an organic solution, powder, emulsifiable concentrate, water solution, or flowable formulation, which can be diluted with water by the seed treater for use in seed treating apparatus. Under certain conditions, it may be desirable to dissolve the antidote in an organic solvent or carrier for use as a seed treatment or the pure compound alone may be used under properly controlled conditions.

For antidote seed-coating or for antidotes applied to soil in granular or liquid formulations, suitable carriers may be either solids, such as talc, sand, clay, diatomaceous earth, sawdust, calcium carbonate, and the like, or liquids, such as water, kerosene, acetone, benzene, toluene, xylene, and the like, in which the active antidote may be either dissolved or dispersed. Emulsifying agents are used to achieve a suitable emulsion if two immiscible liquids are used as a carrier. Wetting agents may also be used to aid in dispersing the active antidote in liquids used as a carrier in which the antidote is not completely soluble. Emulsifying agents and wetting agents are sold under numerous tradenames and trademarks and may be either pure compounds, mixtures of compounds of the same general groups, or they may be mixtures of compounds of different classes. Typical satisfactory surface active agents which may be used are alkali metal higher-alkylarylsulfonates such as sodium dodecylbenzenesulfonate, and the sodium salts of alkylnaphthalenesulfonic acids, fatty alcohol sulfates such as the sodium salts of monoesters of sulfuric acid with n-aliphatic alcohols containing 8-18 carbon atoms, long-chain quaternary ammonium compounds, sodium salts of petroleum-derived alkylsulfonic acids, polyethylene sorbitan monooleate, alkylaryl polyether alcohols, water-soluble lignin sulfonate salts, alkali casein compositions, longchain alcohols usually containing 10-18 carbon atoms, and condensation products of ethylene oxide with fatty acids, alkylphenols, and mercaptans.

The following examples describe preparation of herbicide formulations, antidote formulations, and herbicide+antidote formulations, and use of these formulations, under field test conditions.

EXAMPLE 293

A commercially-available formulation of alachor (herbicide TM 6) in emulsifiable concentrate form (LASSO ® herbicide, Monsanto Co., St. Louis, Mo.) was used for the field tests. The formulation contained 45.1 % by wt alachlor (480 g/l or 4 lbs/gal) and 54.9 % by wt inert ingredients.

EXAMPLE 294

An emulsifiable concentrate formulation containing herbicide compound TM 10 was prepared with the following components:

| | % by wt. |
|---|---|
| Herbicide #10: butachlor (92% tech) | 65.95 |
| Atlox 3404F emulsifier; ICI Specialty Chemicals, Wilmington, Del. | 2.25 |
| Atlox 3409F emulsifier; ICI Specialty Chemicals, Wilmington, Del. | 2.75 |
| T-500-100 solvent (mixture of C9 aromatic compounds); Tenneco Chemical Co., Atlanta, Ga. | 29.02 |
| GE AG-78 antifoaming agent (polysiloxane); General Electric Co., Waterford, N.Y. | 0.01 |
| Methyl violet (30% solution as the oleate); Dye specialties Co., Jersey City, N.J. | 0.02 |

These components were mixed together at room temperature until a uniform blend was obtained. The formulation had a specific gravity of 1.0008 observed at 25° C. calculated against water at 15.6° C., and a flash point of 41° C. The formulation showed good to perfect emulsion bloom at water-hardness concentrations of 114 ppm and 1000 ppm and was 100 percent stable after one hour at each water-hardness test concentration. The formulation contained 600 g/l (5 lb/gal) of herbicide compound TM 10.

EXAMPLE 295

An emulsifiable concentrate formulation containing acetochlor (herbicide compound TM 11) was prepared with the following components:

| | % by wt. |
|---|---|
| Herbicide #11: acetochlor (93.5% tech) | 92.00 |
| Witco C-5438 emulsifier (blend of aionic/non-ionic emulsifiers in ethylene glycol); Witco Chemical Co., New York, N.Y. | 7.96 |
| GE AG-78 antifoaming agent (polysiloxane); General Electric Co., Waterford, N.Y. | 0.02 |
| Methyl violet dye; Dye Specialities Co., Jersey City, N.J. | 0.017 |

These components were mixed together at room temperature until a uniform blend was obtained. The formulation had a specific gravity of 1.1167 observed at 25° C. and calculated against water at 15.6° C., and had a flash point above 100° C. (tag closed-cup method). The formulation showed perfect emulsion bloom at water-hardness concentrations of 114 ppm, 342 ppm and 1000 ppm, and was 100 percent stable after one hour at each water-hardness concentration. The formulation was blue and contained 960 g/l (8 lb/gal) of acetochlor compound.

EXAMPLE 296

An emulsifiable concentrate formulation containing herbicide compound TM 15 was prepared with the following components:

| | % by wt. |
|---|---|
| Herbicide #15: 2-chloro-2'-methyl-6'-methoxy-N-(isopropoxymethyl)-acetanilide (78% tech.) | 41.16 |
| FLOMO 50H emulsifier (50% solution of calcium dodecylbenzene sulfonate in mineral spirits); De Soto Chemical Co., Chicago, Ill. | 1.79 |
| FLOMO 14D emulsifier (reaction product of dodecyl phenol and 14 mols ethylene oxide); De Soto Chemical Co., Chicago, Ill. | 1.91 |
| FLOMO XH emulsifier (block copolymer of propylene oxide and ethylene oxide); De Soto Chemical Co., Chicago, Ill. | 0.93 |
| FLOMO 54C emulsifier (castor oil ethoxylated with 54 moles ethylene oxide); De Soto Chemical Co., Chicago, Ill. | 0.17 |
| Naphtha Solvent | 0.20 |
| Monochlorobenzene Solvent | 53.84 |

These components were mixed together at room temperature until a uniform blend was obtained. The formulation had a specific gravity of 1.1213 observed at 25° C. and calculated against water at 15.6° C., a solution point at 2° C., and a flash point less than 38° C. The formulation showed perfect emulsion bloom at water-hardness concentrations of 114 ppm and 342 ppm, and very good bloom at 1000 ppm, and was 100 percent stable after one hour at each test concentration. The formulation contained 360 g/l (3 lb/gal) of herbicide compound TM 15.

EXAMPLE 297

Other, non-commercially available herbicide formulations used in the field tests were prepared in emulsifiable-concentrate form in accordance with procedures such as described in Examples 294-296. These herbicides and their concentrations of active ingredient were as follows:

| Herbicide Cpd. # | Concentration of Active Ingredient |
|---|---|
| 9 | 600 g/l; 5 lb/gal |

| Herbicide Cpd. # | Concentration of Active Ingredient |
|---|---|
| 18 | 480 g/l; 4 lb/gal |
| 31 | 480 g/l; 4 lb/gal |
| 39 | 480 g/l; 4 lb/gal |

EXAMPLE 298

An emulsifiable concentrate formulation containing antidote compound TM 1 was prepared with the following components:

| | % by wt. |
|---|---|
| Antidote #1: methyl diphenylmethoxyacetate (100% tech.) | 47.04 |
| Atlox 3437F emulsifier; ICI Specialty Chemicals, Wilmington, Del. | 4.67 |
| Atlox 3438F emulsifier; ICI Specialty Chemicals, Wilmington, Del. | 0.33 |
| T-400 solvent (mixture of $C_9$ aromatic compounds); Tenneco Chemical Co., Atlanta, Ga. | 33.57 |
| Monochlorobenzene solvent | 14.39 |

These components were mixed together at room temperature until a uniform blend was obtained. The formulation had a specific gravity of 1.0195 observed at 25° C. calculated against water at 15.6° C., and a solution point less than 0° C. The formulation showed perfect emulsion bloom at water-hardness concentrations of 114 ppm and 1000 ppm and was 100 percent stable after one hour at each water-hardness test concentration. The formulation contained 480 g/l (4 lb/gal) of antidote compound TM 1.

EXAMPLE 299

An emulsifiable concentrate formulation containing antidote compound TM 1 was prepared with the following components:

| | % by wt. |
|---|---|
| Antidote #1: methyl diphenylmethoxyacetate (95% tech.) | 13.00 |
| Stepan Agent 45 emulsifier; Stepan Chemical Co., Northfield, Ill. | 5.00 |
| T-400 solvent (mixture of $C_9$ aromatic compounds); Tenneco Chemical Co., Atlanta, Ga. | 57.40 |
| Monochlorobenzene solvent | 24.60 |

These components were mixed together at room temperature until a uniform blend was obtained. The formulation had a specific gravity of 0.9724 observed at 25° C. calculated against water at 15.6° C., a solution point of 0° C., and a flash point of 38° C. The formulation showed no bloom because it floated on water. The emulsion was observed as 100 percent stable after one hour at each water-hardness test concentration. The formulation contained 120 g/l (1 lb/gal) of antidote compound TM 1.

EXAMPLE 300

An emulsifiable concentrate formulation containing antidote compound TM 9 was prepared with the following components:

| | % by wt. |
|---|---|
| Antidote #9: 2,2,2-trifluoroethyl diphenylmethoxyacetate (99% tech.) | 45.06 |
| FLOMO 50H emulsifier (50% solution of calcium dodecylbenzene sulfonate in mineral spirits); De Soto Chemical Co., Chicago, Ill. | 0.40 |
| FLOMO 14D emulsifier (reaction product of dodecyl phenol and 14 mols ethylene oxide); De Soto Chemical Co., Chicago, Ill. | 2.74 |
| FLOMO XH emulsifier (block copolymer of propylene oxide and ethylene oxide); De Soto Chemical Co., Chicago, Ill. | 1.33 |
| FLOMO 54C emulsifier (castor oil ethoxylated with 54 moles ethylene oxide); De Soto Chemical Co., Chicago, Ill. | 0.24 |
| Naphtha Solvent | 0.29 |
| T-400 solvent (mixture of $C_9$ aromatic compounds); Tenneco Chemical Co., Atlanta, Ga. | 24.97 |
| Monochlorobenzene Solvent | 24.97 |

These components were mixed together at room temperature until a uniform blend was obtained. The formulation had a specific gravity of 1.0759 observed at 25° C. and calculated against water at 15.6° C., and a flash point above 38° C. The formulation showed very good emulsion bloom at a water-hardness concentration of 114 ppm, and perfect bloom at 342 ppm and 1000 ppm, and was 100 percent stable after one hour at each test concentration. The formulation contained 480 g/l (4 lb/gal) of antidote compound TM 9.

EXAMPLE 301

An emulsifiable concentrate formulation containing antidote compound TM 11 was prepared with the following components:

| | % by wt. |
|---|---|
| Antidote #11: 1,1-dimethylethylammonium phenyl[3-(trifluoromethyl)-phenyl]methoxyacetate | 32.10 |
| FLOMO 50H emulsifier (50% solution of calcium dodecylbenzene sulfonate in mineral spirits); De Soto Chemical Co., Chicago, Ill. | 1.79 |
| FLOMO 14D emulsifier (reaction product of dodecyl phenol and 14 mols ethylene oxide); De Soto Chemical Co., Chicago, Ill. | 1.91 |
| FLOMO XH emulsifier (block copolymer of propylene oxide and ethylene oxide); De Soto Chemical Co., Chicago, Ill. | 0.93 |
| FLOMO 54C emulsifier (caster oil ethoxylated with 54 moles ethylene oxide); De Soto Chemical Co., Chicago, Ill. | 0.17 |
| Naphtha Solvent | 0.20 |
| Monochlorobenzene Solvent | 62.90 |

These components were mixed together at room temperature until a uniform blend was obtained. The formulation had a specific gravity of 1.1215 observed at 25° C. and calculated against water at 15.6° C., and a flash point less than 38° C. The formulation showed good emulsion bloom at water-hardness concentrations of 114 ppm, 342 ppm and 1000 ppm, and had a cream layer 1 cm in thickness at each test concentration. The formulation contained 360 g/l (3 lb/gal) of antidote compound TM 11.

EXAMPLE 302

Antidote compound TM 11 in crystalline form was converted to a 20% powder for use in field tests. The powder was prepared with the following components:

|  | % by wt. |
|---|---|
| Antidote #11: 1,1-dimethylethyl-ammonium phenyl[3-(trifluoromethyl)-phenyl]methoxyacetate | 20.00 |
| Barden clay carrier; J. M. Huber Co., Havre de Grace, Md. | 80.00 |

These components were mixed together until uniformly dispersed and then further blended and ground in a hammer mill to a fine powder of particle size from about 50 microns to about 100 microns in diameter.

EXAMPLE 303

An emulsifiable concentrate formulation containing antidote compound TM 16 was prepared with the following components:

|  | % by wt. |
|---|---|
| Antidote #16: S-ethyl 2-(diphenyl-methoxy)ethanethioate | 22.72 |
| FLOMO 50H emulsifier (50% solution of calcium dodecylbenzene sulfonate in mineral spirits); De Soto Chemical Co., Chicago, Ill. | 3.75 |
| FLOMO 54C emulsifier (castor oil ethoxylated with 54 moles ethylene oxide); De Soto Chemical Co., Chicago, Ill. | 3.75 |
| Monochlorobenzene solvent | 69.78 |

These components were mixed together at room temperature until a uniform blend was obtained. The formulation had a solution point of 0° C., and a flash point less than 38° C. The formulation showed perfect emulsion bloom at water-hardness concentrations of 4 ppm, 342 ppm and 1000 ppm, and was 100 percent stable after one hour at each test concentration. The formulation was dark brown and contained 240 g/1 (2 lb/gal) of antidote compound TM 16.

EXAMPLE 304

Antidote compound TM 16 in crystalline form was converted to a 50% sticky powder for use in field tests. The powder was prepared the following components:

|  | % by wt. |
|---|---|
| Antidote #16: S-ethyl 2-(diphenyl-methoxyethanethioate | 50.00 |
| Micro-Cel E diatomaceous earth; Johns-Manville Co., Los Angeles, Ca. | 25.00 |
| Dipropylene Glycol | 25.00 |

These components were mixed together until uniformly dispersed and then further blended and ground in a hammer mill to a fine powder of particle size from about 50 microns to about 100 microns in diameter.

EXAMPLE 305

Antidote compound TM 22 in crystalline form was converted to a 25% wettable powder for use in formulation field tests. The wettable powder was prepared with the following components.

|  | % by wt. |
|---|---|
| Antidote #22: bis(2,6-dimethylphenyl)-methoxyacetic acid | 25.00 |
| Reax 45-A dispersant (modified sodium salts of sulfonated lignin); Westvaco Chem. Div., Winder, Ga. | 4.00 |
| Aerosol OTB dispersant (dioctyl ester of sodium sulfosuccinic acid), American Cyanamid Co., Stamford, Conn. | 4.00 |
| Barden clay carrier; J. M. Huber Co., Havre de Grace, Md. | 67.00 |

These components were mixed together until uniform and then further blended and ground in a hammer mill to a fine powder of particle size from about 50 microns to about 100 microns in diameter.

EXAMPLE 306

Antidote compound TM 22 in crystalline form was converted to a 50% powder for use in field tests. The powder was prepared with the following components:

|  | % by wt. |
|---|---|
| Antidote #22: bis(2,6-dimethylphenyl)-methoxyacetic acid | 50.0 |
| Micro-Cel E diatomaceous earth; Johns-Manville Co., Los Angeles, Ca. | 25.0 |
| Barden Clay carrier; J. M. Huber Co., Havre de Grace, Md. | 25.0 |

These components were mixed together until uniformly dispersed and then further blended and ground in a hammer mill to a fine powder of particle size from about 50 microns to about 100 microns in diameter.

EXAMPLE 307

An emulsifiable concentrate formulation containing antidote compound TM 23 was prepared with the following components:

|  | % by wt. |
|---|---|
| Antidote #23: 3-nitrophenyl diphenylmethoxyacetate (98% tech) | 10.96 |
| FLOMO 54C emulsifier (castor oil ethoxylated with 54 moles ethylene oxide); De Soto Chemical Co., Chicago, Ill. | 5.90 |
| FLOMO 50H emulsifier (50% solution of calcium dodecylbenzene sulfonate in mineral spirits); De Soto Chemical Co., Chicago, Ill. | 3.90 |
| FLOMO XD emulsifier (block copolymer of ethyleneoxide and propylene oxide); De Soto Chemical Co., Chicago, Ill. | 0.20 |
| Monochlorobenzene solvent | 79.03 |

These components were mixed together at room temperature until a uniform blend was obtained. The formulation had a specific gravity of 1.1173 observed at 25° C. calculated against water at 15.6° C., and a solution point of 0° C. and a flash point of less than 38° C. The formulation showed perfect emulsion bloom at water-hardness concentrations of 114 ppm, 342 ppm and 1000 ppm and was 100 percent stable after one hour at each test concentration. The formulation was amber and contained 120 g/1 (1 lb/gal) of antidote compound TM 23.

EXAMPLE 308

Antidote compound TM 23 in crystalline form was converted to a 50% powder for use in field tests. The powder was prepared with the following components:

|  | % by wt. |
|---|---|
| Antidote #23: 3-nitrophenyl diphenylmethoxyacetate | 50.00 |
| Barden clay carrier; J. M. Huber Co., Havre de Grace, Md. | 25.00 |
| Micro-Cel E diatomaceous earth; Johns-Manville Co., Los Angeles, Ca. | 25.00 |

These components were mixed together until uniformly dispersed and then further blended and ground in a hammer mill to a fine powder of particle size from about 50 microns to about 100 microns in diameter.

EXAMPLE 309

An emulsifiable concentrate formulation containing antidote compound TM 24 was prepared with the following components:

|  | % by wt. |
|---|---|
| Antidote #24: ethyl bis(2,6-dimethylphenyl) methoxyacetate (95% tech.) | 25.02 |
| FLOMO 50H emulsifier (50% solution of calcium dodecylbenzene sulfonate in mineral spirits); De Soto Chemical Co., Chicago, Ill. | 5.56 |
| FLOMO 54C emulsifier (castor oil ethoxylated with 54 moles ethylene oxide); De Soto Chemical Co., Chicago, Ill. | 4.44 |
| T-400 solvent (mixture of $C_9$ aromatic compounds); Tenneco Chemical Co., Atlanta, Ga. | 32.49 |
| Monochlorobenzene solvent | 32.49 |

These components were mixed together at room temperature until a uniform blend was obtained. The formulation had a specific gravity of 1.10145 observed at 25° C. calculated against water at 15.6° C., a solution point less than 0° C., and a flash point of 38° C. The formulation showed very good emulsion bloom at waterhardness concentrations of 114 ppm, 342 ppm, and 1000 ppm, and was 100 percent stable after one hour at each test concentration. The formulation was brown in color and contained 240 g/1 (2 lb/gal) of antidote compound TM 24.

EXAMPLE 310

Antidote compound TM 24 in crystalline form was converted to a 50% sticky powder for use in field tests. The wettable powder was prepared with the following components:

|  | % by wt. |
|---|---|
| Antidote #24: ethyl bis(2,6-dimethyl-phenyl)methoxyacetate | 50.00 |
| Micro-Cel E diatomaceous earth; Johns-Manville Co., Los Angeles, Ca. | 25.00 |
| Dipropylene Glycol | 25.00 |

These components were mixed together until uniformly dispersed and then further blended and ground in a hammer mill to a fine powder of particle size from about 50 microns to about 100 microns in diameter.

EXAMPLE 311

Antidote compound TM 27 in crystalline form was converted to a 25% sticky powder for use in field tests. The powder was prepared with the following components:

|  | % by wt. |
|---|---|
| Antidote #27: 1-cyano-1-methylethyl diphenylmethoxyacetate | 25.0 |
| Micro-Cel E diatomaceous earth; Johns-Manville Co., Los Angeles, Ca. | 50.00 |
| Dipropylene Glycol | 25.0 |

These components were mixed together until uniformly dispersed and then further blended and ground in a hammer mill to a fine powder of particle size from about 50 microns to about 100 microns in diameter.

EXAMPLE 312

Antidote-coated crop seed was prepared by placing a measured quantity of seed in a plastic container along with a measured quantity of the powder formulation containing antidote compound The powder formulation was prepared by procedures of Examples 302, 304, 305, 306, 308, 310 or 311. The crop seed was previously treated with the fungicide captan (Chevron Chemical Co., San Francisco, Calif.) and with the insecticide methoxychlor (E.I. duPont de Nemours & Co. Wilmington, Del.). The plastic container containing seed and powder formulation was shaken until all seed was thoroughly coated with the formulation. Antidote-coated crop seed was prepared having antidote at concentrations in a range typically from 1/32% to ⅛%, wt./wt., antidote-on-seed.

EXAMPLE 313

Formulations were prepared for field testing to determine the comparative effects of herbicide alone, herbicide-and-antidote in combination, and antidote alone. The herbicide and/or antidote formulations were applied by tank-mix spraying. Also, the herbicide-antidote interactions were evaluated with the antidote as a seed coating. For each formulation, a tractor-mounted 20-liter spray tank was filled about half-full with water. For the herbicide formulations containing no antidote, an appropriate amount of emulsifiable concentrate (as described in Examples 293-297) was added directly to a tank. For the antidote-containing tank-mix formulations, the antidote in wettable powder form or in emulsifiable form was added to a tank. Then for the herbicide + antidote formulation, antidote wettable powder or emulsifiable concentrate was added to a tank containing herbicide. Each tank-mix formulation was agitated sufficiently to ensure a uniform suspension. The relative amounts of water, herbicide emulsifiable concentrate, and antidote, added to the tank were calculated for each formulation based upon a formulation spraying rate of 280 l/ha (30 gal/acre) in order to achieve various field application rates of herbicide and antidote, as appropriate, for the rates shown in the following tests. Each formulation was sprayed on three replicate plots, with a small-plot tractor-mounted sprayer with a 3 meter (10 ft) boom delivering 280 l/ha (30 gal/ac) at 2 atm pressure (30 psi), unless otherwise specified. The treatments were made to silt loam topsoil containing approximately one percent organic matter and were selected in a random manner in order to normalize variations in plot soil conditions. Three control plots were established which were not treated with herbicide or with antidote formulations. Where appropriate, crop seed used in the field tests was treated prior to planting with Vitavax fungicide, or captan fungicide, or the insecticide methoxychlor.

EXAMPLE 314

Formulations of butachlor (herbicide cpd. TM 10) and tank-mix safened butachlor (with antidote cpd. TM 1) were pre-emergent surface-applied in side-by-side field plots to determine their relative inhibition of grassy weeds and injury to direct-seeded upland rice in eastern Missouri. Eight rows of Brazos rice seed, treated with Vitavax fungicide, and four rows of barnyardgrass seed were planted 3 cm deep at a heavy seeding rate in Ray silt loam topsoil using a 12-row Planet Jr. planter. The test formulations of butachlor, safened butachlor, and a control formulation of antidote without herbicide, were prepared as described in the foregoing Examples. The plots (2×5 m; 7×15 ft) were sprayed with a $CO_2$-pressurized small-plot back-pack sprayer at a rate of 280 l/ha (30 gal/ac). Test observations, taken at 24 days after treatment by three observers, are reported in Table X.

| Field Conditions at Treatment: | |
|---|---|
| Wind speed: | 8-15 Km/hr (5-9 mph) |
| Air temperature: | 33° C. (92° F.) |
| Soil temperature: | 30° C. (86° F.) |
| Relative humidity: | 44% |
| Soil moisture: | slightly cloddy, dry surface; adequate subsurface moisture. |
| Climatic Conditions First-Three Weeks: | |
| Average air temp.: | Hi/Lo 31° C. (87° F.)/19° C. (67° F.) |
| Extreme air temp.: | Hi/Lo 36° C. (97° F.)/13° C. (55° F.) |
| Rainfall: | 8.9 cm (3.5 in) total |
| Irrigation: | 1 cm (0.5") overhead 4 days after treatment. |

TABLE X

| Formulation (kg/ha) | | % Inhibition | |
|---|---|---|---|
| Herbicide #10 | Antidote #1 | Rice | Barnyard-Grass |
| 0 | 0 | 0 | 0 |
| 2.24 | 0 | 20 | 85 |
| 4.48 | 0 | 23 | 97 |
| 8.96 | 0 | 32 | 99 |
| 0 | 1.12 | 0 | 0 |
| 2.24 | 1.12 | 7 | 92 |
| 4.48 | 1.12 | 10 | 96 |
| 8.96 | 1.12 | 20 | 97 |
| 0 | 2.24 | 0 | 0 |
| 2.24 | 2.24 | 10 | 82 |
| 4.48 | 2.24 | 15 | 88 |
| 8.96 | 2.24 | 13 | 97 |
| 0 | 4.48 | 0 | 0 |
| 2.24 | 4.48 | 10 | 87 |
| 4.48 | 4.48 | 23 | 97 |
| 8.96 | 4.48 | 15 | 98 |

EXAMPLE 315

Formulations of alachlor (herbicide cpd. TM 4) and tank-mix safened alachlor (separately with antidote cpd. TM 9 and TM 11) were pre-emergent surface-applied in side-by-side field plots to determine their relative inhibition of grassy and broadleaf weeds in the presence of grain sorghum in eastern Missouri. Four rows of DeKalb E59+ grain sorghum seed were planted 2-3 cm (¾-1 in) deep in Ray silt loam topsoil at a seeding rate of at least 22 Kg/ha (20 lb/ac). Test formulations of alachlor, safened alachlor and a control formulation of antidote without herbicide, were prepared as described in the foregoing Examples. The plots (2×8 m; 7×25 ft) were sprayed with a $CO_2$-pressurized small-plot back-pack sprayer at a rate of 280 l/ha (30 gal/ac). Test observations are reported in Table XI.

| Field Conditions at Treatment: | |
|---|---|
| Wind speed: | 8-14 Km/hr (5-9 mph) |
| Air temperature: | 24° C. (75° F.) |
| Soil moisture: | surface dry, moist @ seed depth |

TABLE XI

| Formulation | | % Inhibition | | |
|---|---|---|---|---|
| Herbicide #6 (kg/ha) | Antidote #9/#11 (kg/ha) | Grain Sorghum a/b | Giant Foxtail a/b | Pigweed a/b |
| 0 | 0 | 0/0 | 0/0 | 0/0 |
| 1.12 | 0 | 22/3 | 100/97 | 100/100 |
| 2.24 | 0 | 62/32 | 100/100 | 100/100 |
| 4.48 | 0 | 88/70 | 100/100 | 100/100 |
| 0 | | 0/0 | 0/0 | 0/0 |
| 1.12 | #9 1.12 | 14/0 | 100/100 | 100/100 |
| 2.24 | #9 1.12 | 27/8 | 100/95 | 100/100 |
| 4.48 | #9 1.12 | 62/33 | 100/100 | 100/100 |
| 0 | #9 2.24 | 0/0 | 0/0 | 0/0 |
| 1.12 | #9 2.24 | 15/7 | 100/98 | 100/100 |
| 2.24 | #9 2.24 | 30/10 | 100/100 | 100/100 |
| 4.48 | #9 2.24 | 41/8 | 100/98 | 100/100 |
| 0 | #9 4.48 | 0/0 | 0/0 | 0/0 |
| 1.12 | #9 4.48 | 8/0 | 99/100 | 99/100 |
| 2.24 | #9 4.48 | 24/3 | 100/100 | 100/100 |
| 4.48 | #9 4.48 | 37/12 | 100/100 | 100/100 |
| 0 | | 0/0 | 0/0 | 0/0 |
| 1.12 | #11 1.12 | 18/10 | 100/100 | 100/100 |
| 2.24 | #11 1.12 | 37/18 | 100/100 | 100/100 |
| 4.48 | #11 1.12 | 65/45 | 100/100 | 100/100 |
| 0 | #11 2.24 | 0/0 | 0/0 | 0/0 |
| 1.12 | #11 2.24 | 7/0 | 100/100 | 100/100 |
| 2.24 | #11 2.24 | 18/3 | 100/100 | 100/100 |
| 4.48 | #11 2.24 | 46/32 | 100/100 | 100/100 |
| 0 | #11 4.48 | 2/0 | 0/0 | 0/0 |
| 1.12 | #11 4.48 | 9/0 | 100/100 | 100/100 |
| 2.24 | #11 4.48 | 12/3 | 100/100 | 100/100 |
| 4.48 | #11 4.48 | 42/18 | 100/100 | 100/100 | a = Observations taken at 21 days after treatment.
b = Observations taken at 58 days after treatment.

EXAMPLE 316

Formulations of four acetanilide herbicides a (cpds TM 6, TM 11, TM 15 and TM 18) were individually surface-applied pre-emergent to side-by-side field plots to determine their relative injury to grain sorghum and corn grown from seed treated with antidote compound TM 11. DeKalb E59+ hybrid grain sorghum seed and DeKalb corn seed were treated with antidote TM 11 in an 80% powder formulation (prepared as described in the foregoing Examples) at a rate of ⅛% antidote-on-seed (wt/wt). Six rows of each seed were planted in Ray silt loam soil to a depth of 1.9-2.5 cm (¾-1 in) using a 12-row Planet Jr. planter at a seeding rate of at least 22 kg/ha (20 lb/ac) for the sorghum seed and at a rate of 147,000 seed/ha (64,000 seed/ac) for the corn seed. The herbicide test and control formulations were prepared and surface-applied to the field plots (3×12 m; 11×15 ft) as described in Example 313. Test observations are reported in Table XII.

| Field Conditions at Treatment: |
|---|

-continued

| | |
|---|---|
| Wind speed: | 0-5 Km/hr (0-3 mph) |
| Air temperature: | 27° C. (80° F.) |
| Soil moisture: | surface dry, moist @ seed depth |
| Climatic Conditions First–Three Weeks: | |
| Average air temp.: | Hi/Lo 32° C. (90° F.)/20° C. (68° F.) |
| Extreme air temp.: | Hi/Lo 35° C. (95° F.)/16° C. (61° F.) |
| Rainfall: | 3.3 cm (1.31 in) total |
| Irrigation: | 2.5 cm (1.0 in) 2 days after treatment |

TABLE XII

| | % Injury | | | |
|---|---|---|---|---|
| | Seed Without Antidote | | Antidote #11 on Seed (⅛%) | |
| Herbicide # — (kg/ha) | Sorghum a/b | Corn a/b | Sorghum a/b | Corn a/b |
| 0 | 0/0 | 0/0 | 0/0 | 0/0 |
| #6  4.48 | 94/80 | 11/0 | 40/16 | 3/7 |
|     6.72 | 99/99 | 9/5 | 57/29 | 23/7 |
| #11  2.24 | 96/80 | 13/3 | 72/67 | 5/4 |
|      6.72 | 100/100 | 28/15 | 87/63 | 13/5 |
| #15  2.24 | 94/86 | 48/20 | 61/71 | 14/18 |
|      6.72 | 100/100 | 89/90 | 100/90 | 42/46 |
| #18  2.24 | 99/13 | 8/13 | 56/49 | 8/3 |
|      6.72 | 100/29 | 37/29 | 92/99 | 17/13 | a = Observations taken at 29 days after treatment.
b = Observations taken at 64 days after treatment.

EXAMPLE 317

Formulations of alachlor (herbicide cpd. TM 6) and tank-mix safened alachlor (with antidote cpd. TM 23) were pre-plant-incorporated in side-by-side field plots to determine their relative injury to winter wheat in eastern Missouri. Test formulations of alachlor, safened alachlor, and a control formulation of antidote without herbicide, were prepared as described in the foregoing Examples. The plots (3×8 m; 11×25 ft) were sprayed with a CO$_2$-pressurized small-plot back-pack sprayer at a rate of 280 l/ha (30 gal/ac). A Ferguson Tilrovator was used to incorporate the formulations to a depth of about 2.5 cm (1 in). A John Deere drill planter was used to plant Pike winter wheat seed to a depth of about 4 cm (1½ in) at a seeding rate of about 99 kg/ha (90 lb/ac). Test observations taken 28 days after treatment, are reported in Table XIII.

| Field Conditions at Treatment: | |
|---|---|
| Wind speed: | 0-5 Km/hr (0-3 mph) |
| Air temperature: | 29° C. (85° F.) |
| Soil moisture: | surface dry, moist @ seed depth |
| Climatic Conditions First–Three Weeks: | |
| Rainfall: | 12.6 cm (4.97 in) total |
| Irrigation: | 2.5 cm (1.0 in) 4 days after treatment |

TABLE XIII

| Herbicide #6 (kg/ha) | Antidote #23 (kg/ha) | % Inhibition Wheat |
|---|---|---|
| 0 | 0 | 0 |
| 1.12 | 0 | 70 |
| 2.24 | 0 | 81 |
| 4.48 | 0 | 92 |
| 0 | 1.12 | 0 |
| 1.12 | 1.12 | 58 |
| 2.24 | 1.12 | 83 |
| 4.48 | 1.12 | 90 |
| 0 | 2.24 | 0 |
| 1.12 | 2.24 | 56 |
| 2.24 | 2.24 | 85 |
| 4.48 | 2.24 | 90 |
| 0 | 4.48 | 0 |

TABLE XIII-continued

| Herbicide #6 (kg/ha) | Antidote #23 (kg/ha) | % Inhibition Wheat |
|---|---|---|
| 1.12 | 4.48 | 45 |
| 2.24 | 4.48 | 72 |
| 4.48 | 4.48 | 85 |

EXAMPLE 318

Formulations of butachlor (herbicide cpd. TM 10) and tank-mix safened butachlor (separately with antidote cpd. TM 16, TM 22 and TM 24) were pre-plantincorporated in side-by-side field plots to determine their relative injury to direct-seeded rice in eastern Missouri. Test formulations of butachlor, safened butachlor, and a control formulation of antidote without herbicide, were prepared as described in the foregoing Examples. The plots (3×8 m; 10×25 ft) were sprayed with a CO$_2$-pressurized small-plot back-pack sprayer at a rate of 280 l/ha (30 gal/ac). A Ferguson Tilrovator was used to incorporate the formulations into Black Stick soil. A John Deere drill planter was used to plant Bellbonnete rice at a seeding rate of 108 kg/ha (98 lb/ac). Test observations are reported in Table XIV.

| Field Conditions at Treatment: | |
|---|---|
| Wind speed: | calm |
| Air temperature: | 32° C. (90° F.) |
| Soil temperature: | 32° C. (90° F.) |
| Soil moisture: | surface dry, dry @ seed depth |
| Climatic Conditions First–Four Weeks: | |
| Rainfall: | 6.5 cm (2.56 in) total |
| Irrigation: | 1.8 cm (¾ in) one day after treatment |

TABLE XIV

| Formulation | | % Inhibition Rice | |
|---|---|---|---|
| Herbicide #10 (kg/ha) | Antidote Tank Mix Ratio Herbicide:Antidote | a | b |
| 0 | — | 0 | 0 |
| 1.12 | — | 23 | 23 |
| 3.36 | — | 37 | 47 |
| 6.72 | — | 53 | 58 |
| 1.12 | #16 8:1 | 23 | 18 |
| 3.36 | #16 8:1 | 30 | 35 |
| 6.72 | #16 8:1 | 47 | 47 |
| 1.12 | #16 4:1 | 23 | 28 |
| 3.36 | #16 4:1 | 37 | 35 |
| 6.72 | #16 4:1 | 43 | 47 |
| 0 | — | 0 | 0 |
| 1.12 | #16 2:1 | 25 | 22 |
| 3.36 | #16 2:1 | 28 | 32 |
| 6.72 | #16 2:1 | 25 | 35 |
| 1.12 | #22 8:1 | 20 | 22 |
| 3.36 | #22 8:1 | 28 | 30 |
| 6.72 | #22 8:1 | 32 | 41 |
| 1.12 | #22 4:1 | 23 | 18 |
| 3.36 | #22 4:1 | 28 | 25 |
| 6.72 | #22 4:1 | 30 | 30 |
| 0 | — | 0 | 0 |
| 1.12 | #22 2:1 | 25 | 12 |
| 3.36 | #22 2:1 | 30 | 17 |
| 6.72 | #22 2:1 | 30 | 17 |
| 1.12 | #24 8:1 | 15 | 12 |
| 3.36 | #24 8:1 | 20 | 18 |
| 6.72 | #24 8:1 | 27 | 30 |
| 1.12 | #24 4:1 | 12 | 18 |
| 3.36 | #24 4:1 | 28 | 25 |
| 6.72 | #24 4:1 | 33 | 25 |
| 0 | 0 | 0 | 0 |
| 1.12 | #24 2:1 | 18 | 13 |
| 3.36 | #24 2:1 | 28 | 17 |

TABLE XIV-continued

| Formulation | | % Inhibition Rice | |
|---|---|---|---|
| Herbicide #10 (kg/ha) | Antidote Tank Mix Ratio Herbicide:Antidote | a | b |
| 6.72 | #24 2:1 | 27 | 17 | a = Observations taken at 24 days after treatment.
b = Observations taken at 37 days after treatment.

EXAMPLE 319

Formulations of four acetanilide herbicides (cpds. TM 6, TM 10, TM 31 and TM 39) were individually pre-plant-incorporated in side-by-side field plots to determine their relative inhibition of barnyardgrass and injury to rice plants grown from direct-seeded rice seeds treated separately with antidote compounds TM 16, TM 22 and TM 24. LaBelle rice seed was treated separately with the three antidotes in 50% sticky powder formulations (prepared as described in the foregoing Examples) at antidote-on-seed rates of 1/32%, 1/16% or ⅛%. The formulations were sprayed and incorporated into silty loam soil plots (3×5 m; 11×15 ft), and the rice seed was drilled into the soil at a seeding rate of 110 kg/ha (100 lb/ac). Test observations are reported in Table XV.

| Field Conditions at Treatment: | |
|---|---|
| Wind speed: | calm |
| Air temperature: | 34° C. (94° F.) |
| Soil temperature: | 28° C. (83° F.) |
| Soil moisture: | surface dry, slight moisture @ seed depth |
| Climatic Conditions First-Three Weeks: | |
| Rainfall: | 4.72 cm (1.86 in) total |
| Irrigation: | 1.9 cm (¾ in) one day after treatment |

TABLE XV

| Antidote # _ wt/wt % on Rice Seed | Herbicide # (kg/ha) | | | | | | |
|---|---|---|---|---|---|---|---|
| | #10 1.12 | #10 3.36 | #6 1.12 | #6 3.36 | #39 1.12 | #39 3.36 | #31 1.12 |
| % RICE INHIBITION | | | | | | | |
| — 0 | 27 | 47 | 98 | 99 | 83 | 98 | 99 |
| #16 | | | | | | | |
| 1/32 0 | 12 | 23 | 85 | 99 | 53 | 99 | 99 |
| 1/16 0 | 12 | 18 | 63 | 95 | 37 | 95 | 99 |
| ⅛ 0 | 7 | 18 | 45 | 95 | 28 | 96 | 98 |
| #22 | | | | | | | |
| 1/32 0 | 8 | 18 | 80 | 99 | 42 | 99 | 99 |
| 1/16 0 | 13 | 20 | 80 | 97 | 43 | 98 | 98 |
| ⅛ 0 | 7 | 15 | 80 | 99 | 23 | 98 | 99 |
| #24 | | | | | | | |
| 1/32 0 | 10 | 20 | 78 | 99 | 45 | 99 | 99 |
| 1/16 0 | 10 | 15 | 70 | 95 | 35 | 97 | 99 |
| ⅛ 0 | 0 | 13 | 70 | 98 | 23 | 95 | 99 |
| % BARNYARDGRASS INHIBITION | | | | | | | |
| — 0 | 100 | 100 | 100 | 100 | 100 | 100 | 100 |
| #16 | | | | | | | |
| 1/32 0 | 98 | 100 | 100 | 100 | 100 | 100 | 100 |
| 1/16 0 | 100 | 100 | 100 | 100 | 100 | 100 | 100 |
| ⅛ 0 | 100 | 100 | 100 | 100 | 100 | 100 | 100 |
| #22 | | | | | | | |
| 1/32 0 | 100 | 100 | 100 | 100 | 100 | 100 | 100 |
| 1/16 0 | 100 | 100 | 100 | 100 | 100 | 100 | 100 |
| ⅛ 0 | 100 | 100 | 100 | 100 | 100 | 100 | 100 |
| #24 | | | | | | | |
| 1/32 0 | 100 | 100 | 100 | 100 | 100 | 100 | 100 |
| 1/16 0 | 100 | 100 | 100 | 100 | 100 | 100 | 100 |
| ⅛ 0 | 100 | 100 | 100 | 100 | 100 | 100 | 100 |

EXAMPLE 320

Formulations of butachlor (herbicide cpd TM 10) and tank-mix safened butachlor (separately with antidote cpd. TM 1, TM 16, TM 22, TM 24 and TM 27) were pre-plant-incorporated in side-by-side field plots to determine their relative injury to direct seeded rice in eastern Missouri. Test formulations of butachlor, safened butachlor and a control formulation of antidote without herbicide, were prepared as described in the foregoing Examples. The plots (5×5 m; 15×15 ft) were sprayed with a small-plot tractor sprayer at a rate of 280 l/ha (30 gal/ac). A rototiller was used to incorporate the formulations into silty clay loam soil to a depth of about 2 to 5 cm (1 to 2 in). A John Deere drill planter was used to plant Labelle (Indica-type) rice at a seeding rate of 121 kg/ha (110 lb/ac). Test observations are reported in Table XVI.

| Field Conditions at Treatment: | |
|---|---|
| Wind speed: | calm |
| Air temperature: | 32° C. (90° F.) |
| Soil temperature: | 29° C. (85° F.) |
| Soil moisture: | surface dry, dry @ seed depth |
| Climatic Conditions First-Four Weeks: | |
| Rainfall: | 0.5 cm (0.20 in.) 18 days after treatment; |
| Irrigation: | 1.8 cm (¾ in) @ 1, 6 and 12 days after treatment |

TABLE XVI

| Herbicide #10 (kg/ha) | Antidote #_ (kg/ha) | Tank Mix Ratio Herbicide:Antidote | Rice Inhibition (%) | |
|---|---|---|---|---|
| | | | a | b |
| 0 | — | — | 0 | 0 |
| 3.36 | — | — | 82 | 57 |
| 6.72 | — | — | 92 | 70 |
| — | #1 6.72 | — | 0 | 0 |
| — | #16 6.72 | — | 0 | 0 |
| — | #22 6.72 | — | 0 | 0 |
| — | #24 6.72 | — | 0 | 0 |
| 3.36 | #1 0.84 | 4:1 | 40 | 22 |
| 6.72 | #1 1.68 | 4:1 | 48 | 28 |
| 3.36 | #1 1.68 | 2:1 | 37 | 18 |
| 6.72 | #1 3.36 | 2:1 | 35 | 22 |
| 3.36 | #1 3.36 | 1:1 | 22 | 17 |
| 6.72 | #1 6.72 | 1:1 | 25 | 18 |
| 3.36 | #16 0.84 | 4:1 | 30 | 22 |
| 6.72 | #16 1.68 | 4:1 | 45 | 33 |
| 3.36 | #16 1.68 | 2:1 | 27 | 13 |
| 6.72 | #16 3.36 | 2:1 | 37 | 25 |
| 3.36 | #16 3.36 | 1:1 | 27 | 12 |
| 6.72 | #16 6.72 | 1:1 | 33 | 18 |
| 3.36 | #22 0.84 | 4:1 | 27 | 17 |
| 6.72 | #22 1.68 | 4:1 | 37 | 25 |
| 3.36 | #22 1.68 | 2:1 | 27 | 18 |
| 6.72 | #22 3.36 | 2:1 | 40 | 27 |
| 3.36 | #22 3.36 | 1:1 | 27 | 17 |
| 6.72 | #22 6.72 | 1:1 | 35 | 22 |
| 3.36 | #24 0.84 | 4:1 | 25 | 13 |
| 6.72 | #24 1.68 | 4:1 | 32 | 22 |
| 3.36 | #24 1.68 | 2:1 | 18 | 10 |
| 6.72 | #24 3.36 | 2:1 | 28 | 20 |
| 3.36 | #24 3.36 | 1:1 | 22 | 7 |
| 6.72 | #24 6.72 | 1:1 | 30 | 17 |
| 3.36 | #27 0.84 | 4:1 | — | — |
| 6.72 | #27 1.68 | 4:1 | 45 | 28 |
| 3.36 | #27 1.68 | 2:1 | 40 | 32 |
| 6.72 | #27 3.36 | 2:1 | 32 | 22 |
| 3.36 | #27 3.36 | 1:1 | 23 | 13 |
| 6.72 | #27 6.72 | 1:1 | 28 | 22 | a = Observations taken at 12 days after treatment.
b = Observations taken at 22 days after treatment.

Although this invention has been described with respect to specific embodiments, the details of these

What is claimed is:

1. Compound of the formula

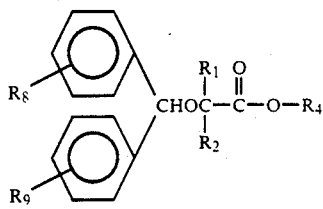

wherein $R_1$ and $R_2$ are H;

$R_4$ is H, alkyl, alkenyl, alkynyl, haloalkyl, cycloalkyl, alkoxyalkyl, alkoxycarbonylalkyl, alkylthioalkyl, hydroxyalkyl, phenyl or benzyl and, when not self-inclusive, said $R_4$ members substituted with alkyl, cycloalkyl, alkoxy, haloalkyl, phenyl, halophenyl, alkoxyphenyl or nitro groups and $R_8$ and $R_9$ are independently H, alkyl, alkoxy, halo or haloalkyl; provided that:

(a) when $R_4$ is H, $R_8$ and/or $R_9$ cannot be H, methyl, ethyl or halogen and (b) when $R_8$ and/or $R_9$ are H, halogen or $CF_3$, $R_4$ cannot be methyl, ethyl, n-propyl, 2-ethoxyethyl or diphenylmethyl.

2. Compound according to claim 1 wherein $R_4$ is selected from the group consisting of H, lower alkyl, $C_{2-5}$ alkenyl or alkynyl, benzyl, phenyl, pyridylmethyl and when not self-inclusive said $R_4$ members substituted with halo, haloloweralkyl, nitro or cyano groups.

3. Compound of claim 2 which is 1,1-dimethylethyl diphenylmethoxyacetate.

4. Compound of claim 2 which is benzyl diphenylmethoxyacetate.

5. Compound of claim 2 which is 1-methylethyl diphenylmethoxyacetate.

6. Compound of claim 2 which is 2,2,2-trifluoroethyl diphenylmethoxyacetate.

7. Compound of claim 2 which is phenyl diphenylmethoxyacetate.

8. Compound of claim 2 which is 2,2,3,3-tetrafluoropropyl diphenylmethoxyacetate.

9. Compound of claim 2 which is 1-methyl-2,2,2-trifluoroethyl phenyl]3-(trifluoromethyl)phenyl]methoxyacetate.

10. Compound of claim 2 which is 4-chlorobenzyl diphenylmethoxyacetate.

11. Compound of claim 2 which is bis(2,6-dimethylphenyl)methoxyacetic acid.

12. Compound of claim 2 which is 3-nitrophenyl diphenylmethoxyacetate.

13. Compound of claim 2 which is ethyl bis(2,6-dimethylphenyl)methoxyacetate.

14. Compound of claim 2 which is 3-pyridinylmethyl diphenylmethoxyacetate.

15. Compound of claim 2 which is 1-cyano-1-methylethyl diphenylmethoxyacetate.

16. Compound of claim 2 which is 2-cyanoethyl diphenylmethoxyacetate.

17. Compound of claim 2 which is 1-cyano-1-methylethyl bis(2,6-dimethylphenyl)methoxyacetate.

18. Compound of claim 2 which is 1-methyl-2-propynyl diphenylmethoxyacetate.

19. Compound of claim 2 which is 3-nitrophenyl (4-chlorophenyl)phenylmethoxyacetate.

20. Compound of claim 2 which is 1-cyano-1-methylethyl (4-chlorophenyl)phenylmethoxyacetate.

21. Compound of claim 2 which is 1-ethyl-2-propynyl diphenylmethoxyacetate.

22. Compound of claim 2 which is 2-propenyl (4-chlorophenyl)phenylmethoxyacetate.

* * * * *